US007462608B2

(12) United States Patent
Chen et al.

(10) Patent No.: US 7,462,608 B2
(45) Date of Patent: Dec. 9, 2008

(54) NON NUCLEOSIDE REVERSE TRANSCRIPTASE INHIBITORS

(75) Inventors: James M. Chen, San Ramon, CA (US); Xiaowu Chen, San Mateo, CA (US); Choung U. Kim, San Carlos, CA (US); William A. Lee, Los Altos, CA (US); Christopher P. Lee, San Francisco, CA (US); Peter H. Nelson, Los Altos, CA (US); James D. Tario, San Mateo, CA (US); Lianhong Xu, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 736 days.

(21) Appl. No.: 10/424,130

(22) Filed: Apr. 25, 2003

(65) Prior Publication Data

US 2005/0197320 A1 Sep. 8, 2005

Related U.S. Application Data

(60) Provisional application No. 60/375,834, filed on Apr. 26, 2002, provisional application No. 60/375,779, filed on Apr. 26, 2002, provisional application No. 60/375,665, filed on Apr. 26, 2002, provisional application No. 60/375,622, filed on Apr. 26, 2002.

(51) Int. Cl.
*A61K 31/665* (2006.01)
*C07D 265/18* (2006.01)

(52) U.S. Cl. .......................... 514/75; 544/90
(58) Field of Classification Search .................. 544/90; 514/230.5, 75
See application file for complete search history.

(56) References Cited

U.S. PATENT DOCUMENTS

| 5,413,996 | A | 5/1995 | Bodor |
| 5,670,497 | A | 9/1997 | Bold et al. |
| 5,750,343 | A | 5/1998 | Maag et al. |
| 5,750,493 | A | 5/1998 | Schinazi et al. |
| 5,874,577 | A | 2/1999 | Chen et al. |
| 5,914,332 | A | 6/1999 | Chen et al. |
| 6,072,053 | A | 6/2000 | Vince et al. |
| 6,312,662 | B1 | 11/2001 | Robinson et al. |
| 6,767,900 | B2 | 7/2004 | Ubasawa et al. |
| 2001/0031773 | A1 | 10/2001 | Camden |
| 2003/0109498 | A1 | 6/2003 | Yuasa et al. |

FOREIGN PATENT DOCUMENTS

| EP | 0 267 050 | 5/1988 |
| EP | 0 441 192 | 1/1991 |
| EP | 0 465 297 | 1/1992 |
| EP | 0 531 597 | 3/1993 |
| EP | 0 632 048 | 1/1995 |
| EP | 0 786 455 | 7/1997 |
| EP | 0 852 233 | 7/1998 |
| EP | 0 919 562 | 6/1999 |
| EP | 1 295 879 | 3/2003 |
| WO | WO 88/06158 | 8/1988 |
| WO | WO 91/19721 | 12/1991 |
| WO | WO 92/00988 | 1/1992 |
| WO | WO 92/18520 | 10/1992 |
| WO | WO 93/12123 | 6/1993 |
| WO | WO 93/24510 | 12/1993 |
| WO | WO 96/14314 | 5/1996 |
| WO | WO 96/40156 | 12/1996 |
| WO | WO 98/04569 | 2/1998 |
| WO | WO 98/11906 | 3/1998 |
| WO | WO 99/62921 | 12/1999 |
| WO | WO 00/04033 | 1/2000 |
| WO | WO 01/13957 | 3/2001 |
| WO | WO 01/17982 | 3/2001 |
| WO | WO 01/19320 | 3/2001 |
| WO | WO 01/46204 | 6/2001 |
| WO | WO 01/64693 | 9/2001 |
| WO | WO 01/96329 | 12/2001 |
| WO | WO 02/03997 | 1/2002 |
| WO | WO 02/06292 | 1/2002 |
| WO | WO 02/08241 | 1/2002 |
| WO | WO 02/14344 | 2/2002 |
| WO | WO 02/057425 | 7/2002 |
| WO | WO 02/100415 | 12/2002 |
| WO | WO 03/028737 | 4/2003 |
| WO | WO 03/050129 | 6/2003 |
| WO | WO 03/059255 | 7/2003 |
| WO | WO 03/064383 | 8/2003 |
| WO | WO 03/066005 | 8/2003 |
| WO | WO 03/080078 | 10/2003 |
| WO | WO 03/090690 | 11/2003 |
| WO | WO 2004/096234 | 11/2004 |
| WO | WO 2005/011709 | 2/2005 |

OTHER PUBLICATIONS

U.S. Appl. No. 10/832,915, commonly owned.*
U.S. Appl. No. 11/106,363, commonly owned.*
U.S. Appl. No. 11/258,621, commonly owned.*
Menendez-Aria, Luis. "Targeting HIV: an antiretroviral therapy and development of drug resistance," *Trends in Pharm. Sciences*, vol. 23 (8), pp. 381-388.*
Abdel-Meguid, Sherin S. et al., Inhibition of Human Immunodeficiency Virus-1 Protease by a $C_2$-Symmetric Phosphinate. Synthesis and Crystallographic Analysis, *Biochemistry*, 1993, 1543-1572, vol. 32, No. 31.

(Continued)

*Primary Examiner*—Joseph McKane
*Assistant Examiner*—Janet L Coppins
(74) *Attorney, Agent, or Firm*—Mark L. Bosse

(57) ABSTRACT

Phosphorus-substituted imidazole compounds with anti-HIV properties having use as therapeutics and for other industrial purposes are disclosed. The compositions inhibit reverse transcriptase activity and are useful therapeutically for the inhibition of such enzymes, as well as in assays for the detection of such enzymes.

75 Claims, 153 Drawing Sheets

OTHER PUBLICATIONS

Allen, Lee F. et al., CI-1040 (PDI84352), a Targeted Signal Transduction Inhibitor of MEK (MAPKK), *Seminars in Oncology*, Oct. 2003, pp. 105-106, vol. 30, No. 5, Elsevier Inc.

Bantia, Shanta et al., Purine nucleoside phosphorylase inhibitor BCX-1777 (Immucillin-H)—a novel potent and orally active immunosuppressive agent, *International Immunopharmacology*, 2001, pp. 1199-1210, Elsevier Science B.V.

Beauchamp, Lilia M., et al., Guanine, Pyrazolo[3,4-d]pyrimidine, and Triazolo[4,5-d]pyrimidine(8-Azaguanine) Phosphonate Acyclic Derivatives as Inhibitors of Purine Nucleoside Phosphorylase, *Journal of Medicinal Chemistry*, 1996, pp. 949-956, American Chemical Society.

Bohandi D. W. et al., A-420983: a potent, orally active inhibitor of Ick with efficacy in a model of transplant rejection, *Bioorganic & Medicinal Chemistry Letters*, 2004, vol. 14.

Bzowska, Agnieszka et al., Purine nucleoside phosphorylases: properties, functions, and clinical aspects, *Pharmacology & Therapeutics*, 2000, pp. 349-425, vol. 88, Elsevier Science Inc.

Chapman, H. et al., Practical Synthesis, Separation, and Stereochemical Assignment of the PMPA Pro-Drug GS-7340, Nucleosides, Nucleotides & Nucleic Acids, 2001, pp. 621-628, vol. 20, Nos. 4-7, Marcel Dekker, Inc.

Clark, Jeremy L. et al., Mycophenolic Acid Analogues as Potential Agents Against West Nile Virus Infection.

Conklyn, Maryrose et al., The JAK3 inhibitor CP-690550 selectively reduces NK and CD8+ cell numbers in cynomolgus monkey blood following chronic oral dosing, *Journal of Leukocyte Biology*, Dec. 2004, pp. 1-8, vol. 76, The Society for Leukocyte Biology.

De Clereq, E., Highlights in the Development of New Antiviral Agents, *Mini Reviews in Medicinal Chemistry*, 2002, 163-175, vol. 2, No. 2., Bentham Science Publishers, Ltd.

De Clercq, Erik, New Developments in Anti-HIV Chemotherapy, *Current Medicinal Chemistry*, 2001, 1543-1572, vol. 8, No. 13, Bentham Science Publishers Ltd.

Dvorakova, Hana et al., Synthesis of 2'-Aminomethyl Derivatives of N-(2-(Phosphonomethoxy)ethyl) Nucleotide Analogues as Potential Antiviral Agents, *J. Med. Chem.*, 1996, 3263-3268. vol. 38, No. 17.

Evans, Gary B., Exploring Structure—Activity Relationships of Transition State Analogues of Human Purine Nucleoside Phosphorylase, *J. Med. Chem.*, 2003, 3412-3423, vol. 46, No. 15, American Chemical Society.

Gumina, Giuseppe et al., Advances in antiviral agents for hepatitis B virus, *Antiviral Chemistry & Chemotherapy*, 2001, 93-112, vol. 12, Suppl. 1, International Medical Press.

Gobec, S. et al., Phosphonate inhibitors of antiget 85C, a crucial enzyme involved in the biosynthesis of the mycobacterium tuberculosis cell wall, *Bioorganic and Medicinal Chemistry Letters*, 2004, vol. 14.

Hegedus, Louis S. et al., Synthesis of 4'-Methyl and 4'-cyano Carbocyclic 2',3'-Didehydro Nucleoside Analogues via 1,4-Addition to Substituted Cyclopentenones, *J. Org. Chem.*, 2004, 8492-8495, vol. 69, No. 24, American Chemical Society.

Herczegh P., et al., Osteoadsorptive bisphosphonate derivatives of fluoroquinolone antibacterials, *J. Med. Chem.*, 2002, vol. 45.

Hirabayashi, Hideki et al., Bone-Specific Drug Delivery Systems, *Clinical Pharacokinetics*, 2003, 1319-1330, vol. 42, No. 15.

Holy A. et al., Synthesis, *Cllect. Czech. Chem. Commun.*, 1989, vol. 54, pp. 2190-2210.

Jain, Jugnu et al., Characterization of Pharmacological Efficacy of VX-148, a New, Potent Immunosuppressive Inosine 5'-Monophosphate Dehydrogenase Inhibitor, *Journal of Pharmacology and Experimental Therapeutics*, 2002, 1272-1277, vol. 302, No. 3, The American Society for Pharmacology and Experimental Therapeutics.

Karpenko, Inna L. et al., Synthesis and Antiherpetic Activity of Acyclovir Phosphonates, *Nucleosides, Nucleotides & Nucleic Acids*, 2003, 319-328, vol. 22, No. 3, Marcel Dekker, Inc.

Kato, Keisuke et al., Stereoselective synthesis of 4'-.alpha.-alkyclcarbovir derivatives based on an asymmetric synthesis or chemo-enzymatic procedure, *Chemical & Pharmaceutical Bulletin*, 1999, 1256-1264, vol. 49, No. 9, Pharmaceutical Society of Japan.

Kato, Keisuke et al., Enantio- and diastereoselective syntheis of 4'-.α.-substituted carbocyclic nucleosides, *Tetrahedron: Asymmetry*, 1998, 911-914, vol. 9, Elsevier Science Ltd.

Kilpatrick, J. Michael, Intravenous and oral pharmacokinetic study of BCX-1777, a novel purine nucleoside phosphorylase transition-state inhibitor, In vivo effects on blood 2'-deoxyguanosine in primates, *International Immunopharmacology*, 2003, 541-548, vol. 3, Elsevier Science B.V.

Kim, Choung Un et al., Regiospecific and Highly Stereoselective Electrophilic Addition to Furanoid Glycals: Synthesis of Phosphonate Nucleotide Analogues with Potent Activity against HIV, *J. Org. Chem.*, 1991, 2642-2647, vol. 56, No. 8, American Chemical Society.

Kinsky, Stephen C. et al., Inhibition of cell proliferation by putative metabolites and non-degradable analogs of methotrexate-.gamma.-dimyristoylphosphatidylethanolamine, *Biochimica et Biphysica Acta*, 19878, 211-218, vol. 917, No. 2., Elsevier Science Publishers B.V.

Kinsky, Stephen C. et al., Effect of liposomes sentitized with methotrexate-γ-dimyristoylphosphatidylethanolamine on cells that are resistant to methotrexate, *Biochimica et Biophysica Acta*, 1986, 129-135, vol. 885, Elsevier Science Publishers B.V.

Kinsky, Stephen C. et al., Circumvention of the methotrexate transport system by methotrexate-phosphatidylethanolamine derivatives effect of fatty acid chain length, *Biochimica et Biophysica Acta*, 1987, 96-103, vol. 921, Elsevier Science Publishers B.V.

Ko, Ok Hyun et al., Efficient synthesis of novel carbocyclic nucleosides via sequential Claisen rearrangement and ring-closing metathesis, *Tetrahedron Letters*, 2002, 6399-6402, vol. 43, Elsevier Science Ltd.

Lewandowicz, Andrzej et al., Achieving the Ultimate Physiological Goal in Transition State Analogue Inhibitors for Purine Nucleoside Phosphorylase, *The Journal of Biological Chemistry*, 2003, 31465-31468, vol. 278, No. 34, The American Society for Biochemistry and Molecular Biology, Inc.

Menendez-Arias, Luis et al. Targeting HIV: antiretroviral therapy and development of drug resistance, *Trends in Pharmacological Sciences*, 2002, 381-388, vol. 23, No. 8, Elsevier Science, Ltd.

Ono-Nita, Suzane Kioko et al., Novel Nucleoside Analogue MCC-478 (LY582563) Is Effective against Wild-Type or Lamivudine-Resistant Hepatitis B Virus, *Antimicrobial Agents and Chemotherapy*, 2002, 2602-2605, vol. 46, No. 8, American Society for Microbiology.

Pankiewicz, Krzysztof W., Novel Mycophenolic Adenine Bis(phosphonate) Analogues As Potential Differentiation Agents against Human Leukemia, *J. Med. Chem.*, 2002 703-712, vol. 45, No. 3, American Chemical Society.

Parang, Keykavous et al., Novel Approaches for Designing 5'-O-Ester Prodrugs of 3'-Azido-2', 3'-dideoxythymidine (AZT), *Current Medicinal Chemistry*, 2000, 995-1039, vol. 7, No. 10, Bentham Science Publishers Ltd.

Prashad, Mahavir et al., An Efficient and Large-Scale Enantioselective Synthesis of PNP405: A Purine Nucleoside Phosphorylase Inhibitor, *J. Org. Chem.*, 2002, 6612-6617, vol. 67, No. 19, American Chemical Society.

Ray, Adrian S. et al., Role of Purine Nucleoside Phosphorylase in Interactions between 2', 3'-Dideoxyinosine and Allopurinal, Ganciclovir, or Tenofovir, Antimicrobial Agents and Chemotherapy, 2004, 1089-1095, vol. 48, No. 4, American Society for Microbiology.

Reed, Leff et al., Antidiabetic PPARγ Ligands: An update on Compounds in development, *Curr. Med. Chem.—Imun., Endoc. & Metab. Agents*, 2002, 33-47, vol. 2, No. 1, Bentham Science Publishers Ltd.

Roberts, Stanley M., Development of the route to the new anti-AIDS drug abacavir: A highlight of academic/industry laison, *IDrugs*, 1998, 896-899, vol. 1, No. 8, Current Drugs Ltd.

Rosowsky, Andre et al., Methotrexate Analogues—27, *Biochemical Pharmacology*, 1986, 3327-3333, vol. 35, No. 19, Pergamon Journals Ltd.

Rosowsky, Andre et al., Methotrexate Analogues, 32, Chain Extension, α-Carboxyl Replacement by Sulfonate and Phosphonate: Effect on Enzyme Binding and Cell-Growth Inhibition, *J. Med. Chem.*, 1988, 1326-1331, vol. 31, No. 7, American Chemical Society.

Schultz, C., Prodrugs of biologically active phosphate esters, *Bioorganic & Medicinal Chemistry*, 2003, 885-898, vol. 11, Elsevier Science Ltd., GB.

Sekiya, Kouichi et al., 2-Amino-6-arylthio-9-[2-(phosphonomethoxy) ethyl) purine Bis(2,2,2-trifluoroethyl) Esters as Novel HBV-Specific Antiviral Reagents, Journal of Medicinal Chemistry, 2002, 3138-3142, vol. 45, No. 14, American Chemical Society.

Shi, Wuxian et al., *Plasmodium falciparum* Purine Nucleoside Phosphorylase, The Journal of Biological Chemistry, 2004, 18103-18106, vol. 279, No. 18, The American Society of Biochemistry and Molecular Biology, Inc.

Sintchak, Michael D. et al., The structure of inosine 5'-monophosphate dehydrogenase and the design of novel inhibitors, Immunopharmachology, 2000, 163-184, vol. 47, Elsevier.

Srinivas, Ranga V. et al., Metabolism and In Vitro Antiretroviral Activities of Bis(Pivaloyloxymethyl) Prodrugs of Acyclic Nucleoside Phosphonates, Antimicrobial Agents and Chemotherapy, 1993, 2247-2250, vol. 37, No. 10, American Society for Microbiology.

Sturtz, Georges et al., Su rune nouvelle approche de pharmacomodulation du methotrexate: synthese d'analogues gem-diphosphoniques d'amethopterine et de la N-10 deaza amethopterine, Medicinal Chemistry, C. R. Acad. Sci. Paris, 1990, vol. 10, No. 2, 739-742, Academie des Sciences.

Sturtz, Georges et al., Analogues phosphonoglutamiques d'amethopterine (methotrexate), Eur. J. Med. Chem—Chim. Ther., 1984, 267-273, vol. 19, No. 3.

Sturtz, G. et al., Synthesis of gem-biphosphonic methotrexate conjugates and their biological response towards Walker's osteosarcoma, *Eur. J. Med. Chem.*, 1993, 899-903, vol. 28, Elsevier.

Sturtz, G. et al., A study of the delivery-targeting concept applied to antineoplasic drugs active on human osteosarcoma, I. Synthesis and biological activity in nude mice carrying human osteosarcoma xenografts of gem-bisphosphonic methotrexate analogues, Eur J. Med. Chem., 1992, 825-833, vol. 27, No. 8, Elsevier.

Vielhaber, Bernd, Bericht vom 3rd International Workshop on Salvage Therapy for HIV-Infection, *Deutsche Aids-Hilfe e.V. FaxReport zu HIV und AIDS*, 2000, 12-14.

Waegell W. et al. A420983, a novel, small molecule inhibitor of LCK prevents allograft rejection, Transplantation Proceedings, 2002, 1411-1417, vol. 34.

Wroblewski, Andrzej et al., Synthesis of (1R,2S)- and (1S,2S)-3-(4-carbamoyl-1,2,3-triazol-1-yl)-1,2-dihydroxypropylphosphonates, Tetrahedron: Asymmetry, 2004, 1457-1464, vol. 15, Elsevier.

\* cited by examiner

Scheme A

Scheme 1 Example 2

Scheme 1 Example 3

Scheme 1 Example 6

Scheme 3 Example 2

Scheme 4 Example 2

Scheme 2

Scheme 8

Scheme 9

Scheme 11

Scheme 18

Scheme 19

Scheme 20

Scheme 21

Scheme 22

Scheme 23

Scheme 24

Scheme 26

Scheme 1

Scheme 2

Example 2

Example 3

Scheme 2

Scheme 1

Scheme 1

Scheme 3

Example 3

Example 2

Scheme 6

R$_1$: defined as above but contains OH, NH$_2$

Example 4

Scheme 1

Example 1

Scheme 2

Scheme 4

Example 4

Scheme 1

Example 1

Scheme 2

Example 2

Scheme 5

Example 3

Example 4

Scheme 7

Example 5

Scheme 3

Scheme 5

Scheme 7

Scheme 2

Scheme 3

5-membered heterocycle with linkPO(R₁)(R₂) attached at heterocycle 6-membered heterocycle with linkPO(R₁)(R₂) attached at heterocycle Scheme 2

Scheme 3

NON NUCLEOSIDE REVERSE TRANSCRIPTASE INHIBITORS

This non-provisional application claims the benefit of Provisional Application No. 60/375,622, filed Apr. 26, 2002, Provisional Application No. 60/375,779 filed Apr. 26, 2002, Provisional Application No. 60/375,834 filed Apr. 26, 2002 and Provisional Application No. 60/375,665 filed Apr. 26, 2002, which are incorporated herein by reference. Additionally, copending applications filed concurrently with this application are also incorporated herein by reference in their entirety.

FIELD OF THE INVENTION

The invention relates generally to compounds with antiviral activity and more specifically with anti-HIV properties.

BACKGROUND OF THE INVENTION

Human immunodeficiency virus (HIV) infection and related disease is a major public health problem worldwide. The retrovirus human immunodeficiency virus type 1 (HIV-1), a member of the primate lentivirus family (DeClercq E (1994) Annals of the New York Academy of Sciences, 724: 438-456; Barre-Sinoussi F (1996) Lancet, 348:31-35), is generally accepted to be the causative agent of acquired immunodeficiency syndrome (AIDS) Tarrago et al FASEB Journal 1994, 8:497-503). AIDS is the result of repeated replication of HIV-1 and a decrease in immune capacity, most prominently a fall in the number of CD4+ lymphocytes. The mature virus has a single stranded RNA genome that encodes 15 proteins (Frankel et al (1998) Annual Review of Biochemistry, 67:1-25; Katz et al (1994) Annual Review of Biochemistry, 63:133-173), including three key enzymes: (i) protease (Prt) (von der Helm K (1996) Biological Chemistry, 377:765-774); (ii) reverse transcriptase (RT) (Hottiger et al (1996) Biological Chemistry Hoppe-Seyler, 377:97-120), an enzyme unique to retroviruses; and (iii) integrase (Asante et al (1999) Advances in Virus Research 52:351-369; Wlodawer A (1999) Advances in Virus Research 52:335-350; Esposito et al (1999) Advances in Virus Research 52:319-333). Protease is responsible for processing the viral precursor polyproteins, integrase is responsible for the integration of the double stranded DNA form of the viral genome into host DNA and RT is the key enzyme in the replication of the viral genome. In viral replication, RT acts as both an RNA- and a DNA-dependent DNA polymerase, to convert the single stranded RNA genome into double stranded DNA. Since virally encoded Reverse Transcriptase (RT) mediates specific reactions during the natural reproduction of the virus, inhibition of HIV RT is an important therapeutic target for treatment of HIV infection and related disease.

Until 1995, the only drugs approved in the United States were nucleoside inhibitors of RT (Smith et al (1994) Clinical Investigator, 17:226-243). Since then, two new classes of agents, protease inhibitors and non-nucleoside RT inhibitors (NNRTI), and more than ten new drugs have been approved (Johnson et al (2000) Advances in Internal Medicine, 45 (1-40; Porche D J (1999) Nursing Clinics of North America, 34:95-112). There are now three classes of drugs available: (1) the original nucleoside RT inhibitors, (2) protease inhibitors, and (3) the non-nucleoside RT inhibitors (NNRTI). Nucleoside RT inhibitors include zidovudine, didanosine (NIH), zalcitabine (NIH), lamivudine (BioChem Pharma Inc) and abacavir (Glaxo Wellcome plc). See Johnson V A (1995) Journal of Infectious Diseases, 171 :Suppl 2:S140-S149; Venrura et al (1999) Archives of Virology, 144:513-523; and Venrura et al Archives of Virology 1999, 144 (513-523).

Approved protease inhibitor drugs include saquinavir (Hoffmann-La Roche Inc, Noble et al (1996) Drugs, 52:1, 93-112), ritonavir (Abbott Laboratories), indinavir (Merck & Co Inc), nelfinavir (Agouron Pharmaceuticals Inc) and amprenavir (Vertex Pharmaceuticals Inc). Approved NNRTI include nevirapine (Boehringer Ingelheim Corp, Grob et al (1992) AIDS Research and Human Retroviruses, 8:145-152; Pollard et al (1998) Clinical Therapeutics, 20:1071-1092), delavirdine (Pharmacia & Upjohn Inc, Freimuth W W (1996) Advances in Experimental Medicine and Biology, 394:279-289) and efavirenz (DuPont Pharmaceuticals Co, Adkins et al (1998) Drugs, 56:6, 1055-1066). Capravirine is an orally administered NNRTI therapeutic candidate (Brown W. (2000) Current Opinion in Anti-Infective Investigational Drugs 2(3):286-94).

RT can be inhibited by both nucleoside and non-nucleoside drugs (Venrura et al (1999) Archives of Virology, 144:513-523; Matthee et al (1999) Planta Medica 65:493-506). The nucleoside inhibitors act as competitive inhibitors, competing with the natural substrates or as chain terminators (Mayers D (1996) AIDS 10:Suppl 1, S9-S13; Villahermosa et al (1997) Biochemistry, 36:13223-13231; Klarmann et al (2000) Journal of Biological Chemistry, 275:359-366). The nucleoside inhibitors, including zidovudine, didanosine and zalcitabine, remain first-line therapies against HIV-1. However, extended use of these drugs leads to the development of HIV variants that are resistant to them (Moyle G J (1997) Journal of Antimicrobial Chemotherapy, 40:6, 765-777; Smith et al (1994) Clinical Investigator 17:226-243). This development of resistance has been associated with specific point mutations in the HIV pol gene, encoding RT.

The non-nucleoside inhibitors act by interacting with a non-substrate-binding site on the enzyme, i.e. allosterically (Proudfoot J R (1998) Current Opinion in Therapeutic Patents, 8:8, 971-982; DeClercq E (1998) Antiviral Research 38:3, 153-179; DeClercq E (1999) Farmaco 54:1-2, 26-45; Katlama C (1999) International Journal of Clinical Practice, 103:Suppl 16-20; Pederson et al (1999) Antiviral Chemistry and Chemotherapy 10:258-314). The NNRTI drugs have now gained a place in the arsenal of treatments for HIV-1 infection (Spence et al (1995) Science 267:988-993), acting non-competitively by interacting with a specific site on the RT that is near to, but distinct from, the active site where the nucleoside inhibitors bind. Several relevant crystal structures of HIV-1 RT complexed with the non-nucleoside inhibitors have been reported, expanding the understanding of how these inhibitors operate (Schafer-W et al (1993)Journal of Medicinal Chemistry 36:726-732).

Although drugs targeting reverse transcriptase and protease are in wide use and have shown effectiveness, particularly when employed in combination, toxicity and development of resistant strains have limited their usefulness (Palella, et al N. Engl. J. Med. (1998) 338:853-860; Richman, D. D. Nature (2001) 410:995-1001).

Combination therapy with RT inhibitors has proven to be highly effective in suppressing viral replication to unquantifiable levels for a sustained period of time. Also, combination therapy with RT and Prt inhibitors have shown synergistic effects in suppressing HIV replication. Unfortunately, 30 to 50% of patients currently fail combination therapy due to the development of drug resistance, non-compliance with complicated dosing regimens, pharmacokinetic interactions, toxicity, and lack of potency. Therefore, there is a need for new HIV-1 inhibitors that are synergistic in combination with other HIV inhibitors.

Assay methods capable of determining the presence, absence or amounts of HIV RT are of practical utility in the search for inhibitors as well as for diagnosing the presence of HIV.

Inhibition of HIV RT is an object of the invention. Inhibitors of HIV RT are useful to limit the establishment and progression of infection by HIV as well as in diagnostic assays for HIV RT, both of which are further objects of the invention. Preparation of compositions capable of inhibiting HIV RT is also an object of the invention.

There is a need for HIV RT inhibitors having improved antiviral and pharmacokinetic properties, including enhanced activity against development of HIV resistance, improved oral bioavailability, greater potency and extended effective half-life in vivo. New HIV RT inhibitors should be active against mutant HIV strains, have distinct resistance profiles, fewer side effects, less complicated dosing schedules, and orally active. In particular, there is a need for a less onerous dosage regimen, such as one pill, once per day.

Improving the delivery of drugs and other agents to target cells and tissues has been the focus of considerable research for many years. Though many attempts have been made to develop effective methods for importing biologically active molecules into cells, both in vivo and in vitro, none has proved to be entirely satisfactory. Optimizing the association of the inhibitory drug with its intracellular target, while minimizing intercellular redistribution of the drug, e.g. to neighboring cells, is often difficult or inefficient.

Most agents currently administered to a patient parenterally are not targeted, resulting in systemic delivery of the agent to cells and tissues of the body where it is unnecessary, and often undesirable. This may result in adverse drug side effects, and often limits the dose of a drug (e.g., cytotoxic agents and other anti-cancer or anti-viral drugs) that can be administered. By comparison, although oral administration of drugs is generally recognized as a convenient and economical method of administration, oral administration can result in either (a) uptake of the drug through the cellular and tissue barriers, e.g. blood/brain, epithelial, cell membrane, resulting in undesirable systemic distribution, or (b) temporary residence of the drug within the gastrointestinal tract. Accordingly, a major goal has been to develop methods for specifically targeting agents to cells and tissues. Benefits of such treatment includes avoiding the general physiological effects of inappropriate delivery of such agents to other cells and tissues, such as uninfected cells.

Intracellular targeting may be achieved by methods and compositions which allow accumulation or retention of biologically active agents inside cells.

SUMMARY OF THE INVENTION

The present invention provides compositions and methods for inhibition of HIV. Compositions of the invention include new imidazole compounds substituted on a carbon atom of the imidazole ring with a sulfur group, and having at least one phosphonate group. Accordingly, the invention includes compounds having Formula I:

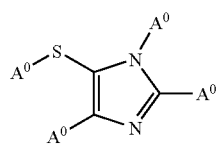

I wherein $A^0$ is $A^1$, $A^2$ or $W^3$. Compounds of the invention include at least one $A^1$ which comprises at least one phosphonate group. In another aspect, the invention includes compounds having Formula II:

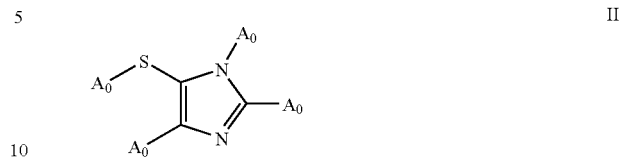

II wherein $A_0$ is $A_1$, $A_2$ or $W_3$. Formula II includes at least one $A_1$ which comprises at least one phosphonate group.

In one aspect, a compound or composition of the invention is provided that further comprises a pharmaceutically-acceptable carrier.

In another aspect of the invention, phosphonate analogs of known approved and experimental non-nucleoside RT inhibitors (NNRTI) are provided which include:
  Capravirine-like phosphonate NNRTI compounds
  PETT-like phosphonate NNRTI compounds
  Pyrazole-like phosphonate NNRTI compounds
  Urea-PETT-like phosphonate NNRTI compounds
  Nevaripine-like phosphonate NNRTI compounds
  Quinazolinone-like phosphonate NNRTI compounds
  Efavirenz-like phosphonate NNRTI compounds
  Benzophenone-like phosphonate NNRTI compounds
  Pyrimidine-like phosphonate NNRTI compounds
  SJ3366-like phosphonate NNRTI compounds
  Delavirdine-like phosphonate NNRTI compounds
  Emivirine-like phosphonate NNRTI compounds
  Loviride-like phosphonate NNRTI compounds
  UC781-like phosphonate NNRTI compounds as well as analogs and pharmaceutically acceptable salts, hydrates, and formulations thereof.

In another aspect of the invention the activity of HIV reverse transcriptase (RT) is inhibited by a method comprising the step of treating a sample suspected of containing HIV RT with a compound or composition of the invention.

Another aspect of the invention provides a method for inhibiting the activity of HIV RT comprising the step of contacting a sample suspected of containing HIV RT with the composition embodiments of the invention.

Another aspect of the invention provides a pharmaceutical combination comprising an effective amount of a compound of the invention and a second compound having anti-HIV properties.

Another aspect of the invention provides a method for the treatment or prevention of the symptoms or effects of an HIV infection in an infected animal, which comprises administering to, i.e. treating said animal with a pharmaceutical combination comprising an effective amount of a compound of the invention and a second compound having anti-HIV properties.

In other aspects, novel methods for syntheses of the compounds of this invention are provided.

DETAILED DESCRIPTION OF EXEMPLARY EMBODIMENTS

Figure 1:
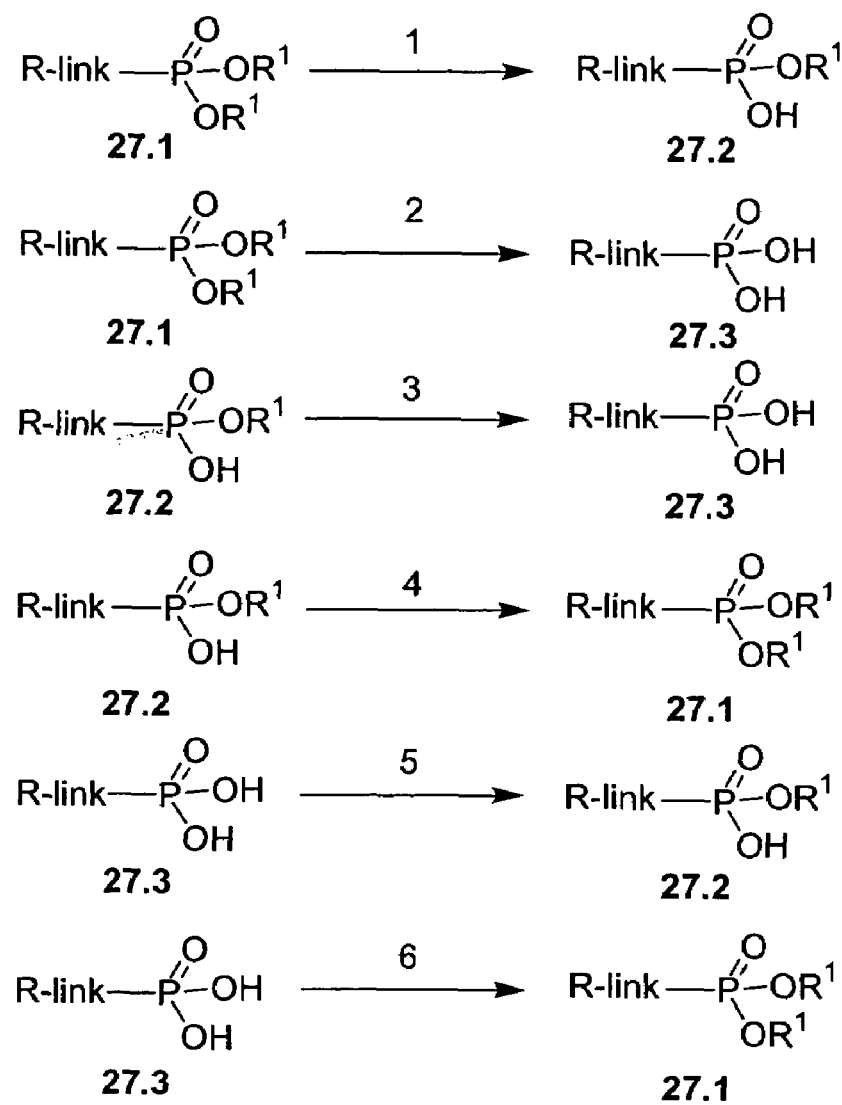
FIG. 1 illustrates scheme A which is described in detail herein below.
Figure 2A:
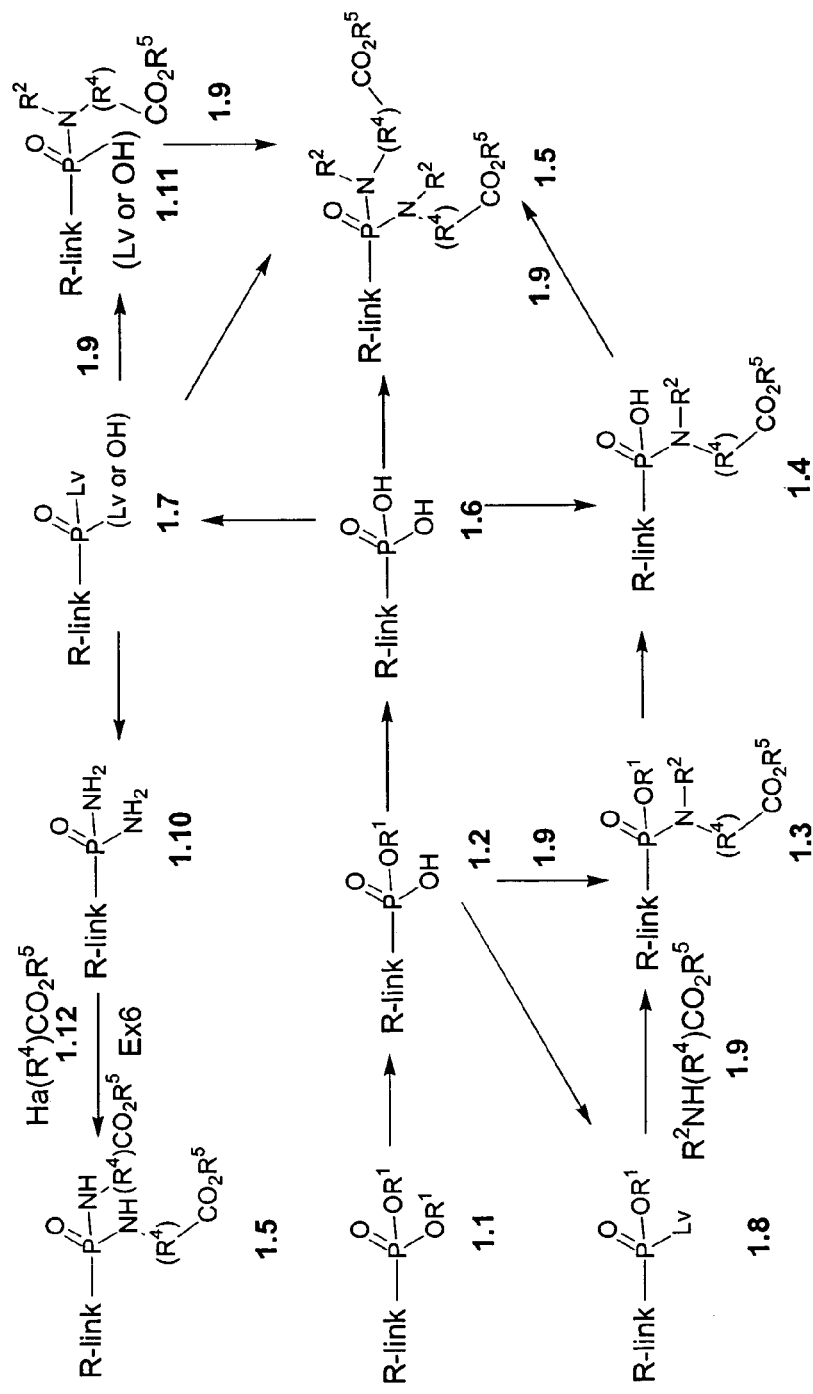
FIGS. 2A-H depict Scheme 1 which is described in detail herein below.
Figure 2B:
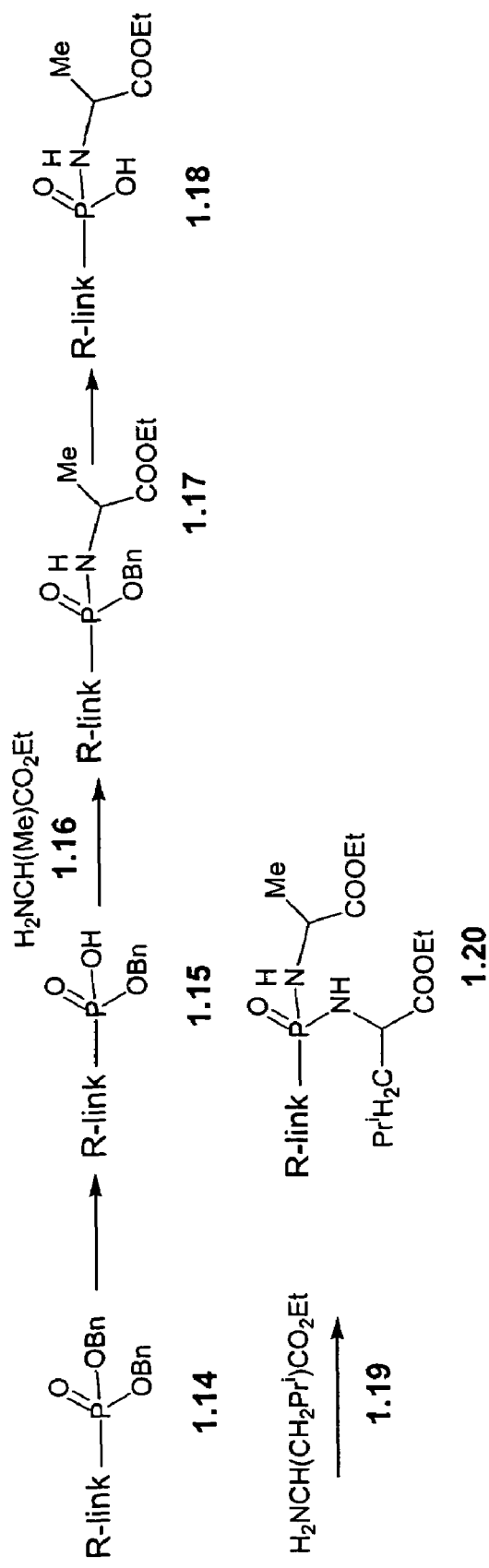
Figure 2C:
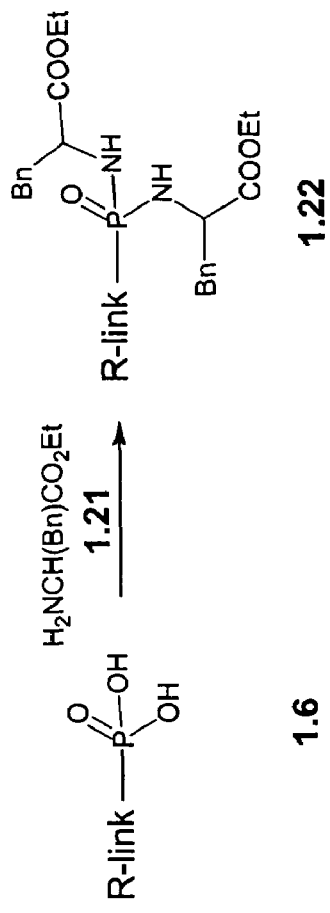
Figure 2D:
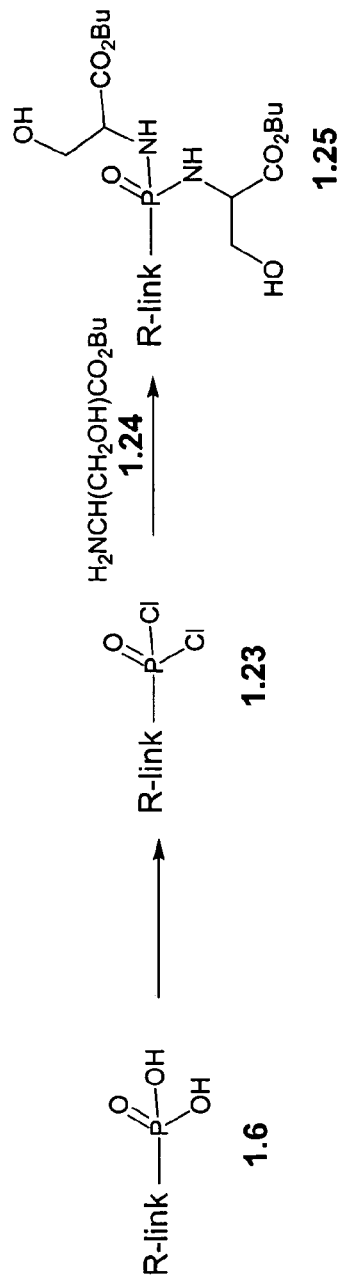
Figure 2E:
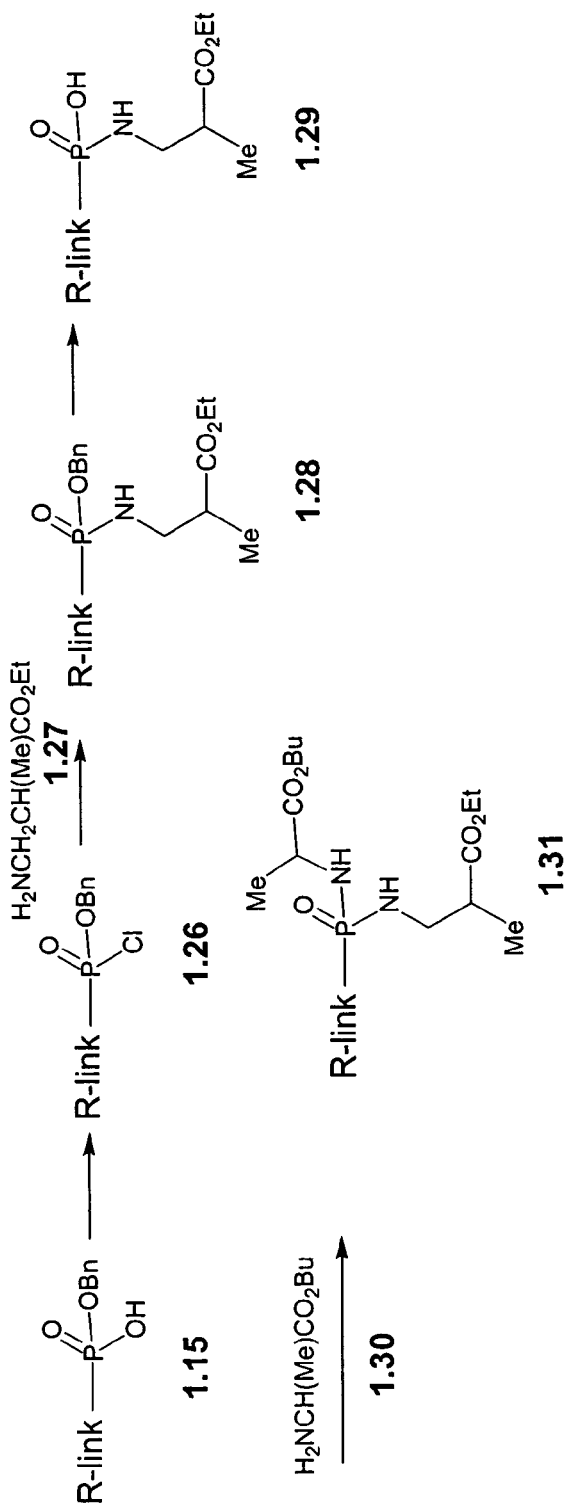
Figure 2F:
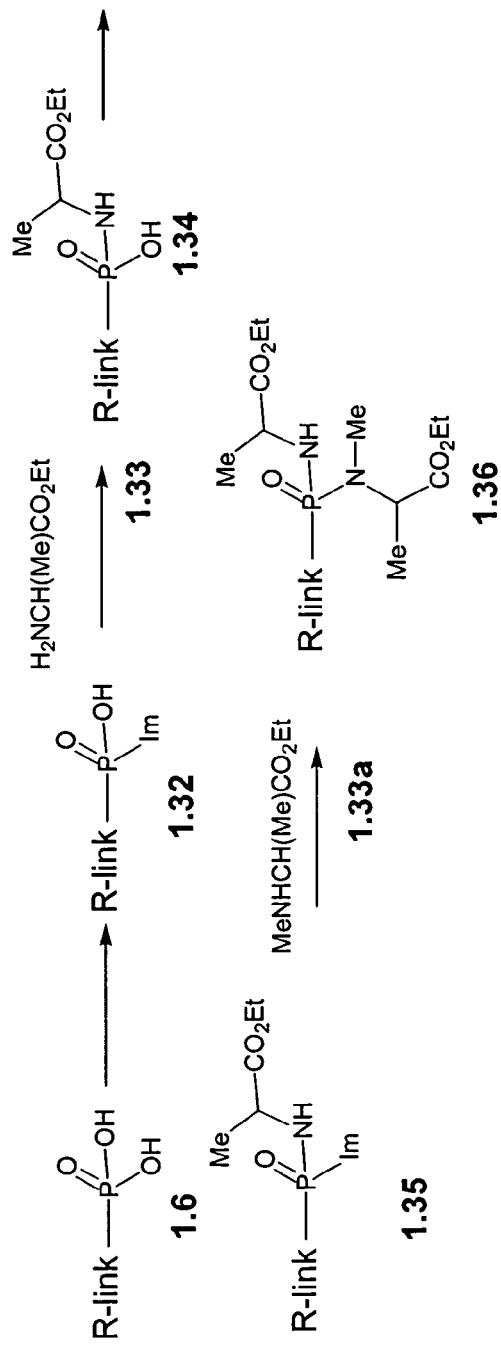
Figure 2G:
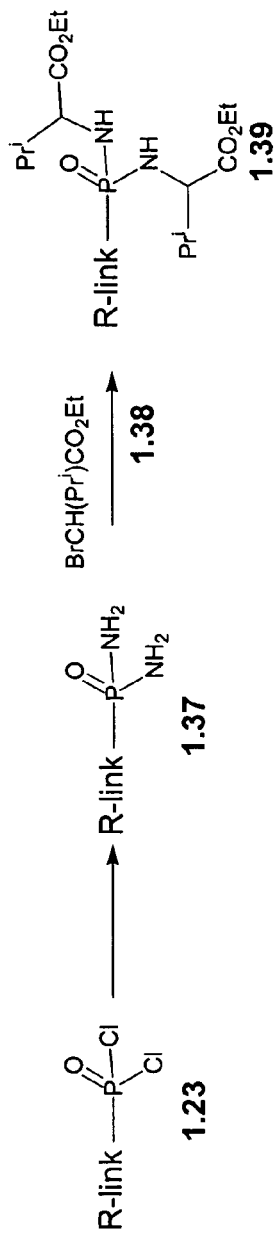
Figure 2H:
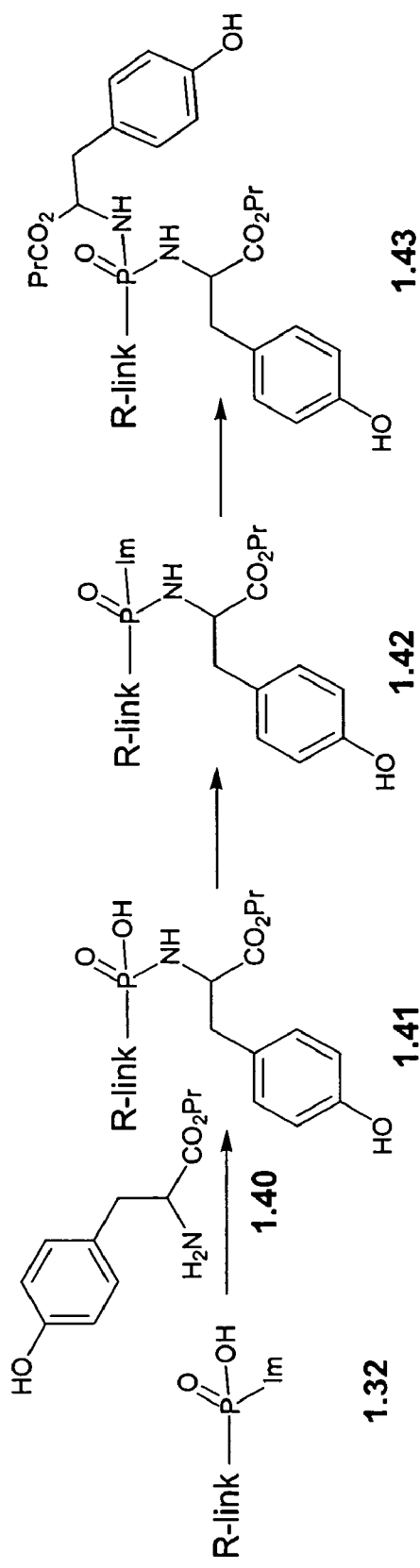
Figure 3A:
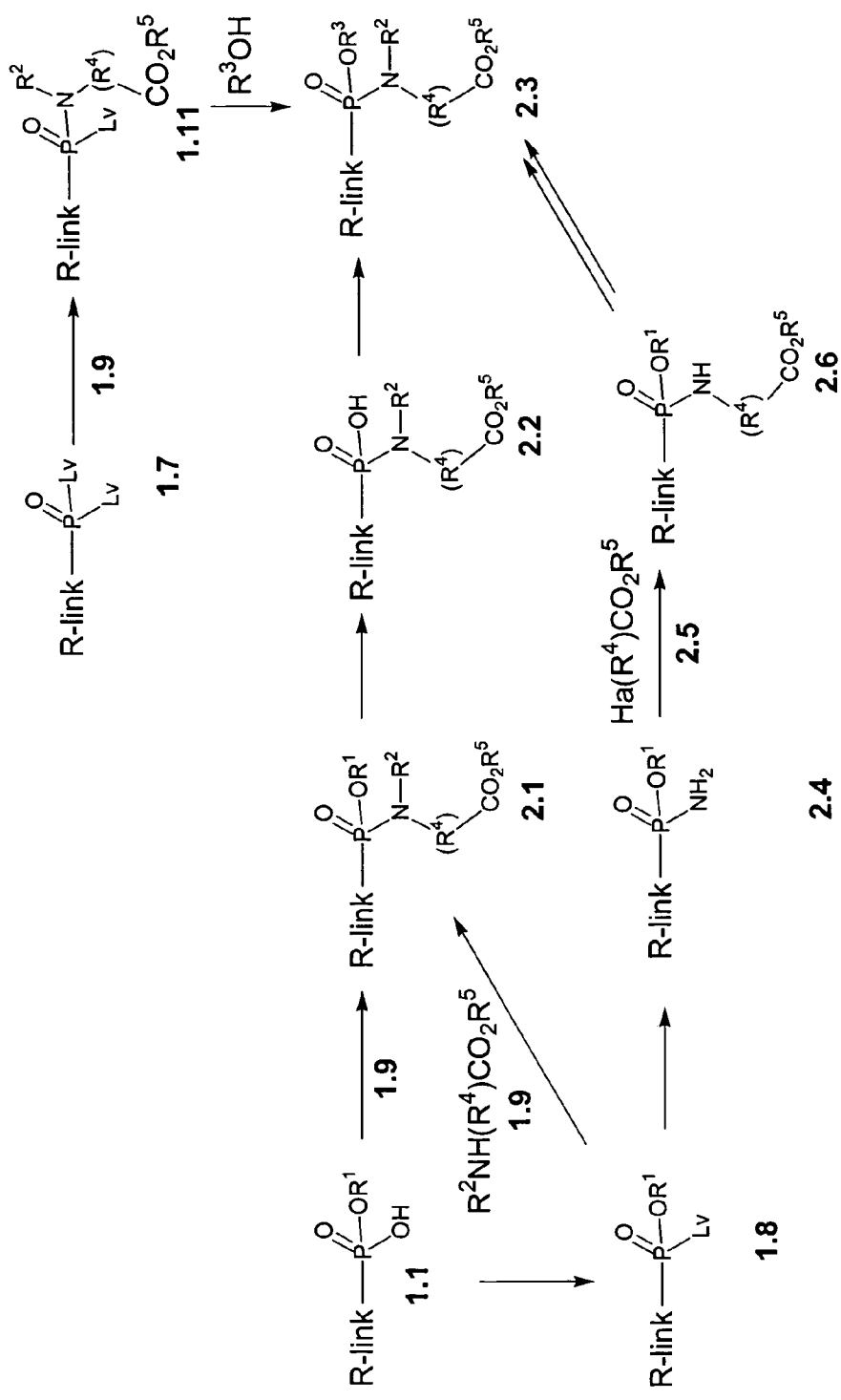
FIGS. 3A-F depict Scheme 2 which is described in detail herein below.
Figure 3B:
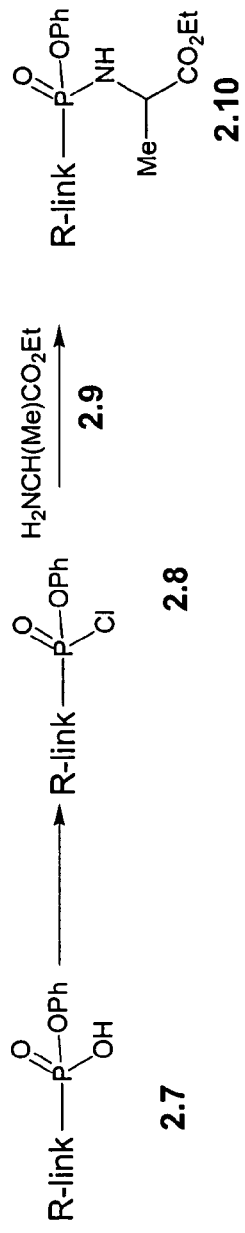
Figure 3C:
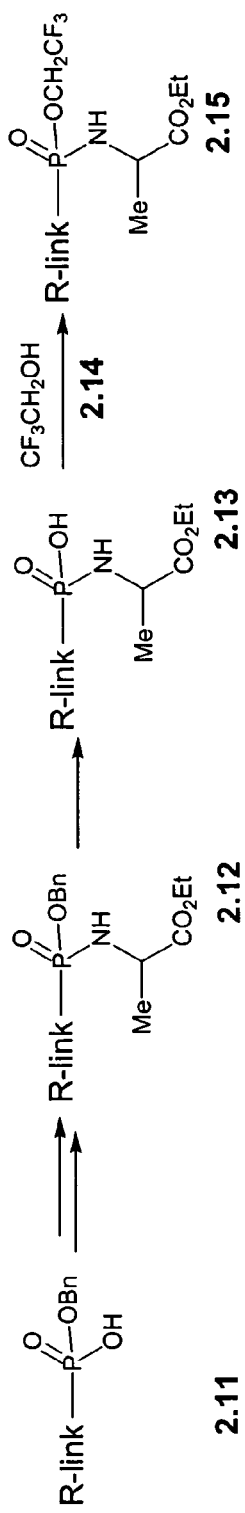
Figure 3D:
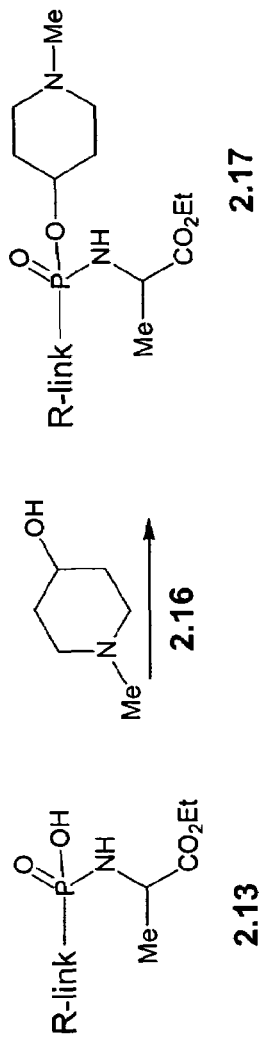
Figure 3E:
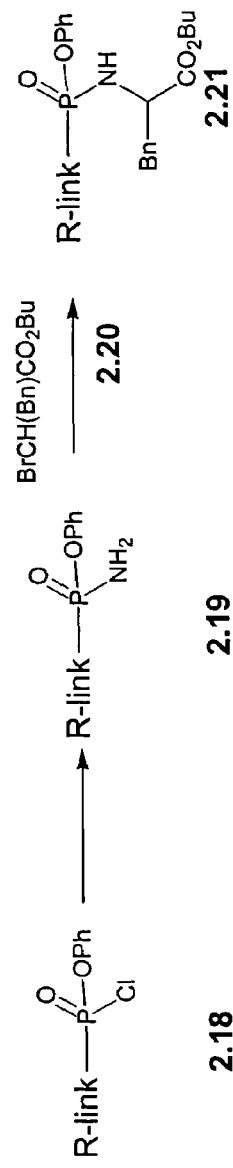
Figure 3F:
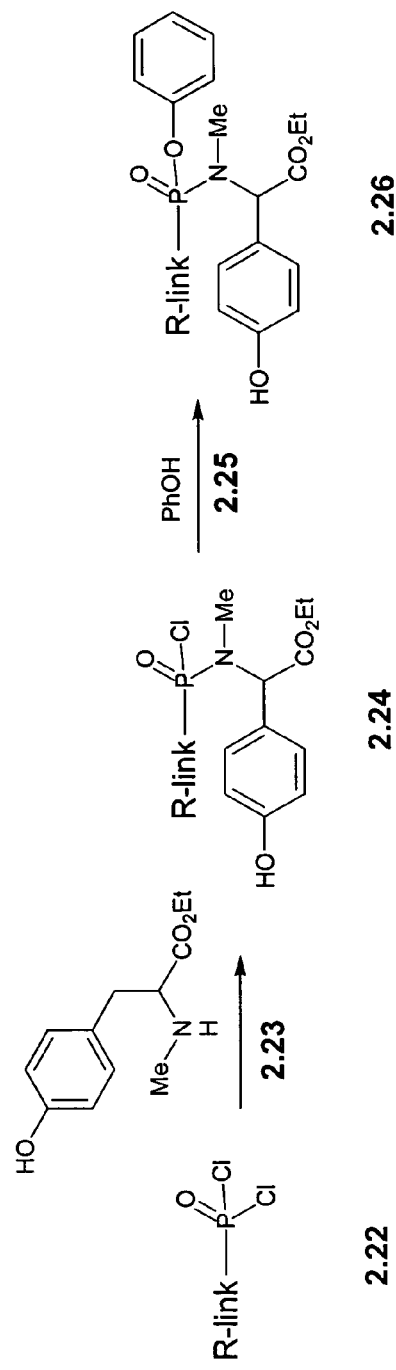
Figure 4A:
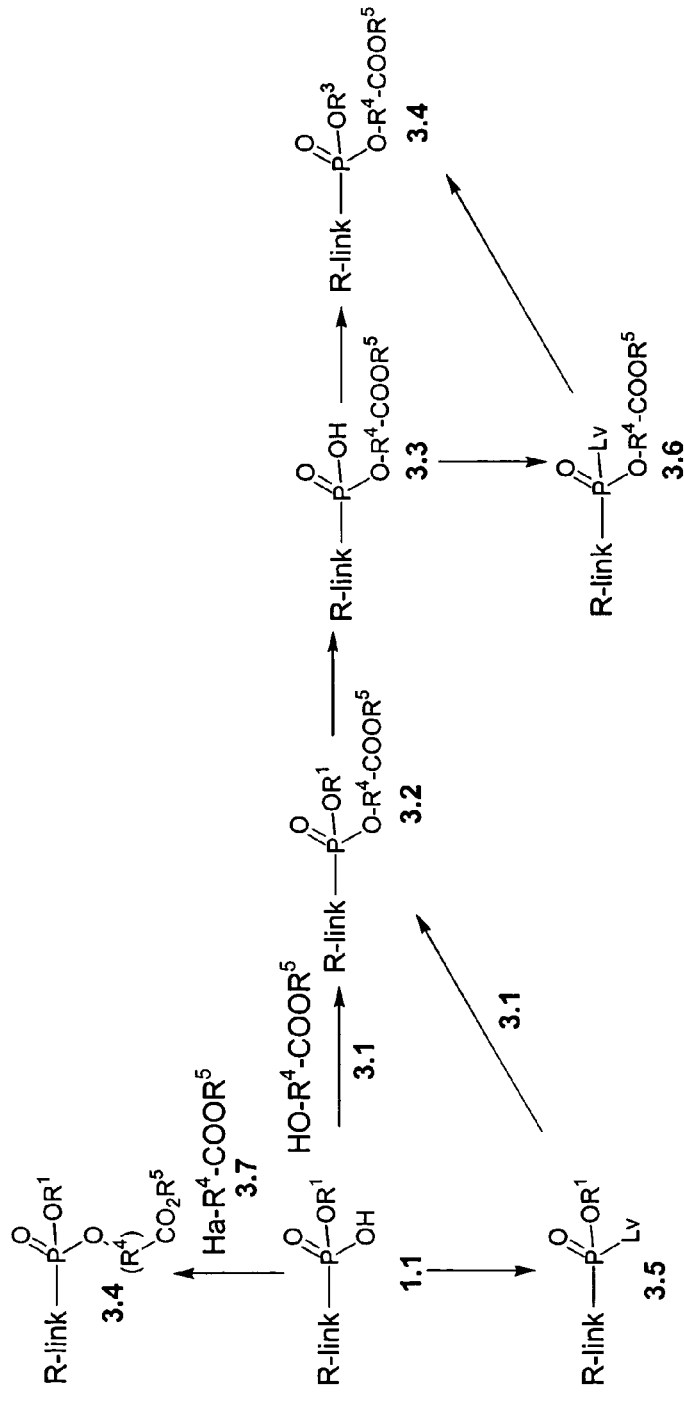
FIGS. 4A-F depict Scheme 3 which is described in detail herein below.
Figure 4B:
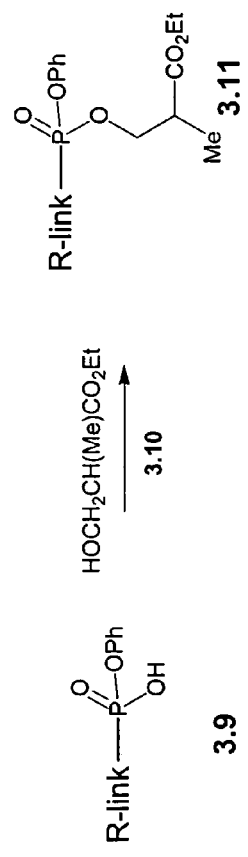
Figure 4C:
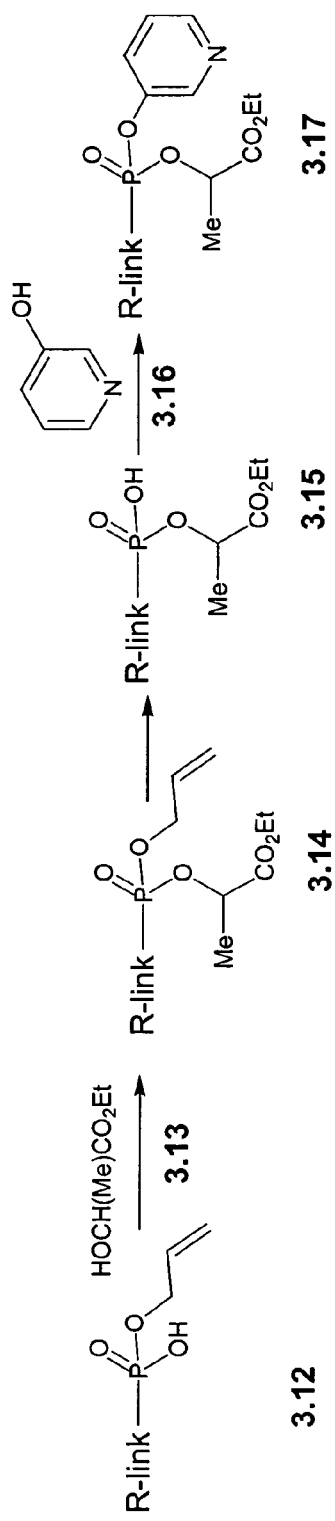
Figure 4D:
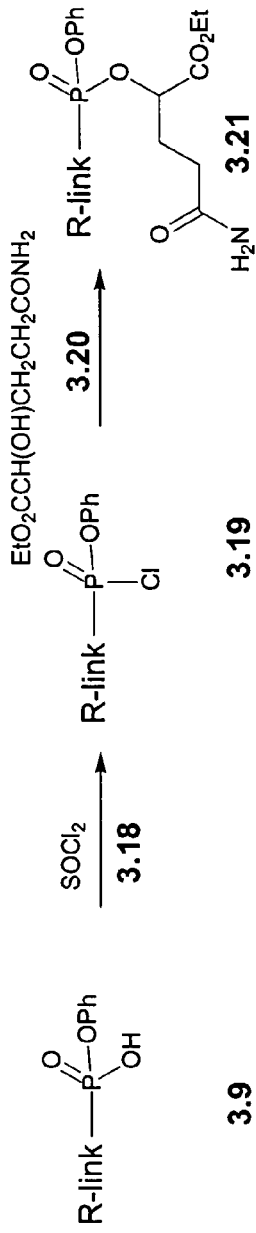
Figure 4E:
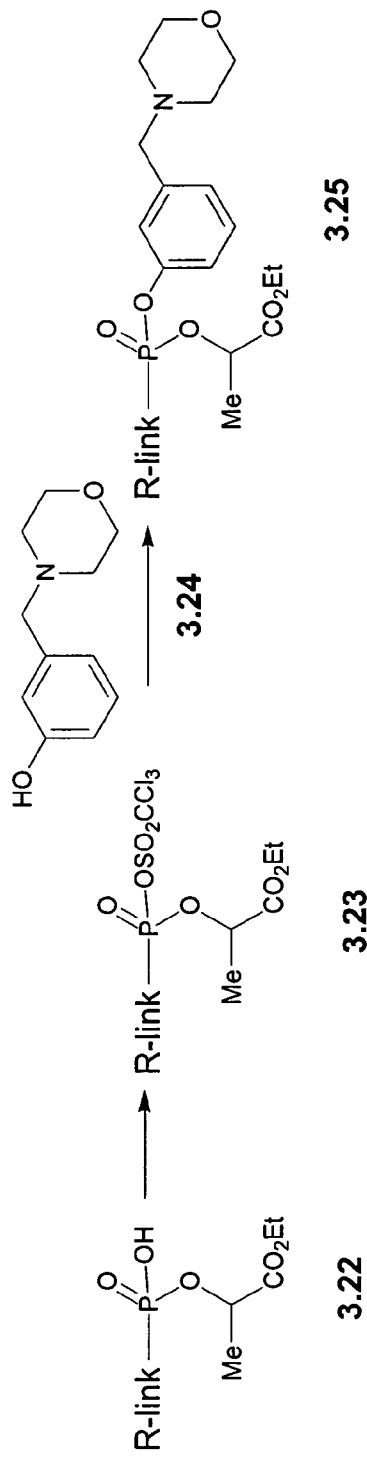
Figure 4F:
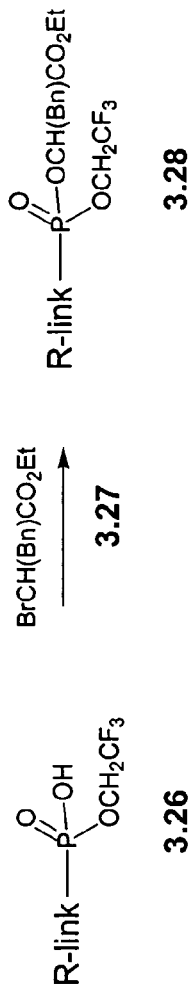
Figure 5A:
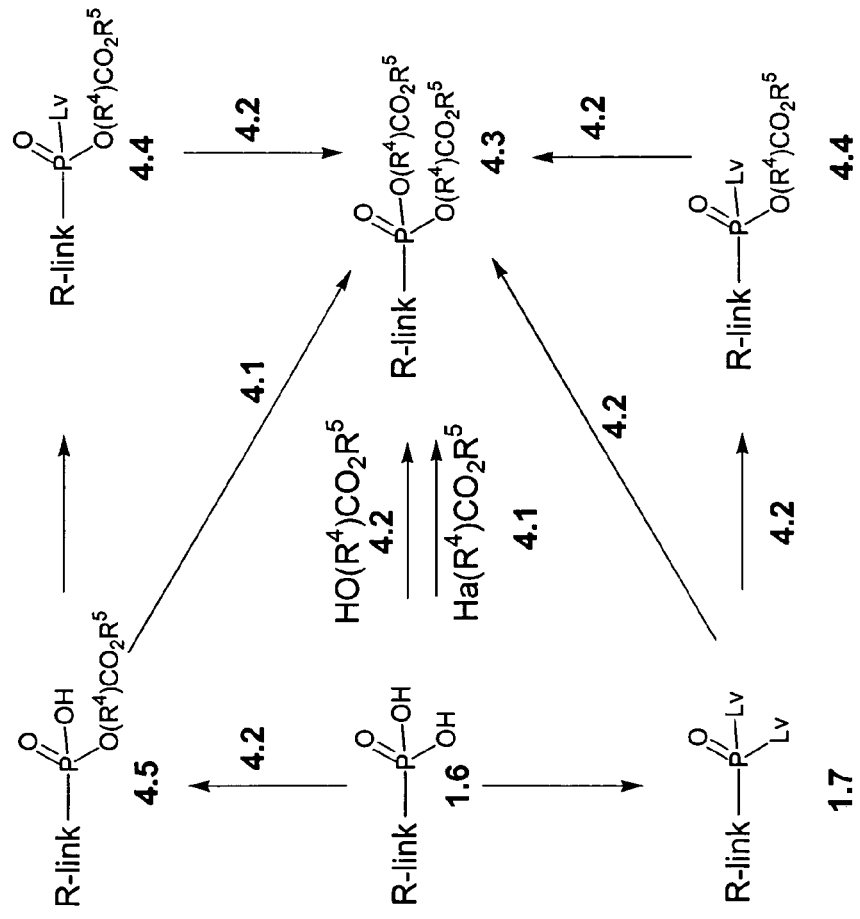
FIGS. 5A-E depict Scheme 4 which is described in detail herein below.
Figure 5B:
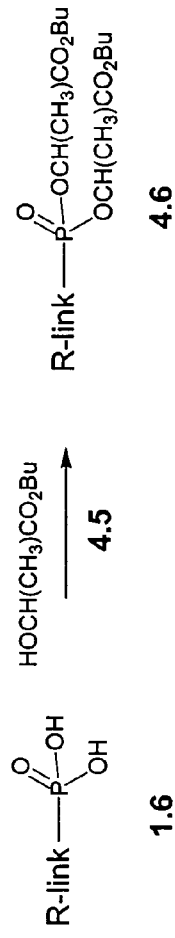
Figure 5C:
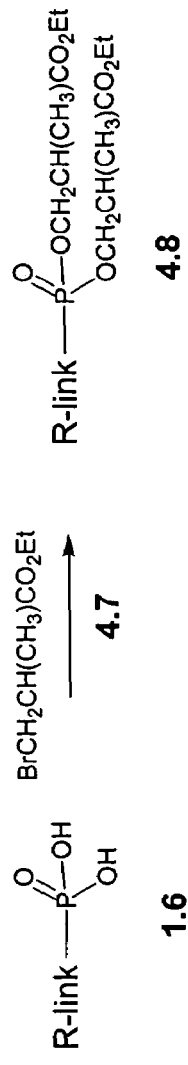
Figure 5D:
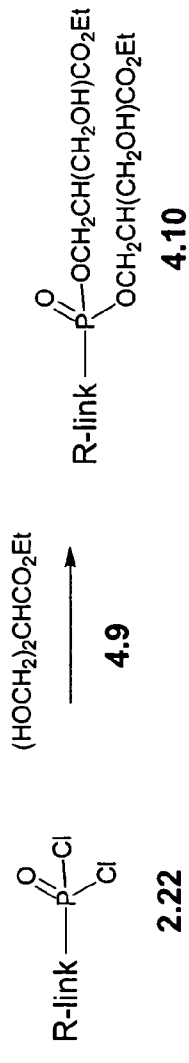
Figure 5E:
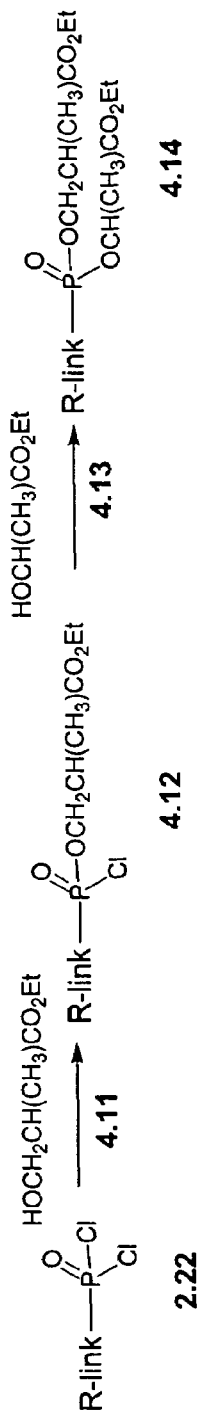

Reference will now be made in detail to certain embodiments of the invention, examples of which are illustrated in the accompanying descriptions, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

Definitions

Unless stated otherwise, the following terms and phrases as used herein are intended to have the following meanings:

The terms "phosphonate" and "phosphonate group" mean a functional group or moiety within a molecule that comprises at least one phosphorus-carbon bond, and at least one phosphorus-oxygen double bond. The phosphorus atom is further substituted with oxygen, sulfur, and nitrogen substituents. As defined herein, "phosphonate" and "phosphonate group" include molecules with phosphonic acid, phosphonic monoester, phosphonic diester, phosphonamidate, phosphondiamidate, and phosphonthioate functional groups.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in Textbook of Drug Design and Development (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy.

Exemplary prodrug moieties include the hydrolytically sensitive or labile acyloxymethyl esters —$CH_2OC(=O)OR^9$ and acyloxymethyl carbonates —$CH_2OC(=O)OR^9$ where $R^9$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al (1983) *J Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2OC(=O)C(CH_3)_3$. An exemplary acyloxymethyl carbonate prodrug moiety is pivaloyloxymethylcarbonate (POC) —$CH_2OC(=O)OC(CH_3)_3$.

Aryl esters of phosphorus groups, especially phenyl esters, are reported to enhance oral bioavailability (DeLambert et al (1994) *J. Med. Chem.* 37: 498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho-orpara-position may accelerate the hydrolysis. Benzyl analogs with an acylated phenol or an alkylated phenol may generate the phenolic compound through the action of enzymes, e.g. esterases, oxidases, etc., which in turn undergoes cleavage at the benzylic C—O bond to generate the phosphoric acid and the quinone methide intermediate. Examples of this class of prodrugs are described by Mitchell et al (1992) *J. Chem. Soc. Perkin Trans.* I 2345; Brook et al WO 91/19721. Still other benzylic prodrugs have been described containing a carboxylic ester-containing group attached to the benzylic methylene (Glazier et al WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al (1993) *Antiviral Res.*, 22: 155-174; Benzaria et al (1996) *J. Med. Chem.* 39: 4958). Cyclic phosphonate esters have also been described as prodrugs of phosphorus-containing compounds (Erion et al, U.S. Pat. No. 6,312,662).

"Pharmaceutically acceptable prodrug" refer to a compound that is metabolized in the host, for example hydrolyzed or oxidized, by either enzymatic action or by general acid or base solvolysis, to form an active ingredient. Typical examples of prodrugs of the compounds of the invention have biologically labile protecting groups on a functional moiety of the compound. Prodrugs include compounds that can be oxidized, reduced, aminated, deaminated, esterified, deesterified, alkylated, dealkylated, acylated, deacylated, phosphorylated, dephosphorylated, or other functional group change or conversion involving forming or breaking chemical bonds on the prodrug.

"Protecting group" refers to a moiety of a compound that masks or alters the properties of a functional group or the properties of the compound as a whole. The chemical substructure of a protecting group varies widely. One function of a protecting group is to serve as intermediates in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

Any reference to any of the compounds of the invention also includes a reference to a physiologically acceptable salt thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of an hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$).

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to: ethylene or vinyl (—$CH=CH_2$), allyl (—$CH_2CH=CH_2$), cyclopentenyl (—$C_5H_7$), and 5-hexenyl (—$CH_2CH_2CH_2CH_2CH=CH_2$).

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—$CH_2$C≡CH).

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—$CH_2$C≡C—), and 4-pentynyl (—$CH_2CH_2CH_2$C≡CH—).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Substituted alkyl", "substituted aryl", and "substituted arylalkyl" mean alkyl, aryl, and arylalkyl respectively, in which one or more hydrogen atoms are each independently replaced with a substituent. Typical substituents include, but are not limited to, —X, —R, —O—, —OR, —SR, —S⁻, —NR₂, —NR₃, =NR, —CX₃, —CN, —OCN, —SCN, —N=C=O, —NCS, —NO, —NO₂, =N₂, —N₃, NC(=O) R, —C(=O)R, —C(=O)NRR —S(=O)₂O⁻, —S(=O)₂ OH, —S(=O)₂R, —OS(=O)₂OR, —S(=O)₂NR, —S(=O)R, —OP(=O)O₂RR, —P(=O)O₂RR —P(=O) (O⁻)₂, —P(=O)(OH)₂, —C(=O)R, —C(=O)X, —C(S)R, —C(O)OR, —C(O)O⁻, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, or prodrug moiety. Alkylene, alkenylene, and alkynylene groups may also be similarly substituted.

"Heterocycle" as used herein includes by way of example and not limitation these heterocycles described in Paquette, Leo A.; "Principles of Modem Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" means a saturated, unsaturated or aromatic ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

"Linker" or "link" means a chemical moiety comprising a covalent bond or a chain of atoms that covalently attaches a phosphonate group to a drug. Linkers include portions of substituents $A^1$ and $A^3$ enumerated in Formula I, or substituents $A_1$ and $A_3$ enumerated in Formula II, which include moieties such as: repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate. The terms "racemic mixture" and "racemate" refer to an equimolar mixture of two enantiomeric species, devoid of optical activity.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Non-Nucleotide Reverse Transcriptase Inhibitor (NNRTI) Compounds

The compounds of the invention include those with anti-HIV activity. In particular, the compounds include non-nucleotide reverse transcriptase inhibitors (NNRTI). The compounds of the inventions bear a phosphonate group, which may be a prodrug moiety.

In one embodiment of the invention, one identifies compounds that may fall within the generic scope of the documents cited under the definition of the term CLC (Capravirine-like compound) but which further comprise a phosphonate group, e.g. a phosphonate diester, phosphonamidate-ester prodrug, or a bis-phosphonamidate-ester (Jiang et al, US 2002/0173490 A1).

Whenever a compound described herein is substituted with more than one of the same designated group, e.g., "$R^1$" or "$R^{6a}$", then it will be understood that the groups may be the same or different, i.e., each group is independently selected. Wavy lines indicate the site of covalent bond attachments to the adjoining groups, moieties, or atoms.

Compounds of the invention are set forth in the Schemes, Examples, and claims below and include compounds of Formula I and Formula II. Formula I compounds have the general structure:

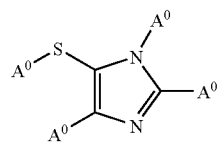

I

Compounds of the invention also include the Formulas:

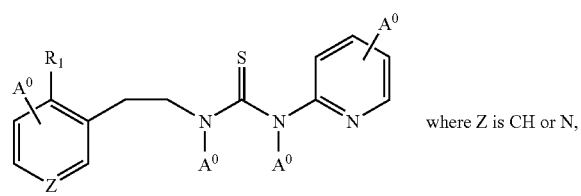

where Z is CH or N,

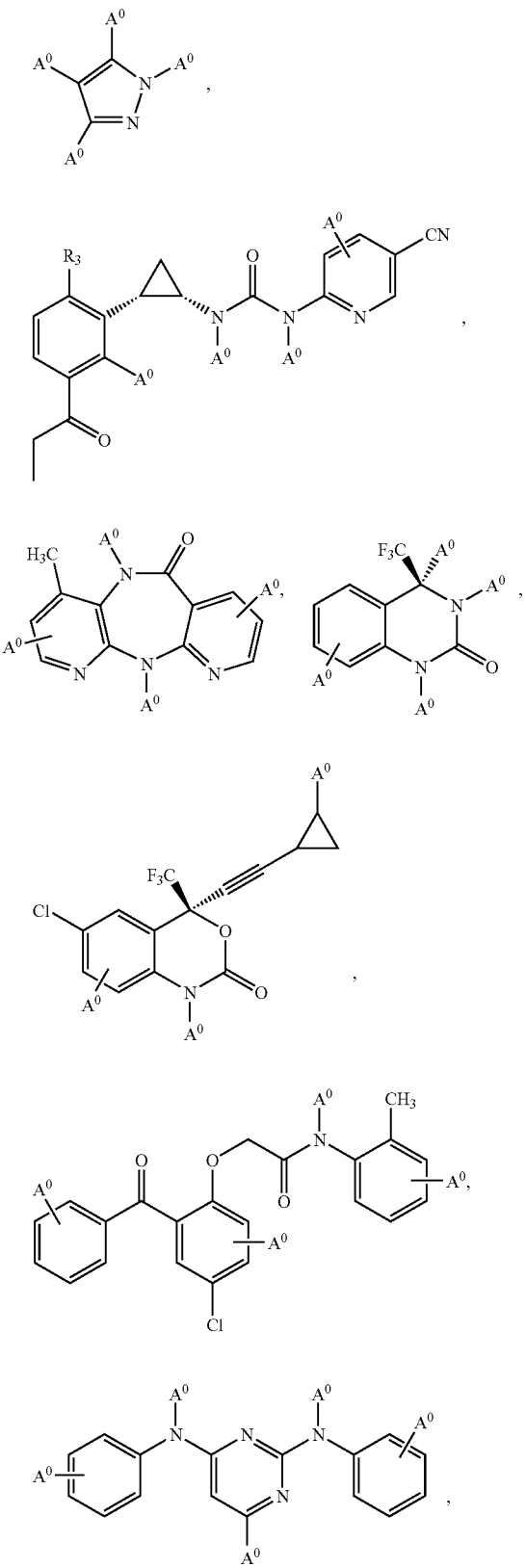

-continued

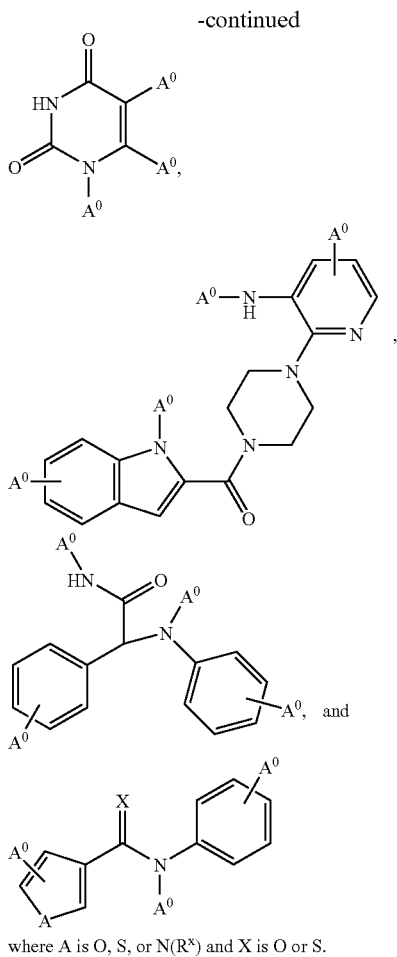

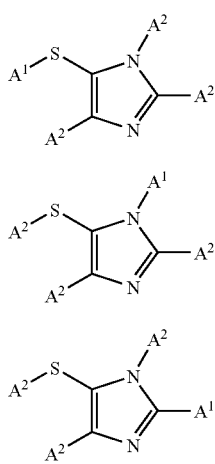

where A is O, S, or N(R$^x$) and X is O or S.

The above Formulas are substituted with one or more covalently attached A$^0$ groups, including simultaneous substitutions at any or all A$^0$.

A$^0$ is A$^1$, A$^2$ or W$^3$ with the proviso that the compound includes at least one A$^1$. Exemplary embodiments of Formula I include Ia, Ib, Ic, and Id:

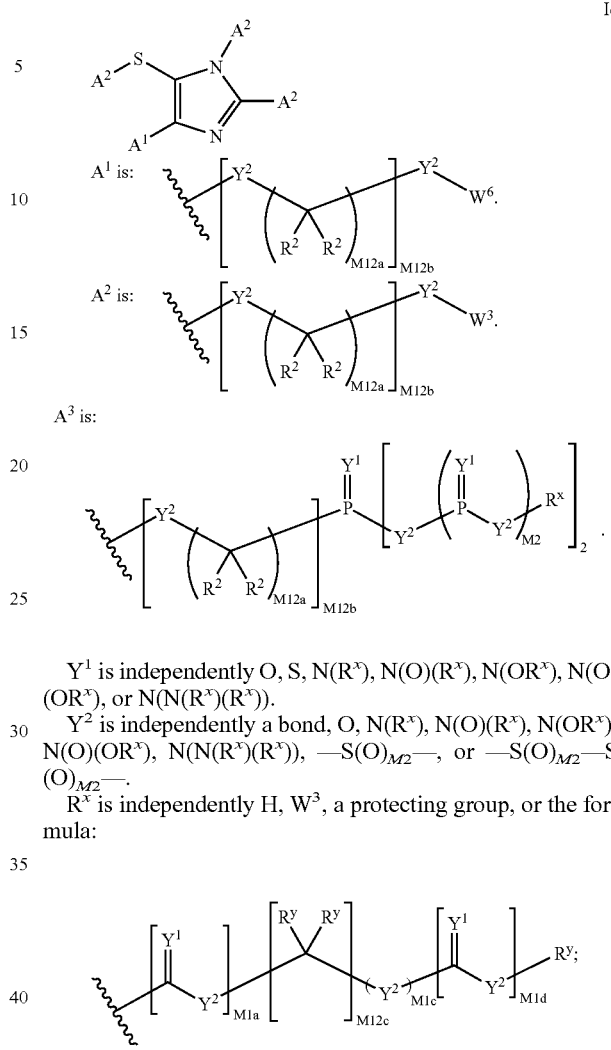

Y$^1$ is independently O, S, N(R$^x$), N(O)(R$^x$), N(OR$^x$), N(O)(OR$^x$), or N(N(R$^x$)(R$^x$)).

Y$^2$ is independently a bond, O, N(R$^x$), N(O)(R$^x$), N(OR$^x$), N(O)(OR$^x$), N(N(R$^x$)(R$^x$)), —S(O)$_{M2}$—, or —S(O)$_{M2}$—S(O)$_{M2}$—.

R$^x$ is independently H, W$^3$, a protecting group, or the formula:

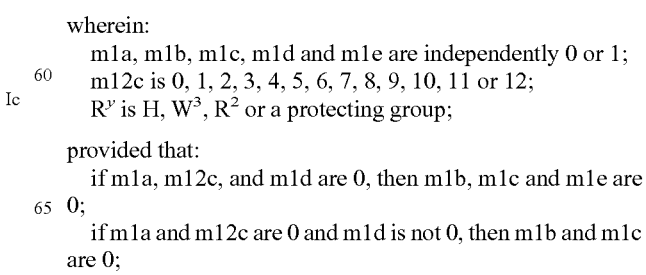

wherein:
M1a, M1c, and M1d are independently 0 or 1;
M12c is 0, 1, 2, 3, 4, 5, 6, 7, 8, 9, 10, 11 or 12; and
R$^y$ is independently H, W$^3$, R$^2$ or a protecting group.
Alternatively, Rx is a group of the formula:

wherein:
m1a, m1b, m1c, m1d and m1e are independently 0 or 1;
m12c is 0, 1, 2, 3, 4, 5, 6, 7, 8, 9, 10, 11 or 12;
R$^y$ is H, W$^3$, R$^2$ or a protecting group;

provided that:
if m1a, m12c, and m1d are 0, then m1b, m1c and m1e are 0;
if m1a and m12c are 0 and m1d is not 0, then m1b and m1c are 0;

if m1a and m1d are 0 and m12c is not 0, then m1b and at least one of m1c and m1e are 0;

if m1a is 0 and m12c and m1d are not 0, then m1b is 0;

if m12c and m1d are 0 and m1a is not 0, then at least two of m1b, m1c and m1e are 0;

if m12c is 0 and m1a and m1d are not 0, then at least one of m1b and m1c are 0; and if m1d is 0 and m1a and m12c are not 0, then at least one of m1c and m1e are 0.

$R^1$ is independently H or alkyl of 1 to 18 carbon atoms.

$R^2$ is independently H, $R^1$, $R^3$ or $R^4$ wherein each $R^4$ is independently substituted with 0 to 3 $R^3$ groups. Alternatively, taken together at a carbon atom, two $R^2$ groups form a ring, i.e. a spiro carbon. The ring may be, for example, cyclopropyl, cyclobutyl, cyclopentyl, or cyclohexyl. The ring may be substituted with 0 to 3 $R^3$ groups.

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$.

$R^{3a}$ is F, Cl, Br, I, —CN, $N_3$ or —$NO_2$.

$R^{3b}$ is $Y^1$.

$R^{3c}$ is —$R^x$, —$N(R^x)(R^x)$, —$SR^x$, —$S(O)R^x$, —$S(O)_2R^x$, —$S(O)(OR^x)$, —$S(O)_2(OR^x)$, —$OC(Y^1)R^x$, —$OC(Y^1)OR^x$, —$OC(Y^1)(N(R^x)(R^x))$, —$SC(Y^1)R^x$, —$SC(Y^1)OR^x$, —$SC(Y^1)(N(R^x)(R^x))$, —$N(R^x)C(Y^1)R^x$, —$N(R^x)C(Y^1)OR^x$, or —$N(R^x)C(Y^1)(N(R^x)(R^x))$.

$R^{3d}$ is —$C(Y^1)R^x$, —$C(Y^1)OR^x$ or —$C(Y^1)(N(R^x)(R^x))$.

$R^4$ is an alkyl of 1 to 18 carbon atoms, alkenyl of 2 to 18 carbon atoms, or alkynyl of 2 to 18 carbon atoms.

$R^5$ is $R^4$ wherein each $R^4$ is substituted with 0 to 3 $R^3$ groups.

$R^{5a}$a is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups.

$W^3$ is $W^4$ or $W^5$.

$W^4$ is $R^5$, —$C(Y^1)R^5$, —$C(Y^1)W^5$, —$SO_2R^5$, or —$SO_2W^5$.

$W^5$ is carbocycle or heterocycle wherein $W^5$ is independently substituted with 0 to 3 $R^2$ groups.

$W^{3a}$ is $W^{4a}$ or $W^{5a}$.

$W^{4a}$ is $R^{5a}$, —$C(Y^1)R^{5a}$, —$C(Y)W^{5a}$, —$SO_2R^{5a}$, or —$SO_2W^{5a}$.

$W^{5a}$ is a multivalent substituted carbocycle or heterocycle wherein $W^{5a}$ may be independently substituted with 0 to 3 $R^2$ groups, $Y^2$ and $A^3$.

$W^6$ is $W^3$ independently substituted with 1, 2, or 3 $A^3$ groups.

M2 is 0, 1 or 2;

M12a is 1, 2, 3, 4, 5, 6, 7, 8, 9, 10, 11 or 12; and

M12b is 0, 1, 2, 3, 4, 5, 6, 7, 8, 9, 10, 11 or 12.

W5 and W5a carbocycles and W5 and W5a heterocycles may be independently substituted with 0 to 3 $R^2$ groups. $W^5$ and $W^{5a}$ may be a saturated, unsaturated or aromatic ring comprising a mono- or bicyclic carbocycle or heterocycle. $W^5$ and $W^{5a}$ may have 3 to 10 ring atoms, e.g., 3 to 7 ring atoms. The $W^5$ and $W^{5a}$ rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

A $W^5$ or $W^{5a}$ heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). $W^5$ heterocyclic monocycles may have 3 to 6 ring atoms (2 to 5 carbon atoms and 1 to 2 heteroatoms selected from N, O, and S); or 5 or 6 ring atoms (3 to 5 carbon atoms and 1 to 2 heteroatoms selected from N and S). $W^5$ and $W^{5a}$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected f N and S) arranged as a bicyclo [5,6] or [6,6] system. The $W^5$ and $W^{5a}$ heterocycle may be bonded to $Y^2$ through a carbon, nitrogen, sulfur or other atom by a stable covalent bond.

$W^5$ and $W^{5a}$ heterocycles include for example, pyridyl, dihydropyridyl isomers, piperidine, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl. $W^5$ and $W^{5a}$ also includes, but is not limited to, examples such as:

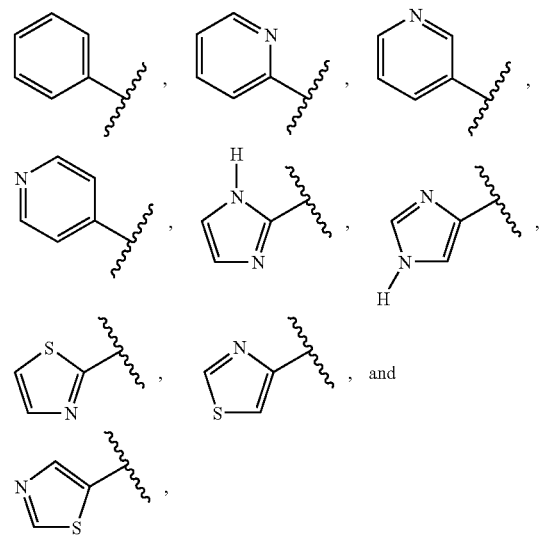

$W^5$ and $W^{5a}$ carbocycles and heterocycles may be independently substituted with 0 to 3 $R^2$ groups, as defined above. For example, substituted $W^5$ and $W^{5a}$ carbocycles include:

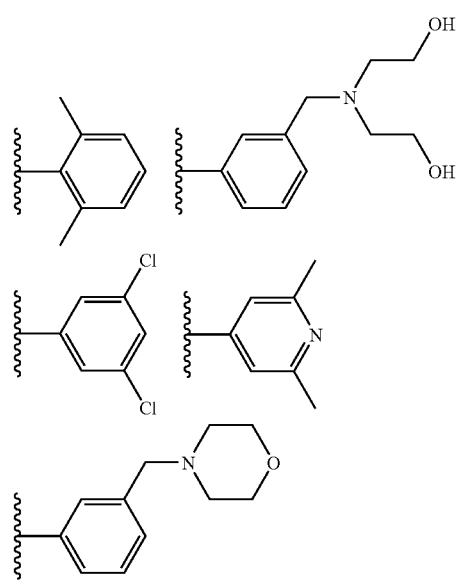

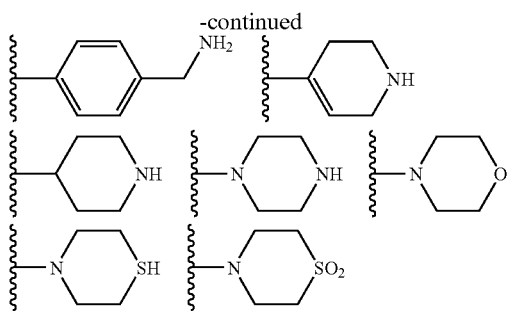

Examples of substituted phenyl carbocycles include:

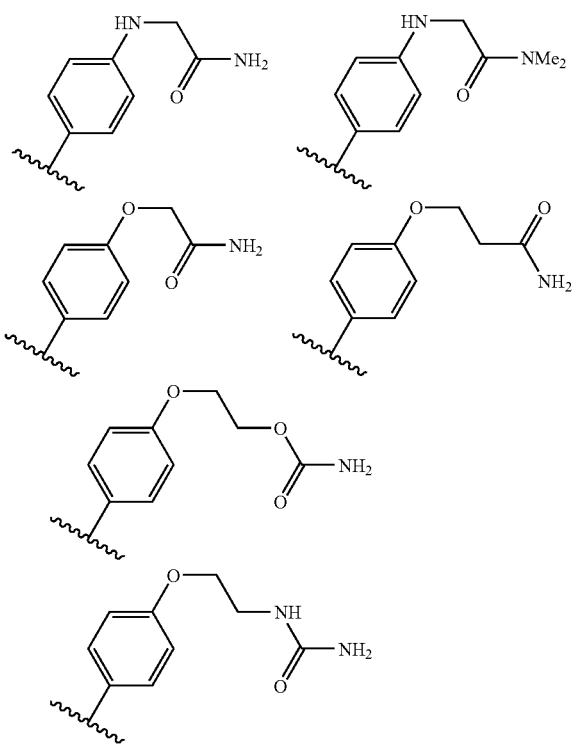

Embodiments of $A^1$ include:

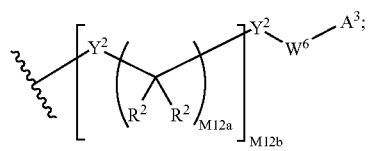

and where one or more $Y^2$ are a bond, such as:

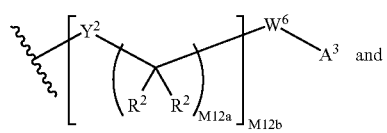

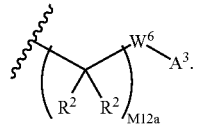

Embodiments of $A^3$ include where M2 is 0, such as:

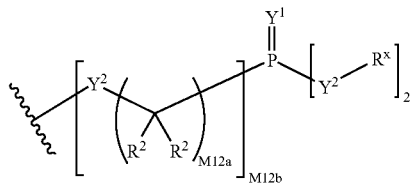

and where M12b is 1, $Y^1$ is oxygen, and $Y^{2b}$ is oxygen (O) or nitrogen (N($R^x$)) such as:

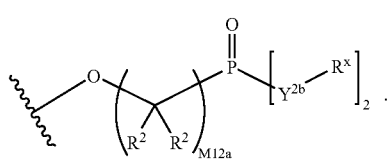

Another embodiment of $A^3$ includes:

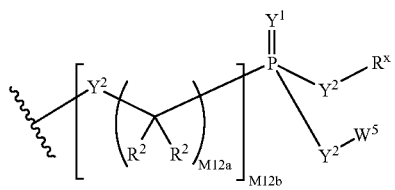

where $W^5$ is a carbocycle such as phenyl or substituted phenyl. Such embodiments include:

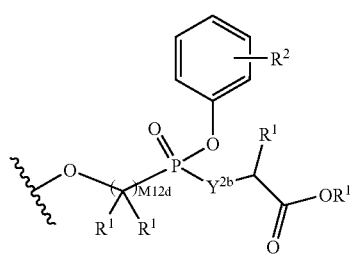

where $Y^{2b}$ is O or N($R^x$); M12d is 1, 2, 3, 4, 5, 6, 7 or 8; and the phenyl carbocycle is substituted with 0 to 3 $R^2$ groups. Such embodiments of $A^3$ include phenyl phosphonamidate-alanate esters and phenyl phosphonate-lactate esters:

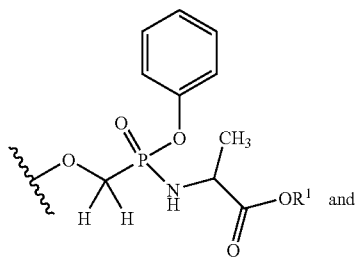 and

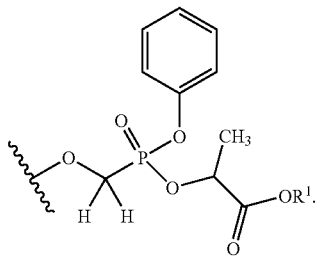

Embodiments of $R^x$ include esters, carbamates, carbonates, thioesters, amides, thioamides, and urea groups:

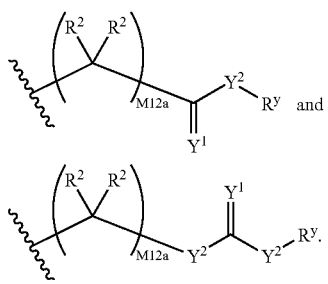

Embodiments of $A^2$ include where $W^3$ is $W^5$, such as:

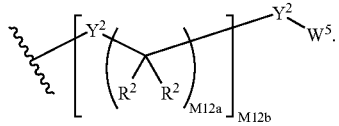

Alternatively, $A^2$ is phenyl, substituted phenyl, benzyl, substituted benzyl, pyridyl or substituted pyridyl.

Embodiments of Formula Ic include:

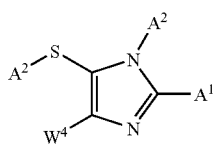

where $W^4$ may be $R^4$, such as isopropyl. Such an embodiment of Formula Ic may also include:

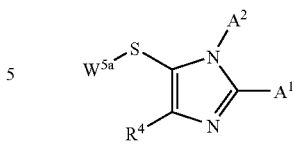

where $W^{5a}$ is a carbocycle or heterocycle and $W^{5a}$ is optionally and independently substituted with 1, 2, or 3 $R^2$ groups. For example, $W^{5a}$ may be 3,5-dichlorophenyl.

An embodiment of Formula Ic may include where $A^1$ is:

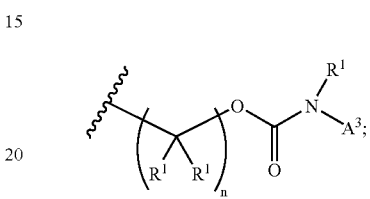

n is an integer from 1 to 18; $A^3$ is of the formula:

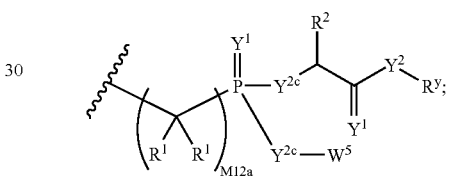

and $Y^{2c}$ is O, N($R^y$) or S. For example, $R^1$ may be H and n may be 1.

Embodiments of Formula Ib include:

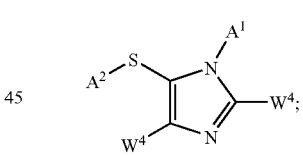

where $A^1$ comprises a phosphonate group attached to the imidazole nitrogen through a heterocycle linker, such as:

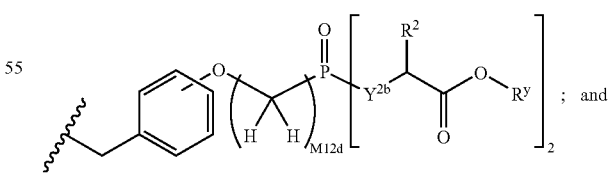

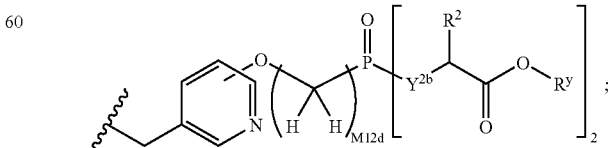

where $Y^{2b}$ is O or $N(R^2)$; and M12d is 1, 2, 3, 4, 5, 6, 7 or 8. The $A^3$ unit may be attached at any of the $W^6$ carbocycle or heterocycle ring positions.

Further embodiments of Formula Ib include:

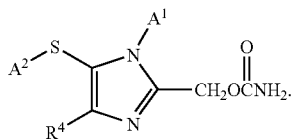

PETT-like phosphonate NNRTI compounds include the formulas:

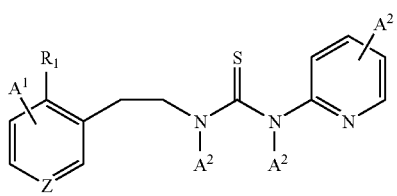

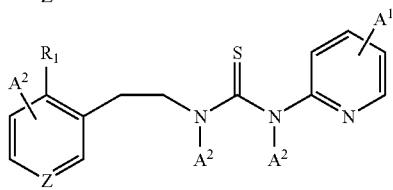

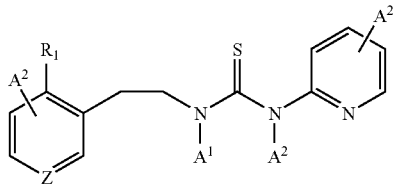

and

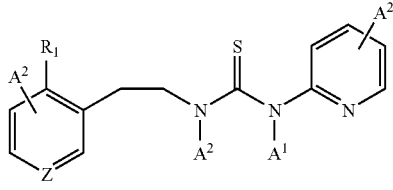

Pyrazole-like phosphonate NNRTI compounds include the formulas:

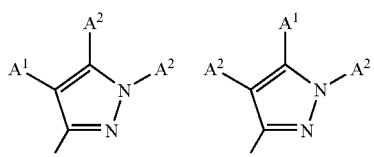

and

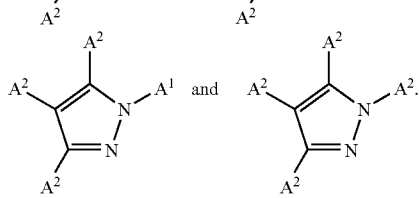

Urea-PETT-like phosphonate NNRTI compounds include the formulas:

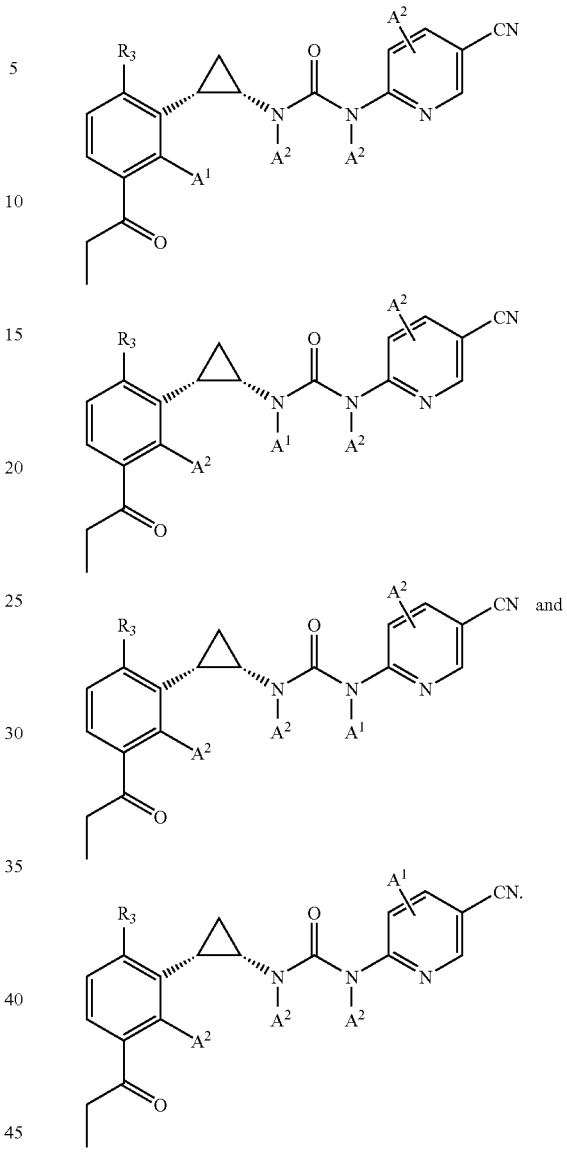

Nevaripine-like phosphonate NNRTI compounds include the formulas:

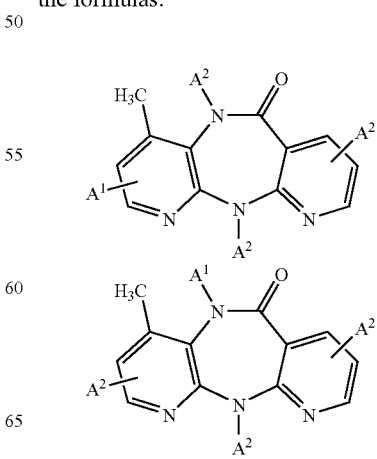

-continued
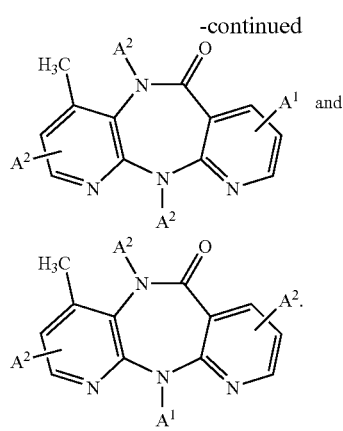
and
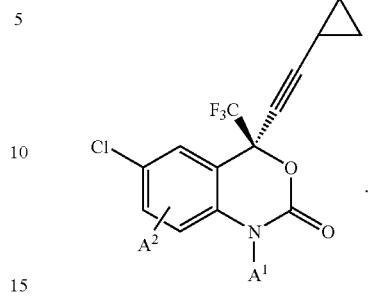
Benzophenone-like phosphonate NNRTI compounds include the formulas:
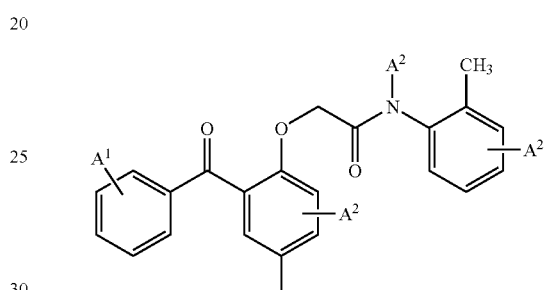
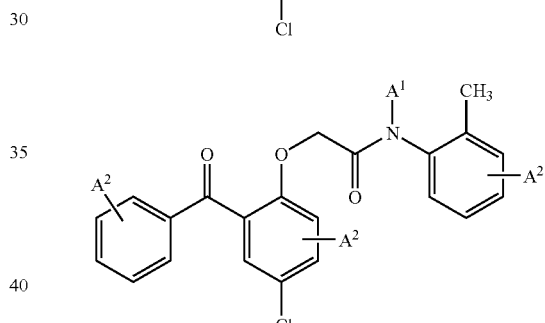
Quinazolinone-like phosphonate NNRTI compounds include the formulas:
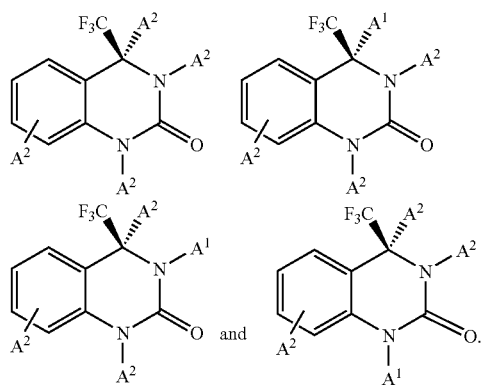
Efavirenz-like phosphonate NNRTI compounds include the formulas:
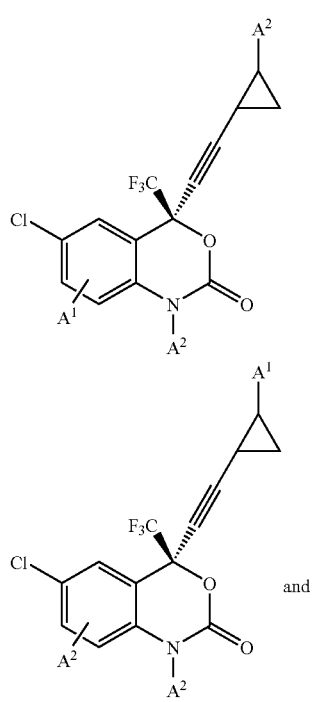
and
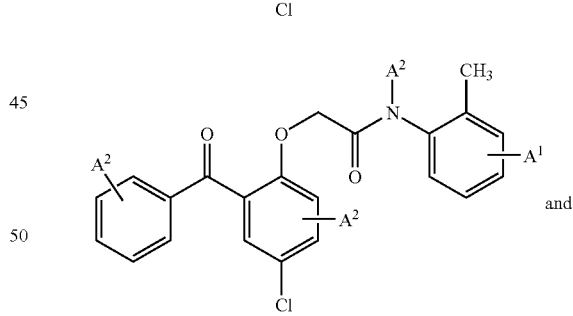
and
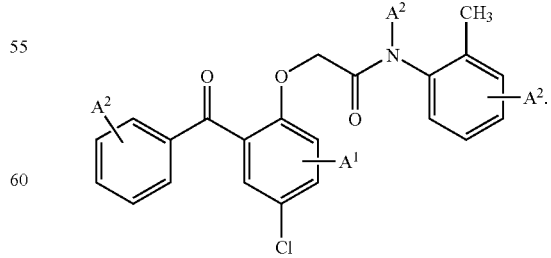
Pyrimidine-like phosphonate NNRTI compounds include the formulas:

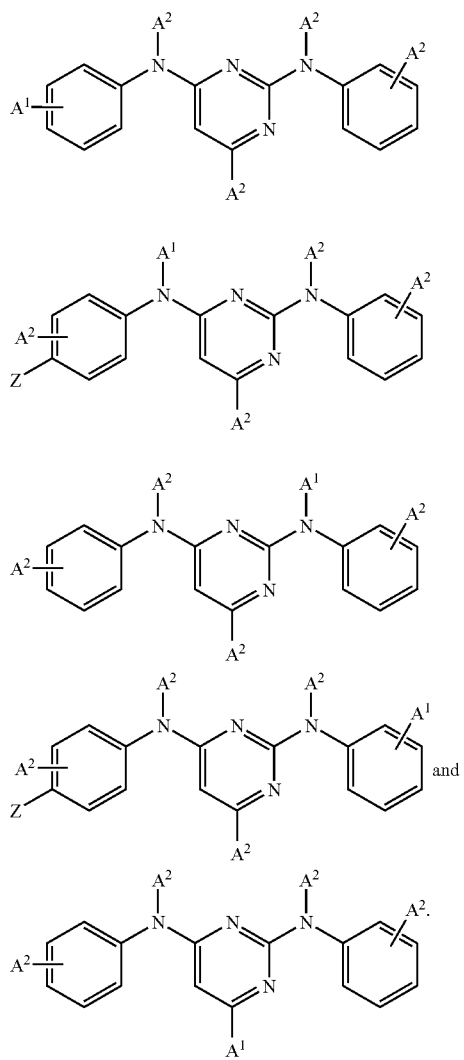
SJ3366-like phosphonate NNRTI compounds and Emivirine-like phosphonate NNRTI compounds include the formulas:
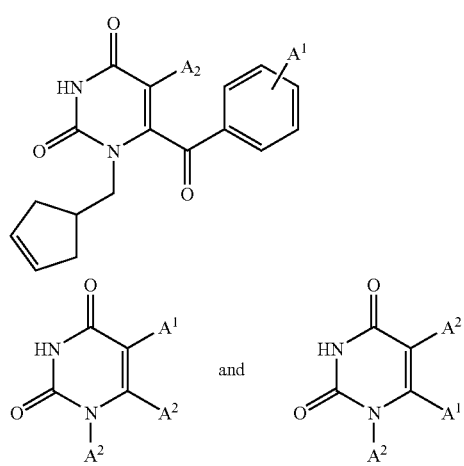
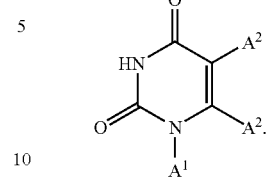
-continued
Delavirdine-like phosphonate NNRTI compounds include the formulas:
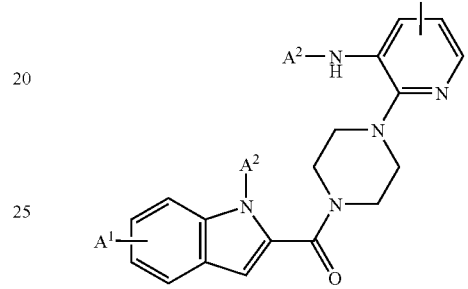
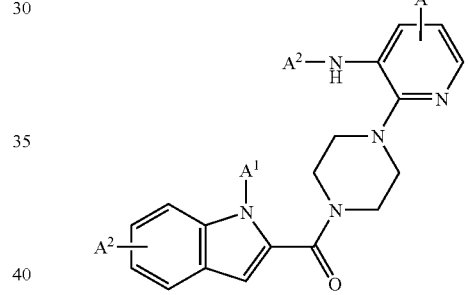
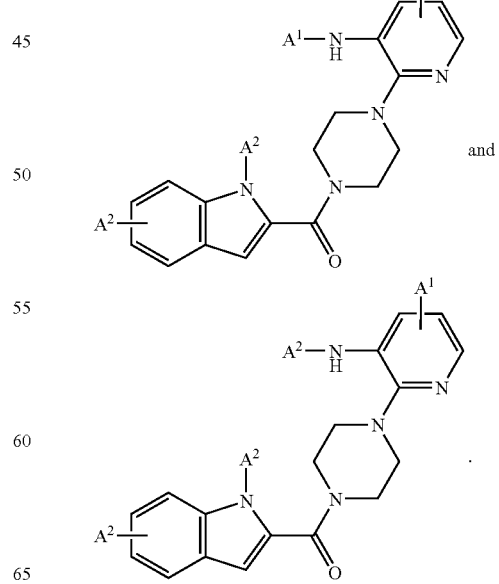

UC781-like phosphonate NNRTI compounds include the formulas:

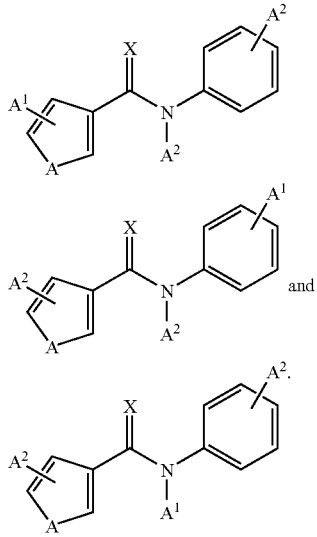

Loviride-like phosphonate NNRTI compounds include the formulas:

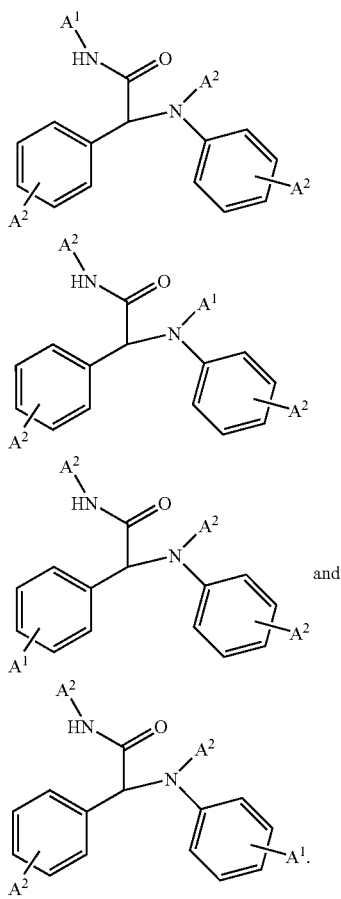

Formula II compounds include Ia and IIb which have the general structures, including:

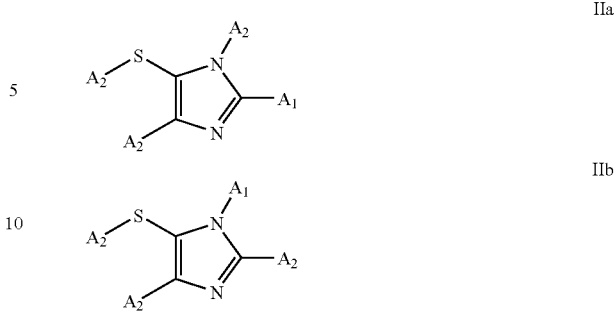

wherein $A_1$ is —$(X_2$—$(C(R_2)(R_2))_{m1}$—$X_3)_{m1}$—$W_3$, and $W_3$ is substituted with 1 to 3 $A_3$ groups.

$A_2$ is —$(X_2$—$(C(R_2)(R_2))_{m1}$—$X_3)_{m1}$—$W_3$.

$A_3$ is —$(X_2$—$(C(R_2)(R_2))_{m1}$—$X_3)_{m1}$—$P(Y_1)(Y_1R_{6a})(Y_1R_{6a})$.

$X_2$ and $X_3$ are independently a bond, —O—, —N($R_2$)—, —N(O$R_2$)—, —N(N($R_2$)($R_2$))—, —S—, —SO—, or —SO$_2$—.

Each $Y_1$ is independently O, N($R_2$), N(O$R_2$), or N(N($R_2$)($R_2$)), wherein each $Y_1$ is bound by two single bonds or one double bond.

$R_1$ is independently H or alkyl of 1 to 12 carbon atoms.

$R_2$ is independently H, $R_3$ or $R_4$ wherein each $R_4$ is independently substituted with 0 to 3 $R_3$ groups. Alternatively, taken together at a carbon atom, two $R_2$ groups form a ring, i.e. a spiro carbon. The ring may be, for example, cyclopropyl, cyclobutyl, cyclopentyl, or cyclohexyl. The ring may be substituted with 0 to 3 $R_3$ groups.

$R_3$ is independently F, Cl, Br, I, —CN, $N_3$, —NO$_2$, —OR$_{6a}$, —OR$_1$, —N(R$_1$)$_2$, —N(R$_1$)(R$_{6b}$), —N(R$_{6b}$)$_2$, —SR$_1$, —SR$_{6a}$, —S(O)R$_1$, —S(O)$_2$R$_1$, —S(O)OR$_1$, —S(O)OR$_{6a}$, —S(O)$_2$OR$_1$, —S(O)$_2$OR$_{6a}$, —C(O)OR$_1$, —C(O)R$_{6c}$, —C(O)OR$_{6a}$, —OC(O)R$_1$, —N(R$_1$)(C(O)R$_1$), —N(R$_{6b}$)(C(O)R$_1$), —N(R$_1$)(C(O)OR$_1$), —N(R$_{6b}$)(C(O)OR$_1$), —C(O)N(R$_1$)$_2$, —C(O)N(R$_{6b}$)(R$_1$), —C(O)N(R$_{6b}$)$_2$, —C(NR$_1$)(N(R$_1$)$_2$), —C(N(R$_{6b}$))(N(R$_1$)$_2$), —C(N(R$_1$))(N(R$_1$)(R$_{6b}$)), —C(N(R$_{6b}$))(N(R$_1$)(R$_{6b}$)), —C(N(R$_1$))(N(R$_{6b}$)$_2$), —C(N(R$_{6b}$))(N(R$_{6b}$)$_2$), —N(R$_1$)C(N(R$_1$))(N(R$_1$)$_2$), —N(R$_1$)C(N(R$_1$))(N(R$_1$)(R$_{6b}$)), —N(R$_1$)C(N(R$_{6b}$))(N(R$_1$)$_2$), —N(R$_{6b}$)C(N(R$_1$))(N(R$_1$)$_2$), —N(R$_{6b}$)C(N(R$_{6b}$))(N(R$_1$)$_2$), —N(R$_{6b}$)C(N(R$_1$))N(R$_1$)(R$_{6b}$), —N(R$_1$)C(N(R$_{6b}$))(N(R$_1$)(R$_{6b}$)), —N(R$_1$)C(N(R$_1$))(N(R$_{6b}$)$_2$), —N(R$_{6b}$)C(N(R$_{6b}$))(N(R$_1$)(R$_{6b}$)), —N(R$_6$b)C(N(R$_1$))(N(R$_{6b}$)$_2$), —N(R$_1$)C(N(R$_{6b}$))(N(R$_{6b}$)$_2$), —N(R$_{6b}$)C(N(R$_{6b}$))(N(R$_{6b}$)$_2$), =O, =S, =N(R$_1$), =N(R$_{6b}$) or $W_5$.

$R_4$ is independently alkyl of 1 to 12 carbon atoms, alkenyl of 2 to 12 carbon atoms, or alkynyl of 2 to 12 carbon atoms.

$R_5$ is independently $R_4$ wherein each $R_4$ is substituted with 0 to 3 $R_3$ groups.

$R_{5a}$ is independently alkylene of 1 to 12 carbon atoms, alkenylene of 2 to 12 carbon atoms, or alkynylene of 2-12 carbon atoms any one of which alkylene, alkenylene or alkynylene is substituted with 0-3 $R_3$ groups.

$R_{6a}$ is independently H or an ether- or ester-forming group.

$R_{6b}$ is independently H, a protecting group for amino or the residue of a carboxyl-containing compound.

$R_{6c}$ is independently H or the residue of an amino-containing compound.

$W_3$ is $W_4$ or $W_5$.

$W_4$ is $R_5$, —C($Y_1$)R$_5$, —C($Y_1$)W$_5$, —SO$_2$R$_5$, or —SO$_2$W$_5$.

W₅ is carbocycle or heterocycle wherein W₅ is independently substituted with 0 to 3 R₂ groups.

W$_{3a}$ is W$_{4a}$ or W$_{5a}$.

W$_{4a}$ is R$_{5a}$, —C(Y₁)R$_{5a}$, —C(Y₁)W$_{5a}$, —SO₂R$_{5a}$, or —SO₂W$_{5a}$.

W$_{5a}$ is carbocycle or heterocycle wherein W₅ is independently substituted with 0 to 3 R₂ groups.

W₆ is independently substituted with 1, 2, or 3 A₃ groups.

m1 is independently an integer from 0 to 12, wherein the sum of all m1's within each individual embodiment of A₁, A₂ or A₃ is 12 or less; and m2 is independently an integer from 0 to 2.

One embodiment of Formula II is where A1 is —(C(R2)(R2))m1-W3, wherein W3 is substituted with 1 A3 group; A2 is —(C(R2)(R2))m1-W3; and A3 is —(C(R2)(R2)(R2))m1-P(Y1)(Y1R6a)(Y1R6a).

Exemplary Enumerated Compounds

By way of example and not limitation, embodiments of the invention are named below in tabular format (Table 100). These embodiments are of the general formula "MBF":

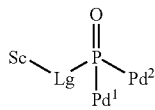

MBF

Each embodiment of MBF is depicted as a substituted nucleus (Sc) in which the nucleus is designated by a number and each substituent is designated in order by letter or number. Tables 1.1 to 1.5 are a schedule of nuclei used in forming the embodiments of Table 100. Each nucleus (Sc) is given a number designation from Tables 1.1 to 1.5, and this designation appears first in each embodiment name. Similarly, Tables 10.1 to 10.19 and 20.1 to 20.36 list the selected linking groups (Lg) and prodrug (Pd¹ and Pd²) substituents, again by letter or number designation, respectively.

Accordingly, each named embodiment of Table 100 is depicted by a number designating the nucleus from Table 1.1-1.5, followed by a letter designating the linking group (Lg) from Table 10.1-10.19, and two numbers designating the two prodrug groups (Pd¹ and Pd²) from Table 20.1-20.36. In graphical tabular form, each embodiment of Table 100 appears as a name having the syntax:

Sc.Lg.Pd¹.Pd²

Thus, structure 58, Example 27, is represented by 12.AH.247.247.

12.AH.247.247

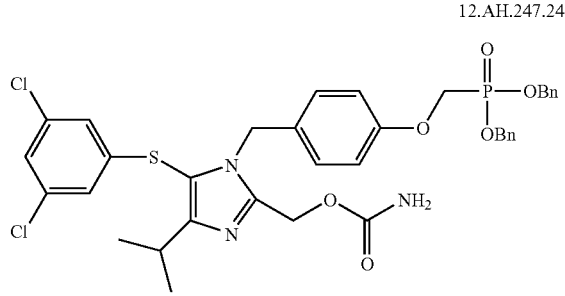

Each Sc group is shown having a tilda ("~"). The tilda is the point of covalent attachment of Sc to Lg. Q¹ and Q² of the linking groups (Lg), it should be understood, do not represent groups or atoms but are simply connectivity designations. Q¹ is the site of the covalent bond to the nucleus (Sc) and Q² is the site of the covalent bond to the phosphorous atom of formula MBF. Each prodrug group (Pd¹ and Pd²) are covalently bonded to the phosphorous atom of MBF at the tilda symbol ("~"). Some embodiments of Tables 10.1-10.19 and 20.1-20.36 may be designated as a combination of letters and numbers (Table 10. 1-10.19) or number and letter (Table 20.1-20.36). For example there are Table 10 entries for BJ1 and BJ2. In any event, entries of Table 10.1-10.19 always begin with a letter and those of Table 20.1-20.36 always begin with a number. When a nucleus (Sc) is shown enclosed within square brackets ("[]") and a covalent bond extends outside the brackets, the point of covalent attachment of Sc to Lg may be at any substitutable site on SC. Selection of the point of attachment is described herein. By way of example and not limitation, the point of attachment is selected from those depicted in the schemes and examples.

TABLE 1.1

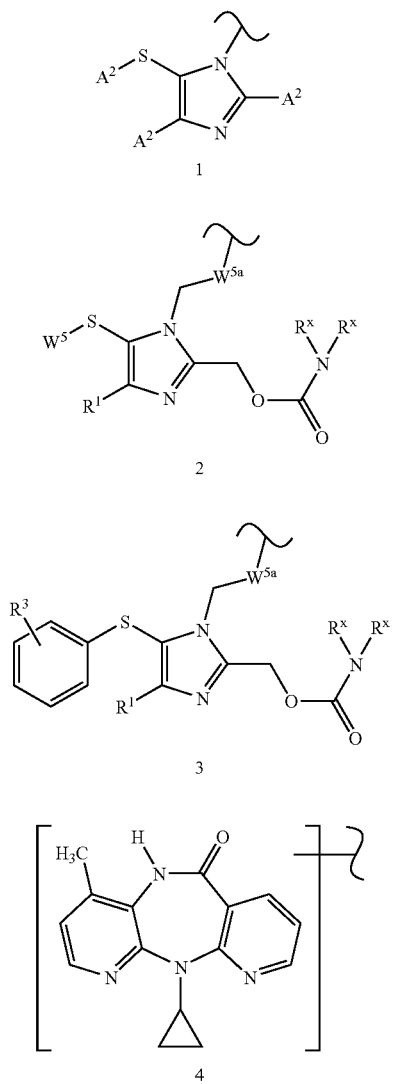

TABLE 1.2
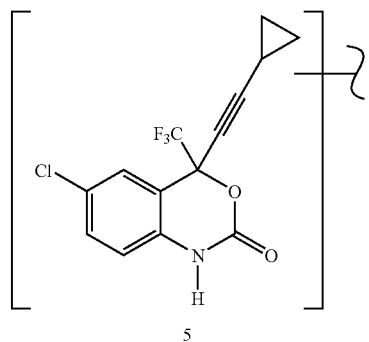
5
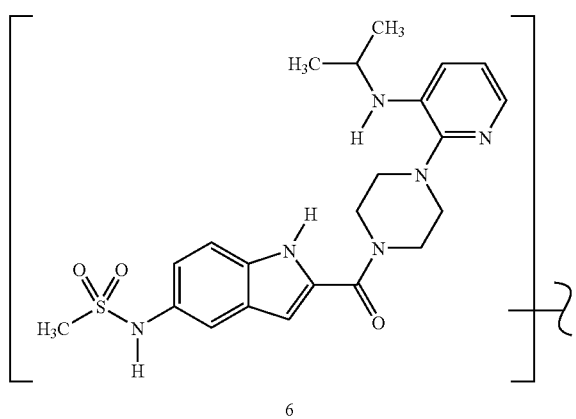
6
TABLE 1.3
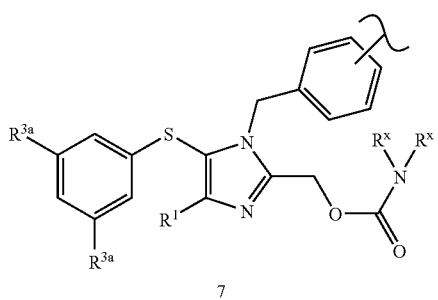
7
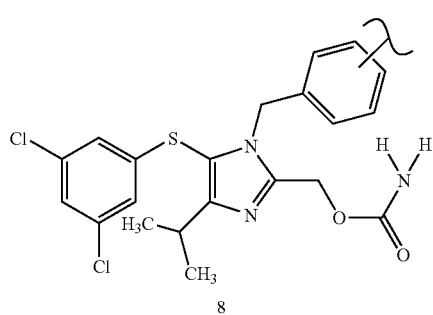
8
TABLE 1.3-continued
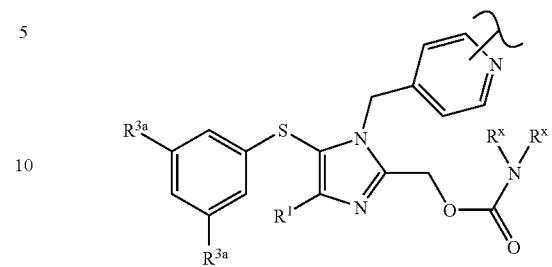
9
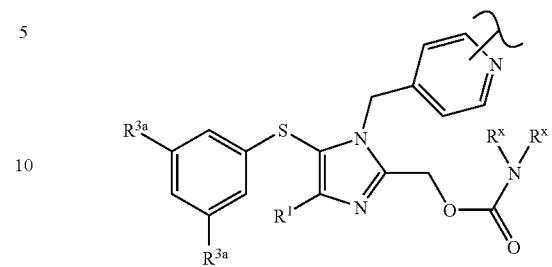
10
TABLE 1.4
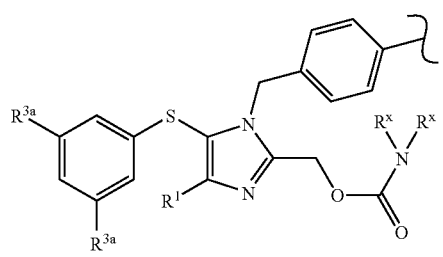
11
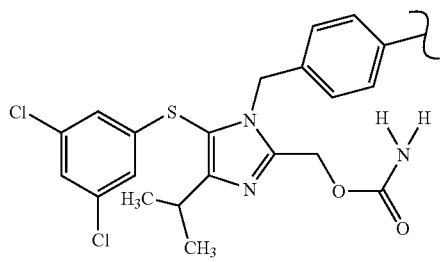
12
TABLE 1.5
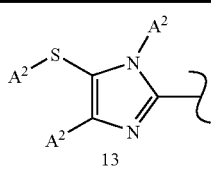
13

TABLE 1.5-continued
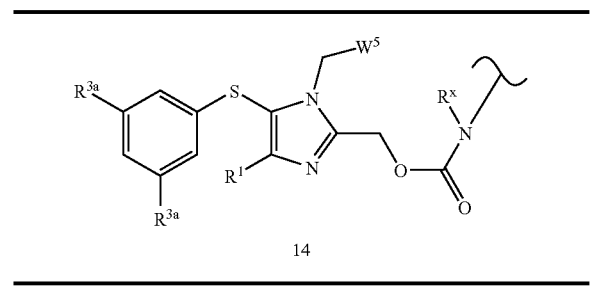
TABLE 10.1
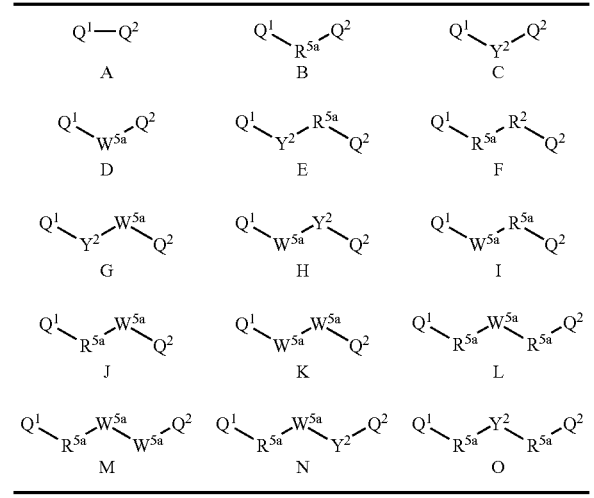
TABLE 10.2
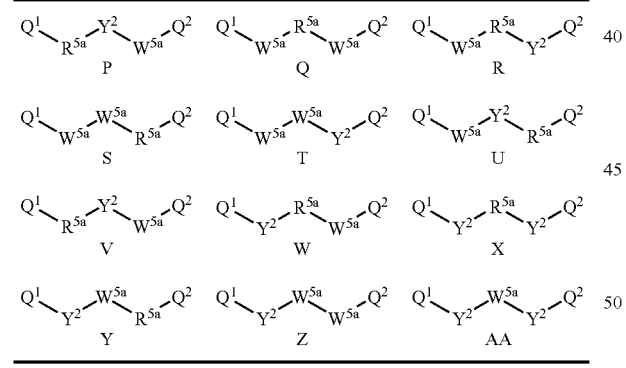
TABLE 10.3
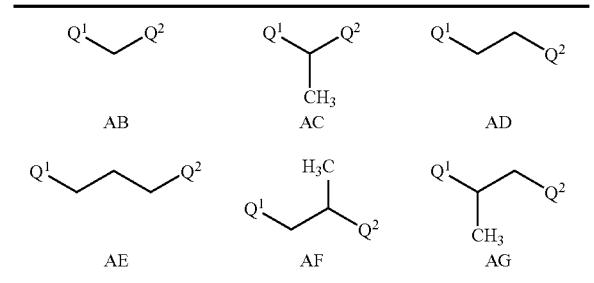
TABLE 10.3-continued
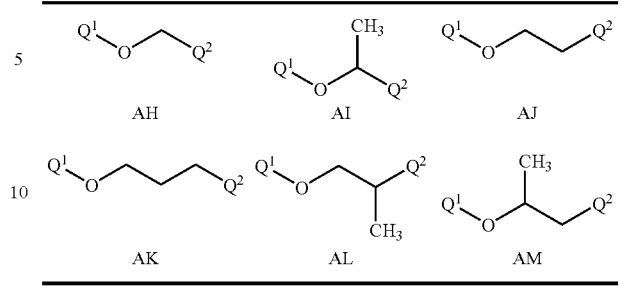
TABLE 10.4
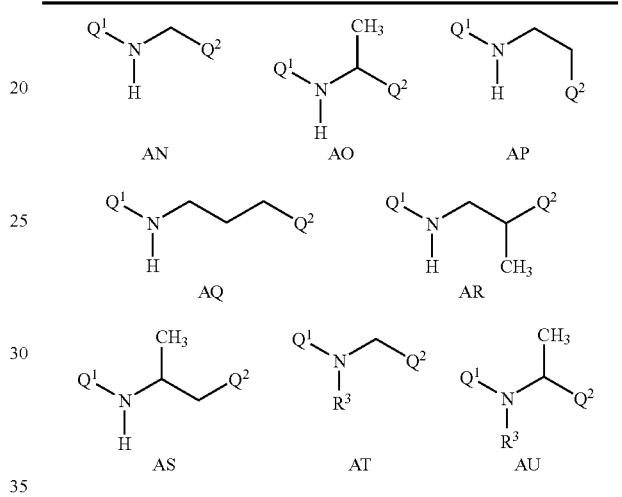
TABLE 10.5
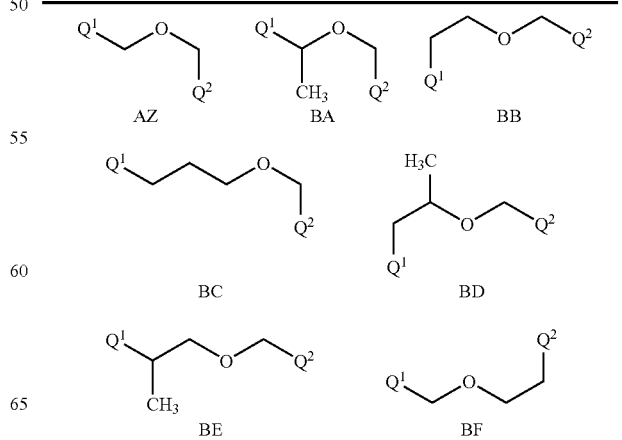

TABLE 10.5-continued
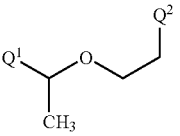 BG
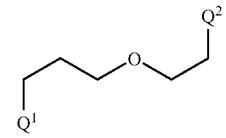 BH
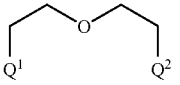 BI
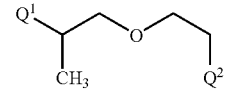 BJ2
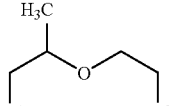 BJ1
TABLE 10.6
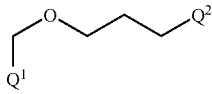 BK
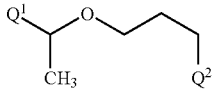 BL
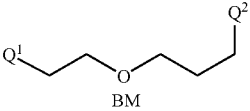 BM
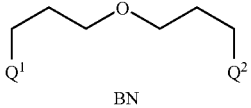 BN
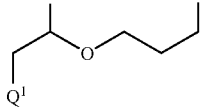 BO
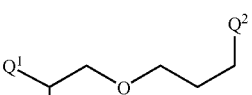 BP
TABLE 10.7
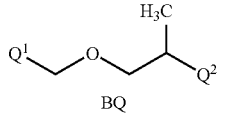 BQ
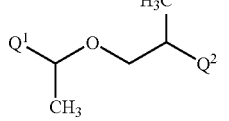 BR
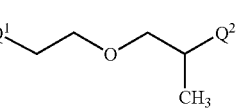 BS
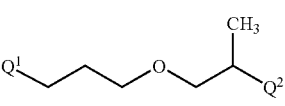 BT
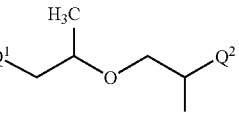 BU
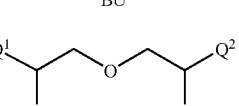 BV
TABLE 10.8
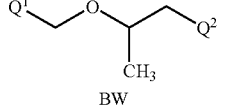 BW
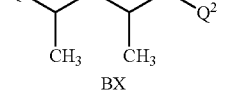 BX
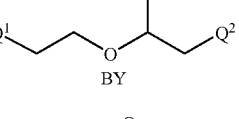 BY
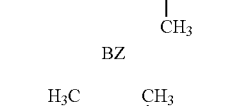 BZ
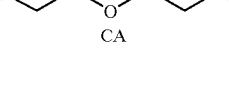 CA TABLE 10.8-continued
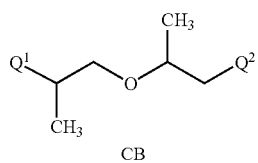
CB
TABLE 10.9
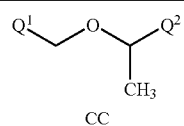
CC
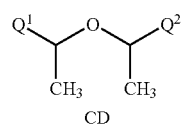
CD
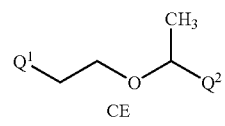
CE
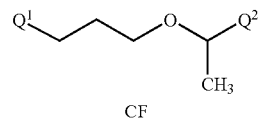
CF
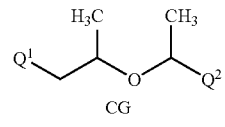
CG
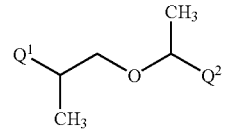
CH
TABLE 10.10
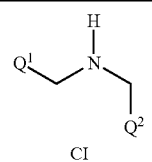
CI
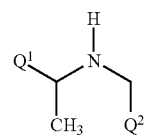
CJ
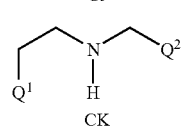
CK
TABLE 10.10-continued
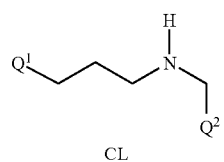
CL
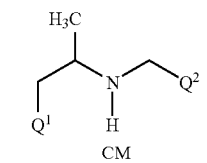
CM
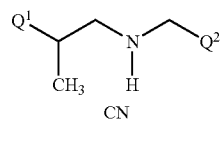
CN
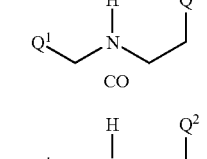
CO
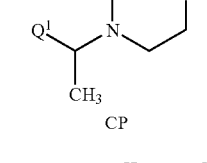
CP
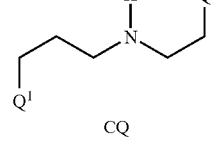
CQ
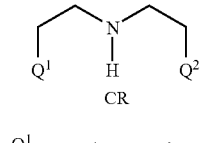
CR
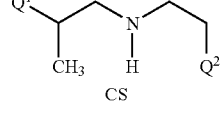
CS
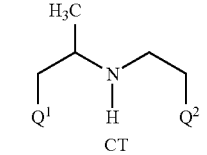
CT
TABLE 10.11
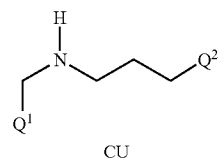
CU TABLE 10.11-continued
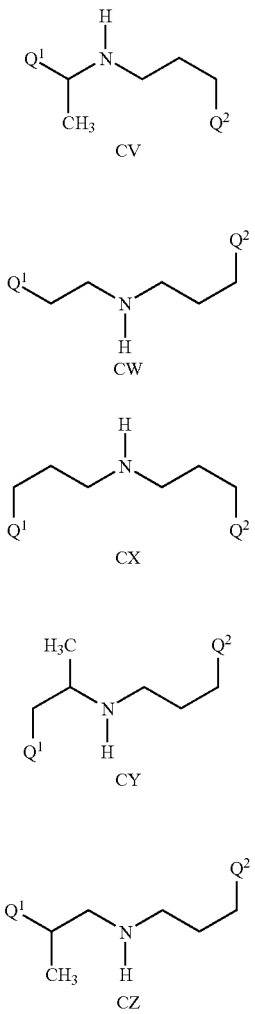
TABLE 10.12
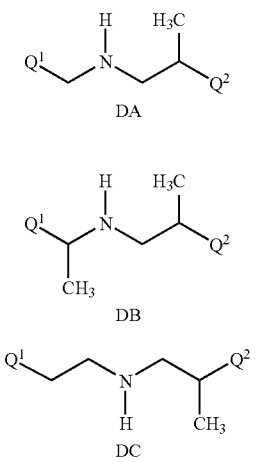
TABLE 10.12-continued
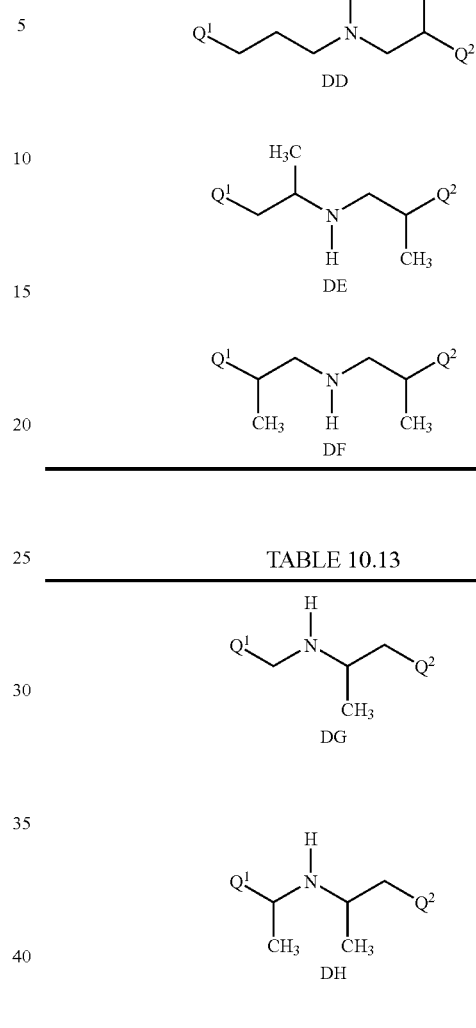
TABLE 10.13
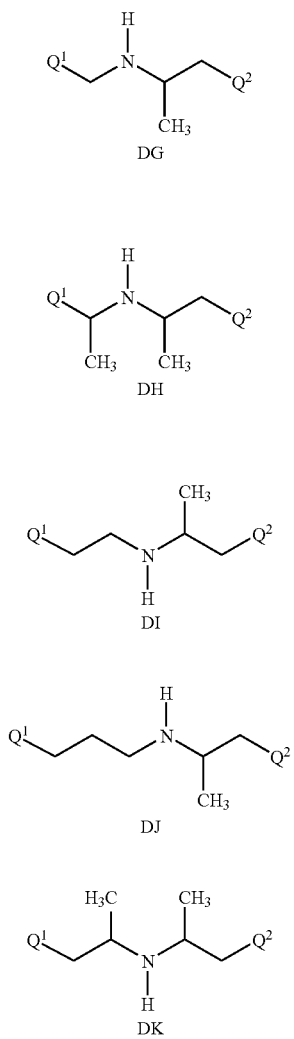

TABLE 10.13-continued
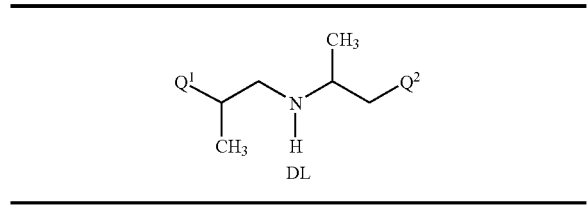
DL
TABLE 10.14
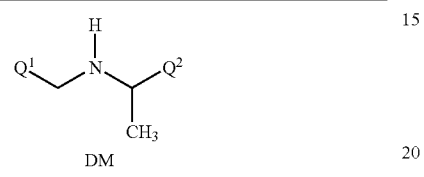
DM
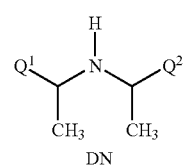
DN
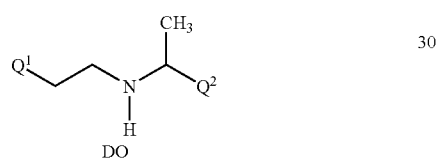
DO
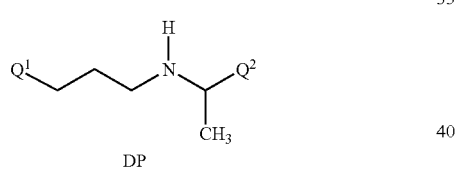
DP
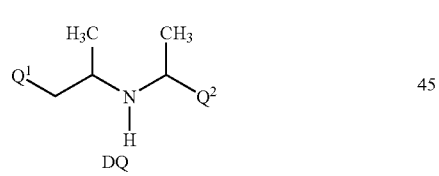
DQ
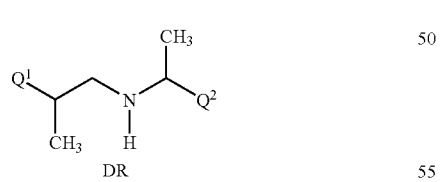
DR
TABLE 10.15
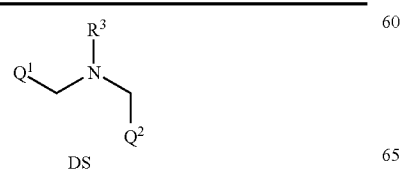
DS
TABLE 10.15-continued
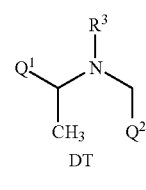
DT
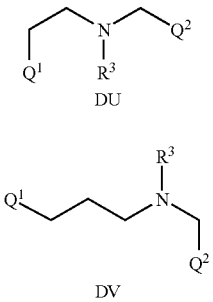
DU
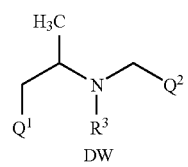
DV
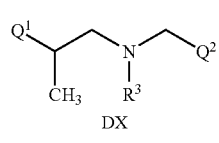
DW
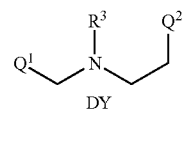
DX
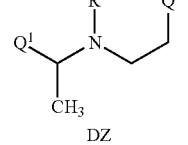
DY
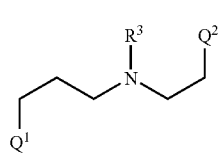
DZ
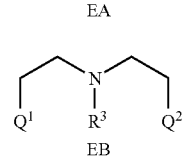
EA
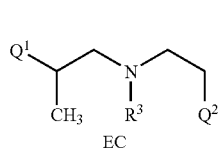
EB
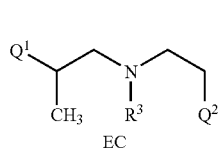
EC TABLE 10.15-continued
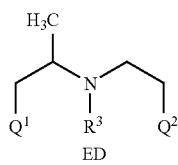
ED
TABLE 10.16
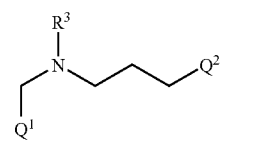
EE
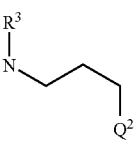
EF
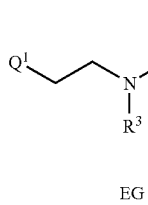
EG
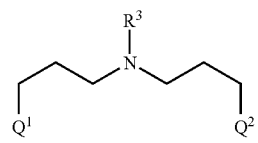
EH
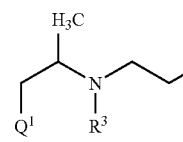
EI
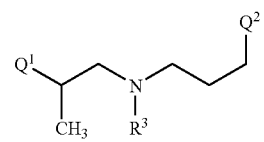
EJ
TABLE 10.17
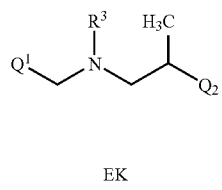
EK
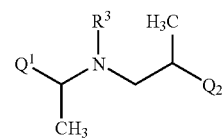
EL
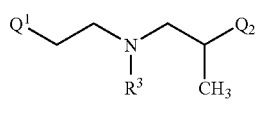
EM
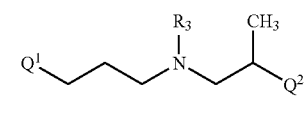
EN
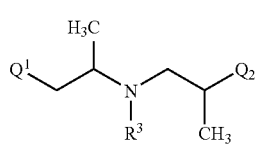
EO
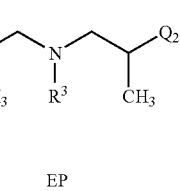
EP
TABLE 10.18
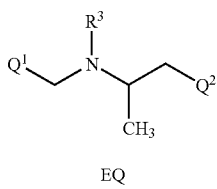
EQ
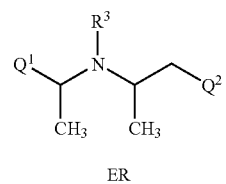
ER
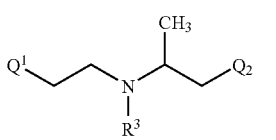
ES
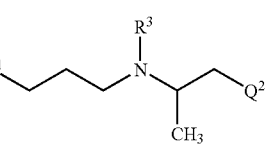
ET
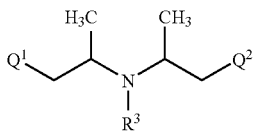
EU
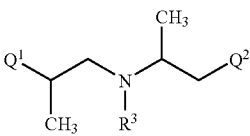
EV
TABLE 10.19
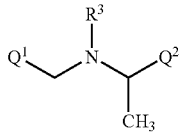
EW
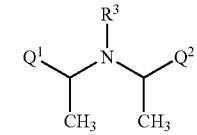
EX
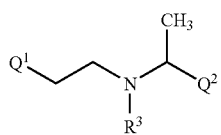
EY
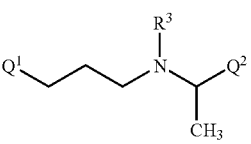
EZ
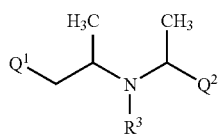
FA
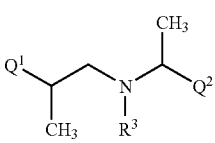
FB
TABLE 20.1
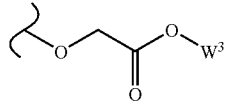
1
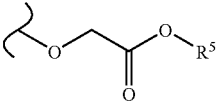
2
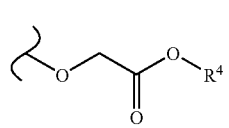
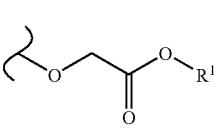

TABLE 20.1-continued
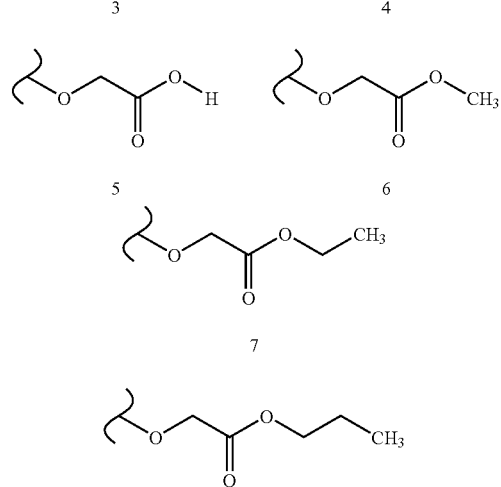
TABLE 20.2
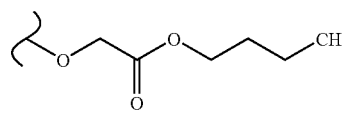
9
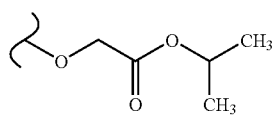
10
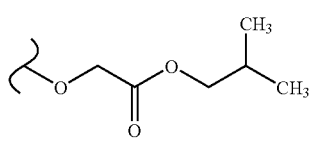
11
TABLE 20.3
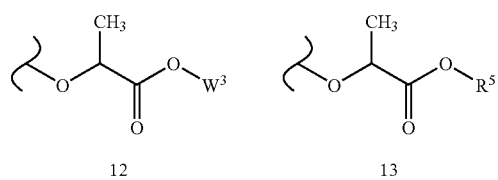
TABLE 20.3-continued
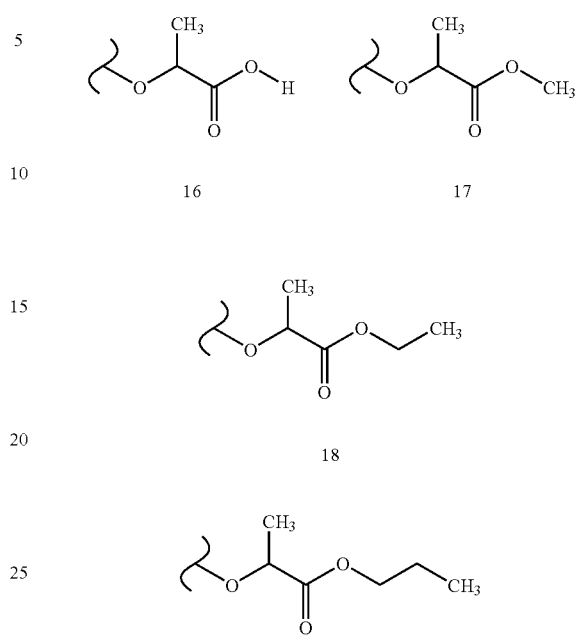
TABLE 20.4
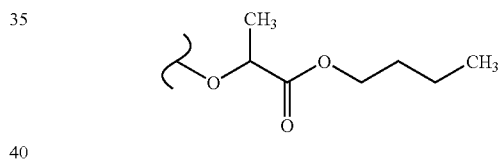
20
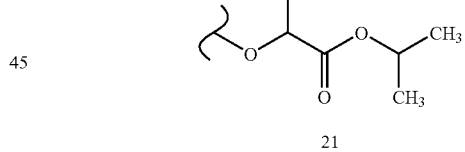
21
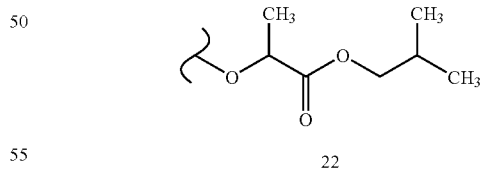
22
TABLE 20.5
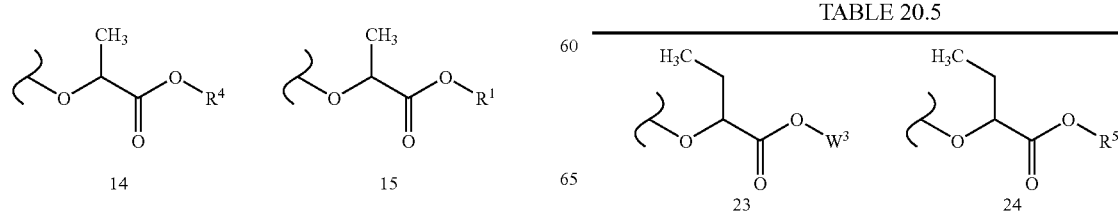

TABLE 20.5-continued
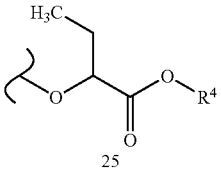
25
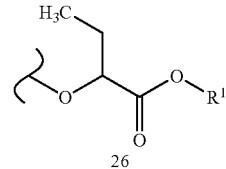
26
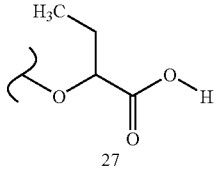
27
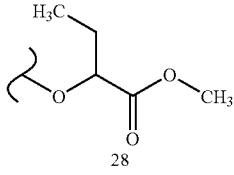
28
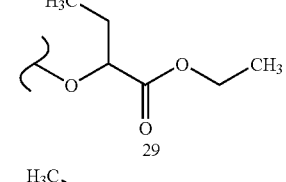
29
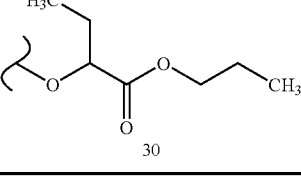
30
TABLE 20.6
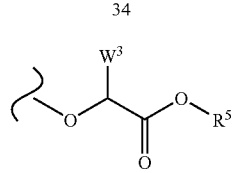
31
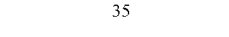
32
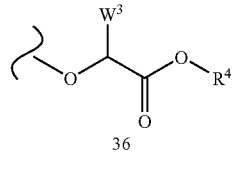
33
TABLE 20.7
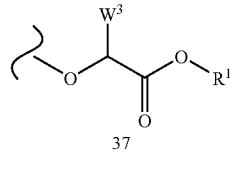
TABLE 20.7-continued
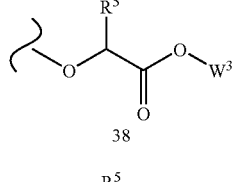
34
35
36
37
38
39
40
41
TABLE 20.8
42
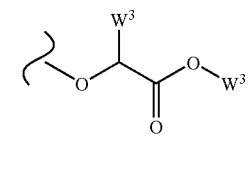

TABLE 20.8-continued
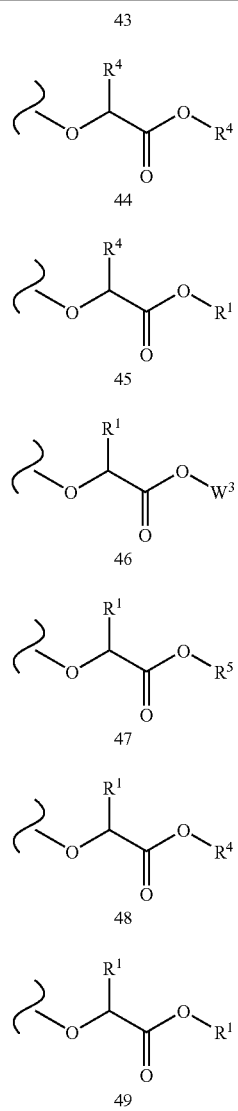
TABLE 20.9
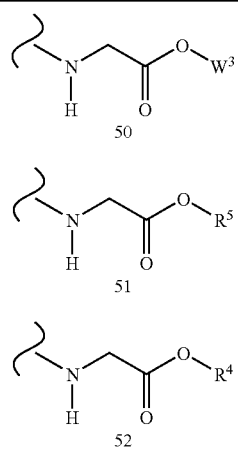
TABLE 20.9-continued
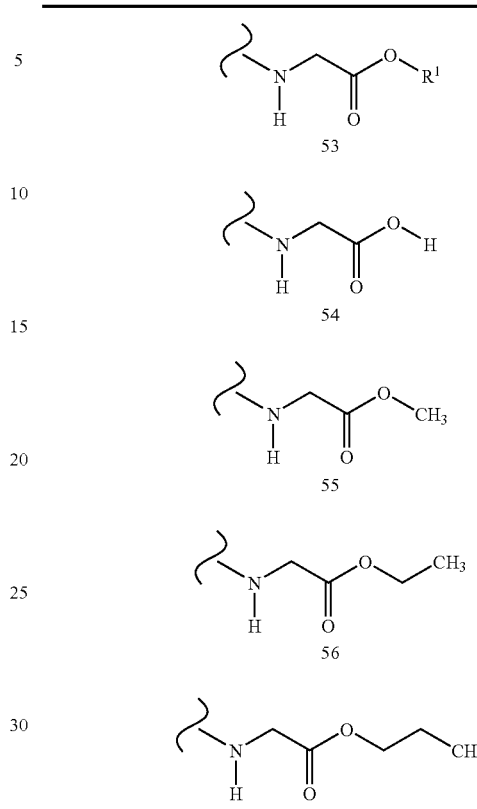
TABLE 20.10
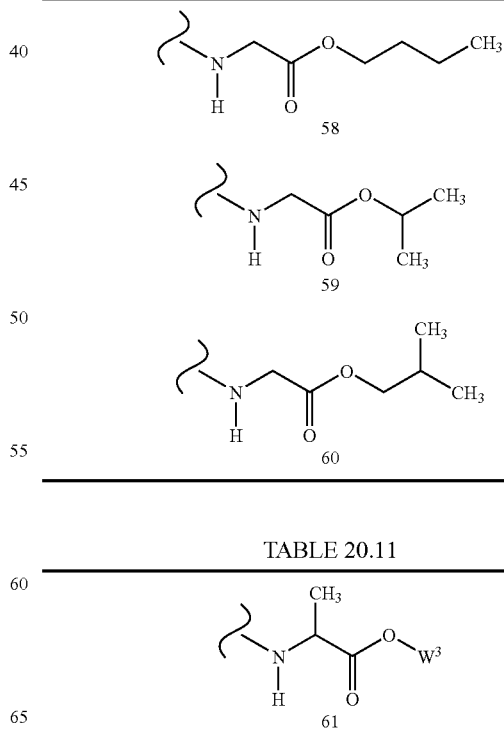

TABLE 20.11-continued
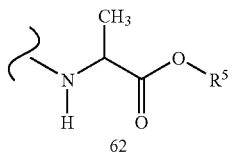
62
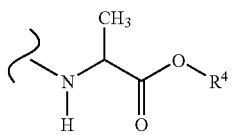
63
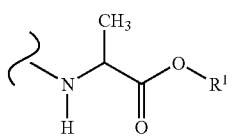
64
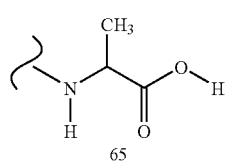
65
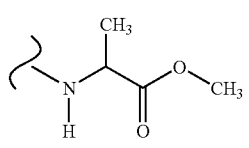
66
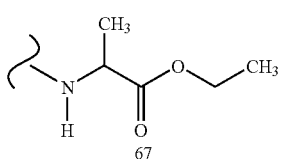
67
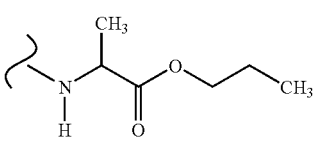
68
TABLE 20.12
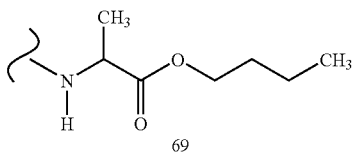
69
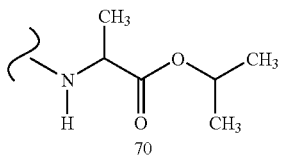
70
TABLE 20.12-continued
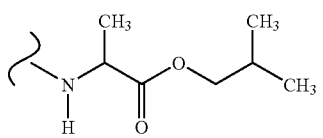
71
TABLE 20.13
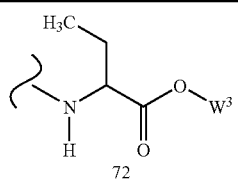
72
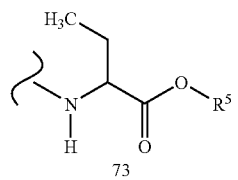
73
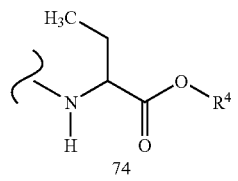
74
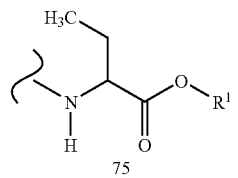
75
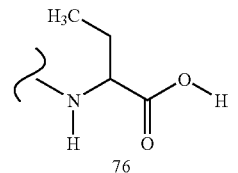
76
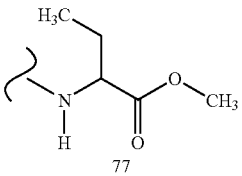
77
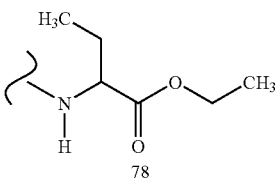
78

TABLE 20.13-continued
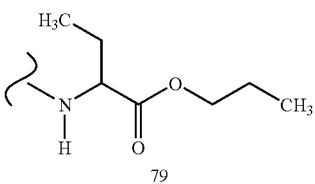
79
TABLE 20.14
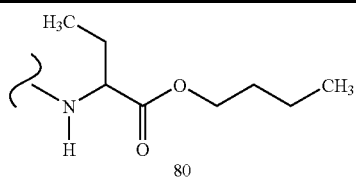
80
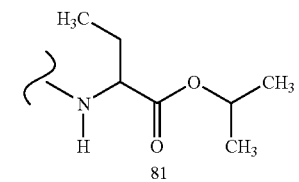
81
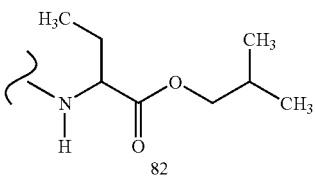
82
TABLE 20.15
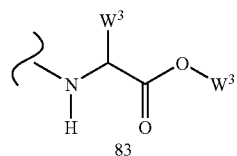
83
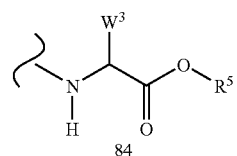
84
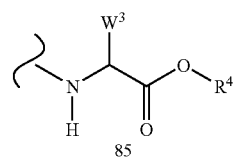
85
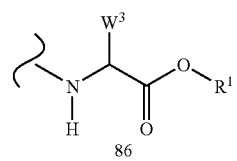
86
TABLE 20.15-continued
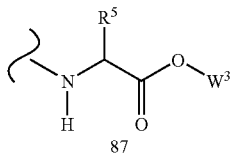
87
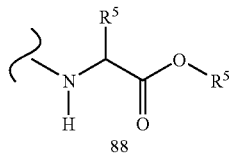
88
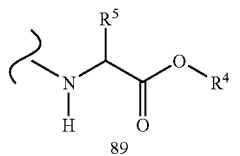
89
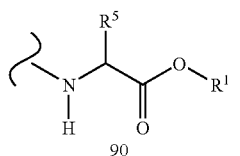
90
TABLE 20.16
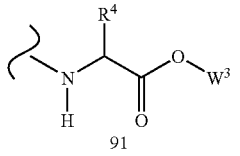
91
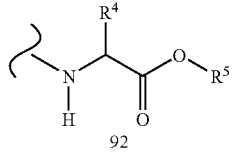
92
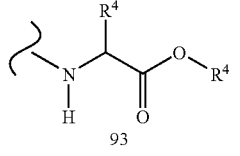
93
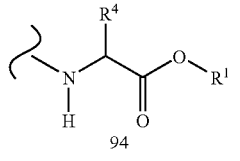
94
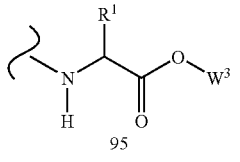
95

TABLE 20.16-continued
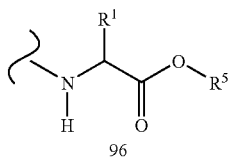
96
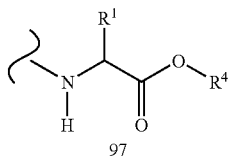
97
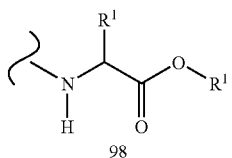
98
TABLE 20.17
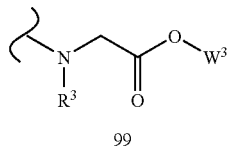
99
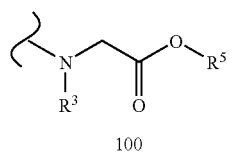
100
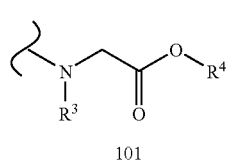
101
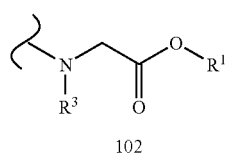
102
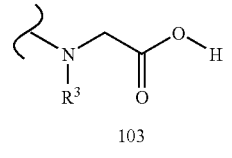
103
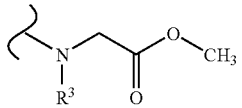
104
TABLE 20.17-continued
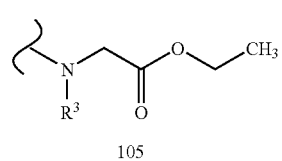
105
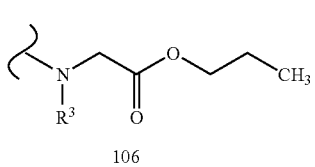
106
TABLE 20.18
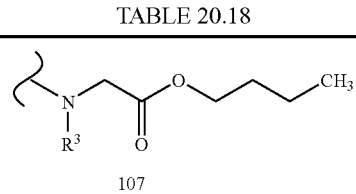
107
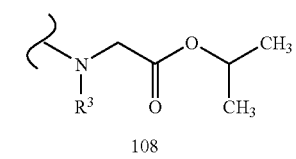
108
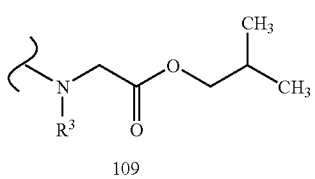
109
TABLE 20.19
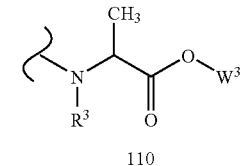
110
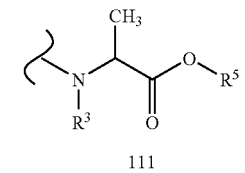
111
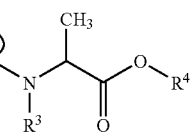
112

TABLE 20.19-continued

113
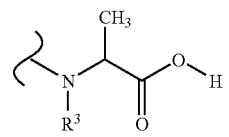
114
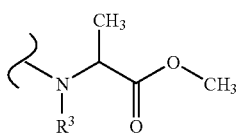
115
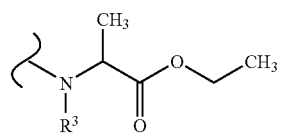
116
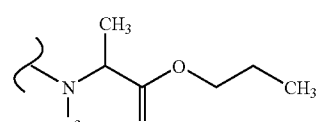
117
TABLE 20.20
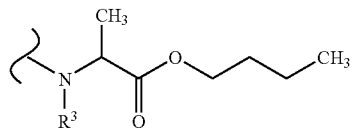
118
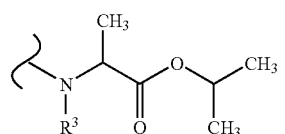
119
TABLE 20.20-continued
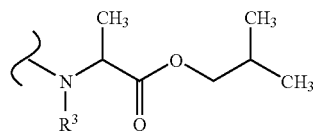
120
TABLE 20.21
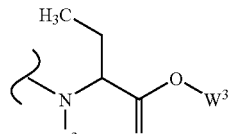
121
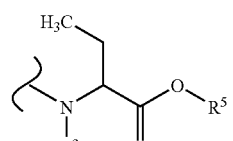
122
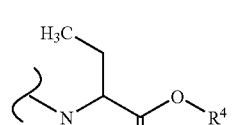
123
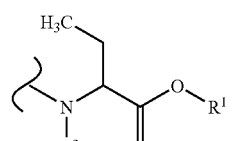
124
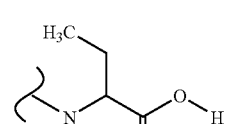
125
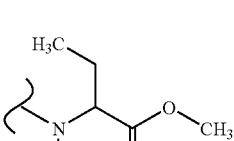
126

TABLE 20.21-continued
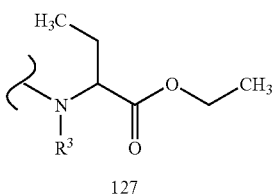
127
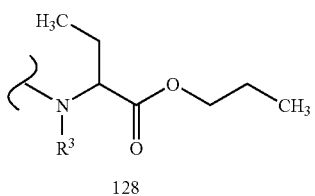
128
TABLE 20.22
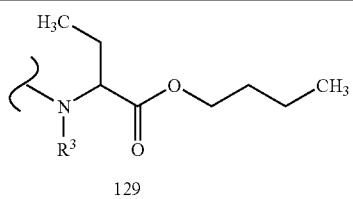
129
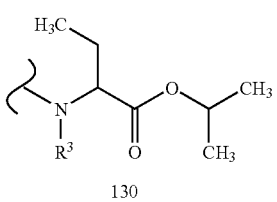
130
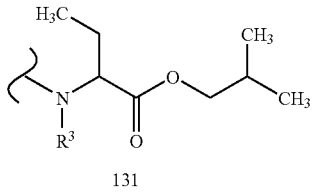
131
TABLE 20.23
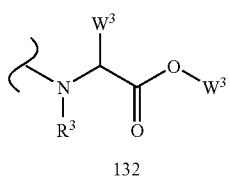
132
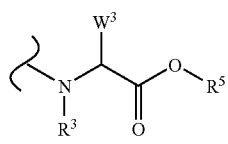
133
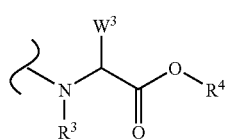
134
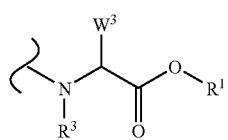
135
TABLE 20.23-continued
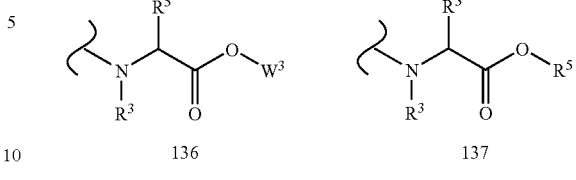
136    137
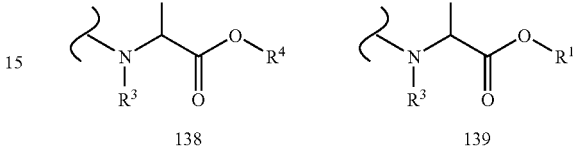
138    139
TABLE 20.24
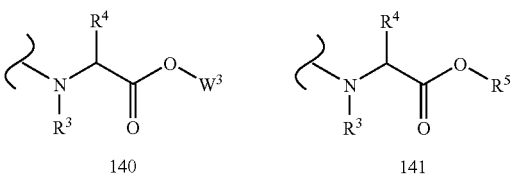
140    141
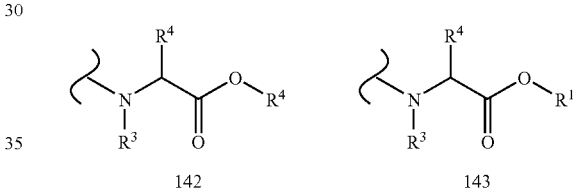
142    143
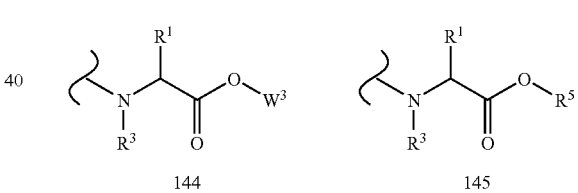
144    145
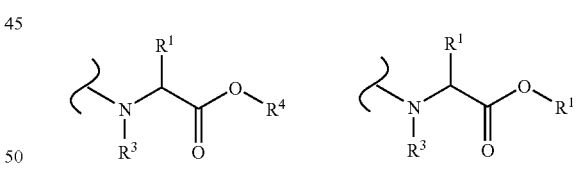
146    147
TABLE 20.25
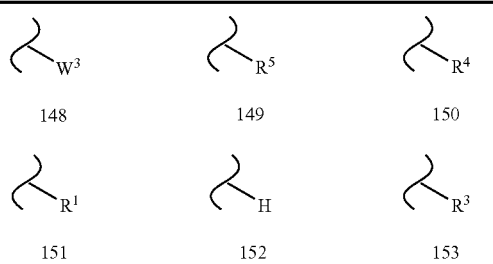
148    149    150
151    152    153

TABLE 20.25-continued
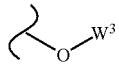
TABLE 20.26
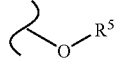
TABLE 20.27
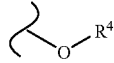
TABLE 20.27-continued
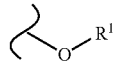
TABLE 20.28
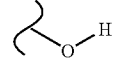

TABLE 20.29
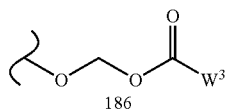
186
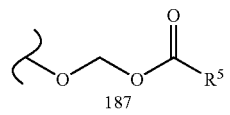
187
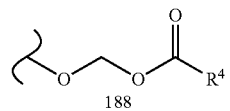
188
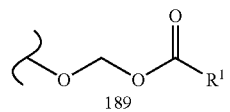
189
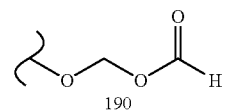
190
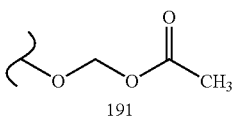
191
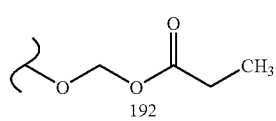
192
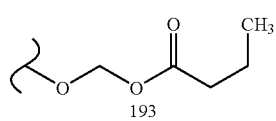
193
TABLE 20.30
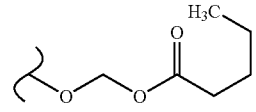
194
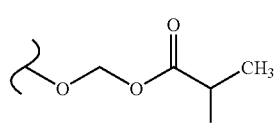
195
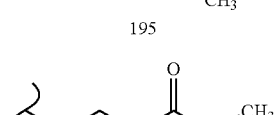
196
TABLE 20.30-continued
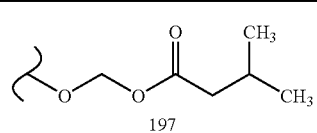
197
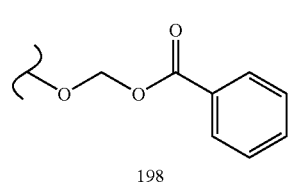
198
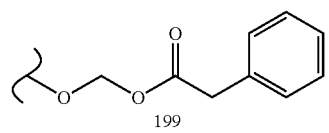
199
TABLE 20.31
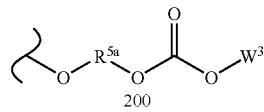
200
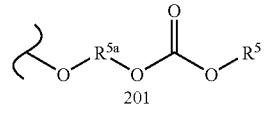
201
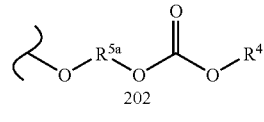
202
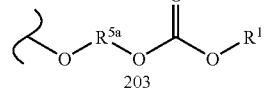
203
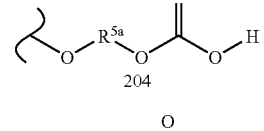
204
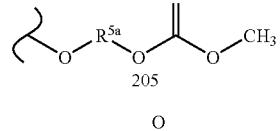
205
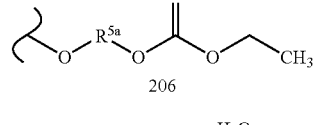
206
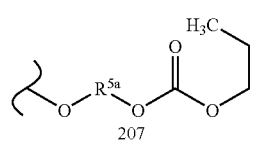
207

TABLE 20.32
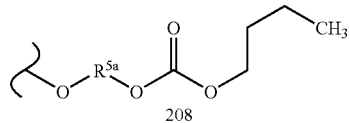
208
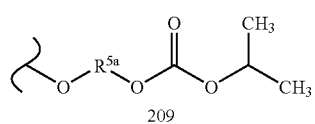
209
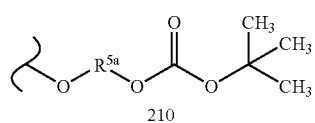
210
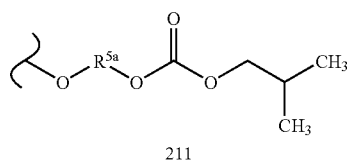
211
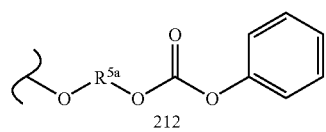
212
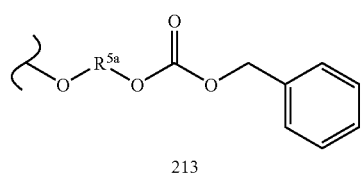
213
TABLE 20.33
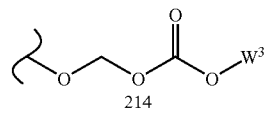
214
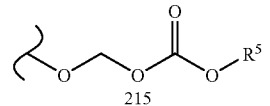
215
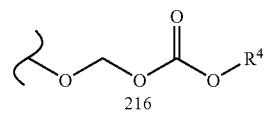
216
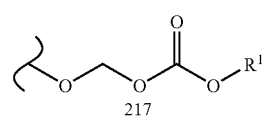
217
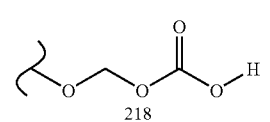
218
TABLE 20.33-continued
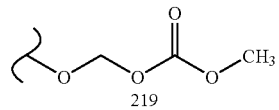
219
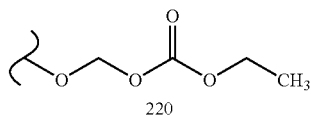
220
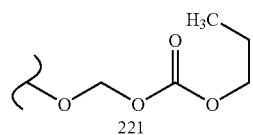
221
TABLE 20.34
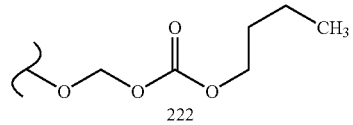
222
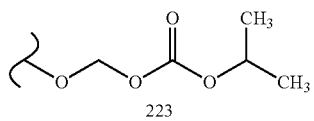
223
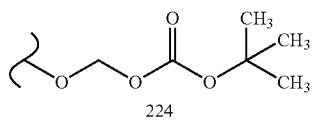
224
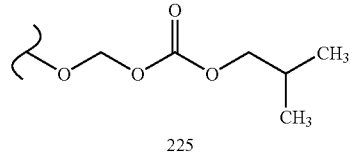
225
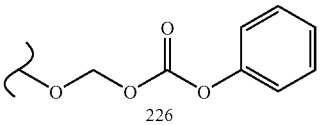
226
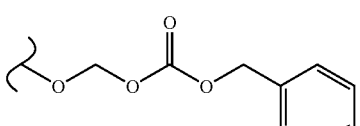
227
TABLE 20.35
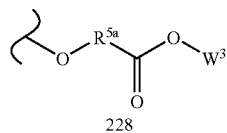
228

TABLE 20.35-continued
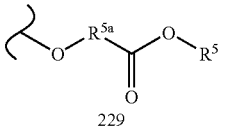
229
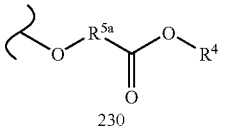
230
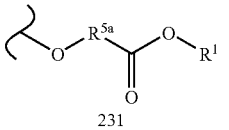
231
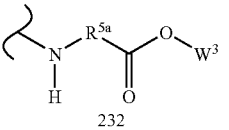
232
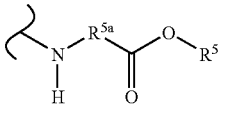
233
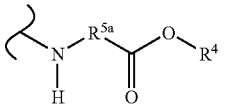
234
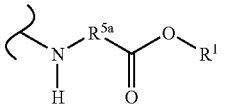
235
TABLE 20.36
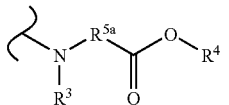
236
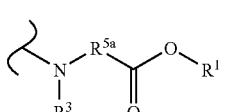
237
TABLE 20.36-continued
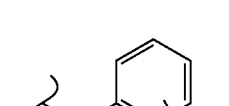
238
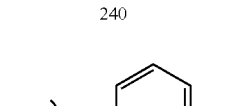
239
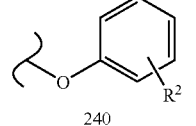
240
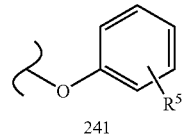
241
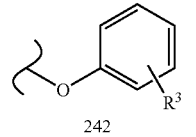
242
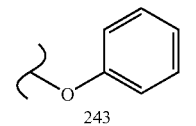
243
TABLE 20.37
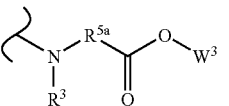
244
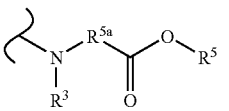
245
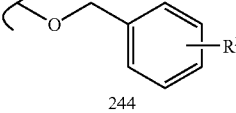
246
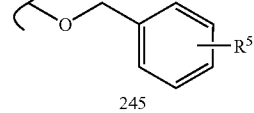
247
TABLE 100
Prodrugs of 1.B
1.B.228.228; 1.B.228.229; 1.B.228.230; 1.B.228.231; 1.B.228.236; 1.B.228.237; 1.B.228.238;
1.B.228.239; 1.B.228.154; 1.B.228.157; 1.B.228.166; 1.B.228.169; 1.B.228.172; 1.B.228.175;
1.B.228.240; 1.B.228.244; 1.B.229.228; 1.B.229.229; 1.B.229.230; 1.B.229.231; 1.B.229.236;
1.B.229.237; 1.B.229.238; 1.B.229.239; 1.B.229.154; 1.B.229.157; 1.B.229.166; 1.B.229.169;

TABLE 100-continued

1.B.229.172; 1.B.229.175; 1.B.229.240; 1.B.229.244; 1.B.230.228; 1.B.230.229; 1.B.230.230;
1.B.230.231; 1.B.230.236; 1.B.230.237; 1.B.230.238; 1.B.230.239; 1.B.230.154; 1.B.230.157;
1.B.230.166; 1.B.230.169; 1.B.230.172; 1.B.230.175; 1.B.230.240; 1.B.230.244; 1.B.231.228;
1.B.231.229; 1.B.231.230; 1.B.231.231; 1.B.231.236; 1.B.231.237; 1.B.231.238; 1.B.231.239;
1.B.231.154; 1.B.231.157; 1.B.231.166; 1.B.231.169; 1.B.231.172; 1.B.231.175; 1.B.231.240;
1.B.231.244; 1.B.236.228; 1.B.236.229; 1.B.236.230; 1.B.236.231; 1.B.236.236; 1.B.236.237;
1.B.236.238; 1.B.236.239; 1.B.236.154; 1.B.236.157; 1.B.236.166; 1.B.236.169; 1.B.236.172;
1.B.236.175; 1.B.236.240; 1.B.236.244; 1.B.237.228; 1.B.237.229; 1.B.237.230; 1.B.237.231;
1.B.237.236; 1.B.237.237; 1.B.237.238; 1.B.237.239; 1.B.237.154; 1.B.237.157; 1.B.237.166;
1.B.237.169; 1.B.237.172; 1.B.237.175; 1.B.237.240; 1.B.237.244; 1.B.238.228; 1.B.238.229;
1.B.238.230; 1.B.238.231; 1.B.238.236; 1.B.238.237; 1.B.238.238; 1.B.238.239; 1.B.238.154;
1.B.238.157; 1.B.238.166; 1.B.238.169; 1.B.238.172; 1.B.238.175; 1.B.238.240; 1.B.238.244;
1.B.239.228; 1.B.239.229; 1.B.239.230; 1.B.239.231; 1.B.239.236; 1.B.239.237; 1.B.239.238;
1.B.239.239; 1.B.239.154; 1.B.239.157; 1.B.239.166; 1.B.239.169; 1.B.239.172; 1.B.239.175;
1.B.239.240; 1.B.239.244; 1.B.154.228; 1.B.154.229; 1.B.154.230; 1.B.154.231; 1.B.154.236;
1.B.154.237; 1.B.154.238; 1.B.154.239; 1.B.154.154; 1.B.154.157; 1.B.154.166; 1.B.154.169;
1.B.154.172; 1.B.154.175; 1.B.154.240; 1.B.154.244; 1.B.157.228; 1.B.157.229; 1.B.157.230;
1.B.157.231; 1.B.157.236; 1.B.157.237; 1.B.157.238; 1.B.157.239; 1.B.157.154; 1.B.157.157;
1.B.157.166; 1.B.157.169; 1.B.157.172; 1.B.157.175; 1.B.157.240; 1.B.157.244; 1.B.166.228;
1.B.166.229; 1.B.166.230; 1.B.166.231; 1.B.166.236; 1.B.166.237; 1.B.166.238; 1.B.166.239;
1.B.166.154; 1.B.166.157; 1.B.166.166; 1.B.166.169; 1.B.166.172; 1.B.166.175; 1.B.166.240;
1.B.166.244; 1.B.169.228; 1.B.169.229; 1.B.169.230; 1.B.169.231; 1.B.169.236; 1.B.169.237;
1.B.169.238; 1.B.169.239; 1.B.169.154; 1.B.169.157; 1.B.169.166; 1.B.169.169; 1.B.169.172;
1.B.169.175; 1.B.169.240; 1.B.169.244; 1.B.172.228; 1.B.172.229; 1.B.172.230; 1.B.172.231;
1.B.172.236; 1.B.172.237; 1.B.172.238; 1.B.172.239; 1.B.172.154; 1.B.172.157; 1.B.172.166;
1.B.172.169; 1.B.172.172; 1.B.172.175; 1.B.172.240; 1.B.172.244; 1.B.175.228; 1.B.175.229;
1.B.175.230; 1.B.175.231; 1.B.175.236; 1.B.175.237; 1.B.175.238; 1.B.175.239; 1.B.175.154;
1.B.175.157; 1.B.175.166; 1.B.175.169; 1.B.175.172; 1.B.175.175; 1.B.175.240; 1.B.175.244;
1.B.240.228; 1.B.240.229; 1.B.240.230; 1.B.240.231; 1.B.240.236; 1.B.240.237; 1.B.240.238;
1.B.240.239; 1.B.240.154; 1.B.240.157; 1.B.240.166; 1.B.240.169; 1.B.240.172; 1.B.240.175;
1.B.240.240; 1.B.240.244; 1.B.244.228; 1.B.244.229; 1.B.244.230; 1.B.244.231; 1.B.244.236;
1.B.244.237; 1.B.244.238; 1.B.244.239; 1.B.244.154; 1.B.244.157; 1.B.244.166; 1.B.244.169;
1.B.244.172; 1.B.244.175; 1.B.244.240; 1.B.244.244;

Prodrugs of 1.D

1.D.228.228; 1.D.228.229; 1.D.228.230; 1.D.228.231; 1.D.228.236; 1.D.228.237;
1.D.228.238; 1.D.228.239; 1.D.228.154; 1.D.228.157; 1.D.228.166; 1.D.228.169; 1.D.228.172;
1.D.228.175; 1.D.228.240; 1.D.228.244; 1.D.229.228; 1.D.229.229; 1.D.229.230; 1.D.229.231;
1.D.229.236; 1.D.229.237; 1.D.229.238; 1.D.229.239; 1.D.229.154; 1.D.229.157; 1.D.229.166;
1.D.229.169; 1.D.229.172; 1.D.229.175; 1.D.229.240; 1.D.229.244; 1.D.230.228; 1.D.230.229;
1.D.230.230; 1.D.230.231; 1.D.230.236; 1.D.230.237; 1.D.230.238; 1.D.230.239; 1.D.230.154;
1.D.230.157; 1.D.230.166; 1.D.230.169; 1.D.230.172; 1.D.230.175; 1.D.230.240; 1.D.230.244;
1.D.231.228; 1.D.231.229; 1.D.231.230; 1.D.231.231; 1.D.231.236; 1.D.231.237; 1.D.231.238;
1.D.231.239; 1.D.231.154; 1.D.231.157; 1.D.231.166; 1.D.231.169; 1.D.231.172; 1.D.231.175;
1.D.231.240; 1.D.231.244; 1.D.236.228; 1.D.236.229; 1.D.236.230; 1.D.236.231; 1.D.236.236;
1.D.236.237; 1.D.236.238; 1.D.236.239; 1.D.236.154; 1.D.236.157; 1.D.236.166; 1.D.236.169;
1.D.236.172; 1.D.236.175; 1.D.236.240; 1.D.236.244; 1.D.237.228; 1.D.237.229; 1.D.237.230;
1.D.237.231; 1.D.237.236; 1.D.237.237; 1.D.237.238; 1.D.237.239; 1.D.237.154; 1.D.237.157;
1.D.237.166; 1.D.237.169; 1.D.237.172; 1.D.237.175; 1.D.237.240; 1.D.237.244; 1.D.238.228;
1.D.238.229; 1.D.238.230; 1.D.238.231; 1.D.238.236; 1.D.238.237; 1.D.238.238; 1.D.238.239;
1.D.238.154; 1.D.238.157; 1.D.238.166; 1.D.238.169; 1.D.238.172; 1.D.238.175; 1.D.238.240;
1.D.238.244; 1.D.239.228; 1.D.239.229; 1.D.239.230; 1.D.239.231; 1.D.239.236; 1.D.239.237;
1.D.239.238; 1.D.239.239; 1.D.239.154; 1.D.239.157; 1.D.239.166; 1.D.239.169; 1.D.239.172;
1.D.239.175; 1.D.239.240; 1.D.239.244; 1.D.154.228; 1.D.154.229; 1.D.154.230; 1.D.154.231;
1.D.154.236; 1.D.154.237; 1.D.154.238; 1.D.154.239; 1.D.154.154; 1.D.154.157; 1.D.154.166;
1.D.154.169; 1.D.154.172; 1.D.154.175; 1.D.154.240; 1.D.154.244; 1.D.157.228; 1.D.157.229;
1.D.157.230; 1.D.157.231; 1.D.157.236; 1.D.157.237; 1.D.157.238; 1.D.157.239; 1.D.157.154;
1.D.157.157; 1.D.157.166; 1.D.157.169; 1.D.157.172; 1.D.157.175; 1.D.157.240; 1.D.157.244;
1.D.166.228; 1.D.166.229; 1.D.166.230; 1.D.166.231; 1.D.166.236; 1.D.166.237; 1.D.166.238;
1.D.166.239; 1.D.166.154; 1.D.166.157; 1.D.166.166; 1.D.166.169; 1.D.166.172; 1.D.166.175;
1.D.166.240; 1.D.166.244; 1.D.169.228; 1.D.169.229; 1.D.169.230; 1.D.169.231; 1.D.169.236;
1.D.169.237; 1.D.169.238; 1.D.169.239; 1.D.169.154; 1.D.169.157; 1.D.169.166; 1.D.169.169;
1.D.169.172; 1.D.169.175; 1.D.169.240; 1.D.169.244; 1.D.172.228; 1.D.172.229; 1.D.172.230;
1.D.172.231; 1.D.172.236; 1.D.172.237; 1.D.172.238; 1.D.172.239; 1.D.172.154; 1.D.172.157;
1.D.172.166; 1.D.172.169; 1.D.172.172; 1.D.172.175; 1.D.172.240; 1.D.172.244; 1.D.175.228;
1.D.175.229; 1.D.175.230; 1.D.175.231; 1.D.175.236; 1.D.175.237; 1.D.175.238; 1.D.175.239;
1.D.175.154; 1.D.175.157; 1.D.175.166; 1.D.175.169; 1.D.175.172; 1.D.175.175; 1.D.175.240;
1.D.175.244; 1.D.240.228; 1.D.240.229; 1.D.240.230; 1.D.240.231; 1.D.240.236; 1.D.240.237;
1.D.240.238; 1.D.240.239; 1.D.240.154; 1.D.240.157; 1.D.240.166; 1.D.240.169; 1.D.240.172;
1.D.240.175; 1.D.240.240; 1.D.240.244; 1.D.244.228; 1.D.244.229; 1.D.244.230; 1.D.244.231;
1.D.244.236; 1.D.244.237; 1.D.244.238; 1.D.244.239; 1.D.244.154; 1.D.244.157; 1.D.244.166;
1.D.244.169; 1.D.244.172; 1.D.244.175; 1.D.244.240; 1.D.244.244;

Prodrugs of 1.E

1.E.228.228; 1.E.228.229; 1.E.228.230; 1.E.228.231; 1.E.228.236; 1.E.228.237; 1.E.228.238;
1.E.228.239; 1.E.228.154; 1.E.228.157; 1.E.228.166; 1.E.228.169; 1.E.228.172; 1.E.228.175;
1.E.228.240; 1.E.228.244; 1.E.229.228; 1.E.229.229; 1.E.229.230; 1.E.229.231; 1.E.229.236;
1.E.229.237; 1.E.229.238; 1.E.229.239; 1.E.229.154; 1.E.229.157; 1.E.229.166; 1.E.229.169;
1.E.229.172; 1.E.229.175; 1.E.229.240; 1.E.229.244; 1.E.230.228; 1.E.230.229; 1.E.230.230;

TABLE 100-continued

1.E.230.231; 1.E.230.236; 1.E.230.237; 1.E.230.238; 1.E.230.239; 1.E.230.154; 1.E.230.157;
1.E.230.166; 1.E.230.169; 1.E.230.172; 1.E.230.175; 1.E.230.240; 1.E.230.244; 1.E.231.228;
1.E.231.229; 1.E.231.230; 1.E.231.231; 1.E.231.236; 1.E.231.237; 1.E.231.238; 1.E.231.239;
1.E.231.154; 1.E.231.157; 1.E.231.166; 1.E.231.169; 1.E.231.172; 1.E.231.175; 1.E.231.240;
1.E.231.244; 1.E.236.228; 1.E.236.229; 1.E.236.230; 1.E.236.231; 1.E.236.236; 1.E.236.237;
1.E.236.238; 1.E.236.239; 1.E.236.154; 1.E.236.157; 1.E.236.166; 1.E.236.169; 1.E.236.172;
1.E.236.175; 1.E.236.240; 1.E.236.244; 1.E.237.228; 1.E.237.229; 1.E.237.230; 1.E.237.231;
1.E.237.236; 1.E.237.237; 1.E.237.238; 1.E.237.239; 1.E.237.154; 1.E.237.157; 1.E.237.166;
1.E.237.169; 1.E.237.172; 1.E.237.175; 1.E.237.240; 1.E.237.244; 1.E.238.228; 1.E.238.229;
1.E.238.230; 1.E.238.231; 1.E.238.236; 1.E.238.237; 1.E.238.238; 1.E.238.239; 1.E.238.154;
1.E.238.157; 1.E.238.166; 1.E.238.169; 1.E.238.172; 1.E.238.175; 1.E.238.240; 1.E.238.244;
1.E.239.228; 1.E.239.229; 1.E.239.230; 1.E.239.231; 1.E.239.236; 1.E.239.237; 1.E.239.238;
1.E.239.239; 1.E.239.154; 1.E.239.157; 1.E.239.166; 1.E.239.169; 1.E.239.172; 1.E.239.175;
1.E.239.240; 1.E.239.244; 1.E.154.228; 1.E.154.229; 1.E.154.230; 1.E.154.231; 1.E.154.236;
1.E.154.237; 1.E.154.238; 1.E.154.239; 1.E.154.154; 1.E.154.157; 1.E.154.166; 1.E.154.169;
1.E.154.172; 1.E.154.175; 1.E.154.240; 1.E.154.244; 1.E.157.228; 1.E.157.229; 1.E.157.230;
1.E.157.231; 1.E.157.236; 1.E.157.237; 1.E.157.238; 1.E.157.239; 1.E.157.154; 1.E.157.157;
1.E.157.166; 1.E.157.169; 1.E.157.172; 1.E.157.175; 1.E.157.240; 1.E.157.244; 1.E.166.228;
1.E.166.229; 1.E.166.230; 1.E.166.231; 1.E.166.236; 1.E.166.237; 1.E.166.238; 1.E.166.239;
1.E.166.154; 1.E.166.157; 1.E.166.166; 1.E.166.169; 1.E.166.172; 1.E.166.175; 1.E.166.240;
1.E.166.244; 1.E.169.228; 1.E.169.229; 1.E.169.230; 1.E.169.231; 1.E.169.236; 1.E.169.237;
1.E.169.238; 1.E.169.239; 1.E.169.154; 1.E.169.157; 1.E.169.166; 1.E.169.169; 1.E.169.172;
1.E.169.175; 1.E.169.240; 1.E.169.244; 1.E.172.228; 1.E.172.229; 1.E.172.230; 1.E.172.231;
1.E.172.236; 1.E.172.237; 1.E.172.238; 1.E.172.239; 1.E.172.154; 1.E.172.157; 1.E.172.166;
1.E.172.169; 1.E.172.172; 1.E.172.175; 1.E.172.240; 1.E.172.244; 1.E.175.228; 1.E.175.229;
1.E.175.230; 1.E.175.231; 1.E.175.236; 1.E.175.237; 1.E.175.238; 1.E.175.239; 1.E.175.154;
1.E.175.157; 1.E.175.166; 1.E.175.169; 1.E.175.172; 1.E.175.175; 1.E.175.240; 1.E.175.244;
1.E.240.228; 1.E.240.229; 1.E.240.230; 1.E.240.231; 1.E.240.236; 1.E.240.237; 1.E.240.238;
1.E.240.239; 1.E.240.154; 1.E.240.157; 1.E.240.166; 1.E.240.169; 1.E.240.172; 1.E.240.175;
1.E.240.240; 1.E.240.244; 1.E.244.228; 1.E.244.229; 1.E.244.230; 1.E.244.231; 1.E.244.236;
1.E.244.237; 1.E.244.238; 1.E.244.239; 1.E.244.154; 1.E.244.157; 1.E.244.166; 1.E.244.169;
1.E.244.172; 1.E.244.175; 1.E.244.240; 1.E.244.244;
Prodrugs of 1.G 1.G.228.228; 1.G.228.229; 1.G.228.230; 1.G.228.231; 1.G.228.236; 1.G.228.237;
1.G.228.238; 1.G.228.239; 1.G.228.154; 1.G.228.157; 1.G.228.166; 1.G.228.169; 1.G.228.172;
1.G.228.175; 1.G.228.240; 1.G.228.244; 1.G.229.228; 1.G.229.229; 1.G.229.230; 1.G.229.231;
1.G.229.236; 1.G.229.237; 1.G.229.238; 1.G.229.239; 1.G.229.154; 1.G.229.157; 1.G.229.166;
1.G.229.169; 1.G.229.172; 1.G.229.175; 1.G.229.240; 1.G.229.244; 1.G.230.228; 1.G.230.229;
1.G.230.230; 1.G.230.231; 1.G.230.236; 1.G.230.237; 1.G.230.238; 1.G.230.239; 1.G.230.154;
1.G.230.157; 1.G.230.166; 1.G.230.169; 1.G.230.172; 1.G.230.175; 1.G.230.240; 1.G.230.244;
1.G.231.228; 1.G.231.229; 1.G.231.230; 1.G.231.231; 1.G.231.236; 1.G.231.237; 1.G.231.238;
1.G.231.239; 1.G.231.154; 1.G.231.157; 1.G.231.166; 1.G.231.169; 1.G.231.172; 1.G.231.175;
1.G.231.240; 1.G.231.244; 1.G.236.228; 1.G.236.229; 1.G.236.230; 1.G.236.231; 1.G.236.236;
1.G.236.237; 1.G.236.238; 1.G.236.239; 1.G.236.154; 1.G.236.157; 1.G.236.166; 1.G.236.169;
1.G.236.172; 1.G.236.175; 1.G.236.240; 1.G.236.244; 1.G.237.228; 1.G.237.229; 1.G.237.230;
1.G.237.231; 1.G.237.236; 1.G.237.237; 1.G.237.238; 1.G.237.239; 1.G.237.154; 1.G.237.157;
1.G.237.166; 1.G.237.169; 1.G.237.172; 1.G.237.175; 1.G.237.240; 1.G.237.244; 1.G.238.228;
1.G.238.229; 1.G.238.230; 1.G.238.231; 1.G.238.236; 1.G.238.237; 1.G.238.238; 1.G.238.239;
1.G.238.154; 1.G.238.157; 1.G.238.166; 1.G.238.169; 1.G.238.172; 1.G.238.175; 1.G.238.240;
1.G.238.244; 1.G.239.228; 1.G.239.229; 1.G.239.230; 1.G.239.231; 1.G.239.236; 1.G.239.237;
1.G.239.238; 1.G.239.239; 1.G.239.154; 1.G.239.157; 1.G.239.166; 1.G.239.169; 1.G.239.172;
1.G.239.175; 1.G.239.240; 1.G.239.244; 1.G.154.228; 1.G.154.229; 1.G.154.230; 1.G.154.231;
1.G.154.236; 1.G.154.237; 1.G.154.238; 1.G.154.239; 1.G.154.154; 1.G.154.157; 1.G.154.166;
1.G.154.169; 1.G.154.172; 1.G.154.175; 1.G.154.240; 1.G.154.244; 1.G.157.228; 1.G.157.229;
1.G.157.230; 1.G.157.231; 1.G.157.236; 1.G.157.237; 1.G.157.238; 1.G.157.239; 1.G.157.154;
1.G.157.157; 1.G.157.166; 1.G.157.169; 1.G.157.172; 1.G.157.175; 1.G.157.240; 1.G.157.244;
1.G.166.228; 1.G.166.229; 1.G.166.230; 1.G.166.231; 1.G.166.236; 1.G.166.237; 1.G.166.238;
1.G.166.239; 1.G.166.154; 1.G.166.157; 1.G.166.166; 1.G.166.169; 1.G.166.172; 1.G.166.175;
1.G.166.240; 1.G.166.244; 1.G.169.228; 1.G.169.229; 1.G.169.230; 1.G.169.231; 1.G.169.236;
1.G.169.237; 1.G.169.238; 1.G.169.239; 1.G.169.154; 1.G.169.157; 1.G.169.166; 1.G.169.169;
1.G.169.172; 1.G.169.175; 1.G.169.240; 1.G.169.244; 1.G.172.228; 1.G.172.229; 1.G.172.230;
1.G.172.231; 1.G.172.236; 1.G.172.237; 1.G.172.238; 1.G.172.239; 1.G.172.154; 1.G.172.157;
1.G.172.166; 1.G.172.169; 1.G.172.172; 1.G.172.175; 1.G.172.240; 1.G.172.244; 1.G.175.228;
1.G.175.229; 1.G.175.230; 1.G.175.231; 1.G.175.236; 1.G.175.237; 1.G.175.238; 1.G.175.239;
1.G.175.154; 1.G.175.157; 1.G.175.166; 1.G.175.169; 1.G.175.172; 1.G.175.175; 1.G.175.240;
1.G.175.244; 1.G.240.228; 1.G.240.229; 1.G.240.230; 1.G.240.231; 1.G.240.236; 1.G.240.237;
1.G.240.238; 1.G.240.239; 1.G.240.154; 1.G.240.157; 1.G.240.166; 1.G.240.169; 1.G.240.172;
1.G.240.175; 1.G.240.240; 1.G.240.244; 1.G.244.228; 1.G.244.229; 1.G.244.230; 1.G.244.231;
1.G.244.236; 1.G.244.237; 1.G.244.238; 1.G.244.239; 1.G.244.154; 1.G.244.157; 1.G.244.166;
1.G.244.169; 1.G.244.172; 1.G.244.175; 1.G.244.240; 1.G.244.244;
Prodrugs of 1.I 1.I.228.228; 1.I.228.229; 1.I.228.230; 1.I.228.231; 1.I.228.236; 1.I.228.237; 1.I.228.238;
1.I.228.239; 1.I.228.154; 1.I.228.157; 1.I.228.166; 1.I.228.169; 1.I.228.172; 1.I.228.175;
1.I.228.240; 1.I.228.244; 1.I.229.228; 1.I.229.229; 1.I.229.230; 1.I.229.231; 1.I.229.236;
1.I.229.237; 1.I.229.238; 1.I.229.239; 1.I.229.154; 1.I.229.157; 1.I.229.166; 1.I.229.169;
1.I.229.172; 1.I.229.175; 1.I.229.240; 1.I.229.244; 1.I.230.228; 1.I.230.229; 1.I.230.230;
1.I.230.231; 1.I.230.236; 1.I.230.237; 1.I.230.238; 1.I.230.239; 1.I.230.154; 1.I.230.157;

TABLE 100-continued

1.I.230.166; 1.I.230.169; 1.I.230.172; 1.I.230.175; 1.I.230.240; 1.I.230.244; 1.I.231.228;
1.I.231.229; 1.I.231.230; 1.I.231.231; 1.I.231.236; 1.I.231.237; 1.I.231.238; 1.I.231.239;
1.I.231.154; 1.I.231.157; 1.I.231.166; 1.I.231.169; 1.I.231.172; 1.I.231.175; 1.I.231.240;
1.I.231.244; 1.I.236.228; 1.I.236.229; 1.I.236.230; 1.I.236.231; 1.I.236.236; 1.I.236.237;
1.I.236.238; 1.I.236.239; 1.I.236.154; 1.I.236.157; 1.I.236.166; 1.I.236.169; 1.I.236.172;
1.I.236.175; 1.I.236.240; 1.I.236.244; 1.I.237.228; 1.I.237.229; 1.I.237.230; 1.I.237.231;
1.I.237.236; 1.I.237.237; 1.I.237.238; 1.I.237.239; 1.I.237.154; 1.I.237.157; 1.I.237.166;
1.I.237.169; 1.I.237.172; 1.I.237.175; 1.I.237.240; 1.I.237.244; 1.I.238.228; 1.I.238.229;
1.I.238.230; 1.I.238.231; 1.I.238.236; 1.I.238.237; 1.I.238.238; 1.I.238.239; 1.I.238.154;
1.I.238.157; 1.I.238.166; 1.I.238.169; 1.I.238.172; 1.I.238.175; 1.I.238.240; 1.I.238.244;
1.I.239.228; 1.I.239.229; 1.I.239.230; 1.I.239.231; 1.I.239.236; 1.I.239.237; 1.I.239.238;
1.I.239.239; 1.I.239.154; 1.I.239.157; 1.I.239.166; 1.I.239.169; 1.I.239.172; 1.I.239.175;
1.I.239.240; 1.I.239.244; 1.I.154.228; 1.I.154.229; 1.I.154.230; 1.I.154.231; 1.I.154.236;
1.I.154.237; 1.I.154.238; 1.I.154.239; 1.I.154.154; 1.I.154.157; 1.I.154.166; 1.I.154.169;
1.I.154.172; 1.I.154.175; 1.I.154.240; 1.I.154.244; 1.I.157.228; 1.I.157.229; 1.I.157.230;
1.I.157.231; 1.I.157.236; 1.I.157.237; 1.I.157.238; 1.I.157.239; 1.I.157.154; 1.I.157.157;
1.I.157.166; 1.I.157.169; 1.I.157.172; 1.I.157.175; 1.I.157.240; 1.I.157.244; 1.I.166.228;
1.I.166.229; 1.I.166.230; 1.I.166.231; 1.I.166.236; 1.I.166.237; 1.I.166.238; 1.I.166.239;
1.I.166.154; 1.I.166.157; 1.I.166.166; 1.I.166.169; 1.I.166.172; 1.I.166.175; 1.I.166.240;
1.I.166.244; 1.I.169.228; 1.I.169.229; 1.I.169.230; 1.I.169.231; 1.I.169.236; 1.I.169.237;
1.I.169.238; 1.I.169.239; 1.I.169.154; 1.I.169.157; 1.I.169.166; 1.I.169.169; 1.I.169.172;
1.I.169.175; 1.I.169.240; 1.I.169.244; 1.I.172.228; 1.I.172.229; 1.I.172.230; 1.I.172.231;
1.I.172.236; 1.I.172.237; 1.I.172.238; 1.I.172.239; 1.I.172.154; 1.I.172.157; 1.I.172.166;
1.I.172.169; 1.I.172.172; 1.I.172.175; 1.I.172.240; 1.I.172.244; 1.I.175.228; 1.I.175.229;
1.I.175.230; 1.I.175.231; 1.I.175.236; 1.I.175.237; 1.I.175.238; 1.I.175.239; 1.I.175.154;
1.I.175.157; 1.I.175.166; 1.I.175.169; 1.I.175.172; 1.I.175.175; 1.I.175.240; 1.I.175.244;
1.I.240.228; 1.I.240.229; 1.I.240.230; 1.I.240.231; 1.I.240.236; 1.I.240.237; 1.I.240.238;
1.I.240.239; 1.I.240.154; 1.I.240.157; 1.I.240.166; 1.I.240.169; 1.I.240.172; 1.I.240.175;
1.I.240.240; 1.I.240.244; 1.I.244.228; 1.I.244.229; 1.I.244.230; 1.I.244.231; 1.I.244.236;
1.I.244.237; 1.I.244.238; 1.I.244.239; 1.I.244.154; 1.I.244.157; 1.I.244.166; 1.I.244.169;
1.I.244.172; 1.I.244.175; 1.I.244.240; 1.I.244.244;

Prodrugs of 1.J

1.J.228.228; 1.J.228.229; 1.J.228.230; 1.J.228.231; 1.J.228.236; 1.J.228.237; 1.J.228.238;
1.J.228.239; 1.J.228.154; 1.J.228.157; 1.J.228.166; 1.J.228.169; 1.J.228.172; 1.J.228.175;
1.J.228.240; 1.J.228.244; 1.J.229.228; 1.J.229.229; 1.J.229.230; 1.J.229.231; 1.J.229.236;
1.J.229.237; 1.J.229.238; 1.J.229.239; 1.J.229.154; 1.J.229.157; 1.J.229.166; 1.J.229.169;
1.J.229.172; 1.J.229.175; 1.J.229.240; 1.J.229.244; 1.J.230.228; 1.J.230.229; 1.J.230.230;
1.J.230.231; 1.J.230.236; 1.J.230.237; 1.J.230.238; 1.J.230.239; 1.J.230.154; 1.J.230.157;
1.J.230.166; 1.J.230.169; 1.J.230.172; 1.J.230.175; 1.J.230.240; 1.J.230.244; 1.J.231.228;
1.J.231.229; 1.J.231.230; 1.J.231.231; 1.J.231.236; 1.J.231.237; 1.J.231.238; 1.J.231.239;
1.J.231.154; 1.J.231.157; 1.J.231.166; 1.J.231.169; 1.J.231.172; 1.J.231.175; 1.J.231.240;
1.J.231.244; 1.J.236.228; 1.J.236.229; 1.J.236.230; 1.J.236.231; 1.J.236.236; 1.J.236.237;
1.J.236.238; 1.J.236.239; 1.J.236.154; 1.J.236.157; 1.J.236.166; 1.J.236.169; 1.J.236.172;
1.J.236.175; 1.J.236.240; 1.J.236.244; 1.J.237.228; 1.J.237.229; 1.J.237.230; 1.J.237.231;
1.J.237.236; 1.J.237.237; 1.J.237.238; 1.J.237.239; 1.J.237.154; 1.J.237.157; 1.J.237.166;
1.J.237.169; 1.J.237.172; 1.J.237.175; 1.J.237.240; 1.J.237.244; 1.J.238.228; 1.J.238.229;
1.J.238.230; 1.J.238.231; 1.J.238.236; 1.J.238.237; 1.J.238.238; 1.J.238.239; 1.J.238.154;
1.J.238.157; 1.J.238.166; 1.J.238.169; 1.J.238.172; 1.J.238.175; 1.J.238.240; 1.J.238.244;
1.J.239.228; 1.J.239.229; 1.J.239.230; 1.J.239.231; 1.J.239.236; 1.J.239.237; 1.J.239.238;
1.J.239.239; 1.J.239.154; 1.J.239.157; 1.J.239.166; 1.J.239.169; 1.J.239.172; 1.J.239.175;
1.J.239.240; 1.J.239.244; 1.J.154.228; 1.J.154.229; 1.J.154.230; 1.J.154.231; 1.J.154.236;
1.J.154.237; 1.J.154.238; 1.J.154.239; 1.J.154.154; 1.J.154.157; 1.J.154.166; 1.J.154.169;
1.J.154.172; 1.J.154.175; 1.J.154.240; 1.J.154.244; 1.J.157.228; 1.J.157.229; 1.J.157.230;
1.J.157.231; 1.J.157.236; 1.J.157.237; 1.J.157.238; 1.J.157.239; 1.J.157.154; 1.J.157.157;
1.J.157.166; 1.J.157.169; 1.J.157.172; 1.J.157.175; 1.J.157.240; 1.J.157.244; 1.J.166.228;
1.J.166.229; 1.J.166.230; 1.J.166.231; 1.J.166.236; 1.J.166.237; 1.J.166.238; 1.J.166.239;
1.J.166.154; 1.J.166.157; 1.J.166.166; 1.J.166.169; 1.J.166.172; 1.J.166.175; 1.J.166.240;
1.J.166.244; 1.J.169.228; 1.J.169.229; 1.J.169.230; 1.J.169.231; 1.J.169.236; 1.J.169.237;
1.J.169.238; 1.J.169.239; 1.J.169.154; 1.J.169.157; 1.J.169.166; 1.J.169.169; 1.J.169.172;
1.J.169.175; 1.J.169.240; 1.J.169.244; 1.J.172.228; 1.J.172.229; 1.J.172.230; 1.J.172.231;
1.J.172.236; 1.J.172.237; 1.J.172.238; 1.J.172.239; 1.J.172.154; 1.J.172.157; 1.J.172.166;
1.J.172.169; 1.J.172.172; 1.J.172.175; 1.J.172.240; 1.J.172.244; 1.J.175.228; 1.J.175.229;
1.J.175.230; 1.J.175.231; 1.J.175.236; 1.J.175.237; 1.J.175.238; 1.J.175.239; 1.J.175.154;
1.J.175.157; 1.J.175.166; 1.J.175.169; 1.J.175.172; 1.J.175.175; 1.J.175.240; 1.J.175.244;
1.J.240.228; 1.J.240.229; 1.J.240.230; 1.J.240.231; 1.J.240.236; 1.J.240.237; 1.J.240.238;
1.J.240.239; 1.J.240.154; 1.J.240.157; 1.J.240.166; 1.J.240.169; 1.J.240.172; 1.J.240.175;
1.J.240.240; 1.J.240.244; 1.J.244.228; 1.J.244.229; 1.J.244.230; 1.J.244.231; 1.J.244.236;
1.J.244.237; 1.J.244.238; 1.J.244.239; 1.J.244.154; 1.J.244.157; 1.J.244.166; 1.J.244.169;
1.J.244.172; 1.J.244.175; 1.J.244.240; 1.J.244.244;

Prodrugs of 1.L

1.L.228.228; 1.L.228.229; 1.L.228.230; 1.L.228.231; 1.L.228.236; 1.L.228.237; 1.L.228.238;
1.L.228.239; 1.L.228.154; 1.L.228.157; 1.L.228.166; 1.L.228.169; 1.L.228.172; 1.L.228.175;
1.L.228.240; 1.L.228.244; 1.L.229.228; 1.L.229.229; 1.L.229.230; 1.L.229.231; 1.L.229.236;
1.L.229.237; 1.L.229.238; 1.L.229.239; 1.L.229.154; 1.L.229.157; 1.L.229.166; 1.L.229.169;
1.L.229.172; 1.L.229.175; 1.L.229.240; 1.L.229.244; 1.L.230.228; 1.L.230.229; 1.L.230.230;
1.L.230.231; 1.L.230.236; 1.L.230.237; 1.L.230.238; 1.L.230.239; 1.L.230.154; 1.L.230.157;
1.L.230.166; 1.L.230.169; 1.L.230.172; 1.L.230.175; 1.L.230.240; 1.L.230.244; 1.L.231.228;

TABLE 100-continued

1.L.231.229; 1.L.231.230; 1.L.231.231; 1.L.231.236; 1.L.231.237; 1.L.231.238; 1.L.231.239; 1.L.231.154; 1.L.231.157; 1.L.231.166; 1.L.231.169; 1.L.231.172; 1.L.231.175; 1.L.231.240; 1.L.231.244; 1.L.236.228; 1.L.236.229; 1.L.236.230; 1.L.236.231; 1.L.236.236; 1.L.236.237; 1.L.236.238; 1.L.236.239; 1.L.236.154; 1.L.236.157; 1.L.236.166; 1.L.236.169; 1.L.236.172; 1.L.236.175; 1.L.236.240; 1.L.236.244; 1.L.237.228; 1.L.237.229; 1.L.237.230; 1.L.237.231; 1.L.237.236; 1.L.237.237; 1.L.237.238; 1.L.237.239; 1.L.237.154; 1.L.237.157; 1.L.237.166; 1.L.237.169; 1.L.237.172; 1.L.237.175; 1.L.237.240; 1.L.237.244; 1.L.238.228; 1.L.238.229; 1.L.238.230; 1.L.238.231; 1.L.238.236; 1.L.238.237; 1.L.238.238; 1.L.238.239; 1.L.238.154; 1.L.238.157; 1.L.238.166; 1.L.238.169; 1.L.238.172; 1.L.238.175; 1.L.238.240; 1.L.238.244; 1.L.239.228; 1.L.239.229; 1.L.239.230; 1.L.239.231; 1.L.239.236; 1.L.239.237; 1.L.239.238; 1.L.239.239; 1.L.239.154; 1.L.239.157; 1.L.239.166; 1.L.239.169; 1.L.239.172; 1.L.239.175; 1.L.239.240; 1.L.239.244; 1.L.154.228; 1.L.154.229; 1.L.154.230; 1.L.154.231; 1.L.154.236; 1.L.154.237; 1.L.154.238; 1.L.154.239; 1.L.154.154; 1.L.154.157; 1.L.154.166; 1.L.154.169; 1.L.154.172; 1.L.154.175; 1.L.154.240; 1.L.154.244; 1.L.157.228; 1.L.157.229; 1.L.157.230; 1.L.157.231; 1.L.157.236; 1.L.157.237; 1.L.157.238; 1.L.157.239; 1.L.157.154; 1.L.157.157; 1.L.157.166; 1.L.157.169; 1.L.157.172; 1.L.157.175; 1.L.157.240; 1.L.157.244; 1.L.166.228; 1.L.166.229; 1.L.166.230; 1.L.166.231; 1.L.166.236; 1.L.166.237; 1.L.166.238; 1.L.166.239; 1.L.166.154; 1.L.166.157; 1.L.166.166; 1.L.166.169; 1.L.166.172; 1.L.166.175; 1.L.166.240; 1.L.166.244; 1.L.169.228; 1.L.169.229; 1.L.169.230; 1.L.169.231; 1.L.169.236; 1.L.169.237; 1.L.169.238; 1.L.169.239; 1.L.169.154; 1.L.169.157; 1.L.169.166; 1.L.169.169; 1.L.169.172; 1.L.169.175; 1.L.169.240; 1.L.169.244; 1.L.172.228; 1.L.172.229; 1.L.172.230; 1.L.172.231; 1.L.172.236; 1.L.172.237; 1.L.172.238; 1.L.172.239; 1.L.172.154; 1.L.172.157; 1.L.172.166; 1.L.172.169; 1.L.172.172; 1.L.172.175; 1.L.172.240; 1.L.172.244; 1.L.175.228; 1.L.175.229; 1.L.175.230; 1.L.175.231; 1.L.175.236; 1.L.175.237; 1.L.175.238; 1.L.175.239; 1.L.175.154; 1.L.175.157; 1.L.175.166; 1.L.175.169; 1.L.175.172; 1.L.175.175; 1.L.175.240; 1.L.175.244; 1.L.240.228; 1.L.240.229; 1.L.240.230; 1.L.240.231; 1.L.240.236; 1.L.240.237; 1.L.240.238; 1.L.240.239; 1.L.240.154; 1.L.240.157; 1.L.240.166; 1.L.240.169; 1.L.240.172; 1.L.240.175; 1.L.240.240; 1.L.240.244; 1.L.244.228; 1.L.244.229; 1.L.244.230; 1.L.244.231; 1.L.244.236; 1.L.244.237; 1.L.244.238; 1.L.244.239; 1.L.244.154; 1.L.244.157; 1.L.244.166; 1.L.244.169; 1.L.244.172; 1.L.244.175; 1.L.244.240; 1.L.244.244;

Prodrugs of 1.O

1.O.228.228; 1.O.228.229; 1.O.228.230; 1.O.228.231; 1.O.228.236; 1.O.228.237; 1.O.228.238; 1.O.228.239; 1.O.228.154; 1.O.228.157; 1.O.228.166; 1.O.228.169; 1.O.228.172; 1.O.228.175; 1.O.228.240; 1.O.228.244; 1.O.229.228; 1.O.229.229; 1.O.229.230; 1.O.229.231; 1.O.229.236; 1.O.229.237; 1.O.229.238; 1.O.229.239; 1.O.229.154; 1.O.229.157; 1.O.229.166; 1.O.229.169; 1.O.229.172; 1.O.229.175; 1.O.229.240; 1.O.229.244; 1.O.230.228; 1.O.230.229; 1.O.230.230; 1.O.230.231; 1.O.230.236; 1.O.230.237; 1.O.230.238; 1.O.230.239; 1.O.230.154; 1.O.230.157; 1.O.230.166; 1.O.230.169; 1.O.230.172; 1.O.230.175; 1.O.230.240; 1.O.230.244; 1.O.231.228; 1.O.231.229; 1.O.231.230; 1.O.231.231; 1.O.231.236; 1.O.231.237; 1.O.231.238; 1.O.231.239; 1.O.231.154; 1.O.231.157; 1.O.231.166; 1.O.231.169; 1.O.231.172; 1.O.231.175; 1.O.231.240; 1.O.231.244; 1.O.236.228; 1.O.236.229; 1.O.236.230; 1.O.236.231; 1.O.236.236; 1.O.236.237; 1.O.236.238; 1.O.236.239; 1.O.236.154; 1.O.236.157; 1.O.236.166; 1.O.236.169; 1.O.236.172; 1.O.236.175; 1.O.236.240; 1.O.236.244; 1.O.237.228; 1.O.237.229; 1.O.237.230; 1.O.237.231; 1.O.237.236; 1.O.237.237; 1.O.237.238; 1.O.237.239; 1.O.237.154; 1.O.237.157; 1.O.237.166; 1.O.237.169; 1.O.237.172; 1.O.237.175; 1.O.237.240; 1.O.237.244; 1.O.238.228; 1.O.238.229; 1.O.238.230; 1.O.238.231; 1.O.238.236; 1.O.238.237; 1.O.238.238; 1.O.238.239; 1.O.238.154; 1.O.238.157; 1.O.238.166; 1.O.238.169; 1.O.238.172; 1.O.238.175; 1.O.238.240; 1.O.238.244; 1.O.239.228; 1.O.239.229; 1.O.239.230; 1.O.239.231; 1.O.239.236; 1.O.239.237; 1.O.239.238; 1.O.239.239; 1.O.239.154; 1.O.239.157; 1.O.239.166; 1.O.239.169; 1.O.239.172; 1.O.239.175; 1.O.239.240; 1.O.239.244; 1.O.154.228; 1.O.154.229; 1.O.154.230; 1.O.154.231; 1.O.154.236; 1.O.154.237; 1.O.154.238; 1.O.154.239; 1.O.154.154; 1.O.154.157; 1.O.154.166; 1.O.154.169; 1.O.154.172; 1.O.154.175; 1.O.154.240; 1.O.154.244; 1.O.157.228; 1.O.157.229; 1.O.157.230; 1.O.157.231; 1.O.157.236; 1.O.157.237; 1.O.157.238; 1.O.157.239; 1.O.157.154; 1.O.157.157; 1.O.157.166; 1.O.157.169; 1.O.157.172; 1.O.157.175; 1.O.157.240; 1.O.157.244; 1.O.166.228; 1.O.166.229; 1.O.166.230; 1.O.166.231; 1.O.166.236; 1.O.166.237; 1.O.166.238; 1.O.166.239; 1.O.166.154; 1.O.166.157; 1.O.166.166; 1.O.166.169; 1.O.166.172; 1.O.166.175; 1.O.166.240; 1.O.166.244; 1.O.169.228; 1.O.169.229; 1.O.169.230; 1.O.169.231; 1.O.169.236; 1.O.169.237; 1.O.169.238; 1.O.169.239; 1.O.169.154; 1.O.169.157; 1.O.169.166; 1.O.169.169; 1.O.169.172; 1.O.169.175; 1.O.169.240; 1.O.169.244; 1.O.172.228; 1.O.172.229; 1.O.172.230; 1.O.172.231; 1.O.172.236; 1.O.172.237; 1.O.172.238; 1.O.172.239; 1.O.172.154; 1.O.172.157; 1.O.172.166; 1.O.172.169; 1.O.172.172; 1.O.172.175; 1.O.172.240; 1.O.172.244; 1.O.175.228; 1.O.175.229; 1.O.175.230; 1.O.175.231; 1.O.175.236; 1.O.175.237; 1.O.175.238; 1.O.175.239; 1.O.175.154; 1.O.175.157; 1.O.175.166; 1.O.175.169; 1.O.175.172; 1.O.175.175; 1.O.175.240; 1.O.175.244; 1.O.240.228; 1.O.240.229; 1.O.240.230; 1.O.240.231; 1.O.240.236; 1.O.240.237; 1.O.240.238; 1.O.240.239; 1.O.240.154; 1.O.240.157; 1.O.240.166; 1.O.240.169; 1.O.240.172; 1.O.240.175; 1.O.240.240; 1.O.240.244; 1.O.244.228; 1.O.244.229; 1.O.244.230; 1.O.244.231; 1.O.244.236; 1.O.244.237; 1.O.244.238; 1.O.244.239; 1.O.244.154; 1.O.244.157; 1.O.244.166; 1.O.244.169; 1.O.244.172; 1.O.244.175; 1.O.244.240; 1.O.244.244;

Prodrugs of 1.P

1.P.228.228; 1.P.228.229; 1.P.228.230; 1.P.228.231; 1.P.228.236; 1.P.228.237; 1.P.228.238; 1.P.228.239; 1.P.228.154; 1.P.228.157; 1.P.228.166; 1.P.228.169; 1.P.228.172; 1.P.228.175; 1.P.228.240; 1.P.228.244; 1.P.229.228; 1.P.229.229; 1.P.229.230; 1.P.229.231; 1.P.229.236; 1.P.229.237; 1.P.229.238; 1.P.229.239; 1.P.229.154; 1.P.229.157; 1.P.229.166; 1.P.229.169; 1.P.229.172; 1.P.229.175; 1.P.229.240; 1.P.229.244; 1.P.230.228; 1.P.230.229; 1.P.230.230; 1.P.230.231; 1.P.230.236; 1.P.230.237; 1.P.230.238; 1.P.230.239; 1.P.230.154; 1.P.230.157; 1.P.230.166; 1.P.230.169; 1.P.230.172; 1.P.230.175; 1.P.230.240; 1.P.230.244; 1.P.231.228; 1.P.231.229; 1.P.231.230; 1.P.231.231; 1.P.231.236; 1.P.231.237; 1.P.231.238; 1.P.231.239;

TABLE 100-continued

1.P.231.154; 1.P.231.157; 1.P.231.166; 1.P.231.169; 1.P.231.172; 1.P.231.175; 1.P.231.240;
1.P.231.244; 1.P.236.228; 1.P.236.229; 1.P.236.230; 1.P.236.231; 1.P.236.236; 1.P.236.237;
1.P.236.238; 1.P.236.239; 1.P.236.154; 1.P.236.157; 1.P.236.166; 1.P.236.169; 1.P.236.172;
1.P.236.175; 1.P.236.240; 1.P.236.244; 1.P.237.228; 1.P.237.229; 1.P.237.230; 1.P.237.231;
1.P.237.236; 1.P.237.237; 1.P.237.238; 1.P.237.239; 1.P.237.154; 1.P.237.157; 1.P.237.166;
1.P.237.169; 1.P.237.172; 1.P.237.175; 1.P.237.240; 1.P.237.244; 1.P.238.228; 1.P.238.229;
1.P.238.230; 1.P.238.231; 1.P.238.236; 1.P.238.237; 1.P.238.238; 1.P.238.239; 1.P.238.154;
1.P.238.157; 1.P.238.166; 1.P.238.169; 1.P.238.172; 1.P.238.175; 1.P.238.240; 1.P.238.244;
1.P.239.228; 1.P.239.229; 1.P.239.230; 1.P.239.231; 1.P.239.236; 1.P.239.237; 1.P.239.238;
1.P.239.239; 1.P.239.154; 1.P.239.157; 1.P.239.166; 1.P.239.169; 1.P.239.172; 1.P.239.175;
1.P.239.240; 1.P.239.244; 1.P.154.228; 1.P.154.229; 1.P.154.230; 1.P.154.231; 1.P.154.236;
1.P.154.237; 1.P.154.238; 1.P.154.239; 1.P.154.154; 1.P.154.157; 1.P.154.166; 1.P.154.169;
1.P.154.172; 1.P.154.175; 1.P.154.240; 1.P.154.244; 1.P.157.228; 1.P.157.229; 1.P.157.230;
1.P.157.231; 1.P.157.236; 1.P.157.237; 1.P.157.238; 1.P.157.239; 1.P.157.154; 1.P.157.157;
1.P.157.166; 1.P.157.169; 1.P.157.172; 1.P.157.175; 1.P.157.240; 1.P.157.244; 1.P.166.228;
1.P.166.229; 1.P.166.230; 1.P.166.231; 1.P.166.236; 1.P.166.237; 1.P.166.238; 1.P.166.239;
1.P.166.154; 1.P.166.157; 1.P.166.166; 1.P.166.169; 1.P.166.172; 1.P.166.175; 1.P.166.240;
1.P.166.244; 1.P.169.228; 1.P.169.229; 1.P.169.230; 1.P.169.231; 1.P.169.236; 1.P.169.237;
1.P.169.238; 1.P.169.239; 1.P.169.154; 1.P.169.157; 1.P.169.166; 1.P.169.169; 1.P.169.172;
1.P.169.175; 1.P.169.240; 1.P.169.244; 1.P.172.228; 1.P.172.229; 1.P.172.230; 1.P.172.231;
1.P.172.236; 1.P.172.237; 1.P.172.238; 1.P.172.239; 1.P.172.154; 1.P.172.157; 1.P.172.166;
1.P.172.169; 1.P.172.172; 1.P.172.175; 1.P.172.240; 1.P.172.244; 1.P.175.228; 1.P.175.229;
1.P.175.230; 1.P.175.231; 1.P.175.236; 1.P.175.237; 1.P.175.238; 1.P.175.239; 1.P.175.154;
1.P.175.157; 1.P.175.166; 1.P.175.169; 1.P.175.172; 1.P.175.175; 1.P.175.240; 1.P.175.244;
1.P.240.228; 1.P.240.229; 1.P.240.230; 1.P.240.231; 1.P.240.236; 1.P.240.237; 1.P.240.238;
1.P.240.239; 1.P.240.154; 1.P.240.157; 1.P.240.166; 1.P.240.169; 1.P.240.172; 1.P.240.175;
1.P.240.240; 1.P.240.244; 1.P.244.228; 1.P.244.229; 1.P.244.230; 1.P.244.231; 1.P.244.236;
1.P.244.237; 1.P.244.238; 1.P.244.239; 1.P.244.154; 1.P.244.157; 1.P.244.166; 1.P.244.169;
1.P.244.172; 1.P.244.175; 1.P.244.240; 1.P.244.244;
Prodrugs of 1.U 1.U.228.228; 1.U.228.229; 1.U.228.230; 1.U.228.231; 1.U.228.236; 1.U.228.237;
1.U.228.238; 1.U.228.239; 1.U.228.154; 1.U.228.157; 1.U.228.166; 1.U.228.169; 1.U.228.172;
1.U.228.175; 1.U.228.240; 1.U.228.244; 1.U.229.228; 1.U.229.229; 1.U.229.230; 1.U.229.231;
1.U.229.236; 1.U.229.237; 1.U.229.238; 1.U.229.239; 1.U.229.154; 1.U.229.157; 1.U.229.166;
1.U.229.169; 1.U.229.172; 1.U.229.175; 1.U.229.240; 1.U.229.244; 1.U.230.228; 1.U.230.229;
1.U.230.230; 1.U.230.231; 1.U.230.236; 1.U.230.237; 1.U.230.238; 1.U.230.239; 1.U.230.154;
1.U.230.157; 1.U.230.166; 1.U.230.169; 1.U.230.172; 1.U.230.175; 1.U.230.240; 1.U.230.244;
1.U.231.228; 1.U.231.229; 1.U.231.230; 1.U.231.231; 1.U.231.236; 1.U.231.237; 1.U.231.238;
1.U.231.239; 1.U.231.154; 1.U.231.157; 1.U.231.166; 1.U.231.169; 1.U.231.172; 1.U.231.175;
1.U.231.240; 1.U.231.244; 1.U.236.228; 1.U.236.229; 1.U.236.230; 1.U.236.231; 1.U.236.236;
1.U.236.237; 1.U.236.238; 1.U.236.239; 1.U.236.154; 1.U.236.157; 1.U.236.166; 1.U.236.169;
1.U.236.172; 1.U.236.175; 1.U.236.240; 1.U.236.244; 1.U.237.228; 1.U.237.229; 1.U.237.230;
1.U.237.231; 1.U.237.236; 1.U.237.237; 1.U.237.238; 1.U.237.239; 1.U.237.154; 1.U.237.157;
1.U.237.166; 1.U.237.169; 1.U.237.172; 1.U.237.175; 1.U.237.240; 1.U.237.244; 1.U.238.228;
1.U.238.229; 1.U.238.230; 1.U.238.231; 1.U.238.236; 1.U.238.237; 1.U.238.238; 1.U.238.239;
1.U.238.154; 1.U.238.157; 1.U.238.166; 1.U.238.169; 1.U.238.172; 1.U.238.175; 1.U.238.240;
1.U.238.244; 1.U.239.228; 1.U.239.229; 1.U.239.230; 1.U.239.231; 1.U.239.236; 1.U.239.237;
1.U.239.238; 1.U.239.239; 1.U.239.154; 1.U.239.157; 1.U.239.166; 1.U.239.169; 1.U.239.172;
1.U.239.175; 1.U.239.240; 1.U.239.244; 1.U.154.228; 1.U.154.229; 1.U.154.230; 1.U.154.231;
1.U.154.236; 1.U.154.237; 1.U.154.238; 1.U.154.239; 1.U.154.154; 1.U.154.157; 1.U.154.166;
1.U.154.169; 1.U.154.172; 1.U.154.175; 1.U.154.240; 1.U.154.244; 1.U.157.228; 1.U.157.229;
1.U.157.230; 1.U.157.231; 1.U.157.236; 1.U.157.237; 1.U.157.238; 1.U.157.239; 1.U.157.154;
1.U.157.157; 1.U.157.166; 1.U.157.169; 1.U.157.172; 1.U.157.175; 1.U.157.240; 1.U.157.244;
1.U.166.228; 1.U.166.229; 1.U.166.230; 1.U.166.231; 1.U.166.236; 1.U.166.237; 1.U.166.238;
1.U.166.239; 1.U.166.154; 1.U.166.157; 1.U.166.166; 1.U.166.169; 1.U.166.172; 1.U.166.175;
1.U.166.240; 1.U.166.244; 1.U.169.228; 1.U.169.229; 1.U.169.230; 1.U.169.231; 1.U.169.236;
1.U.169.237; 1.U.169.238; 1.U.169.239; 1.U.169.154; 1.U.169.157; 1.U.169.166; 1.U.169.169;
1.U.169.172; 1.U.169.175; 1.U.169.240; 1.U.169.244; 1.U.172.228; 1.U.172.229; 1.U.172.230;
1.U.172.231; 1.U.172.236; 1.U.172.237; 1.U.172.238; 1.U.172.239; 1.U.172.154; 1.U.172.157;
1.U.172.166; 1.U.172.169; 1.U.172.172; 1.U.172.175; 1.U.172.240; 1.U.172.244; 1.U.175.228;
1.U.175.229; 1.U.175.230; 1.U.175.231; 1.U.175.236; 1.U.175.237; 1.U.175.238; 1.U.175.239;
1.U.175.154; 1.U.175.157; 1.U.175.166; 1.U.175.169; 1.U.175.172; 1.U.175.175; 1.U.175.240;
1.U.175.244; 1.U.240.228; 1.U.240.229; 1.U.240.230; 1.U.240.231; 1.U.240.236; 1.U.240.237;
1.U.240.238; 1.U.240.239; 1.U.240.154; 1.U.240.157; 1.U.240.166; 1.U.240.169; 1.U.240.172;
1.U.240.175; 1.U.240.240; 1.U.240.244; 1.U.244.228; 1.U.244.229; 1.U.244.230; 1.U.244.231;
1.U.244.236; 1.U.244.237; 1.U.244.238; 1.U.244.239; 1.U.244.154; 1.U.244.157; 1.U.244.166;
1.U.244.169; 1.U.244.172; 1.U.244.175; 1.U.244.240; 1.U.244.244;
Prodrugs of 1.W 1.W.228.228; 1.W.228.229; 1.W.228.230; 1.W.228.231; 1.W.228.236; 1.W.228.237;
1.W.228.238; 1.W.228.239; 1.W.228.154; 1.W.228.157; 1.W.228.166; 1.W.228.169;
1.W.228.172; 1.W.228.175; 1.W.228.240; 1.W.228.244; 1.W.229.228; 1.W.229.229;
1.W.229.230; 1.W.229.231; 1.W.229.236; 1.W.229.237; 1.W.229.238; 1.W.229.239;
1.W.229.154; 1.W.229.157; 1.W.229.166; 1.W.229.169; 1.W.229.172; 1.W.229.175;
1.W.229.240; 1.W.229.244; 1.W.230.228; 1.W.230.229; 1.W.230.230; 1.W.230.231;
1.W.230.236; 1.W.230.237; 1.W.230.238; 1.W.230.239; 1.W.230.154; 1.W.230.157;
1.W.230.166; 1.W.230.169; 1.W.230.172; 1.W.230.175; 1.W.230.240; 1.W.230.244;
1.W.231.228; 1.W.231.229; 1.W.231.230; 1.W.231.231; 1.W.231.236; 1.W.231.237;

TABLE 100-continued

1.W.231.238; 1.W.231.239; 1.W.231.154; 1.W.231.157; 1.W.231.166; 1.W.231.169;
1.W.231.172; 1.W.231.175; 1.W.231.240; 1.W.231.244; 1.W.236.228; 1.W.236.229;
1.W.236.230; 1.W.236.231; 1.W.236.236; 1.W.236.237; 1.W.236.238; 1.W.236.239;
1.W.236.154; 1.W.236.157; 1.W.236.166; 1.W.236.169; 1.W.236.172; 1.W.236.175;
1.W.236.240; 1.W.236.244; 1.W.237.228; 1.W.237.229; 1.W.237.230; 1.W.237.231;
1.W.237.236; 1.W.237.237; 1.W.237.238; 1.W.237.239; 1.W.237.154; 1.W.237.157;
1.W.237.166; 1.W.237.169; 1.W.237.172; 1.W.237.175; 1.W.237.240; 1.W.237.244;
1.W.238.228; 1.W.238.229; 1.W.238.230; 1.W.238.231; 1.W.238.236; 1.W.238.237;
1.W.238.238; 1.W.238.239; 1.W.238.154; 1.W.238.157; 1.W.238.166; 1.W.238.169;
1.W.238.172; 1.W.238.175; 1.W.238.240; 1.W.238.244; 1.W.239.228; 1.W.239.229;
1.W.239.230; 1.W.239.231; 1.W.239.236; 1.W.239.237; 1.W.239.238; 1.W.239.239;
1.W.239.154; 1.W.239.157; 1.W.239.166; 1.W.239.169; 1.W.239.172; 1.W.239.175;
1.W.239.240; 1.W.239.244; 1.W.154.228; 1.W.154.229; 1.W.154.230; 1.W.154.231;
1.W.154.236; 1.W.154.237; 1.W.154.238; 1.W.154.239; 1.W.154.154; 1.W.154.157;
1.W.154.166; 1.W.154.169; 1.W.154.172; 1.W.154.175; 1.W.154.240; 1.W.154.244;
1.W.157.228; 1.W.157.229; 1.W.157.230; 1.W.157.231; 1.W.157.236; 1.W.157.237;
1.W.157.238; 1.W.157.239; 1.W.157.154; 1.W.157.157; 1.W.157.166; 1.W.157.169;
1.W.157.172; 1.W.157.175; 1.W.157.240; 1.W.157.244; 1.W.166.228; 1.W.166.229;
1.W.166.230; 1.W.166.231; 1.W.166.236; 1.W.166.237; 1.W.166.238; 1.W.166.239;
1.W.166.154; 1.W.166.157; 1.W.166.166; 1.W.166.169; 1.W.166.172; 1.W.166.175;
1.W.166.240; 1.W.166.244; 1.W.169.228; 1.W.169.229; 1.W.169.230; 1.W.169.231;
1.W.169.236; 1.W.169.237; 1.W.169.238; 1.W.169.239; 1.W.169.154; 1.W.169.157;
1.W.169.166; 1.W.169.169; 1.W.169.172; 1.W.169.175; 1.W.169.240; 1.W.169.244;
1.W.172.228; 1.W.172.229; 1.W.172.230; 1.W.172.231; 1.W.172.236; 1.W.172.237;
1.W.172.238; 1.W.172.239; 1.W.172.154; 1.W.172.157; 1.W.172.166; 1.W.172.169;
1.W.172.172; 1.W.172.175; 1.W.172.240; 1.W.172.244; 1.W.175.228; 1.W.175.229;
1.W.175.230; 1.W.175.231; 1.W.175.236; 1.W.175.237; 1.W.175.238; 1.W.175.239;
1.W.175.154; 1.W.175.157; 1.W.175.166; 1.W.175.169; 1.W.175.172; 1.W.175.175;
1.W.175.240; 1.W.175.244; 1.W.240.228; 1.W.240.229; 1.W.240.230; 1.W.240.231;
1.W.240.236; 1.W.240.237; 1.W.240.238; 1.W.240.239; 1.W.240.154; 1.W.240.157;
1.W.240.166; 1.W.240.169; 1.W.240.172; 1.W.240.175; 1.W.240.240; 1.W.240.244;
1.W.244.228; 1.W.244.229; 1.W.244.230; 1.W.244.231; 1.W.244.236; 1.W.244.237;
1.W.244.238; 1.W.244.239; 1.W.244.154; 1.W.244.157; 1.W.244.166; 1.W.244.169;
1.W.244.172; 1.W.244.175; 1.W.244.240; 1.W.244.244;
Prodrugs of 1.Y 1.Y.228.228; 1.Y.228.229; 1.Y.228.230; 1.Y.228.231; 1.Y.228.236; 1.Y.228.237; 1.Y.228.238;
1.Y.228.239; 1.Y.228.154; 1.Y.228.157; 1.Y.228.166; 1.Y.228.169; 1.Y.228.172; 1.Y.228.175;
1.Y.228.240; 1.Y.228.244; 1.Y.229.228; 1.Y.229.229; 1.Y.229.230; 1.Y.229.231; 1.Y.229.236;
1.Y.229.237; 1.Y.229.238; 1.Y.229.239; 1.Y.229.154; 1.Y.229.157; 1.Y.229.166; 1.Y.229.169;
1.Y.229.172; 1.Y.229.175; 1.Y.229.240; 1.Y.229.244; 1.Y.230.228; 1.Y.230.229; 1.Y.230.230;
1.Y.230.231; 1.Y.230.236; 1.Y.230.237; 1.Y.230.238; 1.Y.230.239; 1.Y.230.154; 1.Y.230.157;
1.Y.230.166; 1.Y.230.169; 1.Y.230.172; 1.Y.230.175; 1.Y.230.240; 1.Y.230.244; 1.Y.231.228;
1.Y.231.229; 1.Y.231.230; 1.Y.231.231; 1.Y.231.236; 1.Y.231.237; 1.Y.231.238; 1.Y.231.239;
1.Y.231.154; 1.Y.231.157; 1.Y.231.166; 1.Y.231.169; 1.Y.231.172; 1.Y.231.175; 1.Y.231.240;
1.Y.231.244; 1.Y.236.228; 1.Y.236.229; 1.Y.236.230; 1.Y.236.231; 1.Y.236.236; 1.Y.236.237;
1.Y.236.238; 1.Y.236.239; 1.Y.236.154; 1.Y.236.157; 1.Y.236.166; 1.Y.236.169; 1.Y.236.172;
1.Y.236.175; 1.Y.236.240; 1.Y.236.244; 1.Y.237.228; 1.Y.237.229; 1.Y.237.230; 1.Y.237.231;
1.Y.237.236; 1.Y.237.237; 1.Y.237.238; 1.Y.237.239; 1.Y.237.154; 1.Y.237.157; 1.Y.237.166;
1.Y.237.169; 1.Y.237.172; 1.Y.237.175; 1.Y.237.240; 1.Y.237.244; 1.Y.238.228; 1.Y.238.229;
1.Y.238.230; 1.Y.238.231; 1.Y.238.236; 1.Y.238.237; 1.Y.238.238; 1.Y.238.239; 1.Y.238.154;
1.Y.238.157; 1.Y.238.166; 1.Y.238.169; 1.Y.238.172; 1.Y.238.175; 1.Y.238.240; 1.Y.238.244;
1.Y.239.228; 1.Y.239.229; 1.Y.239.230; 1.Y.239.231; 1.Y.239.236; 1.Y.239.237; 1.Y.239.238;
1.Y.239.239; 1.Y.239.154; 1.Y.239.157; 1.Y.239.166; 1.Y.239.169; 1.Y.239.172; 1.Y.239.175;
1.Y.239.240; 1.Y.239.244; 1.Y.154.228; 1.Y.154.229; 1.Y.154.230; 1.Y.154.231; 1.Y.154.236;
1.Y.154.237; 1.Y.154.238; 1.Y.154.239; 1.Y.154.154; 1.Y.154.157; 1.Y.154.166; 1.Y.154.169;
1.Y.154.172; 1.Y.154.175; 1.Y.154.240; 1.Y.154.244; 1.Y.157.228; 1.Y.157.229; 1.Y.157.230;
1.Y.157.231; 1.Y.157.236; 1.Y.157.237; 1.Y.157.238; 1.Y.157.239; 1.Y.157.154; 1.Y.157.157;
1.Y.157.166; 1.Y.157.169; 1.Y.157.172; 1.Y.157.175; 1.Y.157.240; 1.Y.157.244; 1.Y.166.228;
1.Y.166.229; 1.Y.166.230; 1.Y.166.231; 1.Y.166.236; 1.Y.166.237; 1.Y.166.238; 1.Y.166.239;
1.Y.166.154; 1.Y.166.157; 1.Y.166.166; 1.Y.166.169; 1.Y.166.172; 1.Y.166.175; 1.Y.166.240;
1.Y.166.244; 1.Y.169.228; 1.Y.169.229; 1.Y.169.230; 1.Y.169.231; 1.Y.169.236; 1.Y.169.237;
1.Y.169.238; 1.Y.169.239; 1.Y.169.154; 1.Y.169.157; 1.Y.169.166; 1.Y.169.169; 1.Y.169.172;
1.Y.169.175; 1.Y.169.240; 1.Y.169.244; 1.Y.172.228; 1.Y.172.229; 1.Y.172.230; 1.Y.172.231;
1.Y.172.236; 1.Y.172.237; 1.Y.172.238; 1.Y.172.239; 1.Y.172.154; 1.Y.172.157; 1.Y.172.166;
1.Y.172.169; 1.Y.172.172; 1.Y.172.175; 1.Y.172.240; 1.Y.172.244; 1.Y.175.228; 1.Y.175.229;
1.Y.175.230; 1.Y.175.231; 1.Y.175.236; 1.Y.175.237; 1.Y.175.238; 1.Y.175.239; 1.Y.175.154;
1.Y.175.157; 1.Y.175.166; 1.Y.175.169; 1.Y.175.172; 1.Y.175.175; 1.Y.175.240; 1.Y.175.244;
1.Y.240.228; 1.Y.240.229; 1.Y.240.230; 1.Y.240.231; 1.Y.240.236; 1.Y.240.237; 1.Y.240.238;
1.Y.240.239; 1.Y.240.154; 1.Y.240.157; 1.Y.240.166; 1.Y.240.169; 1.Y.240.172; 1.Y.240.175;
1.Y.240.240; 1.Y.240.244; 1.Y.244.228; 1.Y.244.229; 1.Y.244.230; 1.Y.244.231; 1.Y.244.236;
1.Y.244.237; 1.Y.244.238; 1.Y.244.239; 1.Y.244.154; 1.Y.244.157; 1.Y.244.166; 1.Y.244.169;
1.Y.244.172; 1.Y.244.175; 1.Y.244.240; 1.Y.244.244;
Prodrugs of 2.B 2.B.228.228; 2.B.228.229; 2.B.228.230; 2.B.228.231; 2.B.228.236; 2.B.228.237; 2.B.228.238;
2.B.228.239; 2.B.228.154; 2.B.228.157; 2.B.228.166; 2.B.228.169; 2.B.228.172; 2.B.228.175;
2.B.228.240; 2.B.228.244; 2.B.229.228; 2.B.229.229; 2.B.229.230; 2.B.229.231; 2.B.229.236;
2.B.229.237; 2.B.229.238; 2.B.229.239; 2.B.229.154; 2.B.229.157; 2.B.229.166; 2.B.229.169;

TABLE 100-continued

2.B.229.172; 2.B.229.175; 2.B.229.240; 2.B.229.244; 2.B.230.228; 2.B.230.229; 2.B.230.230; 2.B.230.231; 2.B.230.236; 2.B.230.237; 2.B.230.238; 2.B.230.239; 2.B.230.154; 2.B.230.157; 2.B.230.166; 2.B.230.169; 2.B.230.172; 2.B.230.175; 2.B.230.240; 2.B.230.244; 2.B.231.228; 2.B.231.229; 2.B.231.230; 2.B.231.231; 2.B.231.236; 2.B.231.237; 2.B.231.238; 2.B.231.239; 2.B.231.154; 2.B.231.157; 2.B.231.166; 2.B.231.169; 2.B.231.172; 2.B.231.175; 2.B.231.240; 2.B.231.244; 2.B.236.228; 2.B.236.229; 2.B.236.230; 2.B.236.231; 2.B.236.236; 2.B.236.237; 2.B.236.238; 2.B.236.239; 2.B.236.154; 2.B.236.157; 2.B.236.166; 2.B.236.169; 2.B.236.172; 2.B.236.175; 2.B.236.240; 2.B.236.244; 2.B.237.228; 2.B.237.229; 2.B.237.230; 2.B.237.231; 2.B.237.236; 2.B.237.237; 2.B.237.238; 2.B.237.239; 2.B.237.154; 2.B.237.157; 2.B.237.166; 2.B.237.169; 2.B.237.172; 2.B.237.175; 2.B.237.240; 2.B.237.244; 2.B.238.228; 2.B.238.229; 2.B.238.230; 2.B.238.231; 2.B.238.236; 2.B.238.237; 2.B.238.238; 2.B.238.239; 2.B.238.154; 2.B.238.157; 2.B.238.166; 2.B.238.169; 2.B.238.172; 2.B.238.175; 2.B.238.240; 2.B.238.244; 2.B.239.228; 2.B.239.229; 2.B.239.230; 2.B.239.231; 2.B.239.236; 2.B.239.237; 2.B.239.238; 2.B.239.239; 2.B.239.154; 2.B.239.157; 2.B.239.166; 2.B.239.169; 2.B.239.172; 2.B.239.175; 2.B.239.240; 2.B.239.244; 2.B.154.228; 2.B.154.229; 2.B.154.230; 2.B.154.231; 2.B.154.236; 2.B.154.237; 2.B.154.238; 2.B.154.239; 2.B.154.154; 2.B.154.157; 2.B.154.166; 2.B.154.169; 2.B.154.172; 2.B.154.175; 2.B.154.240; 2.B.154.244; 2.B.157.228; 2.B.157.229; 2.B.157.230; 2.B.157.231; 2.B.157.236; 2.B.157.237; 2.B.157.238; 2.B.157.239; 2.B.157.154; 2.B.157.157; 2.B.157.166; 2.B.157.169; 2.B.157.172; 2.B.157.175; 2.B.157.240; 2.B.157.244; 2.B.166.228; 2.B.166.229; 2.B.166.230; 2.B.166.231; 2.B.166.236; 2.B.166.237; 2.B.166.238; 2.B.166.239; 2.B.166.154; 2.B.166.157; 2.B.166.166; 2.B.166.169; 2.B.166.172; 2.B.166.175; 2.B.166.240; 2.B.166.244; 2.B.169.228; 2.B.169.229; 2.B.169.230; 2.B.169.231; 2.B.169.236; 2.B.169.237; 2.B.169.238; 2.B.169.239; 2.B.169.154; 2.B.169.157; 2.B.169.166; 2.B.169.169; 2.B.169.172; 2.B.169.175; 2.B.169.240; 2.B.169.244; 2.B.172.228; 2.B.172.229; 2.B.172.230; 2.B.172.231; 2.B.172.236; 2.B.172.237; 2.B.172.238; 2.B.172.239; 2.B.172.154; 2.B.172.157; 2.B.172.166; 2.B.172.169; 2.B.172.172; 2.B.172.175; 2.B.172.240; 2.B.172.244; 2.B.175.228; 2.B.175.229; 2.B.175.230; 2.B.175.231; 2.B.175.236; 2.B.175.237; 2.B.175.238; 2.B.175.239; 2.B.175.154; 2.B.175.157; 2.B.175.166; 2.B.175.169; 2.B.175.172; 2.B.175.175; 2.B.175.240; 2.B.175.244; 2.B.240.228; 2.B.240.229; 2.B.240.230; 2.B.240.231; 2.B.240.236; 2.B.240.237; 2.B.240.238; 2.B.240.239; 2.B.240.154; 2.B.240.157; 2.B.240.166; 2.B.240.169; 2.B.240.172; 2.B.240.175; 2.B.240.240; 2.B.240.244; 2.B.244.228; 2.B.244.229; 2.B.244.230; 2.B.244.231; 2.B.244.236; 2.B.244.237; 2.B.244.238; 2.B.244.239; 2.B.244.154; 2.B.244.157; 2.B.244.166; 2.B.244.169; 2.B.244.172; 2.B.244.175; 2.B.244.240; 2.B.244.244;

Prodrugs of 2.D

2.D.228.228; 2.D.228.229; 2.D.228.230; 2.D.228.231; 2.D.228.236; 2.D.228.237; 2.D.228.238; 2.D.228.239; 2.D.228.154; 2.D.228.157; 2.D.228.166; 2.D.228.169; 2.D.228.172; 2.D.228.175; 2.D.228.240; 2.D.228.244; 2.D.229.228; 2.D.229.229; 2.D.229.230; 2.D.229.231; 2.D.229.236; 2.D.229.237; 2.D.229.238; 2.D.229.239; 2.D.229.154; 2.D.229.157; 2.D.229.166; 2.D.229.169; 2.D.229.172; 2.D.229.175; 2.D.229.240; 2.D.229.244; 2.D.230.228; 2.D.230.229; 2.D.230.230; 2.D.230.231; 2.D.230.236; 2.D.230.237; 2.D.230.238; 2.D.230.239; 2.D.230.154; 2.D.230.157; 2.D.230.166; 2.D.230.169; 2.D.230.172; 2.D.230.175; 2.D.230.240; 2.D.230.244; 2.D.231.228; 2.D.231.229; 2.D.231.230; 2.D.231.231; 2.D.231.236; 2.D.231.237; 2.D.231.238; 2.D.231.239; 2.D.231.154; 2.D.231.157; 2.D.231.166; 2.D.231.169; 2.D.231.172; 2.D.231.175; 2.D.231.240; 2.D.231.244; 2.D.236.228; 2.D.236.229; 2.D.236.230; 2.D.236.231; 2.D.236.236; 2.D.236.237; 2.D.236.238; 2.D.236.239; 2.D.236.154; 2.D.236.157; 2.D.236.166; 2.D.236.169; 2.D.236.172; 2.D.236.175; 2.D.236.240; 2.D.236.244; 2.D.237.228; 2.D.237.229; 2.D.237.230; 2.D.237.231; 2.D.237.236; 2.D.237.237; 2.D.237.238; 2.D.237.239; 2.D.237.154; 2.D.237.157; 2.D.237.166; 2.D.237.169; 2.D.237.172; 2.D.237.175; 2.D.237.240; 2.D.237.244; 2.D.238.228; 2.D.238.229; 2.D.238.230; 2.D.238.231; 2.D.238.236; 2.D.238.237; 2.D.238.238; 2.D.238.239; 2.D.238.154; 2.D.238.157; 2.D.238.166; 2.D.238.169; 2.D.238.172; 2.D.238.175; 2.D.238.240; 2.D.238.244; 2.D.239.228; 2.D.239.229; 2.D.239.230; 2.D.239.231; 2.D.239.236; 2.D.239.237; 2.D.239.238; 2.D.239.239; 2.D.239.154; 2.D.239.157; 2.D.239.166; 2.D.239.169; 2.D.239.172; 2.D.239.175; 2.D.239.240; 2.D.239.244; 2.D.154.228; 2.D.154.229; 2.D.154.230; 2.D.154.231; 2.D.154.236; 2.D.154.237; 2.D.154.238; 2.D.154.239; 2.D.154.154; 2.D.154.157; 2.D.154.166; 2.D.154.169; 2.D.154.172; 2.D.154.175; 2.D.154.240; 2.D.154.244; 2.D.157.228; 2.D.157.229; 2.D.157.230; 2.D.157.231; 2.D.157.236; 2.D.157.237; 2.D.157.238; 2.D.157.239; 2.D.157.154; 2.D.157.157; 2.D.157.166; 2.D.157.169; 2.D.157.172; 2.D.157.175; 2.D.157.240; 2.D.157.244; 2.D.166.228; 2.D.166.229; 2.D.166.230; 2.D.166.231; 2.D.166.236; 2.D.166.237; 2.D.166.238; 2.D.166.239; 2.D.166.154; 2.D.166.157; 2.D.166.166; 2.D.166.169; 2.D.166.172; 2.D.166.175; 2.D.166.240; 2.D.166.244; 2.D.169.228; 2.D.169.229; 2.D.169.230; 2.D.169.231; 2.D.169.236; 2.D.169.237; 2.D.169.238; 2.D.169.239; 2.D.169.154; 2.D.169.157; 2.D.169.166; 2.D.169.169; 2.D.169.172; 2.D.169.175; 2.D.169.240; 2.D.169.244; 2.D.172.228; 2.D.172.229; 2.D.172.230; 2.D.172.231; 2.D.172.236; 2.D.172.237; 2.D.172.238; 2.D.172.239; 2.D.172.154; 2.D.172.157; 2.D.172.166; 2.D.172.169; 2.D.172.172; 2.D.172.175; 2.D.172.240; 2.D.172.244; 2.D.175.228; 2.D.175.229; 2.D.175.230; 2.D.175.231; 2.D.175.236; 2.D.175.237; 2.D.175.238; 2.D.175.239; 2.D.175.154; 2.D.175.157; 2.D.175.166; 2.D.175.169; 2.D.175.172; 2.D.175.175; 2.D.175.240; 2.D.175.244; 2.D.240.228; 2.D.240.229; 2.D.240.230; 2.D.240.231; 2.D.240.236; 2.D.240.237; 2.D.240.238; 2.D.240.239; 2.D.240.154; 2.D.240.157; 2.D.240.166; 2.D.240.169; 2.D.240.172; 2.D.240.175; 2.D.240.240; 2.D.240.244; 2.D.244.228; 2.D.244.229; 2.D.244.230; 2.D.244.231; 2.D.244.236; 2.D.244.237; 2.D.244.238; 2.D.244.239; 2.D.244.154; 2.D.244.157; 2.D.244.166; 2.D.244.169; 2.D.244.172; 2.D.244.175; 2.D.244.240; 2.D.244.244;

Prodrugs of 2.E

2.E.228.228; 2.E.228.229; 2.E.228.230; 2.E.228.231; 2.E.228.236; 2.E.228.237; 2.E.228.238; 2.E.228.239; 2.E.228.154; 2.E.228.157; 2.E.228.166; 2.E.228.169; 2.E.228.172; 2.E.228.175; 2.E.228.240; 2.E.228.244; 2.E.229.228; 2.E.229.229; 2.E.229.230; 2.E.229.231; 2.E.229.236; 2.E.229.237; 2.E.229.238; 2.E.229.239; 2.E.229.154; 2.E.229.157; 2.E.229.166; 2.E.229.169; 2.E.229.172; 2.E.229.175; 2.E.229.240; 2.E.229.244; 2.E.230.228; 2.E.230.229; 2.E.230.230;

TABLE 100-continued

2.E.230.231; 2.E.230.236; 2.E.230.237; 2.E.230.238; 2.E.230.239; 2.E.230.154; 2.E.230.157;
2.E.230.166; 2.E.230.169; 2.E.230.172; 2.E.230.175; 2.E.230.240; 2.E.230.244; 2.E.231.228;
2.E.231.229; 2.E.231.230; 2.E.231.231; 2.E.231.236; 2.E.231.237; 2.E.231.238; 2.E.231.239;
2.E.231.154; 2.E.231.157; 2.E.231.166; 2.E.231.169; 2.E.231.172; 2.E.231.175; 2.E.231.240;
2.E.231.244; 2.E.236.228; 2.E.236.229; 2.E.236.230; 2.E.236.231; 2.E.236.236; 2.E.236.237;
2.E.236.238; 2.E.236.239; 2.E.236.154; 2.E.236.157; 2.E.236.166; 2.E.236.169; 2.E.236.172;
2.E.236.175; 2.E.236.240; 2.E.236.244; 2.E.237.228; 2.E.237.229; 2.E.237.230; 2.E.237.231;
2.E.237.236; 2.E.237.237; 2.E.237.238; 2.E.237.239; 2.E.237.154; 2.E.237.157; 2.E.237.166;
2.E.237.169; 2.E.237.172; 2.E.237.175; 2.E.237.240; 2.E.237.244; 2.E.238.228; 2.E.238.229;
2.E.238.230; 2.E.238.231; 2.E.238.236; 2.E.238.237; 2.E.238.238; 2.E.238.239; 2.E.238.154;
2.E.238.157; 2.E.238.166; 2.E.238.169; 2.E.238.172; 2.E.238.175; 2.E.238.240; 2.E.238.244;
2.E.239.228; 2.E.239.229; 2.E.239.230; 2.E.239.231; 2.E.239.236; 2.E.239.237; 2.E.239.238;
2.E.239.239; 2.E.239.154; 2.E.239.157; 2.E.239.166; 2.E.239.169; 2.E.239.172; 2.E.239.175;
2.E.239.240; 2.E.239.244; 2.E.154.228; 2.E.154.229; 2.E.154.230; 2.E.154.231; 2.E.154.236;
2.E.154.237; 2.E.154.238; 2.E.154.239; 2.E.154.154; 2.E.154.157; 2.E.154.166; 2.E.154.169;
2.E.154.172; 2.E.154.175; 2.E.154.240; 2.E.154.244; 2.E.157.228; 2.E.157.229; 2.E.157.230;
2.E.157.231; 2.E.157.236; 2.E.157.237; 2.E.157.238; 2.E.157.239; 2.E.157.154; 2.E.157.157;
2.E.157.166; 2.E.157.169; 2.E.157.172; 2.E.157.175; 2.E.157.240; 2.E.157.244; 2.E.166.228;
2.E.166.229; 2.E.166.230; 2.E.166.231; 2.E.166.236; 2.E.166.237; 2.E.166.238; 2.E.166.239;
2.E.166.154; 2.E.166.157; 2.E.166.166; 2.E.166.169; 2.E.166.172; 2.E.166.175; 2.E.166.240;
2.E.166.244; 2.E.169.228; 2.E.169.229; 2.E.169.230; 2.E.169.231; 2.E.169.236; 2.E.169.237;
2.E.169.238; 2.E.169.239; 2.E.169.154; 2.E.169.157; 2.E.169.166; 2.E.169.169; 2.E.169.172;
2.E.169.175; 2.E.169.240; 2.E.169.244; 2.E.172.228; 2.E.172.229; 2.E.172.230; 2.E.172.231;
2.E.172.236; 2.E.172.237; 2.E.172.238; 2.E.172.239; 2.E.172.154; 2.E.172.157; 2.E.172.166;
2.E.172.169; 2.E.172.172; 2.E.172.175; 2.E.172.240; 2.E.172.244; 2.E.175.228; 2.E.175.229;
2.E.175.230; 2.E.175.231; 2.E.175.236; 2.E.175.237; 2.E.175.238; 2.E.175.239; 2.E.175.154;
2.E.175.157; 2.E.175.166; 2.E.175.169; 2.E.175.172; 2.E.175.175; 2.E.175.240; 2.E.175.244;
2.E.240.228; 2.E.240.229; 2.E.240.230; 2.E.240.231; 2.E.240.236; 2.E.240.237; 2.E.240.238;
2.E.240.239; 2.E.240.154; 2.E.240.157; 2.E.240.166; 2.E.240.169; 2.E.240.172; 2.E.240.175;
2.E.240.240; 2.E.240.244; 2.E.244.228; 2.E.244.229; 2.E.244.230; 2.E.244.231; 2.E.244.236;
2.E.244.237; 2.E.244.238; 2.E.244.239; 2.E.244.154; 2.E.244.157; 2.E.244.166; 2.E.244.169;
2.E.244.172; 2.E.244.175; 2.E.244.240; 2.E.244.244;
Prodrugs of 2.G 2.G.228.228; 2.G.228.229; 2.G.228.230; 2.G.228.231; 2.G.228.236; 2.G.228.237;
2.G.228.238; 2.G.228.239; 2.G.228.154; 2.G.228.157; 2.G.228.166; 2.G.228.169; 2.G.228.172;
2.G.228.175; 2.G.228.240; 2.G.228.244; 2.G.229.228; 2.G.229.229; 2.G.229.230; 2.G.229.231;
2.G.229.236; 2.G.229.237; 2.G.229.238; 2.G.229.239; 2.G.229.154; 2.G.229.157; 2.G.229.166;
2.G.229.169; 2.G.229.172; 2.G.229.175; 2.G.229.240; 2.G.229.244; 2.G.230.228; 2.G.230.229;
2.G.230.230; 2.G.230.231; 2.G.230.236; 2.G.230.237; 2.G.230.238; 2.G.230.239; 2.G.230.154;
2.G.230.157; 2.G.230.166; 2.G.230.169; 2.G.230.172; 2.G.230.175; 2.G.230.240; 2.G.230.244;
2.G.231.228; 2.G.231.229; 2.G.231.230; 2.G.231.231; 2.G.231.236; 2.G.231.237; 2.G.231.238;
2.G.231.239; 2.G.231.154; 2.G.231.157; 2.G.231.166; 2.G.231.169; 2.G.231.172; 2.G.231.175;
2.G.231.240; 2.G.231.244; 2.G.236.228; 2.G.236.229; 2.G.236.230; 2.G.236.231; 2.G.236.236;
2.G.236.237; 2.G.236.238; 2.G.236.239; 2.G.236.154; 2.G.236.157; 2.G.236.166; 2.G.236.169;
2.G.236.172; 2.G.236.175; 2.G.236.240; 2.G.236.244; 2.G.237.228; 2.G.237.229; 2.G.237.230;
2.G.237.231; 2.G.237.236; 2.G.237.237; 2.G.237.238; 2.G.237.239; 2.G.237.154; 2.G.237.157;
2.G.237.166; 2.G.237.169; 2.G.237.172; 2.G.237.175; 2.G.237.240; 2.G.237.244; 2.G.238.228;
2.G.238.229; 2.G.238.230; 2.G.238.231; 2.G.238.236; 2.G.238.237; 2.G.238.238; 2.G.238.239;
2.G.238.154; 2.G.238.157; 2.G.238.166; 2.G.238.169; 2.G.238.172; 2.G.238.175; 2.G.238.240;
2.G.238.244; 2.G.239.228; 2.G.239.229; 2.G.239.230; 2.G.239.231; 2.G.239.236; 2.G.239.237;
2.G.239.238; 2.G.239.239; 2.G.239.154; 2.G.239.157; 2.G.239.166; 2.G.239.169; 2.G.239.172;
2.G.239.175; 2.G.239.240; 2.G.239.244; 2.G.154.228; 2.G.154.229; 2.G.154.230; 2.G.154.231;
2.G.154.236; 2.G.154.237; 2.G.154.238; 2.G.154.239; 2.G.154.154; 2.G.154.157; 2.G.154.166;
2.G.154.169; 2.G.154.172; 2.G.154.175; 2.G.154.240; 2.G.154.244; 2.G.157.228; 2.G.157.229;
2.G.157.230; 2.G.157.231; 2.G.157.236; 2.G.157.237; 2.G.157.238; 2.G.157.239; 2.G.157.154;
2.G.157.157; 2.G.157.166; 2.G.157.169; 2.G.157.172; 2.G.157.175; 2.G.157.240; 2.G.157.244;
2.G.166.228; 2.G.166.229; 2.G.166.230; 2.G.166.231; 2.G.166.236; 2.G.166.237; 2.G.166.238;
2.G.166.239; 2.G.166.154; 2.G.166.157; 2.G.166.166; 2.G.166.169; 2.G.166.172; 2.G.166.175;
2.G.166.240; 2.G.166.244; 2.G.169.228; 2.G.169.229; 2.G.169.230; 2.G.169.231; 2.G.169.236;
2.G.169.237; 2.G.169.238; 2.G.169.239; 2.G.169.154; 2.G.169.157; 2.G.169.166; 2.G.169.169;
2.G.169.172; 2.G.169.175; 2.G.169.240; 2.G.169.244; 2.G.172.228; 2.G.172.229; 2.G.172.230;
2.G.172.231; 2.G.172.236; 2.G.172.237; 2.G.172.238; 2.G.172.239; 2.G.172.154; 2.G.172.157;
2.G.172.166; 2.G.172.169; 2.G.172.172; 2.G.172.175; 2.G.172.240; 2.G.172.244; 2.G.175.228;
2.G.175.229; 2.G.175.230; 2.G.175.231; 2.G.175.236; 2.G.175.237; 2.G.175.238; 2.G.175.239;
2.G.175.154; 2.G.175.157; 2.G.175.166; 2.G.175.169; 2.G.175.172; 2.G.175.175; 2.G.175.240;
2.G.175.244; 2.G.240.228; 2.G.240.229; 2.G.240.230; 2.G.240.231; 2.G.240.236; 2.G.240.237;
2.G.240.238; 2.G.240.239; 2.G.240.154; 2.G.240.157; 2.G.240.166; 2.G.240.169; 2.G.240.172;
2.G.240.175; 2.G.240.240; 2.G.240.244; 2.G.244.228; 2.G.244.229; 2.G.244.230; 2.G.244.231;
2.G.244.236; 2.G.244.237; 2.G.244.238; 2.G.244.239; 2.G.244.154; 2.G.244.157; 2.G.244.166;
2.G.244.169; 2.G.244.172; 2.G.244.175; 2.G.244.240; 2.G.244.244;
Prodrugs of 2.I 2.I.228.228; 2.I.228.229; 2.I.228.230; 2.I.228.231; 2.I.228.236; 2.I.228.237; 2.I.228.238;
2.I.228.239; 2.I.228.154; 2.I.228.157; 2.I.228.166; 2.I.228.169; 2.I.228.172; 2.I.228.175;
2.I.228.240; 2.I.228.244; 2.I.229.228; 2.I.229.229; 2.I.229.230; 2.I.229.231; 2.I.229.236;
2.I.229.237; 2.I.229.238; 2.I.229.239; 2.I.229.154; 2.I.229.157; 2.I.229.166; 2.I.229.169;
2.I.229.172; 2.I.229.175; 2.I.229.240; 2.I.229.244; 2.I.230.228; 2.I.230.229; 2.I.230.230;
2.I.230.231; 2.I.230.236; 2.I.230.237; 2.I.230.238; 2.I.230.239; 2.I.230.154; 2.I.230.157;

TABLE 100-continued

2.I.230.166; 2.I.230.169; 2.I.230.172; 2.I.230.175; 2.I.230.240; 2.I.230.244; 2.I.231.228;
2.I.231.229; 2.I.231.230; 2.I.231.231; 2.I.231.236; 2.I.231.237; 2.I.231.238; 2.I.231.239;
2.I.231.154; 2.I.231.157; 2.I.231.166; 2.I.231.169; 2.I.231.172; 2.I.231.175; 2.I.231.240;
2.I.231.244; 2.I.236.228; 2.I.236.229; 2.I.236.230; 2.I.236.231; 2.I.236.236; 2.I.236.237;
2.I.236.238; 2.I.236.239; 2.I.236.154; 2.I.236.157; 2.I.236.166; 2.I.236.169; 2.I.236.172;
2.I.236.175; 2.I.236.240; 2.I.236.244; 2.I.237.228; 2.I.237.229; 2.I.237.230; 2.I.237.231;
2.I.237.236; 2.I.237.237; 2.I.237.238; 2.I.237.239; 2.I.237.154; 2.I.237.157; 2.I.237.166;
2.I.237.169; 2.I.237.172; 2.I.237.175; 2.I.237.240; 2.I.237.244; 2.I.238.228; 2.I.238.229;
2.I.238.230; 2.I.238.231; 2.I.238.236; 2.I.238.237; 2.I.238.238; 2.I.238.239; 2.I.238.154;
2.I.238.157; 2.I.238.166; 2.I.238.169; 2.I.238.172; 2.I.238.175; 2.I.238.240; 2.I.238.244;
2.I.239.228; 2.I.239.229; 2.I.239.230; 2.I.239.231; 2.I.239.236; 2.I.239.237; 2.I.239.238;
2.I.239.239; 2.I.239.154; 2.I.239.157; 2.I.239.166; 2.I.239.169; 2.I.239.172; 2.I.239.175;
2.I.239.240; 2.I.239.244; 2.I.154.228; 2.I.154.229; 2.I.154.230; 2.I.154.231; 2.I.154.236;
2.I.154.237; 2.I.154.238; 2.I.154.239; 2.I.154.154; 2.I.154.157; 2.I.154.166; 2.I.154.169;
2.I.154.172; 2.I.154.175; 2.I.154.240; 2.I.154.244; 2.I.157.228; 2.I.157.229; 2.I.157.230;
2.I.157.231; 2.I.157.236; 2.I.157.237; 2.I.157.238; 2.I.157.239; 2.I.157.154; 2.I.157.157;
2.I.157.166; 2.I.157.169; 2.I.157.172; 2.I.157.175; 2.I.157.240; 2.I.157.244; 2.I.166.228;
2.I.166.229; 2.I.166.230; 2.I.166.231; 2.I.166.236; 2.I.166.237; 2.I.166.238; 2.I.166.239;
2.I.166.154; 2.I.166.157; 2.I.166.166; 2.I.166.169; 2.I.166.172; 2.I.166.175; 2.I.166.240;
2.I.166.244; 2.I.169.228; 2.I.169.229; 2.I.169.230; 2.I.169.231; 2.I.169.236; 2.I.169.237;
2.I.169.238; 2.I.169.239; 2.I.169.154; 2.I.169.157; 2.I.169.166; 2.I.169.169; 2.I.169.172;
2.I.169.175; 2.I.169.240; 2.I.169.244; 2.I.172.228; 2.I.172.229; 2.I.172.230; 2.I.172.231;
2.I.172.236; 2.I.172.237; 2.I.172.238; 2.I.172.239; 2.I.172.154; 2.I.172.157; 2.I.172.166;
2.I.172.169; 2.I.172.172; 2.I.172.175; 2.I.172.240; 2.I.172.244; 2.I.175.228; 2.I.175.229;
2.I.175.230; 2.I.175.231; 2.I.175.236; 2.I.175.237; 2.I.175.238; 2.I.175.239; 2.I.175.154;
2.I.175.157; 2.I.175.166; 2.I.175.169; 2.I.175.172; 2.I.175.175; 2.I.175.240; 2.I.175.244;
2.I.240.228; 2.I.240.229; 2.I.240.230; 2.I.240.231; 2.I.240.236; 2.I.240.237; 2.I.240.238;
2.I.240.239; 2.I.240.154; 2.I.240.157; 2.I.240.166; 2.I.240.169; 2.I.240.172; 2.I.240.175;
2.I.240.240; 2.I.240.244; 2.I.244.228; 2.I.244.229; 2.I.244.230; 2.I.244.231; 2.I.244.236;
2.I.244.237; 2.I.244.238; 2.I.244.239; 2.I.244.154; 2.I.244.157; 2.I.244.166; 2.I.244.169;
2.I.244.172; 2.I.244.175; 2.I.244.240; 2.I.244.244;

Prodrugs of 2.J

2.J.228.228; 2.J.228.229; 2.J.228.230; 2.J.228.231; 2.J.228.236; 2.J.228.237; 2.J.228.238;
2.J.228.239; 2.J.228.154; 2.J.228.157; 2.J.228.166; 2.J.228.169; 2.J.228.172; 2.J.228.175;
2.J.228.240; 2.J.228.244; 2.J.229.228; 2.J.229.229; 2.J.229.230; 2.J.229.231; 2.J.229.236;
2.J.229.237; 2.J.229.238; 2.J.229.239; 2.J.229.154; 2.J.229.157; 2.J.229.166; 2.J.229.169;
2.J.229.172; 2.J.229.175; 2.J.229.240; 2.J.229.244; 2.J.230.228; 2.J.230.229; 2.J.230.230;
2.J.230.231; 2.J.230.236; 2.J.230.237; 2.J.230.238; 2.J.230.239; 2.J.230.154; 2.J.230.157;
2.J.230.166; 2.J.230.169; 2.J.230.172; 2.J.230.175; 2.J.230.240; 2.J.230.244; 2.J.231.228;
2.J.231.229; 2.J.231.230; 2.J.231.231; 2.J.231.236; 2.J.231.237; 2.J.231.238; 2.J.231.239;
2.J.231.154; 2.J.231.157; 2.J.231.166; 2.J.231.169; 2.J.231.172; 2.J.231.175; 2.J.231.240;
2.J.231.244; 2.J.236.228; 2.J.236.229; 2.J.236.230; 2.J.236.231; 2.J.236.236; 2.J.236.237;
2.J.236.238; 2.J.236.239; 2.J.236.154; 2.J.236.157; 2.J.236.166; 2.J.236.169; 2.J.236.172;
2.J.236.175; 2.J.236.240; 2.J.236.244; 2.J.237.228; 2.J.237.229; 2.J.237.230; 2.J.237.231;
2.J.237.236; 2.J.237.237; 2.J.237.238; 2.J.237.239; 2.J.237.154; 2.J.237.157; 2.J.237.166;
2.J.237.169; 2.J.237.172; 2.J.237.175; 2.J.237.240; 2.J.237.244; 2.J.238.228; 2.J.238.229;
2.J.238.230; 2.J.238.231; 2.J.238.236; 2.J.238.237; 2.J.238.238; 2.J.238.239; 2.J.238.154;
2.J.238.157; 2.J.238.166; 2.J.238.169; 2.J.238.172; 2.J.238.175; 2.J.238.240; 2.J.238.244;
2.J.239.228; 2.J.239.229; 2.J.239.230; 2.J.239.231; 2.J.239.236; 2.J.239.237; 2.J.239.238;
2.J.239.239; 2.J.239.154; 2.J.239.157; 2.J.239.166; 2.J.239.169; 2.J.239.172; 2.J.239.175;
2.J.239.240; 2.J.239.244; 2.J.154.228; 2.J.154.229; 2.J.154.230; 2.J.154.231; 2.J.154.236;
2.J.154.237; 2.J.154.238; 2.J.154.239; 2.J.154.154; 2.J.154.157; 2.J.154.166; 2.J.154.169;
2.J.154.172; 2.J.154.175; 2.J.154.240; 2.J.154.244; 2.J.157.228; 2.J.157.229; 2.J.157.230;
2.J.157.231; 2.J.157.236; 2.J.157.237; 2.J.157.238; 2.J.157.239; 2.J.157.154; 2.J.157.157;
2.J.157.166; 2.J.157.169; 2.J.157.172; 2.J.157.175; 2.J.157.240; 2.J.157.244; 2.J.166.228;
2.J.166.229; 2.J.166.230; 2.J.166.231; 2.J.166.236; 2.J.166.237; 2.J.166.238; 2.J.166.239;
2.J.166.154; 2.J.166.157; 2.J.166.166; 2.J.166.169; 2.J.166.172; 2.J.166.175; 2.J.166.240;
2.J.166.244; 2.J.169.228; 2.J.169.229; 2.J.169.230; 2.J.169.231; 2.J.169.236; 2.J.169.237;
2.J.169.238; 2.J.169.239; 2.J.169.154; 2.J.169.157; 2.J.169.166; 2.J.169.169; 2.J.169.172;
2.J.169.175; 2.J.169.240; 2.J.169.244; 2.J.172.228; 2.J.172.229; 2.J.172.230; 2.J.172.231;
2.J.172.236; 2.J.172.237; 2.J.172.238; 2.J.172.239; 2.J.172.154; 2.J.172.157; 2.J.172.166;
2.J.172.169; 2.J.172.172; 2.J.172.175; 2.J.172.240; 2.J.172.244; 2.J.175.228; 2.J.175.229;
2.J.175.230; 2.J.175.231; 2.J.175.236; 2.J.175.237; 2.J.175.238; 2.J.175.239; 2.J.175.154;
2.J.175.157; 2.J.175.166; 2.J.175.169; 2.J.175.172; 2.J.175.175; 2.J.175.240; 2.J.175.244;
2.J.240.228; 2.J.240.229; 2.J.240.230; 2.J.240.231; 2.J.240.236; 2.J.240.237; 2.J.240.238;
2.J.240.239; 2.J.240.154; 2.J.240.157; 2.J.240.166; 2.J.240.169; 2.J.240.172; 2.J.240.175;
2.J.240.240; 2.J.240.244; 2.J.244.228; 2.J.244.229; 2.J.244.230; 2.J.244.231; 2.J.244.236;
2.J.244.237; 2.J.244.238; 2.J.244.239; 2.J.244.154; 2.J.244.157; 2.J.244.166; 2.J.244.169;
2.J.244.172; 2.J.244.175; 2.J.244.240; 2.J.244.244;

Prodrugs of 2.L

2.L.228.228; 2.L.228.229; 2.L.228.230; 2.L.228.231; 2.L.228.236; 2.L.228.237; 2.L.228.238;
2.L.228.239; 2.L.228.154; 2.L.228.157; 2.L.228.166; 2.L.228.169; 2.L.228.172; 2.L.228.175;
2.L.228.240; 2.L.228.244; 2.L.229.228; 2.L.229.229; 2.L.229.230; 2.L.229.231; 2.L.229.236;
2.L.229.237; 2.L.229.238; 2.L.229.239; 2.L.229.154; 2.L.229.157; 2.L.229.166; 2.L.229.169;
2.L.229.172; 2.L.229.175; 2.L.229.240; 2.L.229.244; 2.L.230.228; 2.L.230.229; 2.L.230.230;
2.L.230.231; 2.L.230.236; 2.L.230.237; 2.L.230.238; 2.L.230.239; 2.L.230.154; 2.L.230.157;
2.L.230.166; 2.L.230.169; 2.L.230.172; 2.L.230.175; 2.L.230.240; 2.L.230.244; 2.L.231.228;

TABLE 100-continued

2.L.231.229; 2.L.231.230; 2.L.231.231; 2.L.231.236; 2.L.231.237; 2.L.231.238; 2.L.231.239;
2.L.231.154; 2.L.231.157; 2.L.231.166; 2.L.231.169; 2.L.231.172; 2.L.231.175; 2.L.231.240;
2.L.231.244; 2.L.236.228; 2.L.236.229; 2.L.236.230; 2.L.236.231; 2.L.236.236; 2.L.236.237;
2.L.236.238; 2.L.236.239; 2.L.236.154; 2.L.236.157; 2.L.236.166; 2.L.236.169; 2.L.236.172;
2.L.236.175; 2.L.236.240; 2.L.236.244; 2.L.237.228; 2.L.237.229; 2.L.237.230; 2.L.237.231;
2.L.237.236; 2.L.237.237; 2.L.237.238; 2.L.237.239; 2.L.237.154; 2.L.237.157; 2.L.237.166;
2.L.237.169; 2.L.237.172; 2.L.237.175; 2.L.237.240; 2.L.237.244; 2.L.238.228; 2.L.238.229;
2.L.238.230; 2.L.238.231; 2.L.238.236; 2.L.238.237; 2.L.238.238; 2.L.238.239; 2.L.238.154;
2.L.238.157; 2.L.238.166; 2.L.238.169; 2.L.238.172; 2.L.238.175; 2.L.238.240; 2.L.238.244;
2.L.239.228; 2.L.239.229; 2.L.239.230; 2.L.239.231; 2.L.239.236; 2.L.239.237; 2.L.239.238;
2.L.239.239; 2.L.239.154; 2.L.239.157; 2.L.239.166; 2.L.239.169; 2.L.239.172; 2.L.239.175;
2.L.239.240; 2.L.239.244; 2.L.154.228; 2.L.154.229; 2.L.154.230; 2.L.154.231; 2.L.154.236;
2.L.154.237; 2.L.154.238; 2.L.154.239; 2.L.154.154; 2.L.154.157; 2.L.154.166; 2.L.154.169;
2.L.154.172; 2.L.154.175; 2.L.154.240; 2.L.154.244; 2.L.157.228; 2.L.157.229; 2.L.157.230;
2.L.157.231; 2.L.157.236; 2.L.157.237; 2.L.157.238; 2.L.157.239; 2.L.157.154; 2.L.157.157;
2.L.157.166; 2.L.157.169; 2.L.157.172; 2.L.157.175; 2.L.157.240; 2.L.157.244; 2.L.166.228;
2.L.166.229; 2.L.166.230; 2.L.166.231; 2.L.166.236; 2.L.166.237; 2.L.166.238; 2.L.166.239;
2.L.166.154; 2.L.166.157; 2.L.166.166; 2.L.166.169; 2.L.166.172; 2.L.166.175; 2.L.166.240;
2.L.166.244; 2.L.169.228; 2.L.169.229; 2.L.169.230; 2.L.169.231; 2.L.169.236; 2.L.169.237;
2.L.169.238; 2.L.169.239; 2.L.169.154; 2.L.169.157; 2.L.169.166; 2.L.169.169; 2.L.169.172;
2.L.169.175; 2.L.169.240; 2.L.169.244; 2.L.172.228; 2.L.172.229; 2.L.172.230; 2.L.172.231;
2.L.172.236; 2.L.172.237; 2.L.172.238; 2.L.172.239; 2.L.172.154; 2.L.172.157; 2.L.172.166;
2.L.172.169; 2.L.172.172; 2.L.172.175; 2.L.172.240; 2.L.172.244; 2.L.175.228; 2.L.175.229;
2.L.175.230; 2.L.175.231; 2.L.175.236; 2.L.175.237; 2.L.175.238; 2.L.175.239; 2.L.175.154;
2.L.175.157; 2.L.175.166; 2.L.175.169; 2.L.175.172; 2.L.175.175; 2.L.175.240; 2.L.175.244;
2.L.240.228; 2.L.240.229; 2.L.240.230; 2.L.240.231; 2.L.240.236; 2.L.240.237; 2.L.240.238;
2.L.240.239; 2.L.240.154; 2.L.240.157; 2.L.240.166; 2.L.240.169; 2.L.240.172; 2.L.240.175;
2.L.240.240; 2.L.240.244; 2.L.244.228; 2.L.244.229; 2.L.244.230; 2.L.244.231; 2.L.244.236;
2.L.244.237; 2.L.244.238; 2.L.244.239; 2.L.244.154; 2.L.244.157; 2.L.244.166; 2.L.244.169;
2.L.244.172; 2.L.244.175; 2.L.244.240; 2.L.244.244;
Prodrugs of 2.O 2.O.228.228; 2.O.228.229; 2.O.228.230; 2.O.228.231; 2.O.228.236; 2.O.228.237;
2.O.228.238; 2.O.228.239; 2.O.228.154; 2.O.228.157; 2.O.228.166; 2.O.228.169; 2.O.228.172;
2.O.228.175; 2.O.228.240; 2.O.228.244; 2.O.229.228; 2.O.229.229; 2.O.229.230; 2.O.229.231;
2.O.229.236; 2.O.229.237; 2.O.229.238; 2.O.229.239; 2.O.229.154; 2.O.229.157; 2.O.229.166;
2.O.229.169; 2.O.229.172; 2.O.229.175; 2.O.229.240; 2.O.229.244; 2.O.230.228; 2.O.230.229;
2.O.230.230; 2.O.230.231; 2.O.230.236; 2.O.230.237; 2.O.230.238; 2.O.230.239; 2.O.230.154;
2.O.230.157; 2.O.230.166; 2.O.230.169; 2.O.230.172; 2.O.230.175; 2.O.230.240; 2.O.230.244;
2.O.231.228; 2.O.231.229; 2.O.231.230; 2.O.231.231; 2.O.231.236; 2.O.231.237; 2.O.231.238;
2.O.231.239; 2.O.231.154; 2.O.231.157; 2.O.231.166; 2.O.231.169; 2.O.231.172; 2.O.231.175;
2.O.231.240; 2.O.231.244; 2.O.236.228; 2.O.236.229; 2.O.236.230; 2.O.236.231; 2.O.236.236;
2.O.236.237; 2.O.236.238; 2.O.236.239; 2.O.236.154; 2.O.236.157; 2.O.236.166; 2.O.236.169;
2.O.236.172; 2.O.236.175; 2.O.236.240; 2.O.236.244; 2.O.237.228; 2.O.237.229; 2.O.237.230;
2.O.237.231; 2.O.237.236; 2.O.237.237; 2.O.237.238; 2.O.237.239; 2.O.237.154; 2.O.237.157;
2.O.237.166; 2.O.237.169; 2.O.237.172; 2.O.237.175; 2.O.237.240; 2.O.237.244; 2.O.238.228;
2.O.238.229; 2.O.238.230; 2.O.238.231; 2.O.238.236; 2.O.238.237; 2.O.238.238; 2.O.238.239;
2.O.238.154; 2.O.238.157; 2.O.238.166; 2.O.238.169; 2.O.238.172; 2.O.238.175; 2.O.238.240;
2.O.238.244; 2.O.239.228; 2.O.239.229; 2.O.239.230; 2.O.239.231; 2.O.239.236; 2.O.239.237;
2.O.239.238; 2.O.239.239; 2.O.239.154; 2.O.239.157; 2.O.239.166; 2.O.239.169; 2.O.239.172;
2.O.239.175; 2.O.239.240; 2.O.239.244; 2.O.154.228; 2.O.154.229; 2.O.154.230; 2.O.154.231;
2.O.154.236; 2.O.154.237; 2.O.154.238; 2.O.154.239; 2.O.154.154; 2.O.154.157; 2.O.154.166;
2.O.154.169; 2.O.154.172; 2.O.154.175; 2.O.154.240; 2.O.154.244; 2.O.157.228; 2.O.157.229;
2.O.157.230; 2.O.157.231; 2.O.157.236; 2.O.157.237; 2.O.157.238; 2.O.157.239; 2.O.157.154;
2.O.157.157; 2.O.157.166; 2.O.157.169; 2.O.157.172; 2.O.157.175; 2.O.157.240; 2.O.157.244;
2.O.166.228; 2.O.166.229; 2.O.166.230; 2.O.166.231; 2.O.166.236; 2.O.166.237; 2.O.166.238;
2.O.166.239; 2.O.166.154; 2.O.166.157; 2.O.166.166; 2.O.166.169; 2.O.166.172; 2.O.166.175;
2.O.166.240; 2.O.166.244; 2.O.169.228; 2.O.169.229; 2.O.169.230; 2.O.169.231; 2.O.169.236;
2.O.169.237; 2.O.169.238; 2.O.169.239; 2.O.169.154; 2.O.169.157; 2.O.169.166; 2.O.169.169;
2.O.169.172; 2.O.169.175; 2.O.169.240; 2.O.169.244; 2.O.172.228; 2.O.172.229; 2.O.172.230;
2.O.172.231; 2.O.172.236; 2.O.172.237; 2.O.172.238; 2.O.172.239; 2.O.172.154; 2.O.172.157;
2.O.172.166; 2.O.172.169; 2.O.172.172; 2.O.172.175; 2.O.172.240; 2.O.172.244; 2.O.175.228;
2.O.175.229; 2.O.175.230; 2.O.175.231; 2.O.175.236; 2.O.175.237; 2.O.175.238; 2.O.175.239;
2.O.175.154; 2.O.175.157; 2.O.175.166; 2.O.175.169; 2.O.175.172; 2.O.175.175; 2.O.175.240;
2.O.175.244; 2.O.240.228; 2.O.240.229; 2.O.240.230; 2.O.240.231; 2.O.240.236; 2.O.240.237;
2.O.240.238; 2.O.240.239; 2.O.240.154; 2.O.240.157; 2.O.240.166; 2.O.240.169; 2.O.240.172;
2.O.240.175; 2.O.240.240; 2.O.240.244; 2.O.244.228; 2.O.244.229; 2.O.244.230; 2.O.244.231;
2.O.244.236; 2.O.244.237; 2.O.244.238; 2.O.244.239; 2.O.244.154; 2.O.244.157; 2.O.244.166;
2.O.244.169; 2.O.244.172; 2.O.244.175; 2.O.244.240; 2.O.244.244;
Prodrugs of 2.P 2.P.228.228; 2.P.228.229; 2.P.228.230; 2.P.228.231; 2.P.228.236; 2.P.228.237; 2.P.228.238;
2.P.228.239; 2.P.228.154; 2.P.228.157; 2.P.228.166; 2.P.228.169; 2.P.228.172; 2.P.228.175;
2.P.228.240; 2.P.228.244; 2.P.229.228; 2.P.229.229; 2.P.229.230; 2.P.229.231; 2.P.229.236;
2.P.229.237; 2.P.229.238; 2.P.229.239; 2.P.229.154; 2.P.229.157; 2.P.229.166; 2.P.229.169;
2.P.229.172; 2.P.229.175; 2.P.229.240; 2.P.229.244; 2.P.230.228; 2.P.230.229; 2.P.230.230;
2.P.230.231; 2.P.230.236; 2.P.230.237; 2.P.230.238; 2.P.230.239; 2.P.230.154; 2.P.230.157;
2.P.230.166; 2.P.230.169; 2.P.230.172; 2.P.230.175; 2.P.230.240; 2.P.230.244; 2.P.231.228;
2.P.231.229; 2.P.231.230; 2.P.231.231; 2.P.231.236; 2.P.231.237; 2.P.231.238; 2.P.231.239;

TABLE 100-continued

2.P.231.154; 2.P.231.157; 2.P.231.166; 2.P.231.169; 2.P.231.172; 2.P.231.175; 2.P.231.240;
2.P.231.244; 2.P.236.228; 2.P.236.229; 2.P.236.230; 2.P.236.231; 2.P.236.236; 2.P.236.237;
2.P.236.238; 2.P.236.239; 2.P.236.154; 2.P.236.157; 2.P.236.166; 2.P.236.169; 2.P.236.172;
2.P.236.175; 2.P.236.240; 2.P.236.244; 2.P.237.228; 2.P.237.229; 2.P.237.230; 2.P.237.231;
2.P.237.236; 2.P.237.237; 2.P.237.238; 2.P.237.239; 2.P.237.154; 2.P.237.157; 2.P.237.166;
2.P.237.169; 2.P.237.172; 2.P.237.175; 2.P.237.240; 2.P.237.244; 2.P.238.228; 2.P.238.229;
2.P.238.230; 2.P.238.231; 2.P.238.236; 2.P.238.237; 2.P.238.238; 2.P.238.239; 2.P.238.154;
2.P.238.157; 2.P.238.166; 2.P.238.169; 2.P.238.172; 2.P.238.175; 2.P.238.240; 2.P.238.244;
2.P.239.228; 2.P.239.229; 2.P.239.230; 2.P.239.231; 2.P.239.236; 2.P.239.237; 2.P.239.238;
2.P.239.239; 2.P.239.154; 2.P.239.157; 2.P.239.166; 2.P.239.169; 2.P.239.172; 2.P.239.175;
2.P.239.240; 2.P.239.244; 2.P.154.228; 2.P.154.229; 2.P.154.230; 2.P.154.231; 2.P.154.236;
2.P.154.237; 2.P.154.238; 2.P.154.239; 2.P.154.154; 2.P.154.157; 2.P.154.166; 2.P.154.169;
2.P.154.172; 2.P.154.175; 2.P.154.240; 2.P.154.244; 2.P.157.228; 2.P.157.229; 2.P.157.230;
2.P.157.231; 2.P.157.236; 2.P.157.237; 2.P.157.238; 2.P.157.239; 2.P.157.154; 2.P.157.157;
2.P.157.166; 2.P.157.169; 2.P.157.172; 2.P.157.175; 2.P.157.240; 2.P.157.244; 2.P.166.228;
2.P.166.229; 2.P.166.230; 2.P.166.231; 2.P.166.236; 2.P.166.237; 2.P.166.238; 2.P.166.239;
2.P.166.154; 2.P.166.157; 2.P.166.166; 2.P.166.169; 2.P.166.172; 2.P.166.175; 2.P.166.240;
2.P.166.244; 2.P.169.228; 2.P.169.229; 2.P.169.230; 2.P.169.231; 2.P.169.236; 2.P.169.237;
2.P.169.238; 2.P.169.239; 2.P.169.154; 2.P.169.157; 2.P.169.166; 2.P.169.169; 2.P.169.172;
2.P.169.175; 2.P.169.240; 2.P.169.244; 2.P.172.228; 2.P.172.229; 2.P.172.230; 2.P.172.231;
2.P.172.236; 2.P.172.237; 2.P.172.238; 2.P.172.239; 2.P.172.154; 2.P.172.157; 2.P.172.166;
2.P.172.169; 2.P.172.172; 2.P.172.175; 2.P.172.240; 2.P.172.244; 2.P.175.228; 2.P.175.229;
2.P.175.230; 2.P.175.231; 2.P.175.236; 2.P.175.237; 2.P.175.238; 2.P.175.239; 2.P.175.154;
2.P.175.157; 2.P.175.166; 2.P.175.169; 2.P.175.172; 2.P.175.175; 2.P.175.240; 2.P.175.244;
2.P.240.228; 2.P.240.229; 2.P.240.230; 2.P.240.231; 2.P.240.236; 2.P.240.237; 2.P.240.238;
2.P.240.239; 2.P.240.154; 2.P.240.157; 2.P.240.166; 2.P.240.169; 2.P.240.172; 2.P.240.175;
2.P.240.240; 2.P.240.244; 2.P.244.228; 2.P.244.229; 2.P.244.230; 2.P.244.231; 2.P.244.236;
2.P.244.237; 2.P.244.238; 2.P.244.239; 2.P.244.154; 2.P.244.157; 2.P.244.166; 2.P.244.169;
2.P.244.172; 2.P.244.175; 2.P.244.240; 2.P.244.244;

Prodrugs of 2.U

2.U.228.228; 2.U.228.229; 2.U.228.230; 2.U.228.231; 2.U.228.236; 2.U.228.237;
2.U.228.238; 2.U.228.239; 2.U.228.154; 2.U.228.157; 2.U.228.166; 2.U.228.169; 2.U.228.172;
2.U.228.175; 2.U.228.240; 2.U.228.244; 2.U.229.228; 2.U.229.229; 2.U.229.230; 2.U.229.231;
2.U.229.236; 2.U.229.237; 2.U.229.238; 2.U.229.239; 2.U.229.154; 2.U.229.157; 2.U.229.166;
2.U.229.169; 2.U.229.172; 2.U.229.175; 2.U.229.240; 2.U.229.244; 2.U.230.228; 2.U.230.229;
2.U.230.230; 2.U.230.231; 2.U.230.236; 2.U.230.237; 2.U.230.238; 2.U.230.239; 2.U.230.154;
2.U.230.157; 2.U.230.166; 2.U.230.169; 2.U.230.172; 2.U.230.175; 2.U.230.240; 2.U.230.244;
2.U.231.228; 2.U.231.229; 2.U.231.230; 2.U.231.231; 2.U.231.236; 2.U.231.237; 2.U.231.238;
2.U.231.239; 2.U.231.154; 2.U.231.157; 2.U.231.166; 2.U.231.169; 2.U.231.172; 2.U.231.175;
2.U.231.240; 2.U.231.244; 2.U.236.228; 2.U.236.229; 2.U.236.230; 2.U.236.231; 2.U.236.236;
2.U.236.237; 2.U.236.238; 2.U.236.239; 2.U.236.154; 2.U.236.157; 2.U.236.166; 2.U.236.169;
2.U.236.172; 2.U.236.175; 2.U.236.240; 2.U.236.244; 2.U.237.228; 2.U.237.229; 2.U.237.230;
2.U.237.231; 2.U.237.236; 2.U.237.237; 2.U.237.238; 2.U.237.239; 2.U.237.154; 2.U.237.157;
2.U.237.166; 2.U.237.169; 2.U.237.172; 2.U.237.175; 2.U.237.240; 2.U.237.244; 2.U.238.228;
2.U.238.229; 2.U.238.230; 2.U.238.231; 2.U.238.236; 2.U.238.237; 2.U.238.238; 2.U.238.239;
2.U.238.154; 2.U.238.157; 2.U.238.166; 2.U.238.169; 2.U.238.172; 2.U.238.175; 2.U.238.240;
2.U.238.244; 2.U.239.228; 2.U.239.229; 2.U.239.230; 2.U.239.231; 2.U.239.236; 2.U.239.237;
2.U.239.238; 2.U.239.239; 2.U.239.154; 2.U.239.157; 2.U.239.166; 2.U.239.169; 2.U.239.172;
2.U.239.175; 2.U.239.240; 2.U.239.244; 2.U.154.228; 2.U.154.229; 2.U.154.230; 2.U.154.231;
2.U.154.236; 2.U.154.237; 2.U.154.238; 2.U.154.239; 2.U.154.154; 2.U.154.157; 2.U.154.166;
2.U.154.169; 2.U.154.172; 2.U.154.175; 2.U.154.240; 2.U.154.244; 2.U.157.228; 2.U.157.229;
2.U.157.230; 2.U.157.231; 2.U.157.236; 2.U.157.237; 2.U.157.238; 2.U.157.239; 2.U.157.154;
2.U.157.157; 2.U.157.166; 2.U.157.169; 2.U.157.172; 2.U.157.175; 2.U.157.240; 2.U.157.244;
2.U.166.228; 2.U.166.229; 2.U.166.230; 2.U.166.231; 2.U.166.236; 2.U.166.237; 2.U.166.238;
2.U.166.239; 2.U.166.154; 2.U.166.157; 2.U.166.166; 2.U.166.169; 2.U.166.172; 2.U.166.175;
2.U.166.240; 2.U.166.244; 2.U.169.228; 2.U.169.229; 2.U.169.230; 2.U.169.231; 2.U.169.236;
2.U.169.237; 2.U.169.238; 2.U.169.239; 2.U.169.154; 2.U.169.157; 2.U.169.166; 2.U.169.169;
2.U.169.172; 2.U.169.175; 2.U.169.240; 2.U.169.244; 2.U.172.228; 2.U.172.229; 2.U.172.230;
2.U.172.231; 2.U.172.236; 2.U.172.237; 2.U.172.238; 2.U.172.239; 2.U.172.154; 2.U.172.157;
2.U.172.166; 2.U.172.169; 2.U.172.172; 2.U.172.175; 2.U.172.240; 2.U.172.244; 2.U.175.228;
2.U.175.229; 2.U.175.230; 2.U.175.231; 2.U.175.236; 2.U.175.237; 2.U.175.238; 2.U.175.239;
2.U.175.154; 2.U.175.157; 2.U.175.166; 2.U.175.169; 2.U.175.172; 2.U.175.175; 2.U.175.240;
2.U.175.244; 2.U.240.228; 2.U.240.229; 2.U.240.230; 2.U.240.231; 2.U.240.236; 2.U.240.237;
2.U.240.238; 2.U.240.239; 2.U.240.154; 2.U.240.157; 2.U.240.166; 2.U.240.169; 2.U.240.172;
2.U.240.175; 2.U.240.240; 2.U.240.244; 2.U.244.228; 2.U.244.229; 2.U.244.230; 2.U.244.231;
2.U.244.236; 2.U.244.237; 2.U.244.238; 2.U.244.239; 2.U.244.154; 2.U.244.157; 2.U.244.166;
2.U.244.169; 2.U.244.172; 2.U.244.175; 2.U.244.240; 2.U.244.244;

Prodrugs of 2.W

2.W.228.228; 2.W.228.229; 2.W.228.230; 2.W.228.231; 2.W.228.236; 2.W.228.237;
2.W.228.238; 2.W.228.239; 2.W.228.154; 2.W.228.157; 2.W.228.166; 2.W.228.169;
2.W.228.172; 2.W.228.175; 2.W.228.240; 2.W.228.244; 2.W.229.228; 2.W.229.229;
2.W.229.230; 2.W.229.231; 2.W.229.236; 2.W.229.237; 2.W.229.238; 2.W.229.239;
2.W.229.154; 2.W.229.157; 2.W.229.166; 2.W.229.169; 2.W.229.172; 2.W.229.175;
2.W.229.240; 2.W.229.244; 2.W.230.228; 2.W.230.229; 2.W.230.230; 2.W.230.231;
2.W.230.236; 2.W.230.237; 2.W.230.238; 2.W.230.239; 2.W.230.154; 2.W.230.157;
2.W.230.166; 2.W.230.169; 2.W.230.172; 2.W.230.175; 2.W.230.240; 2.W.230.244;
2.W.231.228; 2.W.231.229; 2.W.231.230; 2.W.231.231; 2.W.231.236; 2.W.231.237;

TABLE 100-continued

2.W.231.238; 2.W.231.239; 2.W.231.154; 2.W.231.157; 2.W.231.166; 2.W.231.169;
2.W.231.172; 2.W.231.175; 2.W.231.240; 2.W.231.244; 2.W.236.228; 2.W.236.229;
2.W.236.230; 2.W.236.231; 2.W.236.236; 2.W.236.237; 2.W.236.238; 2.W.236.239;
2.W.236.154; 2.W.236.157; 2.W.236.166; 2.W.236.169; 2.W.236.172; 2.W.236.175;
2.W.236.240; 2.W.236.244; 2.W.237.228; 2.W.237.229; 2.W.237.230; 2.W.237.231;
2.W.237.236; 2.W.237.237; 2.W.237.238; 2.W.237.239; 2.W.237.154; 2.W.237.157;
2.W.237.166; 2.W.237.169; 2.W.237.172; 2.W.237.175; 2.W.237.240; 2.W.237.244;
2.W.238.228; 2.W.238.229; 2.W.238.230; 2.W.238.231; 2.W.238.236; 2.W.238.237;
2.W.238.238; 2.W.238.239; 2.W.238.154; 2.W.238.157; 2.W.238.166; 2.W.238.169;
2.W.238.172; 2.W.238.175; 2.W.238.240; 2.W.238.244; 2.W.239.228; 2.W.239.229;
2.W.239.230; 2.W.239.231; 2.W.239.236; 2.W.239.237; 2.W.239.238; 2.W.239.239;
2.W.239.154; 2.W.239.157; 2.W.239.166; 2.W.239.169; 2.W.239.172; 2.W.239.175;
2.W.239.240; 2.W.239.244; 2.W.154.228; 2.W.154.229; 2.W.154.230; 2.W.154.231;
2.W.154.236; 2.W.154.237; 2.W.154.238; 2.W.154.239; 2.W.154.154; 2.W.154.157;
2.W.154.166; 2.W.154.169; 2.W.154.172; 2.W.154.175; 2.W.154.240; 2.W.154.244;
2.W.157.228; 2.W.157.229; 2.W.157.230; 2.W.157.231; 2.W.157.236; 2.W.157.237;
2.W.157.238; 2.W.157.239; 2.W.157.154; 2.W.157.157; 2.W.157.166; 2.W.157.169;
2.W.157.172; 2.W.157.175; 2.W.157.240; 2.W.157.244; 2.W.166.228; 2.W.166.229;
2.W.166.230; 2.W.166.231; 2.W.166.236; 2.W.166.237; 2.W.166.238; 2.W.166.239;
2.W.166.154; 2.W.166.157; 2.W.166.166; 2.W.166.169; 2.W.166.172; 2.W.166.175;
2.W.166.240; 2.W.166.244; 2.W.169.228; 2.W.169.229; 2.W.169.230; 2.W.169.231;
2.W.169.236; 2.W.169.237; 2.W.169.238; 2.W.169.239; 2.W.169.154; 2.W.169.157;
2.W.169.166; 2.W.169.169; 2.W.169.172; 2.W.169.175; 2.W.169.240; 2.W.169.244;
2.W.172.228; 2.W.172.229; 2.W.172.230; 2.W.172.231; 2.W.172.236; 2.W.172.237;
2.W.172.238; 2.W.172.239; 2.W.172.154; 2.W.172.157; 2.W.172.166; 2.W.172.169;
2.W.172.172; 2.W.172.175; 2.W.172.240; 2.W.172.244; 2.W.175.228; 2.W.175.229;
2.W.175.230; 2.W.175.231; 2.W.175.236; 2.W.175.237; 2.W.175.238; 2.W.175.239;
2.W.175.154; 2.W.175.157; 2.W.175.166; 2.W.175.169; 2.W.175.172; 2.W.175.175;
2.W.175.240; 2.W.175.244; 2.W.240.228; 2.W.240.229; 2.W.240.230; 2.W.240.231;
2.W.240.236; 2.W.240.237; 2.W.240.238; 2.W.240.239; 2.W.240.154; 2.W.240.157;
2.W.240.166; 2.W.240.169; 2.W.240.172; 2.W.240.175; 2.W.240.240; 2.W.240.244;
2.W.244.228; 2.W.244.229; 2.W.244.230; 2.W.244.231; 2.W.244.236; 2.W.244.237;
2.W.244.238; 2.W.244.239; 2.W.244.154; 2.W.244.157; 2.W.244.166; 2.W.244.169;
2.W.244.172; 2.W.244.175; 2.W.244.240; 2.W.244.244;
Prodrugs of 2.Y 2.Y.228.228; 2.Y.228.229; 2.Y.228.230; 2.Y.228.231; 2.Y.228.236; 2.Y.228.237; 2.Y.228.238;
2.Y.228.239; 2.Y.228.154; 2.Y.228.157; 2.Y.228.166; 2.Y.228.169; 2.Y.228.172; 2.Y.228.175;
2.Y.228.240; 2.Y.228.244; 2.Y.229.228; 2.Y.229.229; 2.Y.229.230; 2.Y.229.231; 2.Y.229.236;
2.Y.229.237; 2.Y.229.238; 2.Y.229.239; 2.Y.229.154; 2.Y.229.157; 2.Y.229.166; 2.Y.229.169;
2.Y.229.172; 2.Y.229.175; 2.Y.229.240; 2.Y.229.244; 2.Y.230.228; 2.Y.230.229; 2.Y.230.230;
2.Y.230.231; 2.Y.230.236; 2.Y.230.237; 2.Y.230.238; 2.Y.230.239; 2.Y.230.154; 2.Y.230.157;
2.Y.230.166; 2.Y.230.169; 2.Y.230.172; 2.Y.230.175; 2.Y.230.240; 2.Y.230.244; 2.Y.231.228;
2.Y.231.229; 2.Y.231.230; 2.Y.231.231; 2.Y.231.236; 2.Y.231.237; 2.Y.231.238; 2.Y.231.239;
2.Y.231.154; 2.Y.231.157; 2.Y.231.166; 2.Y.231.169; 2.Y.231.172; 2.Y.231.175; 2.Y.231.240;
2.Y.231.244; 2.Y.236.228; 2.Y.236.229; 2.Y.236.230; 2.Y.236.231; 2.Y.236.236; 2.Y.236.237;
2.Y.236.238; 2.Y.236.239; 2.Y.236.154; 2.Y.236.157; 2.Y.236.166; 2.Y.236.169; 2.Y.236.172;
2.Y.236.175; 2.Y.236.240; 2.Y.236.244; 2.Y.237.228; 2.Y.237.229; 2.Y.237.230; 2.Y.237.231;
2.Y.237.236; 2.Y.237.237; 2.Y.237.238; 2.Y.237.239; 2.Y.237.154; 2.Y.237.157; 2.Y.237.166;
2.Y.237.169; 2.Y.237.172; 2.Y.237.175; 2.Y.237.240; 2.Y.237.244; 2.Y.238.228; 2.Y.238.229;
2.Y.238.230; 2.Y.238.231; 2.Y.238.236; 2.Y.238.237; 2.Y.238.238; 2.Y.238.239; 2.Y.238.154;
2.Y.238.157; 2.Y.238.166; 2.Y.238.169; 2.Y.238.172; 2.Y.238.175; 2.Y.238.240; 2.Y.238.244;
2.Y.239.228; 2.Y.239.229; 2.Y.239.230; 2.Y.239.231; 2.Y.239.236; 2.Y.239.237; 2.Y.239.238;
2.Y.239.239; 2.Y.239.154; 2.Y.239.157; 2.Y.239.166; 2.Y.239.169; 2.Y.239.172; 2.Y.239.175;
2.Y.239.240; 2.Y.239.244; 2.Y.154.228; 2.Y.154.229; 2.Y.154.230; 2.Y.154.231; 2.Y.154.236;
2.Y.154.237; 2.Y.154.238; 2.Y.154.239; 2.Y.154.154; 2.Y.154.157; 2.Y.154.166; 2.Y.154.169;
2.Y.154.172; 2.Y.154.175; 2.Y.154.240; 2.Y.154.244; 2.Y.157.228; 2.Y.157.229; 2.Y.157.230;
2.Y.157.231; 2.Y.157.236; 2.Y.157.237; 2.Y.157.238; 2.Y.157.239; 2.Y.157.154; 2.Y.157.157;
2.Y.157.166; 2.Y.157.169; 2.Y.157.172; 2.Y.157.175; 2.Y.157.240; 2.Y.157.244; 2.Y.166.228;
2.Y.166.229; 2.Y.166.230; 2.Y.166.231; 2.Y.166.236; 2.Y.166.237; 2.Y.166.238; 2.Y.166.239;
2.Y.166.154; 2.Y.166.157; 2.Y.166.166; 2.Y.166.169; 2.Y.166.172; 2.Y.166.175; 2.Y.166.240;
2.Y.166.244; 2.Y.169.228; 2.Y.169.229; 2.Y.169.230; 2.Y.169.231; 2.Y.169.236; 2.Y.169.237;
2.Y.169.238; 2.Y.169.239; 2.Y.169.154; 2.Y.169.157; 2.Y.169.166; 2.Y.169.169; 2.Y.169.172;
2.Y.169.175; 2.Y.169.240; 2.Y.169.244; 2.Y.172.228; 2.Y.172.229; 2.Y.172.230; 2.Y.172.231;
2.Y.172.236; 2.Y.172.237; 2.Y.172.238; 2.Y.172.239; 2.Y.172.154; 2.Y.172.157; 2.Y.172.166;
2.Y.172.169; 2.Y.172.172; 2.Y.172.175; 2.Y.172.240; 2.Y.172.244; 2.Y.175.228; 2.Y.175.229;
2.Y.175.230; 2.Y.175.231; 2.Y.175.236; 2.Y.175.237; 2.Y.175.238; 2.Y.175.239; 2.Y.175.154;
2.Y.175.157; 2.Y.175.166; 2.Y.175.169; 2.Y.175.172; 2.Y.175.175; 2.Y.175.240; 2.Y.175.244;
2.Y.240.228; 2.Y.240.229; 2.Y.240.230; 2.Y.240.231; 2.Y.240.236; 2.Y.240.237; 2.Y.240.238;
2.Y.240.239; 2.Y.240.154; 2.Y.240.157; 2.Y.240.166; 2.Y.240.169; 2.Y.240.172; 2.Y.240.175;
2.Y.240.240; 2.Y.240.244; 2.Y.244.228; 2.Y.244.229; 2.Y.244.230; 2.Y.244.231; 2.Y.244.236;
2.Y.244.237; 2.Y.244.238; 2.Y.244.239; 2.Y.244.154; 2.Y.244.157; 2.Y.244.166; 2.Y.244.169;
2.Y.244.172; 2.Y.244.175; 2.Y.244.240; 2.Y.244.244;
Prodrugs of 3.B 3.B.228.228; 3.B.228.229; 3.B.228.230; 3.B.228.231; 3.B.228.236; 3.B.228.237; 3.B.228.238;
3.B.228.239; 3.B.228.154; 3.B.228.157; 3.B.228.166; 3.B.228.169; 3.B.228.172; 3.B.228.175;
3.B.228.240; 3.B.228.244; 3.B.229.228; 3.B.229.229; 3.B.229.230; 3.B.229.231; 3.B.229.236;
3.B.229.237; 3.B.229.238; 3.B.229.239; 3.B.229.154; 3.B.229.157; 3.B.229.166; 3.B.229.169;

TABLE 100-continued

3.B.229.172; 3.B.229.175; 3.B.229.240; 3.B.229.244; 3.B.230.228; 3.B.230.229; 3.B.230.230;
3.B.230.231; 3.B.230.236; 3.B.230.237; 3.B.230.238; 3.B.230.239; 3.B.230.154; 3.B.230.157;
3.B.230.166; 3.B.230.169; 3.B.230.172; 3.B.230.175; 3.B.230.240; 3.B.230.244; 3.B.231.228;
3.B.231.229; 3.B.231.230; 3.B.231.231; 3.B.231.236; 3.B.231.237; 3.B.231.238; 3.B.231.239;
3.B.231.154; 3.B.231.157; 3.B.231.166; 3.B.231.169; 3.B.231.172; 3.B.231.175; 3.B.231.240;
3.B.231.244; 3.B.236.228; 3.B.236.229; 3.B.236.230; 3.B.236.231; 3.B.236.236; 3.B.236.237;
3.B.236.238; 3.B.236.239; 3.B.236.154; 3.B.236.157; 3.B.236.166; 3.B.236.169; 3.B.236.172;
3.B.236.175; 3.B.236.240; 3.B.236.244; 3.B.237.228; 3.B.237.229; 3.B.237.230; 3.B.237.231;
3.B.237.236; 3.B.237.237; 3.B.237.238; 3.B.237.239; 3.B.237.154; 3.B.237.157; 3.B.237.166;
3.B.237.169; 3.B.237.172; 3.B.237.175; 3.B.237.240; 3.B.237.244; 3.B.238.228; 3.B.238.229;
3.B.238.230; 3.B.238.231; 3.B.238.236; 3.B.238.237; 3.B.238.238; 3.B.238.239; 3.B.238.154;
3.B.238.157; 3.B.238.166; 3.B.238.169; 3.B.238.172; 3.B.238.175; 3.B.238.240; 3.B.238.244;
3.B.239.228; 3.B.239.229; 3.B.239.230; 3.B.239.231; 3.B.239.236; 3.B.239.237; 3.B.239.238;
3.B.239.239; 3.B.239.154; 3.B.239.157; 3.B.239.166; 3.B.239.169; 3.B.239.172; 3.B.239.175;
3.B.239.240; 3.B.239.244; 3.B.154.228; 3.B.154.229; 3.B.154.230; 3.B.154.231; 3.B.154.236;
3.B.154.237; 3.B.154.238; 3.B.154.239; 3.B.154.154; 3.B.154.157; 3.B.154.166; 3.B.154.169;
3.B.154.172; 3.B.154.175; 3.B.154.240; 3.B.154.244; 3.B.157.228; 3.B.157.229; 3.B.157.230;
3.B.157.231; 3.B.157.236; 3.B.157.237; 3.B.157.238; 3.B.157.239; 3.B.157.154; 3.B.157.157;
3.B.157.166; 3.B.157.169; 3.B.157.172; 3.B.157.175; 3.B.157.240; 3.B.157.244; 3.B.166.228;
3.B.166.229; 3.B.166.230; 3.B.166.231; 3.B.166.236; 3.B.166.237; 3.B.166.238; 3.B.166.239;
3.B.166.154; 3.B.166.157; 3.B.166.166; 3.B.166.169; 3.B.166.172; 3.B.166.175; 3.B.166.240;
3.B.166.244; 3.B.169.228; 3.B.169.229; 3.B.169.230; 3.B.169.231; 3.B.169.236; 3.B.169.237;
3.B.169.238; 3.B.169.239; 3.B.169.154; 3.B.169.157; 3.B.169.166; 3.B.169.169; 3.B.169.172;
3.B.169.175; 3.B.169.240; 3.B.169.244; 3.B.172.228; 3.B.172.229; 3.B.172.230; 3.B.172.231;
3.B.172.236; 3.B.172.237; 3.B.172.238; 3.B.172.239; 3.B.172.154; 3.B.172.157; 3.B.172.166;
3.B.172.169; 3.B.172.172; 3.B.172.175; 3.B.172.240; 3.B.172.244; 3.B.175.228; 3.B.175.229;
3.B.175.230; 3.B.175.231; 3.B.175.236; 3.B.175.237; 3.B.175.238; 3.B.175.239; 3.B.175.154;
3.B.175.157; 3.B.175.166; 3.B.175.169; 3.B.175.172; 3.B.175.175; 3.B.175.240; 3.B.175.244;
3.B.240.228; 3.B.240.229; 3.B.240.230; 3.B.240.231; 3.B.240.236; 3.B.240.237; 3.B.240.238;
3.B.240.239; 3.B.240.154; 3.B.240.157; 3.B.240.166; 3.B.240.169; 3.B.240.172; 3.B.240.175;
3.B.240.240; 3.B.240.244; 3.B.244.228; 3.B.244.229; 3.B.244.230; 3.B.244.231; 3.B.244.236;
3.B.244.237; 3.B.244.238; 3.B.244.239; 3.B.244.154; 3.B.244.157; 3.B.244.166; 3.B.244.169;
3.B.244.172; 3.B.244.175; 3.B.244.240; 3.B.244.244;
Prodrugs of 3.D 3.D.228.228; 3.D.228.229; 3.D.228.230; 3.D.228.231; 3.D.228.236; 3.D.228.237;
3.D.228.238; 3.D.228.239; 3.D.228.154; 3.D.228.157; 3.D.228.166; 3.D.228.169; 3.D.228.172;
3.D.228.175; 3.D.228.240; 3.D.228.244; 3.D.229.228; 3.D.229.229; 3.D.229.230; 3.D.229.231;
3.D.229.236; 3.D.229.237; 3.D.229.238; 3.D.229.239; 3.D.229.154; 3.D.229.157; 3.D.229.166;
3.D.229.169; 3.D.229.172; 3.D.229.175; 3.D.229.240; 3.D.229.244; 3.D.230.228; 3.D.230.229;
3.D.230.230; 3.D.230.231; 3.D.230.236; 3.D.230.237; 3.D.230.238; 3.D.230.239; 3.D.230.154;
3.D.230.157; 3.D.230.166; 3.D.230.169; 3.D.230.172; 3.D.230.175; 3.D.230.240; 3.D.230.244;
3.D.231.228; 3.D.231.229; 3.D.231.230; 3.D.231.231; 3.D.231.236; 3.D.231.237; 3.D.231.238;
3.D.231.239; 3.D.231.154; 3.D.231.157; 3.D.231.166; 3.D.231.169; 3.D.231.172; 3.D.231.175;
3.D.231.240; 3.D.231.244; 3.D.236.228; 3.D.236.229; 3.D.236.230; 3.D.236.231; 3.D.236.236;
3.D.236.237; 3.D.236.238; 3.D.236.239; 3.D.236.154; 3.D.236.157; 3.D.236.166; 3.D.236.169;
3.D.236.172; 3.D.236.175; 3.D.236.240; 3.D.236.244; 3.D.237.228; 3.D.237.229; 3.D.237.230;
3.D.237.231; 3.D.237.236; 3.D.237.237; 3.D.237.238; 3.D.237.239; 3.D.237.154; 3.D.237.157;
3.D.237.166; 3.D.237.169; 3.D.237.172; 3.D.237.175; 3.D.237.240; 3.D.237.244; 3.D.238.228;
3.D.238.229; 3.D.238.230; 3.D.238.231; 3.D.238.236; 3.D.238.237; 3.D.238.238; 3.D.238.239;
3.D.238.154; 3.D.238.157; 3.D.238.166; 3.D.238.169; 3.D.238.172; 3.D.238.175; 3.D.238.240;
3.D.238.244; 3.D.239.228; 3.D.239.229; 3.D.239.230; 3.D.239.231; 3.D.239.236; 3.D.239.237;
3.D.239.238; 3.D.239.239; 3.D.239.154; 3.D.239.157; 3.D.239.166; 3.D.239.169; 3.D.239.172;
3.D.239.175; 3.D.239.240; 3.D.239.244; 3.D.154.228; 3.D.154.229; 3.D.154.230; 3.D.154.231;
3.D.154.236; 3.D.154.237; 3.D.154.238; 3.D.154.239; 3.D.154.154; 3.D.154.157; 3.D.154.166;
3.D.154.169; 3.D.154.172; 3.D.154.175; 3.D.154.240; 3.D.154.244; 3.D.157.228; 3.D.157.229;
3.D.157.230; 3.D.157.231; 3.D.157.236; 3.D.157.237; 3.D.157.238; 3.D.157.239; 3.D.157.154;
3.D.157.157; 3.D.157.166; 3.D.157.169; 3.D.157.172; 3.D.157.175; 3.D.157.240; 3.D.157.244;
3.D.166.228; 3.D.166.229; 3.D.166.230; 3.D.166.231; 3.D.166.236; 3.D.166.237; 3.D.166.238;
3.D.166.239; 3.D.166.154; 3.D.166.157; 3.D.166.166; 3.D.166.169; 3.D.166.172; 3.D.166.175;
3.D.166.240; 3.D.166.244; 3.D.169.228; 3.D.169.229; 3.D.169.230; 3.D.169.231; 3.D.169.236;
3.D.169.237; 3.D.169.238; 3.D.169.239; 3.D.169.154; 3.D.169.157; 3.D.169.166; 3.D.169.169;
3.D.169.172; 3.D.169.175; 3.D.169.240; 3.D.169.244; 3.D.172.228; 3.D.172.229; 3.D.172.230;
3.D.172.231; 3.D.172.236; 3.D.172.237; 3.D.172.238; 3.D.172.239; 3.D.172.154; 3.D.172.157;
3.D.172.166; 3.D.172.169; 3.D.172.172; 3.D.172.175; 3.D.172.240; 3.D.172.244; 3.D.175.228;
3.D.175.229; 3.D.175.230; 3.D.175.231; 3.D.175.236; 3.D.175.237; 3.D.175.238; 3.D.175.239;
3.D.175.154; 3.D.175.157; 3.D.175.166; 3.D.175.169; 3.D.175.172; 3.D.175.175; 3.D.175.240;
3.D.175.244; 3.D.240.228; 3.D.240.229; 3.D.240.230; 3.D.240.231; 3.D.240.236; 3.D.240.237;
3.D.240.238; 3.D.240.239; 3.D.240.154; 3.D.240.157; 3.D.240.166; 3.D.240.169; 3.D.240.172;
3.D.240.175; 3.D.240.240; 3.D.240.244; 3.D.244.228; 3.D.244.229; 3.D.244.230; 3.D.244.231;
3.D.244.236; 3.D.244.237; 3.D.244.238; 3.D.244.239; 3.D.244.154; 3.D.244.157; 3.D.244.166;
3.D.244.169; 3.D.244.172; 3.D.244.175; 3.D.244.240; 3.D.244.244;
Prodrugs of 3.E 3.E.228.228; 3.E.228.229; 3.E.228.230; 3.E.228.231; 3.E.228.236; 3.E.228.237; 3.E.228.238;
3.E.228.239; 3.E.228.154; 3.E.228.157; 3.E.228.166; 3.E.228.169; 3.E.228.172; 3.E.228.175;
3.E.228.240; 3.E.228.244; 3.E.229.228; 3.E.229.229; 3.E.229.230; 3.E.229.231; 3.E.229.236;
3.E.229.237; 3.E.229.238; 3.E.229.239; 3.E.229.154; 3.E.229.157; 3.E.229.166; 3.E.229.169;
3.E.229.172; 3.E.229.175; 3.E.229.240; 3.E.229.244; 3.E.230.228; 3.E.230.229; 3.E.230.230;

TABLE 100-continued

3.E.230.231; 3.E.230.236; 3.E.230.237; 3.E.230.238; 3.E.230.239; 3.E.230.154; 3.E.230.157; 3.E.230.166; 3.E.230.169; 3.E.230.172; 3.E.230.175; 3.E.230.240; 3.E.230.244; 3.E.231.228; 3.E.231.229; 3.E.231.230; 3.E.231.231; 3.E.231.236; 3.E.231.237; 3.E.231.238; 3.E.231.239; 3.E.231.154; 3.E.231.157; 3.E.231.166; 3.E.231.169; 3.E.231.172; 3.E.231.175; 3.E.231.240; 3.E.231.244; 3.E.236.228; 3.E.236.229; 3.E.236.230; 3.E.236.231; 3.E.236.236; 3.E.236.237; 3.E.236.238; 3.E.236.239; 3.E.236.154; 3.E.236.157; 3.E.236.166; 3.E.236.169; 3.E.236.172; 3.E.236.175; 3.E.236.240; 3.E.236.244; 3.E.237.228; 3.E.237.229; 3.E.237.230; 3.E.237.231; 3.E.237.236; 3.E.237.237; 3.E.237.238; 3.E.237.239; 3.E.237.154; 3.E.237.157; 3.E.237.166; 3.E.237.169; 3.E.237.172; 3.E.237.175; 3.E.237.240; 3.E.237.244; 3.E.238.228; 3.E.238.229; 3.E.238.230; 3.E.238.231; 3.E.238.236; 3.E.238.237; 3.E.238.238; 3.E.238.239; 3.E.238.154; 3.E.238.157; 3.E.238.166; 3.E.238.169; 3.E.238.172; 3.E.238.175; 3.E.238.240; 3.E.238.244; 3.E.239.228; 3.E.239.229; 3.E.239.230; 3.E.239.231; 3.E.239.236; 3.E.239.237; 3.E.239.238; 3.E.239.239; 3.E.239.154; 3.E.239.157; 3.E.239.166; 3.E.239.169; 3.E.239.172; 3.E.239.175; 3.E.239.240; 3.E.239.244; 3.E.154.228; 3.E.154.229; 3.E.154.230; 3.E.154.231; 3.E.154.236; 3.E.154.237; 3.E.154.238; 3.E.154.239; 3.E.154.154; 3.E.154.157; 3.E.154.166; 3.E.154.169; 3.E.154.172; 3.E.154.175; 3.E.154.240; 3.E.154.244; 3.E.157.228; 3.E.157.229; 3.E.157.230; 3.E.157.231; 3.E.157.236; 3.E.157.237; 3.E.157.238; 3.E.157.239; 3.E.157.154; 3.E.157.157; 3.E.157.166; 3.E.157.169; 3.E.157.172; 3.E.157.175; 3.E.157.240; 3.E.157.244; 3.E.166.228; 3.E.166.229; 3.E.166.230; 3.E.166.231; 3.E.166.236; 3.E.166.237; 3.E.166.238; 3.E.166.239; 3.E.166.154; 3.E.166.157; 3.E.166.166; 3.E.166.169; 3.E.166.172; 3.E.166.175; 3.E.166.240; 3.E.166.244; 3.E.169.228; 3.E.169.229; 3.E.169.230; 3.E.169.231; 3.E.169.236; 3.E.169.237; 3.E.169.238; 3.E.169.239; 3.E.169.154; 3.E.169.157; 3.E.169.166; 3.E.169.169; 3.E.169.172; 3.E.169.175; 3.E.169.240; 3.E.169.244; 3.E.172.228; 3.E.172.229; 3.E.172.230; 3.E.172.231; 3.E.172.236; 3.E.172.237; 3.E.172.238; 3.E.172.239; 3.E.172.154; 3.E.172.157; 3.E.172.166; 3.E.172.169; 3.E.172.172; 3.E.172.175; 3.E.172.240; 3.E.172.244; 3.E.175.228; 3.E.175.229; 3.E.175.230; 3.E.175.231; 3.E.175.236; 3.E.175.237; 3.E.175.238; 3.E.175.239; 3.E.175.154; 3.E.175.157; 3.E.175.166; 3.E.175.169; 3.E.175.172; 3.E.175.175; 3.E.175.240; 3.E.175.244; 3.E.240.228; 3.E.240.229; 3.E.240.230; 3.E.240.231; 3.E.240.236; 3.E.240.237; 3.E.240.238; 3.E.240.239; 3.E.240.154; 3.E.240.157; 3.E.240.166; 3.E.240.169; 3.E.240.172; 3.E.240.175; 3.E.240.240; 3.E.240.244; 3.E.244.228; 3.E.244.229; 3.E.244.230; 3.E.244.231; 3.E.244.236; 3.E.244.237; 3.E.244.238; 3.E.244.239; 3.E.244.154; 3.E.244.157; 3.E.244.166; 3.E.244.169; 3.E.244.172; 3.E.244.175; 3.E.244.240; 3.E.244.244;
Prodrugs of 3.G 3.G.228.228; 3.G.228.229; 3.G.228.230; 3.G.228.231; 3.G.228.236; 3.G.228.237; 3.G.228.238; 3.G.228.239; 3.G.228.154; 3.G.228.157; 3.G.228.166; 3.G.228.169; 3.G.228.172; 3.G.228.175; 3.G.228.240; 3.G.228.244; 3.G.229.228; 3.G.229.229; 3.G.229.230; 3.G.229.231; 3.G.229.236; 3.G.229.237; 3.G.229.238; 3.G.229.239; 3.G.229.154; 3.G.229.157; 3.G.229.166; 3.G.229.169; 3.G.229.172; 3.G.229.175; 3.G.229.240; 3.G.229.244; 3.G.230.228; 3.G.230.229; 3.G.230.230; 3.G.230.231; 3.G.230.236; 3.G.230.237; 3.G.230.238; 3.G.230.239; 3.G.230.154; 3.G.230.157; 3.G.230.166; 3.G.230.169; 3.G.230.172; 3.G.230.175; 3.G.230.240; 3.G.230.244; 3.G.231.228; 3.G.231.229; 3.G.231.230; 3.G.231.231; 3.G.231.236; 3.G.231.237; 3.G.231.238; 3.G.231.239; 3.G.231.154; 3.G.231.157; 3.G.231.166; 3.G.231.169; 3.G.231.172; 3.G.231.175; 3.G.231.240; 3.G.231.244; 3.G.236.228; 3.G.236.229; 3.G.236.230; 3.G.236.231; 3.G.236.236; 3.G.236.237; 3.G.236.238; 3.G.236.239; 3.G.236.154; 3.G.236.157; 3.G.236.166; 3.G.236.169; 3.G.236.172; 3.G.236.175; 3.G.236.240; 3.G.236.244; 3.G.237.228; 3.G.237.229; 3.G.237.230; 3.G.237.231; 3.G.237.236; 3.G.237.237; 3.G.237.238; 3.G.237.239; 3.G.237.154; 3.G.237.157; 3.G.237.166; 3.G.237.169; 3.G.237.172; 3.G.237.175; 3.G.237.240; 3.G.237.244; 3.G.238.228; 3.G.238.229; 3.G.238.230; 3.G.238.231; 3.G.238.236; 3.G.238.237; 3.G.238.238; 3.G.238.239; 3.G.238.154; 3.G.238.157; 3.G.238.166; 3.G.238.169; 3.G.238.172; 3.G.238.175; 3.G.238.240; 3.G.238.244; 3.G.239.228; 3.G.239.229; 3.G.239.230; 3.G.239.231; 3.G.239.236; 3.G.239.237; 3.G.239.238; 3.G.239.239; 3.G.239.154; 3.G.239.157; 3.G.239.166; 3.G.239.169; 3.G.239.172; 3.G.239.175; 3.G.239.240; 3.G.239.244; 3.G.154.228; 3.G.154.229; 3.G.154.230; 3.G.154.231; 3.G.154.236; 3.G.154.237; 3.G.154.238; 3.G.154.239; 3.G.154.154; 3.G.154.157; 3.G.154.166; 3.G.154.169; 3.G.154.172; 3.G.154.175; 3.G.154.240; 3.G.154.244; 3.G.157.228; 3.G.157.229; 3.G.157.230; 3.G.157.231; 3.G.157.236; 3.G.157.237; 3.G.157.238; 3.G.157.239; 3.G.157.154; 3.G.157.157; 3.G.157.166; 3.G.157.169; 3.G.157.172; 3.G.157.175; 3.G.157.240; 3.G.157.244; 3.G.166.228; 3.G.166.229; 3.G.166.230; 3.G.166.231; 3.G.166.236; 3.G.166.237; 3.G.166.238; 3.G.166.239; 3.G.166.154; 3.G.166.157; 3.G.166.166; 3.G.166.169; 3.G.166.172; 3.G.166.175; 3.G.166.240; 3.G.166.244; 3.G.169.228; 3.G.169.229; 3.G.169.230; 3.G.169.231; 3.G.169.236; 3.G.169.237; 3.G.169.238; 3.G.169.239; 3.G.169.154; 3.G.169.157; 3.G.169.166; 3.G.169.169; 3.G.169.172; 3.G.169.175; 3.G.169.240; 3.G.169.244; 3.G.172.228; 3.G.172.229; 3.G.172.230; 3.G.172.231; 3.G.172.236; 3.G.172.237; 3.G.172.238; 3.G.172.239; 3.G.172.154; 3.G.172.157; 3.G.172.166; 3.G.172.169; 3.G.172.172; 3.G.172.175; 3.G.172.240; 3.G.172.244; 3.G.175.228; 3.G.175.229; 3.G.175.230; 3.G.175.231; 3.G.175.236; 3.G.175.237; 3.G.175.238; 3.G.175.239; 3.G.175.154; 3.G.175.157; 3.G.175.166; 3.G.175.169; 3.G.175.172; 3.G.175.175; 3.G.175.240; 3.G.175.244; 3.G.240.228; 3.G.240.229; 3.G.240.230; 3.G.240.231; 3.G.240.236; 3.G.240.237; 3.G.240.238; 3.G.240.239; 3.G.240.154; 3.G.240.157; 3.G.240.166; 3.G.240.169; 3.G.240.172; 3.G.240.175; 3.G.240.240; 3.G.240.244; 3.G.244.228; 3.G.244.229; 3.G.244.230; 3.G.244.231; 3.G.244.236; 3.G.244.237; 3.G.244.238; 3.G.244.239; 3.G.244.154; 3.G.244.157; 3.G.244.166; 3.G.244.169; 3.G.244.172; 3.G.244.175; 3.G.244.240; 3.G.244.244;
Prodrugs of 3.I 3.I.228.228; 3.I.228.229; 3.I.228.230; 3.I.228.231; 3.I.228.236; 3.I.228.237; 3.I.228.238; 3.I.228.239; 3.I.228.154; 3.I.228.157; 3.I.228.166; 3.I.228.169; 3.I.228.172; 3.I.228.175; 3.I.228.240; 3.I.228.244; 3.I.229.228; 3.I.229.229; 3.I.229.230; 3.I.229.231; 3.I.229.236; 3.I.229.237; 3.I.229.238; 3.I.229.239; 3.I.229.154; 3.I.229.157; 3.I.229.166; 3.I.229.169; 3.I.229.172; 3.I.229.175; 3.I.229.240; 3.I.229.244; 3.I.230.228; 3.I.230.229; 3.I.230.230; 3.I.230.231; 3.I.230.236; 3.I.230.237; 3.I.230.238; 3.I.230.239; 3.I.230.154; 3.I.230.157;

TABLE 100-continued

3.I.230.166; 3.I.230.169; 3.I.230.172; 3.I.230.175; 3.I.230.240; 3.I.230.244; 3.I.231.228;
3.I.231.229; 3.I.231.230; 3.I.231.231; 3.I.231.236; 3.I.231.237; 3.I.231.238; 3.I.231.239;
3.I.231.154; 3.I.231.157; 3.I.231.166; 3.I.231.169; 3.I.231.172; 3.I.231.175; 3.I.231.240;
3.I.231.244; 3.I.236.228; 3.I.236.229; 3.I.236.230; 3.I.236.231; 3.I.236.236; 3.I.236.237;
3.I.236.238; 3.I.236.239; 3.I.236.154; 3.I.236.157; 3.I.236.166; 3.I.236.169; 3.I.236.172;
3.I.236.175; 3.I.236.240; 3.I.236.244; 3.I.237.228; 3.I.237.229; 3.I.237.230; 3.I.237.231;
3.I.237.236; 3.I.237.237; 3.I.237.238; 3.I.237.239; 3.I.237.154; 3.I.237.157; 3.I.237.166;
3.I.237.169; 3.I.237.172; 3.I.237.175; 3.I.237.240; 3.I.237.244; 3.I.238.228; 3.I.238.229;
3.I.238.230; 3.I.238.231; 3.I.238.236; 3.I.238.237; 3.I.238.238; 3.I.238.239; 3.I.238.154;
3.I.238.157; 3.I.238.166; 3.I.238.169; 3.I.238.172; 3.I.238.175; 3.I.238.240; 3.I.238.244;
3.I.239.228; 3.I.239.229; 3.I.239.230; 3.I.239.231; 3.I.239.236; 3.I.239.237; 3.I.239.238;
3.I.239.239; 3.I.239.154; 3.I.239.157; 3.I.239.166; 3.I.239.169; 3.I.239.172; 3.I.239.175;
3.I.239.240; 3.I.239.244; 3.I.154.228; 3.I.154.229; 3.I.154.230; 3.I.154.231; 3.I.154.236;
3.I.154.237; 3.I.154.238; 3.I.154.239; 3.I.154.154; 3.I.154.157; 3.I.154.166; 3.I.154.169;
3.I.154.172; 3.I.154.175; 3.I.154.240; 3.I.154.244; 3.I.157.228; 3.I.157.229; 3.I.157.230;
3.I.157.231; 3.I.157.236; 3.I.157.237; 3.I.157.238; 3.I.157.239; 3.I.157.154; 3.I.157.157;
3.I.157.166; 3.I.157.169; 3.I.157.172; 3.I.157.175; 3.I.157.240; 3.I.157.244; 3.I.166.228;
3.I.166.229; 3.I.166.230; 3.I.166.231; 3.I.166.236; 3.I.166.237; 3.I.166.238; 3.I.166.239;
3.I.166.154; 3.I.166.157; 3.I.166.166; 3.I.166.169; 3.I.166.172; 3.I.166.175; 3.I.166.240;
3.I.166.244; 3.I.169.228; 3.I.169.229; 3.I.169.230; 3.I.169.231; 3.I.169.236; 3.I.169.237;
3.I.169.238; 3.I.169.239; 3.I.169.154; 3.I.169.157; 3.I.169.166; 3.I.169.169; 3.I.169.172;
3.I.169.175; 3.I.169.240; 3.I.169.244; 3.I.172.228; 3.I.172.229; 3.I.172.230; 3.I.172.231;
3.I.172.236; 3.I.172.237; 3.I.172.238; 3.I.172.239; 3.I.172.154; 3.I.172.157; 3.I.172.166;
3.I.172.169; 3.I.172.172; 3.I.172.175; 3.I.172.240; 3.I.172.244; 3.I.175.228; 3.I.175.229;
3.I.175.230; 3.I.175.231; 3.I.175.236; 3.I.175.237; 3.I.175.238; 3.I.175.239; 3.I.175.154;
3.I.175.157; 3.I.175.166; 3.I.175.169; 3.I.175.172; 3.I.175.175; 3.I.175.240; 3.I.175.244;
3.I.240.228; 3.I.240.229; 3.I.240.230; 3.I.240.231; 3.I.240.236; 3.I.240.237; 3.I.240.238;
3.I.240.239; 3.I.240.154; 3.I.240.157; 3.I.240.166; 3.I.240.169; 3.I.240.172; 3.I.240.175;
3.I.240.240; 3.I.240.244; 3.I.244.228; 3.I.244.229; 3.I.244.230; 3.I.244.231; 3.I.244.236;
3.I.244.237; 3.I.244.238; 3.I.244.239; 3.I.244.154; 3.I.244.157; 3.I.244.166; 3.I.244.169;
3.I.244.172; 3.I.244.175; 3.I.244.240; 3.I.244.244;
Prodrugs of 3.J 3.J.228.228; 3.J.228.229; 3.J.228.230; 3.J.228.231; 3.J.228.236; 3.J.228.237; 3.J.228.238;
3.J.228.239; 3.J.228.154; 3.J.228.157; 3.J.228.166; 3.J.228.169; 3.J.228.172; 3.J.228.175;
3.J.228.240; 3.J.228.244; 3.J.229.228; 3.J.229.229; 3.J.229.230; 3.J.229.231; 3.J.229.236;
3.J.229.237; 3.J.229.238; 3.J.229.239; 3.J.229.154; 3.J.229.157; 3.J.229.166; 3.J.229.169;
3.J.229.172; 3.J.229.175; 3.J.229.240; 3.J.229.244; 3.J.230.228; 3.J.230.229; 3.J.230.230;
3.J.230.231; 3.J.230.236; 3.J.230.237; 3.J.230.238; 3.J.230.239; 3.J.230.154; 3.J.230.157;
3.J.230.166; 3.J.230.169; 3.J.230.172; 3.J.230.175; 3.J.230.240; 3.J.230.244; 3.J.231.228;
3.J.231.229; 3.J.231.230; 3.J.231.231; 3.J.231.236; 3.J.231.237; 3.J.231.238; 3.J.231.239;
3.J.231.154; 3.J.231.157; 3.J.231.166; 3.J.231.169; 3.J.231.172; 3.J.231.175; 3.J.231.240;
3.J.231.244; 3.J.236.228; 3.J.236.229; 3.J.236.230; 3.J.236.231; 3.J.236.236; 3.J.236.237;
3.J.236.238; 3.J.236.239; 3.J.236.154; 3.J.236.157; 3.J.236.166; 3.J.236.169; 3.J.236.172;
3.J.236.175; 3.J.236.240; 3.J.236.244; 3.J.237.228; 3.J.237.229; 3.J.237.230; 3.J.237.231;
3.J.237.236; 3.J.237.237; 3.J.237.238; 3.J.237.239; 3.J.237.154; 3.J.237.157; 3.J.237.166;
3.J.237.169; 3.J.237.172; 3.J.237.175; 3.J.237.240; 3.J.237.244; 3.J.238.228; 3.J.238.229;
3.J.238.230; 3.J.238.231; 3.J.238.236; 3.J.238.237; 3.J.238.238; 3.J.238.239; 3.J.238.154;
3.J.238.157; 3.J.238.166; 3.J.238.169; 3.J.238.172; 3.J.238.175; 3.J.238.240; 3.J.238.244;
3.J.239.228; 3.J.239.229; 3.J.239.230; 3.J.239.231; 3.J.239.236; 3.J.239.237; 3.J.239.238;
3.J.239.239; 3.J.239.154; 3.J.239.157; 3.J.239.166; 3.J.239.169; 3.J.239.172; 3.J.239.175;
3.J.239.240; 3.J.239.244; 3.J.154.228; 3.J.154.229; 3.J.154.230; 3.J.154.231; 3.J.154.236;
3.J.154.237; 3.J.154.238; 3.J.154.239; 3.J.154.154; 3.J.154.157; 3.J.154.166; 3.J.154.169;
3.J.154.172; 3.J.154.175; 3.J.154.240; 3.J.154.244; 3.J.157.228; 3.J.157.229; 3.J.157.230;
3.J.157.231; 3.J.157.236; 3.J.157.237; 3.J.157.238; 3.J.157.239; 3.J.157.154; 3.J.157.157;
3.J.157.166; 3.J.157.169; 3.J.157.172; 3.J.157.175; 3.J.157.240; 3.J.157.244; 3.J.166.228;
3.J.166.229; 3.J.166.230; 3.J.166.231; 3.J.166.236; 3.J.166.237; 3.J.166.238; 3.J.166.239;
3.J.166.154; 3.J.166.157; 3.J.166.166; 3.J.166.169; 3.J.166.172; 3.J.166.175; 3.J.166.240;
3.J.166.244; 3.J.169.228; 3.J.169.229; 3.J.169.230; 3.J.169.231; 3.J.169.236; 3.J.169.237;
3.J.169.238; 3.J.169.239; 3.J.169.154; 3.J.169.157; 3.J.169.166; 3.J.169.169; 3.J.169.172;
3.J.169.175; 3.J.169.240; 3.J.169.244; 3.J.172.228; 3.J.172.229; 3.J.172.230; 3.J.172.231;
3.J.172.236; 3.J.172.237; 3.J.172.238; 3.J.172.239; 3.J.172.154; 3.J.172.157; 3.J.172.166;
3.J.172.169; 3.J.172.172; 3.J.172.175; 3.J.172.240; 3.J.172.244; 3.J.175.228; 3.J.175.229;
3.J.175.230; 3.J.175.231; 3.J.175.236; 3.J.175.237; 3.J.175.238; 3.J.175.239; 3.J.175.154;
3.J.175.157; 3.J.175.166; 3.J.175.169; 3.J.175.172; 3.J.175.175; 3.J.175.240; 3.J.175.244;
3.J.240.228; 3.J.240.229; 3.J.240.230; 3.J.240.231; 3.J.240.236; 3.J.240.237; 3.J.240.238;
3.J.240.239; 3.J.240.154; 3.J.240.157; 3.J.240.166; 3.J.240.169; 3.J.240.172; 3.J.240.175;
3.J.240.240; 3.J.240.244; 3.J.244.228; 3.J.244.229; 3.J.244.230; 3.J.244.231; 3.J.244.236;
3.J.244.237; 3.J.244.238; 3.J.244.239; 3.J.244.154; 3.J.244.157; 3.J.244.166; 3.J.244.169;
3.J.244.172; 3.J.244.175; 3.J.244.240; 3.J.244.244;
Prodrugs of 3.L 3.L.228.228; 3.L.228.229; 3.L.228.230; 3.L.228.231; 3.L.228.236; 3.L.228.237; 3.L.228.238;
3.L.228.239; 3.L.228.154; 3.L.228.157; 3.L.228.166; 3.L.228.169; 3.L.228.172; 3.L.228.175;
3.L.228.240; 3.L.228.244; 3.L.229.228; 3.L.229.229; 3.L.229.230; 3.L.229.231; 3.L.229.236;
3.L.229.237; 3.L.229.238; 3.L.229.239; 3.L.229.154; 3.L.229.157; 3.L.229.166; 3.L.229.169;
3.L.229.172; 3.L.229.175; 3.L.229.240; 3.L.229.244; 3.L.230.228; 3.L.230.229; 3.L.230.230;
3.L.230.231; 3.L.230.236; 3.L.230.237; 3.L.230.238; 3.L.230.239; 3.L.230.154; 3.L.230.157;
3.L.230.166; 3.L.230.169; 3.L.230.172; 3.L.230.175; 3.L.230.240; 3.L.230.244; 3.L.231.228;

TABLE 100-continued

3.L.231.229; 3.L.231.230; 3.L.231.231; 3.L.231.236; 3.L.231.237; 3.L.231.238; 3.L.231.239;
3.L.231.154; 3.L.231.157; 3.L.231.166; 3.L.231.169; 3.L.231.172; 3.L.231.175; 3.L.231.240;
3.L.231.244; 3.L.236.228; 3.L.236.229; 3.L.236.230; 3.L.236.231; 3.L.236.236; 3.L.236.237;
3.L.236.238; 3.L.236.239; 3.L.236.154; 3.L.236.157; 3.L.236.166; 3.L.236.169; 3.L.236.172;
3.L.236.175; 3.L.236.240; 3.L.236.244; 3.L.237.228; 3.L.237.229; 3.L.237.230; 3.L.237.231;
3.L.237.236; 3.L.237.237; 3.L.237.238; 3.L.237.239; 3.L.237.154; 3.L.237.157; 3.L.237.166;
3.L.237.169; 3.L.237.172; 3.L.237.175; 3.L.237.240; 3.L.237.244; 3.L.238.228; 3.L.238.229;
3.L.238.230; 3.L.238.231; 3.L.238.236; 3.L.238.237; 3.L.238.238; 3.L.238.239; 3.L.238.154;
3.L.238.157; 3.L.238.166; 3.L.238.169; 3.L.238.172; 3.L.238.175; 3.L.238.240; 3.L.238.244;
3.L.239.228; 3.L.239.229; 3.L.239.230; 3.L.239.231; 3.L.239.236; 3.L.239.237; 3.L.239.238;
3.L.239.239; 3.L.239.154; 3.L.239.157; 3.L.239.166; 3.L.239.169; 3.L.239.172; 3.L.239.175;
3.L.239.240; 3.L.239.244; 3.L.154.228; 3.L.154.229; 3.L.154.230; 3.L.154.231; 3.L.154.236;
3.L.154.237; 3.L.154.238; 3.L.154.239; 3.L.154.154; 3.L.154.157; 3.L.154.166; 3.L.154.169;
3.L.154.172; 3.L.154.175; 3.L.154.240; 3.L.154.244; 3.L.157.228; 3.L.157.229; 3.L.157.230;
3.L.157.231; 3.L.157.236; 3.L.157.237; 3.L.157.238; 3.L.157.239; 3.L.157.154; 3.L.157.157;
3.L.157.166; 3.L.157.169; 3.L.157.172; 3.L.157.175; 3.L.157.240; 3.L.157.244; 3.L.166.228;
3.L.166.229; 3.L.166.230; 3.L.166.231; 3.L.166.236; 3.L.166.237; 3.L.166.238; 3.L.166.239;
3.L.166.154; 3.L.166.157; 3.L.166.166; 3.L.166.169; 3.L.166.172; 3.L.166.175; 3.L.166.240;
3.L.166.244; 3.L.169.228; 3.L.169.229; 3.L.169.230; 3.L.169.231; 3.L.169.236; 3.L.169.237;
3.L.169.238; 3.L.169.239; 3.L.169.154; 3.L.169.157; 3.L.169.166; 3.L.169.169; 3.L.169.172;
3.L.169.175; 3.L.169.240; 3.L.169.244; 3.L.172.228; 3.L.172.229; 3.L.172.230; 3.L.172.231;
3.L.172.236; 3.L.172.237; 3.L.172.238; 3.L.172.239; 3.L.172.154; 3.L.172.157; 3.L.172.166;
3.L.172.169; 3.L.172.172; 3.L.172.175; 3.L.172.240; 3.L.172.244; 3.L.175.228; 3.L.175.229;
3.L.175.230; 3.L.175.231; 3.L.175.236; 3.L.175.237; 3.L.175.238; 3.L.175.239; 3.L.175.154;
3.L.175.157; 3.L.175.166; 3.L.175.169; 3.L.175.172; 3.L.175.175; 3.L.175.240; 3.L.175.244;
3.L.240.228; 3.L.240.229; 3.L.240.230; 3.L.240.231; 3.L.240.236; 3.L.240.237; 3.L.240.238;
3.L.240.239; 3.L.240.154; 3.L.240.157; 3.L.240.166; 3.L.240.169; 3.L.240.172; 3.L.240.175;
3.L.240.240; 3.L.240.244; 3.L.244.228; 3.L.244.229; 3.L.244.230; 3.L.244.231; 3.L.244.236;
3.L.244.237; 3.L.244.238; 3.L.244.239; 3.L.244.154; 3.L.244.157; 3.L.244.166; 3.L.244.169;
3.L.244.172; 3.L.244.175; 3.L.244.240; 3.L.244.244;

Prodrugs of 3.O

3.O.228.228; 3.O.228.229; 3.O.228.230; 3.O.228.231; 3.O.228.236; 3.O.228.237;
3.O.228.238; 3.O.228.239; 3.O.228.154; 3.O.228.157; 3.O.228.166; 3.O.228.169; 3.O.228.172;
3.O.228.175; 3.O.228.240; 3.O.228.244; 3.O.229.228; 3.O.229.229; 3.O.229.230; 3.O.229.231;
3.O.229.236; 3.O.229.237; 3.O.229.238; 3.O.229.239; 3.O.229.154; 3.O.229.157; 3.O.229.166;
3.O.229.169; 3.O.229.172; 3.O.229.175; 3.O.229.240; 3.O.229.244; 3.O.230.228; 3.O.230.229;
3.O.230.230; 3.O.230.231; 3.O.230.236; 3.O.230.237; 3.O.230.238; 3.O.230.239; 3.O.230.154;
3.O.230.157; 3.O.230.166; 3.O.230.169; 3.O.230.172; 3.O.230.175; 3.O.230.240; 3.O.230.244;
3.O.231.228; 3.O.231.229; 3.O.231.230; 3.O.231.231; 3.O.231.236; 3.O.231.237; 3.O.231.238;
3.O.231.239; 3.O.231.154; 3.O.231.157; 3.O.231.166; 3.O.231.169; 3.O.231.172; 3.O.231.175;
3.O.231.240; 3.O.231.244; 3.O.236.228; 3.O.236.229; 3.O.236.230; 3.O.236.231; 3.O.236.236;
3.O.236.237; 3.O.236.238; 3.O.236.239; 3.O.236.154; 3.O.236.157; 3.O.236.166; 3.O.236.169;
3.O.236.172; 3.O.236.175; 3.O.236.240; 3.O.236.244; 3.O.237.228; 3.O.237.229; 3.O.237.230;
3.O.237.231; 3.O.237.236; 3.O.237.237; 3.O.237.238; 3.O.237.239; 3.O.237.154; 3.O.237.157;
3.O.237.166; 3.O.237.169; 3.O.237.172; 3.O.237.175; 3.O.237.240; 3.O.237.244; 3.O.238.228;
3.O.238.229; 3.O.238.230; 3.O.238.231; 3.O.238.236; 3.O.238.237; 3.O.238.238; 3.O.238.239;
3.O.238.154; 3.O.238.157; 3.O.238.166; 3.O.238.169; 3.O.238.172; 3.O.238.175; 3.O.238.240;
3.O.238.244; 3.O.239.228; 3.O.239.229; 3.O.239.230; 3.O.239.231; 3.O.239.236; 3.O.239.237;
3.O.239.238; 3.O.239.239; 3.O.239.154; 3.O.239.157; 3.O.239.166; 3.O.239.169; 3.O.239.172;
3.O.239.175; 3.O.239.240; 3.O.239.244; 3.O.154.228; 3.O.154.229; 3.O.154.230; 3.O.154.231;
3.O.154.236; 3.O.154.237; 3.O.154.238; 3.O.154.239; 3.O.154.154; 3.O.154.157; 3.O.154.166;
3.O.154.169; 3.O.154.172; 3.O.154.175; 3.O.154.240; 3.O.154.244; 3.O.157.228; 3.O.157.229;
3.O.157.230; 3.O.157.231; 3.O.157.236; 3.O.157.237; 3.O.157.238; 3.O.157.239; 3.O.157.154;
3.O.157.157; 3.O.157.166; 3.O.157.169; 3.O.157.172; 3.O.157.175; 3.O.157.240; 3.O.157.244;
3.O.166.228; 3.O.166.229; 3.O.166.230; 3.O.166.231; 3.O.166.236; 3.O.166.237; 3.O.166.238;
3.O.166.239; 3.O.166.154; 3.O.166.157; 3.O.166.166; 3.O.166.169; 3.O.166.172; 3.O.166.175;
3.O.166.240; 3.O.166.244; 3.O.169.228; 3.O.169.229; 3.O.169.230; 3.O.169.231; 3.O.169.236;
3.O.169.237; 3.O.169.238; 3.O.169.239; 3.O.169.154; 3.O.169.157; 3.O.169.166; 3.O.169.169;
3.O.169.172; 3.O.169.175; 3.O.169.240; 3.O.169.244; 3.O.172.228; 3.O.172.229; 3.O.172.230;
3.O.172.231; 3.O.172.236; 3.O.172.237; 3.O.172.238; 3.O.172.239; 3.O.172.154; 3.O.172.157;
3.O.172.166; 3.O.172.169; 3.O.172.172; 3.O.172.175; 3.O.172.240; 3.O.172.244; 3.O.175.228;
3.O.175.229; 3.O.175.230; 3.O.175.231; 3.O.175.236; 3.O.175.237; 3.O.175.238; 3.O.175.239;
3.O.175.154; 3.O.175.157; 3.O.175.166; 3.O.175.169; 3.O.175.172; 3.O.175.175; 3.O.175.240;
3.O.175.244; 3.O.240.228; 3.O.240.229; 3.O.240.230; 3.O.240.231; 3.O.240.236; 3.O.240.237;
3.O.240.238; 3.O.240.239; 3.O.240.154; 3.O.240.157; 3.O.240.166; 3.O.240.169; 3.O.240.172;
3.O.240.175; 3.O.240.240; 3.O.240.244; 3.O.244.228; 3.O.244.229; 3.O.244.230; 3.O.244.231;
3.O.244.236; 3.O.244.237; 3.O.244.238; 3.O.244.239; 3.O.244.154; 3.O.244.157; 3.O.244.166;
3.O.244.169; 3.O.244.172; 3.O.244.175; 3.O.244.240; 3.O.244.244;

Prodrugs of 3.P

3.P.228.228; 3.P.228.229; 3.P.228.230; 3.P.228.231; 3.P.228.236; 3.P.228.237; 3.P.228.238;
3.P.228.239; 3.P.228.154; 3.P.228.157; 3.P.228.166; 3.P.228.169; 3.P.228.172; 3.P.228.175;
3.P.228.240; 3.P.228.244; 3.P.229.228; 3.P.229.229; 3.P.229.230; 3.P.229.231; 3.P.229.236;
3.P.229.237; 3.P.229.238; 3.P.229.239; 3.P.229.154; 3.P.229.157; 3.P.229.166; 3.P.229.169;
3.P.229.172; 3.P.229.175; 3.P.229.240; 3.P.229.244; 3.P.230.228; 3.P.230.229; 3.P.230.230;
3.P.230.231; 3.P.230.236; 3.P.230.237; 3.P.230.238; 3.P.230.239; 3.P.230.154; 3.P.230.157;
3.P.230.166; 3.P.230.169; 3.P.230.172; 3.P.230.175; 3.P.230.240; 3.P.230.244; 3.P.231.228;
3.P.231.229; 3.P.231.230; 3.P.231.231; 3.P.231.236; 3.P.231.237; 3.P.231.238; 3.P.231.239;

TABLE 100-continued

3.P.231.154; 3.P.231.157; 3.P.231.166; 3.P.231.169; 3.P.231.172; 3.P.231.175; 3.P.231.240;
3.P.231.244; 3.P.236.228; 3.P.236.229; 3.P.236.230; 3.P.236.231; 3.P.236.236; 3.P.236.237;
3.P.236.238; 3.P.236.239; 3.P.236.154; 3.P.236.157; 3.P.236.166; 3.P.236.169; 3.P.236.172;
3.P.236.175; 3.P.236.240; 3.P.236.244; 3.P.237.228; 3.P.237.229; 3.P.237.230; 3.P.237.231;
3.P.237.236; 3.P.237.237; 3.P.237.238; 3.P.237.239; 3.P.237.154; 3.P.237.157; 3.P.237.166;
3.P.237.169; 3.P.237.172; 3.P.237.175; 3.P.237.240; 3.P.237.244; 3.P.238.228; 3.P.238.229;
3.P.238.230; 3.P.238.231; 3.P.238.236; 3.P.238.237; 3.P.238.238; 3.P.238.239; 3.P.238.154;
3.P.238.157; 3.P.238.166; 3.P.238.169; 3.P.238.172; 3.P.238.175; 3.P.238.240; 3.P.238.244;
3.P.239.228; 3.P.239.229; 3.P.239.230; 3.P.239.231; 3.P.239.236; 3.P.239.237; 3.P.239.238;
3.P.239.239; 3.P.239.154; 3.P.239.157; 3.P.239.166; 3.P.239.169; 3.P.239.172; 3.P.239.175;
3.P.239.240; 3.P.239.244; 3.P.154.228; 3.P.154.229; 3.P.154.230; 3.P.154.231; 3.P.154.236;
3.P.154.237; 3.P.154.238; 3.P.154.239; 3.P.154.154; 3.P.154.157; 3.P.154.166; 3.P.154.169;
3.P.154.172; 3.P.154.175; 3.P.154.240; 3.P.154.244; 3.P.157.228; 3.P.157.229; 3.P.157.230;
3.P.157.231; 3.P.157.236; 3.P.157.237; 3.P.157.238; 3.P.157.239; 3.P.157.154; 3.P.157.157;
3.P.157.166; 3.P.157.169; 3.P.157.172; 3.P.157.175; 3.P.157.240; 3.P.157.244; 3.P.166.228;
3.P.166.229; 3.P.166.230; 3.P.166.231; 3.P.166.236; 3.P.166.237; 3.P.166.238; 3.P.166.239;
3.P.166.154; 3.P.166.157; 3.P.166.166; 3.P.166.169; 3.P.166.172; 3.P.166.175; 3.P.166.240;
3.P.166.244; 3.P.169.228; 3.P.169.229; 3.P.169.230; 3.P.169.231; 3.P.169.236; 3.P.169.237;
3.P.169.238; 3.P.169.239; 3.P.169.154; 3.P.169.157; 3.P.169.166; 3.P.169.169; 3.P.169.172;
3.P.169.175; 3.P.169.240; 3.P.169.244; 3.P.172.228; 3.P.172.229; 3.P.172.230; 3.P.172.231;
3.P.172.236; 3.P.172.237; 3.P.172.238; 3.P.172.239; 3.P.172.154; 3.P.172.157; 3.P.172.166;
3.P.172.169; 3.P.172.172; 3.P.172.175; 3.P.172.240; 3.P.172.244; 3.P.175.228; 3.P.175.229;
3.P.175.230; 3.P.175.231; 3.P.175.236; 3.P.175.237; 3.P.175.238; 3.P.175.239; 3.P.175.154;
3.P.175.157; 3.P.175.166; 3.P.175.169; 3.P.175.172; 3.P.175.175; 3.P.175.240; 3.P.175.244;
3.P.240.228; 3.P.240.229; 3.P.240.230; 3.P.240.231; 3.P.240.236; 3.P.240.237; 3.P.240.238;
3.P.240.239; 3.P.240.154; 3.P.240.157; 3.P.240.166; 3.P.240.169; 3.P.240.172; 3.P.240.175;
3.P.240.240; 3.P.240.244; 3.P.244.228; 3.P.244.229; 3.P.244.230; 3.P.244.231; 3.P.244.236;
3.P.244.237; 3.P.244.238; 3.P.244.239; 3.P.244.154; 3.P.244.157; 3.P.244.166; 3.P.244.169;
3.P.244.172; 3.P.244.175; 3.P.244.240; 3.P.244.244;
Prodrugs of 3.U 3.U.228.228; 3.U.228.229; 3.U.228.230; 3.U.228.231; 3.U.228.236; 3.U.228.237;
3.U.228.238; 3.U.228.239; 3.U.228.154; 3.U.228.157; 3.U.228.166; 3.U.228.169; 3.U.228.172;
3.U.228.175; 3.U.228.240; 3.U.228.244; 3.U.229.228; 3.U.229.229; 3.U.229.230; 3.U.229.231;
3.U.229.236; 3.U.229.237; 3.U.229.238; 3.U.229.239; 3.U.229.154; 3.U.229.157; 3.U.229.166;
3.U.229.169; 3.U.229.172; 3.U.229.175; 3.U.229.240; 3.U.229.244; 3.U.230.228; 3.U.230.229;
3.U.230.230; 3.U.230.231; 3.U.230.236; 3.U.230.237; 3.U.230.238; 3.U.230.239; 3.U.230.154;
3.U.230.157; 3.U.230.166; 3.U.230.169; 3.U.230.172; 3.U.230.175; 3.U.230.240; 3.U.230.244;
3.U.231.228; 3.U.231.229; 3.U.231.230; 3.U.231.231; 3.U.231.236; 3.U.231.237; 3.U.231.238;
3.U.231.239; 3.U.231.154; 3.U.231.157; 3.U.231.166; 3.U.231.169; 3.U.231.172; 3.U.231.175;
3.U.231.240; 3.U.231.244; 3.U.236.228; 3.U.236.229; 3.U.236.230; 3.U.236.231; 3.U.236.236;
3.U.236.237; 3.U.236.238; 3.U.236.239; 3.U.236.154; 3.U.236.157; 3.U.236.166; 3.U.236.169;
3.U.236.172; 3.U.236.175; 3.U.236.240; 3.U.236.244; 3.U.237.228; 3.U.237.229; 3.U.237.230;
3.U.237.231; 3.U.237.236; 3.U.237.237; 3.U.237.238; 3.U.237.239; 3.U.237.154; 3.U.237.157;
3.U.237.166; 3.U.237.169; 3.U.237.172; 3.U.237.175; 3.U.237.240; 3.U.237.244; 3.U.238.228;
3.U.238.229; 3.U.238.230; 3.U.238.231; 3.U.238.236; 3.U.238.237; 3.U.238.238; 3.U.238.239;
3.U.238.154; 3.U.238.157; 3.U.238.166; 3.U.238.169; 3.U.238.172; 3.U.238.175; 3.U.238.240;
3.U.238.244; 3.U.239.228; 3.U.239.229; 3.U.239.230; 3.U.239.231; 3.U.239.236; 3.U.239.237;
3.U.239.238; 3.U.239.239; 3.U.239.154; 3.U.239.157; 3.U.239.166; 3.U.239.169; 3.U.239.172;
3.U.239.175; 3.U.239.240; 3.U.239.244; 3.U.154.228; 3.U.154.229; 3.U.154.230; 3.U.154.231;
3.U.154.236; 3.U.154.237; 3.U.154.238; 3.U.154.239; 3.U.154.154; 3.U.154.157; 3.U.154.166;
3.U.154.169; 3.U.154.172; 3.U.154.175; 3.U.154.240; 3.U.154.244; 3.U.157.228; 3.U.157.229;
3.U.157.230; 3.U.157.231; 3.U.157.236; 3.U.157.237; 3.U.157.238; 3.U.157.239; 3.U.157.154;
3.U.157.157; 3.U.157.166; 3.U.157.169; 3.U.157.172; 3.U.157.175; 3.U.157.240; 3.U.157.244;
3.U.166.228; 3.U.166.229; 3.U.166.230; 3.U.166.231; 3.U.166.236; 3.U.166.237; 3.U.166.238;
3.U.166.239; 3.U.166.154; 3.U.166.157; 3.U.166.166; 3.U.166.169; 3.U.166.172; 3.U.166.175;
3.U.166.240; 3.U.166.244; 3.U.169.228; 3.U.169.229; 3.U.169.230; 3.U.169.231; 3.U.169.236;
3.U.169.237; 3.U.169.238; 3.U.169.239; 3.U.169.154; 3.U.169.157; 3.U.169.166; 3.U.169.169;
3.U.169.172; 3.U.169.175; 3.U.169.240; 3.U.169.244; 3.U.172.228; 3.U.172.229; 3.U.172.230;
3.U.172.231; 3.U.172.236; 3.U.172.237; 3.U.172.238; 3.U.172.239; 3.U.172.154; 3.U.172.157;
3.U.172.166; 3.U.172.169; 3.U.172.172; 3.U.172.175; 3.U.172.240; 3.U.172.244; 3.U.175.228;
3.U.175.229; 3.U.175.230; 3.U.175.231; 3.U.175.236; 3.U.175.237; 3.U.175.238; 3.U.175.239;
3.U.175.154; 3.U.175.157; 3.U.175.166; 3.U.175.169; 3.U.175.172; 3.U.175.175; 3.U.175.240;
3.U.175.244; 3.U.240.228; 3.U.240.229; 3.U.240.230; 3.U.240.231; 3.U.240.236; 3.U.240.237;
3.U.240.238; 3.U.240.239; 3.U.240.154; 3.U.240.157; 3.U.240.166; 3.U.240.169; 3.U.240.172;
3.U.240.175; 3.U.240.240; 3.U.240.244; 3.U.244.228; 3.U.244.229; 3.U.244.230; 3.U.244.231;
3.U.244.236; 3.U.244.237; 3.U.244.238; 3.U.244.239; 3.U.244.154; 3.U.244.157; 3.U.244.166;
3.U.244.169; 3.U.244.172; 3.U.244.175; 3.U.244.240; 3.U.244.244;
Prodrugs of 3.W 3.W.228.228; 3.W.228.229; 3.W.228.230; 3.W.228.231; 3.W.228.236; 3.W.228.237;
3.W.228.238; 3.W.228.239; 3.W.228.154; 3.W.228.157; 3.W.228.166; 3.W.228.169;
3.W.228.172; 3.W.228.175; 3.W.228.240; 3.W.228.244; 3.W.229.228; 3.W.229.229;
3.W.229.230; 3.W.229.231; 3.W.229.236; 3.W.229.237; 3.W.229.238; 3.W.229.239;
3.W.229.154; 3.W.229.157; 3.W.229.166; 3.W.229.169; 3.W.229.172; 3.W.229.175;
3.W.229.240; 3.W.229.244; 3.W.230.228; 3.W.230.229; 3.W.230.230; 3.W.230.231;
3.W.230.236; 3.W.230.237; 3.W.230.238; 3.W.230.239; 3.W.230.154; 3.W.230.157;
3.W.230.166; 3.W.230.169; 3.W.230.172; 3.W.230.175; 3.W.230.240; 3.W.230.244;
3.W.231.228; 3.W.231.229; 3.W.231.230; 3.W.231.231; 3.W.231.236; 3.W.231.237;

TABLE 100-continued

3.W.231.238; 3.W.231.239; 3.W.231.154; 3.W.231.157; 3.W.231.166; 3.W.231.169;
3.W.231.172; 3.W.231.175; 3.W.231.240; 3.W.231.244; 3.W.236.228; 3.W.236.229;
3.W.236.230; 3.W.236.231; 3.W.236.236; 3.W.236.237; 3.W.236.238; 3.W.236.239;
3.W.236.154; 3.W.236.157; 3.W.236.166; 3.W.236.169; 3.W.236.172; 3.W.236.175;
3.W.236.240; 3.W.236.244; 3.W.237.228; 3.W.237.229; 3.W.237.230; 3.W.237.231;
3.W.237.236; 3.W.237.237; 3.W.237.238; 3.W.237.239; 3.W.237.154; 3.W.237.157;
3.W.237.166; 3.W.237.169; 3.W.237.172; 3.W.237.175; 3.W.237.240; 3.W.237.244;
3.W.238.228; 3.W.238.229; 3.W.238.230; 3.W.238.231; 3.W.238.236; 3.W.238.237;
3.W.238.238; 3.W.238.239; 3.W.238.154; 3.W.238.157; 3.W.238.166; 3.W.238.169;
3.W.238.172; 3.W.238.175; 3.W.238.240; 3.W.238.244; 3.W.239.228; 3.W.239.229;
3.W.239.230; 3.W.239.231; 3.W.239.236; 3.W.239.237; 3.W.239.238; 3.W.239.239;
3.W.239.154; 3.W.239.157; 3.W.239.166; 3.W.239.169; 3.W.239.172; 3.W.239.175;
3.W.239.240; 3.W.239.244; 3.W.154.228; 3.W.154.229; 3.W.154.230; 3.W.154.231;
3.W.154.236; 3.W.154.237; 3.W.154.238; 3.W.154.239; 3.W.154.154; 3.W.154.157;
3.W.154.166; 3.W.154.169; 3.W.154.172; 3.W.154.175; 3.W.154.240; 3.W.154.244;
3.W.157.228; 3.W.157.229; 3.W.157.230; 3.W.157.231; 3.W.157.236; 3.W.157.237;
3.W.157.238; 3.W.157.239; 3.W.157.154; 3.W.157.157; 3.W.157.166; 3.W.157.169;
3.W.157.172; 3.W.157.175; 3.W.157.240; 3.W.157.244; 3.W.166.228; 3.W.166.229;
3.W.166.230; 3.W.166.231; 3.W.166.236; 3.W.166.237; 3.W.166.238; 3.W.166.239;
3.W.166.154; 3.W.166.157; 3.W.166.166; 3.W.166.169; 3.W.166.172; 3.W.166.175;
3.W.166.240; 3.W.166.244; 3.W.169.228; 3.W.169.229; 3.W.169.230; 3.W.169.231;
3.W.169.236; 3.W.169.237; 3.W.169.238; 3.W.169.239; 3.W.169.154; 3.W.169.157;
3.W.169.166; 3.W.169.169; 3.W.169.172; 3.W.169.175; 3.W.169.240; 3.W.169.244;
3.W.172.228; 3.W.172.229; 3.W.172.230; 3.W.172.231; 3.W.172.236; 3.W.172.237;
3.W.172.238; 3.W.172.239; 3.W.172.154; 3.W.172.157; 3.W.172.166; 3.W.172.169;
3.W.172.172; 3.W.172.175; 3.W.172.240; 3.W.172.244; 3.W.175.228; 3.W.175.229;
3.W.175.230; 3.W.175.231; 3.W.175.236; 3.W.175.237; 3.W.175.238; 3.W.175.239;
3.W.175.154; 3.W.175.157; 3.W.175.166; 3.W.175.169; 3.W.175.172; 3.W.175.175;
3.W.175.240; 3.W.175.244; 3.W.240.228; 3.W.240.229; 3.W.240.230; 3.W.240.231;
3.W.240.236; 3.W.240.237; 3.W.240.238; 3.W.240.239; 3.W.240.154; 3.W.240.157;
3.W.240.166; 3.W.240.169; 3.W.240.172; 3.W.240.175; 3.W.240.240; 3.W.240.244;
3.W.244.228; 3.W.244.229; 3.W.244.230; 3.W.244.231; 3.W.244.236; 3.W.244.237;
3.W.244.238; 3.W.244.239; 3.W.244.154; 3.W.244.157; 3.W.244.166; 3.W.244.169;
3.W.244.172; 3.W.244.175; 3.W.244.240; 3.W.244.244;
Prodrugs of 3.Y 3.Y.228.228; 3.Y.228.229; 3.Y.228.230; 3.Y.228.231; 3.Y.228.236; 3.Y.228.237; 3.Y.228.238;
3.Y.228.239; 3.Y.228.154; 3.Y.228.157; 3.Y.228.166; 3.Y.228.169; 3.Y.228.172; 3.Y.228.175;
3.Y.228.240; 3.Y.228.244; 3.Y.229.228; 3.Y.229.229; 3.Y.229.230; 3.Y.229.231; 3.Y.229.236;
3.Y.229.237; 3.Y.229.238; 3.Y.229.239; 3.Y.229.154; 3.Y.229.157; 3.Y.229.166; 3.Y.229.169;
3.Y.229.172; 3.Y.229.175; 3.Y.229.240; 3.Y.229.244; 3.Y.230.228; 3.Y.230.229; 3.Y.230.230;
3.Y.230.231; 3.Y.230.236; 3.Y.230.237; 3.Y.230.238; 3.Y.230.239; 3.Y.230.154; 3.Y.230.157;
3.Y.230.166; 3.Y.230.169; 3.Y.230.172; 3.Y.230.175; 3.Y.230.240; 3.Y.230.244; 3.Y.231.228;
3.Y.231.229; 3.Y.231.230; 3.Y.231.231; 3.Y.231.236; 3.Y.231.237; 3.Y.231.238; 3.Y.231.239;
3.Y.231.154; 3.Y.231.157; 3.Y.231.166; 3.Y.231.169; 3.Y.231.172; 3.Y.231.175; 3.Y.231.240;
3.Y.231.244; 3.Y.236.228; 3.Y.236.229; 3.Y.236.230; 3.Y.236.231; 3.Y.236.236; 3.Y.236.237;
3.Y.236.238; 3.Y.236.239; 3.Y.236.154; 3.Y.236.157; 3.Y.236.166; 3.Y.236.169; 3.Y.236.172;
3.Y.236.175; 3.Y.236.240; 3.Y.236.244; 3.Y.237.228; 3.Y.237.229; 3.Y.237.230; 3.Y.237.231;
3.Y.237.236; 3.Y.237.237; 3.Y.237.238; 3.Y.237.239; 3.Y.237.154; 3.Y.237.157; 3.Y.237.166;
3.Y.237.169; 3.Y.237.172; 3.Y.237.175; 3.Y.237.240; 3.Y.237.244; 3.Y.238.228; 3.Y.238.229;
3.Y.238.230; 3.Y.238.231; 3.Y.238.236; 3.Y.238.237; 3.Y.238.238; 3.Y.238.239; 3.Y.238.154;
3.Y.238.157; 3.Y.238.166; 3.Y.238.169; 3.Y.238.172; 3.Y.238.175; 3.Y.238.240; 3.Y.238.244;
3.Y.239.228; 3.Y.239.229; 3.Y.239.230; 3.Y.239.231; 3.Y.239.236; 3.Y.239.237; 3.Y.239.238;
3.Y.239.239; 3.Y.239.154; 3.Y.239.157; 3.Y.239.166; 3.Y.239.169; 3.Y.239.172; 3.Y.239.175;
3.Y.239.240; 3.Y.239.244; 3.Y.154.228; 3.Y.154.229; 3.Y.154.230; 3.Y.154.231; 3.Y.154.236;
3.Y.154.237; 3.Y.154.238; 3.Y.154.239; 3.Y.154.154; 3.Y.154.157; 3.Y.154.166; 3.Y.154.169;
3.Y.154.172; 3.Y.154.175; 3.Y.154.240; 3.Y.154.244; 3.Y.157.228; 3.Y.157.229; 3.Y.157.230;
3.Y.157.231; 3.Y.157.236; 3.Y.157.237; 3.Y.157.238; 3.Y.157.239; 3.Y.157.154; 3.Y.157.157;
3.Y.157.166; 3.Y.157.169; 3.Y.157.172; 3.Y.157.175; 3.Y.157.240; 3.Y.157.244; 3.Y.166.228;
3.Y.166.229; 3.Y.166.230; 3.Y.166.231; 3.Y.166.236; 3.Y.166.237; 3.Y.166.238; 3.Y.166.239;
3.Y.166.154; 3.Y.166.157; 3.Y.166.166; 3.Y.166.169; 3.Y.166.172; 3.Y.166.175; 3.Y.166.240;
3.Y.166.244; 3.Y.169.228; 3.Y.169.229; 3.Y.169.230; 3.Y.169.231; 3.Y.169.236; 3.Y.169.237;
3.Y.169.238; 3.Y.169.239; 3.Y.169.154; 3.Y.169.157; 3.Y.169.166; 3.Y.169.169; 3.Y.169.172;
3.Y.169.175; 3.Y.169.240; 3.Y.169.244; 3.Y.172.228; 3.Y.172.229; 3.Y.172.230; 3.Y.172.231;
3.Y.172.236; 3.Y.172.237; 3.Y.172.238; 3.Y.172.239; 3.Y.172.154; 3.Y.172.157; 3.Y.172.166;
3.Y.172.169; 3.Y.172.172; 3.Y.172.175; 3.Y.172.240; 3.Y.172.244; 3.Y.175.228; 3.Y.175.229;
3.Y.175.230; 3.Y.175.231; 3.Y.175.236; 3.Y.175.237; 3.Y.175.238; 3.Y.175.239; 3.Y.175.154;
3.Y.175.157; 3.Y.175.166; 3.Y.175.169; 3.Y.175.172; 3.Y.175.175; 3.Y.175.240; 3.Y.175.244;
3.Y.240.228; 3.Y.240.229; 3.Y.240.230; 3.Y.240.231; 3.Y.240.236; 3.Y.240.237; 3.Y.240.238;
3.Y.240.239; 3.Y.240.154; 3.Y.240.157; 3.Y.240.166; 3.Y.240.169; 3.Y.240.172; 3.Y.240.175;
3.Y.240.240; 3.Y.240.244; 3.Y.244.228; 3.Y.244.229; 3.Y.244.230; 3.Y.244.231; 3.Y.244.236;
3.Y.244.237; 3.Y.244.238; 3.Y.244.239; 3.Y.244.154; 3.Y.244.157; 3.Y.244.166; 3.Y.244.169;
3.Y.244.172; 3.Y.244.175; 3.Y.244.240; 3.Y.244.244;
Prodrugs of 4.B 4.B.228.228; 4.B.228.229; 4.B.228.230; 4.B.228.231; 4.B.228.236; 4.B.228.237; 4.B.228.238;
4.B.228.239; 4.B.228.154; 4.B.228.157; 4.B.228.166; 4.B.228.169; 4.B.228.172; 4.B.228.175;
4.B.228.240; 4.B.228.244; 4.B.229.228; 4.B.229.229; 4.B.229.230; 4.B.229.231; 4.B.229.236;
4.B.229.237; 4.B.229.238; 4.B.229.239; 4.B.229.154; 4.B.229.157; 4.B.229.166; 4.B.229.169;

TABLE 100-continued

4.B.229.172; 4.B.229.175; 4.B.229.240; 4.B.229.244; 4.B.230.228; 4.B.230.229; 4.B.230.230; 4.B.230.231; 4.B.230.236; 4.B.230.237; 4.B.230.238; 4.B.230.239; 4.B.230.154; 4.B.230.157; 4.B.230.166; 4.B.230.169; 4.B.230.172; 4.B.230.175; 4.B.230.240; 4.B.230.244; 4.B.231.228; 4.B.231.229; 4.B.231.230; 4.B.231.231; 4.B.231.236; 4.B.231.237; 4.B.231.238; 4.B.231.239; 4.B.231.154; 4.B.231.157; 4.B.231.166; 4.B.231.169; 4.B.231.172; 4.B.231.175; 4.B.231.240; 4.B.231.244; 4.B.236.228; 4.B.236.229; 4.B.236.230; 4.B.236.231; 4.B.236.236; 4.B.236.237; 4.B.236.238; 4.B.236.239; 4.B.236.154; 4.B.236.157; 4.B.236.166; 4.B.236.169; 4.B.236.172; 4.B.236.175; 4.B.236.240; 4.B.236.244; 4.B.237.228; 4.B.237.229; 4.B.237.230; 4.B.237.231; 4.B.237.236; 4.B.237.237; 4.B.237.238; 4.B.237.239; 4.B.237.154; 4.B.237.157; 4.B.237.166; 4.B.237.169; 4.B.237.172; 4.B.237.175; 4.B.237.240; 4.B.237.244; 4.B.238.228; 4.B.238.229; 4.B.238.230; 4.B.238.231; 4.B.238.236; 4.B.238.237; 4.B.238.238; 4.B.238.239; 4.B.238.154; 4.B.238.157; 4.B.238.166; 4.B.238.169; 4.B.238.172; 4.B.238.175; 4.B.238.240; 4.B.238.244; 4.B.239.228; 4.B.239.229; 4.B.239.230; 4.B.239.231; 4.B.239.236; 4.B.239.237; 4.B.239.238; 4.B.239.239; 4.B.239.154; 4.B.239.157; 4.B.239.166; 4.B.239.169; 4.B.239.172; 4.B.239.175; 4.B.239.240; 4.B.239.244; 4.B.154.228; 4.B.154.229; 4.B.154.230; 4.B.154.231; 4.B.154.236; 4.B.154.237; 4.B.154.238; 4.B.154.239; 4.B.154.154; 4.B.154.157; 4.B.154.166; 4.B.154.169; 4.B.154.172; 4.B.154.175; 4.B.154.240; 4.B.154.244; 4.B.157.228; 4.B.157.229; 4.B.157.230; 4.B.157.231; 4.B.157.236; 4.B.157.237; 4.B.157.238; 4.B.157.239; 4.B.157.154; 4.B.157.157; 4.B.157.166; 4.B.157.169; 4.B.157.172; 4.B.157.175; 4.B.157.240; 4.B.157.244; 4.B.166.228; 4.B.166.229; 4.B.166.230; 4.B.166.231; 4.B.166.236; 4.B.166.237; 4.B.166.238; 4.B.166.239; 4.B.166.154; 4.B.166.157; 4.B.166.166; 4.B.166.169; 4.B.166.172; 4.B.166.175; 4.B.166.240; 4.B.166.244; 4.B.169.228; 4.B.169.229; 4.B.169.230; 4.B.169.231; 4.B.169.236; 4.B.169.237; 4.B.169.238; 4.B.169.239; 4.B.169.154; 4.B.169.157; 4.B.169.166; 4.B.169.169; 4.B.169.172; 4.B.169.175; 4.B.169.240; 4.B.169.244; 4.B.172.228; 4.B.172.229; 4.B.172.230; 4.B.172.231; 4.B.172.236; 4.B.172.237; 4.B.172.238; 4.B.172.239; 4.B.172.154; 4.B.172.157; 4.B.172.166; 4.B.172.169; 4.B.172.172; 4.B.172.175; 4.B.172.240; 4.B.172.244; 4.B.175.228; 4.B.175.229; 4.B.175.230; 4.B.175.231; 4.B.175.236; 4.B.175.237; 4.B.175.238; 4.B.175.239; 4.B.175.154; 4.B.175.157; 4.B.175.166; 4.B.175.169; 4.B.175.172; 4.B.175.175; 4.B.175.240; 4.B.175.244; 4.B.240.228; 4.B.240.229; 4.B.240.230; 4.B.240.231; 4.B.240.236; 4.B.240.237; 4.B.240.238; 4.B.240.239; 4.B.240.154; 4.B.240.157; 4.B.240.166; 4.B.240.169; 4.B.240.172; 4.B.240.175; 4.B.240.240; 4.B.240.244; 4.B.244.228; 4.B.244.229; 4.B.244.230; 4.B.244.231; 4.B.244.236; 4.B.244.237; 4.B.244.238; 4.B.244.239; 4.B.244.154; 4.B.244.157; 4.B.244.166; 4.B.244.169; 4.B.244.172; 4.B.244.175; 4.B.244.240; 4.B.244.244;

Prodrugs of 4.D

4.D.228.228; 4.D.228.229; 4.D.228.230; 4.D.228.231; 4.D.228.236; 4.D.228.237; 4.D.228.238; 4.D.228.239; 4.D.228.154; 4.D.228.157; 4.D.228.166; 4.D.228.169; 4.D.228.172; 4.D.228.175; 4.D.228.240; 4.D.228.244; 4.D.229.228; 4.D.229.229; 4.D.229.230; 4.D.229.231; 4.D.229.236; 4.D.229.237; 4.D.229.238; 4.D.229.239; 4.D.229.154; 4.D.229.157; 4.D.229.166; 4.D.229.169; 4.D.229.172; 4.D.229.175; 4.D.229.240; 4.D.229.244; 4.D.230.228; 4.D.230.229; 4.D.230.230; 4.D.230.231; 4.D.230.236; 4.D.230.237; 4.D.230.238; 4.D.230.239; 4.D.230.154; 4.D.230.157; 4.D.230.166; 4.D.230.169; 4.D.230.172; 4.D.230.175; 4.D.230.240; 4.D.230.244; 4.D.231.228; 4.D.231.229; 4.D.231.230; 4.D.231.231; 4.D.231.236; 4.D.231.237; 4.D.231.238; 4.D.231.239; 4.D.231.154; 4.D.231.157; 4.D.231.166; 4.D.231.169; 4.D.231.172; 4.D.231.175; 4.D.231.240; 4.D.231.244; 4.D.236.228; 4.D.236.229; 4.D.236.230; 4.D.236.231; 4.D.236.236; 4.D.236.237; 4.D.236.238; 4.D.236.239; 4.D.236.154; 4.D.236.157; 4.D.236.166; 4.D.236.169; 4.D.236.172; 4.D.236.175; 4.D.236.240; 4.D.236.244; 4.D.237.228; 4.D.237.229; 4.D.237.230; 4.D.237.231; 4.D.237.236; 4.D.237.237; 4.D.237.238; 4.D.237.239; 4.D.237.154; 4.D.237.157; 4.D.237.166; 4.D.237.169; 4.D.237.172; 4.D.237.175; 4.D.237.240; 4.D.237.244; 4.D.238.228; 4.D.238.229; 4.D.238.230; 4.D.238.231; 4.D.238.236; 4.D.238.237; 4.D.238.238; 4.D.238.239; 4.D.238.154; 4.D.238.157; 4.D.238.166; 4.D.238.169; 4.D.238.172; 4.D.238.175; 4.D.238.240; 4.D.238.244; 4.D.239.228; 4.D.239.229; 4.D.239.230; 4.D.239.231; 4.D.239.236; 4.D.239.237; 4.D.239.238; 4.D.239.239; 4.D.239.154; 4.D.239.157; 4.D.239.166; 4.D.239.169; 4.D.239.172; 4.D.239.175; 4.D.239.240; 4.D.239.244; 4.D.154.228; 4.D.154.229; 4.D.154.230; 4.D.154.231; 4.D.154.236; 4.D.154.237; 4.D.154.238; 4.D.154.239; 4.D.154.154; 4.D.154.157; 4.D.154.166; 4.D.154.169; 4.D.154.172; 4.D.154.175; 4.D.154.240; 4.D.154.244; 4.D.157.228; 4.D.157.229; 4.D.157.230; 4.D.157.231; 4.D.157.236; 4.D.157.237; 4.D.157.238; 4.D.157.239; 4.D.157.154; 4.D.157.157; 4.D.157.166; 4.D.157.169; 4.D.157.172; 4.D.157.175; 4.D.157.240; 4.D.157.244; 4.D.166.228; 4.D.166.229; 4.D.166.230; 4.D.166.231; 4.D.166.236; 4.D.166.237; 4.D.166.238; 4.D.166.239; 4.D.166.154; 4.D.166.157; 4.D.166.166; 4.D.166.169; 4.D.166.172; 4.D.166.175; 4.D.166.240; 4.D.166.244; 4.D.169.228; 4.D.169.229; 4.D.169.230; 4.D.169.231; 4.D.169.236; 4.D.169.237; 4.D.169.238; 4.D.169.239; 4.D.169.154; 4.D.169.157; 4.D.169.166; 4.D.169.169; 4.D.169.172; 4.D.169.175; 4.D.169.240; 4.D.169.244; 4.D.172.228; 4.D.172.229; 4.D.172.230; 4.D.172.231; 4.D.172.236; 4.D.172.237; 4.D.172.238; 4.D.172.239; 4.D.172.154; 4.D.172.157; 4.D.172.166; 4.D.172.169; 4.D.172.172; 4.D.172.175; 4.D.172.240; 4.D.172.244; 4.D.175.228; 4.D.175.229; 4.D.175.230; 4.D.175.231; 4.D.175.236; 4.D.175.237; 4.D.175.238; 4.D.175.239; 4.D.175.154; 4.D.175.157; 4.D.175.166; 4.D.175.169; 4.D.175.172; 4.D.175.175; 4.D.175.240; 4.D.175.244; 4.D.240.228; 4.D.240.229; 4.D.240.230; 4.D.240.231; 4.D.240.236; 4.D.240.237; 4.D.240.238; 4.D.240.239; 4.D.240.154; 4.D.240.157; 4.D.240.166; 4.D.240.169; 4.D.240.172; 4.D.240.175; 4.D.240.240; 4.D.240.244; 4.D.244.228; 4.D.244.229; 4.D.244.230; 4.D.244.231; 4.D.244.236; 4.D.244.237; 4.D.244.238; 4.D.244.239; 4.D.244.154; 4.D.244.157; 4.D.244.166; 4.D.244.169; 4.D.244.172; 4.D.244.175; 4.D.244.240; 4.D.244.244;

Prodrugs of 4.E

4.E.228.228; 4.E.228.229; 4.E.228.230; 4.E.228.231; 4.E.228.236; 4.E.228.237; 4.E.228.238; 4.E.228.239; 4.E.228.154; 4.E.228.157; 4.E.228.166; 4.E.228.169; 4.E.228.172; 4.E.228.175; 4.E.228.240; 4.E.228.244; 4.E.229.228; 4.E.229.229; 4.E.229.230; 4.E.229.231; 4.E.229.236; 4.E.229.237; 4.E.229.238; 4.E.229.239; 4.E.229.154; 4.E.229.157; 4.E.229.166; 4.E.229.169; 4.E.229.172; 4.E.229.175; 4.E.229.240; 4.E.229.244; 4.E.230.228; 4.E.230.229; 4.E.230.230;

TABLE 100-continued

4.E.230.231; 4.E.230.236; 4.E.230.237; 4.E.230.238; 4.E.230.239; 4.E.230.154; 4.E.230.157;
4.E.230.166; 4.E.230.169; 4.E.230.172; 4.E.230.175; 4.E.230.240; 4.E.230.244; 4.E.231.228;
4.E.231.229; 4.E.231.230; 4.E.231.231; 4.E.231.236; 4.E.231.237; 4.E.231.238; 4.E.231.239;
4.E.231.154; 4.E.231.157; 4.E.231.166; 4.E.231.169; 4.E.231.172; 4.E.231.175; 4.E.231.240;
4.E.231.244; 4.E.236.228; 4.E.236.229; 4.E.236.230; 4.E.236.231; 4.E.236.236; 4.E.236.237;
4.E.236.238; 4.E.236.239; 4.E.236.154; 4.E.236.157; 4.E.236.166; 4.E.236.169; 4.E.236.172;
4.E.236.175; 4.E.236.240; 4.E.236.244; 4.E.237.228; 4.E.237.229; 4.E.237.230; 4.E.237.231;
4.E.237.236; 4.E.237.237; 4.E.237.238; 4.E.237.239; 4.E.237.154; 4.E.237.157; 4.E.237.166;
4.E.237.169; 4.E.237.172; 4.E.237.175; 4.E.237.240; 4.E.237.244; 4.E.238.228; 4.E.238.229;
4.E.238.230; 4.E.238.231; 4.E.238.236; 4.E.238.237; 4.E.238.238; 4.E.238.239; 4.E.238.154;
4.E.238.157; 4.E.238.166; 4.E.238.169; 4.E.238.172; 4.E.238.175; 4.E.238.240; 4.E.238.244;
4.E.239.228; 4.E.239.229; 4.E.239.230; 4.E.239.231; 4.E.239.236; 4.E.239.237; 4.E.239.238;
4.E.239.239; 4.E.239.154; 4.E.239.157; 4.E.239.166; 4.E.239.169; 4.E.239.172; 4.E.239.175;
4.E.239.240; 4.E.239.244; 4.E.154.228; 4.E.154.229; 4.E.154.230; 4.E.154.231; 4.E.154.236;
4.E.154.237; 4.E.154.238; 4.E.154.239; 4.E.154.154; 4.E.154.157; 4.E.154.166; 4.E.154.169;
4.E.154.172; 4.E.154.175; 4.E.154.240; 4.E.154.244; 4.E.157.228; 4.E.157.229; 4.E.157.230;
4.E.157.231; 4.E.157.236; 4.E.157.237; 4.E.157.238; 4.E.157.239; 4.E.157.154; 4.E.157.157;
4.E.157.166; 4.E.157.169; 4.E.157.172; 4.E.157.175; 4.E.157.240; 4.E.157.244; 4.E.166.228;
4.E.166.229; 4.E.166.230; 4.E.166.231; 4.E.166.236; 4.E.166.237; 4.E.166.238; 4.E.166.239;
4.E.166.154; 4.E.166.157; 4.E.166.166; 4.E.166.169; 4.E.166.172; 4.E.166.175; 4.E.166.240;
4.E.166.244; 4.E.169.228; 4.E.169.229; 4.E.169.230; 4.E.169.231; 4.E.169.236; 4.E.169.237;
4.E.169.238; 4.E.169.239; 4.E.169.154; 4.E.169.157; 4.E.169.166; 4.E.169.169; 4.E.169.172;
4.E.169.175; 4.E.169.240; 4.E.169.244; 4.E.172.228; 4.E.172.229; 4.E.172.230; 4.E.172.231;
4.E.172.236; 4.E.172.237; 4.E.172.238; 4.E.172.239; 4.E.172.154; 4.E.172.157; 4.E.172.166;
4.E.172.169; 4.E.172.172; 4.E.172.175; 4.E.172.240; 4.E.172.244; 4.E.175.228; 4.E.175.229;
4.E.175.230; 4.E.175.231; 4.E.175.236; 4.E.175.237; 4.E.175.238; 4.E.175.239; 4.E.175.154;
4.E.175.157; 4.E.175.166; 4.E.175.169; 4.E.175.172; 4.E.175.175; 4.E.175.240; 4.E.175.244;
4.E.240.228; 4.E.240.229; 4.E.240.230; 4.E.240.231; 4.E.240.236; 4.E.240.237; 4.E.240.238;
4.E.240.239; 4.E.240.154; 4.E.240.157; 4.E.240.166; 4.E.240.169; 4.E.240.172; 4.E.240.175;
4.E.240.240; 4.E.240.244; 4.E.244.228; 4.E.244.229; 4.E.244.230; 4.E.244.231; 4.E.244.236;
4.E.244.237; 4.E.244.238; 4.E.244.239; 4.E.244.154; 4.E.244.157; 4.E.244.166; 4.E.244.169;
4.E.244.172; 4.E.244.175; 4.E.244.240; 4.E.244.244;
Prodrugs of 4.G 4.G.228.228; 4.G.228.229; 4.G.228.230; 4.G.228.231; 4.G.228.236; 4.G.228.237;
4.G.228.238; 4.G.228.239; 4.G.228.154; 4.G.228.157; 4.G.228.166; 4.G.228.169; 4.G.228.172;
4.G.228.175; 4.G.228.240; 4.G.228.244; 4.G.229.228; 4.G.229.229; 4.G.229.230; 4.G.229.231;
4.G.229.236; 4.G.229.237; 4.G.229.238; 4.G.229.239; 4.G.229.154; 4.G.229.157; 4.G.229.166;
4.G.229.169; 4.G.229.172; 4.G.229.175; 4.G.229.240; 4.G.229.244; 4.G.230.228; 4.G.230.229;
4.G.230.230; 4.G.230.231; 4.G.230.236; 4.G.230.237; 4.G.230.238; 4.G.230.239; 4.G.230.154;
4.G.230.157; 4.G.230.166; 4.G.230.169; 4.G.230.172; 4.G.230.175; 4.G.230.240; 4.G.230.244;
4.G.231.228; 4.G.231.229; 4.G.231.230; 4.G.231.231; 4.G.231.236; 4.G.231.237; 4.G.231.238;
4.G.231.239; 4.G.231.154; 4.G.231.157; 4.G.231.166; 4.G.231.169; 4.G.231.172; 4.G.231.175;
4.G.231.240; 4.G.231.244; 4.G.236.228; 4.G.236.229; 4.G.236.230; 4.G.236.231; 4.G.236.236;
4.G.236.237; 4.G.236.238; 4.G.236.239; 4.G.236.154; 4.G.236.157; 4.G.236.166; 4.G.236.169;
4.G.236.172; 4.G.236.175; 4.G.236.240; 4.G.236.244; 4.G.237.228; 4.G.237.229; 4.G.237.230;
4.G.237.231; 4.G.237.236; 4.G.237.237; 4.G.237.238; 4.G.237.239; 4.G.237.154; 4.G.237.157;
4.G.237.166; 4.G.237.169; 4.G.237.172; 4.G.237.175; 4.G.237.240; 4.G.237.244; 4.G.238.228;
4.G.238.229; 4.G.238.230; 4.G.238.231; 4.G.238.236; 4.G.238.237; 4.G.238.238; 4.G.238.239;
4.G.238.154; 4.G.238.157; 4.G.238.166; 4.G.238.169; 4.G.238.172; 4.G.238.175; 4.G.238.240;
4.G.238.244; 4.G.239.228; 4.G.239.229; 4.G.239.230; 4.G.239.231; 4.G.239.236; 4.G.239.237;
4.G.239.238; 4.G.239.239; 4.G.239.154; 4.G.239.157; 4.G.239.166; 4.G.239.169; 4.G.239.172;
4.G.239.175; 4.G.239.240; 4.G.239.244; 4.G.154.228; 4.G.154.229; 4.G.154.230; 4.G.154.231;
4.G.154.236; 4.G.154.237; 4.G.154.238; 4.G.154.239; 4.G.154.154; 4.G.154.157; 4.G.154.166;
4.G.154.169; 4.G.154.172; 4.G.154.175; 4.G.154.240; 4.G.154.244; 4.G.157.228; 4.G.157.229;
4.G.157.230; 4.G.157.231; 4.G.157.236; 4.G.157.237; 4.G.157.238; 4.G.157.239; 4.G.157.154;
4.G.157.157; 4.G.157.166; 4.G.157.169; 4.G.157.172; 4.G.157.175; 4.G.157.240; 4.G.157.244;
4.G.166.228; 4.G.166.229; 4.G.166.230; 4.G.166.231; 4.G.166.236; 4.G.166.237; 4.G.166.238;
4.G.166.239; 4.G.166.154; 4.G.166.157; 4.G.166.166; 4.G.166.169; 4.G.166.172; 4.G.166.175;
4.G.166.240; 4.G.166.244; 4.G.169.228; 4.G.169.229; 4.G.169.230; 4.G.169.231; 4.G.169.236;
4.G.169.237; 4.G.169.238; 4.G.169.239; 4.G.169.154; 4.G.169.157; 4.G.169.166; 4.G.169.169;
4.G.169.172; 4.G.169.175; 4.G.169.240; 4.G.169.244; 4.G.172.228; 4.G.172.229; 4.G.172.230;
4.G.172.231; 4.G.172.236; 4.G.172.237; 4.G.172.238; 4.G.172.239; 4.G.172.154; 4.G.172.157;
4.G.172.166; 4.G.172.169; 4.G.172.172; 4.G.172.175; 4.G.172.240; 4.G.172.244; 4.G.175.228;
4.G.175.229; 4.G.175.230; 4.G.175.231; 4.G.175.236; 4.G.175.237; 4.G.175.238; 4.G.175.239;
4.G.175.154; 4.G.175.157; 4.G.175.166; 4.G.175.169; 4.G.175.172; 4.G.175.175; 4.G.175.240;
4.G.175.244; 4.G.240.228; 4.G.240.229; 4.G.240.230; 4.G.240.231; 4.G.240.236; 4.G.240.237;
4.G.240.238; 4.G.240.239; 4.G.240.154; 4.G.240.157; 4.G.240.166; 4.G.240.169; 4.G.240.172;
4.G.240.175; 4.G.240.240; 4.G.240.244; 4.G.244.228; 4.G.244.229; 4.G.244.230; 4.G.244.231;
4.G.244.236; 4.G.244.237; 4.G.244.238; 4.G.244.239; 4.G.244.154; 4.G.244.157; 4.G.244.166;
4.G.244.169; 4.G.244.172; 4.G.244.175; 4.G.244.240; 4.G.244.244;
Prodrugs of 4.I 4.I.228.228; 4.I.228.229; 4.I.228.230; 4.I.228.231; 4.I.228.236; 4.I.228.237; 4.I.228.238;
4.I.228.239; 4.I.228.154; 4.I.228.157; 4.I.228.166; 4.I.228.169; 4.I.228.172; 4.I.228.175;
4.I.228.240; 4.I.228.244; 4.I.229.228; 4.I.229.229; 4.I.229.230; 4.I.229.231; 4.I.229.236;
4.I.229.237; 4.I.229.238; 4.I.229.239; 4.I.229.154; 4.I.229.157; 4.I.229.166; 4.I.229.169;
4.I.229.172; 4.I.229.175; 4.I.229.240; 4.I.229.244; 4.I.230.228; 4.I.230.229; 4.I.230.230;
4.I.230.231; 4.I.230.236; 4.I.230.237; 4.I.230.238; 4.I.230.239; 4.I.230.154; 4.I.230.157;

TABLE 100-continued

4.I.230.166; 4.I.230.169; 4.I.230.172; 4.I.230.175; 4.I.230.240; 4.I.230.244; 4.I.231.228;
4.I.231.229; 4.I.231.230; 4.I.231.231; 4.I.231.236; 4.I.231.237; 4.I.231.238; 4.I.231.239;
4.I.231.154; 4.I.231.157; 4.I.231.166; 4.I.231.169; 4.I.231.172; 4.I.231.175; 4.I.231.240;
4.I.231.244; 4.I.236.228; 4.I.236.229; 4.I.236.230; 4.I.236.231; 4.I.236.236; 4.I.236.237;
4.I.236.238; 4.I.236.239; 4.I.236.154; 4.I.236.157; 4.I.236.166; 4.I.236.169; 4.I.236.172;
4.I.236.175; 4.I.236.240; 4.I.236.244; 4.I.237.228; 4.I.237.229; 4.I.237.230; 4.I.237.231;
4.I.237.236; 4.I.237.237; 4.I.237.238; 4.I.237.239; 4.I.237.154; 4.I.237.157; 4.I.237.166;
4.I.237.169; 4.I.237.172; 4.I.237.175; 4.I.237.240; 4.I.237.244; 4.I.238.228; 4.I.238.229;
4.I.238.230; 4.I.238.231; 4.I.238.236; 4.I.238.237; 4.I.238.238; 4.I.238.239; 4.I.238.154;
4.I.238.157; 4.I.238.166; 4.I.238.169; 4.I.238.172; 4.I.238.175; 4.I.238.240; 4.I.238.244;
4.I.239.228; 4.I.239.229; 4.I.239.230; 4.I.239.231; 4.I.239.236; 4.I.239.237; 4.I.239.238;
4.I.239.239; 4.I.239.154; 4.I.239.157; 4.I.239.166; 4.I.239.169; 4.I.239.172; 4.I.239.175;
4.I.239.240; 4.I.239.244; 4.I.154.228; 4.I.154.229; 4.I.154.230; 4.I.154.231; 4.I.154.236;
4.I.154.237; 4.I.154.238; 4.I.154.239; 4.I.154.154; 4.I.154.157; 4.I.154.166; 4.I.154.169;
4.I.154.172; 4.I.154.175; 4.I.154.240; 4.I.154.244; 4.I.157.228; 4.I.157.229; 4.I.157.230;
4.I.157.231; 4.I.157.236; 4.I.157.237; 4.I.157.238; 4.I.157.239; 4.I.157.154; 4.I.157.157;
4.I.157.166; 4.I.157.169; 4.I.157.172; 4.I.157.175; 4.I.157.240; 4.I.157.244; 4.I.166.228;
4.I.166.229; 4.I.166.230; 4.I.166.231; 4.I.166.236; 4.I.166.237; 4.I.166.238; 4.I.166.239;
4.I.166.154; 4.I.166.157; 4.I.166.166; 4.I.166.169; 4.I.166.172; 4.I.166.175; 4.I.166.240;
4.I.166.244; 4.I.169.228; 4.I.169.229; 4.I.169.230; 4.I.169.231; 4.I.169.236; 4.I.169.237;
4.I.169.238; 4.I.169.239; 4.I.169.154; 4.I.169.157; 4.I.169.166; 4.I.169.169; 4.I.169.172;
4.I.169.175; 4.I.169.240; 4.I.169.244; 4.I.172.228; 4.I.172.229; 4.I.172.230; 4.I.172.231;
4.I.172.236; 4.I.172.237; 4.I.172.238; 4.I.172.239; 4.I.172.154; 4.I.172.157; 4.I.172.166;
4.I.172.169; 4.I.172.172; 4.I.172.175; 4.I.172.240; 4.I.172.244; 4.I.175.228; 4.I.175.229;
4.I.175.230; 4.I.175.231; 4.I.175.236; 4.I.175.237; 4.I.175.238; 4.I.175.239; 4.I.175.154;
4.I.175.157; 4.I.175.166; 4.I.175.169; 4.I.175.172; 4.I.175.175; 4.I.175.240; 4.I.175.244;
4.I.240.228; 4.I.240.229; 4.I.240.230; 4.I.240.231; 4.I.240.236; 4.I.240.237; 4.I.240.238;
4.I.240.239; 4.I.240.154; 4.I.240.157; 4.I.240.166; 4.I.240.169; 4.I.240.172; 4.I.240.175;
4.I.240.240; 4.I.240.244; 4.I.244.228; 4.I.244.229; 4.I.244.230; 4.I.244.231; 4.I.244.236;
4.I.244.237; 4.I.244.238; 4.I.244.239; 4.I.244.154; 4.I.244.157; 4.I.244.166; 4.I.244.169;
4.I.244.172; 4.I.244.175; 4.I.244.240; 4.I.244.244;
Prodrugs of 4.J 4.J.228.228; 4.J.228.229; 4.J.228.230; 4.J.228.231; 4.J.228.236; 4.J.228.237; 4.J.228.238;
4.J.228.239; 4.J.228.154; 4.J.228.157; 4.J.228.166; 4.J.228.169; 4.J.228.172; 4.J.228.175;
4.J.228.240; 4.J.228.244; 4.J.229.228; 4.J.229.229; 4.J.229.230; 4.J.229.231; 4.J.229.236;
4.J.229.237; 4.J.229.238; 4.J.229.239; 4.J.229.154; 4.J.229.157; 4.J.229.166; 4.J.229.169;
4.J.229.172; 4.J.229.175; 4.J.229.240; 4.J.229.244; 4.J.230.228; 4.J.230.229; 4.J.230.230;
4.J.230.231; 4.J.230.236; 4.J.230.237; 4.J.230.238; 4.J.230.239; 4.J.230.154; 4.J.230.157;
4.J.230.166; 4.J.230.169; 4.J.230.172; 4.J.230.175; 4.J.230.240; 4.J.230.244; 4.J.231.228;
4.J.231.229; 4.J.231.230; 4.J.231.231; 4.J.231.236; 4.J.231.237; 4.J.231.238; 4.J.231.239;
4.J.231.154; 4.J.231.157; 4.J.231.166; 4.J.231.169; 4.J.231.172; 4.J.231.175; 4.J.231.240;
4.J.231.244; 4.J.236.228; 4.J.236.229; 4.J.236.230; 4.J.236.231; 4.J.236.236; 4.J.236.237;
4.J.236.238; 4.J.236.239; 4.J.236.154; 4.J.236.157; 4.J.236.166; 4.J.236.169; 4.J.236.172;
4.J.236.175; 4.J.236.240; 4.J.236.244; 4.J.237.228; 4.J.237.229; 4.J.237.230; 4.J.237.231;
4.J.237.236; 4.J.237.237; 4.J.237.238; 4.J.237.239; 4.J.237.154; 4.J.237.157; 4.J.237.166;
4.J.237.169; 4.J.237.172; 4.J.237.175; 4.J.237.240; 4.J.237.244; 4.J.238.228; 4.J.238.229;
4.J.238.230; 4.J.238.231; 4.J.238.236; 4.J.238.237; 4.J.238.238; 4.J.238.239; 4.J.238.154;
4.J.238.157; 4.J.238.166; 4.J.238.169; 4.J.238.172; 4.J.238.175; 4.J.238.240; 4.J.238.244;
4.J.239.228; 4.J.239.229; 4.J.239.230; 4.J.239.231; 4.J.239.236; 4.J.239.237; 4.J.239.238;
4.J.239.239; 4.J.239.154; 4.J.239.157; 4.J.239.166; 4.J.239.169; 4.J.239.172; 4.J.239.175;
4.J.239.240; 4.J.239.244; 4.J.154.228; 4.J.154.229; 4.J.154.230; 4.J.154.231; 4.J.154.236;
4.J.154.237; 4.J.154.238; 4.J.154.239; 4.J.154.154; 4.J.154.157; 4.J.154.166; 4.J.154.169;
4.J.154.172; 4.J.154.175; 4.J.154.240; 4.J.154.244; 4.J.157.228; 4.J.157.229; 4.J.157.230;
4.J.157.231; 4.J.157.236; 4.J.157.237; 4.J.157.238; 4.J.157.239; 4.J.157.154; 4.J.157.157;
4.J.157.166; 4.J.157.169; 4.J.157.172; 4.J.157.175; 4.J.157.240; 4.J.157.244; 4.J.166.228;
4.J.166.229; 4.J.166.230; 4.J.166.231; 4.J.166.236; 4.J.166.237; 4.J.166.238; 4.J.166.239;
4.J.166.154; 4.J.166.157; 4.J.166.166; 4.J.166.169; 4.J.166.172; 4.J.166.175; 4.J.166.240;
4.J.166.244; 4.J.169.228; 4.J.169.229; 4.J.169.230; 4.J.169.231; 4.J.169.236; 4.J.169.237;
4.J.169.238; 4.J.169.239; 4.J.169.154; 4.J.169.157; 4.J.169.166; 4.J.169.169; 4.J.169.172;
4.J.169.175; 4.J.169.240; 4.J.169.244; 4.J.172.228; 4.J.172.229; 4.J.172.230; 4.J.172.231;
4.J.172.236; 4.J.172.237; 4.J.172.238; 4.J.172.239; 4.J.172.154; 4.J.172.157; 4.J.172.166;
4.J.172.169; 4.J.172.172; 4.J.172.175; 4.J.172.240; 4.J.172.244; 4.J.175.228; 4.J.175.229;
4.J.175.230; 4.J.175.231; 4.J.175.236; 4.J.175.237; 4.J.175.238; 4.J.175.239; 4.J.175.154;
4.J.175.157; 4.J.175.166; 4.J.175.169; 4.J.175.172; 4.J.175.175; 4.J.175.240; 4.J.175.244;
4.J.240.228; 4.J.240.229; 4.J.240.230; 4.J.240.231; 4.J.240.236; 4.J.240.237; 4.J.240.238;
4.J.240.239; 4.J.240.154; 4.J.240.157; 4.J.240.166; 4.J.240.169; 4.J.240.172; 4.J.240.175;
4.J.240.240; 4.J.240.244; 4.J.244.228; 4.J.244.229; 4.J.244.230; 4.J.244.231; 4.J.244.236;
4.J.244.237; 4.J.244.238; 4.J.244.239; 4.J.244.154; 4.J.244.157; 4.J.244.166; 4.J.244.169;
4.J.244.172; 4.J.244.175; 4.J.244.240; 4.J.244.244;
Prodrugs of 4.L 4.L.228.228; 4.L.228.229; 4.L.228.230; 4.L.228.231; 4.L.228.236; 4.L.228.237; 4.L.228.238;
4.L.228.239; 4.L.228.154; 4.L.228.157; 4.L.228.166; 4.L.228.169; 4.L.228.172; 4.L.228.175;
4.L.228.240; 4.L.228.244; 4.L.229.228; 4.L.229.229; 4.L.229.230; 4.L.229.231; 4.L.229.236;
4.L.229.237; 4.L.229.238; 4.L.229.239; 4.L.229.154; 4.L.229.157; 4.L.229.166; 4.L.229.169;
4.L.229.172; 4.L.229.175; 4.L.229.240; 4.L.229.244; 4.L.230.228; 4.L.230.229; 4.L.230.230;
4.L.230.231; 4.L.230.236; 4.L.230.237; 4.L.230.238; 4.L.230.239; 4.L.230.154; 4.L.230.157;
4.L.230.166; 4.L.230.169; 4.L.230.172; 4.L.230.175; 4.L.230.240; 4.L.230.244; 4.L.231.228;

TABLE 100-continued

4.L.231.229; 4.L.231.230; 4.L.231.231; 4.L.231.236; 4.L.231.237; 4.L.231.238; 4.L.231.239;
4.L.231.154; 4.L.231.157; 4.L.231.166; 4.L.231.169; 4.L.231.172; 4.L.231.175; 4.L.231.240;
4.L.231.244; 4.L.236.228; 4.L.236.229; 4.L.236.230; 4.L.236.231; 4.L.236.236; 4.L.236.237;
4.L.236.238; 4.L.236.239; 4.L.236.154; 4.L.236.157; 4.L.236.166; 4.L.236.169; 4.L.236.172;
4.L.236.175; 4.L.236.240; 4.L.236.244; 4.L.237.228; 4.L.237.229; 4.L.237.230; 4.L.237.231;
4.L.237.236; 4.L.237.237; 4.L.237.238; 4.L.237.239; 4.L.237.154; 4.L.237.157; 4.L.237.166;
4.L.237.169; 4.L.237.172; 4.L.237.175; 4.L.237.240; 4.L.237.244; 4.L.238.228; 4.L.238.229;
4.L.238.230; 4.L.238.231; 4.L.238.236; 4.L.238.237; 4.L.238.238; 4.L.238.239; 4.L.238.154;
4.L.238.157; 4.L.238.166; 4.L.238.169; 4.L.238.172; 4.L.238.175; 4.L.238.240; 4.L.238.244;
4.L.239.228; 4.L.239.229; 4.L.239.230; 4.L.239.231; 4.L.239.236; 4.L.239.237; 4.L.239.238;
4.L.239.239; 4.L.239.154; 4.L.239.157; 4.L.239.166; 4.L.239.169; 4.L.239.172; 4.L.239.175;
4.L.239.240; 4.L.239.244; 4.L.154.228; 4.L.154.229; 4.L.154.230; 4.L.154.231; 4.L.154.236;
4.L.154.237; 4.L.154.238; 4.L.154.239; 4.L.154.154; 4.L.154.157; 4.L.154.166; 4.L.154.169;
4.L.154.172; 4.L.154.175; 4.L.154.240; 4.L.154.244; 4.L.157.228; 4.L.157.229; 4.L.157.230;
4.L.157.231; 4.L.157.236; 4.L.157.237; 4.L.157.238; 4.L.157.239; 4.L.157.154; 4.L.157.157;
4.L.157.166; 4.L.157.169; 4.L.157.172; 4.L.157.175; 4.L.157.240; 4.L.157.244; 4.L.166.228;
4.L.166.229; 4.L.166.230; 4.L.166.231; 4.L.166.236; 4.L.166.237; 4.L.166.238; 4.L.166.239;
4.L.166.154; 4.L.166.157; 4.L.166.166; 4.L.166.169; 4.L.166.172; 4.L.166.175; 4.L.166.240;
4.L.166.244; 4.L.169.228; 4.L.169.229; 4.L.169.230; 4.L.169.231; 4.L.169.236; 4.L.169.237;
4.L.169.238; 4.L.169.239; 4.L.169.154; 4.L.169.157; 4.L.169.166; 4.L.169.169; 4.L.169.172;
4.L.169.175; 4.L.169.240; 4.L.169.244; 4.L.172.228; 4.L.172.229; 4.L.172.230; 4.L.172.231;
4.L.172.236; 4.L.172.237; 4.L.172.238; 4.L.172.239; 4.L.172.154; 4.L.172.157; 4.L.172.166;
4.L.172.169; 4.L.172.172; 4.L.172.175; 4.L.172.240; 4.L.172.244; 4.L.175.228; 4.L.175.229;
4.L.175.230; 4.L.175.231; 4.L.175.236; 4.L.175.237; 4.L.175.238; 4.L.175.239; 4.L.175.154;
4.L.175.157; 4.L.175.166; 4.L.175.169; 4.L.175.172; 4.L.175.175; 4.L.175.240; 4.L.175.244;
4.L.240.228; 4.L.240.229; 4.L.240.230; 4.L.240.231; 4.L.240.236; 4.L.240.237; 4.L.240.238;
4.L.240.239; 4.L.240.154; 4.L.240.157; 4.L.240.166; 4.L.240.169; 4.L.240.172; 4.L.240.175;
4.L.240.240; 4.L.240.244; 4.L.244.228; 4.L.244.229; 4.L.244.230; 4.L.244.231; 4.L.244.236;
4.L.244.237; 4.L.244.238; 4.L.244.239; 4.L.244.154; 4.L.244.157; 4.L.244.166; 4.L.244.169;
4.L.244.172; 4.L.244.175; 4.L.244.240; 4.L.244.244;
Prodrugs of 4.O 4.O.228.228; 4.O.228.229; 4.O.228.230; 4.O.228.231; 4.O.228.236; 4.O.228.237;
4.O.228.238; 4.O.228.239; 4.O.228.154; 4.O.228.157; 4.O.228.166; 4.O.228.169; 4.O.228.172;
4.O.228.175; 4.O.228.240; 4.O.228.244; 4.O.229.228; 4.O.229.229; 4.O.229.230; 4.O.229.231;
4.O.229.236; 4.O.229.237; 4.O.229.238; 4.O.229.239; 4.O.229.154; 4.O.229.157; 4.O.229.166;
4.O.229.169; 4.O.229.172; 4.O.229.175; 4.O.229.240; 4.O.229.244; 4.O.230.228; 4.O.230.229;
4.O.230.230; 4.O.230.231; 4.O.230.236; 4.O.230.237; 4.O.230.238; 4.O.230.239; 4.O.230.154;
4.O.230.157; 4.O.230.166; 4.O.230.169; 4.O.230.172; 4.O.230.175; 4.O.230.240; 4.O.230.244;
4.O.231.228; 4.O.231.229; 4.O.231.230; 4.O.231.231; 4.O.231.236; 4.O.231.237; 4.O.231.238;
4.O.231.239; 4.O.231.154; 4.O.231.157; 4.O.231.166; 4.O.231.169; 4.O.231.172; 4.O.231.175;
4.O.231.240; 4.O.231.244; 4.O.236.228; 4.O.236.229; 4.O.236.230; 4.O.236.231; 4.O.236.236;
4.O.236.237; 4.O.236.238; 4.O.236.239; 4.O.236.154; 4.O.236.157; 4.O.236.166; 4.O.236.169;
4.O.236.172; 4.O.236.175; 4.O.236.240; 4.O.236.244; 4.O.237.228; 4.O.237.229; 4.O.237.230;
4.O.237.231; 4.O.237.236; 4.O.237.237; 4.O.237.238; 4.O.237.239; 4.O.237.154; 4.O.237.157;
4.O.237.166; 4.O.237.169; 4.O.237.172; 4.O.237.175; 4.O.237.240; 4.O.237.244; 4.O.238.228;
4.O.238.229; 4.O.238.230; 4.O.238.231; 4.O.238.236; 4.O.238.237; 4.O.238.238; 4.O.238.239;
4.O.238.154; 4.O.238.157; 4.O.238.166; 4.O.238.169; 4.O.238.172; 4.O.238.175; 4.O.238.240;
4.O.238.244; 4.O.239.228; 4.O.239.229; 4.O.239.230; 4.O.239.231; 4.O.239.236; 4.O.239.237;
4.O.239.238; 4.O.239.239; 4.O.239.154; 4.O.239.157; 4.O.239.166; 4.O.239.169; 4.O.239.172;
4.O.239.175; 4.O.239.240; 4.O.239.244; 4.O.154.228; 4.O.154.229; 4.O.154.230; 4.O.154.231;
4.O.154.236; 4.O.154.237; 4.O.154.238; 4.O.154.239; 4.O.154.154; 4.O.154.157; 4.O.154.166;
4.O.154.169; 4.O.154.172; 4.O.154.175; 4.O.154.240; 4.O.154.244; 4.O.157.228; 4.O.157.229;
4.O.157.230; 4.O.157.231; 4.O.157.236; 4.O.157.237; 4.O.157.238; 4.O.157.239; 4.O.157.154;
4.O.157.157; 4.O.157.166; 4.O.157.169; 4.O.157.172; 4.O.157.175; 4.O.157.240; 4.O.157.244;
4.O.166.228; 4.O.166.229; 4.O.166.230; 4.O.166.231; 4.O.166.236; 4.O.166.237; 4.O.166.238;
4.O.166.239; 4.O.166.154; 4.O.166.157; 4.O.166.166; 4.O.166.169; 4.O.166.172; 4.O.166.175;
4.O.166.240; 4.O.166.244; 4.O.169.228; 4.O.169.229; 4.O.169.230; 4.O.169.231; 4.O.169.236;
4.O.169.237; 4.O.169.238; 4.O.169.239; 4.O.169.154; 4.O.169.157; 4.O.169.166; 4.O.169.169;
4.O.169.172; 4.O.169.175; 4.O.169.240; 4.O.169.244; 4.O.172.228; 4.O.172.229; 4.O.172.230;
4.O.172.231; 4.O.172.236; 4.O.172.237; 4.O.172.238; 4.O.172.239; 4.O.172.154; 4.O.172.157;
4.O.172.166; 4.O.172.169; 4.O.172.172; 4.O.172.175; 4.O.172.240; 4.O.172.244; 4.O.175.228;
4.O.175.229; 4.O.175.230; 4.O.175.231; 4.O.175.236; 4.O.175.237; 4.O.175.238; 4.O.175.239;
4.O.175.154; 4.O.175.157; 4.O.175.166; 4.O.175.169; 4.O.175.172; 4.O.175.175; 4.O.175.240;
4.O.175.244; 4.O.240.228; 4.O.240.229; 4.O.240.230; 4.O.240.231; 4.O.240.236; 4.O.240.237;
4.O.240.238; 4.O.240.239; 4.O.240.154; 4.O.240.157; 4.O.240.166; 4.O.240.169; 4.O.240.172;
4.O.240.175; 4.O.240.240; 4.O.240.244; 4.O.244.228; 4.O.244.229; 4.O.244.230; 4.O.244.231;
4.O.244.236; 4.O.244.237; 4.O.244.238; 4.O.244.239; 4.O.244.154; 4.O.244.157; 4.O.244.166;
4.O.244.169; 4.O.244.172; 4.O.244.175; 4.O.244.240; 4.O.244.244;
Prodrugs of 4.P 4.P.228.228; 4.P.228.229; 4.P.228.230; 4.P.228.231; 4.P.228.236; 4.P.228.237; 4.P.228.238;
4.P.228.239; 4.P.228.154; 4.P.228.157; 4.P.228.166; 4.P.228.169; 4.P.228.172; 4.P.228.175;
4.P.228.240; 4.P.228.244; 4.P.229.228; 4.P.229.229; 4.P.229.230; 4.P.229.231; 4.P.229.236;
4.P.229.237; 4.P.229.238; 4.P.229.239; 4.P.229.154; 4.P.229.157; 4.P.229.166; 4.P.229.169;
4.P.229.172; 4.P.229.175; 4.P.229.240; 4.P.229.244; 4.P.230.228; 4.P.230.229; 4.P.230.230;
4.P.230.231; 4.P.230.236; 4.P.230.237; 4.P.230.238; 4.P.230.239; 4.P.230.154; 4.P.230.157;
4.P.230.166; 4.P.230.169; 4.P.230.172; 4.P.230.175; 4.P.230.240; 4.P.230.244; 4.P.231.228;
4.P.231.229; 4.P.231.230; 4.P.231.231; 4.P.231.236; 4.P.231.237; 4.P.231.238; 4.P.231.239;

TABLE 100-continued

4.P.231.154; 4.P.231.157; 4.P.231.166; 4.P.231.169; 4.P.231.172; 4.P.231.175; 4.P.231.240;
4.P.231.244; 4.P.236.228; 4.P.236.229; 4.P.236.230; 4.P.236.231; 4.P.236.236; 4.P.236.237;
4.P.236.238; 4.P.236.239; 4.P.236.154; 4.P.236.157; 4.P.236.166; 4.P.236.169; 4.P.236.172;
4.P.236.175; 4.P.236.240; 4.P.236.244; 4.P.237.228; 4.P.237.229; 4.P.237.230; 4.P.237.231;
4.P.237.236; 4.P.237.237; 4.P.237.238; 4.P.237.239; 4.P.237.154; 4.P.237.157; 4.P.237.166;
4.P.237.169; 4.P.237.172; 4.P.237.175; 4.P.237.240; 4.P.237.244; 4.P.238.228; 4.P.238.229;
4.P.238.230; 4.P.238.231; 4.P.238.236; 4.P.238.237; 4.P.238.238; 4.P.238.239; 4.P.238.154;
4.P.238.157; 4.P.238.166; 4.P.238.169; 4.P.238.172; 4.P.238.175; 4.P.238.240; 4.P.238.244;
4.P.239.228; 4.P.239.229; 4.P.239.230; 4.P.239.231; 4.P.239.236; 4.P.239.237; 4.P.239.238;
4.P.239.239; 4.P.239.154; 4.P.239.157; 4.P.239.166; 4.P.239.169; 4.P.239.172; 4.P.239.175;
4.P.239.240; 4.P.239.244; 4.P.154.228; 4.P.154.229; 4.P.154.230; 4.P.154.231; 4.P.154.236;
4.P.154.237; 4.P.154.238; 4.P.154.239; 4.P.154.154; 4.P.154.157; 4.P.154.166; 4.P.154.169;
4.P.154.172; 4.P.154.175; 4.P.154.240; 4.P.154.244; 4.P.157.228; 4.P.157.229; 4.P.157.230;
4.P.157.231; 4.P.157.236; 4.P.157.237; 4.P.157.238; 4.P.157.239; 4.P.157.154; 4.P.157.157;
4.P.157.166; 4.P.157.169; 4.P.157.172; 4.P.157.175; 4.P.157.240; 4.P.157.244; 4.P.166.228;
4.P.166.229; 4.P.166.230; 4.P.166.231; 4.P.166.236; 4.P.166.237; 4.P.166.238; 4.P.166.239;
4.P.166.154; 4.P.166.157; 4.P.166.166; 4.P.166.169; 4.P.166.172; 4.P.166.175; 4.P.166.240;
4.P.166.244; 4.P.169.228; 4.P.169.229; 4.P.169.230; 4.P.169.231; 4.P.169.236; 4.P.169.237;
4.P.169.238; 4.P.169.239; 4.P.169.154; 4.P.169.157; 4.P.169.166; 4.P.169.169; 4.P.169.172;
4.P.169.175; 4.P.169.240; 4.P.169.244; 4.P.172.228; 4.P.172.229; 4.P.172.230; 4.P.172.231;
4.P.172.236; 4.P.172.237; 4.P.172.238; 4.P.172.239; 4.P.172.154; 4.P.172.157; 4.P.172.166;
4.P.172.169; 4.P.172.172; 4.P.172.175; 4.P.172.240; 4.P.172.244; 4.P.175.228; 4.P.175.229;
4.P.175.230; 4.P.175.231; 4.P.175.236; 4.P.175.237; 4.P.175.238; 4.P.175.239; 4.P.175.154;
4.P.175.157; 4.P.175.166; 4.P.175.169; 4.P.175.172; 4.P.175.175; 4.P.175.240; 4.P.175.244;
4.P.240.228; 4.P.240.229; 4.P.240.230; 4.P.240.231; 4.P.240.236; 4.P.240.237; 4.P.240.238;
4.P.240.239; 4.P.240.154; 4.P.240.157; 4.P.240.166; 4.P.240.169; 4.P.240.172; 4.P.240.175;
4.P.240.240; 4.P.240.244; 4.P.244.228; 4.P.244.229; 4.P.244.230; 4.P.244.231; 4.P.244.236;
4.P.244.237; 4.P.244.238; 4.P.244.239; 4.P.244.154; 4.P.244.157; 4.P.244.166; 4.P.244.169;
4.P.244.172; 4.P.244.175; 4.P.244.240; 4.P.244.244;

Prodrugs of 4.U

4.U.228.228; 4.U.228.229; 4.U.228.230; 4.U.228.231; 4.U.228.236; 4.U.228.237;
4.U.228.238; 4.U.228.239; 4.U.228.154; 4.U.228.157; 4.U.228.166; 4.U.228.169; 4.U.228.172;
4.U.228.175; 4.U.228.240; 4.U.228.244; 4.U.229.228; 4.U.229.229; 4.U.229.230; 4.U.229.231;
4.U.229.236; 4.U.229.237; 4.U.229.238; 4.U.229.239; 4.U.229.154; 4.U.229.157; 4.U.229.166;
4.U.229.169; 4.U.229.172; 4.U.229.175; 4.U.229.240; 4.U.229.244; 4.U.230.228; 4.U.230.229;
4.U.230.230; 4.U.230.231; 4.U.230.236; 4.U.230.237; 4.U.230.238; 4.U.230.239; 4.U.230.154;
4.U.230.157; 4.U.230.166; 4.U.230.169; 4.U.230.172; 4.U.230.175; 4.U.230.240; 4.U.230.244;
4.U.231.228; 4.U.231.229; 4.U.231.230; 4.U.231.231; 4.U.231.236; 4.U.231.237; 4.U.231.238;
4.U.231.239; 4.U.231.154; 4.U.231.157; 4.U.231.166; 4.U.231.169; 4.U.231.172; 4.U.231.175;
4.U.231.240; 4.U.231.244; 4.U.236.228; 4.U.236.229; 4.U.236.230; 4.U.236.231; 4.U.236.236;
4.U.236.237; 4.U.236.238; 4.U.236.239; 4.U.236.154; 4.U.236.157; 4.U.236.166; 4.U.236.169;
4.U.236.172; 4.U.236.175; 4.U.236.240; 4.U.236.244; 4.U.237.228; 4.U.237.229; 4.U.237.230;
4.U.237.231; 4.U.237.236; 4.U.237.237; 4.U.237.238; 4.U.237.239; 4.U.237.154; 4.U.237.157;
4.U.237.166; 4.U.237.169; 4.U.237.172; 4.U.237.175; 4.U.237.240; 4.U.237.244; 4.U.238.228;
4.U.238.229; 4.U.238.230; 4.U.238.231; 4.U.238.236; 4.U.238.237; 4.U.238.238; 4.U.238.239;
4.U.238.154; 4.U.238.157; 4.U.238.166; 4.U.238.169; 4.U.238.172; 4.U.238.175; 4.U.238.240;
4.U.238.244; 4.U.239.228; 4.U.239.229; 4.U.239.230; 4.U.239.231; 4.U.239.236; 4.U.239.237;
4.U.239.238; 4.U.239.239; 4.U.239.154; 4.U.239.157; 4.U.239.166; 4.U.239.169; 4.U.239.172;
4.U.239.175; 4.U.239.240; 4.U.239.244; 4.U.154.228; 4.U.154.229; 4.U.154.230; 4.U.154.231;
4.U.154.236; 4.U.154.237; 4.U.154.238; 4.U.154.239; 4.U.154.154; 4.U.154.157; 4.U.154.166;
4.U.154.169; 4.U.154.172; 4.U.154.175; 4.U.154.240; 4.U.154.244; 4.U.157.228; 4.U.157.229;
4.U.157.230; 4.U.157.231; 4.U.157.236; 4.U.157.237; 4.U.157.238; 4.U.157.239; 4.U.157.154;
4.U.157.157; 4.U.157.166; 4.U.157.169; 4.U.157.172; 4.U.157.175; 4.U.157.240; 4.U.157.244;
4.U.166.228; 4.U.166.229; 4.U.166.230; 4.U.166.231; 4.U.166.236; 4.U.166.237; 4.U.166.238;
4.U.166.239; 4.U.166.154; 4.U.166.157; 4.U.166.166; 4.U.166.169; 4.U.166.172; 4.U.166.175;
4.U.166.240; 4.U.166.244; 4.U.169.228; 4.U.169.229; 4.U.169.230; 4.U.169.231; 4.U.169.236;
4.U.169.237; 4.U.169.238; 4.U.169.239; 4.U.169.154; 4.U.169.157; 4.U.169.166; 4.U.169.169;
4.U.169.172; 4.U.169.175; 4.U.169.240; 4.U.169.244; 4.U.172.228; 4.U.172.229; 4.U.172.230;
4.U.172.231; 4.U.172.236; 4.U.172.237; 4.U.172.238; 4.U.172.239; 4.U.172.154; 4.U.172.157;
4.U.172.166; 4.U.172.169; 4.U.172.172; 4.U.172.175; 4.U.172.240; 4.U.172.244; 4.U.175.228;
4.U.175.229; 4.U.175.230; 4.U.175.231; 4.U.175.236; 4.U.175.237; 4.U.175.238; 4.U.175.239;
4.U.175.154; 4.U.175.157; 4.U.175.166; 4.U.175.169; 4.U.175.172; 4.U.175.175; 4.U.175.240;
4.U.175.244; 4.U.240.228; 4.U.240.229; 4.U.240.230; 4.U.240.231; 4.U.240.236; 4.U.240.237;
4.U.240.238; 4.U.240.239; 4.U.240.154; 4.U.240.157; 4.U.240.166; 4.U.240.169; 4.U.240.172;
4.U.240.175; 4.U.240.240; 4.U.240.244; 4.U.244.228; 4.U.244.229; 4.U.244.230; 4.U.244.231;
4.U.244.236; 4.U.244.237; 4.U.244.238; 4.U.244.239; 4.U.244.154; 4.U.244.157; 4.U.244.166;
4.U.244.169; 4.U.244.172; 4.U.244.175; 4.U.244.240; 4.U.244.244;

Prodrugs of 4.W

4.W.228.228; 4.W.228.229; 4.W.228.230; 4.W.228.231; 4.W.228.236; 4.W.228.237;
4.W.228.238; 4.W.228.239; 4.W.228.154; 4.W.228.157; 4.W.228.166; 4.W.228.169;
4.W.228.172; 4.W.228.175; 4.W.228.240; 4.W.228.244; 4.W.229.228; 4.W.229.229;
4.W.229.230; 4.W.229.231; 4.W.229.236; 4.W.229.237; 4.W.229.238; 4.W.229.239;
4.W.229.154; 4.W.229.157; 4.W.229.166; 4.W.229.169; 4.W.229.172; 4.W.229.175;
4.W.229.240; 4.W.229.244; 4.W.230.228; 4.W.230.229; 4.W.230.230; 4.W.230.231;
4.W.230.236; 4.W.230.237; 4.W.230.238; 4.W.230.239; 4.W.230.154; 4.W.230.157;
4.W.230.166; 4.W.230.169; 4.W.230.172; 4.W.230.175; 4.W.230.240; 4.W.230.244;
4.W.231.228; 4.W.231.229; 4.W.231.230; 4.W.231.231; 4.W.231.236; 4.W.231.237;

TABLE 100-continued

4.W.231.238; 4.W.231.239; 4.W.231.154; 4.W.231.157; 4.W.231.166; 4.W.231.169;
4.W.231.172; 4.W.231.175; 4.W.231.240; 4.W.231.244; 4.W.236.228; 4.W.236.229;
4.W.236.230; 4.W.236.231; 4.W.236.236; 4.W.236.237; 4.W.236.238; 4.W.236.239;
4.W.236.154; 4.W.236.157; 4.W.236.166; 4.W.236.169; 4.W.236.172; 4.W.236.175;
4.W.236.240; 4.W.236.244; 4.W.237.228; 4.W.237.229; 4.W.237.230; 4.W.237.231;
4.W.237.236; 4.W.237.237; 4.W.237.238; 4.W.237.239; 4.W.237.154; 4.W.237.157;
4.W.237.166; 4.W.237.169; 4.W.237.172; 4.W.237.175; 4.W.237.240; 4.W.237.244;
4.W.238.228; 4.W.238.229; 4.W.238.230; 4.W.238.231; 4.W.238.236; 4.W.238.237;
4.W.238.238; 4.W.238.239; 4.W.238.154; 4.W.238.157; 4.W.238.166; 4.W.238.169;
4.W.238.172; 4.W.238.175; 4.W.238.240; 4.W.238.244; 4.W.239.228; 4.W.239.229;
4.W.239.230; 4.W.239.231; 4.W.239.236; 4.W.239.237; 4.W.239.238; 4.W.239.239;
4.W.239.154; 4.W.239.157; 4.W.239.166; 4.W.239.169; 4.W.239.172; 4.W.239.175;
4.W.239.240; 4.W.239.244; 4.W.154.228; 4.W.154.229; 4.W.154.230; 4.W.154.231;
4.W.154.236; 4.W.154.237; 4.W.154.238; 4.W.154.239; 4.W.154.154; 4.W.154.157;
4.W.154.166; 4.W.154.169; 4.W.154.172; 4.W.154.175; 4.W.154.240; 4.W.154.244;
4.W.157.228; 4.W.157.229; 4.W.157.230; 4.W.157.231; 4.W.157.236; 4.W.157.237;
4.W.157.238; 4.W.157.239; 4.W.157.154; 4.W.157.157; 4.W.157.166; 4.W.157.169;
4.W.157.172; 4.W.157.175; 4.W.157.240; 4.W.157.244; 4.W.166.228; 4.W.166.229;
4.W.166.230; 4.W.166.231; 4.W.166.236; 4.W.166.237; 4.W.166.238; 4.W.166.239;
4.W.166.154; 4.W.166.157; 4.W.166.166; 4.W.166.169; 4.W.166.172; 4.W.166.175;
4.W.166.240; 4.W.166.244; 4.W.169.228; 4.W.169.229; 4.W.169.230; 4.W.169.231;
4.W.169.236; 4.W.169.237; 4.W.169.238; 4.W.169.239; 4.W.169.154; 4.W.169.157;
4.W.169.166; 4.W.169.169; 4.W.169.172; 4.W.169.175; 4.W.169.240; 4.W.169.244;
4.W.172.228; 4.W.172.229; 4.W.172.230; 4.W.172.231; 4.W.172.236; 4.W.172.237;
4.W.172.238; 4.W.172.239; 4.W.172.154; 4.W.172.157; 4.W.172.166; 4.W.172.169;
4.W.172.172; 4.W.172.175; 4.W.172.240; 4.W.172.244; 4.W.175.228; 4.W.175.229;
4.W.175.230; 4.W.175.231; 4.W.175.236; 4.W.175.237; 4.W.175.238; 4.W.175.239;
4.W.175.154; 4.W.175.157; 4.W.175.166; 4.W.175.169; 4.W.175.172; 4.W.175.175;
4.W.175.240; 4.W.175.244; 4.W.240.228; 4.W.240.229; 4.W.240.230; 4.W.240.231;
4.W.240.236; 4.W.240.237; 4.W.240.238; 4.W.240.239; 4.W.240.154; 4.W.240.157;
4.W.240.166; 4.W.240.169; 4.W.240.172; 4.W.240.175; 4.W.240.240; 4.W.240.244;
4.W.244.228; 4.W.244.229; 4.W.244.230; 4.W.244.231; 4.W.244.236; 4.W.244.237;
4.W.244.238; 4.W.244.239; 4.W.244.154; 4.W.244.157; 4.W.244.166; 4.W.244.169;
4.W.244.172; 4.W.244.175; 4.W.244.240; 4.W.244.244;
Prodrugs of 4.Y 4.Y.228.228; 4.Y.228.229; 4.Y.228.230; 4.Y.228.231; 4.Y.228.236; 4.Y.228.237; 4.Y.228.238;
4.Y.228.239; 4.Y.228.154; 4.Y.228.157; 4.Y.228.166; 4.Y.228.169; 4.Y.228.172; 4.Y.228.175;
4.Y.228.240; 4.Y.228.244; 4.Y.229.228; 4.Y.229.229; 4.Y.229.230; 4.Y.229.231; 4.Y.229.236;
4.Y.229.237; 4.Y.229.238; 4.Y.229.239; 4.Y.229.154; 4.Y.229.157; 4.Y.229.166; 4.Y.229.169;
4.Y.229.172; 4.Y.229.175; 4.Y.229.240; 4.Y.229.244; 4.Y.230.228; 4.Y.230.229; 4.Y.230.230;
4.Y.230.231; 4.Y.230.236; 4.Y.230.237; 4.Y.230.238; 4.Y.230.239; 4.Y.230.154; 4.Y.230.157;
4.Y.230.166; 4.Y.230.169; 4.Y.230.172; 4.Y.230.175; 4.Y.230.240; 4.Y.230.244; 4.Y.231.228;
4.Y.231.229; 4.Y.231.230; 4.Y.231.231; 4.Y.231.236; 4.Y.231.237; 4.Y.231.238; 4.Y.231.239;
4.Y.231.154; 4.Y.231.157; 4.Y.231.166; 4.Y.231.169; 4.Y.231.172; 4.Y.231.175; 4.Y.231.240;
4.Y.231.244; 4.Y.236.228; 4.Y.236.229; 4.Y.236.230; 4.Y.236.231; 4.Y.236.236; 4.Y.236.237;
4.Y.236.238; 4.Y.236.239; 4.Y.236.154; 4.Y.236.157; 4.Y.236.166; 4.Y.236.169; 4.Y.236.172;
4.Y.236.175; 4.Y.236.240; 4.Y.236.244; 4.Y.237.228; 4.Y.237.229; 4.Y.237.230; 4.Y.237.231;
4.Y.237.236; 4.Y.237.237; 4.Y.237.238; 4.Y.237.239; 4.Y.237.154; 4.Y.237.157; 4.Y.237.166;
4.Y.237.169; 4.Y.237.172; 4.Y.237.175; 4.Y.237.240; 4.Y.237.244; 4.Y.238.228; 4.Y.238.229;
4.Y.238.230; 4.Y.238.231; 4.Y.238.236; 4.Y.238.237; 4.Y.238.238; 4.Y.238.239; 4.Y.238.154;
4.Y.238.157; 4.Y.238.166; 4.Y.238.169; 4.Y.238.172; 4.Y.238.175; 4.Y.238.240; 4.Y.238.244;
4.Y.239.228; 4.Y.239.229; 4.Y.239.230; 4.Y.239.231; 4.Y.239.236; 4.Y.239.237; 4.Y.239.238;
4.Y.239.239; 4.Y.239.154; 4.Y.239.157; 4.Y.239.166; 4.Y.239.169; 4.Y.239.172; 4.Y.239.175;
4.Y.239.240; 4.Y.239.244; 4.Y.154.228; 4.Y.154.229; 4.Y.154.230; 4.Y.154.231; 4.Y.154.236;
4.Y.154.237; 4.Y.154.238; 4.Y.154.239; 4.Y.154.154; 4.Y.154.157; 4.Y.154.166; 4.Y.154.169;
4.Y.154.172; 4.Y.154.175; 4.Y.154.240; 4.Y.154.244; 4.Y.157.228; 4.Y.157.229; 4.Y.157.230;
4.Y.157.231; 4.Y.157.236; 4.Y.157.237; 4.Y.157.238; 4.Y.157.239; 4.Y.157.154; 4.Y.157.157;
4.Y.157.166; 4.Y.157.169; 4.Y.157.172; 4.Y.157.175; 4.Y.157.240; 4.Y.157.244; 4.Y.166.228;
4.Y.166.229; 4.Y.166.230; 4.Y.166.231; 4.Y.166.236; 4.Y.166.237; 4.Y.166.238; 4.Y.166.239;
4.Y.166.154; 4.Y.166.157; 4.Y.166.166; 4.Y.166.169; 4.Y.166.172; 4.Y.166.175; 4.Y.166.240;
4.Y.166.244; 4.Y.169.228; 4.Y.169.229; 4.Y.169.230; 4.Y.169.231; 4.Y.169.236; 4.Y.169.237;
4.Y.169.238; 4.Y.169.239; 4.Y.169.154; 4.Y.169.157; 4.Y.169.166; 4.Y.169.169; 4.Y.169.172;
4.Y.169.175; 4.Y.169.240; 4.Y.169.244; 4.Y.172.228; 4.Y.172.229; 4.Y.172.230; 4.Y.172.231;
4.Y.172.236; 4.Y.172.237; 4.Y.172.238; 4.Y.172.239; 4.Y.172.154; 4.Y.172.157; 4.Y.172.166;
4.Y.172.169; 4.Y.172.172; 4.Y.172.175; 4.Y.172.240; 4.Y.172.244; 4.Y.175.228; 4.Y.175.229;
4.Y.175.230; 4.Y.175.231; 4.Y.175.236; 4.Y.175.237; 4.Y.175.238; 4.Y.175.239; 4.Y.175.154;
4.Y.175.157; 4.Y.175.166; 4.Y.175.169; 4.Y.175.172; 4.Y.175.175; 4.Y.175.240; 4.Y.175.244;
4.Y.240.228; 4.Y.240.229; 4.Y.240.230; 4.Y.240.231; 4.Y.240.236; 4.Y.240.237; 4.Y.240.238;
4.Y.240.239; 4.Y.240.154; 4.Y.240.157; 4.Y.240.166; 4.Y.240.169; 4.Y.240.172; 4.Y.240.175;
4.Y.240.240; 4.Y.240.244; 4.Y.244.228; 4.Y.244.229; 4.Y.244.230; 4.Y.244.231; 4.Y.244.236;
4.Y.244.237; 4.Y.244.238; 4.Y.244.239; 4.Y.244.154; 4.Y.244.157; 4.Y.244.166; 4.Y.244.169;
4.Y.244.172; 4.Y.244.175; 4.Y.244.240; 4.Y.244.244;
Prodrugs of 5.B 5.B.228.228; 5.B.228.229; 5.B.228.230; 5.B.228.231; 5.B.228.236; 5.B.228.237; 5.B.228.238;
5.B.228.239; 5.B.228.154; 5.B.228.157; 5.B.228.166; 5.B.228.169; 5.B.228.172; 5.B.228.175;
5.B.228.240; 5.B.228.244; 5.B.229.228; 5.B.229.229; 5.B.229.230; 5.B.229.231; 5.B.229.236;
5.B.229.237; 5.B.229.238; 5.B.229.239; 5.B.229.154; 5.B.229.157; 5.B.229.166; 5.B.229.169;

TABLE 100-continued

5.B.229.172; 5.B.229.175; 5.B.229.240; 5.B.229.244; 5.B.230.228; 5.B.230.229; 5.B.230.230; 5.B.230.231; 5.B.230.236; 5.B.230.237; 5.B.230.238; 5.B.230.239; 5.B.230.154; 5.B.230.157; 5.B.230.166; 5.B.230.169; 5.B.230.172; 5.B.230.175; 5.B.230.240; 5.B.230.244; 5.B.231.228; 5.B.231.229; 5.B.231.230; 5.B.231.231; 5.B.231.236; 5.B.231.237; 5.B.231.238; 5.B.231.239; 5.B.231.154; 5.B.231.157; 5.B.231.166; 5.B.231.169; 5.B.231.172; 5.B.231.175; 5.B.231.240; 5.B.231.244; 5.B.236.228; 5.B.236.229; 5.B.236.230; 5.B.236.231; 5.B.236.236; 5.B.236.237; 5.B.236.238; 5.B.236.239; 5.B.236.154; 5.B.236.157; 5.B.236.166; 5.B.236.169; 5.B.236.172; 5.B.236.175; 5.B.236.240; 5.B.236.244; 5.B.237.228; 5.B.237.229; 5.B.237.230; 5.B.237.231; 5.B.237.236; 5.B.237.237; 5.B.237.238; 5.B.237.239; 5.B.237.154; 5.B.237.157; 5.B.237.166; 5.B.237.169; 5.B.237.172; 5.B.237.175; 5.B.237.240; 5.B.237.244; 5.B.238.228; 5.B.238.229; 5.B.238.230; 5.B.238.231; 5.B.238.236; 5.B.238.237; 5.B.238.238; 5.B.238.239; 5.B.238.154; 5.B.238.157; 5.B.238.166; 5.B.238.169; 5.B.238.172; 5.B.238.175; 5.B.238.240; 5.B.238.244; 5.B.239.228; 5.B.239.229; 5.B.239.230; 5.B.239.231; 5.B.239.236; 5.B.239.237; 5.B.239.238; 5.B.239.239; 5.B.239.154; 5.B.239.157; 5.B.239.166; 5.B.239.169; 5.B.239.172; 5.B.239.175; 5.B.239.240; 5.B.239.244; 5.B.154.228; 5.B.154.229; 5.B.154.230; 5.B.154.231; 5.B.154.236; 5.B.154.237; 5.B.154.238; 5.B.154.239; 5.B.154.154; 5.B.154.157; 5.B.154.166; 5.B.154.169; 5.B.154.172; 5.B.154.175; 5.B.154.240; 5.B.154.244; 5.B.157.228; 5.B.157.229; 5.B.157.230; 5.B.157.231; 5.B.157.236; 5.B.157.237; 5.B.157.238; 5.B.157.239; 5.B.157.154; 5.B.157.157; 5.B.157.166; 5.B.157.169; 5.B.157.172; 5.B.157.175; 5.B.157.240; 5.B.157.244; 5.B.166.228; 5.B.166.229; 5.B.166.230; 5.B.166.231; 5.B.166.236; 5.B.166.237; 5.B.166.238; 5.B.166.239; 5.B.166.154; 5.B.166.157; 5.B.166.166; 5.B.166.169; 5.B.166.172; 5.B.166.175; 5.B.166.240; 5.B.166.244; 5.B.169.228; 5.B.169.229; 5.B.169.230; 5.B.169.231; 5.B.169.236; 5.B.169.237; 5.B.169.238; 5.B.169.239; 5.B.169.154; 5.B.169.157; 5.B.169.166; 5.B.169.169; 5.B.169.172; 5.B.169.175; 5.B.169.240; 5.B.169.244; 5.B.172.228; 5.B.172.229; 5.B.172.230; 5.B.172.231; 5.B.172.236; 5.B.172.237; 5.B.172.238; 5.B.172.239; 5.B.172.154; 5.B.172.157; 5.B.172.166; 5.B.172.169; 5.B.172.172; 5.B.172.175; 5.B.172.240; 5.B.172.244; 5.B.175.228; 5.B.175.229; 5.B.175.230; 5.B.175.231; 5.B.175.236; 5.B.175.237; 5.B.175.238; 5.B.175.239; 5.B.175.154; 5.B.175.157; 5.B.175.166; 5.B.175.169; 5.B.175.172; 5.B.175.175; 5.B.175.240; 5.B.175.244; 5.B.240.228; 5.B.240.229; 5.B.240.230; 5.B.240.231; 5.B.240.236; 5.B.240.237; 5.B.240.238; 5.B.240.239; 5.B.240.154; 5.B.240.157; 5.B.240.166; 5.B.240.169; 5.B.240.172; 5.B.240.175; 5.B.240.240; 5.B.240.244; 5.B.244.228; 5.B.244.229; 5.B.244.230; 5.B.244.231; 5.B.244.236; 5.B.244.237; 5.B.244.238; 5.B.244.239; 5.B.244.154; 5.B.244.157; 5.B.244.166; 5.B.244.169; 5.B.244.172; 5.B.244.175; 5.B.244.240; 5.B.244.244;

Prodrugs of 5.D

5.D.228.228; 5.D.228.229; 5.D.228.230; 5.D.228.231; 5.D.228.236; 5.D.228.237; 5.D.228.238; 5.D.228.239; 5.D.228.154; 5.D.228.157; 5.D.228.166; 5.D.228.169; 5.D.228.172; 5.D.228.175; 5.D.228.240; 5.D.228.244; 5.D.229.228; 5.D.229.229; 5.D.229.230; 5.D.229.231; 5.D.229.236; 5.D.229.237; 5.D.229.238; 5.D.229.239; 5.D.229.154; 5.D.229.157; 5.D.229.166; 5.D.229.169; 5.D.229.172; 5.D.229.175; 5.D.229.240; 5.D.229.244; 5.D.230.228; 5.D.230.229; 5.D.230.230; 5.D.230.231; 5.D.230.236; 5.D.230.237; 5.D.230.238; 5.D.230.239; 5.D.230.154; 5.D.230.157; 5.D.230.166; 5.D.230.169; 5.D.230.172; 5.D.230.175; 5.D.230.240; 5.D.230.244; 5.D.231.228; 5.D.231.229; 5.D.231.230; 5.D.231.231; 5.D.231.236; 5.D.231.237; 5.D.231.238; 5.D.231.239; 5.D.231.154; 5.D.231.157; 5.D.231.166; 5.D.231.169; 5.D.231.172; 5.D.231.175; 5.D.231.240; 5.D.231.244; 5.D.236.228; 5.D.236.229; 5.D.236.230; 5.D.236.231; 5.D.236.236; 5.D.236.237; 5.D.236.238; 5.D.236.239; 5.D.236.154; 5.D.236.157; 5.D.236.166; 5.D.236.169; 5.D.236.172; 5.D.236.175; 5.D.236.240; 5.D.236.244; 5.D.237.228; 5.D.237.229; 5.D.237.230; 5.D.237.231; 5.D.237.236; 5.D.237.237; 5.D.237.238; 5.D.237.239; 5.D.237.154; 5.D.237.157; 5.D.237.166; 5.D.237.169; 5.D.237.172; 5.D.237.175; 5.D.237.240; 5.D.237.244; 5.D.238.228; 5.D.238.229; 5.D.238.230; 5.D.238.231; 5.D.238.236; 5.D.238.237; 5.D.238.238; 5.D.238.239; 5.D.238.154; 5.D.238.157; 5.D.238.166; 5.D.238.169; 5.D.238.172; 5.D.238.175; 5.D.238.240; 5.D.238.244; 5.D.239.228; 5.D.239.229; 5.D.239.230; 5.D.239.231; 5.D.239.236; 5.D.239.237; 5.D.239.238; 5.D.239.239; 5.D.239.154; 5.D.239.157; 5.D.239.166; 5.D.239.169; 5.D.239.172; 5.D.239.175; 5.D.239.240; 5.D.239.244; 5.D.154.228; 5.D.154.229; 5.D.154.230; 5.D.154.231; 5.D.154.236; 5.D.154.237; 5.D.154.238; 5.D.154.239; 5.D.154.154; 5.D.154.157; 5.D.154.166; 5.D.154.169; 5.D.154.172; 5.D.154.175; 5.D.154.240; 5.D.154.244; 5.D.157.228; 5.D.157.229; 5.D.157.230; 5.D.157.231; 5.D.157.236; 5.D.157.237; 5.D.157.238; 5.D.157.239; 5.D.157.154; 5.D.157.157; 5.D.157.166; 5.D.157.169; 5.D.157.172; 5.D.157.175; 5.D.157.240; 5.D.157.244; 5.D.166.228; 5.D.166.229; 5.D.166.230; 5.D.166.231; 5.D.166.236; 5.D.166.237; 5.D.166.238; 5.D.166.239; 5.D.166.154; 5.D.166.157; 5.D.166.166; 5.D.166.169; 5.D.166.172; 5.D.166.175; 5.D.166.240; 5.D.166.244; 5.D.169.228; 5.D.169.229; 5.D.169.230; 5.D.169.231; 5.D.169.236; 5.D.169.237; 5.D.169.238; 5.D.169.239; 5.D.169.154; 5.D.169.157; 5.D.169.166; 5.D.169.169; 5.D.169.172; 5.D.169.175; 5.D.169.240; 5.D.169.244; 5.D.172.228; 5.D.172.229; 5.D.172.230; 5.D.172.231; 5.D.172.236; 5.D.172.237; 5.D.172.238; 5.D.172.239; 5.D.172.154; 5.D.172.157; 5.D.172.166; 5.D.172.169; 5.D.172.172; 5.D.172.175; 5.D.172.240; 5.D.172.244; 5.D.175.228; 5.D.175.229; 5.D.175.230; 5.D.175.231; 5.D.175.236; 5.D.175.237; 5.D.175.238; 5.D.175.239; 5.D.175.154; 5.D.175.157; 5.D.175.166; 5.D.175.169; 5.D.175.172; 5.D.175.175; 5.D.175.240; 5.D.175.244; 5.D.240.228; 5.D.240.229; 5.D.240.230; 5.D.240.231; 5.D.240.236; 5.D.240.237; 5.D.240.238; 5.D.240.239; 5.D.240.154; 5.D.240.157; 5.D.240.166; 5.D.240.169; 5.D.240.172; 5.D.240.175; 5.D.240.240; 5.D.240.244; 5.D.244.228; 5.D.244.229; 5.D.244.230; 5.D.244.231; 5.D.244.236; 5.D.244.237; 5.D.244.238; 5.D.244.239; 5.D.244.154; 5.D.244.157; 5.D.244.166; 5.D.244.169; 5.D.244.172; 5.D.244.175; 5.D.244.240; 5.D.244.244;

Prodrugs of 5.E

5.E.228.228; 5.E.228.229; 5.E.228.230; 5.E.228.231; 5.E.228.236; 5.E.228.237; 5.E.228.238; 5.E.228.239; 5.E.228.154; 5.E.228.157; 5.E.228.166; 5.E.228.169; 5.E.228.172; 5.E.228.175; 5.E.228.240; 5.E.228.244; 5.E.229.228; 5.E.229.229; 5.E.229.230; 5.E.229.231; 5.E.229.236; 5.E.229.237; 5.E.229.238; 5.E.229.239; 5.E.229.154; 5.E.229.157; 5.E.229.166; 5.E.229.169; 5.E.229.172; 5.E.229.175; 5.E.229.240; 5.E.229.244; 5.E.230.228; 5.E.230.229; 5.E.230.230;

TABLE 100-continued

5.E.230.231; 5.E.230.236; 5.E.230.237; 5.E.230.238; 5.E.230.239; 5.E.230.154; 5.E.230.157;
5.E.230.166; 5.E.230.169; 5.E.230.172; 5.E.230.175; 5.E.230.240; 5.E.230.244; 5.E.231.228;
5.E.231.229; 5.E.231.230; 5.E.231.231; 5.E.231.236; 5.E.231.237; 5.E.231.238; 5.E.231.239;
5.E.231.154; 5.E.231.157; 5.E.231.166; 5.E.231.169; 5.E.231.172; 5.E.231.175; 5.E.231.240;
5.E.231.244; 5.E.236.228; 5.E.236.229; 5.E.236.230; 5.E.236.231; 5.E.236.236; 5.E.236.237;
5.E.236.238; 5.E.236.239; 5.E.236.154; 5.E.236.157; 5.E.236.166; 5.E.236.169; 5.E.236.172;
5.E.236.175; 5.E.236.240; 5.E.236.244; 5.E.237.228; 5.E.237.229; 5.E.237.230; 5.E.237.231;
5.E.237.236; 5.E.237.237; 5.E.237.238; 5.E.237.239; 5.E.237.154; 5.E.237.157; 5.E.237.166;
5.E.237.169; 5.E.237.172; 5.E.237.175; 5.E.237.240; 5.E.237.244; 5.E.238.228; 5.E.238.229;
5.E.238.230; 5.E.238.231; 5.E.238.236; 5.E.238.237; 5.E.238.238; 5.E.238.239; 5.E.238.154;
5.E.238.157; 5.E.238.166; 5.E.238.169; 5.E.238.172; 5.E.238.175; 5.E.238.240; 5.E.238.244;
5.E.239.228; 5.E.239.229; 5.E.239.230; 5.E.239.231; 5.E.239.236; 5.E.239.237; 5.E.239.238;
5.E.239.239; 5.E.239.154; 5.E.239.157; 5.E.239.166; 5.E.239.169; 5.E.239.172; 5.E.239.175;
5.E.239.240; 5.E.239.244; 5.E.154.228; 5.E.154.229; 5.E.154.230; 5.E.154.231; 5.E.154.236;
5.E.154.237; 5.E.154.238; 5.E.154.239; 5.E.154.154; 5.E.154.157; 5.E.154.166; 5.E.154.169;
5.E.154.172; 5.E.154.175; 5.E.154.240; 5.E.154.244; 5.E.157.228; 5.E.157.229; 5.E.157.230;
5.E.157.231; 5.E.157.236; 5.E.157.237; 5.E.157.238; 5.E.157.239; 5.E.157.154; 5.E.157.157;
5.E.157.166; 5.E.157.169; 5.E.157.172; 5.E.157.175; 5.E.157.240; 5.E.157.244; 5.E.166.228;
5.E.166.229; 5.E.166.230; 5.E.166.231; 5.E.166.236; 5.E.166.237; 5.E.166.238; 5.E.166.239;
5.E.166.154; 5.E.166.157; 5.E.166.166; 5.E.166.169; 5.E.166.172; 5.E.166.175; 5.E.166.240;
5.E.166.244; 5.E.169.228; 5.E.169.229; 5.E.169.230; 5.E.169.231; 5.E.169.236; 5.E.169.237;
5.E.169.238; 5.E.169.239; 5.E.169.154; 5.E.169.157; 5.E.169.166; 5.E.169.169; 5.E.169.172;
5.E.169.175; 5.E.169.240; 5.E.169.244; 5.E.172.228; 5.E.172.229; 5.E.172.230; 5.E.172.231;
5.E.172.236; 5.E.172.237; 5.E.172.238; 5.E.172.239; 5.E.172.154; 5.E.172.157; 5.E.172.166;
5.E.172.169; 5.E.172.172; 5.E.172.175; 5.E.172.240; 5.E.172.244; 5.E.175.228; 5.E.175.229;
5.E.175.230; 5.E.175.231; 5.E.175.236; 5.E.175.237; 5.E.175.238; 5.E.175.239; 5.E.175.154;
5.E.175.157; 5.E.175.166; 5.E.175.169; 5.E.175.172; 5.E.175.175; 5.E.175.240; 5.E.175.244;
5.E.240.228; 5.E.240.229; 5.E.240.230; 5.E.240.231; 5.E.240.236; 5.E.240.237; 5.E.240.238;
5.E.240.239; 5.E.240.154; 5.E.240.157; 5.E.240.166; 5.E.240.169; 5.E.240.172; 5.E.240.175;
5.E.240.240; 5.E.240.244; 5.E.244.228; 5.E.244.229; 5.E.244.230; 5.E.244.231; 5.E.244.236;
5.E.244.237; 5.E.244.238; 5.E.244.239; 5.E.244.154; 5.E.244.157; 5.E.244.166; 5.E.244.169;
5.E.244.172; 5.E.244.175; 5.E.244.240; 5.E.244.244;
Prodrugs of 5.G 5.G.228.228; 5.G.228.229; 5.G.228.230; 5.G.228.231; 5.G.228.236; 5.G.228.237;
5.G.228.238; 5.G.228.239; 5.G.228.154; 5.G.228.157; 5.G.228.166; 5.G.228.169; 5.G.228.172;
5.G.228.175; 5.G.228.240; 5.G.228.244; 5.G.229.228; 5.G.229.229; 5.G.229.230; 5.G.229.231;
5.G.229.236; 5.G.229.237; 5.G.229.238; 5.G.229.239; 5.G.229.154; 5.G.229.157; 5.G.229.166;
5.G.229.169; 5.G.229.172; 5.G.229.175; 5.G.229.240; 5.G.229.244; 5.G.230.228; 5.G.230.229;
5.G.230.230; 5.G.230.231; 5.G.230.236; 5.G.230.237; 5.G.230.238; 5.G.230.239; 5.G.230.154;
5.G.230.157; 5.G.230.166; 5.G.230.169; 5.G.230.172; 5.G.230.175; 5.G.230.240; 5.G.230.244;
5.G.231.228; 5.G.231.229; 5.G.231.230; 5.G.231.231; 5.G.231.236; 5.G.231.237; 5.G.231.238;
5.G.231.239; 5.G.231.154; 5.G.231.157; 5.G.231.166; 5.G.231.169; 5.G.231.172; 5.G.231.175;
5.G.231.240; 5.G.231.244; 5.G.236.228; 5.G.236.229; 5.G.236.230; 5.G.236.231; 5.G.236.236;
5.G.236.237; 5.G.236.238; 5.G.236.239; 5.G.236.154; 5.G.236.157; 5.G.236.166; 5.G.236.169;
5.G.236.172; 5.G.236.175; 5.G.236.240; 5.G.236.244; 5.G.237.228; 5.G.237.229; 5.G.237.230;
5.G.237.231; 5.G.237.236; 5.G.237.237; 5.G.237.238; 5.G.237.239; 5.G.237.154; 5.G.237.157;
5.G.237.166; 5.G.237.169; 5.G.237.172; 5.G.237.175; 5.G.237.240; 5.G.237.244; 5.G.238.228;
5.G.238.229; 5.G.238.230; 5.G.238.231; 5.G.238.236; 5.G.238.237; 5.G.238.238; 5.G.238.239;
5.G.238.154; 5.G.238.157; 5.G.238.166; 5.G.238.169; 5.G.238.172; 5.G.238.175; 5.G.238.240;
5.G.238.244; 5.G.239.228; 5.G.239.229; 5.G.239.230; 5.G.239.231; 5.G.239.236; 5.G.239.237;
5.G.239.238; 5.G.239.239; 5.G.239.154; 5.G.239.157; 5.G.239.166; 5.G.239.169; 5.G.239.172;
5.G.239.175; 5.G.239.240; 5.G.239.244; 5.G.154.228; 5.G.154.229; 5.G.154.230; 5.G.154.231;
5.G.154.236; 5.G.154.237; 5.G.154.238; 5.G.154.239; 5.G.154.154; 5.G.154.157; 5.G.154.166;
5.G.154.169; 5.G.154.172; 5.G.154.175; 5.G.154.240; 5.G.154.244; 5.G.157.228; 5.G.157.229;
5.G.157.230; 5.G.157.231; 5.G.157.236; 5.G.157.237; 5.G.157.238; 5.G.157.239; 5.G.157.154;
5.G.157.157; 5.G.157.166; 5.G.157.169; 5.G.157.172; 5.G.157.175; 5.G.157.240; 5.G.157.244;
5.G.166.228; 5.G.166.229; 5.G.166.230; 5.G.166.231; 5.G.166.236; 5.G.166.237; 5.G.166.238;
5.G.166.239; 5.G.166.154; 5.G.166.157; 5.G.166.166; 5.G.166.169; 5.G.166.172; 5.G.166.175;
5.G.166.240; 5.G.166.244; 5.G.169.228; 5.G.169.229; 5.G.169.230; 5.G.169.231; 5.G.169.236;
5.G.169.237; 5.G.169.238; 5.G.169.239; 5.G.169.154; 5.G.169.157; 5.G.169.166; 5.G.169.169;
5.G.169.172; 5.G.169.175; 5.G.169.240; 5.G.169.244; 5.G.172.228; 5.G.172.229; 5.G.172.230;
5.G.172.231; 5.G.172.236; 5.G.172.237; 5.G.172.238; 5.G.172.239; 5.G.172.154; 5.G.172.157;
5.G.172.166; 5.G.172.169; 5.G.172.172; 5.G.172.175; 5.G.172.240; 5.G.172.244; 5.G.175.228;
5.G.175.229; 5.G.175.230; 5.G.175.231; 5.G.175.236; 5.G.175.237; 5.G.175.238; 5.G.175.239;
5.G.175.154; 5.G.175.157; 5.G.175.166; 5.G.175.169; 5.G.175.172; 5.G.175.175; 5.G.175.240;
5.G.175.244; 5.G.240.228; 5.G.240.229; 5.G.240.230; 5.G.240.231; 5.G.240.236; 5.G.240.237;
5.G.240.238; 5.G.240.239; 5.G.240.154; 5.G.240.157; 5.G.240.166; 5.G.240.169; 5.G.240.172;
5.G.240.175; 5.G.240.240; 5.G.240.244; 5.G.244.228; 5.G.244.229; 5.G.244.230; 5.G.244.231;
5.G.244.236; 5.G.244.237; 5.G.244.238; 5.G.244.239; 5.G.244.154; 5.G.244.157; 5.G.244.166;
5.G.244.169; 5.G.244.172; 5.G.244.175; 5.G.244.240; 5.G.244.244;
Prodrugs of 5.I 5.I.228.228; 5.I.228.229; 5.I.228.230; 5.I.228.231; 5.I.228.236; 5.I.228.237; 5.I.228.238;
5.I.228.239; 5.I.228.154; 5.I.228.157; 5.I.228.166; 5.I.228.169; 5.I.228.172; 5.I.228.175;
5.I.228.240; 5.I.228.244; 5.I.229.228; 5.I.229.229; 5.I.229.230; 5.I.229.231; 5.I.229.236;
5.I.229.237; 5.I.229.238; 5.I.229.239; 5.I.229.154; 5.I.229.157; 5.I.229.166; 5.I.229.169;
5.I.229.172; 5.I.229.175; 5.I.229.240; 5.I.229.244; 5.I.230.228; 5.I.230.229; 5.I.230.230;
5.I.230.231; 5.I.230.236; 5.I.230.237; 5.I.230.238; 5.I.230.239; 5.I.230.154; 5.I.230.157;

TABLE 100-continued

5.I.230.166; 5.I.230.169; 5.I.230.172; 5.I.230.175; 5.I.230.240; 5.I.230.244; 5.I.231.228;
5.I.231.229; 5.I.231.230; 5.I.231.231; 5.I.231.236; 5.I.231.237; 5.I.231.238; 5.I.231.239;
5.I.231.154; 5.I.231.157; 5.I.231.166; 5.I.231.169; 5.I.231.172; 5.I.231.175; 5.I.231.240;
5.I.231.244; 5.I.236.228; 5.I.236.229; 5.I.236.230; 5.I.236.231; 5.I.236.236; 5.I.236.237;
5.I.236.238; 5.I.236.239; 5.I.236.154; 5.I.236.157; 5.I.236.166; 5.I.236.169; 5.I.236.172;
5.I.236.175; 5.I.236.240; 5.I.236.244; 5.I.237.228; 5.I.237.229; 5.I.237.230; 5.I.237.231;
5.I.237.236; 5.I.237.237; 5.I.237.238; 5.I.237.239; 5.I.237.154; 5.I.237.157; 5.I.237.166;
5.I.237.169; 5.I.237.172; 5.I.237.175; 5.I.237.240; 5.I.237.244; 5.I.238.228; 5.I.238.229;
5.I.238.230; 5.I.238.231; 5.I.238.236; 5.I.238.237; 5.I.238.238; 5.I.238.239; 5.I.238.154;
5.I.238.157; 5.I.238.166; 5.I.238.169; 5.I.238.172; 5.I.238.175; 5.I.238.240; 5.I.238.244;
5.I.239.228; 5.I.239.229; 5.I.239.230; 5.I.239.231; 5.I.239.236; 5.I.239.237; 5.I.239.238;
5.I.239.239; 5.I.239.154; 5.I.239.157; 5.I.239.166; 5.I.239.169; 5.I.239.172; 5.I.239.175;
5.I.239.240; 5.I.239.244; 5.I.154.228; 5.I.154.229; 5.I.154.230; 5.I.154.231; 5.I.154.236;
5.I.154.237; 5.I.154.238; 5.I.154.239; 5.I.154.154; 5.I.154.157; 5.I.154.166; 5.I.154.169;
5.I.154.172; 5.I.154.175; 5.I.154.240; 5.I.154.244; 5.I.157.228; 5.I.157.229; 5.I.157.230;
5.I.157.231; 5.I.157.236; 5.I.157.237; 5.I.157.238; 5.I.157.239; 5.I.157.154; 5.I.157.157;
5.I.157.166; 5.I.157.169; 5.I.157.172; 5.I.157.175; 5.I.157.240; 5.I.157.244; 5.I.166.228;
5.I.166.229; 5.I.166.230; 5.I.166.231; 5.I.166.236; 5.I.166.237; 5.I.166.238; 5.I.166.239;
5.I.166.154; 5.I.166.157; 5.I.166.166; 5.I.166.169; 5.I.166.172; 5.I.166.175; 5.I.166.240;
5.I.166.244; 5.I.169.228; 5.I.169.229; 5.I.169.230; 5.I.169.231; 5.I.169.236; 5.I.169.237;
5.I.169.238; 5.I.169.239; 5.I.169.154; 5.I.169.157; 5.I.169.166; 5.I.169.169; 5.I.169.172;
5.I.169.175; 5.I.169.240; 5.I.169.244; 5.I.172.228; 5.I.172.229; 5.I.172.230; 5.I.172.231;
5.I.172.236; 5.I.172.237; 5.I.172.238; 5.I.172.239; 5.I.172.154; 5.I.172.157; 5.I.172.166;
5.I.172.169; 5.I.172.172; 5.I.172.175; 5.I.172.240; 5.I.172.244; 5.I.175.228; 5.I.175.229;
5.I.175.230; 5.I.175.231; 5.I.175.236; 5.I.175.237; 5.I.175.238; 5.I.175.239; 5.I.175.154;
5.I.175.157; 5.I.175.166; 5.I.175.169; 5.I.175.172; 5.I.175.175; 5.I.175.240; 5.I.175.244;
5.I.240.228; 5.I.240.229; 5.I.240.230; 5.I.240.231; 5.I.240.236; 5.I.240.237; 5.I.240.238;
5.I.240.239; 5.I.240.154; 5.I.240.157; 5.I.240.166; 5.I.240.169; 5.I.240.172; 5.I.240.175;
5.I.240.240; 5.I.240.244; 5.I.244.228; 5.I.244.229; 5.I.244.230; 5.I.244.231; 5.I.244.236;
5.I.244.237; 5.I.244.238; 5.I.244.239; 5.I.244.154; 5.I.244.157; 5.I.244.166; 5.I.244.169;
5.I.244.172; 5.I.244.175; 5.I.244.240; 5.I.244.244;
Prodrugs of 5.J 5.J.228.228; 5.J.228.229; 5.J.228.230; 5.J.228.231; 5.J.228.236; 5.J.228.237; 5.J.228.238;
5.J.228.239; 5.J.228.154; 5.J.228.157; 5.J.228.166; 5.J.228.169; 5.J.228.172; 5.J.228.175;
5.J.228.240; 5.J.228.244; 5.J.229.228; 5.J.229.229; 5.J.229.230; 5.J.229.231; 5.J.229.236;
5.J.229.237; 5.J.229.238; 5.J.229.239; 5.J.229.154; 5.J.229.157; 5.J.229.166; 5.J.229.169;
5.J.229.172; 5.J.229.175; 5.J.229.240; 5.J.229.244; 5.J.230.228; 5.J.230.229; 5.J.230.230;
5.J.230.231; 5.J.230.236; 5.J.230.237; 5.J.230.238; 5.J.230.239; 5.J.230.154; 5.J.230.157;
5.J.230.166; 5.J.230.169; 5.J.230.172; 5.J.230.175; 5.J.230.240; 5.J.230.244; 5.J.231.228;
5.J.231.229; 5.J.231.230; 5.J.231.231; 5.J.231.236; 5.J.231.237; 5.J.231.238; 5.J.231.239;
5.J.231.154; 5.J.231.157; 5.J.231.166; 5.J.231.169; 5.J.231.172; 5.J.231.175; 5.J.231.240;
5.J.231.244; 5.J.236.228; 5.J.236.229; 5.J.236.230; 5.J.236.231; 5.J.236.236; 5.J.236.237;
5.J.236.238; 5.J.236.239; 5.J.236.154; 5.J.236.157; 5.J.236.166; 5.J.236.169; 5.J.236.172;
5.J.236.175; 5.J.236.240; 5.J.236.244; 5.J.237.228; 5.J.237.229; 5.J.237.230; 5.J.237.231;
5.J.237.236; 5.J.237.237; 5.J.237.238; 5.J.237.239; 5.J.237.154; 5.J.237.157; 5.J.237.166;
5.J.237.169; 5.J.237.172; 5.J.237.175; 5.J.237.240; 5.J.237.244; 5.J.238.228; 5.J.238.229;
5.J.238.230; 5.J.238.231; 5.J.238.236; 5.J.238.237; 5.J.238.238; 5.J.238.239; 5.J.238.154;
5.J.238.157; 5.J.238.166; 5.J.238.169; 5.J.238.172; 5.J.238.175; 5.J.238.240; 5.J.238.244;
5.J.239.228; 5.J.239.229; 5.J.239.230; 5.J.239.231; 5.J.239.236; 5.J.239.237; 5.J.239.238;
5.J.239.239; 5.J.239.154; 5.J.239.157; 5.J.239.166; 5.J.239.169; 5.J.239.172; 5.J.239.175;
5.J.239.240; 5.J.239.244; 5.J.154.228; 5.J.154.229; 5.J.154.230; 5.J.154.231; 5.J.154.236;
5.J.154.237; 5.J.154.238; 5.J.154.239; 5.J.154.154; 5.J.154.157; 5.J.154.166; 5.J.154.169;
5.J.154.172; 5.J.154.175; 5.J.154.240; 5.J.154.244; 5.J.157.228; 5.J.157.229; 5.J.157.230;
5.J.157.231; 5.J.157.236; 5.J.157.237; 5.J.157.238; 5.J.157.239; 5.J.157.154; 5.J.157.157;
5.J.157.166; 5.J.157.169; 5.J.157.172; 5.J.157.175; 5.J.157.240; 5.J.157.244; 5.J.166.228;
5.J.166.229; 5.J.166.230; 5.J.166.231; 5.J.166.236; 5.J.166.237; 5.J.166.238; 5.J.166.239;
5.J.166.154; 5.J.166.157; 5.J.166.166; 5.J.166.169; 5.J.166.172; 5.J.166.175; 5.J.166.240;
5.J.166.244; 5.J.169.228; 5.J.169.229; 5.J.169.230; 5.J.169.231; 5.J.169.236; 5.J.169.237;
5.J.169.238; 5.J.169.239; 5.J.169.154; 5.J.169.157; 5.J.169.166; 5.J.169.169; 5.J.169.172;
5.J.169.175; 5.J.169.240; 5.J.169.244; 5.J.172.228; 5.J.172.229; 5.J.172.230; 5.J.172.231;
5.J.172.236; 5.J.172.237; 5.J.172.238; 5.J.172.239; 5.J.172.154; 5.J.172.157; 5.J.172.166;
5.J.172.169; 5.J.172.172; 5.J.172.175; 5.J.172.240; 5.J.172.244; 5.J.175.228; 5.J.175.229;
5.J.175.230; 5.J.175.231; 5.J.175.236; 5.J.175.237; 5.J.175.238; 5.J.175.239; 5.J.175.154;
5.J.175.157; 5.J.175.166; 5.J.175.169; 5.J.175.172; 5.J.175.175; 5.J.175.240; 5.J.175.244;
5.J.240.228; 5.J.240.229; 5.J.240.230; 5.J.240.231; 5.J.240.236; 5.J.240.237; 5.J.240.238;
5.J.240.239; 5.J.240.154; 5.J.240.157; 5.J.240.166; 5.J.240.169; 5.J.240.172; 5.J.240.175;
5.J.240.240; 5.J.240.244; 5.J.244.228; 5.J.244.229; 5.J.244.230; 5.J.244.231; 5.J.244.236;
5.J.244.237; 5.J.244.238; 5.J.244.239; 5.J.244.154; 5.J.244.157; 5.J.244.166; 5.J.244.169;
5.J.244.172; 5.J.244.175; 5.J.244.240; 5.J.244.244;
Prodrugs of 5.L 5.L.228.228; 5.L.228.229; 5.L.228.230; 5.L.228.231; 5.L.228.236; 5.L.228.237; 5.L.228.238;
5.L.228.239; 5.L.228.154; 5.L.228.157; 5.L.228.166; 5.L.228.169; 5.L.228.172; 5.L.228.175;
5.L.228.240; 5.L.228.244; 5.L.229.228; 5.L.229.229; 5.L.229.230; 5.L.229.231; 5.L.229.236;
5.L.229.237; 5.L.229.238; 5.L.229.239; 5.L.229.154; 5.L.229.157; 5.L.229.166; 5.L.229.169;
5.L.229.172; 5.L.229.175; 5.L.229.240; 5.L.229.244; 5.L.230.228; 5.L.230.229; 5.L.230.230;
5.L.230.231; 5.L.230.236; 5.L.230.237; 5.L.230.238; 5.L.230.239; 5.L.230.154; 5.L.230.157;
5.L.230.166; 5.L.230.169; 5.L.230.172; 5.L.230.175; 5.L.230.240; 5.L.230.244; 5.L.231.228;

TABLE 100-continued

5.L.231.229; 5.L.231.230; 5.L.231.231; 5.L.231.236; 5.L.231.237; 5.L.231.238; 5.L.231.239;
5.L.231.154; 5.L.231.157; 5.L.231.166; 5.L.231.169; 5.L.231.172; 5.L.231.175; 5.L.231.240;
5.L.231.244; 5.L.236.228; 5.L.236.229; 5.L.236.230; 5.L.236.231; 5.L.236.236; 5.L.236.237;
5.L.236.238; 5.L.236.239; 5.L.236.154; 5.L.236.157; 5.L.236.166; 5.L.236.169; 5.L.236.172;
5.L.236.175; 5.L.236.240; 5.L.236.244; 5.L.237.228; 5.L.237.229; 5.L.237.230; 5.L.237.231;
5.L.237.236; 5.L.237.237; 5.L.237.238; 5.L.237.239; 5.L.237.154; 5.L.237.157; 5.L.237.166;
5.L.237.169; 5.L.237.172; 5.L.237.175; 5.L.237.240; 5.L.237.244; 5.L.238.228; 5.L.238.229;
5.L.238.230; 5.L.238.231; 5.L.238.236; 5.L.238.237; 5.L.238.238; 5.L.238.239; 5.L.238.154;
5.L.238.157; 5.L.238.166; 5.L.238.169; 5.L.238.172; 5.L.238.175; 5.L.238.240; 5.L.238.244;
5.L.239.228; 5.L.239.229; 5.L.239.230; 5.L.239.231; 5.L.239.236; 5.L.239.237; 5.L.239.238;
5.L.239.239; 5.L.239.154; 5.L.239.157; 5.L.239.166; 5.L.239.169; 5.L.239.172; 5.L.239.175;
5.L.239.240; 5.L.239.244; 5.L.154.228; 5.L.154.229; 5.L.154.230; 5.L.154.231; 5.L.154.236;
5.L.154.237; 5.L.154.238; 5.L.154.239; 5.L.154.154; 5.L.154.157; 5.L.154.166; 5.L.154.169;
5.L.154.172; 5.L.154.175; 5.L.154.240; 5.L.154.244; 5.L.157.228; 5.L.157.229; 5.L.157.230;
5.L.157.231; 5.L.157.236; 5.L.157.237; 5.L.157.238; 5.L.157.239; 5.L.157.154; 5.L.157.157;
5.L.157.166; 5.L.157.169; 5.L.157.172; 5.L.157.175; 5.L.157.240; 5.L.157.244; 5.L.166.228;
5.L.166.229; 5.L.166.230; 5.L.166.231; 5.L.166.236; 5.L.166.237; 5.L.166.238; 5.L.166.239;
5.L.166.154; 5.L.166.157; 5.L.166.166; 5.L.166.169; 5.L.166.172; 5.L.166.175; 5.L.166.240;
5.L.166.244; 5.L.169.228; 5.L.169.229; 5.L.169.230; 5.L.169.231; 5.L.169.236; 5.L.169.237;
5.L.169.238; 5.L.169.239; 5.L.169.154; 5.L.169.157; 5.L.169.166; 5.L.169.169; 5.L.169.172;
5.L.169.175; 5.L.169.240; 5.L.169.244; 5.L.172.228; 5.L.172.229; 5.L.172.230; 5.L.172.231;
5.L.172.236; 5.L.172.237; 5.L.172.238; 5.L.172.239; 5.L.172.154; 5.L.172.157; 5.L.172.166;
5.L.172.169; 5.L.172.172; 5.L.172.175; 5.L.172.240; 5.L.172.244; 5.L.175.228; 5.L.175.229;
5.L.175.230; 5.L.175.231; 5.L.175.236; 5.L.175.237; 5.L.175.238; 5.L.175.239; 5.L.175.154;
5.L.175.157; 5.L.175.166; 5.L.175.169; 5.L.175.172; 5.L.175.175; 5.L.175.240; 5.L.175.244;
5.L.240.228; 5.L.240.229; 5.L.240.230; 5.L.240.231; 5.L.240.236; 5.L.240.237; 5.L.240.238;
5.L.240.239; 5.L.240.154; 5.L.240.157; 5.L.240.166; 5.L.240.169; 5.L.240.172; 5.L.240.175;
5.L.240.240; 5.L.240.244; 5.L.244.228; 5.L.244.229; 5.L.244.230; 5.L.244.231; 5.L.244.236;
5.L.244.237; 5.L.244.238; 5.L.244.239; 5.L.244.154; 5.L.244.157; 5.L.244.166; 5.L.244.169;
5.L.244.172; 5.L.244.175; 5.L.244.240; 5.L.244.244;
Prodrugs of 5.O 5.O.228.228; 5.O.228.229; 5.O.228.230; 5.O.228.231; 5.O.228.236; 5.O.228.237;
5.O.228.238; 5.O.228.239; 5.O.228.154; 5.O.228.157; 5.O.228.166; 5.O.228.169; 5.O.228.172;
5.O.228.175; 5.O.228.240; 5.O.228.244; 5.O.229.228; 5.O.229.229; 5.O.229.230; 5.O.229.231;
5.O.229.236; 5.O.229.237; 5.O.229.238; 5.O.229.239; 5.O.229.154; 5.O.229.157; 5.O.229.166;
5.O.229.169; 5.O.229.172; 5.O.229.175; 5.O.229.240; 5.O.229.244; 5.O.230.228; 5.O.230.229;
5.O.230.230; 5.O.230.231; 5.O.230.236; 5.O.230.237; 5.O.230.238; 5.O.230.239; 5.O.230.154;
5.O.230.157; 5.O.230.166; 5.O.230.169; 5.O.230.172; 5.O.230.175; 5.O.230.240; 5.O.230.244;
5.O.231.228; 5.O.231.229; 5.O.231.230; 5.O.231.231; 5.O.231.236; 5.O.231.237; 5.O.231.238;
5.O.231.239; 5.O.231.154; 5.O.231.157; 5.O.231.166; 5.O.231.169; 5.O.231.172; 5.O.231.175;
5.O.231.240; 5.O.231.244; 5.O.236.228; 5.O.236.229; 5.O.236.230; 5.O.236.231; 5.O.236.236;
5.O.236.237; 5.O.236.238; 5.O.236.239; 5.O.236.154; 5.O.236.157; 5.O.236.166; 5.O.236.169;
5.O.236.172; 5.O.236.175; 5.O.236.240; 5.O.236.244; 5.O.237.228; 5.O.237.229; 5.O.237.230;
5.O.237.231; 5.O.237.236; 5.O.237.237; 5.O.237.238; 5.O.237.239; 5.O.237.154; 5.O.237.157;
5.O.237.166; 5.O.237.169; 5.O.237.172; 5.O.237.175; 5.O.237.240; 5.O.237.244; 5.O.238.228;
5.O.238.229; 5.O.238.230; 5.O.238.231; 5.O.238.236; 5.O.238.237; 5.O.238.238; 5.O.238.239;
5.O.238.154; 5.O.238.157; 5.O.238.166; 5.O.238.169; 5.O.238.172; 5.O.238.175; 5.O.238.240;
5.O.238.244; 5.O.239.228; 5.O.239.229; 5.O.239.230; 5.O.239.231; 5.O.239.236; 5.O.239.237;
5.O.239.238; 5.O.239.239; 5.O.239.154; 5.O.239.157; 5.O.239.166; 5.O.239.169; 5.O.239.172;
5.O.239.175; 5.O.239.240; 5.O.239.244; 5.O.154.228; 5.O.154.229; 5.O.154.230; 5.O.154.231;
5.O.154.236; 5.O.154.237; 5.O.154.238; 5.O.154.239; 5.O.154.154; 5.O.154.157; 5.O.154.166;
5.O.154.169; 5.O.154.172; 5.O.154.175; 5.O.154.240; 5.O.154.244; 5.O.157.228; 5.O.157.229;
5.O.157.230; 5.O.157.231; 5.O.157.236; 5.O.157.237; 5.O.157.238; 5.O.157.239; 5.O.157.154;
5.O.157.157; 5.O.157.166; 5.O.157.169; 5.O.157.172; 5.O.157.175; 5.O.157.240; 5.O.157.244;
5.O.166.228; 5.O.166.229; 5.O.166.230; 5.O.166.231; 5.O.166.236; 5.O.166.237; 5.O.166.238;
5.O.166.239; 5.O.166.154; 5.O.166.157; 5.O.166.166; 5.O.166.169; 5.O.166.172; 5.O.166.175;
5.O.166.240; 5.O.166.244; 5.O.169.228; 5.O.169.229; 5.O.169.230; 5.O.169.231; 5.O.169.236;
5.O.169.237; 5.O.169.238; 5.O.169.239; 5.O.169.154; 5.O.169.157; 5.O.169.166; 5.O.169.169;
5.O.169.172; 5.O.169.175; 5.O.169.240; 5.O.169.244; 5.O.172.228; 5.O.172.229; 5.O.172.230;
5.O.172.231; 5.O.172.236; 5.O.172.237; 5.O.172.238; 5.O.172.239; 5.O.172.154; 5.O.172.157;
5.O.172.166; 5.O.172.169; 5.O.172.172; 5.O.172.175; 5.O.172.240; 5.O.172.244; 5.O.175.228;
5.O.175.229; 5.O.175.230; 5.O.175.231; 5.O.175.236; 5.O.175.237; 5.O.175.238; 5.O.175.239;
5.O.175.154; 5.O.175.157; 5.O.175.166; 5.O.175.169; 5.O.175.172; 5.O.175.175; 5.O.175.240;
5.O.175.244; 5.O.240.228; 5.O.240.229; 5.O.240.230; 5.O.240.231; 5.O.240.236; 5.O.240.237;
5.O.240.238; 5.O.240.239; 5.O.240.154; 5.O.240.157; 5.O.240.166; 5.O.240.169; 5.O.240.172;
5.O.240.175; 5.O.240.240; 5.O.240.244; 5.O.244.228; 5.O.244.229; 5.O.244.230; 5.O.244.231;
5.O.244.236; 5.O.244.237; 5.O.244.238; 5.O.244.239; 5.O.244.154; 5.O.244.157; 5.O.244.166;
5.O.244.169; 5.O.244.172; 5.O.244.175; 5.O.244.240; 5.O.244.244;
Prodrugs of 5.P 5.P.228.228; 5.P.228.229; 5.P.228.230; 5.P.228.231; 5.P.228.236; 5.P.228.237; 5.P.228.238;
5.P.228.239; 5.P.228.154; 5.P.228.157; 5.P.228.166; 5.P.228.169; 5.P.228.172; 5.P.228.175;
5.P.228.240; 5.P.228.244; 5.P.229.228; 5.P.229.229; 5.P.229.230; 5.P.229.231; 5.P.229.236;
5.P.229.237; 5.P.229.238; 5.P.229.239; 5.P.229.154; 5.P.229.157; 5.P.229.166; 5.P.229.169;
5.P.229.172; 5.P.229.175; 5.P.229.240; 5.P.229.244; 5.P.230.228; 5.P.230.229; 5.P.230.230;
5.P.230.231; 5.P.230.236; 5.P.230.237; 5.P.230.238; 5.P.230.239; 5.P.230.154; 5.P.230.157;
5.P.230.166; 5.P.230.169; 5.P.230.172; 5.P.230.175; 5.P.230.240; 5.P.230.244; 5.P.231.228;
5.P.231.229; 5.P.231.230; 5.P.231.231; 5.P.231.236; 5.P.231.237; 5.P.231.238; 5.P.231.239;

TABLE 100-continued

5.P.231.154; 5.P.231.157; 5.P.231.166; 5.P.231.169; 5.P.231.172; 5.P.231.175; 5.P.231.240;
5.P.231.244; 5.P.236.228; 5.P.236.229; 5.P.236.230; 5.P.236.231; 5.P.236.236; 5.P.236.237;
5.P.236.238; 5.P.236.239; 5.P.236.154; 5.P.236.157; 5.P.236.166; 5.P.236.169; 5.P.236.172;
5.P.236.175; 5.P.236.240; 5.P.236.244; 5.P.237.228; 5.P.237.229; 5.P.237.230; 5.P.237.231;
5.P.237.236; 5.P.237.237; 5.P.237.238; 5.P.237.239; 5.P.237.154; 5.P.237.157; 5.P.237.166;
5.P.237.169; 5.P.237.172; 5.P.237.175; 5.P.237.240; 5.P.237.244; 5.P.238.228; 5.P.238.229;
5.P.238.230; 5.P.238.231; 5.P.238.236; 5.P.238.237; 5.P.238.238; 5.P.238.239; 5.P.238.154;
5.P.238.157; 5.P.238.166; 5.P.238.169; 5.P.238.172; 5.P.238.175; 5.P.238.240; 5.P.238.244;
5.P.239.228; 5.P.239.229; 5.P.239.230; 5.P.239.231; 5.P.239.236; 5.P.239.237; 5.P.239.238;
5.P.239.239; 5.P.239.154; 5.P.239.157; 5.P.239.166; 5.P.239.169; 5.P.239.172; 5.P.239.175;
5.P.239.240; 5.P.239.244; 5.P.154.228; 5.P.154.229; 5.P.154.230; 5.P.154.231; 5.P.154.236;
5.P.154.237; 5.P.154.238; 5.P.154.239; 5.P.154.154; 5.P.154.157; 5.P.154.166; 5.P.154.169;
5.P.154.172; 5.P.154.175; 5.P.154.240; 5.P.154.244; 5.P.157.228; 5.P.157.229; 5.P.157.230;
5.P.157.231; 5.P.157.236; 5.P.157.237; 5.P.157.238; 5.P.157.239; 5.P.157.154; 5.P.157.157;
5.P.157.166; 5.P.157.169; 5.P.157.172; 5.P.157.175; 5.P.157.240; 5.P.157.244; 5.P.166.228;
5.P.166.229; 5.P.166.230; 5.P.166.231; 5.P.166.236; 5.P.166.237; 5.P.166.238; 5.P.166.239;
5.P.166.154; 5.P.166.157; 5.P.166.166; 5.P.166.169; 5.P.166.172; 5.P.166.175; 5.P.166.240;
5.P.166.244; 5.P.169.228; 5.P.169.229; 5.P.169.230; 5.P.169.231; 5.P.169.236; 5.P.169.237;
5.P.169.238; 5.P.169.239; 5.P.169.154; 5.P.169.157; 5.P.169.166; 5.P.169.169; 5.P.169.172;
5.P.169.175; 5.P.169.240; 5.P.169.244; 5.P.172.228; 5.P.172.229; 5.P.172.230; 5.P.172.231;
5.P.172.236; 5.P.172.237; 5.P.172.238; 5.P.172.239; 5.P.172.154; 5.P.172.157; 5.P.172.166;
5.P.172.169; 5.P.172.172; 5.P.172.175; 5.P.172.240; 5.P.172.244; 5.P.175.228; 5.P.175.229;
5.P.175.230; 5.P.175.231; 5.P.175.236; 5.P.175.237; 5.P.175.238; 5.P.175.239; 5.P.175.154;
5.P.175.157; 5.P.175.166; 5.P.175.169; 5.P.175.172; 5.P.175.175; 5.P.175.240; 5.P.175.244;
5.P.240.228; 5.P.240.229; 5.P.240.230; 5.P.240.231; 5.P.240.236; 5.P.240.237; 5.P.240.238;
5.P.240.239; 5.P.240.154; 5.P.240.157; 5.P.240.166; 5.P.240.169; 5.P.240.172; 5.P.240.175;
5.P.240.240; 5.P.240.244; 5.P.244.228; 5.P.244.229; 5.P.244.230; 5.P.244.231; 5.P.244.236;
5.P.244.237; 5.P.244.238; 5.P.244.239; 5.P.244.154; 5.P.244.157; 5.P.244.166; 5.P.244.169;
5.P.244.172; 5.P.244.175; 5.P.244.240; 5.P.244.244;

Prodrugs of 5.U

5.U.228.228; 5.U.228.229; 5.U.228.230; 5.U.228.231; 5.U.228.236; 5.U.228.237;
5.U.228.238; 5.U.228.239; 5.U.228.154; 5.U.228.157; 5.U.228.166; 5.U.228.169; 5.U.228.172;
5.U.228.175; 5.U.228.240; 5.U.228.244; 5.U.229.228; 5.U.229.229; 5.U.229.230; 5.U.229.231;
5.U.229.236; 5.U.229.237; 5.U.229.238; 5.U.229.239; 5.U.229.154; 5.U.229.157; 5.U.229.166;
5.U.229.169; 5.U.229.172; 5.U.229.175; 5.U.229.240; 5.U.229.244; 5.U.230.228; 5.U.230.229;
5.U.230.230; 5.U.230.231; 5.U.230.236; 5.U.230.237; 5.U.230.238; 5.U.230.239; 5.U.230.154;
5.U.230.157; 5.U.230.166; 5.U.230.169; 5.U.230.172; 5.U.230.175; 5.U.230.240; 5.U.230.244;
5.U.231.228; 5.U.231.229; 5.U.231.230; 5.U.231.231; 5.U.231.236; 5.U.231.237; 5.U.231.238;
5.U.231.239; 5.U.231.154; 5.U.231.157; 5.U.231.166; 5.U.231.169; 5.U.231.172; 5.U.231.175;
5.U.231.240; 5.U.231.244; 5.U.236.228; 5.U.236.229; 5.U.236.230; 5.U.236.231; 5.U.236.236;
5.U.236.237; 5.U.236.238; 5.U.236.239; 5.U.236.154; 5.U.236.157; 5.U.236.166; 5.U.236.169;
5.U.236.172; 5.U.236.175; 5.U.236.240; 5.U.236.244; 5.U.237.228; 5.U.237.229; 5.U.237.230;
5.U.237.231; 5.U.237.236; 5.U.237.237; 5.U.237.238; 5.U.237.239; 5.U.237.154; 5.U.237.157;
5.U.237.166; 5.U.237.169; 5.U.237.172; 5.U.237.175; 5.U.237.240; 5.U.237.244; 5.U.238.228;
5.U.238.229; 5.U.238.230; 5.U.238.231; 5.U.238.236; 5.U.238.237; 5.U.238.238; 5.U.238.239;
5.U.238.154; 5.U.238.157; 5.U.238.166; 5.U.238.169; 5.U.238.172; 5.U.238.175; 5.U.238.240;
5.U.238.244; 5.U.239.228; 5.U.239.229; 5.U.239.230; 5.U.239.231; 5.U.239.236; 5.U.239.237;
5.U.239.238; 5.U.239.239; 5.U.239.154; 5.U.239.157; 5.U.239.166; 5.U.239.169; 5.U.239.172;
5.U.239.175; 5.U.239.240; 5.U.239.244; 5.U.154.228; 5.U.154.229; 5.U.154.230; 5.U.154.231;
5.U.154.236; 5.U.154.237; 5.U.154.238; 5.U.154.239; 5.U.154.154; 5.U.154.157; 5.U.154.166;
5.U.154.169; 5.U.154.172; 5.U.154.175; 5.U.154.240; 5.U.154.244; 5.U.157.228; 5.U.157.229;
5.U.157.230; 5.U.157.231; 5.U.157.236; 5.U.157.237; 5.U.157.238; 5.U.157.239; 5.U.157.154;
5.U.157.157; 5.U.157.166; 5.U.157.169; 5.U.157.172; 5.U.157.175; 5.U.157.240; 5.U.157.244;
5.U.166.228; 5.U.166.229; 5.U.166.230; 5.U.166.231; 5.U.166.236; 5.U.166.237; 5.U.166.238;
5.U.166.239; 5.U.166.154; 5.U.166.157; 5.U.166.166; 5.U.166.169; 5.U.166.172; 5.U.166.175;
5.U.166.240; 5.U.166.244; 5.U.169.228; 5.U.169.229; 5.U.169.230; 5.U.169.231; 5.U.169.236;
5.U.169.237; 5.U.169.238; 5.U.169.239; 5.U.169.154; 5.U.169.157; 5.U.169.166; 5.U.169.169;
5.U.169.172; 5.U.169.175; 5.U.169.240; 5.U.169.244; 5.U.172.228; 5.U.172.229; 5.U.172.230;
5.U.172.231; 5.U.172.236; 5.U.172.237; 5.U.172.238; 5.U.172.239; 5.U.172.154; 5.U.172.157;
5.U.172.166; 5.U.172.169; 5.U.172.172; 5.U.172.175; 5.U.172.240; 5.U.172.244; 5.U.175.228;
5.U.175.229; 5.U.175.230; 5.U.175.231; 5.U.175.236; 5.U.175.237; 5.U.175.238; 5.U.175.239;
5.U.175.154; 5.U.175.157; 5.U.175.166; 5.U.175.169; 5.U.175.172; 5.U.175.175; 5.U.175.240;
5.U.175.244; 5.U.240.228; 5.U.240.229; 5.U.240.230; 5.U.240.231; 5.U.240.236; 5.U.240.237;
5.U.240.238; 5.U.240.239; 5.U.240.154; 5.U.240.157; 5.U.240.166; 5.U.240.169; 5.U.240.172;
5.U.240.175; 5.U.240.240; 5.U.240.244; 5.U.244.228; 5.U.244.229; 5.U.244.230; 5.U.244.231;
5.U.244.236; 5.U.244.237; 5.U.244.238; 5.U.244.239; 5.U.244.154; 5.U.244.157; 5.U.244.166;
5.U.244.169; 5.U.244.172; 5.U.244.175; 5.U.244.240; 5.U.244.244;

Prodrugs of 5.W

5.W.228.228; 5.W.228.229; 5.W.228.230; 5.W.228.231; 5.W.228.236; 5.W.228.237;
5.W.228.238; 5.W.228.239; 5.W.228.154; 5.W.228.157; 5.W.228.166; 5.W.228.169;
5.W.228.172; 5.W.228.175; 5.W.228.240; 5.W.228.244; 5.W.229.228; 5.W.229.229;
5.W.229.230; 5.W.229.231; 5.W.229.236; 5.W.229.237; 5.W.229.238; 5.W.229.239;
5.W.229.154; 5.W.229.157; 5.W.229.166; 5.W.229.169; 5.W.229.172; 5.W.229.175;
5.W.229.240; 5.W.229.244; 5.W.230.228; 5.W.230.229; 5.W.230.230; 5.W.230.231;
5.W.230.236; 5.W.230.237; 5.W.230.238; 5.W.230.239; 5.W.230.154; 5.W.230.157;
5.W.230.166; 5.W.230.169; 5.W.230.172; 5.W.230.175; 5.W.230.240; 5.W.230.244;
5.W.231.228; 5.W.231.229; 5.W.231.230; 5.W.231.231; 5.W.231.236; 5.W.231.237;

TABLE 100-continued

5.W.231.238; 5.W.231.239; 5.W.231.154; 5.W.231.157; 5.W.231.166; 5.W.231.169;
5.W.231.172; 5.W.231.175; 5.W.231.240; 5.W.231.244; 5.W.236.228; 5.W.236.229;
5.W.236.230; 5.W.236.231; 5.W.236.236; 5.W.236.237; 5.W.236.238; 5.W.236.239;
5.W.236.154; 5.W.236.157; 5.W.236.166; 5.W.236.169; 5.W.236.172; 5.W.236.175;
5.W.236.240; 5.W.236.244; 5.W.237.228; 5.W.237.229; 5.W.237.230; 5.W.237.231;
5.W.237.236; 5.W.237.237; 5.W.237.238; 5.W.237.239; 5.W.237.154; 5.W.237.157;
5.W.237.166; 5.W.237.169; 5.W.237.172; 5.W.237.175; 5.W.237.240; 5.W.237.244;
5.W.238.228; 5.W.238.229; 5.W.238.230; 5.W.238.231; 5.W.238.236; 5.W.238.237;
5.W.238.238; 5.W.238.239; 5.W.238.154; 5.W.238.157; 5.W.238.166; 5.W.238.169;
5.W.238.172; 5.W.238.175; 5.W.238.240; 5.W.238.244; 5.W.239.228; 5.W.239.229;
5.W.239.230; 5.W.239.231; 5.W.239.236; 5.W.239.237; 5.W.239.238; 5.W.239.239;
5.W.239.154; 5.W.239.157; 5.W.239.166; 5.W.239.169; 5.W.239.172; 5.W.239.175;
5.W.239.240; 5.W.239.244; 5.W.154.228; 5.W.154.229; 5.W.154.230; 5.W.154.231;
5.W.154.236; 5.W.154.237; 5.W.154.238; 5.W.154.239; 5.W.154.154; 5.W.154.157;
5.W.154.166; 5.W.154.169; 5.W.154.172; 5.W.154.175; 5.W.154.240; 5.W.154.244;
5.W.157.228; 5.W.157.229; 5.W.157.230; 5.W.157.231; 5.W.157.236; 5.W.157.237;
5.W.157.238; 5.W.157.239; 5.W.157.154; 5.W.157.157; 5.W.157.166; 5.W.157.169;
5.W.157.172; 5.W.157.175; 5.W.157.240; 5.W.157.244; 5.W.166.228; 5.W.166.229;
5.W.166.230; 5.W.166.231; 5.W.166.236; 5.W.166.237; 5.W.166.238; 5.W.166.239;
5.W.166.154; 5.W.166.157; 5.W.166.166; 5.W.166.169; 5.W.166.172; 5.W.166.175;
5.W.166.240; 5.W.166.244; 5.W.169.228; 5.W.169.229; 5.W.169.230; 5.W.169.231;
5.W.169.236; 5.W.169.237; 5.W.169.238; 5.W.169.239; 5.W.169.154; 5.W.169.157;
5.W.169.166; 5.W.169.169; 5.W.169.172; 5.W.169.175; 5.W.169.240; 5.W.169.244;
5.W.172.228; 5.W.172.229; 5.W.172.230; 5.W.172.231; 5.W.172.236; 5.W.172.237;
5.W.172.238; 5.W.172.239; 5.W.172.154; 5.W.172.157; 5.W.172.166; 5.W.172.169;
5.W.172.172; 5.W.172.175; 5.W.172.240; 5.W.172.244; 5.W.175.228; 5.W.175.229;
5.W.175.230; 5.W.175.231; 5.W.175.236; 5.W.175.237; 5.W.175.238; 5.W.175.239;
5.W.175.154; 5.W.175.157; 5.W.175.166; 5.W.175.169; 5.W.175.172; 5.W.175.175;
5.W.175.240; 5.W.175.244; 5.W.240.228; 5.W.240.229; 5.W.240.230; 5.W.240.231;
5.W.240.236; 5.W.240.237; 5.W.240.238; 5.W.240.239; 5.W.240.154; 5.W.240.157;
5.W.240.166; 5.W.240.169; 5.W.240.172; 5.W.240.175; 5.W.240.240; 5.W.240.244;
5.W.244.228; 5.W.244.229; 5.W.244.230; 5.W.244.231; 5.W.244.236; 5.W.244.237;
5.W.244.238; 5.W.244.239; 5.W.244.154; 5.W.244.157; 5.W.244.166; 5.W.244.169;
5.W.244.172; 5.W.244.175; 5.W.244.240; 5.W.244.244;
Prodrugs of 5.Y 5.Y.228.228; 5.Y.228.229; 5.Y.228.230; 5.Y.228.231; 5.Y.228.236; 5.Y.228.237; 5.Y.228.238;
5.Y.228.239; 5.Y.228.154; 5.Y.228.157; 5.Y.228.166; 5.Y.228.169; 5.Y.228.172; 5.Y.228.175;
5.Y.228.240; 5.Y.228.244; 5.Y.229.228; 5.Y.229.229; 5.Y.229.230; 5.Y.229.231; 5.Y.229.236;
5.Y.229.237; 5.Y.229.238; 5.Y.229.239; 5.Y.229.154; 5.Y.229.157; 5.Y.229.166; 5.Y.229.169;
5.Y.229.172; 5.Y.229.175; 5.Y.229.240; 5.Y.229.244; 5.Y.230.228; 5.Y.230.229; 5.Y.230.230;
5.Y.230.231; 5.Y.230.236; 5.Y.230.237; 5.Y.230.238; 5.Y.230.239; 5.Y.230.154; 5.Y.230.157;
5.Y.230.166; 5.Y.230.169; 5.Y.230.172; 5.Y.230.175; 5.Y.230.240; 5.Y.230.244; 5.Y.231.228;
5.Y.231.229; 5.Y.231.230; 5.Y.231.231; 5.Y.231.236; 5.Y.231.237; 5.Y.231.238; 5.Y.231.239;
5.Y.231.154; 5.Y.231.157; 5.Y.231.166; 5.Y.231.169; 5.Y.231.172; 5.Y.231.175; 5.Y.231.240;
5.Y.231.244; 5.Y.236.228; 5.Y.236.229; 5.Y.236.230; 5.Y.236.231; 5.Y.236.236; 5.Y.236.237;
5.Y.236.238; 5.Y.236.239; 5.Y.236.154; 5.Y.236.157; 5.Y.236.166; 5.Y.236.169; 5.Y.236.172;
5.Y.236.175; 5.Y.236.240; 5.Y.236.244; 5.Y.237.228; 5.Y.237.229; 5.Y.237.230; 5.Y.237.231;
5.Y.237.236; 5.Y.237.237; 5.Y.237.238; 5.Y.237.239; 5.Y.237.154; 5.Y.237.157; 5.Y.237.166;
5.Y.237.169; 5.Y.237.172; 5.Y.237.175; 5.Y.237.240; 5.Y.237.244; 5.Y.238.228; 5.Y.238.229;
5.Y.238.230; 5.Y.238.231; 5.Y.238.236; 5.Y.238.237; 5.Y.238.238; 5.Y.238.239; 5.Y.238.154;
5.Y.238.157; 5.Y.238.166; 5.Y.238.169; 5.Y.238.172; 5.Y.238.175; 5.Y.238.240; 5.Y.238.244;
5.Y.239.228; 5.Y.239.229; 5.Y.239.230; 5.Y.239.231; 5.Y.239.236; 5.Y.239.237; 5.Y.239.238;
5.Y.239.239; 5.Y.239.154; 5.Y.239.157; 5.Y.239.166; 5.Y.239.169; 5.Y.239.172; 5.Y.239.175;
5.Y.239.240; 5.Y.239.244; 5.Y.154.228; 5.Y.154.229; 5.Y.154.230; 5.Y.154.231; 5.Y.154.236;
5.Y.154.237; 5.Y.154.238; 5.Y.154.239; 5.Y.154.154; 5.Y.154.157; 5.Y.154.166; 5.Y.154.169;
5.Y.154.172; 5.Y.154.175; 5.Y.154.240; 5.Y.154.244; 5.Y.157.228; 5.Y.157.229; 5.Y.157.230;
5.Y.157.231; 5.Y.157.236; 5.Y.157.237; 5.Y.157.238; 5.Y.157.239; 5.Y.157.154; 5.Y.157.157;
5.Y.157.166; 5.Y.157.169; 5.Y.157.172; 5.Y.157.175; 5.Y.157.240; 5.Y.157.244; 5.Y.166.228;
5.Y.166.229; 5.Y.166.230; 5.Y.166.231; 5.Y.166.236; 5.Y.166.237; 5.Y.166.238; 5.Y.166.239;
5.Y.166.154; 5.Y.166.157; 5.Y.166.166; 5.Y.166.169; 5.Y.166.172; 5.Y.166.175; 5.Y.166.240;
5.Y.166.244; 5.Y.169.228; 5.Y.169.229; 5.Y.169.230; 5.Y.169.231; 5.Y.169.236; 5.Y.169.237;
5.Y.169.238; 5.Y.169.239; 5.Y.169.154; 5.Y.169.157; 5.Y.169.166; 5.Y.169.169; 5.Y.169.172;
5.Y.169.175; 5.Y.169.240; 5.Y.169.244; 5.Y.172.228; 5.Y.172.229; 5.Y.172.230; 5.Y.172.231;
5.Y.172.236; 5.Y.172.237; 5.Y.172.238; 5.Y.172.239; 5.Y.172.154; 5.Y.172.157; 5.Y.172.166;
5.Y.172.169; 5.Y.172.172; 5.Y.172.175; 5.Y.172.240; 5.Y.172.244; 5.Y.175.228; 5.Y.175.229;
5.Y.175.230; 5.Y.175.231; 5.Y.175.236; 5.Y.175.237; 5.Y.175.238; 5.Y.175.239; 5.Y.175.154;
5.Y.175.157; 5.Y.175.166; 5.Y.175.169; 5.Y.175.172; 5.Y.175.175; 5.Y.175.240; 5.Y.175.244;
5.Y.240.228; 5.Y.240.229; 5.Y.240.230; 5.Y.240.231; 5.Y.240.236; 5.Y.240.237; 5.Y.240.238;
5.Y.240.239; 5.Y.240.154; 5.Y.240.157; 5.Y.240.166; 5.Y.240.169; 5.Y.240.172; 5.Y.240.175;
5.Y.240.240; 5.Y.240.244; 5.Y.244.228; 5.Y.244.229; 5.Y.244.230; 5.Y.244.231; 5.Y.244.236;
5.Y.244.237; 5.Y.244.238; 5.Y.244.239; 5.Y.244.154; 5.Y.244.157; 5.Y.244.166; 5.Y.244.169;
5.Y.244.172; 5.Y.244.175; 5.Y.244.240; 5.Y.244.244;
Prodrugs of 6.B 6.B.228.228; 6.B.228.229; 6.B.228.230; 6.B.228.231; 6.B.228.236; 6.B.228.237; 6.B.228.238;
6.B.228.239; 6.B.228.154; 6.B.228.157; 6.B.228.166; 6.B.228.169; 6.B.228.172; 6.B.228.175;
6.B.228.240; 6.B.228.244; 6.B.229.228; 6.B.229.229; 6.B.229.230; 6.B.229.231; 6.B.229.236;
6.B.229.237; 6.B.229.238; 6.B.229.239; 6.B.229.154; 6.B.229.157; 6.B.229.166; 6.B.229.169;

TABLE 100-continued

6.B.229.172; 6.B.229.175; 6.B.229.240; 6.B.229.244; 6.B.230.228; 6.B.230.229; 6.B.230.230;
6.B.230.231; 6.B.230.236; 6.B.230.237; 6.B.230.238; 6.B.230.239; 6.B.230.154; 6.B.230.157;
6.B.230.166; 6.B.230.169; 6.B.230.172; 6.B.230.175; 6.B.230.240; 6.B.230.244; 6.B.231.228;
6.B.231.229; 6.B.231.230; 6.B.231.231; 6.B.231.236; 6.B.231.237; 6.B.231.238; 6.B.231.239;
6.B.231.154; 6.B.231.157; 6.B.231.166; 6.B.231.169; 6.B.231.172; 6.B.231.175; 6.B.231.240;
6.B.231.244; 6.B.236.228; 6.B.236.229; 6.B.236.230; 6.B.236.231; 6.B.236.236; 6.B.236.237;
6.B.236.238; 6.B.236.239; 6.B.236.154; 6.B.236.157; 6.B.236.166; 6.B.236.169; 6.B.236.172;
6.B.236.175; 6.B.236.240; 6.B.236.244; 6.B.237.228; 6.B.237.229; 6.B.237.230; 6.B.237.231;
6.B.237.236; 6.B.237.237; 6.B.237.238; 6.B.237.239; 6.B.237.154; 6.B.237.157; 6.B.237.166;
6.B.237.169; 6.B.237.172; 6.B.237.175; 6.B.237.240; 6.B.237.244; 6.B.238.228; 6.B.238.229;
6.B.238.230; 6.B.238.231; 6.B.238.236; 6.B.238.237; 6.B.238.238; 6.B.238.239; 6.B.238.154;
6.B.238.157; 6.B.238.166; 6.B.238.169; 6.B.238.172; 6.B.238.175; 6.B.238.240; 6.B.238.244;
6.B.239.228; 6.B.239.229; 6.B.239.230; 6.B.239.231; 6.B.239.236; 6.B.239.237; 6.B.239.238;
6.B.239.239; 6.B.239.154; 6.B.239.157; 6.B.239.166; 6.B.239.169; 6.B.239.172; 6.B.239.175;
6.B.239.240; 6.B.239.244; 6.B.154.228; 6.B.154.229; 6.B.154.230; 6.B.154.231; 6.B.154.236;
6.B.154.237; 6.B.154.238; 6.B.154.239; 6.B.154.154; 6.B.154.157; 6.B.154.166; 6.B.154.169;
6.B.154.172; 6.B.154.175; 6.B.154.240; 6.B.154.244; 6.B.157.228; 6.B.157.229; 6.B.157.230;
6.B.157.231; 6.B.157.236; 6.B.157.237; 6.B.157.238; 6.B.157.239; 6.B.157.154; 6.B.157.157;
6.B.157.166; 6.B.157.169; 6.B.157.172; 6.B.157.175; 6.B.157.240; 6.B.157.244; 6.B.166.228;
6.B.166.229; 6.B.166.230; 6.B.166.231; 6.B.166.236; 6.B.166.237; 6.B.166.238; 6.B.166.239;
6.B.166.154; 6.B.166.157; 6.B.166.166; 6.B.166.169; 6.B.166.172; 6.B.166.175; 6.B.166.240;
6.B.166.244; 6.B.169.228; 6.B.169.229; 6.B.169.230; 6.B.169.231; 6.B.169.236; 6.B.169.237;
6.B.169.238; 6.B.169.239; 6.B.169.154; 6.B.169.157; 6.B.169.166; 6.B.169.169; 6.B.169.172;
6.B.169.175; 6.B.169.240; 6.B.169.244; 6.B.172.228; 6.B.172.229; 6.B.172.230; 6.B.172.231;
6.B.172.236; 6.B.172.237; 6.B.172.238; 6.B.172.239; 6.B.172.154; 6.B.172.157; 6.B.172.166;
6.B.172.169; 6.B.172.172; 6.B.172.175; 6.B.172.240; 6.B.172.244; 6.B.175.228; 6.B.175.229;
6.B.175.230; 6.B.175.231; 6.B.175.236; 6.B.175.237; 6.B.175.238; 6.B.175.239; 6.B.175.154;
6.B.175.157; 6.B.175.166; 6.B.175.169; 6.B.175.172; 6.B.175.175; 6.B.175.240; 6.B.175.244;
6.B.240.228; 6.B.240.229; 6.B.240.230; 6.B.240.231; 6.B.240.236; 6.B.240.237; 6.B.240.238;
6.B.240.239; 6.B.240.154; 6.B.240.157; 6.B.240.166; 6.B.240.169; 6.B.240.172; 6.B.240.175;
6.B.240.240; 6.B.240.244; 6.B.244.228; 6.B.244.229; 6.B.244.230; 6.B.244.231; 6.B.244.236;
6.B.244.237; 6.B.244.238; 6.B.244.239; 6.B.244.154; 6.B.244.157; 6.B.244.166; 6.B.244.169;
6.B.244.172; 6.B.244.175; 6.B.244.240; 6.B.244.244;
Prodrugs of 6.D 6.D.228.228; 6.D.228.229; 6.D.228.230; 6.D.228.231; 6.D.228.236; 6.D.228.237;
6.D.228.238; 6.D.228.239; 6.D.228.154; 6.D.228.157; 6.D.228.166; 6.D.228.169; 6.D.228.172;
6.D.228.175; 6.D.228.240; 6.D.228.244; 6.D.229.228; 6.D.229.229; 6.D.229.230; 6.D.229.231;
6.D.229.236; 6.D.229.237; 6.D.229.238; 6.D.229.239; 6.D.229.154; 6.D.229.157; 6.D.229.166;
6.D.229.169; 6.D.229.172; 6.D.229.175; 6.D.229.240; 6.D.229.244; 6.D.230.228; 6.D.230.229;
6.D.230.230; 6.D.230.231; 6.D.230.236; 6.D.230.237; 6.D.230.238; 6.D.230.239; 6.D.230.154;
6.D.230.157; 6.D.230.166; 6.D.230.169; 6.D.230.172; 6.D.230.175; 6.D.230.240; 6.D.230.244;
6.D.231.228; 6.D.231.229; 6.D.231.230; 6.D.231.231; 6.D.231.236; 6.D.231.237; 6.D.231.238;
6.D.231.239; 6.D.231.154; 6.D.231.157; 6.D.231.166; 6.D.231.169; 6.D.231.172; 6.D.231.175;
6.D.231.240; 6.D.231.244; 6.D.236.228; 6.D.236.229; 6.D.236.230; 6.D.236.231; 6.D.236.236;
6.D.236.237; 6.D.236.238; 6.D.236.239; 6.D.236.154; 6.D.236.157; 6.D.236.166; 6.D.236.169;
6.D.236.172; 6.D.236.175; 6.D.236.240; 6.D.236.244; 6.D.237.228; 6.D.237.229; 6.D.237.230;
6.D.237.231; 6.D.237.236; 6.D.237.237; 6.D.237.238; 6.D.237.239; 6.D.237.154; 6.D.237.157;
6.D.237.166; 6.D.237.169; 6.D.237.172; 6.D.237.175; 6.D.237.240; 6.D.237.244; 6.D.238.228;
6.D.238.229; 6.D.238.230; 6.D.238.231; 6.D.238.236; 6.D.238.237; 6.D.238.238; 6.D.238.239;
6.D.238.154; 6.D.238.157; 6.D.238.166; 6.D.238.169; 6.D.238.172; 6.D.238.175; 6.D.238.240;
6.D.238.244; 6.D.239.228; 6.D.239.229; 6.D.239.230; 6.D.239.231; 6.D.239.236; 6.D.239.237;
6.D.239.238; 6.D.239.239; 6.D.239.154; 6.D.239.157; 6.D.239.166; 6.D.239.169; 6.D.239.172;
6.D.239.175; 6.D.239.240; 6.D.239.244; 6.D.154.228; 6.D.154.229; 6.D.154.230; 6.D.154.231;
6.D.154.236; 6.D.154.237; 6.D.154.238; 6.D.154.239; 6.D.154.154; 6.D.154.157; 6.D.154.166;
6.D.154.169; 6.D.154.172; 6.D.154.175; 6.D.154.240; 6.D.154.244; 6.D.157.228; 6.D.157.229;
6.D.157.230; 6.D.157.231; 6.D.157.236; 6.D.157.237; 6.D.157.238; 6.D.157.239; 6.D.157.154;
6.D.157.157; 6.D.157.166; 6.D.157.169; 6.D.157.172; 6.D.157.175; 6.D.157.240; 6.D.157.244;
6.D.166.228; 6.D.166.229; 6.D.166.230; 6.D.166.231; 6.D.166.236; 6.D.166.237; 6.D.166.238;
6.D.166.239; 6.D.166.154; 6.D.166.157; 6.D.166.166; 6.D.166.169; 6.D.166.172; 6.D.166.175;
6.D.166.240; 6.D.166.244; 6.D.169.228; 6.D.169.229; 6.D.169.230; 6.D.169.231; 6.D.169.236;
6.D.169.237; 6.D.169.238; 6.D.169.239; 6.D.169.154; 6.D.169.157; 6.D.169.166; 6.D.169.169;
6.D.169.172; 6.D.169.175; 6.D.169.240; 6.D.169.244; 6.D.172.228; 6.D.172.229; 6.D.172.230;
6.D.172.231; 6.D.172.236; 6.D.172.237; 6.D.172.238; 6.D.172.239; 6.D.172.154; 6.D.172.157;
6.D.172.166; 6.D.172.169; 6.D.172.172; 6.D.172.175; 6.D.172.240; 6.D.172.244; 6.D.175.228;
6.D.175.229; 6.D.175.230; 6.D.175.231; 6.D.175.236; 6.D.175.237; 6.D.175.238; 6.D.175.239;
6.D.175.154; 6.D.175.157; 6.D.175.166; 6.D.175.169; 6.D.175.172; 6.D.175.175; 6.D.175.240;
6.D.175.244; 6.D.240.228; 6.D.240.229; 6.D.240.230; 6.D.240.231; 6.D.240.236; 6.D.240.237;
6.D.240.238; 6.D.240.239; 6.D.240.154; 6.D.240.157; 6.D.240.166; 6.D.240.169; 6.D.240.172;
6.D.240.175; 6.D.240.240; 6.D.240.244; 6.D.244.228; 6.D.244.229; 6.D.244.230; 6.D.244.231;
6.D.244.236; 6.D.244.237; 6.D.244.238; 6.D.244.239; 6.D.244.154; 6.D.244.157; 6.D.244.166;
6.D.244.169; 6.D.244.172; 6.D.244.175; 6.D.244.240; 6.D.244.244;
Prodrugs of 6.E 6.E.228.228; 6.E.228.229; 6.E.228.230; 6.E.228.231; 6.E.228.236; 6.E.228.237; 6.E.228.238;
6.E.228.239; 6.E.228.154; 6.E.228.157; 6.E.228.166; 6.E.228.169; 6.E.228.172; 6.E.228.175;
6.E.228.240; 6.E.228.244; 6.E.229.228; 6.E.229.229; 6.E.229.230; 6.E.229.231; 6.E.229.236;
6.E.229.237; 6.E.229.238; 6.E.229.239; 6.E.229.154; 6.E.229.157; 6.E.229.166; 6.E.229.169;
6.E.229.172; 6.E.229.175; 6.E.229.240; 6.E.229.244; 6.E.230.228; 6.E.230.229; 6.E.230.230;

TABLE 100-continued

6.E.230.231; 6.E.230.236; 6.E.230.237; 6.E.230.238; 6.E.230.239; 6.E.230.154; 6.E.230.157;
6.E.230.166; 6.E.230.169; 6.E.230.172; 6.E.230.175; 6.E.230.240; 6.E.230.244; 6.E.231.228;
6.E.231.229; 6.E.231.230; 6.E.231.231; 6.E.231.236; 6.E.231.237; 6.E.231.238; 6.E.231.239;
6.E.231.154; 6.E.231.157; 6.E.231.166; 6.E.231.169; 6.E.231.172; 6.E.231.175; 6.E.231.240;
6.E.231.244; 6.E.236.228; 6.E.236.229; 6.E.236.230; 6.E.236.231; 6.E.236.236; 6.E.236.237;
6.E.236.238; 6.E.236.239; 6.E.236.154; 6.E.236.157; 6.E.236.166; 6.E.236.169; 6.E.236.172;
6.E.236.175; 6.E.236.240; 6.E.236.244; 6.E.237.228; 6.E.237.229; 6.E.237.230; 6.E.237.231;
6.E.237.236; 6.E.237.237; 6.E.237.238; 6.E.237.239; 6.E.237.154; 6.E.237.157; 6.E.237.166;
6.E.237.169; 6.E.237.172; 6.E.237.175; 6.E.237.240; 6.E.237.244; 6.E.238.228; 6.E.238.229;
6.E.238.230; 6.E.238.231; 6.E.238.236; 6.E.238.237; 6.E.238.238; 6.E.238.239; 6.E.238.154;
6.E.238.157; 6.E.238.166; 6.E.238.169; 6.E.238.172; 6.E.238.175; 6.E.238.240; 6.E.238.244;
6.E.239.228; 6.E.239.229; 6.E.239.230; 6.E.239.231; 6.E.239.236; 6.E.239.237; 6.E.239.238;
6.E.239.239; 6.E.239.154; 6.E.239.157; 6.E.239.166; 6.E.239.169; 6.E.239.172; 6.E.239.175;
6.E.239.240; 6.E.239.244; 6.E.154.228; 6.E.154.229; 6.E.154.230; 6.E.154.231; 6.E.154.236;
6.E.154.237; 6.E.154.238; 6.E.154.239; 6.E.154.154; 6.E.154.157; 6.E.154.166; 6.E.154.169;
6.E.154.172; 6.E.154.175; 6.E.154.240; 6.E.154.244; 6.E.157.228; 6.E.157.229; 6.E.157.230;
6.E.157.231; 6.E.157.236; 6.E.157.237; 6.E.157.238; 6.E.157.239; 6.E.157.154; 6.E.157.157;
6.E.157.166; 6.E.157.169; 6.E.157.172; 6.E.157.175; 6.E.157.240; 6.E.157.244; 6.E.166.228;
6.E.166.229; 6.E.166.230; 6.E.166.231; 6.E.166.236; 6.E.166.237; 6.E.166.238; 6.E.166.239;
6.E.166.154; 6.E.166.157; 6.E.166.166; 6.E.166.169; 6.E.166.172; 6.E.166.175; 6.E.166.240;
6.E.166.244; 6.E.169.228; 6.E.169.229; 6.E.169.230; 6.E.169.231; 6.E.169.236; 6.E.169.237;
6.E.169.238; 6.E.169.239; 6.E.169.154; 6.E.169.157; 6.E.169.166; 6.E.169.169; 6.E.169.172;
6.E.169.175; 6.E.169.240; 6.E.169.244; 6.E.172.228; 6.E.172.229; 6.E.172.230; 6.E.172.231;
6.E.172.236; 6.E.172.237; 6.E.172.238; 6.E.172.239; 6.E.172.154; 6.E.172.157; 6.E.172.166;
6.E.172.169; 6.E.172.172; 6.E.172.175; 6.E.172.240; 6.E.172.244; 6.E.175.228; 6.E.175.229;
6.E.175.230; 6.E.175.231; 6.E.175.236; 6.E.175.237; 6.E.175.238; 6.E.175.239; 6.E.175.154;
6.E.175.157; 6.E.175.166; 6.E.175.169; 6.E.175.172; 6.E.175.175; 6.E.175.240; 6.E.175.244;
6.E.240.228; 6.E.240.229; 6.E.240.230; 6.E.240.231; 6.E.240.236; 6.E.240.237; 6.E.240.238;
6.E.240.239; 6.E.240.154; 6.E.240.157; 6.E.240.166; 6.E.240.169; 6.E.240.172; 6.E.240.175;
6.E.240.240; 6.E.240.244; 6.E.244.228; 6.E.244.229; 6.E.244.230; 6.E.244.231; 6.E.244.236;
6.E.244.237; 6.E.244.238; 6.E.244.239; 6.E.244.154; 6.E.244.157; 6.E.244.166; 6.E.244.169;
6.E.244.172; 6.E.244.175; 6.E.244.240; 6.E.244.244;
Prodrugs of 6.G 6.G.228.228; 6.G.228.229; 6.G.228.230; 6.G.228.231; 6.G.228.236; 6.G.228.237;
6.G.228.238; 6.G.228.239; 6.G.228.154; 6.G.228.157; 6.G.228.166; 6.G.228.169; 6.G.228.172;
6.G.228.175; 6.G.228.240; 6.G.228.244; 6.G.229.228; 6.G.229.229; 6.G.229.230; 6.G.229.231;
6.G.229.236; 6.G.229.237; 6.G.229.238; 6.G.229.239; 6.G.229.154; 6.G.229.157; 6.G.229.166;
6.G.229.169; 6.G.229.172; 6.G.229.175; 6.G.229.240; 6.G.229.244; 6.G.230.228; 6.G.230.229;
6.G.230.230; 6.G.230.231; 6.G.230.236; 6.G.230.237; 6.G.230.238; 6.G.230.239; 6.G.230.154;
6.G.230.157; 6.G.230.166; 6.G.230.169; 6.G.230.172; 6.G.230.175; 6.G.230.240; 6.G.230.244;
6.G.231.228; 6.G.231.229; 6.G.231.230; 6.G.231.231; 6.G.231.236; 6.G.231.237; 6.G.231.238;
6.G.231.239; 6.G.231.154; 6.G.231.157; 6.G.231.166; 6.G.231.169; 6.G.231.172; 6.G.231.175;
6.G.231.240; 6.G.231.244; 6.G.236.228; 6.G.236.229; 6.G.236.230; 6.G.236.231; 6.G.236.236;
6.G.236.237; 6.G.236.238; 6.G.236.239; 6.G.236.154; 6.G.236.157; 6.G.236.166; 6.G.236.169;
6.G.236.172; 6.G.236.175; 6.G.236.240; 6.G.236.244; 6.G.237.228; 6.G.237.229; 6.G.237.230;
6.G.237.231; 6.G.237.236; 6.G.237.237; 6.G.237.238; 6.G.237.239; 6.G.237.154; 6.G.237.157;
6.G.237.166; 6.G.237.169; 6.G.237.172; 6.G.237.175; 6.G.237.240; 6.G.237.244; 6.G.238.228;
6.G.238.229; 6.G.238.230; 6.G.238.231; 6.G.238.236; 6.G.238.237; 6.G.238.238; 6.G.238.239;
6.G.238.154; 6.G.238.157; 6.G.238.166; 6.G.238.169; 6.G.238.172; 6.G.238.175; 6.G.238.240;
6.G.238.244; 6.G.239.228; 6.G.239.229; 6.G.239.230; 6.G.239.231; 6.G.239.236; 6.G.239.237;
6.G.239.238; 6.G.239.239; 6.G.239.154; 6.G.239.157; 6.G.239.166; 6.G.239.169; 6.G.239.172;
6.G.239.175; 6.G.239.240; 6.G.239.244; 6.G.154.228; 6.G.154.229; 6.G.154.230; 6.G.154.231;
6.G.154.236; 6.G.154.237; 6.G.154.238; 6.G.154.239; 6.G.154.154; 6.G.154.157; 6.G.154.166;
6.G.154.169; 6.G.154.172; 6.G.154.175; 6.G.154.240; 6.G.154.244; 6.G.157.228; 6.G.157.229;
6.G.157.230; 6.G.157.231; 6.G.157.236; 6.G.157.237; 6.G.157.238; 6.G.157.239; 6.G.157.154;
6.G.157.157; 6.G.157.166; 6.G.157.169; 6.G.157.172; 6.G.157.175; 6.G.157.240; 6.G.157.244;
6.G.166.228; 6.G.166.229; 6.G.166.230; 6.G.166.231; 6.G.166.236; 6.G.166.237; 6.G.166.238;
6.G.166.239; 6.G.166.154; 6.G.166.157; 6.G.166.166; 6.G.166.169; 6.G.166.172; 6.G.166.175;
6.G.166.240; 6.G.166.244; 6.G.169.228; 6.G.169.229; 6.G.169.230; 6.G.169.231; 6.G.169.236;
6.G.169.237; 6.G.169.238; 6.G.169.239; 6.G.169.154; 6.G.169.157; 6.G.169.166; 6.G.169.169;
6.G.169.172; 6.G.169.175; 6.G.169.240; 6.G.169.244; 6.G.172.228; 6.G.172.229; 6.G.172.230;
6.G.172.231; 6.G.172.236; 6.G.172.237; 6.G.172.238; 6.G.172.239; 6.G.172.154; 6.G.172.157;
6.G.172.166; 6.G.172.169; 6.G.172.172; 6.G.172.175; 6.G.172.240; 6.G.172.244; 6.G.175.228;
6.G.175.229; 6.G.175.230; 6.G.175.231; 6.G.175.236; 6.G.175.237; 6.G.175.238; 6.G.175.239;
6.G.175.154; 6.G.175.157; 6.G.175.166; 6.G.175.169; 6.G.175.172; 6.G.175.175; 6.G.175.240;
6.G.175.244; 6.G.240.228; 6.G.240.229; 6.G.240.230; 6.G.240.231; 6.G.240.236; 6.G.240.237;
6.G.240.238; 6.G.240.239; 6.G.240.154; 6.G.240.157; 6.G.240.166; 6.G.240.169; 6.G.240.172;
6.G.240.175; 6.G.240.240; 6.G.240.244; 6.G.244.228; 6.G.244.229; 6.G.244.230; 6.G.244.231;
6.G.244.236; 6.G.244.237; 6.G.244.238; 6.G.244.239; 6.G.244.154; 6.G.244.157; 6.G.244.166;
6.G.244.169; 6.G.244.172; 6.G.244.175; 6.G.244.240; 6.G.244.244;
Prodrugs of 6.I 6.I.228.228; 6.I.228.229; 6.I.228.230; 6.I.228.231; 6.I.228.236; 6.I.228.237; 6.I.228.238;
6.I.228.239; 6.I.228.154; 6.I.228.157; 6.I.228.166; 6.I.228.169; 6.I.228.172; 6.I.228.175;
6.I.228.240; 6.I.228.244; 6.I.229.228; 6.I.229.229; 6.I.229.230; 6.I.229.231; 6.I.229.236;
6.I.229.237; 6.I.229.238; 6.I.229.239; 6.I.229.154; 6.I.229.157; 6.I.229.166; 6.I.229.169;
6.I.229.172; 6.I.229.175; 6.I.229.240; 6.I.229.244; 6.I.230.228; 6.I.230.229; 6.I.230.230;
6.I.230.231; 6.I.230.236; 6.I.230.237; 6.I.230.238; 6.I.230.239; 6.I.230.154; 6.I.230.157;

TABLE 100-continued

6.I.230.166; 6.I.230.169; 6.I.230.172; 6.I.230.175; 6.I.230.240; 6.I.230.244; 6.I.231.228;
6.I.231.229; 6.I.231.230; 6.I.231.231; 6.I.231.236; 6.I.231.237; 6.I.231.238; 6.I.231.239;
6.I.231.154; 6.I.231.157; 6.I.231.166; 6.I.231.169; 6.I.231.172; 6.I.231.175; 6.I.231.240;
6.I.231.244; 6.I.236.228; 6.I.236.229; 6.I.236.230; 6.I.236.231; 6.I.236.236; 6.I.236.237;
6.I.236.238; 6.I.236.239; 6.I.236.154; 6.I.236.157; 6.I.236.166; 6.I.236.169; 6.I.236.172;
6.I.236.175; 6.I.236.240; 6.I.236.244; 6.I.237.228; 6.I.237.229; 6.I.237.230; 6.I.237.231;
6.I.237.236; 6.I.237.237; 6.I.237.238; 6.I.237.239; 6.I.237.154; 6.I.237.157; 6.I.237.166;
6.I.237.169; 6.I.237.172; 6.I.237.175; 6.I.237.240; 6.I.237.244; 6.I.238.228; 6.I.238.229;
6.I.238.230; 6.I.238.231; 6.I.238.236; 6.I.238.237; 6.I.238.238; 6.I.238.239; 6.I.238.154;
6.I.238.157; 6.I.238.166; 6.I.238.169; 6.I.238.172; 6.I.238.175; 6.I.238.240; 6.I.238.244;
6.I.239.228; 6.I.239.229; 6.I.239.230; 6.I.239.231; 6.I.239.236; 6.I.239.237; 6.I.239.238;
6.I.239.239; 6.I.239.154; 6.I.239.157; 6.I.239.166; 6.I.239.169; 6.I.239.172; 6.I.239.175;
6.I.239.240; 6.I.239.244; 6.I.154.228; 6.I.154.229; 6.I.154.230; 6.I.154.231; 6.I.154.236;
6.I.154.237; 6.I.154.238; 6.I.154.239; 6.I.154.154; 6.I.154.157; 6.I.154.166; 6.I.154.169;
6.I.154.172; 6.I.154.175; 6.I.154.240; 6.I.154.244; 6.I.157.228; 6.I.157.229; 6.I.157.230;
6.I.157.231; 6.I.157.236; 6.I.157.237; 6.I.157.238; 6.I.157.239; 6.I.157.154; 6.I.157.157;
6.I.157.166; 6.I.157.169; 6.I.157.172; 6.I.157.175; 6.I.157.240; 6.I.157.244; 6.I.166.228;
6.I.166.229; 6.I.166.230; 6.I.166.231; 6.I.166.236; 6.I.166.237; 6.I.166.238; 6.I.166.239;
6.I.166.154; 6.I.166.157; 6.I.166.166; 6.I.166.169; 6.I.166.172; 6.I.166.175; 6.I.166.240;
6.I.166.244; 6.I.169.228; 6.I.169.229; 6.I.169.230; 6.I.169.231; 6.I.169.236; 6.I.169.237;
6.I.169.238; 6.I.169.239; 6.I.169.154; 6.I.169.157; 6.I.169.166; 6.I.169.169; 6.I.169.172;
6.I.169.175; 6.I.169.240; 6.I.169.244; 6.I.172.228; 6.I.172.229; 6.I.172.230; 6.I.172.231;
6.I.172.236; 6.I.172.237; 6.I.172.238; 6.I.172.239; 6.I.172.154; 6.I.172.157; 6.I.172.166;
6.I.172.169; 6.I.172.172; 6.I.172.175; 6.I.172.240; 6.I.172.244; 6.I.175.228; 6.I.175.229;
6.I.175.230; 6.I.175.231; 6.I.175.236; 6.I.175.237; 6.I.175.238; 6.I.175.239; 6.I.175.154;
6.I.175.157; 6.I.175.166; 6.I.175.169; 6.I.175.172; 6.I.175.175; 6.I.175.240; 6.I.175.244;
6.I.240.228; 6.I.240.229; 6.I.240.230; 6.I.240.231; 6.I.240.236; 6.I.240.237; 6.I.240.238;
6.I.240.239; 6.I.240.154; 6.I.240.157; 6.I.240.166; 6.I.240.169; 6.I.240.172; 6.I.240.175;
6.I.240.240; 6.I.240.244; 6.I.244.228; 6.I.244.229; 6.I.244.230; 6.I.244.231; 6.I.244.236;
6.I.244.237; 6.I.244.238; 6.I.244.239; 6.I.244.154; 6.I.244.157; 6.I.244.166; 6.I.244.169;
6.I.244.172; 6.I.244.175; 6.I.244.240; 6.I.244.244;
Prodrugs of 6.J 6.J.228.228; 6.J.228.229; 6.J.228.230; 6.J.228.231; 6.J.228.236; 6.J.228.237; 6.J.228.238;
6.J.228.239; 6.J.228.154; 6.J.228.157; 6.J.228.166; 6.J.228.169; 6.J.228.172; 6.J.228.175;
6.J.228.240; 6.J.228.244; 6.J.229.228; 6.J.229.229; 6.J.229.230; 6.J.229.231; 6.J.229.236;
6.J.229.237; 6.J.229.238; 6.J.229.239; 6.J.229.154; 6.J.229.157; 6.J.229.166; 6.J.229.169;
6.J.229.172; 6.J.229.175; 6.J.229.240; 6.J.229.244; 6.J.230.228; 6.J.230.229; 6.J.230.230;
6.J.230.231; 6.J.230.236; 6.J.230.237; 6.J.230.238; 6.J.230.239; 6.J.230.154; 6.J.230.157;
6.J.230.166; 6.J.230.169; 6.J.230.172; 6.J.230.175; 6.J.230.240; 6.J.230.244; 6.J.231.228;
6.J.231.229; 6.J.231.230; 6.J.231.231; 6.J.231.236; 6.J.231.237; 6.J.231.238; 6.J.231.239;
6.J.231.154; 6.J.231.157; 6.J.231.166; 6.J.231.169; 6.J.231.172; 6.J.231.175; 6.J.231.240;
6.J.231.244; 6.J.236.228; 6.J.236.229; 6.J.236.230; 6.J.236.231; 6.J.236.236; 6.J.236.237;
6.J.236.238; 6.J.236.239; 6.J.236.154; 6.J.236.157; 6.J.236.166; 6.J.236.169; 6.J.236.172;
6.J.236.175; 6.J.236.240; 6.J.236.244; 6.J.237.228; 6.J.237.229; 6.J.237.230; 6.J.237.231;
6.J.237.236; 6.J.237.237; 6.J.237.238; 6.J.237.239; 6.J.237.154; 6.J.237.157; 6.J.237.166;
6.J.237.169; 6.J.237.172; 6.J.237.175; 6.J.237.240; 6.J.237.244; 6.J.238.228; 6.J.238.229;
6.J.238.230; 6.J.238.231; 6.J.238.236; 6.J.238.237; 6.J.238.238; 6.J.238.239; 6.J.238.154;
6.J.238.157; 6.J.238.166; 6.J.238.169; 6.J.238.172; 6.J.238.175; 6.J.238.240; 6.J.238.244;
6.J.239.228; 6.J.239.229; 6.J.239.230; 6.J.239.231; 6.J.239.236; 6.J.239.237; 6.J.239.238;
6.J.239.239; 6.J.239.154; 6.J.239.157; 6.J.239.166; 6.J.239.169; 6.J.239.172; 6.J.239.175;
6.J.239.240; 6.J.239.244; 6.J.154.228; 6.J.154.229; 6.J.154.230; 6.J.154.231; 6.J.154.236;
6.J.154.237; 6.J.154.238; 6.J.154.239; 6.J.154.154; 6.J.154.157; 6.J.154.166; 6.J.154.169;
6.J.154.172; 6.J.154.175; 6.J.154.240; 6.J.154.244; 6.J.157.228; 6.J.157.229; 6.J.157.230;
6.J.157.231; 6.J.157.236; 6.J.157.237; 6.J.157.238; 6.J.157.239; 6.J.157.154; 6.J.157.157;
6.J.157.166; 6.J.157.169; 6.J.157.172; 6.J.157.175; 6.J.157.240; 6.J.157.244; 6.J.166.228;
6.J.166.229; 6.J.166.230; 6.J.166.231; 6.J.166.236; 6.J.166.237; 6.J.166.238; 6.J.166.239;
6.J.166.154; 6.J.166.157; 6.J.166.166; 6.J.166.169; 6.J.166.172; 6.J.166.175; 6.J.166.240;
6.J.166.244; 6.J.169.228; 6.J.169.229; 6.J.169.230; 6.J.169.231; 6.J.169.236; 6.J.169.237;
6.J.169.238; 6.J.169.239; 6.J.169.154; 6.J.169.157; 6.J.169.166; 6.J.169.169; 6.J.169.172;
6.J.169.175; 6.J.169.240; 6.J.169.244; 6.J.172.228; 6.J.172.229; 6.J.172.230; 6.J.172.231;
6.J.172.236; 6.J.172.237; 6.J.172.238; 6.J.172.239; 6.J.172.154; 6.J.172.157; 6.J.172.166;
6.J.172.169; 6.J.172.172; 6.J.172.175; 6.J.172.240; 6.J.172.244; 6.J.175.228; 6.J.175.229;
6.J.175.230; 6.J.175.231; 6.J.175.236; 6.J.175.237; 6.J.175.238; 6.J.175.239; 6.J.175.154;
6.J.175.157; 6.J.175.166; 6.J.175.169; 6.J.175.172; 6.J.175.175; 6.J.175.240; 6.J.175.244;
6.J.240.228; 6.J.240.229; 6.J.240.230; 6.J.240.231; 6.J.240.236; 6.J.240.237; 6.J.240.238;
6.J.240.239; 6.J.240.154; 6.J.240.157; 6.J.240.166; 6.J.240.169; 6.J.240.172; 6.J.240.175;
6.J.240.240; 6.J.240.244; 6.J.244.228; 6.J.244.229; 6.J.244.230; 6.J.244.231; 6.J.244.236;
6.J.244.237; 6.J.244.238; 6.J.244.239; 6.J.244.154; 6.J.244.157; 6.J.244.166; 6.J.244.169;
6.J.244.172; 6.J.244.175; 6.J.244.240; 6.J.244.244;
Prodrugs of 6.L 6.L.228.228; 6.L.228.229; 6.L.228.230; 6.L.228.231; 6.L.228.236; 6.L.228.237; 6.L.228.238;
6.L.228.239; 6.L.228.154; 6.L.228.157; 6.L.228.166; 6.L.228.169; 6.L.228.172; 6.L.228.175;
6.L.228.240; 6.L.228.244; 6.L.229.228; 6.L.229.229; 6.L.229.230; 6.L.229.231; 6.L.229.236;
6.L.229.237; 6.L.229.238; 6.L.229.239; 6.L.229.154; 6.L.229.157; 6.L.229.166; 6.L.229.169;
6.L.229.172; 6.L.229.175; 6.L.229.240; 6.L.229.244; 6.L.230.228; 6.L.230.229; 6.L.230.230;
6.L.230.231; 6.L.230.236; 6.L.230.237; 6.L.230.238; 6.L.230.239; 6.L.230.154; 6.L.230.157;
6.L.230.166; 6.L.230.169; 6.L.230.172; 6.L.230.175; 6.L.230.240; 6.L.230.244; 6.L.231.228;

TABLE 100-continued

6.L.231.229; 6.L.231.230; 6.L.231.231; 6.L.231.236; 6.L.231.237; 6.L.231.238; 6.L.231.239;
6.L.231.154; 6.L.231.157; 6.L.231.166; 6.L.231.169; 6.L.231.172; 6.L.231.175; 6.L.231.240;
6.L.231.244; 6.L.236.228; 6.L.236.229; 6.L.236.230; 6.L.236.231; 6.L.236.236; 6.L.236.237;
6.L.236.238; 6.L.236.239; 6.L.236.154; 6.L.236.157; 6.L.236.166; 6.L.236.169; 6.L.236.172;
6.L.236.175; 6.L.236.240; 6.L.236.244; 6.L.237.228; 6.L.237.229; 6.L.237.230; 6.L.237.231;
6.L.237.236; 6.L.237.237; 6.L.237.238; 6.L.237.239; 6.L.237.154; 6.L.237.157; 6.L.237.166;
6.L.237.169; 6.L.237.172; 6.L.237.175; 6.L.237.240; 6.L.237.244; 6.L.238.228; 6.L.238.229;
6.L.238.230; 6.L.238.231; 6.L.238.236; 6.L.238.237; 6.L.238.238; 6.L.238.239; 6.L.238.154;
6.L.238.157; 6.L.238.166; 6.L.238.169; 6.L.238.172; 6.L.238.175; 6.L.238.240; 6.L.238.244;
6.L.239.228; 6.L.239.229; 6.L.239.230; 6.L.239.231; 6.L.239.236; 6.L.239.237; 6.L.239.238;
6.L.239.239; 6.L.239.154; 6.L.239.157; 6.L.239.166; 6.L.239.169; 6.L.239.172; 6.L.239.175;
6.L.239.240; 6.L.239.244; 6.L.154.228; 6.L.154.229; 6.L.154.230; 6.L.154.231; 6.L.154.236;
6.L.154.237; 6.L.154.238; 6.L.154.239; 6.L.154.154; 6.L.154.157; 6.L.154.166; 6.L.154.169;
6.L.154.172; 6.L.154.175; 6.L.154.240; 6.L.154.244; 6.L.157.228; 6.L.157.229; 6.L.157.230;
6.L.157.231; 6.L.157.236; 6.L.157.237; 6.L.157.238; 6.L.157.239; 6.L.157.154; 6.L.157.157;
6.L.157.166; 6.L.157.169; 6.L.157.172; 6.L.157.175; 6.L.157.240; 6.L.157.244; 6.L.166.228;
6.L.166.229; 6.L.166.230; 6.L.166.231; 6.L.166.236; 6.L.166.237; 6.L.166.238; 6.L.166.239;
6.L.166.154; 6.L.166.157; 6.L.166.166; 6.L.166.169; 6.L.166.172; 6.L.166.175; 6.L.166.240;
6.L.166.244; 6.L.169.228; 6.L.169.229; 6.L.169.230; 6.L.169.231; 6.L.169.236; 6.L.169.237;
6.L.169.238; 6.L.169.239; 6.L.169.154; 6.L.169.157; 6.L.169.166; 6.L.169.169; 6.L.169.172;
6.L.169.175; 6.L.169.240; 6.L.169.244; 6.L.172.228; 6.L.172.229; 6.L.172.230; 6.L.172.231;
6.L.172.236; 6.L.172.237; 6.L.172.238; 6.L.172.239; 6.L.172.154; 6.L.172.157; 6.L.172.166;
6.L.172.169; 6.L.172.172; 6.L.172.175; 6.L.172.240; 6.L.172.244; 6.L.175.228; 6.L.175.229;
6.L.175.230; 6.L.175.231; 6.L.175.236; 6.L.175.237; 6.L.175.238; 6.L.175.239; 6.L.175.154;
6.L.175.157; 6.L.175.166; 6.L.175.169; 6.L.175.172; 6.L.175.175; 6.L.175.240; 6.L.175.244;
6.L.240.228; 6.L.240.229; 6.L.240.230; 6.L.240.231; 6.L.240.236; 6.L.240.237; 6.L.240.238;
6.L.240.239; 6.L.240.154; 6.L.240.157; 6.L.240.166; 6.L.240.169; 6.L.240.172; 6.L.240.175;
6.L.240.240; 6.L.240.244; 6.L.244.228; 6.L.244.229; 6.L.244.230; 6.L.244.231; 6.L.244.236;
6.L.244.237; 6.L.244.238; 6.L.244.239; 6.L.244.154; 6.L.244.157; 6.L.244.166; 6.L.244.169;
6.L.244.172; 6.L.244.175; 6.L.244.240; 6.L.244.244;
Prodrugs of 6.O 6.O.228.228; 6.O.228.229; 6.O.228.230; 6.O.228.231; 6.O.228.236; 6.O.228.237;
6.O.228.238; 6.O.228.239; 6.O.228.154; 6.O.228.157; 6.O.228.166; 6.O.228.169; 6.O.228.172;
6.O.228.175; 6.O.228.240; 6.O.228.244; 6.O.229.228; 6.O.229.229; 6.O.229.230; 6.O.229.231;
6.O.229.236; 6.O.229.237; 6.O.229.238; 6.O.229.239; 6.O.229.154; 6.O.229.157; 6.O.229.166;
6.O.229.169; 6.O.229.172; 6.O.229.175; 6.O.229.240; 6.O.229.244; 6.O.230.228; 6.O.230.229;
6.O.230.230; 6.O.230.231; 6.O.230.236; 6.O.230.237; 6.O.230.238; 6.O.230.239; 6.O.230.154;
6.O.230.157; 6.O.230.166; 6.O.230.169; 6.O.230.172; 6.O.230.175; 6.O.230.240; 6.O.230.244;
6.O.231.228; 6.O.231.229; 6.O.231.230; 6.O.231.231; 6.O.231.236; 6.O.231.237; 6.O.231.238;
6.O.231.239; 6.O.231.154; 6.O.231.157; 6.O.231.166; 6.O.231.169; 6.O.231.172; 6.O.231.175;
6.O.231.240; 6.O.231.244; 6.O.236.228; 6.O.236.229; 6.O.236.230; 6.O.236.231; 6.O.236.236;
6.O.236.237; 6.O.236.238; 6.O.236.239; 6.O.236.154; 6.O.236.157; 6.O.236.166; 6.O.236.169;
6.O.236.172; 6.O.236.175; 6.O.236.240; 6.O.236.244; 6.O.237.228; 6.O.237.229; 6.O.237.230;
6.O.237.231; 6.O.237.236; 6.O.237.237; 6.O.237.238; 6.O.237.239; 6.O.237.154; 6.O.237.157;
6.O.237.166; 6.O.237.169; 6.O.237.172; 6.O.237.175; 6.O.237.240; 6.O.237.244; 6.O.238.228;
6.O.238.229; 6.O.238.230; 6.O.238.231; 6.O.238.236; 6.O.238.237; 6.O.238.238; 6.O.238.239;
6.O.238.154; 6.O.238.157; 6.O.238.166; 6.O.238.169; 6.O.238.172; 6.O.238.175; 6.O.238.240;
6.O.238.244; 6.O.239.228; 6.O.239.229; 6.O.239.230; 6.O.239.231; 6.O.239.236; 6.O.239.237;
6.O.239.238; 6.O.239.239; 6.O.239.154; 6.O.239.157; 6.O.239.166; 6.O.239.169; 6.O.239.172;
6.O.239.175; 6.O.239.240; 6.O.239.244; 6.O.154.228; 6.O.154.229; 6.O.154.230; 6.O.154.231;
6.O.154.236; 6.O.154.237; 6.O.154.238; 6.O.154.239; 6.O.154.154; 6.O.154.157; 6.O.154.166;
6.O.154.169; 6.O.154.172; 6.O.154.175; 6.O.154.240; 6.O.154.244; 6.O.157.228; 6.O.157.229;
6.O.157.230; 6.O.157.231; 6.O.157.236; 6.O.157.237; 6.O.157.238; 6.O.157.239; 6.O.157.154;
6.O.157.157; 6.O.157.166; 6.O.157.169; 6.O.157.172; 6.O.157.175; 6.O.157.240; 6.O.157.244;
6.O.166.228; 6.O.166.229; 6.O.166.230; 6.O.166.231; 6.O.166.236; 6.O.166.237; 6.O.166.238;
6.O.166.239; 6.O.166.154; 6.O.166.157; 6.O.166.166; 6.O.166.169; 6.O.166.172; 6.O.166.175;
6.O.166.240; 6.O.166.244; 6.O.169.228; 6.O.169.229; 6.O.169.230; 6.O.169.231; 6.O.169.236;
6.O.169.237; 6.O.169.238; 6.O.169.239; 6.O.169.154; 6.O.169.157; 6.O.169.166; 6.O.169.169;
6.O.169.172; 6.O.169.175; 6.O.169.240; 6.O.169.244; 6.O.172.228; 6.O.172.229; 6.O.172.230;
6.O.172.231; 6.O.172.236; 6.O.172.237; 6.O.172.238; 6.O.172.239; 6.O.172.154; 6.O.172.157;
6.O.172.166; 6.O.172.169; 6.O.172.172; 6.O.172.175; 6.O.172.240; 6.O.172.244; 6.O.175.228;
6.O.175.229; 6.O.175.230; 6.O.175.231; 6.O.175.236; 6.O.175.237; 6.O.175.238; 6.O.175.239;
6.O.175.154; 6.O.175.157; 6.O.175.166; 6.O.175.169; 6.O.175.172; 6.O.175.175; 6.O.175.240;
6.O.175.244; 6.O.240.228; 6.O.240.229; 6.O.240.230; 6.O.240.231; 6.O.240.236; 6.O.240.237;
6.O.240.238; 6.O.240.239; 6.O.240.154; 6.O.240.157; 6.O.240.166; 6.O.240.169; 6.O.240.172;
6.O.240.175; 6.O.240.240; 6.O.240.244; 6.O.244.228; 6.O.244.229; 6.O.244.230; 6.O.244.231;
6.O.244.236; 6.O.244.237; 6.O.244.238; 6.O.244.239; 6.O.244.154; 6.O.244.157; 6.O.244.166;
6.O.244.169; 6.O.244.172; 6.O.244.175; 6.O.244.240; 6.O.244.244;
Prodrugs of 6.P 6.P.228.228; 6.P.228.229; 6.P.228.230; 6.P.228.231; 6.P.228.236; 6.P.228.237; 6.P.228.238;
6.P.228.239; 6.P.228.154; 6.P.228.157; 6.P.228.166; 6.P.228.169; 6.P.228.172; 6.P.228.175;
6.P.228.240; 6.P.228.244; 6.P.229.228; 6.P.229.229; 6.P.229.230; 6.P.229.231; 6.P.229.236;
6.P.229.237; 6.P.229.238; 6.P.229.239; 6.P.229.154; 6.P.229.157; 6.P.229.166; 6.P.229.169;
6.P.229.172; 6.P.229.175; 6.P.229.240; 6.P.229.244; 6.P.230.228; 6.P.230.229; 6.P.230.230;
6.P.230.231; 6.P.230.236; 6.P.230.237; 6.P.230.238; 6.P.230.239; 6.P.230.154; 6.P.230.157;
6.P.230.166; 6.P.230.169; 6.P.230.172; 6.P.230.175; 6.P.230.240; 6.P.230.244; 6.P.231.228;
6.P.231.229; 6.P.231.230; 6.P.231.231; 6.P.231.236; 6.P.231.237; 6.P.231.238; 6.P.231.239;

TABLE 100-continued

6.P.231.154; 6.P.231.157; 6.P.231.166; 6.P.231.169; 6.P.231.172; 6.P.231.175; 6.P.231.240; 6.P.231.244; 6.P.236.228; 6.P.236.229; 6.P.236.230; 6.P.236.231; 6.P.236.236; 6.P.236.237; 6.P.236.238; 6.P.236.239; 6.P.236.154; 6.P.236.157; 6.P.236.166; 6.P.236.169; 6.P.236.172; 6.P.236.175; 6.P.236.240; 6.P.236.244; 6.P.237.228; 6.P.237.229; 6.P.237.230; 6.P.237.231; 6.P.237.236; 6.P.237.237; 6.P.237.238; 6.P.237.239; 6.P.237.154; 6.P.237.157; 6.P.237.166; 6.P.237.169; 6.P.237.172; 6.P.237.175; 6.P.237.240; 6.P.237.244; 6.P.238.228; 6.P.238.229; 6.P.238.230; 6.P.238.231; 6.P.238.236; 6.P.238.237; 6.P.238.238; 6.P.238.239; 6.P.238.154; 6.P.238.157; 6.P.238.166; 6.P.238.169; 6.P.238.172; 6.P.238.175; 6.P.238.240; 6.P.238.244; 6.P.239.228; 6.P.239.229; 6.P.239.230; 6.P.239.231; 6.P.239.236; 6.P.239.237; 6.P.239.238; 6.P.239.239; 6.P.239.154; 6.P.239.157; 6.P.239.166; 6.P.239.169; 6.P.239.172; 6.P.239.175; 6.P.239.240; 6.P.239.244; 6.P.154.228; 6.P.154.229; 6.P.154.230; 6.P.154.231; 6.P.154.236; 6.P.154.237; 6.P.154.238; 6.P.154.239; 6.P.154.154; 6.P.154.157; 6.P.154.166; 6.P.154.169; 6.P.154.172; 6.P.154.175; 6.P.154.240; 6.P.154.244; 6.P.157.228; 6.P.157.229; 6.P.157.230; 6.P.157.231; 6.P.157.236; 6.P.157.237; 6.P.157.238; 6.P.157.239; 6.P.157.154; 6.P.157.157; 6.P.157.166; 6.P.157.169; 6.P.157.172; 6.P.157.175; 6.P.157.240; 6.P.157.244; 6.P.166.228; 6.P.166.229; 6.P.166.230; 6.P.166.231; 6.P.166.236; 6.P.166.237; 6.P.166.238; 6.P.166.239; 6.P.166.154; 6.P.166.157; 6.P.166.166; 6.P.166.169; 6.P.166.172; 6.P.166.175; 6.P.166.240; 6.P.166.244; 6.P.169.228; 6.P.169.229; 6.P.169.230; 6.P.169.231; 6.P.169.236; 6.P.169.237; 6.P.169.238; 6.P.169.239; 6.P.169.154; 6.P.169.157; 6.P.169.166; 6.P.169.169; 6.P.169.172; 6.P.169.175; 6.P.169.240; 6.P.169.244; 6.P.172.228; 6.P.172.229; 6.P.172.230; 6.P.172.231; 6.P.172.236; 6.P.172.237; 6.P.172.238; 6.P.172.239; 6.P.172.154; 6.P.172.157; 6.P.172.166; 6.P.172.169; 6.P.172.172; 6.P.172.175; 6.P.172.240; 6.P.172.244; 6.P.175.228; 6.P.175.229; 6.P.175.230; 6.P.175.231; 6.P.175.236; 6.P.175.237; 6.P.175.238; 6.P.175.239; 6.P.175.154; 6.P.175.157; 6.P.175.166; 6.P.175.169; 6.P.175.172; 6.P.175.175; 6.P.175.240; 6.P.175.244; 6.P.240.228; 6.P.240.229; 6.P.240.230; 6.P.240.231; 6.P.240.236; 6.P.240.237; 6.P.240.238; 6.P.240.239; 6.P.240.154; 6.P.240.157; 6.P.240.166; 6.P.240.169; 6.P.240.172; 6.P.240.175; 6.P.240.240; 6.P.240.244; 6.P.244.228; 6.P.244.229; 6.P.244.230; 6.P.244.231; 6.P.244.236; 6.P.244.237; 6.P.244.238; 6.P.244.239; 6.P.244.154; 6.P.244.157; 6.P.244.166; 6.P.244.169; 6.P.244.172; 6.P.244.175; 6.P.244.240; 6.P.244.244;

Prodrugs of 6.U

6.U.228.228; 6.U.228.229; 6.U.228.230; 6.U.228.231; 6.U.228.236; 6.U.228.237; 6.U.228.238; 6.U.228.239; 6.U.228.154; 6.U.228.157; 6.U.228.166; 6.U.228.169; 6.U.228.172; 6.U.228.175; 6.U.228.240; 6.U.228.244; 6.U.229.228; 6.U.229.229; 6.U.229.230; 6.U.229.231; 6.U.229.236; 6.U.229.237; 6.U.229.238; 6.U.229.239; 6.U.229.154; 6.U.229.157; 6.U.229.166; 6.U.229.169; 6.U.229.172; 6.U.229.175; 6.U.229.240; 6.U.229.244; 6.U.230.228; 6.U.230.229; 6.U.230.230; 6.U.230.231; 6.U.230.236; 6.U.230.237; 6.U.230.238; 6.U.230.239; 6.U.230.154; 6.U.230.157; 6.U.230.166; 6.U.230.169; 6.U.230.172; 6.U.230.175; 6.U.230.240; 6.U.230.244; 6.U.231.228; 6.U.231.229; 6.U.231.230; 6.U.231.231; 6.U.231.236; 6.U.231.237; 6.U.231.238; 6.U.231.239; 6.U.231.154; 6.U.231.157; 6.U.231.166; 6.U.231.169; 6.U.231.172; 6.U.231.175; 6.U.231.240; 6.U.231.244; 6.U.236.228; 6.U.236.229; 6.U.236.230; 6.U.236.231; 6.U.236.236; 6.U.236.237; 6.U.236.238; 6.U.236.239; 6.U.236.154; 6.U.236.157; 6.U.236.166; 6.U.236.169; 6.U.236.172; 6.U.236.175; 6.U.236.240; 6.U.236.244; 6.U.237.228; 6.U.237.229; 6.U.237.230; 6.U.237.231; 6.U.237.236; 6.U.237.237; 6.U.237.238; 6.U.237.239; 6.U.237.154; 6.U.237.157; 6.U.237.166; 6.U.237.169; 6.U.237.172; 6.U.237.175; 6.U.237.240; 6.U.237.244; 6.U.238.228; 6.U.238.229; 6.U.238.230; 6.U.238.231; 6.U.238.236; 6.U.238.237; 6.U.238.238; 6.U.238.239; 6.U.238.154; 6.U.238.157; 6.U.238.166; 6.U.238.169; 6.U.238.172; 6.U.238.175; 6.U.238.240; 6.U.238.244; 6.U.239.228; 6.U.239.229; 6.U.239.230; 6.U.239.231; 6.U.239.236; 6.U.239.237; 6.U.239.238; 6.U.239.239; 6.U.239.154; 6.U.239.157; 6.U.239.166; 6.U.239.169; 6.U.239.172; 6.U.239.175; 6.U.239.240; 6.U.239.244; 6.U.154.228; 6.U.154.229; 6.U.154.230; 6.U.154.231; 6.U.154.236; 6.U.154.237; 6.U.154.238; 6.U.154.239; 6.U.154.154; 6.U.154.157; 6.U.154.166; 6.U.154.169; 6.U.154.172; 6.U.154.175; 6.U.154.240; 6.U.154.244; 6.U.157.228; 6.U.157.229; 6.U.157.230; 6.U.157.231; 6.U.157.236; 6.U.157.237; 6.U.157.238; 6.U.157.239; 6.U.157.154; 6.U.157.157; 6.U.157.166; 6.U.157.169; 6.U.157.172; 6.U.157.175; 6.U.157.240; 6.U.157.244; 6.U.166.228; 6.U.166.229; 6.U.166.230; 6.U.166.231; 6.U.166.236; 6.U.166.237; 6.U.166.238; 6.U.166.239; 6.U.166.154; 6.U.166.157; 6.U.166.166; 6.U.166.169; 6.U.166.172; 6.U.166.175; 6.U.166.240; 6.U.166.244; 6.U.169.228; 6.U.169.229; 6.U.169.230; 6.U.169.231; 6.U.169.236; 6.U.169.237; 6.U.169.238; 6.U.169.239; 6.U.169.154; 6.U.169.157; 6.U.169.166; 6.U.169.169; 6.U.169.172; 6.U.169.175; 6.U.169.240; 6.U.169.244; 6.U.172.228; 6.U.172.229; 6.U.172.230; 6.U.172.231; 6.U.172.236; 6.U.172.237; 6.U.172.238; 6.U.172.239; 6.U.172.154; 6.U.172.157; 6.U.172.166; 6.U.172.169; 6.U.172.172; 6.U.172.175; 6.U.172.240; 6.U.172.244; 6.U.175.228; 6.U.175.229; 6.U.175.230; 6.U.175.231; 6.U.175.236; 6.U.175.237; 6.U.175.238; 6.U.175.239; 6.U.175.154; 6.U.175.157; 6.U.175.166; 6.U.175.169; 6.U.175.172; 6.U.175.175; 6.U.175.240; 6.U.175.244; 6.U.240.228; 6.U.240.229; 6.U.240.230; 6.U.240.231; 6.U.240.236; 6.U.240.237; 6.U.240.238; 6.U.240.239; 6.U.240.154; 6.U.240.157; 6.U.240.166; 6.U.240.169; 6.U.240.172; 6.U.240.175; 6.U.240.240; 6.U.240.244; 6.U.244.228; 6.U.244.229; 6.U.244.230; 6.U.244.231; 6.U.244.236; 6.U.244.237; 6.U.244.238; 6.U.244.239; 6.U.244.154; 6.U.244.157; 6.U.244.166; 6.U.244.169; 6.U.244.172; 6.U.244.175; 6.U.244.240; 6.U.244.244;

Prodrugs of 6.W

6.W.228.228; 6.W.228.229; 6.W.228.230; 6.W.228.231; 6.W.228.236; 6.W.228.237; 6.W.228.238; 6.W.228.239; 6.W.228.154; 6.W.228.157; 6.W.228.166; 6.W.228.169; 6.W.228.172; 6.W.228.175; 6.W.228.240; 6.W.228.244; 6.W.229.228; 6.W.229.229; 6.W.229.230; 6.W.229.231; 6.W.229.236; 6.W.229.237; 6.W.229.238; 6.W.229.239; 6.W.229.154; 6.W.229.157; 6.W.229.166; 6.W.229.169; 6.W.229.172; 6.W.229.175; 6.W.229.240; 6.W.229.244; 6.W.230.228; 6.W.230.229; 6.W.230.230; 6.W.230.231; 6.W.230.236; 6.W.230.237; 6.W.230.238; 6.W.230.239; 6.W.230.154; 6.W.230.157; 6.W.230.166; 6.W.230.169; 6.W.230.172; 6.W.230.175; 6.W.230.240; 6.W.230.244; 6.W.231.228; 6.W.231.229; 6.W.231.230; 6.W.231.231; 6.W.231.236; 6.W.231.237;

TABLE 100-continued

6.W.231.238; 6.W.231.239; 6.W.231.154; 6.W.231.157; 6.W.231.166; 6.W.231.169;
6.W.231.172; 6.W.231.175; 6.W.231.240; 6.W.231.244; 6.W.236.228; 6.W.236.229;
6.W.236.230; 6.W.236.231; 6.W.236.236; 6.W.236.237; 6.W.236.238; 6.W.236.239;
6.W.236.154; 6.W.236.157; 6.W.236.166; 6.W.236.169; 6.W.236.172; 6.W.236.175;
6.W.236.240; 6.W.236.244; 6.W.237.228; 6.W.237.229; 6.W.237.230; 6.W.237.231;
6.W.237.236; 6.W.237.237; 6.W.237.238; 6.W.237.239; 6.W.237.154; 6.W.237.157;
6.W.237.166; 6.W.237.169; 6.W.237.172; 6.W.237.175; 6.W.237.240; 6.W.237.244;
6.W.238.228; 6.W.238.229; 6.W.238.230; 6.W.238.231; 6.W.238.236; 6.W.238.237;
6.W.238.238; 6.W.238.239; 6.W.238.154; 6.W.238.157; 6.W.238.166; 6.W.238.169;
6.W.238.172; 6.W.238.175; 6.W.238.240; 6.W.238.244; 6.W.239.228; 6.W.239.229;
6.W.239.230; 6.W.239.231; 6.W.239.236; 6.W.239.237; 6.W.239.238; 6.W.239.239;
6.W.239.154; 6.W.239.157; 6.W.239.166; 6.W.239.169; 6.W.239.172; 6.W.239.175;
6.W.239.240; 6.W.239.244; 6.W.154.228; 6.W.154.229; 6.W.154.230; 6.W.154.231;
6.W.154.236; 6.W.154.237; 6.W.154.238; 6.W.154.239; 6.W.154.154; 6.W.154.157;
6.W.154.166; 6.W.154.169; 6.W.154.172; 6.W.154.175; 6.W.154.240; 6.W.154.244;
6.W.157.228; 6.W.157.229; 6.W.157.230; 6.W.157.231; 6.W.157.236; 6.W.157.237;
6.W.157.238; 6.W.157.239; 6.W.157.154; 6.W.157.157; 6.W.157.166; 6.W.157.169;
6.W.157.172; 6.W.157.175; 6.W.157.240; 6.W.157.244; 6.W.166.228; 6.W.166.229;
6.W.166.230; 6.W.166.231; 6.W.166.236; 6.W.166.237; 6.W.166.238; 6.W.166.239;
6.W.166.154; 6.W.166.157; 6.W.166.166; 6.W.166.169; 6.W.166.172; 6.W.166.175;
6.W.166.240; 6.W.166.244; 6.W.169.228; 6.W.169.229; 6.W.169.230; 6.W.169.231;
6.W.169.236; 6.W.169.237; 6.W.169.238; 6.W.169.239; 6.W.169.154; 6.W.169.157;
6.W.169.166; 6.W.169.169; 6.W.169.172; 6.W.169.175; 6.W.169.240; 6.W.169.244;
6.W.172.228; 6.W.172.229; 6.W.172.230; 6.W.172.231; 6.W.172.236; 6.W.172.237;
6.W.172.238; 6.W.172.239; 6.W.172.154; 6.W.172.157; 6.W.172.166; 6.W.172.169;
6.W.172.172; 6.W.172.175; 6.W.172.240; 6.W.172.244; 6.W.175.228; 6.W.175.229;
6.W.175.230; 6.W.175.231; 6.W.175.236; 6.W.175.237; 6.W.175.238; 6.W.175.239;
6.W.175.154; 6.W.175.157; 6.W.175.166; 6.W.175.169; 6.W.175.172; 6.W.175.175;
6.W.175.240; 6.W.175.244; 6.W.240.228; 6.W.240.229; 6.W.240.230; 6.W.240.231;
6.W.240.236; 6.W.240.237; 6.W.240.238; 6.W.240.239; 6.W.240.154; 6.W.240.157;
6.W.240.166; 6.W.240.169; 6.W.240.172; 6.W.240.175; 6.W.240.240; 6.W.240.244;
6.W.244.228; 6.W.244.229; 6.W.244.230; 6.W.244.231; 6.W.244.236; 6.W.244.237;
6.W.244.238; 6.W.244.239; 6.W.244.154; 6.W.244.157; 6.W.244.166; 6.W.244.169;
6.W.244.172; 6.W.244.175; 6.W.244.240; 6.W.244.244;

Prodrugs of 6.Y

6.Y.228.228; 6.Y.228.229; 6.Y.228.230; 6.Y.228.231; 6.Y.228.236; 6.Y.228.237;
6.Y.228.238; 6.Y.228.239; 6.Y.228.154; 6.Y.228.157; 6.Y.228.166; 6.Y.228.169; 6.Y.228.172;
6.Y.228.175; 6.Y.228.240; 6.Y.228.244; 6.Y.229.228; 6.Y.229.229; 6.Y.229.230; 6.Y.229.231;
6.Y.229.236; 6.Y.229.237; 6.Y.229.238; 6.Y.229.239; 6.Y.229.154; 6.Y.229.157; 6.Y.229.166;
6.Y.229.169; 6.Y.229.172; 6.Y.229.175; 6.Y.229.240; 6.Y.229.244; 6.Y.230.228; 6.Y.230.229;
6.Y.230.230; 6.Y.230.231; 6.Y.230.236; 6.Y.230.237; 6.Y.230.238; 6.Y.230.239; 6.Y.230.154;
6.Y.230.157; 6.Y.230.166; 6.Y.230.169; 6.Y.230.172; 6.Y.230.175; 6.Y.230.240; 6.Y.230.244;
6.Y.231.228; 6.Y.231.229; 6.Y.231.230; 6.Y.231.231; 6.Y.231.236; 6.Y.231.237; 6.Y.231.238;
6.Y.231.239; 6.Y.231.154; 6.Y.231.157; 6.Y.231.166; 6.Y.231.169; 6.Y.231.172; 6.Y.231.175;
6.Y.231.240; 6.Y.231.244; 6.Y.236.228; 6.Y.236.229; 6.Y.236.230; 6.Y.236.231; 6.Y.236.236;
6.Y.236.237; 6.Y.236.238; 6.Y.236.239; 6.Y.236.154; 6.Y.236.157; 6.Y.236.166; 6.Y.236.169;
6.Y.236.172; 6.Y.236.175; 6.Y.236.240; 6.Y.236.244; 6.Y.237.228; 6.Y.237.229; 6.Y.237.230;
6.Y.237.231; 6.Y.237.236; 6.Y.237.237; 6.Y.237.238; 6.Y.237.239; 6.Y.237.154; 6.Y.237.157;
6.Y.237.166; 6.Y.237.169; 6.Y.237.172; 6.Y.237.175; 6.Y.237.240; 6.Y.237.244; 6.Y.238.228;
6.Y.238.229; 6.Y.238.230; 6.Y.238.231; 6.Y.238.236; 6.Y.238.237; 6.Y.238.238; 6.Y.238.239;
6.Y.238.154; 6.Y.238.157; 6.Y.238.166; 6.Y.238.169; 6.Y.238.172; 6.Y.238.175; 6.Y.238.240;
6.Y.238.244; 6.Y.239.228; 6.Y.239.229; 6.Y.239.230; 6.Y.239.231; 6.Y.239.236; 6.Y.239.237;
6.Y.239.238; 6.Y.239.239; 6.Y.239.154; 6.Y.239.157; 6.Y.239.166; 6.Y.239.169; 6.Y.239.172;
6.Y.239.175; 6.Y.239.240; 6.Y.239.244; 6.Y.154.228; 6.Y.154.229; 6.Y.154.230; 6.Y.154.231;
6.Y.154.236; 6.Y.154.237; 6.Y.154.238; 6.Y.154.239; 6.Y.154.154; 6.Y.154.157; 6.Y.154.166;
6.Y.154.169; 6.Y.154.172; 6.Y.154.175; 6.Y.154.240; 6.Y.154.244; 6.Y.157.228; 6.Y.157.229;
6.Y.157.230; 6.Y.157.231; 6.Y.157.236; 6.Y.157.237; 6.Y.157.238; 6.Y.157.239; 6.Y.157.154;
6.Y.157.157; 6.Y.157.166; 6.Y.157.169; 6.Y.157.172; 6.Y.157.175; 6.Y.157.240; 6.Y.157.244;
6.Y.166.228; 6.Y.166.229; 6.Y.166.230; 6.Y.166.231; 6.Y.166.236; 6.Y.166.237; 6.Y.166.238;
6.Y.166.239; 6.Y.166.154; 6.Y.166.157; 6.Y.166.166; 6.Y.166.169; 6.Y.166.172; 6.Y.166.175;
6.Y.166.240; 6.Y.166.244; 6.Y.169.228; 6.Y.169.229; 6.Y.169.230; 6.Y.169.231; 6.Y.169.236;
6.Y.169.237; 6.Y.169.238; 6.Y.169.239; 6.Y.169.154; 6.Y.169.157; 6.Y.169.166; 6.Y.169.169;
6.Y.169.172; 6.Y.169.175; 6.Y.169.240; 6.Y.169.244; 6.Y.172.228; 6.Y.172.229; 6.Y.172.230;
6.Y.172.231; 6.Y.172.236; 6.Y.172.237; 6.Y.172.238; 6.Y.172.239; 6.Y.172.154; 6.Y.172.157;
6.Y.172.166; 6.Y.172.169; 6.Y.172.172; 6.Y.172.175; 6.Y.172.240; 6.Y.172.244; 6.Y.175.228;
6.Y.175.229; 6.Y.175.230; 6.Y.175.231; 6.Y.175.236; 6.Y.175.237; 6.Y.175.238; 6.Y.175.239;
6.Y.175.154; 6.Y.175.157; 6.Y.175.166; 6.Y.175.169; 6.Y.175.172; 6.Y.175.175; 6.Y.175.240;
6.Y.175.244; 6.Y.240.228; 6.Y.240.229; 6.Y.240.230; 6.Y.240.231; 6.Y.240.236; 6.Y.240.237;
6.Y.240.238; 6.Y.240.239; 6.Y.240.154; 6.Y.240.157; 6.Y.240.166; 6.Y.240.169; 6.Y.240.172;
6.Y.240.175; 6.Y.240.240; 6.Y.240.244; 6.Y.244.228; 6.Y.244.229; 6.Y.244.230; 6.Y.244.231;
6.Y.244.236; 6.Y.244.237; 6.Y.244.238; 6.Y.244.239; 6.Y.244.154; 6.Y.244.157; 6.Y.244.166;
6.Y.244.169; 6.Y.244.172; 6.Y.244.175; 6.Y.244.240; 6.Y.244.244;

Prodrugs of 7.AH

7.AH.4.157; 7.AH.4.158; 7.AH.4.196; 7.AH.4.223; 7.AH.4.240; 7.AH.4.244; 7.AH.4.243;
7.AH.4.247; 7.AH.5.157; 7.AH.5.158; 7.AH.5.196; 7.AH.5.223; 7.AH.5.240; 7.AH.5.244;
7.AH.5.243; 7.AH.5.247; 7.AH.7.157; 7.AH.7.158; 7.AH.7.196; 7.AH.7.223; 7.AH.7.240;
7.AH.7.244; 7.AH.7.243; 7.AH.7.247; 7.AH.15.157; 7.AH.15.158; 7.AH.15.196; 7.AH.15.223;

TABLE 100-continued

7.AH.15.240; 7.AH.15.244; 7.AH.15.243; 7.AH.15.247; 7.AH.16.157; 7.AH.16.158;
7.AH.16.196; 7.AH.16.223; 7.AH.16.240; 7.AH.16.244; 7.AH.16.243; 7.AH.16.247;
7.AH.18.157; 7.AH.18.158; 7.AH.18.196; 7.AH.18.223; 7.AH.18.240; 7.AH.18.244;
7.AH.18.243; 7.AH.18.247; 7.AH.26.157; 7.AH.26.158; 7.AH.26.196; 7.AH.26.223;
7.AH.26.240; 7.AH.26.244; 7.AH.26.243; 7.AH.26.247; 7.AH.27.157; 7.AH.27.158;
7.AH.27.196; 7.AH.27.223; 7.AH.27.240; 7.AH.27.244; 7.AH.27.243; 7.AH.27.247;
7.AH.29.157; 7.AH.29.158; 7.AH.29.196; 7.AH.29.223; 7.AH.29.240; 7.AH.29.244;
7.AH.29.243; 7.AH.29.247; 7.AH.54.157; 7.AH.54.158; 7.AH.54.196; 7.AH.54.223;
7.AH.54.240; 7.AH.54.244; 7.AH.54.243; 7.AH.54.247; 7.AH.55.157; 7.AH.55.158;
7.AH.55.196; 7.AH.55.223; 7.AH.55.240; 7.AH.55.244; 7.AH.55.243; 7.AH.55.247;
7.AH.56.157; 7.AH.56.158; 7.AH.56.196; 7.AH.56.223; 7.AH.56.240; 7.AH.56.244;
7.AH.56.243; 7.AH.56.247; 7.AH.157.157; 7.AH.157.158; 7.AH.157.196; 7.AH.157.223;
7.AH.157.240; 7.AH.157.244; 7.AH.157.243; 7.AH.157.247; 7.AH.196.157; 7.AH.196.158;
7.AH.196.196; 7.AH.196.223; 7.AH.196.240; 7.AH.196.244; 7.AH.196.243; 7.AH.196.247;
7.AH.223.157; 7.AH.223.158; 7.AH.223.196; 7.AH.223.223; 7.AH.223.240; 7.AH.223.244;
7.AH.223.243; 7.AH.223.247; 7.AH.240.157; 7.AH.240.158; 7.AH.240.196; 7.AH.240.223;
7.AH.240.240; 7.AH.240.244; 7.AH.240.243; 7.AH.240.247; 7.AH.244.157; 7.AH.244.158;
7.AH.244.196; 7.AH.244.223; 7.AH.244.240; 7.AH.244.244; 7.AH.244.243; 7.AH.244.247;
7.AH.247.157; 7.AH.247.158; 7.AH.247.196; 7.AH.247.223; 7.AH.247.240; 7.AH.247.244;
7.AH.247.243; 7.AH.247.247;
Prodrugs of 7.AJ 7.AJ.4.157; 7.AJ.4.158; 7.AJ.4.196; 7.AJ.4.223; 7.AJ.4.240; 7.AJ.4.244; 7.AJ.4.243;
7.AJ.4.247; 7.AJ.5.157; 7.AJ.5.158; 7.AJ.5.196; 7.AJ.5.223; 7.AJ.5.240; 7.AJ.5.244; 7.AJ.5.243;
7.AJ.5.247; 7.AJ.7.157; 7.AJ.7.158; 7.AJ.7.196; 7.AJ.7.223; 7.AJ.7.240; 7.AJ.7.244; 7.AJ.7.243;
7.AJ.7.247; 7.AJ.15.157; 7.AJ.15.158; 7.AJ.15.196; 7.AJ.15.223; 7.AJ.15.240; 7.AJ.15.244;
7.AJ.15.243; 7.AJ.15.247; 7.AJ.16.157; 7.AJ.16.158; 7.AJ.16.196; 7.AJ.16.223; 7.AJ.16.240;
7.AJ.16.244; 7.AJ.16.243; 7.AJ.16.247; 7.AJ.18.157; 7.AJ.18.158; 7.AJ.18.196; 7.AJ.18.223;
7.AJ.18.240; 7.AJ.18.244; 7.AJ.18.243; 7.AJ.18.247; 7.AJ.26.157; 7.AJ.26.158; 7.AJ.26.196;
7.AJ.26.223; 7.AJ.26.240; 7.AJ.26.244; 7.AJ.26.243; 7.AJ.26.247; 7.AJ.27.157; 7.AJ.27.158;
7.AJ.27.196; 7.AJ.27.223; 7.AJ.27.240; 7.AJ.27.244; 7.AJ.27.243; 7.AJ.27.247; 7.AJ.29.157;
7.AJ.29.158; 7.AJ.29.196; 7.AJ.29.223; 7.AJ.29.240; 7.AJ.29.244; 7.AJ.29.243; 7.AJ.29.247;
7.AJ.54.157; 7.AJ.54.158; 7.AJ.54.196; 7.AJ.54.223; 7.AJ.54.240; 7.AJ.54.244; 7.AJ.54.243;
7.AJ.54.247; 7.AJ.55.157; 7.AJ.55.158; 7.AJ.55.196; 7.AJ.55.223; 7.AJ.55.240; 7.AJ.55.244;
7.AJ.55.243; 7.AJ.55.247; 7.AJ.56.157; 7.AJ.56.158; 7.AJ.56.196; 7.AJ.56.223; 7.AJ.56.240;
7.AJ.56.244; 7.AJ.56.243; 7.AJ.56.247; 7.AJ.157.157; 7.AJ.157.158; 7.AJ.157.196;
7.AJ.157.223; 7.AJ.157.240; 7.AJ.157.244; 7.AJ.157.243; 7.AJ.157.247; 7.AJ.196.157;
7.AJ.196.158; 7.AJ.196.196; 7.AJ.196.223; 7.AJ.196.240; 7.AJ.196.244; 7.AJ.196.243;
7.AJ.196.247; 7.AJ.223.157; 7.AJ.223.158; 7.AJ.223.196; 7.AJ.223.223; 7.AJ.223.240;
7.AJ.223.244; 7.AJ.223.243; 7.AJ.223.247; 7.AJ.240.157; 7.AJ.240.158; 7.AJ.240.196;
7.AJ.240.223; 7.AJ.240.240; 7.AJ.240.244; 7.AJ.240.243; 7.AJ.240.247; 7.AJ.244.157;
7.AJ.244.158; 7.AJ.244.196; 7.AJ.244.223; 7.AJ.244.240; 7.AJ.244.244; 7.AJ.244.243;
7.AJ.244.247; 7.AJ.247.157; 7.AJ.247.158; 7.AJ.247.196; 7.AJ.247.223; 7.AJ.247.240;
7.AJ.247.244; 7.AJ.247.243; 7.AJ.247.247;
Prodrugs of 7.AN 7.AN.4.157; 7.AN.4.158; 7.AN.4.196; 7.AN.4.223; 7.AN.4.240; 7.AN.4.244; 7.AN.4.243;
7.AN.4.247; 7.AN.5.157; 7.AN.5.158; 7.AN.5.196; 7.AN.5.223; 7.AN.5.240; 7.AN.5.244;
7.AN.5.243; 7.AN.5.247; 7.AN.7.157; 7.AN.7.158; 7.AN.7.196; 7.AN.7.223; 7.AN.7.240;
7.AN.7.244; 7.AN.7.243; 7.AN.7.247; 7.AN.15.157; 7.AN.15.158; 7.AN.15.196; 7.AN.15.223;
7.AN.15.240; 7.AN.15.244; 7.AN.15.243; 7.AN.15.247; 7.AN.16.157; 7.AN.16.158;
7.AN.16.196; 7.AN.16.223; 7.AN.16.240; 7.AN.16.244; 7.AN.16.243; 7.AN.16.247;
7.AN.18.157; 7.AN.18.158; 7.AN.18.196; 7.AN.18.223; 7.AN.18.240; 7.AN.18.244;
7.AN.18.243; 7.AN.18.247; 7.AN.26.157; 7.AN.26.158; 7.AN.26.196; 7.AN.26.223;
7.AN.26.240; 7.AN.26.244; 7.AN.26.243; 7.AN.26.247; 7.AN.27.157; 7.AN.27.158;
7.AN.27.196; 7.AN.27.223; 7.AN.27.240; 7.AN.27.244; 7.AN.27.243; 7.AN.27.247;
7.AN.29.157; 7.AN.29.158; 7.AN.29.196; 7.AN.29.223; 7.AN.29.240; 7.AN.29.244;
7.AN.29.243; 7.AN.29.247; 7.AN.54.157; 7.AN.54.158; 7.AN.54.196; 7.AN.54.223;
7.AN.54.240; 7.AN.54.244; 7.AN.54.243; 7.AN.54.247; 7.AN.55.157; 7.AN.55.158;
7.AN.55.196; 7.AN.55.223; 7.AN.55.240; 7.AN.55.244; 7.AN.55.243; 7.AN.55.247;
7.AN.56.157; 7.AN.56.158; 7.AN.56.196; 7.AN.56.223; 7.AN.56.240; 7.AN.56.244;
7.AN.56.243; 7.AN.56.247; 7.AN.157.157; 7.AN.157.158; 7.AN.157.196; 7.AN.157.223;
7.AN.157.240; 7.AN.157.244; 7.AN.157.243; 7.AN.157.247; 7.AN.196.157; 7.AN.196.158;
7.AN.196.196; 7.AN.196.223; 7.AN.196.240; 7.AN.196.244; 7.AN.196.243; 7.AN.196.247;
7.AN.223.157; 7.AN.223.158; 7.AN.223.196; 7.AN.223.223; 7.AN.223.240; 7.AN.223.244;
7.AN.223.243; 7.AN.223.247; 7.AN.240.157; 7.AN.240.158; 7.AN.240.196; 7.AN.240.223;
7.AN.240.240; 7.AN.240.244; 7.AN.240.243; 7.AN.240.247; 7.AN.244.157; 7.AN.244.158;
7.AN.244.196; 7.AN.244.223; 7.AN.244.240; 7.AN.244.244; 7.AN.244.243; 7.AN.244.247;
7.AN.247.157; 7.AN.247.158; 7.AN.247.196; 7.AN.247.223; 7.AN.247.240; 7.AN.247.244;
7.AN.247.243; 7.AN.247.247;
Prodrugs of 7.AP 7.AP.4.157; 7.AP.4.158; 7.AP.4.196; 7.AP.4.223; 7.AP.4.240; 7.AP.4.244; 7.AP.4.243;
7.AP.4.247; 7.AP.5.157; 7.AP.5.158; 7.AP.5.196; 7.AP.5.223; 7.AP.5.240; 7.AP.5.244;
7.AP.5.243; 7.AP.5.247; 7.AP.7.157; 7.AP.7.158; 7.AP.7.196; 7.AP.7.223; 7.AP.7.240;
7.AP.7.244; 7.AP.7.243; 7.AP.7.247; 7.AP.15.157; 7.AP.15.158; 7.AP.15.196; 7.AP.15.223;
7.AP.15.240; 7.AP.15.244; 7.AP.15.243; 7.AP.15.247; 7.AP.16.157; 7.AP.16.158; 7.AP.16.196;
7.AP.16.223; 7.AP.16.240; 7.AP.16.244; 7.AP.16.243; 7.AP.16.247; 7.AP.18.157; 7.AP.18.158;
7.AP.18.196; 7.AP.18.223; 7.AP.18.240; 7.AP.18.244; 7.AP.18.243; 7.AP.18.247; 7.AP.26.157;

TABLE 100-continued

7.AP.26.158; 7.AP.26.196; 7.AP.26.223; 7.AP.26.240; 7.AP.26.244; 7.AP.26.243; 7.AP.26.247;
7.AP.27.157; 7.AP.27.158; 7.AP.27.196; 7.AP.27.223; 7.AP.27.240; 7.AP.27.244; 7.AP.27.243;
7.AP.27.247; 7.AP.29.157; 7.AP.29.158; 7.AP.29.196; 7.AP.29.223; 7.AP.29.240; 7.AP.29.244;
7.AP.29.243; 7.AP.29.247; 7.AP.54.157; 7.AP.54.158; 7.AP.54.196; 7.AP.54.223; 7.AP.54.240;
7.AP.54.244; 7.AP.54.243; 7.AP.54.247; 7.AP.55.157; 7.AP.55.158; 7.AP.55.196; 7.AP.55.223;
7.AP.55.240; 7.AP.55.244; 7.AP.55.243; 7.AP.55.247; 7.AP.56.157; 7.AP.56.158; 7.AP.56.196;
7.AP.56.223; 7.AP.56.240; 7.AP.56.244; 7.AP.56.243; 7.AP.56.247; 7.AP.157.157;
7.AP.157.158; 7.AP.157.196; 7.AP.157.223; 7.AP.157.240; 7.AP.157.244; 7.AP.157.243;
7.AP.157.247; 7.AP.196.157; 7.AP.196.158; 7.AP.196.196; 7.AP.196.223; 7.AP.196.240;
7.AP.196.244; 7.AP.196.243; 7.AP.196.247; 7.AP.223.157; 7.AP.223.158; 7.AP.223.196;
7.AP.223.223; 7.AP.223.240; 7.AP.223.244; 7.AP.223.243; 7.AP.223.247; 7.AP.240.157;
7.AP.240.158; 7.AP.240.196; 7.AP.240.223; 7.AP.240.240; 7.AP.240.244; 7.AP.240.243;
7.AP.240.247; 7.AP.244.157; 7.AP.244.158; 7.AP.244.196; 7.AP.244.223; 7.AP.244.240;
7.AP.244.244; 7.AP.244.243; 7.AP.244.247; 7.AP.247.157; 7.AP.247.158; 7.AP.247.196;
7.AP.247.223; 7.AP.247.240; 7.AP.247.244; 7.AP.247.243; 7.AP.247.247;
Prodrugs of 7.AZ 7.AZ.4.157; 7.AZ.4.158; 7.AZ.4.196; 7.AZ.4.223; 7.AZ.4.240; 7.AZ.4.244; 7.AZ.4.243;
7.AZ.4.247; 7.AZ.5.157; 7.AZ.5.158; 7.AZ.5.196; 7.AZ.5.223; 7.AZ.5.240; 7.AZ.5.244;
7.AZ.5.243; 7.AZ.5.247; 7.AZ.7.157; 7.AZ.7.158; 7.AZ.7.196; 7.AZ.7.223; 7.AZ.7.240;
7.AZ.7.244; 7.AZ.7.243; 7.AZ.7.247; 7.AZ.15.157; 7.AZ.15.158; 7.AZ.15.196; 7.AZ.15.223;
7.AZ.15.240; 7.AZ.15.244; 7.AZ.15.243; 7.AZ.15.247; 7.AZ.16.157; 7.AZ.16.158;
7.AZ.16.196; 7.AZ.16.223; 7.AZ.16.240; 7.AZ.16.244; 7.AZ.16.243; 7.AZ.16.247;
7.AZ.18.157; 7.AZ.18.158; 7.AZ.18.196; 7.AZ.18.223; 7.AZ.18.240; 7.AZ.18.244;
7.AZ.18.243; 7.AZ.18.247; 7.AZ.26.157; 7.AZ.26.158; 7.AZ.26.196; 7.AZ.26.223;
7.AZ.26.240; 7.AZ.26.244; 7.AZ.26.243; 7.AZ.26.247; 7.AZ.27.157; 7.AZ.27.158;
7.AZ.27.196; 7.AZ.27.223; 7.AZ.27.240; 7.AZ.27.244; 7.AZ.27.243; 7.AZ.27.247;
7.AZ.29.157; 7.AZ.29.158; 7.AZ.29.196; 7.AZ.29.223; 7.AZ.29.240; 7.AZ.29.244;
7.AZ.29.243; 7.AZ.29.247; 7.AZ.54.157; 7.AZ.54.158; 7.AZ.54.196; 7.AZ.54.223;
7.AZ.54.240; 7.AZ.54.244; 7.AZ.54.243; 7.AZ.54.247; 7.AZ.55.157; 7.AZ.55.158;
7.AZ.55.196; 7.AZ.55.223; 7.AZ.55.240; 7.AZ.55.244; 7.AZ.55.243; 7.AZ.55.247;
7.AZ.56.157; 7.AZ.56.158; 7.AZ.56.196; 7.AZ.56.223; 7.AZ.56.240; 7.AZ.56.244;
7.AZ.56.243; 7.AZ.56.247; 7.AZ.157.157; 7.AZ.157.158; 7.AZ.157.196; 7.AZ.157.223;
7.AZ.157.240; 7.AZ.157.244; 7.AZ.157.243; 7.AZ.157.247; 7.AZ.196.157; 7.AZ.196.158;
7.AZ.196.196; 7.AZ.196.223; 7.AZ.196.240; 7.AZ.196.244; 7.AZ.196.243; 7.AZ.196.247;
7.AZ.223.157; 7.AZ.223.158; 7.AZ.223.196; 7.AZ.223.223; 7.AZ.223.240; 7.AZ.223.244;
7.AZ.223.243; 7.AZ.223.247; 7.AZ.240.157; 7.AZ.240.158; 7.AZ.240.196; 7.AZ.240.223;
7.AZ.240.240; 7.AZ.240.244; 7.AZ.240.243; 7.AZ.240.247; 7.AZ.244.157; 7.AZ.244.158;
7.AZ.244.196; 7.AZ.244.223; 7.AZ.244.240; 7.AZ.244.244; 7.AZ.244.243; 7.AZ.244.247;
7.AZ.247.157; 7.AZ.247.158; 7.AZ.247.196; 7.AZ.247.223; 7.AZ.247.240; 7.AZ.247.244;
7.AZ.247.243; 7.AZ.247.247;
Prodrugs of 7.BF 7.BF.4.157; 7.BF.4.158; 7.BF.4.196; 7.BF.4.223; 7.BF.4.240; 7.BF.4.244; 7.BF.4.243;
7.BF.4.247; 7.BF.5.157; 7.BF.5.158; 7.BF.5.196; 7.BF.5.223; 7.BF.5.240; 7.BF.5.244;
7.BF.5.243; 7.BF.5.247; 7.BF.7.157; 7.BF.7.158; 7.BF.7.196; 7.BF.7.223; 7.BF.7.240;
7.BF.7.244; 7.BF.7.243; 7.BF.7.247; 7.BF.15.157; 7.BF.15.158; 7.BF.15.196; 7.BF.15.223;
7.BF.15.240; 7.BF.15.244; 7.BF.15.243; 7.BF.15.247; 7.BF.16.157; 7.BF.16.158; 7.BF.16.196;
7.BF.16.223; 7.BF.16.240; 7.BF.16.244; 7.BF.16.243; 7.BF.16.247; 7.BF.18.157; 7.BF.18.158;
7.BF.18.196; 7.BF.18.223; 7.BF.18.240; 7.BF.18.244; 7.BF.18.243; 7.BF.18.247; 7.BF.26.157;
7.BF.26.158; 7.BF.26.196; 7.BF.26.223; 7.BF.26.240; 7.BF.26.244; 7.BF.26.243; 7.BF.26.247;
7.BF.27.157; 7.BF.27.158; 7.BF.27.196; 7.BF.27.223; 7.BF.27.240; 7.BF.27.244; 7.BF.27.243;
7.BF.27.247; 7.BF.29.157; 7.BF.29.158; 7.BF.29.196; 7.BF.29.223; 7.BF.29.240; 7.BF.29.244;
7.BF.29.243; 7.BF.29.247; 7.BF.54.157; 7.BF.54.158; 7.BF.54.196; 7.BF.54.223; 7.BF.54.240;
7.BF.54.244; 7.BF.54.243; 7.BF.54.247; 7.BF.55.157; 7.BF.55.158; 7.BF.55.196; 7.BF.55.223;
7.BF.55.240; 7.BF.55.244; 7.BF.55.243; 7.BF.55.247; 7.BF.56.157; 7.BF.56.158; 7.BF.56.196;
7.BF.56.223; 7.BF.56.240; 7.BF.56.244; 7.BF.56.243; 7.BF.56.247; 7.BF.157.157;
7.BF.157.158; 7.BF.157.196; 7.BF.157.223; 7.BF.157.240; 7.BF.157.244; 7.BF.157.243;
7.BF.157.247; 7.BF.196.157; 7.BF.196.158; 7.BF.196.196; 7.BF.196.223; 7.BF.196.240;
7.BF.196.244; 7.BF.196.243; 7.BF.196.247; 7.BF.223.157; 7.BF.223.158; 7.BF.223.196;
7.BF.223.223; 7.BF.223.240; 7.BF.223.244; 7.BF.223.243; 7.BF.223.247; 7.BF.240.157;
7.BF.240.158; 7.BF.240.196; 7.BF.240.223; 7.BF.240.240; 7.BF.240.244; 7.BF.240.243;
7.BF.240.247; 7.BF.244.157; 7.BF.244.158; 7.BF.244.196; 7.BF.244.223; 7.BF.244.240;
7.BF.244.244; 7.BF.244.243; 7.BF.244.247; 7.BF.247.157; 7.BF.247.158; 7.BF.247.196;
7.BF.247.223; 7.BF.247.240; 7.BF.247.244; 7.BF.247.243; 7.BF.247.247;
Prodrugs of 7.CI 7.CI.4.157; 7.CI.4.158; 7.CI.4.196; 7.CI.4.223; 7.CI.4.240; 7.CI.4.244; 7.CI.4.243;
7.CI.4.247; 7.CI.5.157; 7.CI.5.158; 7.CI.5.196; 7.CI.5.223; 7.CI.5.240; 7.CI.5.244; 7.CI.5.243;
7.CI.5.247; 7.CI.7.157; 7.CI.7.158; 7.CI.7.196; 7.CI.7.223; 7.CI.7.240; 7.CI.7.244; 7.CI.7.243;
7.CI.7.247; 7.CI.15.157; 7.CI.15.158; 7.CI.15.196; 7.CI.15.223; 7.CI.15.240; 7.CI.15.244;
7.CI.15.243; 7.CI.15.247; 7.CI.16.157; 7.CI.16.158; 7.CI.16.196; 7.CI.16.223; 7.CI.16.240;
7.CI.16.244; 7.CI.16.243; 7.CI.16.247; 7.CI.18.157; 7.CI.18.158; 7.CI.18.196; 7.CI.18.223;
7.CI.18.240; 7.CI.18.244; 7.CI.18.243; 7.CI.18.247; 7.CI.26.157; 7.CI.26.158; 7.CI.26.196;
7.CI.26.223; 7.CI.26.240; 7.CI.26.244; 7.CI.26.243; 7.CI.26.247; 7.CI.27.157; 7.CI.27.158;
7.CI.27.196; 7.CI.27.223; 7.CI.27.240; 7.CI.27.244; 7.CI.27.243; 7.CI.27.247; 7.CI.29.157;
7.CI.29.158; 7.CI.29.196; 7.CI.29.223; 7.CI.29.240; 7.CI.29.244; 7.CI.29.243; 7.CI.29.247;
7.CI.54.157; 7.CI.54.158; 7.CI.54.196; 7.CI.54.223; 7.CI.54.240; 7.CI.54.244; 7.CI.54.243;
7.CI.54.247; 7.CI.55.157; 7.CI.55.158; 7.CI.55.196; 7.CI.55.223; 7.CI.55.240; 7.CI.55.244;

TABLE 100-continued

7.CI.55.243; 7.CI.55.247; 7.CI.56.157; 7.CI.56.158; 7.CI.56.196; 7.CI.56.223; 7.CI.56.240;
7.CI.56.244; 7.CI.56.243; 7.CI.56.247; 7.CI.157.157; 7.CI.157.158; 7.CI.157.196; 7.CI.157.223;
7.CI.157.240; 7.CI.157.244; 7.CI.157.243; 7.CI.157.247; 7.CI.196.157; 7.CI.196.158;
7.CI.196.196; 7.CI.196.223; 7.CI.196.240; 7.CI.196.244; 7.CI.196.243; 7.CI.196.247;
7.CI.223.157; 7.CI.223.158; 7.CI.223.196; 7.CI.223.223; 7.CI.223.240; 7.CI.223.244;
7.CI.223.243; 7.CI.223.247; 7.CI.240.157; 7.CI.240.158; 7.CI.240.196; 7.CI.240.223;
7.CI.240.240; 7.CI.240.244; 7.CI.240.243; 7.CI.240.247; 7.CI.244.157; 7.CI.244.158;
7.CI.244.196; 7.CI.244.223; 7.CI.244.240; 7.CI.244.244; 7.CI.244.243; 7.CI.244.247;
7.CI.247.157; 7.CI.247.158; 7.CI.247.196; 7.CI.247.223; 7.CI.247.240; 7.CI.247.244;
7.CI.247.243; 7.CI.247.247;
Prodrugs of 7.CO 7.CO.4.157; 7.CO.4.158; 7.CO.4.196; 7.CO.4.223; 7.CO.4.240; 7.CO.4.244; 7.CO.4.243;
7.CO.4.247; 7.CO.5.157; 7.CO.5.158; 7.CO.5.196; 7.CO.5.223; 7.CO.5.240; 7.CO.5.244;
7.CO.5.243; 7.CO.5.247; 7.CO.7.157; 7.CO.7.158; 7.CO.7.196; 7.CO.7.223; 7.CO.7.240;
7.CO.7.244; 7.CO.7.243; 7.CO.7.247; 7.CO.15.157; 7.CO.15.158; 7.CO.15.196; 7.CO.15.223;
7.CO.15.240; 7.CO.15.244; 7.CO.15.243; 7.CO.15.247; 7.CO.16.157; 7.CO.16.158;
7.CO.16.196; 7.CO.16.223; 7.CO.16.240; 7.CO.16.244; 7.CO.16.243; 7.CO.16.247;
7.CO.18.157; 7.CO.18.158; 7.CO.18.196; 7.CO.18.223; 7.CO.18.240; 7.CO.18.244;
7.CO.18.243; 7.CO.18.247; 7.CO.26.157; 7.CO.26.158; 7.CO.26.196; 7.CO.26.223;
7.CO.26.240; 7.CO.26.244; 7.CO.26.243; 7.CO.26.247; 7.CO.27.157; 7.CO.27.158;
7.CO.27.196; 7.CO.27.223; 7.CO.27.240; 7.CO.27.244; 7.CO.27.243; 7.CO.27.247;
7.CO.29.157; 7.CO.29.158; 7.CO.29.196; 7.CO.29.223; 7.CO.29.240; 7.CO.29.244;
7.CO.29.243; 7.CO.29.247; 7.CO.54.157; 7.CO.54.158; 7.CO.54.196; 7.CO.54.223;
7.CO.54.240; 7.CO.54.244; 7.CO.54.243; 7.CO.54.247; 7.CO.55.157; 7.CO.55.158;
7.CO.55.196; 7.CO.55.223; 7.CO.55.240; 7.CO.55.244; 7.CO.55.243; 7.CO.55.247;
7.CO.56.157; 7.CO.56.158; 7.CO.56.196; 7.CO.56.223; 7.CO.56.240; 7.CO.56.244;
7.CO.56.243; 7.CO.56.247; 7.CO.157.157; 7.CO.157.158; 7.CO.157.196; 7.CO.157.223;
7.CO.157.240; 7.CO.157.244; 7.CO.157.243; 7.CO.157.247; 7.CO.196.157; 7.CO.196.158;
7.CO.196.196; 7.CO.196.223; 7.CO.196.240; 7.CO.196.244; 7.CO.196.243; 7.CO.196.247;
7.CO.223.157; 7.CO.223.158; 7.CO.223.196; 7.CO.223.223; 7.CO.223.240; 7.CO.223.244;
7.CO.223.243; 7.CO.223.247; 7.CO.240.157; 7.CO.240.158; 7.CO.240.196; 7.CO.240.223;
7.CO.240.240; 7.CO.240.244; 7.CO.240.243; 7.CO.240.247; 7.CO.244.157; 7.CO.244.158;
7.CO.244.196; 7.CO.244.223; 7.CO.244.240; 7.CO.244.244; 7.CO.244.243; 7.CO.244.247;
7.CO.4.157; 7.CO.4.158; 7.CO.4.196; 7.CO.4.223; 7.CO.4.240; 7.CO.4.244; 7.CO.4.243;
7.CO.4.247;
Prodrugs of 8.AH 8.AH.4.157; 8.AH.4.158; 8.AH.4.196; 8.AH.4.223; 8.AH.4.240; 8.AH.4.244; 8.AH.4.243;
8.AH.4.247; 8.AH.5.157; 8.AH.5.158; 8.AH.5.196; 8.AH.5.223; 8.AH.5.240; 8.AH.5.244;
8.AH.5.243; 8.AH.5.247; 8.AH.7.157; 8.AH.7.158; 8.AH.7.196; 8.AH.7.223; 8.AH.7.240;
8.AH.7.244; 8.AH.7.243; 8.AH.7.247; 8.AH.15.157; 8.AH.15.158; 8.AH.15.196; 8.AH.15.223;
8.AH.15.240; 8.AH.15.244; 8.AH.15.243; 8.AH.15.247; 8.AH.16.157; 8.AH.16.158;
8.AH.16.196; 8.AH.16.223; 8.AH.16.240; 8.AH.16.244; 8.AH.16.243; 8.AH.16.247;
8.AH.18.157; 8.AH.18.158; 8.AH.18.196; 8.AH.18.223; 8.AH.18.240; 8.AH.18.244;
8.AH.18.243; 8.AH.18.247; 8.AH.26.157; 8.AH.26.158; 8.AH.26.196; 8.AH.26.223;
8.AH.26.240; 8.AH.26.244; 8.AH.26.243; 8.AH.26.247; 8.AH.27.157; 8.AH.27.158;
8.AH.27.196; 8.AH.27.223; 8.AH.27.240; 8.AH.27.244; 8.AH.27.243; 8.AH.27.247;
8.AH.29.157; 8.AH.29.158; 8.AH.29.196; 8.AH.29.223; 8.AH.29.240; 8.AH.29.244;
8.AH.29.243; 8.AH.29.247; 8.AH.54.157; 8.AH.54.158; 8.AH.54.196; 8.AH.54.223;
8.AH.54.240; 8.AH.54.244; 8.AH.54.243; 8.AH.54.247; 8.AH.55.157; 8.AH.55.158;
8.AH.55.196; 8.AH.55.223; 8.AH.55.240; 8.AH.55.244; 8.AH.55.243; 8.AH.55.247;
8.AH.56.157; 8.AH.56.158; 8.AH.56.196; 8.AH.56.223; 8.AH.56.240; 8.AH.56.244;
8.AH.56.243; 8.AH.56.247; 8.AH.157.157; 8.AH.157.158; 8.AH.157.196; 8.AH.157.223;
8.AH.157.240; 8.AH.157.244; 8.AH.157.243; 8.AH.157.247; 8.AH.196.157; 8.AH.196.158;
8.AH.196.196; 8.AH.196.223; 8.AH.196.240; 8.AH.196.244; 8.AH.196.243; 8.AH.196.247;
8.AH.223.157; 8.AH.223.158; 8.AH.223.196; 8.AH.223.223; 8.AH.223.240; 8.AH.223.244;
8.AH.223.243; 8.AH.223.247; 8.AH.240.157; 8.AH.240.158; 8.AH.240.196; 8.AH.240.223;
8.AH.240.240; 8.AH.240.244; 8.AH.240.243; 8.AH.240.247; 8.AH.244.157; 8.AH.244.158;
8.AH.244.196; 8.AH.244.223; 8.AH.244.240; 8.AH.244.244; 8.AH.244.243; 8.AH.244.247;
8.AH.247.157; 8.AH.247.158; 8.AH.247.196; 8.AH.247.223; 8.AH.247.240; 8.AH.247.244;
8.AH.247.243; 8.AH.247.247;
Prodrugs of 8.AJ 8.AJ.4.157; 8.AJ.4.158; 8.AJ.4.196; 8.AJ.4.223; 8.AJ.4.240; 8.AJ.4.244; 8.AJ.4.243;
8.AJ.4.247; 8.AJ.5.157; 8.AJ.5.158; 8.AJ.5.196; 8.AJ.5.223; 8.AJ.5.240; 8.AJ.5.244; 8.AJ.5.243;
8.AJ.5.247; 8.AJ.7.157; 8.AJ.7.158; 8.AJ.7.196; 8.AJ.7.223; 8.AJ.7.240; 8.AJ.7.244; 8.AJ.7.243;
8.AJ.7.247; 8.AJ.15.157; 8.AJ.15.158; 8.AJ.15.196; 8.AJ.15.223; 8.AJ.15.240; 8.AJ.15.244;
8.AJ.15.243; 8.AJ.15.247; 8.AJ.16.157; 8.AJ.16.158; 8.AJ.16.196; 8.AJ.16.223; 8.AJ.16.240;
8.AJ.16.244; 8.AJ.16.243; 8.AJ.16.247; 8.AJ.18.157; 8.AJ.18.158; 8.AJ.18.196; 8.AJ.18.223;
8.AJ.18.240; 8.AJ.18.244; 8.AJ.18.243; 8.AJ.18.247; 8.AJ.26.157; 8.AJ.26.158; 8.AJ.26.196;
8.AJ.26.223; 8.AJ.26.240; 8.AJ.26.244; 8.AJ.26.243; 8.AJ.26.247; 8.AJ.27.157; 8.AJ.27.158;
8.AJ.27.196; 8.AJ.27.223; 8.AJ.27.240; 8.AJ.27.244; 8.AJ.27.243; 8.AJ.27.247; 8.AJ.29.157;
8.AJ.29.158; 8.AJ.29.196; 8.AJ.29.223; 8.AJ.29.240; 8.AJ.29.244; 8.AJ.29.243; 8.AJ.29.247;
8.AJ.54.157; 8.AJ.54.158; 8.AJ.54.196; 8.AJ.54.223; 8.AJ.54.240; 8.AJ.54.244; 8.AJ.54.243;
8.AJ.54.247; 8.AJ.55.157; 8.AJ.55.158; 8.AJ.55.196; 8.AJ.55.223; 8.AJ.55.240; 8.AJ.55.244;
8.AJ.55.243; 8.AJ.55.247; 8.AJ.56.157; 8.AJ.56.158; 8.AJ.56.196; 8.AJ.56.223; 8.AJ.56.240;
8.AJ.56.244; 8.AJ.56.243; 8.AJ.56.247; 8.AJ.157.157; 8.AJ.157.158; 8.AJ.157.196;
8.AJ.157.223; 8.AJ.157.240; 8.AJ.157.244; 8.AJ.157.243; 8.AJ.157.247; 8.AJ.196.157;

TABLE 100-continued

8.AJ.196.158; 8.AJ.196.196; 8.AJ.196.223; 8.AJ.196.240; 8.AJ.196.244; 8.AJ.196.243; 8.AJ.196.247; 8.AJ.223.157; 8.AJ.223.158; 8.AJ.223.196; 8.AJ.223.223; 8.AJ.223.240; 8.AJ.223.244; 8.AJ.223.243; 8.AJ.223.247; 8.AJ.240.157; 8.AJ.240.158; 8.AJ.240.196; 8.AJ.240.223; 8.AJ.240.240; 8.AJ.240.244; 8.AJ.240.243; 8.AJ.240.247; 8.AJ.244.157; 8.AJ.244.158; 8.AJ.244.196; 8.AJ.244.223; 8.AJ.244.240; 8.AJ.244.244; 8.AJ.244.243; 8.AJ.244.247; 8.AJ.247.157; 8.AJ.247.158; 8.AJ.247.196; 8.AJ.247.223; 8.AJ.247.240; 8.AJ.247.244; 8.AJ.247.243; 8.AJ.247.247;

Prodrugs of 8.AN

8.AN.4.157; 8.AN.4.158; 8.AN.4.196; 8.AN.4.223; 8.AN.4.240; 8.AN.4.244; 8.AN.4.243; 8.AN.4.247; 8.AN.5.157; 8.AN.5.158; 8.AN.5.196; 8.AN.5.223; 8.AN.5.240; 8.AN.5.244; 8.AN.5.243; 8.AN.5.247; 8.AN.7.157; 8.AN.7.158; 8.AN.7.196; 8.AN.7.223; 8.AN.7.240; 8.AN.7.244; 8.AN.7.243; 8.AN.7.247; 8.AN.15.157; 8.AN.15.158; 8.AN.15.196; 8.AN.15.223; 8.AN.15.240; 8.AN.15.244; 8.AN.15.243; 8.AN.15.247; 8.AN.16.157; 8.AN.16.158; 8.AN.16.196; 8.AN.16.223; 8.AN.16.240; 8.AN.16.244; 8.AN.16.243; 8.AN.16.247; 8.AN.18.157; 8.AN.18.158; 8.AN.18.196; 8.AN.18.223; 8.AN.18.240; 8.AN.18.244; 8.AN.18.243; 8.AN.18.247; 8.AN.26.157; 8.AN.26.158; 8.AN.26.196; 8.AN.26.223; 8.AN.26.240; 8.AN.26.244; 8.AN.26.243; 8.AN.26.247; 8.AN.27.157; 8.AN.27.158; 8.AN.27.196; 8.AN.27.223; 8.AN.27.240; 8.AN.27.244; 8.AN.27.243; 8.AN.27.247; 8.AN.29.157; 8.AN.29.158; 8.AN.29.196; 8.AN.29.223; 8.AN.29.240; 8.AN.29.244; 8.AN.29.243; 8.AN.29.247; 8.AN.54.157; 8.AN.54.158; 8.AN.54.196; 8.AN.54.223; 8.AN.54.240; 8.AN.54.244; 8.AN.54.243; 8.AN.54.247; 8.AN.55.157; 8.AN.55.158; 8.AN.55.196; 8.AN.55.223; 8.AN.55.240; 8.AN.55.244; 8.AN.55.243; 8.AN.55.247; 8.AN.56.157; 8.AN.56.158; 8.AN.56.196; 8.AN.56.223; 8.AN.56.240; 8.AN.56.244; 8.AN.56.243; 8.AN.56.247; 8.AN.157.157; 8.AN.157.158; 8.AN.157.196; 8.AN.157.223; 8.AN.157.240; 8.AN.157.244; 8.AN.157.243; 8.AN.157.247; 8.AN.196.157; 8.AN.196.158; 8.AN.196.196; 8.AN.196.223; 8.AN.196.240; 8.AN.196.244; 8.AN.196.243; 8.AN.196.247; 8.AN.223.157; 8.AN.223.158; 8.AN.223.196; 8.AN.223.223; 8.AN.223.240; 8.AN.223.244; 8.AN.223.243; 8.AN.223.247; 8.AN.240.157; 8.AN.240.158; 8.AN.240.196; 8.AN.240.223; 8.AN.240.240; 8.AN.240.244; 8.AN.240.243; 8.AN.240.247; 8.AN.244.157; 8.AN.244.158; 8.AN.244.196; 8.AN.244.223; 8.AN.244.240; 8.AN.244.244; 8.AN.244.243; 8.AN.244.247; 8.AN.247.157; 8.AN.247.158; 8.AN.247.196; 8.AN.247.223; 8.AN.247.240; 8.AN.247.244; 8.AN.247.243; 8.AN.247.247;

Prodrugs of 8.AP

8.AP.4.157; 8.AP.4.158; 8.AP.4.196; 8.AP.4.223; 8.AP.4.240; 8.AP.4.244; 8.AP.4.243; 8.AP.4.247; 8.AP.5.157; 8.AP.5.158; 8.AP.5.196; 8.AP.5.223; 8.AP.5.240; 8.AP.5.244; 8.AP.5.243; 8.AP.5.247; 8.AP.7.157; 8.AP.7.158; 8.AP.7.196; 8.AP.7.223; 8.AP.7.240; 8.AP.7.244; 8.AP.7.243; 8.AP.7.247; 8.AP.15.157; 8.AP.15.158; 8.AP.15.196; 8.AP.15.223; 8.AP.15.240; 8.AP.15.244; 8.AP.15.243; 8.AP.15.247; 8.AP.16.157; 8.AP.16.158; 8.AP.16.196; 8.AP.16.223; 8.AP.16.240; 8.AP.16.244; 8.AP.16.243; 8.AP.16.247; 8.AP.18.157; 8.AP.18.158; 8.AP.18.196; 8.AP.18.223; 8.AP.18.240; 8.AP.18.244; 8.AP.18.243; 8.AP.18.247; 8.AP.26.157; 8.AP.26.158; 8.AP.26.196; 8.AP.26.223; 8.AP.26.240; 8.AP.26.244; 8.AP.26.243; 8.AP.26.247; 8.AP.27.157; 8.AP.27.158; 8.AP.27.196; 8.AP.27.223; 8.AP.27.240; 8.AP.27.244; 8.AP.27.243; 8.AP.27.247; 8.AP.29.157; 8.AP.29.158; 8.AP.29.196; 8.AP.29.223; 8.AP.29.240; 8.AP.29.244; 8.AP.29.243; 8.AP.29.247; 8.AP.54.157; 8.AP.54.158; 8.AP.54.196; 8.AP.54.223; 8.AP.54.240; 8.AP.54.244; 8.AP.54.243; 8.AP.54.247; 8.AP.55.157; 8.AP.55.158; 8.AP.55.196; 8.AP.55.223; 8.AP.55.240; 8.AP.55.244; 8.AP.55.243; 8.AP.55.247; 8.AP.56.157; 8.AP.56.158; 8.AP.56.196; 8.AP.56.223; 8.AP.56.240; 8.AP.56.244; 8.AP.56.243; 8.AP.56.247; 8.AP.157.157; 8.AP.157.158; 8.AP.157.196; 8.AP.157.223; 8.AP.157.240; 8.AP.157.244; 8.AP.157.243; 8.AP.157.247; 8.AP.196.157; 8.AP.196.158; 8.AP.196.196; 8.AP.196.223; 8.AP.196.240; 8.AP.196.244; 8.AP.196.243; 8.AP.196.247; 8.AP.223.157; 8.AP.223.158; 8.AP.223.196; 8.AP.223.223; 8.AP.223.240; 8.AP.223.244; 8.AP.223.243; 8.AP.223.247; 8.AP.240.157; 8.AP.240.158; 8.AP.240.196; 8.AP.240.223; 8.AP.240.240; 8.AP.240.244; 8.AP.240.243; 8.AP.240.247; 8.AP.244.157; 8.AP.244.158; 8.AP.244.196; 8.AP.244.223; 8.AP.244.240; 8.AP.244.244; 8.AP.244.243; 8.AP.244.247; 8.AP.247.157; 8.AP.247.158; 8.AP.247.196; 8.AP.247.223; 8.AP.247.240; 8.AP.247.244; 8.AP.247.243; 8.AP.247.247;

Prodrugs of 8.AZ

8.AZ.4.157; 8.AZ.4.158; 8.AZ.4.196; 8.AZ.4.223; 8.AZ.4.240; 8.AZ.4.244; 8.AZ.4.243; 8.AZ.4.247; 8.AZ.5.157; 8.AZ.5.158; 8.AZ.5.196; 8.AZ.5.223; 8.AZ.5.240; 8.AZ.5.244; 8.AZ.5.243; 8.AZ.5.247; 8.AZ.7.157; 8.AZ.7.158; 8.AZ.7.196; 8.AZ.7.223; 8.AZ.7.240; 8.AZ.7.244; 8.AZ.7.243; 8.AZ.7.247; 8.AZ.15.157; 8.AZ.15.158; 8.AZ.15.196; 8.AZ.15.223; 8.AZ.15.240; 8.AZ.15.244; 8.AZ.15.243; 8.AZ.15.247; 8.AZ.16.157; 8.AZ.16.158; 8.AZ.16.196; 8.AZ.16.223; 8.AZ.16.240; 8.AZ.16.244; 8.AZ.16.243; 8.AZ.16.247; 8.AZ.18.157; 8.AZ.18.158; 8.AZ.18.196; 8.AZ.18.223; 8.AZ.18.240; 8.AZ.18.244; 8.AZ.18.243; 8.AZ.18.247; 8.AZ.26.157; 8.AZ.26.158; 8.AZ.26.196; 8.AZ.26.223; 8.AZ.26.240; 8.AZ.26.244; 8.AZ.26.243; 8.AZ.26.247; 8.AZ.27.157; 8.AZ.27.158; 8.AZ.27.196; 8.AZ.27.223; 8.AZ.27.240; 8.AZ.27.244; 8.AZ.27.243; 8.AZ.27.247; 8.AZ.29.157; 8.AZ.29.158; 8.AZ.29.196; 8.AZ.29.223; 8.AZ.29.240; 8.AZ.29.244; 8.AZ.29.243; 8.AZ.29.247; 8.AZ.54.157; 8.AZ.54.158; 8.AZ.54.196; 8.AZ.54.223; 8.AZ.54.240; 8.AZ.54.244; 8.AZ.54.243; 8.AZ.54.247; 8.AZ.55.157; 8.AZ.55.158; 8.AZ.55.196; 8.AZ.55.223; 8.AZ.55.240; 8.AZ.55.244; 8.AZ.55.243; 8.AZ.55.247; 8.AZ.56.157; 8.AZ.56.158; 8.AZ.56.196; 8.AZ.56.223; 8.AZ.56.240; 8.AZ.56.244; 8.AZ.56.243; 8.AZ.56.247; 8.AZ.157.157; 8.AZ.157.158; 8.AZ.157.196; 8.AZ.157.223; 8.AZ.157.240; 8.AZ.157.244; 8.AZ.157.243; 8.AZ.157.247; 8.AZ.196.157; 8.AZ.196.158; 8.AZ.196.196; 8.AZ.196.223; 8.AZ.196.240; 8.AZ.196.244; 8.AZ.196.243; 8.AZ.196.247; 8.AZ.223.157; 8.AZ.223.158; 8.AZ.223.196; 8.AZ.223.223; 8.AZ.223.240; 8.AZ.223.244; 8.AZ.223.243; 8.AZ.223.247; 8.AZ.240.157; 8.AZ.240.158; 8.AZ.240.196; 8.AZ.240.223;

TABLE 100-continued

8.AZ.240.240; 8.AZ.240.244; 8.AZ.240.243; 8.AZ.240.247; 8.AZ.244.157; 8.AZ.244.158;
8.AZ.244.196; 8.AZ.244.223; 8.AZ.244.240; 8.AZ.244.244; 8.AZ.244.243; 8.AZ.244.247;
8.AZ.247.157; 8.AZ.247.158; 8.AZ.247.196; 8.AZ.247.223; 8.AZ.247.240; 8.AZ.247.244;
8.AZ.247.243; 8.AZ.247.247;

Prodrugs of 8.BF

8.BF.4.157; 8.BF.4.158; 8.BF.4.196; 8.BF.4.223; 8.BF.4.240; 8.BF.4.244; 8.BF.4.243;
8.BF.4.247; 8.BF.5.157; 8.BF.5.158; 8.BF.5.196; 8.BF.5.223; 8.BF.5.240; 8.BF.5.244;
8.BF.5.243; 8.BF.5.247; 8.BF.7.157; 8.BF.7.158; 8.BF.7.196; 8.BF.7.223; 8.BF.7.240;
8.BF.7.244; 8.BF.7.243; 8.BF.7.247; 8.BF.15.157; 8.BF.15.158; 8.BF.15.196; 8.BF.15.223;
8.BF.15.240; 8.BF.15.244; 8.BF.15.243; 8.BF.15.247; 8.BF.16.157; 8.BF.16.158; 8.BF.16.196;
8.BF.16.223; 8.BF.16.240; 8.BF.16.244; 8.BF.16.243; 8.BF.16.247; 8.BF.18.157; 8.BF.18.158;
8.BF.18.196; 8.BF.18.223; 8.BF.18.240; 8.BF.18.244; 8.BF.18.243; 8.BF.18.247; 8.BF.26.157;
8.BF.26.158; 8.BF.26.196; 8.BF.26.223; 8.BF.26.240; 8.BF.26.244; 8.BF.26.243; 8.BF.26.247;
8.BF.27.157; 8.BF.27.158; 8.BF.27.196; 8.BF.27.223; 8.BF.27.240; 8.BF.27.244; 8.BF.27.243;
8.BF.27.247; 8.BF.29.157; 8.BF.29.158; 8.BF.29.196; 8.BF.29.223; 8.BF.29.240; 8.BF.29.244;
8.BF.29.243; 8.BF.29.247; 8.BF.54.157; 8.BF.54.158; 8.BF.54.196; 8.BF.54.223; 8.BF.54.240;
8.BF.54.244; 8.BF.54.243; 8.BF.54.247; 8.BF.55.157; 8.BF.55.158; 8.BF.55.196; 8.BF.55.223;
8.BF.55.240; 8.BF.55.244; 8.BF.55.243; 8.BF.55.247; 8.BF.56.157; 8.BF.56.158; 8.BF.56.196;
8.BF.56.223; 8.BF.56.240; 8.BF.56.244; 8.BF.56.243; 8.BF.56.247; 8.BF.157.157;
8.BF.157.158; 8.BF.157.196; 8.BF.157.223; 8.BF.157.240; 8.BF.157.244; 8.BF.157.243;
8.BF.157.247; 8.BF.196.157; 8.BF.196.158; 8.BF.196.196; 8.BF.196.223; 8.BF.196.240;
8.BF.196.244; 8.BF.196.243; 8.BF.196.247; 8.BF.223.157; 8.BF.223.158; 8.BF.223.196;
8.BF.223.223; 8.BF.223.240; 8.BF.223.244; 8.BF.223.243; 8.BF.223.247; 8.BF.240.157;
8.BF.240.158; 8.BF.240.196; 8.BF.240.223; 8.BF.240.240; 8.BF.240.244; 8.BF.240.243;
8.BF.240.247; 8.BF.244.157; 8.BF.244.158; 8.BF.244.196; 8.BF.244.223; 8.BF.244.240;
8.BF.244.244; 8.BF.244.243; 8.BF.244.247; 8.BF.247.157; 8.BF.247.158; 8.BF.247.196;
8.BF.247.223; 8.BF.247.240; 8.BF.247.244; 8.BF.247.243; 8.BF.247.247;

Prodrugs of 8.CI

8.CI.4.157; 8.CI.4.158; 8.CI.4.196; 8.CI.4.223; 8.CI.4.240; 8.CI.4.244; 8.CI.4.243;
8.CI.4.247; 8.CI.5.157; 8.CI.5.158; 8.CI.5.196; 8.CI.5.223; 8.CI.5.240; 8.CI.5.244; 8.CI.5.243;
8.CI.5.247; 8.CI.7.157; 8.CI.7.158; 8.CI.7.196; 8.CI.7.223; 8.CI.7.240; 8.CI.7.244; 8.CI.7.243;
8.CI.7.247; 8.CI.15.157; 8.CI.15.158; 8.CI.15.196; 8.CI.15.223; 8.CI.15.240; 8.CI.15.244;
8.CI.15.243; 8.CI.15.247; 8.CI.16.157; 8.CI.16.158; 8.CI.16.196; 8.CI.16.223; 8.CI.16.240;
8.CI.16.244; 8.CI.16.243; 8.CI.16.247; 8.CI.18.157; 8.CI.18.158; 8.CI.18.196; 8.CI.18.223;
8.CI.18.240; 8.CI.18.244; 8.CI.18.243; 8.CI.18.247; 8.CI.26.157; 8.CI.26.158; 8.CI.26.196;
8.CI.26.223; 8.CI.26.240; 8.CI.26.244; 8.CI.26.243; 8.CI.26.247; 8.CI.27.157; 8.CI.27.158;
8.CI.27.196; 8.CI.27.223; 8.CI.27.240; 8.CI.27.244; 8.CI.27.243; 8.CI.27.247; 8.CI.29.157;
8.CI.29.158; 8.CI.29.196; 8.CI.29.223; 8.CI.29.240; 8.CI.29.244; 8.CI.29.243; 8.CI.29.247;
8.CI.54.157; 8.CI.54.158; 8.CI.54.196; 8.CI.54.223; 8.CI.54.240; 8.CI.54.244; 8.CI.54.243;
8.CI.54.247; 8.CI.55.157; 8.CI.55.158; 8.CI.55.196; 8.CI.55.223; 8.CI.55.240; 8.CI.55.244;
8.CI.55.243; 8.CI.55.247; 8.CI.56.157; 8.CI.56.158; 8.CI.56.196; 8.CI.56.223; 8.CI.56.240;
8.CI.56.244; 8.CI.56.243; 8.CI.56.247; 8.CI.157.157; 8.CI.157.158; 8.CI.157.196; 8.CI.157.223;
8.CI.157.240; 8.CI.157.244; 8.CI.157.243; 8.CI.157.247; 8.CI.196.157; 8.CI.196.158;
8.CI.196.196; 8.CI.196.223; 8.CI.196.240; 8.CI.196.244; 8.CI.196.243; 8.CI.196.247;
8.CI.223.157; 8.CI.223.158; 8.CI.223.196; 8.CI.223.223; 8.CI.223.240; 8.CI.223.244;
8.CI.223.243; 8.CI.223.247; 8.CI.240.157; 8.CI.240.158; 8.CI.240.196; 8.CI.240.223;
8.CI.240.240; 8.CI.240.244; 8.CI.240.243; 8.CI.240.247; 8.CI.244.157; 8.CI.244.158;
8.CI.244.196; 8.CI.244.223; 8.CI.244.240; 8.CI.244.244; 8.CI.244.243; 8.CI.244.247;
8.CI.247.157; 8.CI.247.158; 8.CI.247.196; 8.CI.247.223; 8.CI.247.240; 8.CI.247.244;
8.CI.247.243; 8.CI.247.247;

Prodrugs of 8.CO

8.CO.4.157; 8.CO.4.158; 8.CO.4.196; 8.CO.4.223; 8.CO.4.240; 8.CO.4.244; 8.CO.4.243;
8.CO.4.247; 8.CO.5.157; 8.CO.5.158; 8.CO.5.196; 8.CO.5.223; 8.CO.5.240; 8.CO.5.244;
8.CO.5.243; 8.CO.5.247; 8.CO.7.157; 8.CO.7.158; 8.CO.7.196; 8.CO.7.223; 8.CO.7.240;
8.CO.7.244; 8.CO.7.243; 8.CO.7.247; 8.CO.15.157; 8.CO.15.158; 8.CO.15.196; 8.CO.15.223;
8.CO.15.240; 8.CO.15.244; 8.CO.15.243; 8.CO.15.247; 8.CO.16.157; 8.CO.16.158;
8.CO.16.196; 8.CO.16.223; 8.CO.16.240; 8.CO.16.244; 8.CO.16.243; 8.CO.16.247;
8.CO.18.157; 8.CO.18.158; 8.CO.18.196; 8.CO.18.223; 8.CO.18.240; 8.CO.18.244;
8.CO.18.243; 8.CO.18.247; 8.CO.26.157; 8.CO.26.158; 8.CO.26.196; 8.CO.26.223;
8.CO.26.240; 8.CO.26.244; 8.CO.26.243; 8.CO.26.247; 8.CO.27.157; 8.CO.27.158;
8.CO.27.196; 8.CO.27.223; 8.CO.27.240; 8.CO.27.244; 8.CO.27.243; 8.CO.27.247;
8.CO.29.157; 8.CO.29.158; 8.CO.29.196; 8.CO.29.223; 8.CO.29.240; 8.CO.29.244;
8.CO.29.243; 8.CO.29.247; 8.CO.54.157; 8.CO.54.158; 8.CO.54.196; 8.CO.54.223;
8.CO.54.240; 8.CO.54.244; 8.CO.54.243; 8.CO.54.247; 8.CO.55.157; 8.CO.55.158;
8.CO.55.196; 8.CO.55.223; 8.CO.55.240; 8.CO.55.244; 8.CO.55.243; 8.CO.55.247;
8.CO.56.157; 8.CO.56.158; 8.CO.56.196; 8.CO.56.223; 8.CO.56.240; 8.CO.56.244;
8.CO.56.243; 8.CO.56.247; 8.CO.157.157; 8.CO.157.158; 8.CO.157.196; 8.CO.157.223;
8.CO.157.240; 8.CO.157.244; 8.CO.157.243; 8.CO.157.247; 8.CO.196.157; 8.CO.196.158;
8.CO.196.196; 8.CO.196.223; 8.CO.196.240; 8.CO.196.244; 8.CO.196.243; 8.CO.196.247;
8.CO.223.157; 8.CO.223.158; 8.CO.223.196; 8.CO.223.223; 8.CO.223.240; 8.CO.223.244;
8.CO.223.243; 8.CO.223.247; 8.CO.240.157; 8.CO.240.158; 8.CO.240.196; 8.CO.240.223;
8.CO.240.240; 8.CO.240.244; 8.CO.240.243; 8.CO.240.247; 8.CO.244.157; 8.CO.244.158;
8.CO.244.196; 8.CO.244.223; 8.CO.244.240; 8.CO.244.244; 8.CO.244.243; 8.CO.244.247;
8.CO.247.157; 8.CO.247.158; 8.CO.247.196; 8.CO.247.223; 8.CO.247.240; 8.CO.247.244;
8.CO.247.243; 8.CO.247.247;

TABLE 100-continued

Prodrugs of 9.AH

9.AH.4.157; 9.AH.4.158; 9.AH.4.196; 9.AH.4.223; 9.AH.4.240; 9.AH.4.244; 9.AH.4.243;
9.AH.4.247; 9.AH.5.157; 9.AH.5.158; 9.AH.5.196; 9.AH.5.223; 9.AH.5.240; 9.AH.5.244;
9.AH.5.243; 9.AH.5.247; 9.AH.7.157; 9.AH.7.158; 9.AH.7.196; 9.AH.7.223; 9.AH.7.240;
9.AH.7.244; 9.AH.7.243; 9.AH.7.247; 9.AH.15.157; 9.AH.15.158; 9.AH.15.196; 9.AH.15.223;
9.AH.15.240; 9.AH.15.244; 9.AH.15.243; 9.AH.15.247; 9.AH.16.157; 9.AH.16.158;
9.AH.16.196; 9.AH.16.223; 9.AH.16.240; 9.AH.16.244; 9.AH.16.243; 9.AH.16.247;
9.AH.18.157; 9.AH.18.158; 9.AH.18.196; 9.AH.18.223; 9.AH.18.240; 9.AH.18.244;
9.AH.18.243; 9.AH.18.247; 9.AH.26.157; 9.AH.26.158; 9.AH.26.196; 9.AH.26.223;
9.AH.26.240; 9.AH.26.244; 9.AH.26.243; 9.AH.26.247; 9.AH.27.157; 9.AH.27.158;
9.AH.27.196; 9.AH.27.223; 9.AH.27.240; 9.AH.27.244; 9.AH.27.243; 9.AH.27.247;
9.AH.29.157; 9.AH.29.158; 9.AH.29.196; 9.AH.29.223; 9.AH.29.240; 9.AH.29.244;
9.AH.29.243; 9.AH.29.247; 9.AH.54.157; 9.AH.54.158; 9.AH.54.196; 9.AH.54.223;
9.AH.54.240; 9.AH.54.244; 9.AH.54.243; 9.AH.54.247; 9.AH.55.157; 9.AH.55.158;
9.AH.55.196; 9.AH.55.223; 9.AH.55.240; 9.AH.55.244; 9.AH.55.243; 9.AH.55.247;
9.AH.56.157; 9.AH.56.158; 9.AH.56.196; 9.AH.56.223; 9.AH.56.240; 9.AH.56.244;
9.AH.56.243; 9.AH.56.247; 9.AH.157.157; 9.AH.157.158; 9.AH.157.196; 9.AH.157.223;
9.AH.157.240; 9.AH.157.244; 9.AH.157.243; 9.AH.157.247; 9.AH.196.157; 9.AH.196.158;
9.AH.196.196; 9.AH.196.223; 9.AH.196.240; 9.AH.196.244; 9.AH.196.243; 9.AH.196.247;
9.AH.223.157; 9.AH.223.158; 9.AH.223.196; 9.AH.223.223; 9.AH.223.240; 9.AH.223.244;
9.AH.223.243; 9.AH.223.247; 9.AH.240.157; 9.AH.240.158; 9.AH.240.196; 9.AH.240.223;
9.AH.240.240; 9.AH.240.244; 9.AH.240.243; 9.AH.240.247; 9.AH.244.157; 9.AH.244.158;
9.AH.244.196; 9.AH.244.223; 9.AH.244.240; 9.AH.244.244; 9.AH.244.243; 9.AH.244.247;
9.AH.247.157; 9.AH.247.158; 9.AH.247.196; 9.AH.247.223; 9.AH.247.240; 9.AH.247.244;
9.AH.247.243; 9.AH.247.247;

Prodrugs of 9.AJ

9.AJ.4.157; 9.AJ.4.158; 9.AJ.4.196; 9.AJ.4.223; 9.AJ.4.240; 9.AJ.4.244; 9.AJ.4.243;
9.AJ.4.247; 9.AJ.5.157; 9.AJ.5.158; 9.AJ.5.196; 9.AJ.5.223; 9.AJ.5.240; 9.AJ.5.244; 9.AJ.5.243;
9.AJ.5.247; 9.AJ.7.157; 9.AJ.7.158; 9.AJ.7.196; 9.AJ.7.223; 9.AJ.7.240; 9.AJ.7.244; 9.AJ.7.243;
9.AJ.7.247; 9.AJ.15.157; 9.AJ.15.158; 9.AJ.15.196; 9.AJ.15.223; 9.AJ.15.240; 9.AJ.15.244;
9.AJ.15.243; 9.AJ.15.247; 9.AJ.16.157; 9.AJ.16.158; 9.AJ.16.196; 9.AJ.16.223; 9.AJ.16.240;
9.AJ.16.244; 9.AJ.16.243; 9.AJ.16.247; 9.AJ.18.157; 9.AJ.18.158; 9.AJ.18.196; 9.AJ.18.223;
9.AJ.18.240; 9.AJ.18.244; 9.AJ.18.243; 9.AJ.18.247; 9.AJ.26.157; 9.AJ.26.158; 9.AJ.26.196;
9.AJ.26.223; 9.AJ.26.240; 9.AJ.26.244; 9.AJ.26.243; 9.AJ.26.247; 9.AJ.27.157; 9.AJ.27.158;
9.AJ.27.196; 9.AJ.27.223; 9.AJ.27.240; 9.AJ.27.244; 9.AJ.27.243; 9.AJ.27.247; 9.AJ.29.157;
9.AJ.29.158; 9.AJ.29.196; 9.AJ.29.223; 9.AJ.29.240; 9.AJ.29.244; 9.AJ.29.243; 9.AJ.29.247;
9.AJ.54.157; 9.AJ.54.158; 9.AJ.54.196; 9.AJ.54.223; 9.AJ.54.240; 9.AJ.54.244; 9.AJ.54.243;
9.AJ.54.247; 9.AJ.55.157; 9.AJ.55.158; 9.AJ.55.196; 9.AJ.55.223; 9.AJ.55.240; 9.AJ.55.244;
9.AJ.55.243; 9.AJ.55.247; 9.AJ.56.157; 9.AJ.56.158; 9.AJ.56.196; 9.AJ.56.223; 9.AJ.56.240;
9.AJ.56.244; 9.AJ.56.243; 9.AJ.56.247; 9.AJ.157.157; 9.AJ.157.158; 9.AJ.157.196;
9.AJ.157.223; 9.AJ.157.240; 9.AJ.157.244; 9.AJ.157.243; 9.AJ.157.247; 9.AJ.196.157;
9.AJ.196.158; 9.AJ.196.196; 9.AJ.196.223; 9.AJ.196.240; 9.AJ.196.244; 9.AJ.196.243;
9.AJ.196.247; 9.AJ.223.157; 9.AJ.223.158; 9.AJ.223.196; 9.AJ.223.223; 9.AJ.223.240;
9.AJ.223.244; 9.AJ.223.243; 9.AJ.223.247; 9.AJ.240.157; 9.AJ.240.158; 9.AJ.240.196;
9.AJ.240.223; 9.AJ.240.240; 9.AJ.240.244; 9.AJ.240.243; 9.AJ.240.247; 9.AJ.244.157;
9.AJ.244.158; 9.AJ.244.196; 9.AJ.244.223; 9.AJ.244.240; 9.AJ.244.244; 9.AJ.244.243;
9.AJ.244.247; 9.AJ.247.157; 9.AJ.247.158; 9.AJ.247.196; 9.AJ.247.223; 9.AJ.247.240;
9.AJ.247.244; 9.AJ.247.243; 9.AJ.247.247;

Prodrugs of 9.AN

9.AN.4.157; 9.AN.4.158; 9.AN.4.196; 9.AN.4.223; 9.AN.4.240; 9.AN.4.244; 9.AN.4.243;
9.AN.4.247; 9.AN.5.157; 9.AN.5.158; 9.AN.5.196; 9.AN.5.223; 9.AN.5.240; 9.AN.5.244;
9.AN.5.243; 9.AN.5.247; 9.AN.7.157; 9.AN.7.158; 9.AN.7.196; 9.AN.7.223; 9.AN.7.240;
9.AN.7.244; 9.AN.7.243; 9.AN.7.247; 9.AN.15.157; 9.AN.15.158; 9.AN.15.196; 9.AN.15.223;
9.AN.15.240; 9.AN.15.244; 9.AN.15.243; 9.AN.15.247; 9.AN.16.157; 9.AN.16.158;
9.AN.16.196; 9.AN.16.223; 9.AN.16.240; 9.AN.16.244; 9.AN.16.243; 9.AN.16.247;
9.AN.18.157; 9.AN.18.158; 9.AN.18.196; 9.AN.18.223; 9.AN.18.240; 9.AN.18.244;
9.AN.18.243; 9.AN.18.247; 9.AN.26.157; 9.AN.26.158; 9.AN.26.196; 9.AN.26.223;
9.AN.26.240; 9.AN.26.244; 9.AN.26.243; 9.AN.26.247; 9.AN.27.157; 9.AN.27.158;
9.AN.27.196; 9.AN.27.223; 9.AN.27.240; 9.AN.27.244; 9.AN.27.243; 9.AN.27.247;
9.AN.29.157; 9.AN.29.158; 9.AN.29.196; 9.AN.29.223; 9.AN.29.240; 9.AN.29.244;
9.AN.29.243; 9.AN.29.247; 9.AN.54.157; 9.AN.54.158; 9.AN.54.196; 9.AN.54.223;
9.AN.54.240; 9.AN.54.244; 9.AN.54.243; 9.AN.54.247; 9.AN.55.157; 9.AN.55.158;
9.AN.55.196; 9.AN.55.223; 9.AN.55.240; 9.AN.55.244; 9.AN.55.243; 9.AN.55.247;
9.AN.56.157; 9.AN.56.158; 9.AN.56.196; 9.AN.56.223; 9.AN.56.240; 9.AN.56.244;
9.AN.56.243; 9.AN.56.247; 9.AN.157.157; 9.AN.157.158; 9.AN.157.196; 9.AN.157.223;
9.AN.157.240; 9.AN.157.244; 9.AN.157.243; 9.AN.157.247; 9.AN.196.157; 9.AN.196.158;
9.AN.196.196; 9.AN.196.223; 9.AN.196.240; 9.AN.196.244; 9.AN.196.243; 9.AN.196.247;
9.AN.223.157; 9.AN.223.158; 9.AN.223.196; 9.AN.223.223; 9.AN.223.240; 9.AN.223.244;
9.AN.223.243; 9.AN.223.247; 9.AN.240.157; 9.AN.240.158; 9.AN.240.196; 9.AN.240.223;
9.AN.240.240; 9.AN.240.244; 9.AN.240.243; 9.AN.240.247; 9.AN.244.157; 9.AN.244.158;
9.AN.244.196; 9.AN.244.223; 9.AN.244.240; 9.AN.244.244; 9.AN.244.243; 9.AN.244.247;
9.AN.247.157; 9.AN.247.158; 9.AN.247.196; 9.AN.247.223; 9.AN.247.240; 9.AN.247.244;
9.AN.247.243; 9.AN.247.247;

TABLE 100-continued

Prodrugs of 9.AP

9.AP.4.157; 9.AP.4.158; 9.AP.4.196; 9.AP.4.223; 9.AP.4.240; 9.AP.4.244; 9.AP.4.243;
9.AP.4.247; 9.AP.5.157; 9.AP.5.158; 9.AP.5.196; 9.AP.5.223; 9.AP.5.240; 9.AP.5.244;
9.AP.5.243; 9.AP.5.247; 9.AP.7.157; 9.AP.7.158; 9.AP.7.196; 9.AP.7.223; 9.AP.7.240;
9.AP.7.244; 9.AP.7.243; 9.AP.7.247; 9.AP.15.157; 9.AP.15.158; 9.AP.15.196; 9.AP.15.223;
9.AP.15.240; 9.AP.15.244; 9.AP.15.243; 9.AP.15.247; 9.AP.16.157; 9.AP.16.158; 9.AP.16.196;
9.AP.16.223; 9.AP.16.240; 9.AP.16.244; 9.AP.16.243; 9.AP.16.247; 9.AP.18.157; 9.AP.18.158;
9.AP.18.196; 9.AP.18.223; 9.AP.18.240; 9.AP.18.244; 9.AP.18.243; 9.AP.18.247; 9.AP.26.157;
9.AP.26.158; 9.AP.26.196; 9.AP.26.223; 9.AP.26.240; 9.AP.26.244; 9.AP.26.243; 9.AP.26.247;
9.AP.27.157; 9.AP.27.158; 9.AP.27.196; 9.AP.27.223; 9.AP.27.240; 9.AP.27.244; 9.AP.27.243;
9.AP.27.247; 9.AP.29.157; 9.AP.29.158; 9.AP.29.196; 9.AP.29.223; 9.AP.29.240; 9.AP.29.244;
9.AP.29.243; 9.AP.29.247; 9.AP.54.157; 9.AP.54.158; 9.AP.54.196; 9.AP.54.223; 9.AP.54.240;
9.AP.54.244; 9.AP.54.243; 9.AP.54.247; 9.AP.55.157; 9.AP.55.158; 9.AP.55.196; 9.AP.55.223;
9.AP.55.240; 9.AP.55.244; 9.AP.55.243; 9.AP.55.247; 9.AP.56.157; 9.AP.56.158; 9.AP.56.196;
9.AP.56.223; 9.AP.56.240; 9.AP.56.244; 9.AP.56.243; 9.AP.56.247; 9.AP.157.157;
9.AP.157.158; 9.AP.157.196; 9.AP.157.223; 9.AP.157.240; 9.AP.157.244; 9.AP.157.243;
9.AP.157.247; 9.AP.196.157; 9.AP.196.158; 9.AP.196.196; 9.AP.196.223; 9.AP.196.240;
9.AP.196.244; 9.AP.196.243; 9.AP.196.247; 9.AP.223.157; 9.AP.223.158; 9.AP.223.196;
9.AP.223.223; 9.AP.223.240; 9.AP.223.244; 9.AP.223.243; 9.AP.223.247; 9.AP.240.157;
9.AP.240.158; 9.AP.240.196; 9.AP.240.223; 9.AP.240.240; 9.AP.240.244; 9.AP.240.243;
9.AP.240.247; 9.AP.244.157; 9.AP.244.158; 9.AP.244.196; 9.AP.244.223; 9.AP.244.240;
9.AP.244.244; 9.AP.244.243; 9.AP.244.247; 9.AP.247.157; 9.AP.247.158; 9.AP.247.196;
9.AP.247.223; 9.AP.247.240; 9.AP.247.244; 9.AP.247.243; 9.AP.247.247;

Prodrugs of 9.AZ

9.AZ.4.157; 9.AZ.4.158; 9.AZ.4.196; 9.AZ.4.223; 9.AZ.4.240; 9.AZ.4.244; 9.AZ.4.243;
9.AZ.4.247; 9.AZ.5.157; 9.AZ.5.158; 9.AZ.5.196; 9.AZ.5.223; 9.AZ.5.240; 9.AZ.5.244;
9.AZ.5.243; 9.AZ.5.247; 9.AZ.7.157; 9.AZ.7.158; 9.AZ.7.196; 9.AZ.7.223; 9.AZ.7.240;
9.AZ.7.244; 9.AZ.7.243; 9.AZ.7.247; 9.AZ.15.157; 9.AZ.15.158; 9.AZ.15.196; 9.AZ.15.223;
9.AZ.15.240; 9.AZ.15.244; 9.AZ.15.243; 9.AZ.15.247; 9.AZ.16.157; 9.AZ.16.158;
9.AZ.16.196; 9.AZ.16.223; 9.AZ.16.240; 9.AZ.16.244; 9.AZ.16.243; 9.AZ.16.247;
9.AZ.18.157; 9.AZ.18.158; 9.AZ.18.196; 9.AZ.18.223; 9.AZ.18.240; 9.AZ.18.244;
9.AZ.18.243; 9.AZ.18.247; 9.AZ.26.157; 9.AZ.26.158; 9.AZ.26.196; 9.AZ.26.223;
9.AZ.26.240; 9.AZ.26.244; 9.AZ.26.243; 9.AZ.26.247; 9.AZ.27.157; 9.AZ.27.158;
9.AZ.27.196; 9.AZ.27.223; 9.AZ.27.240; 9.AZ.27.244; 9.AZ.27.243; 9.AZ.27.247;
9.AZ.29.157; 9.AZ.29.158; 9.AZ.29.196; 9.AZ.29.223; 9.AZ.29.240; 9.AZ.29.244;
9.AZ.29.243; 9.AZ.29.247; 9.AZ.54.157; 9.AZ.54.158; 9.AZ.54.196; 9.AZ.54.223;
9.AZ.54.240; 9.AZ.54.244; 9.AZ.54.243; 9.AZ.54.247; 9.AZ.55.157; 9.AZ.55.158;
9.AZ.55.196; 9.AZ.55.223; 9.AZ.55.240; 9.AZ.55.244; 9.AZ.55.243; 9.AZ.55.247;
9.AZ.56.157; 9.AZ.56.158; 9.AZ.56.196; 9.AZ.56.223; 9.AZ.56.240; 9.AZ.56.244;
9.AZ.56.243; 9.AZ.56.247; 9.AZ.157.157; 9.AZ.157.158; 9.AZ.157.196; 9.AZ.157.223;
9.AZ.157.240; 9.AZ.157.244; 9.AZ.157.243; 9.AZ.157.247; 9.AZ.196.157; 9.AZ.196.158;
9.AZ.196.196; 9.AZ.196.223; 9.AZ.196.240; 9.AZ.196.244; 9.AZ.196.243; 9.AZ.196.247;
9.AZ.223.157; 9.AZ.223.158; 9.AZ.223.196; 9.AZ.223.223; 9.AZ.223.240; 9.AZ.223.244;
9.AZ.223.243; 9.AZ.223.247; 9.AZ.240.157; 9.AZ.240.158; 9.AZ.240.196; 9.AZ.240.223;
9.AZ.240.240; 9.AZ.240.244; 9.AZ.240.243; 9.AZ.240.247; 9.AZ.244.157; 9.AZ.244.158;
9.AZ.244.196; 9.AZ.244.223; 9.AZ.244.240; 9.AZ.244.244; 9.AZ.244.243; 9.AZ.244.247;
9.AZ.247.157; 9.AZ.247.158; 9.AZ.247.196; 9.AZ.247.223; 9.AZ.247.240; 9.AZ.247.244;
9.AZ.247.243; 9.AZ.247.247;

Prodrugs of 9.BF

9.BF.4.157; 9.BF.4.158; 9.BF.4.196; 9.BF.4.223; 9.BF.4.240; 9.BF.4.244; 9.BF.4.243;
9.BF.4.247; 9.BF.5.157; 9.BF.5.158; 9.BF.5.196; 9.BF.5.223; 9.BF.5.240; 9.BF.5.244;
9.BF.5.243; 9.BF.5.247; 9.BF.7.157; 9.BF.7.158; 9.BF.7.196; 9.BF.7.223; 9.BF.7.240;
9.BF.7.244; 9.BF.7.243; 9.BF.7.247; 9.BF.15.157; 9.BF.15.158; 9.BF.15.196; 9.BF.15.223;
9.BF.15.240; 9.BF.15.244; 9.BF.15.243; 9.BF.15.247; 9.BF.16.157; 9.BF.16.158; 9.BF.16.196;
9.BF.16.223; 9.BF.16.240; 9.BF.16.244; 9.BF.16.243; 9.BF.16.247; 9.BF.18.157; 9.BF.18.158;
9.BF.18.196; 9.BF.18.223; 9.BF.18.240; 9.BF.18.244; 9.BF.18.243; 9.BF.18.247; 9.BF.26.157;
9.BF.26.158; 9.BF.26.196; 9.BF.26.223; 9.BF.26.240; 9.BF.26.244; 9.BF.26.243; 9.BF.26.247;
9.BF.27.157; 9.BF.27.158; 9.BF.27.196; 9.BF.27.223; 9.BF.27.240; 9.BF.27.244; 9.BF.27.243;
9.BF.27.247; 9.BF.29.157; 9.BF.29.158; 9.BF.29.196; 9.BF.29.223; 9.BF.29.240; 9.BF.29.244;
9.BF.29.243; 9.BF.29.247; 9.BF.54.157; 9.BF.54.158; 9.BF.54.196; 9.BF.54.223; 9.BF.54.240;
9.BF.54.244; 9.BF.54.243; 9.BF.54.247; 9.BF.55.157; 9.BF.55.158; 9.BF.55.196; 9.BF.55.223;
9.BF.55.240; 9.BF.55.244; 9.BF.55.243; 9.BF.55.247; 9.BF.56.157; 9.BF.56.158; 9.BF.56.196;
9.BF.56.223; 9.BF.56.240; 9.BF.56.244; 9.BF.56.243; 9.BF.56.247; 9.BF.157.157;
9.BF.157.158; 9.BF.157.196; 9.BF.157.223; 9.BF.157.240; 9.BF.157.244; 9.BF.157.243;
9.BF.157.247; 9.BF.196.157; 9.BF.196.158; 9.BF.196.196; 9.BF.196.223; 9.BF.196.240;
9.BF.196.244; 9.BF.196.243; 9.BF.196.247; 9.BF.223.157; 9.BF.223.158; 9.BF.223.196;
9.BF.223.223; 9.BF.223.240; 9.BF.223.244; 9.BF.223.243; 9.BF.223.247; 9.BF.240.157;
9.BF.240.158; 9.BF.240.196; 9.BF.240.223; 9.BF.240.240; 9.BF.240.244; 9.BF.240.243;
9.BF.240.247; 9.BF.244.157; 9.BF.244.158; 9.BF.244.196; 9.BF.244.223; 9.BF.244.240;
9.BF.244.244; 9.BF.244.243; 9.BF.244.247; 9.BF.247.157; 9.BF.247.158; 9.BF.247.196;
9.BF.247.223; 9.BF.247.240; 9.BF.247.244; 9.BF.247.243; 9.BF.247.247;

Prodrugs of 9.CI

9.CI.4.157; 9.CI.4.158; 9.CI.4.196; 9.CI.4.223; 9.CI.4.240; 9.CI.4.244; 9.CI.4.243;
9.CI.4.247; 9.CI.5.157; 9.CI.5.158; 9.CI.5.196; 9.CI.5.223; 9.CI.5.240; 9.CI.5.244; 9.CI.5.243;
9.CI.5.247; 9.CI.7.157; 9.CI.7.158; 9.CI.7.196; 9.CI.7.223; 9.CI.7.240; 9.CI.7.244; 9.CI.7.243;

TABLE 100-continued

9.CI.7.247; 9.CI.15.157; 9.CI.15.158; 9.CI.15.196; 9.CI.15.223; 9.CI.15.240; 9.CI.15.244;
9.CI.15.243; 9.CI.15.247; 9.CI.16.157; 9.CI.16.158; 9.CI.16.196; 9.CI.16.223; 9.CI.16.240;
9.CI.16.244; 9.CI.16.243; 9.CI.16.247; 9.CL.18.157; 9.CI.18.158; 9.CI.18.196; 9.CI.18.223;
9.CI.18.240; 9.CI.18.244; 9.CI.18.243; 9.CI.18.247; 9.CI.26.157; 9.CI.26.158; 9.CI.26.196;
9.CI.26.223; 9.CI.26.240; 9.CI.26.244; 9.CI.26.243; 9.CI.26.247; 9.CI.27.157; 9.CI.27.158;
9.CI.27.196; 9.CI.27.223; 9.CI.27.240; 9.CI.27.244; 9.CI.27.243; 9.CI.27.247; 9.CI.29.157;
9.CI.29.158; 9.CI.29.196; 9.CI.29.223; 9.CI.29.240; 9.CI.29.244; 9.CI.29.243; 9.CI.29.247;
9.CI.54.157; 9.CI.54.158; 9.CI.54.196; 9.CI.54.223; 9.CI.54.240; 9.CI.54.244; 9.CI.54.243;
9.CI.54.247; 9.CI.55.157; 9.CI.55.158; 9.CI.55.196; 9.CI.55.223; 9.CI.55.240; 9.CI.55.244;
9.CI.55.243; 9.CI.55.247; 9.CI.56.157; 9.CI.56.158; 9.CI.56.196; 9.CI.56.223; 9.CI.56.240;
9.CI.56.244; 9.CI.56.243; 9.CI.56.247; 9.CI.157.157; 9.CI.157.158; 9.CI.157.196; 9.CI.157.223;
9.CI.157.240; 9.CI.157.244; 9.CI.157.243; 9.CI.157.247; 9.CI.196.157; 9.CI.196.158;
9.CI.196.196; 9.CI.196.223; 9.CI.196.240; 9.CI.196.244; 9.CI.196.243; 9.CI.196.247;
9.CI.223.157; 9.CI.223.158; 9.CI.223.196; 9.CI.223.223; 9.CI.223.240; 9.CI.223.244;
9.CI.223.243; 9.CI.223.247; 9.CI.240.157; 9.CI.240.158; 9.CI.240.196; 9.CI.240.223;
9.CI.240.240; 9.CI.240.244; 9.CI.240.243; 9.CI.240.247; 9.CI.244.157; 9.CI.244.158;
9.CI.244.196; 9.CI.244.223; 9.CI.244.240; 9.CI.244.244; 9.CI.244.243; 9.CI.244.247;
9.CI.247.157; 9.CI.247.158; 9.CI.247.196; 9.CI.247.223; 9.CI.247.240; 9.CI.247.244;
9.CI.247.243; 9.CI.247.247;

Prodrugs of 9.CO

9.CO.4.157; 9.CO.4.158; 9.CO.4.196; 9.CO.4.223; 9.CO.4.240; 9.CO.4.244; 9.CO.4.243;
9.CO.4.247; 9.CO.5.157; 9.CO.5.158; 9.CO.5.196; 9.CO.5.223; 9.CO.5.240; 9.CO.5.244;
9.CO.5.243; 9.CO.5.247; 9.CO.7.157; 9.CO.7.158; 9.CO.7.196; 9.CO.7.223; 9.CO.7.240;
9.CO.7.244; 9.CO.7.243; 9.CO.7.247; 9.CO.15.157; 9.CO.15.158; 9.CO.15.196; 9.CO.15.223;
9.CO.15.240; 9.CO.15.244; 9.CO.15.243; 9.CO.15.247; 9.CO.16.157; 9.CO.16.158;
9.CO.16.196; 9.CO.16.223; 9.CO.16.240; 9.CO.16.244; 9.CO.16.243; 9.CO.16.247;
9.CO.18.157; 9.CO.18.158; 9.CO.18.196; 9.CO.18.223; 9.CO.18.240; 9.CO.18.244;
9.CO.18.243; 9.CO.18.247; 9.CO.26.157; 9.CO.26.158; 9.CO.26.196; 9.CO.26.223;
9.CO.26.240; 9.CO.26.244; 9.CO.26.243; 9.CO.26.247; 9.CO.27.157; 9.CO.27.158;
9.CO.27.196; 9.CO.27.223; 9.CO.27.240; 9.CO.27.244; 9.CO.27.243; 9.CO.27.247;
9.CO.29.157; 9.CO.29.158; 9.CO.29.196; 9.CO.29.223; 9.CO.29.240; 9.CO.29.244;
9.CO.29.243; 9.CO.29.247; 9.CO.54.157; 9.CO.54.158; 9.CO.54.196; 9.CO.54.223;
9.CO.54.240; 9.CO.54.244; 9.CO.54.243; 9.CO.54.247; 9.CO.55.157; 9.CO.55.158;
9.CO.55.196; 9.CO.55.223; 9.CO.55.240; 9.CO.55.244; 9.CO.55.243; 9.CO.55.247;
9.CO.56.157; 9.CO.56.158; 9.CO.56.196; 9.CO.56.223; 9.CO.56.240; 9.CO.56.244;
9.CO.56.243; 9.CO.56.247; 9.CO.157.157; 9.CO.157.158; 9.CO.157.196; 9.CO.157.223;
9.CO.157.240; 9.CO.157.244; 9.CO.157.243; 9.CO.157.247; 9.CO.196.157; 9.CO.196.158;
9.CO.196.196; 9.CO.196.223; 9.CO.196.240; 9.CO.196.244; 9.CO.196.243; 9.CO.196.247;
9.CO.223.157; 9.CO.223.158; 9.CO.223.196; 9.CO.223.223; 9.CO.223.240; 9.CO.223.244;
9.CO.223.243; 9.CO.223.247; 9.CO.240.157; 9.CO.240.158; 9.CO.240.196; 9.CO.240.223;
9.CO.240.240; 9.CO.240.244; 9.CO.240.243; 9.CO.240.247; 9.CO.244.157; 9.CO.244.158;
9.CO.244.196; 9.CO.244.223; 9.CO.244.240; 9.CO.244.244; 9.CO.244.243; 9.CO.244.247;
9.CO.247.157; 9.CO.247.158; 9.CO.247.196; 9.CO.247.223; 9.CO.247.240; 9.CO.247.244;
9.CO.247.243; 9.CO.247.247;

Prodrugs of 10.AH

10.AH.4.157; 10.AH.4.158; 10.AH.4.196; 10.AH.4.223; 10.AH.4.240; 10.AH.4.244;
10.AH.4.243; 10.AH.4.247; 10.AH.5.157; 10.AH.5.158; 10.AH.5.196; 10.AH.5.223;
10.AH.5.240; 10.AH.5.244; 10.AH.5.243; 10.AH.5.247; 10.AH.7.157; 10.AH.7.158;
10.AH.7.196; 10.AH.7.223; 10.AH.7.240; 10.AH.7.244; 10.AH.7.243; 10.AH.7.247;
10.AH.15.157; 10.AH.15.158; 10.AH.15.196; 10.AH.15.223; 10.AH.15.240; 10.AH.15.244;
10.AH.15.243; 10.AH.15.247; 10.AH.16.157; 10.AH.16.158; 10.AH.16.196; 10.AH.16.223;
10.AH.16.240; 10.AH.16.244; 10.AH.16.243; 10.AH.16.247; 10.AH.18.157; 10.AH.18.158;
10.AH.18.196; 10.AH.18.223; 10.AH.18.240; 10.AH.18.244; 10.AH.18.243; 10.AH.18.247;
10.AH.26.157; 10.AH.26.158; 10.AH.26.196; 10.AH.26.223; 10.AH.26.240; 10.AH.26.244;
10.AH.26.243; 10.AH.26.247; 10.AH.27.157; 10.AH.27.158; 10.AH.27.196; 10.AH.27.223;
10.AH.27.240; 10.AH.27.244; 10.AH.27.243; 10.AH.27.247; 10.AH.29.157; 10.AH.29.158;
10.AH.29.196; 10.AH.29.223; 10.AH.29.240; 10.AH.29.244; 10.AH.29.243; 10.AH.29.247;
10.AH.54.157; 10.AH.54.158; 10.AH.54.196; 10.AH.54.223; 10.AH.54.240; 10.AH.54.244;
10.AH.54.243; 10.AH.54.247; 10.AH.55.157; 10.AH.55.158; 10.AH.55.196; 10.AH.55.223;
10.AH.55.240; 10.AH.55.244; 10.AH.55.243; 10.AH.55.247; 10.AH.56.157; 10.AH.56.158;
10.AH.56.196; 10.AH.56.223; 10.AH.56.240; 10.AH.56.244; 10.AH.56.243; 10.AH.56.247;
10.AH.157.157; 10.AH.157.158; 10.AH.157.196; 10.AH.157.223; 10.AH.157.240;
10.AH.157.244; 10.AH.157.243; 10.AH.157.247; 10.AH.196.157; 10.AH.196.158;
10.AH.196.196; 10.AH.196.223; 10.AH.196.240; 10.AH.196.244; 10.AH.196.243;
10.AH.196.247; 10.AH.223.157; 10.AH.223.158; 10.AH.223.196; 10.AH.223.223;
10.AH.223.240; 10.AH.223.244; 10.AH.223.243; 10.AH.223.247; 10.AH.240.157;
10.AH.240.158; 10.AH.240.196; 10.AH.240.223; 10.AH.240.240; 10.AH.240.244;
10.AH.240.243; 10.AH.240.247; 10.AH.244.157; 10.AH.244.158; 10.AH.244.196;
10.AH.244.223; 10.AH.244.240; 10.AH.244.244; 10.AH.244.243; 10.AH.244.247;
10.AH.247.157; 10.AH.247.158; 10.AH.247.196; 10.AH.247.223; 10.AH.247.240;
10.AH.247.244; 10.AH.247.243; 10.AH.247.247;

Prodrugs of 10.AJ

10.AJ.4.157; 10.AJ.4.158; 10.AJ.4.196; 10.AJ.4.223; 10.AJ.4.240; 10.AJ.4.244; 10.AJ.4.243;
10.AJ.4.247; 10.AJ.5.157; 10.AJ.5.158; 10.AJ.5.196; 10.AJ.5.223; 10.AJ.5.240; 10.AJ.5.244;
10.AJ.5.243; 10.AJ.5.247; 10.AJ.7.157; 10.AJ.7.158; 10.AJ.7.196; 10.AJ.7.223; 10.AJ.7.240;
10.AJ.7.244; 10.AJ.7.243; 10.AJ.7.247; 10.AJ.15.157; 10.AJ.15.158; 10.AJ.15.196;

TABLE 100-continued

10.AJ.15.223; 10.AJ.15.240; 10.AJ.15.244; 10.AJ.15.243; 10.AJ.15.247; 10.AJ.16.157;
10.AJ.16.158; 10.AJ.16.196; 10.AJ.16.223; 10.AJ.16.240; 10.AJ.16.244; 10.AJ.16.243;
10.AJ.16.247; 10.AJ.18.157; 10.AJ.18.158; 10.AJ.18.196; 10.AJ.18.223; 10.AJ.18.240;
10.AJ.18.244; 10.AJ.18.243; 10.AJ.18.247; 10.AJ.26.157; 10.AJ.26.158; 10.AJ.26.196;
10.AJ.26.223; 10.AJ.26.240; 10.AJ.26.244; 10.AJ.26.243; 10.AJ.26.247; 10.AJ.27.157;
10.AJ.27.158; 10.AJ.27.196; 10.AJ.27.223; 10.AJ.27.240; 10.AJ.27.244; 10.AJ.27.243;
10.AJ.27.247; 10.AJ.29.157; 10.AJ.29.158; 10.AJ.29.196; 10.AJ.29.223; 10.AJ.29.240;
10.AJ.29.244; 10.AJ.29.243; 10.AJ.29.247; 10.AJ.54.157; 10.AJ.54.158; 10.AJ.54.196;
10.AJ.54.223; 10.AJ.54.240; 10.AJ.54.244; 10.AJ.54.243; 10.AJ.54.247; 10.AJ.55.157;
10.AJ.55.158; 10.AJ.55.196; 10.AJ.55.223; 10.AJ.55.240; 10.AJ.55.244; 10.AJ.55.243;
10.AJ.55.247; 10.AJ.56.157; 10.AJ.56.158; 10.AJ.56.196; 10.AJ.56.223; 10.AJ.56.240;
10.AJ.56.244; 10.AJ.56.243; 10.AJ.56.247; 10.AJ.157.157; 10.AJ.157.158; 10.AJ.157.196;
10.AJ.157.223; 10.AJ.157.240; 10.AJ.157.244; 10.AJ.157.243; 10.AJ.157.247; 10.AJ.196.157;
10.AJ.196.158; 10.AJ.196.196; 10.AJ.196.223; 10.AJ.196.240; 10.AJ.196.244; 10.AJ.196.243;
10.AJ.196.247; 10.AJ.223.157; 10.AJ.223.158; 10.AJ.223.196; 10.AJ.223.223; 10.AJ.223.240;
10.AJ.223.244; 10.AJ.223.243; 10.AJ.223.247; 10.AJ.240.157; 10.AJ.240.158; 10.AJ.240.196;
10.AJ.240.223; 10.AJ.240.240; 10.AJ.240.244; 10.AJ.240.243; 10.AJ.240.247; 10.AJ.244.157;
10.AJ.244.158; 10.AJ.244.196; 10.AJ.244.223; 10.AJ.244.240; 10.AJ.244.244; 10.AJ.244.243;
10.AJ.244.247; 10.AJ.247.157; 10.AJ.247.158; 10.AJ.247.196; 10.AJ.247.223; 10.AJ.247.240;
10.AJ.247.244; 10.AJ.247.243; 10.AJ.247.247;
Prodrugs of 10.AN 10.AN.4.157; 10.AN.4.158; 10.AN.4.196; 10.AN.4.223; 10.AN.4.240; 10.AN.4.244;
10.AN.4.243; 10.AN.4.247; 10.AN.5.157; 10.AN.5.158; 10.AN.5.196; 10.AN.5.223;
10.AN.5.240; 10.AN.5.244; 10.AN.5.243; 10.AN.5.247; 10.AN.7.157; 10.AN.7.158;
10.AN.7.196; 10.AN.7.223; 10.AN.7.240; 10.AN.7.244; 10.AN.7.243; 10.AN.7.247;
10.AN.15.157; 10.AN.15.158; 10.AN.15.196; 10.AN.15.223; 10.AN.15.240; 10.AN.15.244;
10.AN.15.243; 10.AN.15.247; 10.AN.16.157; 10.AN.16.158; 10.AN.16.196; 10.AN.16.223;
10.AN.16.240; 10.AN.16.244; 10.AN.16.243; 10.AN.16.247; 10.AN.18.157; 10.AN.18.158;
10.AN.18.196; 10.AN.18.223; 10.AN.18.240; 10.AN.18.244; 10.AN.18.243; 10.AN.18.247;
10.AN.26.157; 10.AN.26.158; 10.AN.26.196; 10.AN.26.223; 10.AN.26.240; 10.AN.26.244;
10.AN.26.243; 10.AN.26.247; 10.AN.27.157; 10.AN.27.158; 10.AN.27.196; 10.AN.27.223;
10.AN.27.240; 10.AN.27.244; 10.AN.27.243; 10.AN.27.247; 10.AN.29.157; 10.AN.29.158;
10.AN.29.196; 10.AN.29.223; 10.AN.29.240; 10.AN.29.244; 10.AN.29.243; 10.AN.29.247;
10.AN.54.157; 10.AN.54.158; 10.AN.54.196; 10.AN.54.223; 10.AN.54.240; 10.AN.54.244;
10.AN.54.243; 10.AN.54.247; 10.AN.55.157; 10.AN.55.158; 10.AN.55.196; 10.AN.55.223;
10.AN.55.240; 10.AN.55.244; 10.AN.55.243; 10.AN.55.247; 10.AN.56.157; 10.AN.56.158;
10.AN.56.196; 10.AN.56.223; 10.AN.56.240; 10.AN.56.244; 10.AN.56.243; 10.AN.56.247;
10.AN.157.157; 10.AN.157.158; 10.AN.157.196; 10.AN.157.223; 10.AN.157.240;
10.AN.157.244; 10.AN.157.243; 10.AN.157.247; 10.AN.196.157; 10.AN.196.158;
10.AN.196.196; 10.AN.196.223; 10.AN.196.240; 10.AN.196.244; 10.AN.196.243;
10.AN.196.247; 10.AN.223.157; 10.AN.223.158; 10.AN.223.196; 10.AN.223.223;
10.AN.223.240; 10.AN.223.244; 10.AN.223.243; 10.AN.223.247; 10.AN.240.157;
10.AN.240.158; 10.AN.240.196; 10.AN.240.223; 10.AN.240.240; 10.AN.240.244;
10.AN.240.243; 10.AN.240.247; 10.AN.244.157; 10.AN.244.158; 10.AN.244.196;
10.AN.244.223; 10.AN.244.240; 10.AN.244.244; 10.AN.244.243; 10.AN.244.247;
10.AN.247.157; 10.AN.247.158; 10.AN.247.196; 10.AN.247.223; 10.AN.247.240;
10.AN.247.244; 10.AN.247.243; 10.AN.247.247;
Prodrugs of 10.AP 10.AP.4.157; 10.AP.4.158; 10.AP.4.196; 10.AP.4.223; 10.AP.4.240; 10.AP.4.244;
10.AP.4.243; 10.AP.4.247; 10.AP.5.157; 10.AP.5.158; 10.AP.5.196; 10.AP.5.223; 10.AP.5.240;
10.AP.5.244; 10.AP.5.243; 10.AP.5.247; 10.AP.7.157; 10.AP.7.158; 10.AP.7.196; 10.AP.7.223;
10.AP.7.240; 10.AP.7.244; 10.AP.7.243; 10.AP.7.247; 10.AP.15.157; 10.AP.15.158;
10.AP.15.196; 10.AP.15.223; 10.AP.15.240; 10.AP.15.244; 10.AP.15.243; 10.AP.15.247;
10.AP.16.157; 10.AP.16.158; 10.AP.16.196; 10.AP.16.223; 10.AP.16.240; 10.AP.16.244;
10.AP.16.243; 10.AP.16.247; 10.AP.18.157; 10.AP.18.158; 10.AP.18.196; 10.AP.18.223;
10.AP.18.240; 10.AP.18.244; 10.AP.18.243; 10.AP.18.247; 10.AP.26.157; 10.AP.26.158;
10.AP.26.196; 10.AP.26.223; 10.AP.26.240; 10.AP.26.244; 10.AP.26.243; 10.AP.26.247;
10.AP.27.157; 10.AP.27.158; 10.AP.27.196; 10.AP.27.223; 10.AP.27.240; 10.AP.27.244;
10.AP.27.243; 10.AP.27.247; 10.AP.29.157; 10.AP.29.158; 10.AP.29.196; 10.AP.29.223;
10.AP.29.240; 10.AP.29.244; 10.AP.29.243; 10.AP.29.247; 10.AP.54.157; 10.AP.54.158;
10.AP.54.196; 10.AP.54.223; 10.AP.54.240; 10.AP.54.244; 10.AP.54.243; 10.AP.54.247;
10.AP.55.157; 10.AP.55.158; 10.AP.55.196; 10.AP.55.223; 10.AP.55.240; 10.AP.55.244;
10.AP.55.243; 10.AP.55.247; 10.AP.56.157; 10.AP.56.158; 10.AP.56.196; 10.AP.56.223;
10.AP.56.240; 10.AP.56.244; 10.AP.56.243; 10.AP.56.247; 10.AP.157.157; 10.AP.157.158;
10.AP.157.196; 10.AP.157.223; 10.AP.157.240; 10.AP.157.244; 10.AP.157.243;
10.AP.157.247; 10.AP.196.157; 10.AP.196.158; 10.AP.196.196; 10.AP.196.223;
10.AP.196.240; 10.AP.196.244; 10.AP.196.243; 10.AP.196.247; 10.AP.223.157;
10.AP.223.158; 10.AP.223.196; 10.AP.223.223; 10.AP.223.240; 10.AP.223.244;
10.AP.223.243; 10.AP.223.247; 10.AP.240.157; 10.AP.240.158; 10.AP.240.196;
10.AP.240.223; 10.AP.240.240; 10.AP.240.244; 10.AP.240.243; 10.AP.240.247;
10.AP.244.157; 10.AP.244.158; 10.AP.244.196; 10.AP.244.223; 10.AP.244.240;
10.AP.244.244; 10.AP.244.243; 10.AP.244.247; 10.AP.247.157; 10.AP.247.158;
10.AP.247.196; 10.AP.247.223; 10.AP.247.240; 10.AP.247.244; 10.AP.247.243;
10.AP.247.247;

TABLE 100-continued

Prodrugs of 10.AZ

10.AZ.4.157; 10.AZ.4.158; 10.AZ.4.196; 10.AZ.4.223; 10.AZ.4.240; 10.AZ.4.244;
10.AZ.4.243; 10.AZ.4.247; 10.AZ.5.157; 10.AZ.5.158; 10.AZ.5.196; 10.AZ.5.223;
10.AZ.5.240; 10.AZ.5.244; 10.AZ.5.243; 10.AZ.5.247; 10.AZ.7.157; 10.AZ.7.158;
10.AZ.7.196; 10.AZ.7.223; 10.AZ.7.240; 10.AZ.7.244; 10.AZ.7.243; 10.AZ.7.247;
10.AZ.15.157; 10.AZ.15.158; 10.AZ.15.196; 10.AZ.15.223; 10.AZ.15.240; 10.AZ.15.244;
10.AZ.15.243; 10.AZ.15.247; 10.AZ.16.157; 10.AZ.16.158; 10.AZ.16.196; 10.AZ.16.223;
10.AZ.16.240; 10.AZ.16.244; 10.AZ.16.243; 10.AZ.16.247; 10.AZ.18.157; 10.AZ.18.158;
10.AZ.18.196; 10.AZ.18.223; 10.AZ.18.240; 10.AZ.18.244; 10.AZ.18.243; 10.AZ.18.247;
10.AZ.26.157; 10.AZ.26.158; 10.AZ.26.196; 10.AZ.26.223; 10.AZ.26.240; 10.AZ.26.244;
10.AZ.26.243; 10.AZ.26.247; 10.AZ.27.157; 10.AZ.27.158; 10.AZ.27.196; 10.AZ.27.223;
10.AZ.27.240; 10.AZ.27.244; 10.AZ.27.243; 10.AZ.27.247; 10.AZ.29.157; 10.AZ.29.158;
10.AZ.29.196; 10.AZ.29.223; 10.AZ.29.240; 10.AZ.29.244; 10.AZ.29.243; 10.AZ.29.247;
10.AZ.54.157; 10.AZ.54.158; 10.AZ.54.196; 10.AZ.54.223; 10.AZ.54.240; 10.AZ.54.244;
10.AZ.54.243; 10.AZ.54.247; 10.AZ.55.157; 10.AZ.55.158; 10.AZ.55.196; 10.AZ.55.223;
10.AZ.55.240; 10.AZ.55.244; 10.AZ.55.243; 10.AZ.55.247; 10.AZ.56.157; 10.AZ.56.158;
10.AZ.56.196; 10.AZ.56.223; 10.AZ.56.240; 10.AZ.56.244; 10.AZ.56.243; 10.AZ.56.247;
10.AZ.157.157; 10.AZ.157.158; 10.AZ.157.196; 10.AZ.157.223; 10.AZ.157.240;
10.AZ.157.244; 10.AZ.157.243; 10.AZ.157.247; 10.AZ.196.157; 10.AZ.196.158;
10.AZ.196.196; 10.AZ.196.223; 10.AZ.196.240; 10.AZ.196.244; 10.AZ.196.243;
10.AZ.196.247; 10.AZ.223.157; 10.AZ.223.158; 10.AZ.223.196; 10.AZ.223.223;
10.AZ.223.240; 10.AZ.223.244; 10.AZ.223.243; 10.AZ.223.247; 10.AZ.240.157;
10.AZ.240.158; 10.AZ.240.196; 10.AZ.240.223; 10.AZ.240.240; 10.AZ.240.244;
10.AZ.240.243; 10.AZ.240.247; 10.AZ.244.157; 10.AZ.244.158; 10.AZ.244.196;
10.AZ.244.223; 10.AZ.244.240; 10.AZ.244.244; 10.AZ.244.243; 10.AZ.244.247;
10.AZ.247.157; 10.AZ.247.158; 10.AZ.247.196; 10.AZ.247.223; 10.AZ.247.240;
10.AZ.247.244; 10.AZ.247.243; 10.AZ.247.247;

Prodrugs of 10.BF

10.BF.4.157; 10.BF.4.158; 10.BF.4.196; 10.BF.4.223; 10.BF.4.240; 10.BF.4.244;
10.BF.4.243; 10.BF.4.247; 10.BF.5.157; 10.BF.5.158; 10.BF.5.196; 10.BF.5.223; 10.BF.5.240;
10.BF.5.244; 10.BF.5.243; 10.BF.5.247; 10.BF.7.157; 10.BF.7.158; 10.BF.7.196; 10.BF.7.223;
10.BF.7.240; 10.BF.7.244; 10.BF.7.243; 10.BF.7.247; 10.BF.15.157; 10.BF.15.158;
10.BF.15.196; 10.BF.15.223; 10.BF.15.240; 10.BF.15.244; 10.BF.15.243; 10.BF.15.247;
10.BF.16.157; 10.BF.16.158; 10.BF.16.196; 10.BF.16.223; 10.BF.16.240; 10.BF.16.244;
10.BF.16.243; 10.BF.16.247; 10.BF.18.157; 10.BF.18.158; 10.BF.18.196; 10.BF.18.223;
10.BF.18.240; 10.BF.18.244; 10.BF.18.243; 10.BF.18.247; 10.BF.26.157; 10.BF.26.158;
10.BF.26.196; 10.BF.26.223; 10.BF.26.240; 10.BF.26.244; 10.BF.26.243; 10.BF.26.247;
10.BF.27.157; 10.BF.27.158; 10.BF.27.196; 10.BF.27.223; 10.BF.27.240; 10.BF.27.244;
10.BF.27.243; 10.BF.27.247; 10.BF.29.157; 10.BF.29.158; 10.BF.29.196; 10.BF.29.223;
10.BF.29.240; 10.BF.29.244; 10.BF.29.243; 10.BF.29.247; 10.BF.54.157; 10.BF.54.158;
10.BF.54.196; 10.BF.54.223; 10.BF.54.240; 10.BF.54.244; 10.BF.54.243; 10.BF.54.247;
10.BF.55.157; 10.BF.55.158; 10.BF.55.196; 10.BF.55.223; 10.BF.55.240; 10.BF.55.244;
10.BF.55.243; 10.BF.55.247; 10.BF.56.157; 10.BF.56.158; 10.BF.56.196; 10.BF.56.223;
10.BF.56.240; 10.BF.56.244; 10.BF.56.243; 10.BF.56.247; 10.BF.157.157; 10.BF.157.158;
10.BF.157.196; 10.BF.157.223; 10.BF.157.240; 10.BF.157.244; 10.BF.157.243; 10.BF.157.247;
10.BF.196.157; 10.BF.196.158; 10.BF.196.196; 10.BF.196.223; 10.BF.196.240; 10.BF.196.244;
10.BF.196.243; 10.BF.196.247; 10.BF.223.157; 10.BF.223.158; 10.BF.223.196; 10.BF.223.223;
10.BF.223.240; 10.BF.223.244; 10.BF.223.243; 10.BF.223.247; 10.BF.240.157; 10.BF.240.158;
10.BF.240.196; 10.BF.240.223; 10.BF.240.240; 10.BF.240.244; 10.BF.240.243; 10.BF.240.247;
10.BF.244.157; 10.BF.244.158; 10.BF.244.196; 10.BF.244.223; 10.BF.244.240; 10.BF.244.244;
10.BF.244.243; 10.BF.244.247; 10.BF.247.157; 10.BF.247.158; 10.BF.247.196; 10.BF.247.223;
10.BF.247.240; 10.BF.247.244; 10.BF.247.243; 10.BF.247.247;

Prodrugs of 10.CI

10.CI.4.157; 10.CI.4.158; 10.CI.4.196; 10.CI.4.223; 10.CI.4.240; 10.CI.4.244; 10.CI.4.243;
10.CI.4.247; 10.CI.5.157; 10.CI.5.158; 10.CI.5.196; 10.CI.5.223; 10.CI.5.240; 10.CI.5.244;
10.CI.5.243; 10.CI.5.247; 10.CI.7.157; 10.CI.7.158; 10.CI.7.196; 10.CI.7.223; 10.CI.7.240;
10.CI.7.244; 10.CI.7.243; 10.CI.7.247; 10.CI.15.157; 10.CI.15.158; 10.CI.15.196; 10.CI.15.223;
10.CI.15.240; 10.CI.15.244; 10.CI.15.243; 10.CI.15.247; 10.CI.16.157; 10.CI.16.158;
10.CI.16.196; 10.CI.16.223; 10.CI.16.240; 10.CI.16.244; 10.CI.16.243; 10.CI.16.247;
10.CI.18.157; 10.CI.18.158; 10.CI.18.196; 10.CI.18.223; 10.CI.18.240; 10.CI.18.244;
10.CI.18.243; 10.CI.18.247; 10.CI.26.157; 10.CI.26.158; 10.CI.26.196; 10.CI.26.223;
10.CI.26.240; 10.CI.26.244; 10.CI.26.243; 10.CI.26.247; 10.CI.27.157; 10.CI.27.158;
10.CI.27.196; 10.CI.27.223; 10.CI.27.240; 10.CI.27.244; 10.CI.27.243; 10.CI.27.247;
10.CI.29.157; 10.CI.29.158; 10.CI.29.196; 10.CI.29.223; 10.CI.29.240; 10.CI.29.244;
10.CI.29.243; 10.CI.29.247; 10.CI.54.157; 10.CI.54.158; 10.CI.54.196; 10.CI.54.223;
10.CI.54.240; 10.CI.54.244; 10.CI.54.243; 10.CI.54.247; 10.CI.55.157; 10.CI.55.158;
10.CI.55.196; 10.CI.55.223; 10.CI.55.240; 10.CI.55.244; 10.CI.55.243; 10.CI.55.247;
10.CI.56.157; 10.CI.56.158; 10.CI.56.196; 10.CI.56.223; 10.CI.56.240; 10.CI.56.244;
10.CI.56.243; 10.CI.56.247; 10.CI.157.157; 10.CI.157.158; 10.CI.157.196; 10.CI.157.223;
10.CI.157.240; 10.CI.157.244; 10.CI.157.243; 10.CI.157.247; 10.CI.196.157; 10.CI.196.158;
10.CI.196.196; 10.CI.196.223; 10.CI.196.240; 10.CI.196.244; 10.CI.196.243; 10.CI.196.247;
10.CI.223.157; 10.CI.223.158; 10.CI.223.196; 10.CI.223.223; 10.CI.223.240; 10.CI.223.244;
10.CI.223.243; 10.CI.223.247; 10.CI.240.157; 10.CI.240.158; 10.CI.240.196; 10.CI.240.223;
10.CI.240.240; 10.CI.240.244; 10.CI.240.243; 10.CI.240.247; 10.CI.244.157; 10.CI.244.158;
10.CI.244.196; 10.CI.244.223; 10.CI.244.240; 10.CI.244.244; 10.CI.244.243; 10.CI.244.247;

TABLE 100-continued

10.CI.247.157; 10.CI.247.158; 10.CI.247.196; 10.CI.247.223; 10.CI.247.240; 10.CI.247.244;
10.CI.247.243; 10.CI.247.247;
Prodrugs of 10.CO 10.CO.4.157; 10.CO.4.158; 10.CO.4.196; 10.CO.4.223; 10.CO.4.240; 10.CO.4.244;
10.CO.4.243; 10.CO.4.247; 10.CO.5.157; 10.CO.5.158; 10.CO.5.196; 10.CO.5.223;
10.CO.5.240; 10.CO.5.244; 10.CO.5.243; 10.CO.5.247; 10.CO.7.157; 10.CO.7.158;
10.CO.7.196; 10.CO.7.223; 10.CO.7.240; 10.CO.7.244; 10.CO.7.243; 10.CO.7.247;
10.CO.15.157; 10.CO.15.158; 10.CO.15.196; 10.CO.15.223; 10.CO.15.240; 10.CO.15.244;
10.CO.15.243; 10.CO.15.247; 10.CO.16.157; 10.CO.16.158; 10.CO.16.196; 10.CO.16.223;
10.CO.16.240; 10.CO.16.244; 10.CO.16.243; 10.CO.16.247; 10.CO.18.157; 10.CO.18.158;
10.CO.18.196; 10.CO.18.223; 10.CO.18.240; 10.CO.18.244; 10.CO.18.243; 10.CO.18.247;
10.CO.26.157; 10.CO.26.158; 10.CO.26.196; 10.CO.26.223; 10.CO.26.240; 10.CO.26.244;
10.CO.26.243; 10.CO.26.247; 10.CO.27.157; 10.CO.27.158; 10.CO.27.196; 10.CO.27.223;
10.CO.27.240; 10.CO.27.244; 10.CO.27.243; 10.CO.27.247; 10.CO.29.157; 10.CO.29.158;
10.CO.29.196; 10.CO.29.223; 10.CO.29.240; 10.CO.29.244; 10.CO.29.243; 10.CO.29.247;
10.CO.54.157; 10.CO.54.158; 10.CO.54.196; 10.CO.54.223; 10.CO.54.240; 10.CO.54.244;
10.CO.54.243; 10.CO.54.247; 10.CO.55.157; 10.CO.55.158; 10.CO.55.196; 10.CO.55.223;
10.CO.55.240; 10.CO.55.244; 10.CO.55.243; 10.CO.55.247; 10.CO.56.157; 10.CO.56.158;
10.CO.56.196; 10.CO.56.223; 10.CO.56.240; 10.CO.56.244; 10.CO.56.243; 10.CO.56.247;
10.CO.157.157; 10.CO.157.158; 10.CO.157.196; 10.CO.157.223; 10.CO.157.240;
10.CO.157.244; 10.CO.157.243; 10.CO.157.247; 10.CO.196.157; 10.CO.196.158;
10.CO.196.196; 10.CO.196.223; 10.CO.196.240; 10.CO.196.244; 10.CO.196.243;
10.CO.196.247; 10.CO.223.157; 10.CO.223.158; 10.CO.223.196; 10.CO.223.223;
10.CO.223.240; 10.CO.223.244; 10.CO.223.243; 10.CO.223.247; 10.CO.240.157;
10.CO.240.158; 10.CO.240.196; 10.CO.240.223; 10.CO.240.240; 10.CO.240.244;
10.CO.240.243; 10.CO.240.247; 10.CO.244.157; 10.CO.244.158; 10.CO.244.196;
10.CO.244.223; 10.CO.244.240; 10.CO.244.244; 10.CO.244.243; 10.CO.244.247;
10.CO.247.157; 10.CO.247.158; 10.CO.247.196; 10.CO.247.223; 10.CO.247.240;
10.CO.247.244; 10.CO.247.243; 10.CO.247.247;
Prodrugs of 11.AH 11.AH.4.157; 11.AH.4.158; 11.AH.4.196; 11.AH.4.223; 11.AH.4.240; 11.AH.4.244;
11.AH.4.243; 11.AH.4.247; 11.AH.5.157; 11.AH.5.158; 11.AH.5.196; 11.AH.5.223;
11.AH.5.240; 11.AH.5.244; 11.AH.5.243; 11.AH.5.247; 11.AH.7.157; 11.AH.7.158;
11.AH.7.196; 11.AH.7.223; 11.AH.7.240; 11.AH.7.244; 11.AH.7.243; 11.AH.7.247;
11.AH.15.157; 11.AH.15.158; 11.AH.15.196; 11.AH.15.223; 11.AH.15.240; 11.AH.15.244;
11.AH.15.243; 11.AH.15.247; 11.AH.16.157; 11.AH.16.158; 11.AH.16.196; 11.AH.16.223;
11.AH.16.240; 11.AH.16.244; 11.AH.16.243; 11.AH.16.247; 11.AH.18.157; 11.AH.18.158;
11.AH.18.196; 11.AH.18.223; 11.AH.18.240; 11.AH.18.244; 11.AH.18.243; 11.AH.18.247;
11.AH.26.157; 11.AH.26.158; 11.AH.26.196; 11.AH.26.223; 11.AH.26.240; 11.AH.26.244;
11.AH.26.243; 11.AH.26.247; 11.AH.27.157; 11.AH.27.158; 11.AH.27.196; 11.AH.27.223;
11.AH.27.240; 11.AH.27.244; 11.AH.27.243; 11.AH.27.247; 11.AH.29.157; 11.AH.29.158;
11.AH.29.196; 11.AH.29.223; 11.AH.29.240; 11.AH.29.244; 11.AH.29.243; 11.AH.29.247;
11.AH.54.157; 11.AH.54.158; 11.AH.54.196; 11.AH.54.223; 11.AH.54.240; 11.AH.54.244;
11.AH.54.243; 11.AH.54.247; 11.AH.55.157; 11.AH.55.158; 11.AH.55.196; 11.AH.55.223;
11.AH.55.240; 11.AH.55.244; 11.AH.55.243; 11.AH.55.247; 11.AH.56.157; 11.AH.56.158;
11.AH.56.196; 11.AH.56.223; 11.AH.56.240; 11.AH.56.244; 11.AH.56.243; 11.AH.56.247;
11.AH.157.157; 11.AH.157.158; 11.AH.157.196; 11.AH.157.223; 11.AH.157.240;
11.AH.157.244; 11.AH.157.243; 11.AH.157.247; 11.AH.196.157; 11.AH.196.158;
11.AH.196.196; 11.AH.196.223; 11.AH.196.240; 11.AH.196.244; 11.AH.196.243;
11.AH.196.247; 11.AH.223.157; 11.AH.223.158; 11.AH.223.196; 11.AH.223.223;
11.AH.223.240; 11.AH.223.244; 11.AH.223.243; 11.AH.223.247; 11.AH.240.157;
11.AH.240.158; 11.AH.240.196; 11.AH.240.223; 11.AH.240.240; 11.AH.240.244;
11.AH.240.243; 11.AH.240.247; 11.AH.244.157; 11.AH.244.158; 11.AH.244.196;
11.AH.244.223; 11.AH.244.240; 11.AH.244.244; 11.AH.244.243; 11.AH.244.247;
11.AH.247.157; 11.AH.247.158; 11.AH.247.196; 11.AH.247.223; 11.AH.247.240;
11.AH.247.244; 11.AH.247.243; 11.AH.247.247;
Prodrugs of 11.AJ 11.AJ.4.157; 11.AJ.4.158; 11.AJ.4.196; 11.AJ.4.223; 11.AJ.4.240; 11.AJ.4.244; 11.AJ.4.243;
11.AJ.4.247; 11.AJ.5.157; 11.AJ.5.158; 11.AJ.5.196; 11.AJ.5.223; 11.AJ.5.240; 11.AJ.5.244;
11.AJ.5.243; 11.AJ.5.247; 11.AJ.7.157; 11.AJ.7.158; 11.AJ.7.196; 11.AJ.7.223; 11.AJ.7.240;
11.AJ.7.244; 11.AJ.7.243; 11.AJ.7.247; 11.AJ.15.157; 11.AJ.15.158; 11.AJ.15.196;
11.AJ.15.223; 11.AJ.15.240; 11.AJ.15.244; 11.AJ.15.243; 11.AJ.15.247; 11.AJ.16.157;
11.AJ.16.158; 11.AJ.16.196; 11.AJ.16.223; 11.AJ.16.240; 11.AJ.16.244; 11.AJ.16.243;
11.AJ.16.247; 11.AJ.18.157; 11.AJ.18.158; 11.AJ.18.196; 11.AJ.18.223; 11.AJ.18.240;
11.AJ.18.244; 11.AJ.18.243; 11.AJ.18.247; 11.AJ.26.157; 11.AJ.26.158; 11.AJ.26.196;
11.AJ.26.223; 11.AJ.26.240; 11.AJ.26.244; 11.AJ.26.243; 11.AJ.26.247; 11.AJ.27.157;
11.AJ.27.158; 11.AJ.27.196; 11.AJ.27.223; 11.AJ.27.240; 11.AJ.27.244; 11.AJ.27.243;
11.AJ.27.247; 11.AJ.29.157; 11.AJ.29.158; 11.AJ.29.196; 11.AJ.29.223; 11.AJ.29.240;
11.AJ.29.244; 11.AJ.29.243; 11.AJ.29.247; 11.AJ.54.157; 11.AJ.54.158; 11.AJ.54.196;
11.AJ.54.223; 11.AJ.54.240; 11.AJ.54.244; 11.AJ.54.243; 11.AJ.54.247; 11.AJ.55.157;
11.AJ.55.158; 11.AJ.55.196; 11.AJ.55.223; 11.AJ.55.240; 11.AJ.55.244; 11.AJ.55.243;
11.AJ.55.247; 11.AJ.56.157; 11.AJ.56.158; 11.AJ.56.196; 11.AJ.56.223; 11.AJ.56.240;
11.AJ.56.244; 11.AJ.56.243; 11.AJ.56.247; 11.AJ.157.157; 11.AJ.157.158; 11.AJ.157.196;
11.AJ.157.223; 11.AJ.157.240; 11.AJ.157.244; 11.AJ.157.243; 11.AJ.157.247; 11.AJ.196.157;
11.AJ.196.158; 11.AJ.196.196; 11.AJ.196.223; 11.AJ.196.240; 11.AJ.196.244; 11.AJ.196.243;
11.AJ.196.247; 11.AJ.223.157; 11.AJ.223.158; 11.AJ.223.196; 11.AJ.223.223; 11.AJ.223.240;

TABLE 100-continued

11.AJ.223.244; 11.AJ.223.243; 11.AJ.223.247; 11.AJ.240.157; 11.AJ.240.158; 11.AJ.240.196;
11.AJ.240.223; 11.AJ.240.240; 11.AJ.240.244; 11.AJ.240.243; 11.AJ.240.247; 11.AJ.244.157;
11.AJ.244.158; 11.AJ.244.196; 11.AJ.244.223; 11.AJ.244.240; 11.AJ.244.244; 11.AJ.244.243;
11.AJ.244.247; 11.AJ.247.157; 11.AJ.247.158; 11.AJ.247.196; 11.AJ.247.223; 11.AJ.247.240;
11.AJ.247.244; 11.AJ.247.243; 11.AJ.247.247;

Prodrugs of 11.AN

11.AN.4.157; 11.AN.4.158; 11.AN.4.196; 11.AN.4.223; 11.AN.4.240; 11.AN.4.244;
11.AN.4.243; 11.AN.4.247; 11.AN.5.157; 11.AN.5.158; 11.AN.5.196; 11.AN.5.223;
11.AN.5.240; 11.AN.5.244; 11.AN.5.243; 11.AN.5.247; 11.AN.7.157; 11.AN.7.158;
11.AN.7.196; 11.AN.7.223; 11.AN.7.240; 11.AN.7.244; 11.AN.7.243; 11.AN.7.247;
11.AN.15.157; 11.AN.15.158; 11.AN.15.196; 11.AN.15.223; 11.AN.15.240; 11.AN.15.244;
11.AN.15.243; 11.AN.15.247; 11.AN.16.157; 11.AN.16.158; 11.AN.16.196; 11.AN.16.223;
11.AN.16.240; 11.AN.16.244; 11.AN.16.243; 11.AN.16.247; 11.AN.18.157; 11.AN.18.158;
11.AN.18.196; 11.AN.18.223; 11.AN.18.240; 11.AN.18.244; 11.AN.18.243; 11.AN.18.247;
11.AN.26.157; 11.AN.26.158; 11.AN.26.196; 11.AN.26.223; 11.AN.26.240; 11.AN.26.244;
11.AN.26.243; 11.AN.26.247; 11.AN.27.157; 11.AN.27.158; 11.AN.27.196; 11.AN.27.223;
11.AN.27.240; 11.AN.27.244; 11.AN.27.243; 11.AN.27.247; 11.AN.29.157; 11.AN.29.158;
11.AN.29.196; 11.AN.29.223; 11.AN.29.240; 11.AN.29.244; 11.AN.29.243; 11.AN.29.247;
11.AN.54.157; 11.AN.54.158; 11.AN.54.196; 11.AN.54.223; 11.AN.54.240; 11.AN.54.244;
11.AN.54.243; 11.AN.54.247; 11.AN.55.157; 11.AN.55.158; 11.AN.55.196; 11.AN.55.223;
11.AN.55.240; 11.AN.55.244; 11.AN.55.243; 11.AN.55.247; 11.AN.56.157; 11.AN.56.158;
11.AN.56.196; 11.AN.56.223; 11.AN.56.240; 11.AN.56.244; 11.AN.56.243; 11.AN.56.247;
11.AN.157.157; 11.AN.157.158; 11.AN.157.196; 11.AN.157.223; 11.AN.157.240;
11.AN.157.244; 11.AN.157.243; 11.AN.157.247; 11.AN.196.157; 11.AN.196.158;
11.AN.196.196; 11.AN.196.223; 11.AN.196.240; 11.AN.196.244; 11.AN.196.243;
11.AN.196.247; 11.AN.223.157; 11.AN.223.158; 11.AN.223.196; 11.AN.223.223;
11.AN.223.240; 11.AN.223.244; 11.AN.223.243; 11.AN.223.247; 11.AN.240.157;
11.AN.240.158; 11.AN.240.196; 11.AN.240.223; 11.AN.240.240; 11.AN.240.244;
11.AN.240.243; 11.AN.240.247; 11.AN.244.157; 11.AN.244.158; 11.AN.244.196;
11.AN.244.223; 11.AN.244.240; 11.AN.244.244; 11.AN.244.243; 11.AN.244.247;
11.AN.247.157; 11.AN.247.158; 11.AN.247.196; 11.AN.247.223; 11.AN.247.240;
11.AN.247.244; 11.AN.247.243; 11.AN.247.247;

Prodrugs of 11.AP

11.AP.4.157; 11.AP.4.158; 11.AP.4.196; 11.AP.4.223; 11.AP.4.240; 11.AP.4.244;
11.AP.4.243; 11.AP.4.247; 11.AP.5.157; 11.AP.5.158; 11.AP.5.196; 11.AP.5.223; 11.AP.5.240;
11.AP.5.244; 11.AP.5.243; 11.AP.5.247; 11.AP.7.157; 11.AP.7.158; 11.AP.7.196; 11.AP.7.223;
11.AP.7.240; 11.AP.7.244; 11.AP.7.243; 11.AP.7.247; 11.AP.15.157; 11.AP.15.158;
11.AP.15.196; 11.AP.15.223; 11.AP.15.240; 11.AP.15.244; 11.AP.15.243; 11.AP.15.247;
11.AP.16.157; 11.AP.16.158; 11.AP.16.196; 11.AP.16.223; 11.AP.16.240; 11.AP.16.244;
11.AP.16.243; 11.AP.16.247; 11.AP.18.157; 11.AP.18.158; 11.AP.18.196; 11.AP.18.223;
11.AP.18.240; 11.AP.18.244; 11.AP.18.243; 11.AP.18.247; 11.AP.26.157; 11.AP.26.158;
11.AP.26.196; 11.AP.26.223; 11.AP.26.240; 11.AP.26.244; 11.AP.26.243; 11.AP.26.247;
11.AP.27.157; 11.AP.27.158; 11.AP.27.196; 11.AP.27.223; 11.AP.27.240; 11.AP.27.244;
11.AP.27.243; 11.AP.27.247; 11.AP.29.157; 11.AP.29.158; 11.AP.29.196; 11.AP.29.223;
11.AP.29.240; 11.AP.29.244; 11.AP.29.243; 11.AP.29.247; 11.AP.54.157; 11.AP.54.158;
11.AP.54.196; 11.AP.54.223; 11.AP.54.240; 11.AP.54.244; 11.AP.54.243; 11.AP.54.247;
11.AP.55.157; 11.AP.55.158; 11.AP.55.196; 11.AP.55.223; 11.AP.55.240; 11.AP.55.244;
11.AP.55.243; 11.AP.55.247; 11.AP.56.157; 11.AP.56.158; 11.AP.56.196; 11.AP.56.223;
11.AP.56.240; 11.AP.56.244; 11.AP.56.243; 11.AP.56.247; 11.AP.157.157; 11.AP.157.158;
11.AP.157.196; 11.AP.157.223; 11.AP.157.240; 11.AP.157.244; 11.AP.157.243;
11.AP.157.247; 11.AP.196.157; 11.AP.196.158; 11.AP.196.196; 11.AP.196.223;
11.AP.196.240; 11.AP.196.244; 11.AP.196.243; 11.AP.196.247; 11.AP.223.157;
11.AP.223.158; 11.AP.223.196; 11.AP.223.223; 11.AP.223.240; 11.AP.223.244;
11.AP.223.243; 11.AP.223.247; 11.AP.240.157; 11.AP.240.158; 11.AP.240.196;
11.AP.240.223; 11.AP.240.240; 11.AP.240.244; 11.AP.240.243; 11.AP.240.247;
11.AP.244.157; 11.AP.244.158; 11.AP.244.196; 11.AP.244.223; 11.AP.244.240;
11.AP.244.244; 11.AP.244.243; 11.AP.244.247; 11.AP.247.157; 11.AP.247.158;
11.AP.247.196; 11.AP.247.223; 11.AP.247.240; 11.AP.247.244; 11.AP.247.243;
11.AP.247.247;

Prodrugs of 11.AZ

11.AZ.4.157; 11.AZ.4.158; 11.AZ.4.196; 11.AZ.4.223; 11.AZ.4.240; 11.AZ.4.244;
11.AZ.4.243; 11.AZ.4.247; 11.AZ.5.157; 11.AZ.5.158; 11.AZ.5.196; 11.AZ.5.223;
11.AZ.5.240; 11.AZ.5.244; 11.AZ.5.243; 11.AZ.5.247; 11.AZ.7.157; 11.AZ.7.158;
11.AZ.7.196; 11.AZ.7.223; 11.AZ.7.240; 11.AZ.7.244; 11.AZ.7.243; 11.AZ.7.247;
11.AZ.15.157; 11.AZ.15.158; 11.AZ.15.196; 11.AZ.15.223; 11.AZ.15.240; 11.AZ.15.244;
11.AZ.15.243; 11.AZ.15.247; 11.AZ.16.157; 11.AZ.16.158; 11.AZ.16.196; 11.AZ.16.223;
11.AZ.16.240; 11.AZ.16.244; 11.AZ.16.243; 11.AZ.16.247; 11.AZ.18.157; 11.AZ.18.158;
11.AZ.18.196; 11.AZ.18.223; 11.AZ.18.240; 11.AZ.18.244; 11.AZ.18.243; 11.AZ.18.247;
11.AZ.26.157; 11.AZ.26.158; 11.AZ.26.196; 11.AZ.26.223; 11.AZ.26.240; 11.AZ.26.244;
11.AZ.26.243; 11.AZ.26.247; 11.AZ.27.157; 11.AZ.27.158; 11.AZ.27.196; 11.AZ.27.223;
11.AZ.27.240; 11.AZ.27.244; 11.AZ.27.243; 11.AZ.27.247; 11.AZ.29.157; 11.AZ.29.158;
11.AZ.29.196; 11.AZ.29.223; 11.AZ.29.240; 11.AZ.29.244; 11.AZ.29.243; 11.AZ.29.247;
11.AZ.54.157; 11.AZ.54.158; 11.AZ.54.196; 11.AZ.54.223; 11.AZ.54.240; 11.AZ.54.244;
11.AZ.54.243; 11.AZ.54.247; 11.AZ.55.157; 11.AZ.55.158; 11.AZ.55.196; 11.AZ.55.223;
11.AZ.55.240; 11.AZ.55.244; 11.AZ.55.243; 11.AZ.55.247; 11.AZ.56.157; 11.AZ.56.158;
11.AZ.56.196; 11.AZ.56.223; 11.AZ.56.240; 11.AZ.56.244; 11.AZ.56.243; 11.AZ.56.247;

TABLE 100-continued

11.AZ.157.157; 11.AZ.157.158; 11.AZ.157.196; 11.AZ.157.223; 11.AZ.157.240;
11.AZ.157.244; 11.AZ.157.243; 11.AZ.157.247; 11.AZ.196.157; 11.AZ.196.158;
11.AZ.196.196; 11.AZ.196.223; 11.AZ.196.240; 11.AZ.196.244; 11.AZ.196.243;
11.AZ.196.247; 11.AZ.223.157; 11.AZ.223.158; 11.AZ.223.196; 11.AZ.223.223;
11.AZ.223.240; 11.AZ.223.244; 11.AZ.223.243; 11.AZ.223.247; 11.AZ.240.157;
11.AZ.240.158; 11.AZ.240.196; 11.AZ.240.223; 11.AZ.240.240; 11.AZ.240.244;
11.AZ.240.243; 11.AZ.240.247; 11.AZ.244.157; 11.AZ.244.158; 11.AZ.244.196;
11.AZ.244.223; 11.AZ.244.240; 11.AZ.244.244; 11.AZ.244.243; 11.AZ.244.247;
11.AZ.247.157; 11.AZ.247.158; 11.AZ.247.196; 11.AZ.247.223; 11.AZ.247.240;
11.AZ.247.244; 11.AZ.247.243; 11.AZ.247.247;
Prodrugs of 11.BF 11.BF.4.157; 11.BF.4.158; 11.BF.4.196; 11.BF.4.223; 11.BF.4.240; 11.BF.4.244;
11.BF.4.243; 11.BF.4.247; 11.BF.5.157; 11.BF.5.158; 11.BF.5.196; 11.BF.5.223; 11.BF.5.240;
11.BF.5.244; 11.BF.5.243; 11.BF.5.247; 11.BF.7.157; 11.BF.7.158; 11.BF.7.196; 11.BF.7.223;
11.BF.7.240; 11.BF.7.244; 11.BF.7.243; 11.BF.7.247; 11.BF.15.157; 11.BF.15.158;
11.BF.15.196; 11.BF.15.223; 11.BF.15.240; 11.BF.15.244; 11.BF.15.243; 11.BF.15.247;
11.BF.16.157; 11.BF.16.158; 11.BF.16.196; 11.BF.16.223; 11.BF.16.240; 11.BF.16.244;
11.BF.16.243; 11.BF.16.247; 11.BF.18.157; 11.BF.18.158; 11.BF.18.196; 11.BF.18.223;
11.BF.18.240; 11.BF.18.244; 11.BF.18.243; 11.BF.18.247; 11.BF.26.157; 11.BF.26.158;
11.BF.26.196; 11.BF.26.223; 11.BF.26.240; 11.BF.26.244; 11.BF.26.243; 11.BF.26.247;
11.BF.27.157; 11.BF.27.158; 11.BF.27.196; 11.BF.27.223; 11.BF.27.240; 11.BF.27.244;
11.BF.27.243; 11.BF.27.247; 11.BF.29.157; 11.BF.29.158; 11.BF.29.196; 11.BF.29.223;
11.BF.29.240; 11.BF.29.244; 11.BF.29.243; 11.BF.29.247; 11.BF.54.157; 11.BF.54.158;
11.BF.54.196; 11.BF.54.223; 11.BF.54.240; 11.BF.54.244; 11.BF.54.243; 11.BF.54.247;
11.BF.55.157; 11.BF.55.158; 11.BF.55.196; 11.BF.55.223; 11.BF.55.240; 11.BF.55.244;
11.BF.55.243; 11.BF.55.247; 11.BF.56.157; 11.BF.56.158; 11.BF.56.196; 11.BF.56.223;
11.BF.56.240; 11.BF.56.244; 11.BF.56.243; 11.BF.56.247; 11.BF.157.157; 11.BF.157.158;
11.BF.157.196; 11.BF.157.223; 11.BF.157.240; 11.BF.157.244; 11.BF.157.243; 11.BF.157.247;
11.BF.196.157; 11.BF.196.158; 11.BF.196.196; 11.BF.196.223; 11.BF.196.240; 11.BF.196.244;
11.BF.196.243; 11.BF.196.247; 11.BF.223.157; 11.BF.223.158; 11.BF.223.196; 11.BF.223.223;
11.BF.223.240; 11.BF.223.244; 11.BF.223.243; 11.BF.223.247; 11.BF.240.157; 11.BF.240.158;
11.BF.240.196; 11.BF.240.223; 11.BF.240.240; 11.BF.240.244; 11.BF.240.243; 11.BF.240.247;
11.BF.244.157; 11.BF.244.158; 11.BF.244.196; 11.BF.244.223; 11.BF.244.240; 11.BF.244.244;
11.BF.244.243; 11.BF.244.247; 11.BF.247.157; 11.BF.247.158; 11.BF.247.196; 11.BF.247.223;
11.BF.247.240; 11.BF.247.244; 11.BF.247.243; 11.BF.247.247;
Prodrugs of 11.CI 11.CI.4.157; 11.CI.4.158; 11.CI.4.196; 11.CI.4.223; 11.CI.4.240; 11.CI.4.244; 11.CI.4.243;
11.CI.4.247; 11.CI.5.157; 11.CI.5.158; 11.CI.5.196; 11.CI.5.223; 11.CI.5.240; 11.CI.5.244;
11.CI.5.243; 11.CI.5.247; 11.CI.7.157; 11.CI.7.158; 11.CI.7.196; 11.CI.7.223; 11.CI.7.240;
11.CI.7.244; 11.CI.7.243; 11.CI.7.247; 11.CI.15.157; 11.CI.15.158; 11.CI.15.196; 11.CI.15.223;
11.CI.15.240; 11.CI.15.244; 11.CI.15.243; 11.CI.15.247; 11.CI.16.157; 11.CI.16.158;
11.CI.16.196; 11.CI.16.223; 11.CI.16.240; 11.CI.16.244; 11.CI.16.243; 11.CI.16.247;
11.CI.18.157; 11.CI.18.158; 11.CI.18.196; 11.CI.18.223; 11.CI.18.240; 11.CI.18.244;
11.CI.18.243; 11.CI.18.247; 11.CI.26.157; 11.CI.26.158; 11.CI.26.196; 11.CI.26.223;
11.CI.26.240; 11.CI.26.244; 11.CI.26.243; 11.CI.26.247; 11.CI.27.157; 11.CI.27.158;
11.CI.27.196; 11.CI.27.223; 11.CI.27.240; 11.CI.27.244; 11.CI.27.243; 11.CI.27.247;
11.CI.29.157; 11.CI.29.158; 11.CI.29.196; 11.CI.29.223; 11.CI.29.240; 11.CI.29.244;
11.CI.29.243; 11.CI.29.247; 11.CI.54.157; 11.CI.54.158; 11.CI.54.196; 11.CI.54.223;
11.CI.54.240; 11.CI.54.244; 11.CI.54.243; 11.CI.54.247; 11.CI.55.157; 11.CI.55.158;
11.CI.55.196; 11.CI.55.223; 11.CI.55.240; 11.CI.55.244; 11.CI.55.243; 11.CI.55.247;
11.CI.56.157; 11.CI.56.158; 11.CI.56.196; 11.CI.56.223; 11.CI.56.240; 11.CI.56.244;
11.CI.56.243; 11.CI.56.247; 11.CI.157.157; 11.CI.157.158; 11.CI.157.196; 11.CI.157.223;
11.CI.157.240; 11.CI.157.244; 11.CI.157.243; 11.CI.157.247; 11.CI.196.157; 11.CI.196.158;
11.CI.196.196; 11.CI.196.223; 11.CI.196.240; 11.CI.196.244; 11.CI.196.243; 11.CI.196.247;
11.CI.223.157; 11.CI.223.158; 11.CI.223.196; 11.CI.223.223; 11.CI.223.240; 11.CI.223.244;
11.CI.223.243; 11.CI.223.247; 11.CI.240.157; 11.CI.240.158; 11.CI.240.196; 11.CI.240.223;
11.CI.240.240; 11.CI.240.244; 11.CI.240.243; 11.CI.240.247; 11.CI.244.157; 11.CI.244.158;
11.CI.244.196; 11.CI.244.223; 11.CI.244.240; 11.CI.244.244; 11.CI.244.243; 11.CI.244.247;
11.CI.247.157; 11.CI.247.158; 11.CI.247.196; 11.CI.247.223; 11.CI.247.240; 11.CI.247.244;
11.CI.247.243; 11.CI.247.247;
Prodrugs of 11.CO 11.CO.4.157; 11.CO.4.158; 11.CO.4.196; 11.CO.4.223; 11.CO.4.240; 11.CO.4.244;
11.CO.4.243; 11.CO.4.247; 11.CO.5.157; 11.CO.5.158; 11.CO.5.196; 11.CO.5.223;
11.CO.5.240; 11.CO.5.244; 11.CO.5.243; 11.CO.5.247; 11.CO.7.157; 11.CO.7.158;
11.CO.7.196; 11.CO.7.223; 11.CO.7.240; 11.CO.7.244; 11.CO.7.243; 11.CO.7.247;
11.CO.15.157; 11.CO.15.158; 11.CO.15.196; 11.CO.15.223; 11.CO.15.240; 11.CO.15.244;
11.CO.15.243; 11.CO.15.247; 11.CO.16.157; 11.CO.16.158; 11.CO.16.196; 11.CO.16.223;
11.CO.16.240; 11.CO.16.244; 11.CO.16.243; 11.CO.16.247; 11.CO.18.157; 11.CO.18.158;
11.CO.18.196; 11.CO.18.223; 11.CO.18.240; 11.CO.18.244; 11.CO.18.243; 11.CO.18.247;
11.CO.26.157; 11.CO.26.158; 11.CO.26.196; 11.CO.26.223; 11.CO.26.240; 11.CO.26.244;
11.CO.26.243; 11.CO.26.247; 11.CO.27.157; 11.CO.27.158; 11.CO.27.196; 11.CO.27.223;
11.CO.27.240; 11.CO.27.244; 11.CO.27.243; 11.CO.27.247; 11.CO.29.157; 11.CO.29.158;
11.CO.29.196; 11.CO.29.223; 11.CO.29.240; 11.CO.29.244; 11.CO.29.243; 11.CO.29.247;
11.CO.54.157; 11.CO.54.158; 11.CO.54.196; 11.CO.54.223; 11.CO.54.240; 11.CO.54.244;
11.CO.54.243; 11.CO.54.247; 11.CO.55.157; 11.CO.55.158; 11.CO.55.196; 11.CO.55.223;
11.CO.55.240; 11.CO.55.244; 11.CO.55.243; 11.CO.55.247; 11.CO.56.157; 11.CO.56.158;

TABLE 100-continued

11.CO.56.196; 11.CO.56.223; 11.CO.56.240; 11.CO.56.244; 11.CO.56.243; 11.CO.56.247;
11.CO.157.157; 11.CO.157.158; 11.CO.157.196; 11.CO.157.223; 11.CO.157.240;
11.CO.157.244; 11.CO.157.243; 11.CO.157.247; 11.CO.196.157; 11.CO.196.158;
11.CO.196.196; 11.CO.196.223; 11.CO.196.240; 11.CO.196.244; 11.CO.196.243;
11.CO.196.247; 11.CO.223.157; 11.CO.223.158; 11.CO.223.196; 11.CO.223.223;
11.CO.223.240; 11.CO.223.244; 11.CO.223.243; 11.CO.223.247; 11.CO.240.157;
11.CO.240.158; 11.CO.240.196; 11.CO.240.223; 11.CO.240.240; 11.CO.240.244;
11.CO.240.243; 11.CO.240.247; 11.CO.244.157; 11.CO.244.158; 11.CO.244.196;
11.CO.244.223; 11.CO.244.240; 11.CO.244.244; 11.CO.244.243; 11.CO.244.247;
11.CO.247.157; 11.CO.247.158; 11.CO.247.196; 11.CO.247.223; 11.CO.247.240;
11.CO.247.244; 11.CO.247.243; 11.CO.247.247;

Prodrugs of 12.AH

12.AH.4.157; 12.AH.4.158; 12.AH.4.196; 12.AH.4.223; 12.AH.4.240; 12.AH.4.244;
12.AH.4.243; 12.AH.4.247; 12.AH.5.157; 12.AH.5.158; 12.AH.5.196; 12.AH.5.223;
12.AH.5.240; 12.AH.5.244; 12.AH.5.243; 12.AH.5.247; 12.AH.7.157; 12.AH.7.158;
12.AH.7.196; 12.AH.7.223; 12.AH.7.240; 12.AH.7.244; 12.AH.7.243; 12.AH.7.247;
12.AH.15.157; 12.AH.15.158; 12.AH.15.196; 12.AH.15.223; 12.AH.15.240; 12.AH.15.244;
12.AH.15.243; 12.AH.15.247; 12.AH.16.157; 12.AH.16.158; 12.AH.16.196; 12.AH.16.223;
12.AH.16.240; 12.AH.16.244; 12.AH.16.243; 12.AH.16.247; 12.AH.18.157; 12.AH.18.158;
12.AH.18.196; 12.AH.18.223; 12.AH.18.240; 12.AH.18.244; 12.AH.18.243; 12.AH.18.247;
12.AH.26.157; 12.AH.26.158; 12.AH.26.196; 12.AH.26.223; 12.AH.26.240; 12.AH.26.244;
12.AH.26.243; 12.AH.26.247; 12.AH.27.157; 12.AH.27.158; 12.AH.27.196; 12.AH.27.223;
12.AH.27.240; 12.AH.27.244; 12.AH.27.243; 12.AH.27.247; 12.AH.29.157; 12.AH.29.158;
12.AH.29.196; 12.AH.29.223; 12.AH.29.240; 12.AH.29.244; 12.AH.29.243; 12.AH.29.247;
12.AH.54.157; 12.AH.54.158; 12.AH.54.196; 12.AH.54.223; 12.AH.54.240; 12.AH.54.244;
12.AH.54.243; 12.AH.54.247; 12.AH.55.157; 12.AH.55.158; 12.AH.55.196; 12.AH.55.223;
12.AH.55.240; 12.AH.55.244; 12.AH.55.243; 12.AH.55.247; 12.AH.56.157; 12.AH.56.158;
12.AH.56.196; 12.AH.56.223; 12.AH.56.240; 12.AH.56.244; 12.AH.56.243; 12.AH.56.247;
12.AH.157.157; 12.AH.157.158; 12.AH.157.196; 12.AH.157.223; 12.AH.157.240;
12.AH.157.244; 12.AH.157.243; 12.AH.157.247; 12.AH.196.157; 12.AH.196.158;
12.AH.196.196; 12.AH.196.223; 12.AH.196.240; 12.AH.196.244; 12.AH.196.243;
12.AH.196.247; 12.AH.223.157; 12.AH.223.158; 12.AH.223.196; 12.AH.223.223;
12.AH.223.240; 12.AH.223.244; 12.AH.223.243; 12.AH.223.247; 12.AH.240.157;
12.AH.240.158; 12.AH.240.196; 12.AH.240.223; 12.AH.240.240; 12.AH.240.244;
12.AH.240.243; 12.AH.240.247; 12.AH.244.157; 12.AH.244.158; 12.AH.244.196;
12.AH.244.223; 12.AH.244.240; 12.AH.244.244; 12.AH.244.243; 12.AH.244.247;
12.AH.247.157; 12.AH.247.158; 12.AH.247.196; 12.AH.247.223; 12.AH.247.240;
12.AH.247.244; 12.AH.247.243; 12.AH.247.247;

Prodrugs of 12.AJ

12.AJ.4.157; 12.AJ.4.158; 12.AJ.4.196; 12.AJ.4.223; 12.AJ.4.240; 12.AJ.4.244; 12.AJ.4.243;
12.AJ.4.247; 12.AJ.5.157; 12.AJ.5.158; 12.AJ.5.196; 12.AJ.5.223; 12.AJ.5.240; 12.AJ.5.244;
12.AJ.5.243; 12.AJ.5.247; 12.AJ.7.157; 12.AJ.7.158; 12.AJ.7.196; 12.AJ.7.223; 12.AJ.7.240;
12.AJ.7.244; 12.AJ.7.243; 12.AJ.7.247; 12.AJ.15.157; 12.AJ.15.158; 12.AJ.15.196;
12.AJ.15.223; 12.AJ.15.240; 12.AJ.15.244; 12.AJ.15.243; 12.AJ.15.247; 12.AJ.16.157;
12.AJ.16.158; 12.AJ.16.196; 12.AJ.16.223; 12.AJ.16.240; 12.AJ.16.244; 12.AJ.16.243;
12.AJ.16.247; 12.AJ.18.157; 12.AJ.18.158; 12.AJ.18.196; 12.AJ.18.223; 12.AJ.18.240;
12.AJ.18.244; 12.AJ.18.243; 12.AJ.18.247; 12.AJ.26.157; 12.AJ.26.158; 12.AJ.26.196;
12.AJ.26.223; 12.AJ.26.240; 12.AJ.26.244; 12.AJ.26.243; 12.AJ.26.247; 12.AJ.27.157;
12.AJ.27.158; 12.AJ.27.196; 12.AJ.27.223; 12.AJ.27.240; 12.AJ.27.244; 12.AJ.27.243;
12.AJ.27.247; 12.AJ.29.157; 12.AJ.29.158; 12.AJ.29.196; 12.AJ.29.223; 12.AJ.29.240;
12.AJ.29.244; 12.AJ.29.243; 12.AJ.29.247; 12.AJ.54.157; 12.AJ.54.158; 12.AJ.54.196;
12.AJ.54.223; 12.AJ.54.240; 12.AJ.54.244; 12.AJ.54.243; 12.AJ.54.247; 12.AJ.55.157;
12.AJ.55.158; 12.AJ.55.196; 12.AJ.55.223; 12.AJ.55.240; 12.AJ.55.244; 12.AJ.55.243;
12.AJ.55.247; 12.AJ.56.157; 12.AJ.56.158; 12.AJ.56.196; 12.AJ.56.223; 12.AJ.56.240;
12.AJ.56.244; 12.AJ.56.243; 12.AJ.56.247; 12.AJ.157.157; 12.AJ.157.158; 12.AJ.157.196;
12.AJ.157.223; 12.AJ.157.240; 12.AJ.157.244; 12.AJ.157.243; 12.AJ.157.247; 12.AJ.196.157;
12.AJ.196.158; 12.AJ.196.196; 12.AJ.196.223; 12.AJ.196.240; 12.AJ.196.244; 12.AJ.196.243;
12.AJ.196.247; 12.AJ.223.157; 12.AJ.223.158; 12.AJ.223.196; 12.AJ.223.223; 12.AJ.223.240;
12.AJ.223.244; 12.AJ.223.243; 12.AJ.223.247; 12.AJ.240.157; 12.AJ.240.158; 12.AJ.240.196;
12.AJ.240.223; 12.AJ.240.240; 12.AJ.240.244; 12.AJ.240.243; 12.AJ.240.247; 12.AJ.244.157;
12.AJ.244.158; 12.AJ.244.196; 12.AJ.244.223; 12.AJ.244.240; 12.AJ.244.244; 12.AJ.244.243;
12.AJ.244.247; 12.AJ.247.157; 12.AJ.247.158; 12.AJ.247.196; 12.AJ.247.223; 12.AJ.247.240;
12.AJ.247.244; 12.AJ.247.243; 12.AJ.247.247;

Prodrugs of 12.AN

12.AN.4.157; 12.AN.4.158; 12.AN.4.196; 12.AN.4.223; 12.AN.4.240; 12.AN.4.244;
12.AN.4.243; 12.AN.4.247; 12.AN.5.157; 12.AN.5.158; 12.AN.5.196; 12.AN.5.223;
12.AN.5.240; 12.AN.5.244; 12.AN.5.243; 12.AN.5.247; 12.AN.7.157; 12.AN.7.158;
12.AN.7.196; 12.AN.7.223; 12.AN.7.240; 12.AN.7.244; 12.AN.7.243; 12.AN.7.247;
12.AN.15.157; 12.AN.15.158; 12.AN.15.196; 12.AN.15.223; 12.AN.15.240; 12.AN.15.244;
12.AN.15.243; 12.AN.15.247; 12.AN.16.157; 12.AN.16.158; 12.AN.16.196; 12.AN.16.223;
12.AN.16.240; 12.AN.16.244; 12.AN.16.243; 12.AN.16.247; 12.AN.18.157; 12.AN.18.158;
12.AN.18.196; 12.AN.18.223; 12.AN.18.240; 12.AN.18.244; 12.AN.18.243; 12.AN.18.247;
12.AN.26.157; 12.AN.26.158; 12.AN.26.196; 12.AN.26.223; 12.AN.26.240; 12.AN.26.244;
12.AN.26.243; 12.AN.26.247; 12.AN.27.157; 12.AN.27.158; 12.AN.27.196; 12.AN.27.223;
12.AN.27.240; 12.AN.27.244; 12.AN.27.243; 12.AN.27.247; 12.AN.29.157; 12.AN.29.158;
12.AN.29.196; 12.AN.29.223; 12.AN.29.240; 12.AN.29.244; 12.AN.29.243; 12.AN.29.247;

TABLE 100-continued

12.AN.54.157; 12.AN.54.158; 12.AN.54.196; 12.AN.54.223; 12.AN.54.240; 12.AN.54.244;
12.AN.54.243; 12.AN.54.247; 12.AN.55.157; 12.AN.55.158; 12.AN.55.196; 12.AN.55.223;
12.AN.55.240; 12.AN.55.244; 12.AN.55.243; 12.AN.55.247; 12.AN.56.157; 12.AN.56.158;
12.AN.56.196; 12.AN.56.223; 12.AN.56.240; 12.AN.56.244; 12.AN.56.243; 12.AN.56.247;
12.AN.157.157; 12.AN.157.158; 12.AN.157.196; 12.AN.157.223; 12.AN.157.240;
12.AN.157.244; 12.AN.157.243; 12.AN.157.247; 12.AN.196.157; 12.AN.196.158;
12.AN.196.196; 12.AN.196.223; 12.AN.196.240; 12.AN.196.244; 12.AN.196.243;
12.AN.196.247; 12.AN.223.157; 12.AN.223.158; 12.AN.223.196; 12.AN.223.223;
12.AN.223.240; 12.AN.223.244; 12.AN.223.243; 12.AN.223.247; 12.AN.240.157;
12.AN.240.158; 12.AN.240.196; 12.AN.240.223; 12.AN.240.240; 12.AN.240.244;
12.AN.240.243; 12.AN.240.247; 12.AN.244.157; 12.AN.244.158; 12.AN.244.196;
12.AN.244.223; 12.AN.244.240; 12.AN.244.244; 12.AN.244.243; 12.AN.244.247;
12.AN.247.157; 12.AN.247.158; 12.AN.247.196; 12.AN.247.223; 12.AN.247.240;
12.AN.247.244; 12.AN.247.243; 12.AN.247.247;
Prodrugs of 12.AP 12.AP.4.157; 12.AP.4.158; 12.AP.4.196; 12.AP.4.223; 12.AP.4.240; 12.AP.4.244;
12.AP.4.243; 12.AP.4.247; 12.AP.5.157; 12.AP.5.158; 12.AP.5.196; 12.AP.5.223; 12.AP.5.240;
12.AP.5.244; 12.AP.5.243; 12.AP.5.247; 12.AP.7.157; 12.AP.7.158; 12.AP.7.196; 12.AP.7.223;
12.AP.7.240; 12.AP.7.244; 12.AP.7.243; 12.AP.7.247; 12.AP.15.157; 12.AP.15.158;
12.AP.15.196; 12.AP.15.223; 12.AP.15.240; 12.AP.15.244; 12.AP.15.243; 12.AP.15.247;
12.AP.16.157; 12.AP.16.158; 12.AP.16.196; 12.AP.16.223; 12.AP.16.240; 12.AP.16.244;
12.AP.16.243; 12.AP.16.247; 12.AP.18.157; 12.AP.18.158; 12.AP.18.196; 12.AP.18.223;
12.AP.18.240; 12.AP.18.244; 12.AP.18.243; 12.AP.18.247; 12.AP.26.157; 12.AP.26.158;
12.AP.26.196; 12.AP.26.223; 12.AP.26.240; 12.AP.26.244; 12.AP.26.243; 12.AP.26.247;
12.AP.27.157; 12.AP.27.158; 12.AP.27.196; 12.AP.27.223; 12.AP.27.240; 12.AP.27.244;
12.AP.27.243; 12.AP.27.247; 12.AP.29.157; 12.AP.29.158; 12.AP.29.196; 12.AP.29.223;
12.AP.29.240; 12.AP.29.244; 12.AP.29.243; 12.AP.29.247; 12.AP.54.157; 12.AP.54.158;
12.AP.54.196; 12.AP.54.223; 12.AP.54.240; 12.AP.54.244; 12.AP.54.243; 12.AP.54.247;
12.AP.55.157; 12.AP.55.158; 12.AP.55.196; 12.AP.55.223; 12.AP.55.240; 12.AP.55.244;
12.AP.55.243; 12.AP.55.247; 12.AP.56.157; 12.AP.56.158; 12.AP.56.196; 12.AP.56.223;
12.AP.56.240; 12.AP.56.244; 12.AP.56.243; 12.AP.56.247; 12.AP.157.157; 12.AP.157.158;
12.AP.157.196; 12.AP.157.223; 12.AP.157.240; 12.AP.157.244; 12.AP.157.243;
12.AP.157.247; 12.AP.196.157; 12.AP.196.158; 12.AP.196.196; 12.AP.196.223;
12.AP.196.240; 12.AP.196.244; 12.AP.196.243; 12.AP.196.247; 12.AP.223.157;
12.AP.223.158; 12.AP.223.196; 12.AP.223.223; 12.AP.223.240; 12.AP.223.244;
12.AP.223.243; 12.AP.223.247; 12.AP.240.157; 12.AP.240.158; 12.AP.240.196;
12.AP.240.223; 12.AP.240.240; 12.AP.240.244; 12.AP.240.243; 12.AP.240.247;
12.AP.244.157; 12.AP.244.158; 12.AP.244.196; 12.AP.244.223; 12.AP.244.240;
12.AP.244.244; 12.AP.244.243; 12.AP.244.247; 12.AP.247.157; 12.AP.247.158;
12.AP.247.196; 12.AP.247.223; 12.AP.247.240; 12.AP.247.244; 12.AP.247.243;
12.AP.247.247;
Prodrugs of 12.AZ 12.AZ.4.157; 12.AZ.4.158; 12.AZ.4.196; 12.AZ.4.223; 12.AZ.4.240; 12.AZ.4.244;
12.AZ.4.243; 12.AZ.4.247; 12.AZ.5.157; 12.AZ.5.158; 12.AZ.5.196; 12.AZ.5.223;
12.AZ.5.240; 12.AZ.5.244; 12.AZ.5.243; 12.AZ.5.247; 12.AZ.7.157; 12.AZ.7.158;
12.AZ.7.196; 12.AZ.7.223; 12.AZ.7.240; 12.AZ.7.244; 12.AZ.7.243; 12.AZ.7.247;
12.AZ.15.157; 12.AZ.15.158; 12.AZ.15.196; 12.AZ.15.223; 12.AZ.15.240; 12.AZ.15.244;
12.AZ.15.243; 12.AZ.15.247; 12.AZ.16.157; 12.AZ.16.158; 12.AZ.16.196; 12.AZ.16.223;
12.AZ.16.240; 12.AZ.16.244; 12.AZ.16.243; 12.AZ.16.247; 12.AZ.18.157; 12.AZ.18.158;
12.AZ.18.196; 12.AZ.18.223; 12.AZ.18.240; 12.AZ.18.244; 12.AZ.18.243; 12.AZ.18.247;
12.AZ.26.157; 12.AZ.26.158; 12.AZ.26.196; 12.AZ.26.223; 12.AZ.26.240; 12.AZ.26.244;
12.AZ.26.243; 12.AZ.26.247; 12.AZ.27.157; 12.AZ.27.158; 12.AZ.27.196; 12.AZ.27.223;
12.AZ.27.240; 12.AZ.27.244; 12.AZ.27.243; 12.AZ.27.247; 12.AZ.29.157; 12.AZ.29.158;
12.AZ.29.196; 12.AZ.29.223; 12.AZ.29.240; 12.AZ.29.244; 12.AZ.29.243; 12.AZ.29.247;
12.AZ.54.157; 12.AZ.54.158; 12.AZ.54.196; 12.AZ.54.223; 12.AZ.54.240; 12.AZ.54.244;
12.AZ.54.243; 12.AZ.54.247; 12.AZ.55.157; 12.AZ.55.158; 12.AZ.55.196; 12.AZ.55.223;
12.AZ.55.240; 12.AZ.55.244; 12.AZ.55.243; 12.AZ.55.247; 12.AZ.56.157; 12.AZ.56.158;
12.AZ.56.196; 12.AZ.56.223; 12.AZ.56.240; 12.AZ.56.244; 12.AZ.56.243; 12.AZ.56.247;
12.AZ.157.157; 12.AZ.157.158; 12.AZ.157.196; 12.AZ.157.223; 12.AZ.157.240;
12.AZ.157.244; 12.AZ.157.243; 12.AZ.157.247; 12.AZ.196.157; 12.AZ.196.158;
12.AZ.196.196; 12.AZ.196.223; 12.AZ.196.240; 12.AZ.196.244; 12.AZ.196.243;
12.AZ.196.247; 12.AZ.223.157; 12.AZ.223.158; 12.AZ.223.196; 12.AZ.223.223;
12.AZ.223.240; 12.AZ.223.244; 12.AZ.223.243; 12.AZ.223.247; 12.AZ.240.157;
12.AZ.240.158; 12.AZ.240.196; 12.AZ.240.223; 12.AZ.240.240; 12.AZ.240.244;
12.AZ.240.243; 12.AZ.240.247; 12.AZ.244.157; 12.AZ.244.158; 12.AZ.244.196;
12.AZ.244.223; 12.AZ.244.240; 12.AZ.244.244; 12.AZ.244.243; 12.AZ.244.247;
12.AZ.247.157; 12.AZ.247.158; 12.AZ.247.196; 12.AZ.247.223; 12.AZ.247.240;
12.AZ.247.244; 12.AZ.247.243; 12.AZ.247.247;
Prodrugs of 12.BF 12.BF.4.157; 12.BF.4.158; 12.BF.4.196; 12.BF.4.223; 12.BF.4.240; 12.BF.4.244;
12.BF.4.243; 12.BF.4.247; 12.BF.5.157; 12.BF.5.158; 12.BF.5.196; 12.BF.5.223; 12.BF.5.240;
12.BF.5.244; 12.BF.5.243; 12.BF.5.247; 12.BF.7.157; 12.BF.7.158; 12.BF.7.196; 12.BF.7.223;
12.BF.7.240; 12.BF.7.244; 12.BF.7.243; 12.BF.7.247; 12.BF.15.157; 12.BF.15.158;
12.BF.15.196; 12.BF.15.223; 12.BF.15.240; 12.BF.15.244; 12.BF.15.243; 12.BF.15.247;
12.BF.16.157; 12.BF.16.158; 12.BF.16.196; 12.BF.16.223; 12.BF.16.240; 12.BF.16.244;
12.BF.16.243; 12.BF.16.247; 12.BF.18.157; 12.BF.18.158; 12.BF.18.196; 12.BF.18.223;

TABLE 100-continued

12.BF.18.240; 12.BF.18.244; 12.BF.18.243; 12.BF.18.247; 12.BF.26.157; 12.BF.26.158;
12.BF.26.196; 12.BF.26.223; 12.BF.26.240; 12.BF.26.244; 12.BF.26.243; 12.BF.26.247;
12.BF.27.157; 12.BF.27.158; 12.BF.27.196; 12.BF.27.223; 12.BF.27.240; 12.BF.27.244;
12.BF.27.243; 12.BF.27.247; 12.BF.29.157; 12.BF.29.158; 12.BF.29.196; 12.BF.29.223;
12.BF.29.240; 12.BF.29.244; 12.BF.29.243; 12.BF.29.247; 12.BF.54.157; 12.BF.54.158;
12.BF.54.196; 12.BF.54.223; 12.BF.54.240; 12.BF.54.244; 12.BF.54.243; 12.BF.54.247;
12.BF.55.157; 12.BF.55.158; 12.BF.55.196; 12.BF.55.223; 12.BF.55.240; 12.BF.55.244;
12.BF.55.243; 12.BF.55.247; 12.BF.56.157; 12.BF.56.158; 12.BF.56.196; 12.BF.56.223;
12.BF.56.240; 12.BF.56.244; 12.BF.56.243; 12.BF.56.247; 12.BF.157.157; 12.BF.157.158;
12.BF.157.196; 12.BF.157.223; 12.BF.157.240; 12.BF.157.244; 12.BF.157.243; 12.BF.157.247;
12.BF.196.157; 12.BF.196.158; 12.BF.196.196; 12.BF.196.223; 12.BF.196.240; 12.BF.196.244;
12.BF.196.243; 12.BF.196.247; 12.BF.223.157; 12.BF.223.158; 12.BF.223.196; 12.BF.223.223;
12.BF.223.240; 12.BF.223.244; 12.BF.223.243; 12.BF.223.247; 12.BF.240.157; 12.BF.240.158;
12.BF.240.196; 12.BF.240.223; 12.BF.240.240; 12.BF.240.244; 12.BF.240.243; 12.BF.240.247;
12.BF.244.157; 12.BF.244.158; 12.BF.244.196; 12.BF.244.223; 12.BF.244.240; 12.BF.244.244;
12.BF.244.243; 12.BF.244.247; 12.BF.247.157; 12.BF.247.158; 12.BF.247.196; 12.BF.247.223;
12.BF.247.240; 12.BF.247.244; 12.BF.247.243; 12.BF.247.247;
Prodrugs of 12.CI 12.CI.4.157; 12.CI.4.158; 12.CI.4.196; 12.CI.4.223; 12.CI.4.240; 12.CI.4.244; 12.CI.4.243;
12.CI.4.247; 12.CI.5.157; 12.CI.5.158; 12.CI.5.196; 12.CI.5.223; 12.CI.5.240; 12.CI.5.244;
12.CI.5.243; 12.CI.5.247; 12.CI.7.157; 12.CI.7.158; 12.CI.7.196; 12.CI.7.223; 12.CI.7.240;
12.CI.7.244; 12.CI.7.243; 12.CI.7.247; 12.CI.15.157; 12.CI.15.158; 12.CI.15.196; 12.CI.15.223;
12.CI.15.240; 12.CI.15.244; 12.CI.15.243; 12.CI.15.247; 12.CI.16.157; 12.CI.16.158;
12.CI.16.196; 12.CI.16.223; 12.CI.16.240; 12.CI.16.244; 12.CI.16.243; 12.CI.16.247;
12.CI.18.157; 12.CI.18.158; 12.CI.18.196; 12.CI.18.223; 12.CI.18.240; 12.CI.18.244;
12.CI.18.243; 12.CI.18.247; 12.CI.26.157; 12.CI.26.158; 12.CI.26.196; 12.CI.26.223;
12.CI.26.240; 12.CI.26.244; 12.CI.26.243; 12.CI.26.247; 12.CI.27.157; 12.CI.27.158;
12.CI.27.196; 12.CI.27.223; 12.CI.27.240; 12.CI.27.244; 12.CI.27.243; 12.CI.27.247;
12.CI.29.157; 12.CI.29.158; 12.CI.29.196; 12.CI.29.223; 12.CI.29.240; 12.CI.29.244;
12.CI.29.243; 12.CI.29.247; 12.CI.54.157; 12.CI.54.158; 12.CI.54.196; 12.CI.54.223;
12.CI.54.240; 12.CI.54.244; 12.CI.54.243; 12.CI.54.247; 12.CI.55.157; 12.CI.55.158;
12.CI.55.196; 12.CI.55.223; 12.CI.55.240; 12.CI.55.244; 12.CI.55.243; 12.CI.55.247;
12.CI.56.157; 12.CI.56.158; 12.CI.56.196; 12.CI.56.223; 12.CI.56.240; 12.CI.56.244;
12.CI.56.243; 12.CI.56.247; 12.CI.157.157; 12.CI.157.158; 12.CI.157.196; 12.CI.157.223;
12.CI.157.240; 12.CI.157.244; 12.CI.157.243; 12.CI.157.247; 12.CI.196.157; 12.CI.196.158;
12.CI.196.196; 12.CI.196.223; 12.CI.196.240; 12.CI.196.244; 12.CI.196.243; 12.CI.196.247;
12.CI.223.157; 12.CI.223.158; 12.CI.223.196; 12.CI.223.223; 12.CI.223.240; 12.CI.223.244;
12.CI.223.243; 12.CI.223.247; 12.CI.240.157; 12.CI.240.158; 12.CI.240.196; 12.CI.240.223;
12.CI.240.240; 12.CI.240.244; 12.CI.240.243; 12.CI.240.247; 12.CI.244.157; 12.CI.244.158;
12.CI.244.196; 12.CI.244.223; 12.CI.244.240; 12.CI.244.244; 12.CI.244.243; 12.CI.244.247;
12.CI.247.157; 12.CI.247.158; 12.CI.247.196; 12.CI.247.223; 12.CI.247.240; 12.CI.247.244;
12.CI.247.243; 12.CI.247.247;
Prodrugs of 12.CO 12.CO.4.157; 12.CO.4.158; 12.CO.4.196; 12.CO.4.223; 12.CO.4.240; 12.CO.4.244;
12.CO.4.243; 12.CO.4.247; 12.CO.5.157; 12.CO.5.158; 12.CO.5.196; 12.CO.5.223;
12.CO.5.240; 12.CO.5.244; 12.CO.5.243; 12.CO.5.247; 12.CO.7.157; 12.CO.7.158;
12.CO.7.196; 12.CO.7.223; 12.CO.7.240; 12.CO.7.244; 12.CO.7.243; 12.CO.7.247;
12.CO.15.157; 12.CO.15.158; 12.CO.15.196; 12.CO.15.223; 12.CO.15.240; 12.CO.15.244;
12.CO.15.243; 12.CO.15.247; 12.CO.16.157; 12.CO.16.158; 12.CO.16.196; 12.CO.16.223;
12.CO.16.240; 12.CO.16.244; 12.CO.16.243; 12.CO.16.247; 12.CO.18.157; 12.CO.18.158;
12.CO.18.196; 12.CO.18.223; 12.CO.18.240; 12.CO.18.244; 12.CO.18.243; 12.CO.18.247;
12.CO.26.157; 12.CO.26.158; 12.CO.26.196; 12.CO.26.223; 12.CO.26.240; 12.CO.26.244;
12.CO.26.243; 12.CO.26.247; 12.CO.27.157; 12.CO.27.158; 12.CO.27.196; 12.CO.27.223;
12.CO.27.240; 12.CO.27.244; 12.CO.27.243; 12.CO.27.247; 12.CO.29.157; 12.CO.29.158;
12.CO.29.196; 12.CO.29.223; 12.CO.29.240; 12.CO.29.244; 12.CO.29.243; 12.CO.29.247;
12.CO.54.157; 12.CO.54.158; 12.CO.54.196; 12.CO.54.223; 12.CO.54.240; 12.CO.54.244;
12.CO.54.243; 12.CO.54.247; 12.CO.55.157; 12.CO.55.158; 12.CO.55.196; 12.CO.55.223;
12.CO.55.240; 12.CO.55.244; 12.CO.55.243; 12.CO.55.247; 12.CO.56.157; 12.CO.56.158;
12.CO.56.196; 12.CO.56.223; 12.CO.56.240; 12.CO.56.244; 12.CO.56.243; 12.CO.56.247;
12.CO.157.157; 12.CO.157.158; 12.CO.157.196; 12.CO.157.223; 12.CO.157.240;
12.CO.157.244; 12.CO.157.243; 12.CO.157.247; 12.CO.196.157; 12.CO.196.158;
12.CO.196.196; 12.CO.196.223; 12.CO.196.240; 12.CO.196.244; 12.CO.196.243;
12.CO.196.247; 12.CO.223.157; 12.CO.223.158; 12.CO.223.196; 12.CO.223.223;
12.CO.223.240; 12.CO.223.244; 12.CO.223.243; 12.CO.223.247; 12.CO.240.157;
12.CO.240.158; 12.CO.240.196; 12.CO.240.223; 12.CO.240.240; 12.CO.240.244;
12.CO.240.243; 12.CO.240.247; 12.CO.244.157; 12.CO.244.158; 12.CO.244.196;
12.CO.244.223; 12.CO.244.240; 12.CO.244.244; 12.CO.244.243; 12.CO.244.247;
12.CO.247.157; 12.CO.247.158; 12.CO.247.196; 12.CO.247.223; 12.CO.247.240;
12.CO.247.244; 12.CO.247.243; 12.CO.247.247.
Prodrugs of 13.B 13.B.228.228; 13.B.228.229; 13.B.228.230; 13.B.228.231; 13.B.228.236; 13.B.228.237;
13.B.228.238; 13.B.228.239; 13.B.228.154; 13.B.228.157; 13.B.228.166; 13.B.228.169;
13.B.228.172; 13.B.228.175; 13.B.228.240; 13.B.228.244; 13.B.229.228; 13.B.229.229;
13.B.229.230; 13.B.229.231; 13.B.229.236; 13.B.229.237; 13.B.229.238; 13.B.229.239;
13.B.229.154; 13.B.229.157; 13.B.229.166; 13.B.229.169; 13.B.229.172; 13.B.229.175;
13.B.229.240; 13.B.229.244; 13.B.230.228; 13.B.230.229; 13.B.230.230; 13.B.230.231;

TABLE 100-continued

13.B.230.236; 13.B.230.237; 13.B.230.238; 13.B.230.239; 13.B.230.154; 13.B.230.157;
13.B.230.166; 13.B.230.169; 13.B.230.172; 13.B.230.175; 13.B.230.240; 13.B.230.244;
13.B.231.228; 13.B.231.229; 13.B.231.230; 13.B.231.231; 13.B.231.236; 13.B.231.237;
13.B.231.238; 13.B.231.239; 13.B.231.154; 13.B.231.157; 13.B.231.166; 13.B.231.169;
13.B.231.172; 13.B.231.175; 13.B.231.240; 13.B.231.244; 13.B.236.228; 13.B.236.229;
13.B.236.230; 13.B.236.231; 13.B.236.236; 13.B.236.237; 13.B.236.238; 13.B.236.239;
13.B.236.154; 13.B.236.157; 13.B.236.166; 13.B.236.169; 13.B.236.172; 13.B.236.175;
13.B.236.240; 13.B.236.244; 13.B.237.228; 13.B.237.229; 13.B.237.230; 13.B.237.231;
13.B.237.236; 13.B.237.237; 13.B.237.238; 13.B.237.239; 13.B.237.154; 13.B.237.157;
13.B.237.166; 13.B.237.169; 13.B.237.172; 13.B.237.175; 13.B.237.240; 13.B.237.244;
13.B.238.228; 13.B.238.229; 13.B.238.230; 13.B.238.231; 13.B.238.236; 13.B.238.237;
13.B.238.238; 13.B.238.239; 13.B.238.154; 13.B.238.157; 13.B.238.166; 13.B.238.169;
13.B.238.172; 13.B.238.175; 13.B.238.240; 13.B.238.244; 13.B.239.228; 13.B.239.229;
13.B.239.230; 13.B.239.231; 13.B.239.236; 13.B.239.237; 13.B.239.238; 13.B.239.239;
13.B.239.154; 13.B.239.157; 13.B.239.166; 13.B.239.169; 13.B.239.172; 13.B.239.175;
13.B.239.240; 13.B.239.244; 13.B.154.228; 13.B.154.229; 13.B.154.230; 13.B.154.231;
13.B.154.236; 13.B.154.237; 13.B.154.238; 13.B.154.239; 13.B.154.154; 13.B.154.157;
13.B.154.166; 13.B.154.169; 13.B.154.172; 13.B.154.175; 13.B.154.240; 13.B.154.244;
13.B.157.228; 13.B.157.229; 13.B.157.230; 13.B.157.231; 13.B.157.236; 13.B.157.237;
13.B.157.238; 13.B.157.239; 13.B.157.154; 13.B.157.157; 13.B.157.166; 13.B.157.169;
13.B.157.172; 13.B.157.175; 13.B.157.240; 13.B.157.244; 13.B.166.228; 13.B.166.229;
13.B.166.230; 13.B.166.231; 13.B.166.236; 13.B.166.237; 13.B.166.238; 13.B.166.239;
13.B.166.154; 13.B.166.157; 13.B.166.166; 13.B.166.169; 13.B.166.172; 13.B.166.175;
13.B.166.240; 13.B.166.244; 13.B.169.228; 13.B.169.229; 13.B.169.230; 13.B.169.231;
13.B.169.236; 13.B.169.237; 13.B.169.238; 13.B.169.239; 13.B.169.154; 13.B.169.157;
13.B.169.166; 13.B.169.169; 13.B.169.172; 13.B.169.175; 13.B.169.240; 13.B.169.244;
13.B.172.228; 13.B.172.229; 13.B.172.230; 13.B.172.231; 13.B.172.236; 13.B.172.237;
13.B.172.238; 13.B.172.239; 13.B.172.154; 13.B.172.157; 13.B.172.166; 13.B.172.169;
13.B.172.172; 13.B.172.175; 13.B.172.240; 13.B.172.244; 13.B.175.228; 13.B.175.229;
13.B.175.230; 13.B.175.231; 13.B.175.236; 13.B.175.237; 13.B.175.238; 13.B.175.239;
13.B.175.154; 13.B.175.157; 13.B.175.166; 13.B.175.169; 13.B.175.172; 13.B.175.175;
13.B.175.240; 13.B.175.244; 13.B.240.228; 13.B.240.229; 13.B.240.230; 13.B.240.231;
13.B.240.236; 13.B.240.237; 13.B.240.238; 13.B.240.239; 13.B.240.154; 13.B.240.157;
13.B.240.166; 13.B.240.169; 13.B.240.172; 13.B.240.175; 13.B.240.240; 13.B.240.244;
13.B.244.228; 13.B.244.229; 13.B.244.230; 13.B.244.231; 13.B.244.236; 13.B.244.237;
13.B.244.238; 13.B.244.239; 13.B.244.154; 13.B.244.157; 13.B.244.166; 13.B.244.169;
13.B.244.172; 13.B.244.175; 13.B.244.240; 13.B.244.244;
Prodrugs of 13.D 13.D.228.228; 13.D.228.229; 13.D.228.230; 13.D.228.231; 13.D.228.236; 13.D.228.237;
13.D.228.238; 13.D.228.239; 13.D.228.154; 13.D.228.157; 13.D.228.166; 13.D.228.169;
13.D.228.172; 13.D.228.175; 13.D.228.240; 13.D.228.244; 13.D.229.228; 13.D.229.229;
13.D.229.230; 13.D.229.231; 13.D.229.236; 13.D.229.237; 13.D.229.238; 13.D.229.239;
13.D.229.154; 13.D.229.157; 13.D.229.166; 13.D.229.169; 13.D.229.172; 13.D.229.175;
13.D.229.240; 13.D.229.244; 13.D.230.228; 13.D.230.229; 13.D.230.230; 13.D.230.231;
13.D.230.236; 13.D.230.237; 13.D.230.238; 13.D.230.239; 13.D.230.154; 13.D.230.157;
13.D.230.166; 13.D.230.169; 13.D.230.172; 13.D.230.175; 13.D.230.240; 13.D.230.244;
13.D.231.228; 13.D.231.229; 13.D.231.230; 13.D.231.231; 13.D.231.236; 13.D.231.237;
13.D.231.238; 13.D.231.239; 13.D.231.154; 13.D.231.157; 13.D.231.166; 13.D.231.169;
13.D.231.172; 13.D.231.175; 13.D.231.240; 13.D.231.244; 13.D.236.228; 13.D.236.229;
13.D.236.230; 13.D.236.231; 13.D.236.236; 13.D.236.237; 13.D.236.238; 13.D.236.239;
13.D.236.154; 13.D.236.157; 13.D.236.166; 13.D.236.169; 13.D.236.172; 13.D.236.175;
13.D.236.240; 13.D.236.244; 13.D.237.228; 13.D.237.229; 13.D.237.230; 13.D.237.231;
13.D.237.236; 13.D.237.237; 13.D.237.238; 13.D.237.239; 13.D.237.154; 13.D.237.157;
13.D.237.166; 13.D.237.169; 13.D.237.172; 13.D.237.175; 13.D.237.240; 13.D.237.244;
13.D.238.228; 13.D.238.229; 13.D.238.230; 13.D.238.231; 13.D.238.236; 13.D.238.237;
13.D.238.238; 13.D.238.239; 13.D.238.154; 13.D.238.157; 13.D.238.166; 13.D.238.169;
13.D.238.172; 13.D.238.175; 13.D.238.240; 13.D.238.244; 13.D.239.228; 13.D.239.229;
13.D.239.230; 13.D.239.231; 13.D.239.236; 13.D.239.237; 13.D.239.238; 13.D.239.239;
13.D.239.154; 13.D.239.157; 13.D.239.166; 13.D.239.169; 13.D.239.172; 13.D.239.175;
13.D.239.240; 13.D.239.244; 13.D.154.228; 13.D.154.229; 13.D.154.230; 13.D.154.231;
13.D.154.236; 13.D.154.237; 13.D.154.238; 13.D.154.239; 13.D.154.154; 13.D.154.157;
13.D.154.166; 13.D.154.169; 13.D.154.172; 13.D.154.175; 13.D.154.240; 13.D.154.244;
13.D.157.228; 13.D.157.229; 13.D.157.230; 13.D.157.231; 13.D.157.236; 13.D.157.237;
13.D.157.238; 13.D.157.239; 13.D.157.154; 13.D.157.157; 13.D.157.166; 13.D.157.169;
13.D.157.172; 13.D.157.175; 13.D.157.240; 13.D.157.244; 13.D.166.228; 13.D.166.229;
13.D.166.230; 13.D.166.231; 13.D.166.236; 13.D.166.237; 13.D.166.238; 13.D.166.239;
13.D.166.154; 13.D.166.157; 13.D.166.166; 13.D.166.169; 13.D.166.172; 13.D.166.175;
13.D.166.240; 13.D.166.244; 13.D.169.228; 13.D.169.229; 13.D.169.230; 13.D.169.231;
13.D.169.236; 13.D.169.237; 13.D.169.238; 13.D.169.239; 13.D.169.154; 13.D.169.157;
13.D.169.166; 13.D.169.169; 13.D.169.172; 13.D.169.175; 13.D.169.240; 13.D.169.244;
13.D.172.228; 13.D.172.229; 13.D.172.230; 13.D.172.231; 13.D.172.236; 13.D.172.237;
13.D.172.238; 13.D.172.239; 13.D.172.154; 13.D.172.157; 13.D.172.166; 13.D.172.169;
13.D.172.172; 13.D.172.175; 13.D.172.240; 13.D.172.244; 13.D.175.228; 13.D.175.229;
13.D.175.230; 13.D.175.231; 13.D.175.236; 13.D.175.237; 13.D.175.238; 13.D.175.239;
13.D.175.154; 13.D.175.157; 13.D.175.166; 13.D.175.169; 13.D.175.172; 13.D.175.175;
13.D.175.240; 13.D.175.244; 13.D.240.228; 13.D.240.229; 13.D.240.230; 13.D.240.231;
13.D.240.236; 13.D.240.237; 13.D.240.238; 13.D.240.239; 13.D.240.154; 13.D.240.157;
13.D.240.166; 13.D.240.169; 13.D.240.172; 13.D.240.175; 13.D.240.240; 13.D.240.244;

TABLE 100-continued

13.D.244.228; 13.D.244.229; 13.D.244.230; 13.D.244.231; 13.D.244.236; 13.D.244.237;
13.D.244.238; 13.D.244.239; 13.D.244.154; 13.D.244.157; 13.D.244.166; 13.D.244.169;
13.D.244.172; 13.D.244.175; 13.D.244.240; 13.D.244.244;
Prodrugs of 13.E 13.E.228.228; 13.E.228.229; 13.E.228.230; 13.E.228.231; 13.E.228.236; 13.E.228.237;
13.E.228.238; 13.E.228.239; 13.E.228.154; 13.E.228.157; 13.E.228.166; 13.E.228.169;
13.E.228.172; 13.E.228.175; 13.E.228.240; 13.E.228.244; 13.E.229.228; 13.E.229.229;
13.E.229.230; 13.E.229.231; 13.E.229.236; 13.E.229.237; 13.E.229.238; 13.E.229.239;
13.E.229.154; 13.E.229.157; 13.E.229.166; 13.E.229.169; 13.E.229.172; 13.E.229.175;
13.E.229.240; 13.E.229.244; 13.E.230.228; 13.E.230.229; 13.E.230.230; 13.E.230.231;
13.E.230.236; 13.E.230.237; 13.E.230.238; 13.E.230.239; 13.E.230.154; 13.E.230.157;
13.E.230.166; 13.E.230.169; 13.E.230.172; 13.E.230.175; 13.E.230.240; 13.E.230.244;
13.E.231.228; 13.E.231.229; 13.E.231.230; 13.E.231.231; 13.E.231.236; 13.E.231.237;
13.E.231.238; 13.E.231.239; 13.E.231.154; 13.E.231.157; 13.E.231.166; 13.E.231.169;
13.E.231.172; 13.E.231.175; 13.E.231.240; 13.E.231.244; 13.E.236.228; 13.E.236.229;
13.E.236.230; 13.E.236.231; 13.E.236.236; 13.E.236.237; 13.E.236.238; 13.E.236.239;
13.E.236.154; 13.E.236.157; 13.E.236.166; 13.E.236.169; 13.E.236.172; 13.E.236.175;
13.E.236.240; 13.E.236.244; 13.E.237.228; 13.E.237.229; 13.E.237.230; 13.E.237.231;
13.E.237.236; 13.E.237.237; 13.E.237.238; 13.E.237.239; 13.E.237.154; 13.E.237.157;
13.E.237.166; 13.E.237.169; 13.E.237.172; 13.E.237.175; 13.E.237.240; 13.E.237.244;
13.E.238.228; 13.E.238.229; 13.E.238.230; 13.E.238.231; 13.E.238.236; 13.E.238.237;
13.E.238.238; 13.E.238.239; 13.E.238.154; 13.E.238.157; 13.E.238.166; 13.E.238.169;
13.E.238.172; 13.E.238.175; 13.E.238.240; 13.E.238.244; 13.E.239.228; 13.E.239.229;
13.E.239.230; 13.E.239.231; 13.E.239.236; 13.E.239.237; 13.E.239.238; 13.E.239.239;
13.E.239.154; 13.E.239.157; 13.E.239.166; 13.E.239.169; 13.E.239.172; 13.E.239.175;
13.E.239.240; 13.E.239.244; 13.E.154.228; 13.E.154.229; 13.E.154.230; 13.E.154.231;
13.E.154.236; 13.E.154.237; 13.E.154.238; 13.E.154.239; 13.E.154.154; 13.E.154.157;
13.E.154.166; 13.E.154.169; 13.E.154.172; 13.E.154.175; 13.E.154.240; 13.E.154.244;
13.E.157.228; 13.E.157.229; 13.E.157.230; 13.E.157.231; 13.E.157.236; 13.E.157.237;
13.E.157.238; 13.E.157.239; 13.E.157.154; 13.E.157.157; 13.E.157.166; 13.E.157.169;
13.E.157.172; 13.E.157.175; 13.E.157.240; 13.E.157.244; 13.E.166.228; 13.E.166.229;
13.E.166.230; 13.E.166.231; 13.E.166.236; 13.E.166.237; 13.E.166.238; 13.E.166.239;
13.E.166.154; 13.E.166.157; 13.E.166.166; 13.E.166.169; 13.E.166.172; 13.E.166.175;
13.E.166.240; 13.E.166.244; 13.E.169.228; 13.E.169.229; 13.E.169.230; 13.E.169.231;
13.E.169.236; 13.E.169.237; 13.E.169.238; 13.E.169.239; 13.E.169.154; 13.E.169.157;
13.E.169.166; 13.E.169.169; 13.E.169.172; 13.E.169.175; 13.E.169.240; 13.E.169.244;
13.E.172.228; 13.E.172.229; 13.E.172.230; 13.E.172.231; 13.E.172.236; 13.E.172.237;
13.E.172.238; 13.E.172.239; 13.E.172.154; 13.E.172.157; 13.E.172.166; 13.E.172.169;
13.E.172.172; 13.E.172.175; 13.E.172.240; 13.E.172.244; 13.E.175.228; 13.E.175.229;
13.E.175.230; 13.E.175.231; 13.E.175.236; 13.E.175.237; 13.E.175.238; 13.E.175.239;
13.E.175.154; 13.E.175.157; 13.E.175.166; 13.E.175.169; 13.E.175.172; 13.E.175.175;
13.E.175.240; 13.E.175.244; 13.E.240.228; 13.E.240.229; 13.E.240.230; 13.E.240.231;
13.E.240.236; 13.E.240.237; 13.E.240.238; 13.E.240.239; 13.E.240.154; 13.E.240.157;
13.E.240.166; 13.E.240.169; 13.E.240.172; 13.E.240.175; 13.E.240.240; 13.E.240.244;
13.E.244.228; 13.E.244.229; 13.E.244.230; 13.E.244.231; 13.E.244.236; 13.E.244.237;
13.E.244.238; 13.E.244.239; 13.E.244.154; 13.E.244.157; 13.E.244.166; 13.E.244.169;
13.E.244.172; 13.E.244.175; 13.E.244.240; 13.E.244.244;
Prodrugs of 13.G 13.G.228.228; 13.G.228.229; 13.G.228.230; 13.G.228.231; 13.G.228.236; 13.G.228.237;
13.G.228.238; 13.G.228.239; 13.G.228.154; 13.G.228.157; 13.G.228.166; 13.G.228.169;
13.G.228.172; 13.G.228.175; 13.G.228.240; 13.G.228.244; 13.G.229.228; 13.G.229.229;
13.G.229.230; 13.G.229.231; 13.G.229.236; 13.G.229.237; 13.G.229.238; 13.G.229.239;
13.G.229.154; 13.G.229.157; 13.G.229.166; 13.G.229.169; 13.G.229.172; 13.G.229.175;
13.G.229.240; 13.G.229.244; 13.G.230.228; 13.G.230.229; 13.G.230.230; 13.G.230.231;
13.G.230.236; 13.G.230.237; 13.G.230.238; 13.G.230.239; 13.G.230.154; 13.G.230.157;
13.G.230.166; 13.G.230.169; 13.G.230.172; 13.G.230.175; 13.G.230.240; 13.G.230.244;
13.G.231.228; 13.G.231.229; 13.G.231.230; 13.G.231.231; 13.G.231.236; 13.G.231.237;
13.G.231.238; 13.G.231.239; 13.G.231.154; 13.G.231.157; 13.G.231.166; 13.G.231.169;
13.G.231.172; 13.G.231.175; 13.G.231.240; 13.G.231.244; 13.G.236.228; 13.G.236.229;
13.G.236.230; 13.G.236.231; 13.G.236.236; 13.G.236.237; 13.G.236.238; 13.G.236.239;
13.G.236.154; 13.G.236.157; 13.G.236.166; 13.G.236.169; 13.G.236.172; 13.G.236.175;
13.G.236.240; 13.G.236.244; 13.G.237.228; 13.G.237.229; 13.G.237.230; 13.G.237.231;
13.G.237.236; 13.G.237.237; 13.G.237.238; 13.G.237.239; 13.G.237.154; 13.G.237.157;
13.G.237.166; 13.G.237.169; 13.G.237.172; 13.G.237.175; 13.G.237.240; 13.G.237.244;
13.G.238.228; 13.G.238.229; 13.G.238.230; 13.G.238.231; 13.G.238.236; 13.G.238.237;
13.G.238.238; 13.G.238.239; 13.G.238.154; 13.G.238.157; 13.G.238.166; 13.G.238.169;
13.G.238.172; 13.G.238.175; 13.G.238.240; 13.G.238.244; 13.G.239.228; 13.G.239.229;
13.G.239.230; 13.G.239.231; 13.G.239.236; 13.G.239.237; 13.G.239.238; 13.G.239.239;
13.G.239.154; 13.G.239.157; 13.G.239.166; 13.G.239.169; 13.G.239.172; 13.G.239.175;
13.G.239.240; 13.G.239.244; 13.G.154.228; 13.G.154.229; 13.G.154.230; 13.G.154.231;
13.G.154.236; 13.G.154.237; 13.G.154.238; 13.G.154.239; 13.G.154.154; 13.G.154.157;
13.G.154.166; 13.G.154.169; 13.G.154.172; 13.G.154.175; 13.G.154.240; 13.G.154.244;
13.G.157.228; 13.G.157.229; 13.G.157.230; 13.G.157.231; 13.G.157.236; 13.G.157.237;
13.G.157.238; 13.G.157.239; 13.G.157.154; 13.G.157.157; 13.G.157.166; 13.G.157.169;
13.G.157.172; 13.G.157.175; 13.G.157.240; 13.G.157.244; 13.G.166.228; 13.G.166.229;
13.G.166.230; 13.G.166.231; 13.G.166.236; 13.G.166.237; 13.G.166.238; 13.G.166.239;
13.G.166.154; 13.G.166.157; 13.G.166.166; 13.G.166.169; 13.G.166.172; 13.G.166.175;

TABLE 100-continued

13.G.166.240; 13.G.166.244; 13.G.169.228; 13.G.169.229; 13.G.169.230; 13.G.169.231;
13.G.169.236; 13.G.169.237; 13.G.169.238; 13.G.169.239; 13.G.169.154; 13.G.169.157;
13.G.169.166; 13.G.169.169; 13.G.169.172; 13.G.169.175; 13.G.169.240; 13.G.169.244;
13.G.172.228; 13.G.172.229; 13.G.172.230; 13.G.172.231; 13.G.172.236; 13.G.172.237;
13.G.172.238; 13.G.172.239; 13.G.172.154; 13.G.172.157; 13.G.172.166; 13.G.172.169;
13.G.172.172; 13.G.172.175; 13.G.172.240; 13.G.172.244; 13.G.175.228; 13.G.175.229;
13.G.175.230; 13.G.175.231; 13.G.175.236; 13.G.175.237; 13.G.175.238; 13.G.175.239;
13.G.175.154; 13.G.175.157; 13.G.175.166; 13.G.175.169; 13.G.175.172; 13.G.175.175;
13.G.175.240; 13.G.175.244; 13.G.240.228; 13.G.240.229; 13.G.240.230; 13.G.240.231;
13.G.240.236; 13.G.240.237; 13.G.240.238; 13.G.240.239; 13.G.240.154; 13.G.240.157;
13.G.240.166; 13.G.240.169; 13.G.240.172; 13.G.240.175; 13.G.240.240; 13.G.240.244;
13.G.244.228; 13.G.244.229; 13.G.244.230; 13.G.244.231; 13.G.244.236; 13.G.244.237;
13.G.244.238; 13.G.244.239; 13.G.244.154; 13.G.244.157; 13.G.244.166; 13.G.244.169;
13.G.244.172; 13.G.244.175; 13.G.244.240; 13.G.244.244;
Prodrugs of 13.I 13.I.228.228; 13.I.228.229; 13.I.228.230; 13.I.228.231; 13.I.228.236; 13.I.228.237;
13.I.228.238; 13.I.228.239; 13.I.228.154; 13.I.228.157; 13.I.228.166; 13.I.228.169; 13.I.228.172;
13.I.228.175; 13.I.228.240; 13.I.228.244; 13.I.229.228; 13.I.229.229; 13.I.229.230; 13.I.229.231;
13.I.229.236; 13.I.229.237; 13.I.229.238; 13.I.229.239; 13.I.229.154; 13.I.229.157; 13.I.229.166;
13.I.229.169; 13.I.229.172; 13.I.229.175; 13.I.229.240; 13.I.229.244; 13.I.230.228; 13.I.230.229;
13.I.230.230; 13.I.230.231; 13.I.230.236; 13.I.230.237; 13.I.230.238; 13.I.230.239; 13.I.230.154;
13.I.230.157; 13.I.230.166; 13.I.230.169; 13.I.230.172; 13.I.230.175; 13.I.230.240; 13.I.230.244;
13.I.231.228; 13.I.231.229; 13.I.231.230; 13.I.231.231; 13.I.231.236; 13.I.231.237; 13.I.231.238;
13.I.231.239; 13.I.231.154; 13.I.231.157; 13.I.231.166; 13.I.231.169; 13.I.231.172; 13.I.231.175;
13.I.231.240; 13.I.231.244; 13.I.236.228; 13.I.236.229; 13.I.236.230; 13.I.236.231; 13.I.236.236;
13.I.236.237; 13.I.236.238; 13.I.236.239; 13.I.236.154; 13.I.236.157; 13.I.236.166; 13.I.236.169;
13.I.236.172; 13.I.236.175; 13.I.236.240; 13.I.236.244; 13.I.237.228; 13.I.237.229; 13.I.237.230;
13.I.237.231; 13.I.237.236; 13.I.237.237; 13.I.237.238; 13.I.237.239; 13.I.237.154; 13.I.237.157;
13.I.237.166; 13.I.237.169; 13.I.237.172; 13.I.237.175; 13.I.237.240; 13.I.237.244; 13.I.238.228;
13.I.238.229; 13.I.238.230; 13.I.238.231; 13.I.238.236; 13.I.238.237; 13.I.238.238; 13.I.238.239;
13.I.238.154; 13.I.238.157; 13.I.238.166; 13.I.238.169; 13.I.238.172; 13.I.238.175; 13.I.238.240;
13.I.238.244; 13.I.239.228; 13.I.239.229; 13.I.239.230; 13.I.239.231; 13.I.239.236; 13.I.239.237;
13.I.239.238; 13.I.239.239; 13.I.239.154; 13.I.239.157; 13.I.239.166; 13.I.239.169; 13.I.239.172;
13.I.239.175; 13.I.239.240; 13.I.239.244; 13.I.154.228; 13.I.154.229; 13.I.154.230; 13.I.154.231;
13.I.154.236; 13.I.154.237; 13.I.154.238; 13.I.154.239; 13.I.154.154; 13.I.154.157; 13.I.154.166;
13.I.154.169; 13.I.154.172; 13.I.154.175; 13.I.154.240; 13.I.154.244; 13.I.157.228; 13.I.157.229;
13.I.157.230; 13.I.157.231; 13.I.157.236; 13.I.157.237; 13.I.157.238; 13.I.157.239; 13.I.157.154;
13.I.157.157; 13.I.157.166; 13.I.157.169; 13.I.157.172; 13.I.157.175; 13.I.157.240; 13.I.157.244;
13.I.166.228; 13.I.166.229; 13.I.166.230; 13.I.166.231; 13.I.166.236; 13.I.166.237; 13.I.166.238;
13.I.166.239; 13.I.166.154; 13.I.166.157; 13.I.166.166; 13.I.166.169; 13.I.166.172; 13.I.166.175;
13.I.166.240; 13.I.166.244; 13.I.169.228; 13.I.169.229; 13.I.169.230; 13.I.169.231; 13.I.169.236;
13.I.169.237; 13.I.169.238; 13.I.169.239; 13.I.169.154; 13.I.169.157; 13.I.169.166; 13.I.169.169;
13.I.169.172; 13.I.169.175; 13.I.169.240; 13.I.169.244; 13.I.172.228; 13.I.172.229; 13.I.172.230;
13.I.172.231; 13.I.172.236; 13.I.172.237; 13.I.172.238; 13.I.172.239; 13.I.172.154; 13.I.172.157;
13.I.172.166; 13.I.172.169; 13.I.172.172; 13.I.172.175; 13.I.172.240; 13.I.172.244; 13.I.175.228;
13.I.175.229; 13.I.175.230; 13.I.175.231; 13.I.175.236; 13.I.175.237; 13.I.175.238; 13.I.175.239;
13.I.175.154; 13.I.175.157; 13.I.175.166; 13.I.175.169; 13.I.175.172; 13.I.175.175; 13.I.175.240;
13.I.175.244; 13.I.240.228; 13.I.240.229; 13.I.240.230; 13.I.240.231; 13.I.240.236; 13.I.240.237;
13.I.240.238; 13.I.240.239; 13.I.240.154; 13.I.240.157; 13.I.240.166; 13.I.240.169; 13.I.240.172;
13.I.240.175; 13.I.240.240; 13.I.240.244; 13.I.244.228; 13.I.244.229; 13.I.244.230; 13.I.244.231;
13.I.244.236; 13.I.244.237; 13.I.244.238; 13.I.244.239; 13.I.244.154; 13.I.244.157; 13.I.244.166;
13.I.244.169; 13.I.244.172; 13.I.244.175; 13.I.244.240; 13.I.244.244;
Prodrugs of 13.J 13.J.228.228; 13.J.228.229; 13.J.228.230; 13.J.228.231; 13.J.228.236; 13.J.228.237;
13.J.228.238; 13.J.228.239; 13.J.228.154; 13.J.228.157; 13.J.228.166; 13.J.228.169; 13.J.228.172;
13.J.228.175; 13.J.228.240; 13.J.228.244; 13.J.229.228; 13.J.229.229; 13.J.229.230; 13.J.229.231;
13.J.229.236; 13.J.229.237; 13.J.229.238; 13.J.229.239; 13.J.229.154; 13.J.229.157; 13.J.229.166;
13.J.229.169; 13.J.229.172; 13.J.229.175; 13.J.229.240; 13.J.229.244; 13.J.230.228; 13.J.230.229;
13.J.230.230; 13.J.230.231; 13.J.230.236; 13.J.230.237; 13.J.230.238; 13.J.230.239; 13.J.230.154;
13.J.230.157; 13.J.230.166; 13.J.230.169; 13.J.230.172; 13.J.230.175; 13.J.230.240; 13.J.230.244;
13.J.231.228; 13.J.231.229; 13.J.231.230; 13.J.231.231; 13.J.231.236; 13.J.231.237; 13.J.231.238;
13.J.231.239; 13.J.231.154; 13.J.231.157; 13.J.231.166; 13.J.231.169; 13.J.231.172; 13.J.231.175;
13.J.231.240; 13.J.231.244; 13.J.236.228; 13.J.236.229; 13.J.236.230; 13.J.236.231; 13.J.236.236;
13.J.236.237; 13.J.236.238; 13.J.236.239; 13.J.236.154; 13.J.236.157; 13.J.236.166; 13.J.236.169;
13.J.236.172; 13.J.236.175; 13.J.236.240; 13.J.236.244; 13.J.237.228; 13.J.237.229; 13.J.237.230;
13.J.237.231; 13.J.237.236; 13.J.237.237; 13.J.237.238; 13.J.237.239; 13.J.237.154; 13.J.237.157;
13.J.237.166; 13.J.237.169; 13.J.237.172; 13.J.237.175; 13.J.237.240; 13.J.237.244; 13.J.238.228;
13.J.238.229; 13.J.238.230; 13.J.238.231; 13.J.238.236; 13.J.238.237; 13.J.238.238; 13.J.238.239;
13.J.238.154; 13.J.238.157; 13.J.238.166; 13.J.238.169; 13.J.238.172; 13.J.238.175; 13.J.238.240;
13.J.238.244; 13.J.239.228; 13.J.239.229; 13.J.239.230; 13.J.239.231; 13.J.239.236; 13.J.239.237;
13.J.239.238; 13.J.239.239; 13.J.239.154; 13.J.239.157; 13.J.239.166; 13.J.239.169; 13.J.239.172;
13.J.239.175; 13.J.239.240; 13.J.239.244; 13.J.154.228; 13.J.154.229; 13.J.154.230; 13.J.154.231;
13.J.154.236; 13.J.154.237; 13.J.154.238; 13.J.154.239; 13.J.154.154; 13.J.154.157; 13.J.154.166;
13.J.154.169; 13.J.154.172; 13.J.154.175; 13.J.154.240; 13.J.154.244; 13.J.157.228; 13.J.157.229;
13.J.157.230; 13.J.157.231; 13.J.157.236; 13.J.157.237; 13.J.157.238; 13.J.157.239; 13.J.157.154;
13.J.157.157; 13.J.157.166; 13.J.157.169; 13.J.157.172; 13.J.157.175; 13.J.157.240; 13.J.157.244;
13.J.166.228; 13.J.166.229; 13.J.166.230; 13.J.166.231; 13.J.166.236; 13.J.166.237; 13.J.166.238;

TABLE 100-continued

13.J.166.239; 13.J.166.154; 13.J.166.157; 13.J.166.166; 13.J.166.169; 13.J.166.172; 13.J.166.175;
13.J.166.240; 13.J.166.244; 13.J.169.228; 13.J.169.229; 13.J.169.230; 13.J.169.231; 13.J.169.236;
13.J.169.237; 13.J.169.238; 13.J.169.239; 13.J.169.154; 13.J.169.157; 13.J.169.166; 13.J.169.169;
13.J.169.172; 13.J.169.175; 13.J.169.240; 13.J.169.244; 13.J.172.228; 13.J.172.229; 13.J.172.230;
13.J.172.231; 13.J.172.236; 13.J.172.237; 13.J.172.238; 13.J.172.239; 13.J.172.154; 13.J.172.157;
13.J.172.166; 13.J.172.169; 13.J.172.172; 13.J.172.175; 13.J.172.240; 13.J.172.244; 13.J.175.228;
13.J.175.229; 13.J.175.230; 13.J.175.231; 13.J.175.236; 13.J.175.237; 13.J.175.238; 13.J.175.239;
13.J.175.154; 13.J.175.157; 13.J.175.166; 13.J.175.169; 13.J.175.172; 13.J.175.175; 13.J.175.240;
13.J.175.244; 13.J.240.228; 13.J.240.229; 13.J.240.230; 13.J.240.231; 13.J.240.236; 13.J.240.237;
13.J.240.238; 13.J.240.239; 13.J.240.154; 13.J.240.157; 13.J.240.166; 13.J.240.169; 13.J.240.172;
13.J.240.175; 13.J.240.240; 13.J.240.244; 13.J.244.228; 13.J.244.229; 13.J.244.230; 13.J.244.231;
13.J.244.236; 13.J.244.237; 13.J.244.238; 13.J.244.239; 13.J.244.154; 13.J.244.157; 13.J.244.166;
13.J.244.169; 13.J.244.172; 13.J.244.175; 13.J.244.240; 13.J.244.244;

Prodrugs of 13.L

13.L.228.228; 13.L.228.229; 13.L.228.230; 13.L.228.231; 13.L.228.236; 13.L.228.237;
13.L.228.238; 13.L.228.239; 13.L.228.154; 13.L.228.157; 13.L.228.166; 13.L.228.169;
13.L.228.172; 13.L.228.175; 13.L.228.240; 13.L.228.244; 13.L.229.228; 13.L.229.229;
13.L.229.230; 13.L.229.231; 13.L.229.236; 13.L.229.237; 13.L.229.238; 13.L.229.239;
13.L.229.154; 13.L.229.157; 13.L.229.166; 13.L.229.169; 13.L.229.172; 13.L.229.175;
13.L.229.240; 13.L.229.244; 13.L.230.228; 13.L.230.229; 13.L.230.230; 13.L.230.231;
13.L.230.236; 13.L.230.237; 13.L.230.238; 13.L.230.239; 13.L.230.154; 13.L.230.157;
13.L.230.166; 13.L.230.169; 13.L.230.172; 13.L.230.175; 13.L.230.240; 13.L.230.244;
13.L.231.228; 13.L.231.229; 13.L.231.230; 13.L.231.231; 13.L.231.236; 13.L.231.237;
13.L.231.238; 13.L.231.239; 13.L.231.154; 13.L.231.157; 13.L.231.166; 13.L.231.169;
13.L.231.172; 13.L.231.175; 13.L.231.240; 13.L.231.244; 13.L.236.228; 13.L.236.229;
13.L.236.230; 13.L.236.231; 13.L.236.236; 13.L.236.237; 13.L.236.238; 13.L.236.239;
13.L.236.154; 13.L.236.157; 13.L.236.166; 13.L.236.169; 13.L.236.172; 13.L.236.175;
13.L.236.240; 13.L.236.244; 13.L.237.228; 13.L.237.229; 13.L.237.230; 13.L.237.231;
13.L.237.236; 13.L.237.237; 13.L.237.238; 13.L.237.239; 13.L.237.154; 13.L.237.157;
13.L.237.166; 13.L.237.169; 13.L.237.172; 13.L.237.175; 13.L.237.240; 13.L.237.244;
13.L.238.228; 13.L.238.229; 13.L.238.230; 13.L.238.231; 13.L.238.236; 13.L.238.237;
13.L.238.238; 13.L.238.239; 13.L.238.154; 13.L.238.157; 13.L.238.166; 13.L.238.169;
13.L.238.172; 13.L.238.175; 13.L.238.240; 13.L.238.244; 13.L.239.228; 13.L.239.229;
13.L.239.230; 13.L.239.231; 13.L.239.236; 13.L.239.237; 13.L.239.238; 13.L.239.239;
13.L.239.154; 13.L.239.157; 13.L.239.166; 13.L.239.169; 13.L.239.172; 13.L.239.175;
13.L.239.240; 13.L.239.244; 13.L.154.228; 13.L.154.229; 13.L.154.230; 13.L.154.231;
13.L.154.236; 13.L.154.237; 13.L.154.238; 13.L.154.239; 13.L.154.154; 13.L.154.157;
13.L.154.166; 13.L.154.169; 13.L.154.172; 13.L.154.175; 13.L.154.240; 13.L.154.244;
13.L.157.228; 13.L.157.229; 13.L.157.230; 13.L.157.231; 13.L.157.236; 13.L.157.237;
13.L.157.238; 13.L.157.239; 13.L.157.154; 13.L.157.157; 13.L.157.166; 13.L.157.169;
13.L.157.172; 13.L.157.175; 13.L.157.240; 13.L.157.244; 13.L.166.228; 13.L.166.229;
13.L.166.230; 13.L.166.231; 13.L.166.236; 13.L.166.237; 13.L.166.238; 13.L.166.239;
13.L.166.154; 13.L.166.157; 13.L.166.166; 13.L.166.169; 13.L.166.172; 13.L.166.175;
13.L.166.240; 13.L.166.244; 13.L.169.228; 13.L.169.229; 13.L.169.230; 13.L.169.231;
13.L.169.236; 13.L.169.237; 13.L.169.238; 13.L.169.239; 13.L.169.154; 13.L.169.157;
13.L.169.166; 13.L.169.169; 13.L.169.172; 13.L.169.175; 13.L.169.240; 13.L.169.244;
13.L.172.228; 13.L.172.229; 13.L.172.230; 13.L.172.231; 13.L.172.236; 13.L.172.237;
13.L.172.238; 13.L.172.239; 13.L.172.154; 13.L.172.157; 13.L.172.166; 13.L.172.169;
13.L.172.172; 13.L.172.175; 13.L.172.240; 13.L.172.244; 13.L.175.228; 13.L.175.229;
13.L.175.230; 13.L.175.231; 13.L.175.236; 13.L.175.237; 13.L.175.238; 13.L.175.239;
13.L.175.154; 13.L.175.157; 13.L.175.166; 13.L.175.169; 13.L.175.172; 13.L.175.175;
13.L.175.240; 13.L.175.244; 13.L.240.228; 13.L.240.229; 13.L.240.230; 13.L.240.231;
13.L.240.236; 13.L.240.237; 13.L.240.238; 13.L.240.239; 13.L.240.154; 13.L.240.157;
13.L.240.166; 13.L.240.169; 13.L.240.172; 13.L.240.175; 13.L.240.240; 13.L.240.244;
13.L.244.228; 13.L.244.229; 13.L.244.230; 13.L.244.231; 13.L.244.236; 13.L.244.237;
13.L.244.238; 13.L.244.239; 13.L.244.154; 13.L.244.157; 13.L.244.166; 13.L.244.169;
13.L.244.172; 13.L.244.175; 13.L.244.240; 13.L.244.244;

Prodrugs of 13.O

13.O.228.228; 13.O.228.229; 13.O.228.230; 13.O.228.231; 13.O.228.236; 13.O.228.237;
13.O.228.238; 13.O.228.239; 13.O.228.154; 13.O.228.157; 13.O.228.166; 13.O.228.169;
13.O.228.172; 13.O.228.175; 13.O.228.240; 13.O.228.244; 13.O.229.228; 13.O.229.229;
13.O.229.230; 13.O.229.231; 13.O.229.236; 13.O.229.237; 13.O.229.238; 13.O.229.239;
13.O.229.154; 13.O.229.157; 13.O.229.166; 13.O.229.169; 13.O.229.172; 13.O.229.175;
13.O.229.240; 13.O.229.244; 13.O.230.228; 13.O.230.229; 13.O.230.230; 13.O.230.231;
13.O.230.236; 13.O.230.237; 13.O.230.238; 13.O.230.239; 13.O.230.154; 13.O.230.157;
13.O.230.166; 13.O.230.169; 13.O.230.172; 13.O.230.175; 13.O.230.240; 13.O.230.244;
13.O.231.228; 13.O.231.229; 13.O.231.230; 13.O.231.231; 13.O.231.236; 13.O.231.237;
13.O.231.238; 13.O.231.239; 13.O.231.154; 13.O.231.157; 13.O.231.166; 13.O.231.169;
13.O.231.172; 13.O.231.175; 13.O.231.240; 13.O.231.244; 13.O.236.228; 13.O.236.229;
13.O.236.230; 13.O.236.231; 13.O.236.236; 13.O.236.237; 13.O.236.238; 13.O.236.239;
13.O.236.154; 13.O.236.157; 13.O.236.166; 13.O.236.169; 13.O.236.172; 13.O.236.175;
13.O.236.240; 13.O.236.244; 13.O.237.228; 13.O.237.229; 13.O.237.230; 13.O.237.231;
13.O.237.236; 13.O.237.237; 13.O.237.238; 13.O.237.239; 13.O.237.154; 13.O.237.157;
13.O.237.166; 13.O.237.169; 13.O.237.172; 13.O.237.175; 13.O.237.240; 13.O.237.244;
13.O.238.228; 13.O.238.229; 13.O.238.230; 13.O.238.231; 13.O.238.236; 13.O.238.237;
13.O.238.238; 13.O.238.239; 13.O.238.154; 13.O.238.157; 13.O.238.166; 13.O.238.169;
13.O.238.172; 13.O.238.175; 13.O.238.240; 13.O.238.244; 13.O.239.228; 13.O.239.229;

TABLE 100-continued

13.O.239.230; 13.O.239.231; 13.O.239.236; 13.O.239.237; 13.O.239.238; 13.O.239.239;
13.O.239.154; 13.O.239.157; 13.O.239.166; 13.O.239.169; 13.O.239.172; 13.O.239.175;
13.O.239.240; 13.O.239.244; 13.O.154.228; 13.O.154.229; 13.O.154.230; 13.O.154.231;
13.O.154.236; 13.O.154.237; 13.O.154.238; 13.O.154.239; 13.O.154.154; 13.O.154.157;
13.O.154.166; 13.O.154.169; 13.O.154.172; 13.O.154.175; 13.O.154.240; 13.O.154.244;
13.O.157.228; 13.O.157.229; 13.O.157.230; 13.O.157.231; 13.O.157.236; 13.O.157.237;
13.O.157.238; 13.O.157.239; 13.O.157.154; 13.O.157.157; 13.O.157.166; 13.O.157.169;
13.O.157.172; 13.O.157.175; 13.O.157.240; 13.O.157.244; 13.O.166.228; 13.O.166.229;
13.O.166.230; 13.O.166.231; 13.O.166.236; 13.O.166.237; 13.O.166.238; 13.O.166.239;
13.O.166.154; 13.O.166.157; 13.O.166.166; 13.O.166.169; 13.O.166.172; 13.O.166.175;
13.O.166.240; 13.O.166.244; 13.O.169.228; 13.O.169.229; 13.O.169.230; 13.O.169.231;
13.O.169.236; 13.O.169.237; 13.O.169.238; 13.O.169.239; 13.O.169.154; 13.O.169.157;
13.O.169.166; 13.O.169.169; 13.O.169.172; 13.O.169.175; 13.O.169.240; 13.O.169.244;
13.O.172.228; 13.O.172.229; 13.O.172.230; 13.O.172.231; 13.O.172.236; 13.O.172.237;
13.O.172.238; 13.O.172.239; 13.O.172.154; 13.O.172.157; 13.O.172.166; 13.O.172.169;
13.O.172.172; 13.O.172.175; 13.O.172.240; 13.O.172.244; 13.O.175.228; 13.O.175.229;
13.O.175.230; 13.O.175.231; 13.O.175.236; 13.O.175.237; 13.O.175.238; 13.O.175.239;
13.O.175.154; 13.O.175.157; 13.O.175.166; 13.O.175.169; 13.O.175.172; 13.O.175.175;
13.O.175.240; 13.O.175.244; 13.O.240.228; 13.O.240.229; 13.O.240.230; 13.O.240.231;
13.O.240.236; 13.O.240.237; 13.O.240.238; 13.O.240.239; 13.O.240.154; 13.O.240.157;
13.O.240.166; 13.O.240.169; 13.O.240.172; 13.O.240.175; 13.O.240.240; 13.O.240.244;
13.O.244.228; 13.O.244.229; 13.O.244.230; 13.O.244.231; 13.O.244.236; 13.O.244.237;
13.O.244.238; 13.O.244.239; 13.O.244.154; 13.O.244.157; 13.O.244.166; 13.O.244.169;
13.O.244.172; 13.O.244.175; 13.O.244.240; 13.O.244.244;
Prodrugs of 13.P 13.P.228.228; 13.P.228.229; 13.P.228.230; 13.P.228.231; 13.P.228.236; 13.P.228.237;
13.P.228.238; 13.P.228.239; 13.P.228.154; 13.P.228.157; 13.P.228.166; 13.P.228.169;
13.P.228.172; 13.P.228.175; 13.P.228.240; 13.P.228.244; 13.P.229.228; 13.P.229.229;
13.P.229.230; 13.P.229.231; 13.P.229.236; 13.P.229.237; 13.P.229.238; 13.P.229.239;
13.P.229.154; 13.P.229.157; 13.P.229.166; 13.P.229.169; 13.P.229.172; 13.P.229.175;
13.P.229.240; 13.P.229.244; 13.P.230.228; 13.P.230.229; 13.P.230.230; 13.P.230.231;
13.P.230.236; 13.P.230.237; 13.P.230.238; 13.P.230.239; 13.P.230.154; 13.P.230.157;
13.P.230.166; 13.P.230.169; 13.P.230.172; 13.P.230.175; 13.P.230.240; 13.P.230.244;
13.P.231.228; 13.P.231.229; 13.P.231.230; 13.P.231.231; 13.P.231.236; 13.P.231.237;
13.P.231.238; 13.P.231.239; 13.P.231.154; 13.P.231.157; 13.P.231.166; 13.P.231.169;
13.P.231.172; 13.P.231.175; 13.P.231.240; 13.P.231.244; 13.P.236.228; 13.P.236.229;
13.P.236.230; 13.P.236.231; 13.P.236.236; 13.P.236.237; 13.P.236.238; 13.P.236.239;
13.P.236.154; 13.P.236.157; 13.P.236.166; 13.P.236.169; 13.P.236.172; 13.P.236.175;
13.P.236.240; 13.P.236.244; 13.P.237.228; 13.P.237.229; 13.P.237.230; 13.P.237.231;
13.P.237.236; 13.P.237.237; 13.P.237.238; 13.P.237.239; 13.P.237.154; 13.P.237.157;
13.P.237.166; 13.P.237.169; 13.P.237.172; 13.P.237.175; 13.P.237.240; 13.P.237.244;
13.P.238.228; 13.P.238.229; 13.P.238.230; 13.P.238.231; 13.P.238.236; 13.P.238.237;
13.P.238.238; 13.P.238.239; 13.P.238.154; 13.P.238.157; 13.P.238.166; 13.P.238.169;
13.P.238.172; 13.P.238.175; 13.P.238.240; 13.P.238.244; 13.P.239.228; 13.P.239.229;
13.P.239.230; 13.P.239.231; 13.P.239.236; 13.P.239.237; 13.P.239.238; 13.P.239.239;
13.P.239.154; 13.P.239.157; 13.P.239.166; 13.P.239.169; 13.P.239.172; 13.P.239.175;
13.P.239.240; 13.P.239.244; 13.P.154.228; 13.P.154.229; 13.P.154.230; 13.P.154.231;
13.P.154.236; 13.P.154.237; 13.P.154.238; 13.P.154.239; 13.P.154.154; 13.P.154.157;
13.P.154.166; 13.P.154.169; 13.P.154.172; 13.P.154.175; 13.P.154.240; 13.P.154.244;
13.P.157.228; 13.P.157.229; 13.P.157.230; 13.P.157.231; 13.P.157.236; 13.P.157.237;
13.P.157.238; 13.P.157.239; 13.P.157.154; 13.P.157.157; 13.P.157.166; 13.P.157.169;
13.P.157.172; 13.P.157.175; 13.P.157.240; 13.P.157.244; 13.P.166.228; 13.P.166.229;
13.P.166.230; 13.P.166.231; 13.P.166.236; 13.P.166.237; 13.P.166.238; 13.P.166.239;
13.P.166.154; 13.P.166.157; 13.P.166.166; 13.P.166.169; 13.P.166.172; 13.P.166.175;
13.P.166.240; 13.P.166.244; 13.P.169.228; 13.P.169.229; 13.P.169.230; 13.P.169.231;
13.P.169.236; 13.P.169.237; 13.P.169.238; 13.P.169.239; 13.P.169.154; 13.P.169.157;
13.P.169.166; 13.P.169.169; 13.P.169.172; 13.P.169.175; 13.P.169.240; 13.P.169.244;
13.P.172.228; 13.P.172.229; 13.P.172.230; 13.P.172.231; 13.P.172.236; 13.P.172.237;
13.P.172.238; 13.P.172.239; 13.P.172.154; 13.P.172.157; 13.P.172.166; 13.P.172.169;
13.P.172.172; 13.P.172.175; 13.P.172.240; 13.P.172.244; 13.P.175.228; 13.P.175.229;
13.P.175.230; 13.P.175.231; 13.P.175.236; 13.P.175.237; 13.P.175.238; 13.P.175.239;
13.P.175.154; 13.P.175.157; 13.P.175.166; 13.P.175.169; 13.P.175.172; 13.P.175.175;
13.P.175.240; 13.P.175.244; 13.P.240.228; 13.P.240.229; 13.P.240.230; 13.P.240.231;
13.P.240.236; 13.P.240.237; 13.P.240.238; 13.P.240.239; 13.P.240.154; 13.P.240.157;
13.P.240.166; 13.P.240.169; 13.P.240.172; 13.P.240.175; 13.P.240.240; 13.P.240.244;
13.P.244.228; 13.P.244.229; 13.P.244.230; 13.P.244.231; 13.P.244.236; 13.P.244.237;
13.P.244.238; 13.P.244.239; 13.P.244.154; 13.P.244.157; 13.P.244.166; 13.P.244.169;
13.P.244.172; 13.P.244.175; 13.P.244.240; 13.P.244.244;
Prodrugs of 13.U 13.U.228.228; 13.U.228.229; 13.U.228.230; 13.U.228.231; 13.U.228.236; 13.U.228.237;
13.U.228.238; 13.U.228.239; 13.U.228.154; 13.U.228.157; 13.U.228.166; 13.U.228.169;
13.U.228.172; 13.U.228.175; 13.U.228.240; 13.U.228.244; 13.U.229.228; 13.U.229.229;
13.U.229.230; 13.U.229.231; 13.U.229.236; 13.U.229.237; 13.U.229.238; 13.U.229.239;
13.U.229.154; 13.U.229.157; 13.U.229.166; 13.U.229.169; 13.U.229.172; 13.U.229.175;
13.U.229.240; 13.U.229.244; 13.U.230.228; 13.U.230.229; 13.U.230.230; 13.U.230.231;
13.U.230.236; 13.U.230.237; 13.U.230.238; 13.U.230.239; 13.U.230.154; 13.U.230.157;
13.U.230.166; 13.U.230.169; 13.U.230.172; 13.U.230.175; 13.U.230.240; 13.U.230.244;

TABLE 100-continued

13.U.231.228; 13.U.231.229; 13.U.231.230; 13.U.231.231; 13.U.231.236; 13.U.231.237;
13.U.231.238; 13.U.231.239; 13.U.231.154; 13.U.231.157; 13.U.231.166; 13.U.231.169;
13.U.231.172; 13.U.231.175; 13.U.231.240; 13.U.231.244; 13.U.236.228; 13.U.236.229;
13.U.236.230; 13.U.236.231; 13.U.236.236; 13.U.236.237; 13.U.236.238; 13.U.236.239;
13.U.236.154; 13.U.236.157; 13.U.236.166; 13.U.236.169; 13.U.236.172; 13.U.236.175;
13.U.236.240; 13.U.236.244; 13.U.237.228; 13.U.237.229; 13.U.237.230; 13.U.237.231;
13.U.237.236; 13.U.237.237; 13.U.237.238; 13.U.237.239; 13.U.237.154; 13.U.237.157;
13.U.237.166; 13.U.237.169; 13.U.237.172; 13.U.237.175; 13.U.237.240; 13.U.237.244;
13.U.238.228; 13.U.238.229; 13.U.238.230; 13.U.238.231; 13.U.238.236; 13.U.238.237;
13.U.238.238; 13.U.238.239; 13.U.238.154; 13.U.238.157; 13.U.238.166; 13.U.238.169;
13.U.238.172; 13.U.238.175; 13.U.238.240; 13.U.238.244; 13.U.239.228; 13.U.239.229;
13.U.239.230; 13.U.239.231; 13.U.239.236; 13.U.239.237; 13.U.239.238; 13.U.239.239;
13.U.239.154; 13.U.239.157; 13.U.239.166; 13.U.239.169; 13.U.239.172; 13.U.239.175;
13.U.239.240; 13.U.239.244; 13.U.154.228; 13.U.154.229; 13.U.154.230; 13.U.154.231;
13.U.154.236; 13.U.154.237; 13.U.154.238; 13.U.154.239; 13.U.154.154; 13.U.154.157;
13.U.154.166; 13.U.154.169; 13.U.154.172; 13.U.154.175; 13.U.154.240; 13.U.154.244;
13.U.157.228; 13.U.157.229; 13.U.157.230; 13.U.157.231; 13.U.157.236; 13.U.157.237;
13.U.157.238; 13.U.157.239; 13.U.157.154; 13.U.157.157; 13.U.157.166; 13.U.157.169;
13.U.157.172; 13.U.157.175; 13.U.157.240; 13.U.157.244; 13.U.166.228; 13.U.166.229;
13.U.166.230; 13.U.166.231; 13.U.166.236; 13.U.166.237; 13.U.166.238; 13.U.166.239;
13.U.166.154; 13.U.166.157; 13.U.166.166; 13.U.166.169; 13.U.166.172; 13.U.166.175;
13.U.166.240; 13.U.166.244; 13.U.169.228; 13.U.169.229; 13.U.169.230; 13.U.169.231;
13.U.169.236; 13.U.169.237; 13.U.169.238; 13.U.169.239; 13.U.169.154; 13.U.169.157;
13.U.169.166; 13.U.169.169; 13.U.169.172; 13.U.169.175; 13.U.169.240; 13.U.169.244;
13.U.172.228; 13.U.172.229; 13.U.172.230; 13.U.172.231; 13.U.172.236; 13.U.172.237;
13.U.172.238; 13.U.172.239; 13.U.172.154; 13.U.172.157; 13.U.172.166; 13.U.172.169;
13.U.172.172; 13.U.172.175; 13.U.172.240; 13.U.172.244; 13.U.175.228; 13.U.175.229;
13.U.175.230; 13.U.175.231; 13.U.175.236; 13.U.175.237; 13.U.175.238; 13.U.175.239;
13.U.175.154; 13.U.175.157; 13.U.175.166; 13.U.175.169; 13.U.175.172; 13.U.175.175;
13.U.175.240; 13.U.175.244; 13.U.240.228; 13.U.240.229; 13.U.240.230; 13.U.240.231;
13.U.240.236; 13.U.240.237; 13.U.240.238; 13.U.240.239; 13.U.240.154; 13.U.240.157;
13.U.240.166; 13.U.240.169; 13.U.240.172; 13.U.240.175; 13.U.240.240; 13.U.240.244;
13.U.244.228; 13.U.244.229; 13.U.244.230; 13.U.244.231; 13.U.244.236; 13.U.244.237;
13.U.244.238; 13.U.244.239; 13.U.244.154; 13.U.244.157; 13.U.244.166; 13.U.244.169;
13.U.244.172; 13.U.244.175; 13.U.244.240; 13.U.244.244;
Prodrugs of 13.W 13.W.228.228; 13.W.228.229; 13.W.228.230; 13.W.228.231; 13.W.228.236; 13.W.228.237;
13.W.228.238; 13.W.228.239; 13.W.228.154; 13.W.228.157; 13.W.228.166; 13.W.228.169;
13.W.228.172; 13.W.228.175; 13.W.228.240; 13.W.228.244; 13.W.229.228; 13.W.229.229;
13.W.229.230; 13.W.229.231; 13.W.229.236; 13.W.229.237; 13.W.229.238; 13.W.229.239;
13.W.229.154; 13.W.229.157; 13.W.229.166; 13.W.229.169; 13.W.229.172; 13.W.229.175;
13.W.229.240; 13.W.229.244; 13.W.230.228; 13.W.230.229; 13.W.230.230; 13.W.230.231;
13.W.230.236; 13.W.230.237; 13.W.230.238; 13.W.230.239; 13.W.230.154; 13.W.230.157;
13.W.230.166; 13.W.230.169; 13.W.230.172; 13.W.230.175; 13.W.230.240; 13.W.230.244;
13.W.231.228; 13.W.231.229; 13.W.231.230; 13.W.231.231; 13.W.231.236; 13.W.231.237;
13.W.231.238; 13.W.231.239; 13.W.231.154; 13.W.231.157; 13.W.231.166; 13.W.231.169;
13.W.231.172; 13.W.231.175; 13.W.231.240; 13.W.231.244; 13.W.236.228; 13.W.236.229;
13.W.236.230; 13.W.236.231; 13.W.236.236; 13.W.236.237; 13.W.236.238; 13.W.236.239;
13.W.236.154; 13.W.236.157; 13.W.236.166; 13.W.236.169; 13.W.236.172; 13.W.236.175;
13.W.236.240; 13.W.236.244; 13.W.237.228; 13.W.237.229; 13.W.237.230; 13.W.237.231;
13.W.237.236; 13.W.237.237; 13.W.237.238; 13.W.237.239; 13.W.237.154; 13.W.237.157;
13.W.237.166; 13.W.237.169; 13.W.237.172; 13.W.237.175; 13.W.237.240; 13.W.237.244;
13.W.238.228; 13.W.238.229; 13.W.238.230; 13.W.238.231; 13.W.238.236; 13.W.238.237;
13.W.238.238; 13.W.238.239; 13.W.238.154; 13.W.238.157; 13.W.238.166; 13.W.238.169;
13.W.238.172; 13.W.238.175; 13.W.238.240; 13.W.238.244; 13.W.239.228; 13.W.239.229;
13.W.239.230; 13.W.239.231; 13.W.239.236; 13.W.239.237; 13.W.239.238; 13.W.239.239;
13.W.239.154; 13.W.239.157; 13.W.239.166; 13.W.239.169; 13.W.239.172; 13.W.239.175;
13.W.239.240; 13.W.239.244; 13.W.154.228; 13.W.154.229; 13.W.154.230; 13.W.154.231;
13.W.154.236; 13.W.154.237; 13.W.154.238; 13.W.154.239; 13.W.154.154; 13.W.154.157;
13.W.154.166; 13.W.154.169; 13.W.154.172; 13.W.154.175; 13.W.154.240; 13.W.154.244;
13.W.157.228; 13.W.157.229; 13.W.157.230; 13.W.157.231; 13.W.157.236; 13.W.157.237;
13.W.157.238; 13.W.157.239; 13.W.157.154; 13.W.157.157; 13.W.157.166; 13.W.157.169;
13.W.157.172; 13.W.157.175; 13.W.157.240; 13.W.157.244; 13.W.166.228; 13.W.166.229;
13.W.166.230; 13.W.166.231; 13.W.166.236; 13.W.166.237; 13.W.166.238; 13.W.166.239;
13.W.166.154; 13.W.166.157; 13.W.166.166; 13.W.166.169; 13.W.166.172; 13.W.166.175;
13.W.166.240; 13.W.166.244; 13.W.169.228; 13.W.169.229; 13.W.169.230; 13.W.169.231;
13.W.169.236; 13.W.169.237; 13.W.169.238; 13.W.169.239; 13.W.169.154; 13.W.169.157;
13.W.169.166; 13.W.169.169; 13.W.169.172; 13.W.169.175; 13.W.169.240; 13.W.169.244;
13.W.172.228; 13.W.172.229; 13.W.172.230; 13.W.172.231; 13.W.172.236; 13.W.172.237;
13.W.172.238; 13.W.172.239; 13.W.172.154; 13.W.172.157; 13.W.172.166; 13.W.172.169;
13.W.172.172; 13.W.172.175; 13.W.172.240; 13.W.172.244; 13.W.175.228; 13.W.175.229;
13.W.175.230; 13.W.175.231; 13.W.175.236; 13.W.175.237; 13.W.175.238; 13.W.175.239;
13.W.175.154; 13.W.175.157; 13.W.175.166; 13.W.175.169; 13.W.175.172; 13.W.175.175;
13.W.175.240; 13.W.175.244; 13.W.240.228; 13.W.240.229; 13.W.240.230; 13.W.240.231;
13.W.240.236; 13.W.240.237; 13.W.240.238; 13.W.240.239; 13.W.240.154; 13.W.240.157;
13.W.240.166; 13.W.240.169; 13.W.240.172; 13.W.240.175; 13.W.240.240; 13.W.240.244;
13.W.244.228; 13.W.244.229; 13.W.244.230; 13.W.244.231; 13.W.244.236; 13.W.244.237;

TABLE 100-continued

13.W.244.238; 13.W.244.239; 13.W.244.154; 13.W.244.157; 13.W.244.166; 13.W.244.169;
13.W.244.172; 13.W.244.175; 13.W.244.240; 13.W.244.244;
Prodrugs of 13.Y 13.Y.228.228; 13.Y.228.229; 13.Y.228.230; 13.Y.228.231; 13.Y.228.236; 13.Y.228.237;
13.Y.228.238; 13.Y.228.239; 13.Y.228.154; 13.Y.228.157; 13.Y.228.166; 13.Y.228.169;
13.Y.228.172; 13.Y.228.175; 13.Y.228.240; 13.Y.228.244; 13.Y.229.228; 13.Y.229.229;
13.Y.229.230; 13.Y.229.231; 13.Y.229.236; 13.Y.229.237; 13.Y.229.238; 13.Y.229.239;
13.Y.229.154; 13.Y.229.157; 13.Y.229.166; 13.Y.229.169; 13.Y.229.172; 13.Y.229.175;
13.Y.229.240; 13.Y.229.244; 13.Y.230.228; 13.Y.230.229; 13.Y.230.230; 13.Y.230.231;
13.Y.230.236; 13.Y.230.237; 13.Y.230.238; 13.Y.230.239; 13.Y.230.154; 13.Y.230.157;
13.Y.230.166; 13.Y.230.169; 13.Y.230.172; 13.Y.230.175; 13.Y.230.240; 13.Y.230.244;
13.Y.231.228; 13.Y.231.229; 13.Y.231.230; 13.Y.231.231; 13.Y.231.236; 13.Y.231.237;
13.Y.231.238; 13.Y.231.239; 13.Y.231.154; 13.Y.231.157; 13.Y.231.166; 13.Y.231.169;
13.Y.231.172; 13.Y.231.175; 13.Y.231.240; 13.Y.231.244; 13.Y.236.228; 13.Y.236.229;
13.Y.236.230; 13.Y.236.231; 13.Y.236.236; 13.Y.236.237; 13.Y.236.238; 13.Y.236.239;
13.Y.236.154; 13.Y.236.157; 13.Y.236.166; 13.Y.236.169; 13.Y.236.172; 13.Y.236.175;
13.Y.236.240; 13.Y.236.244; 13.Y.237.228; 13.Y.237.229; 13.Y.237.230; 13.Y.237.231;
13.Y.237.236; 13.Y.237.237; 13.Y.237.238; 13.Y.237.239; 13.Y.237.154; 13.Y.237.157;
13.Y.237.166; 13.Y.237.169; 13.Y.237.172; 13.Y.237.175; 13.Y.237.240; 13.Y.237.244;
13.Y.238.228; 13.Y.238.229; 13.Y.238.230; 13.Y.238.231; 13.Y.238.236; 13.Y.238.237;
13.Y.238.238; 13.Y.238.239; 13.Y.238.154; 13.Y.238.157; 13.Y.238.166; 13.Y.238.169;
13.Y.238.172; 13.Y.238.175; 13.Y.238.240; 13.Y.238.244; 13.Y.239.228; 13.Y.239.229;
13.Y.239.230; 13.Y.239.231; 13.Y.239.236; 13.Y.239.237; 13.Y.239.238; 13.Y.239.239;
13.Y.239.154; 13.Y.239.157; 13.Y.239.166; 13.Y.239.169; 13.Y.239.172; 13.Y.239.175;
13.Y.239.240; 13.Y.239.244; 13.Y.154.228; 13.Y.154.229; 13.Y.154.230; 13.Y.154.231;
13.Y.154.236; 13.Y.154.237; 13.Y.154.238; 13.Y.154.239; 13.Y.154.154; 13.Y.154.157;
13.Y.154.166; 13.Y.154.169; 13.Y.154.172; 13.Y.154.175; 13.Y.154.240; 13.Y.154.244;
13.Y.157.228; 13.Y.157.229; 13.Y.157.230; 13.Y.157.231; 13.Y.157.236; 13.Y.157.237;
13.Y.157.238; 13.Y.157.239; 13.Y.157.154; 13.Y.157.157; 13.Y.157.166; 13.Y.157.169;
13.Y.157.172; 13.Y.157.175; 13.Y.157.240; 13.Y.157.244; 13.Y.166.228; 13.Y.166.229;
13.Y.166.230; 13.Y.166.231; 13.Y.166.236; 13.Y.166.237; 13.Y.166.238; 13.Y.166.239;
13.Y.166.154; 13.Y.166.157; 13.Y.166.166; 13.Y.166.169; 13.Y.166.172; 13.Y.166.175;
13.Y.166.240; 13.Y.166.244; 13.Y.169.228; 13.Y.169.229; 13.Y.169.230; 13.Y.169.231;
13.Y.169.236; 13.Y.169.237; 13.Y.169.238; 13.Y.169.239; 13.Y.169.154; 13.Y.169.157;
13.Y.169.166; 13.Y.169.169; 13.Y.169.172; 13.Y.169.175; 13.Y.169.240; 13.Y.169.244;
13.Y.172.228; 13.Y.172.229; 13.Y.172.230; 13.Y.172.231; 13.Y.172.236; 13.Y.172.237;
13.Y.172.238; 13.Y.172.239; 13.Y.172.154; 13.Y.172.157; 13.Y.172.166; 13.Y.172.169;
13.Y.172.172; 13.Y.172.175; 13.Y.172.240; 13.Y.172.244; 13.Y.175.228; 13.Y.175.229;
13.Y.175.230; 13.Y.175.231; 13.Y.175.236; 13.Y.175.237; 13.Y.175.238; 13.Y.175.239;
13.Y.175.154; 13.Y.175.157; 13.Y.175.166; 13.Y.175.169; 13.Y.175.172; 13.Y.175.175;
13.Y.175.240; 13.Y.175.244; 13.Y.240.228; 13.Y.240.229; 13.Y.240.230; 13.Y.240.231;
13.Y.240.236; 13.Y.240.237; 13.Y.240.238; 13.Y.240.239; 13.Y.240.154; 13.Y.240.157;
13.Y.240.166; 13.Y.240.169; 13.Y.240.172; 13.Y.240.175; 13.Y.240.240; 13.Y.240.244;
13.Y.244.228; 13.Y.244.229; 13.Y.244.230; 13.Y.244.231; 13.Y.244.236; 13.Y.244.237;
13.Y.244.238; 13.Y.244.239; 13.Y.244.154; 13.Y.244.157; 13.Y.244.166; 13.Y.244.169;
13.Y.244.172; 13.Y.244.175; 13.Y.244.240; 13.Y.244.244;
Prodrugs of 14.AH 14.AH.4.157; 14.AH.4.158; 14.AH.4.196; 14.AH.4.223; 14.AH.4.240; 14.AH.4.244;
14.AH.4.243; 14.AH.4.247; 14.AH.5.157; 14.AH.5.158; 14.AH.5.196; 14.AH.5.223;
14.AH.5.240; 14.AH.5.244; 14.AH.5.243; 14.AH.5.247; 14.AH.7.157; 14.AH.7.158;
14.AH.7.196; 14.AH.7.223; 14.AH.7.240; 14.AH.7.244; 14.AH.7.243; 14.AH.7.247;
14.AH.15.157; 14.AH.15.158; 14.AH.15.196; 14.AH.15.223; 14.AH.15.240; 14.AH.15.244;
14.AH.15.243; 14.AH.15.247; 14.AH.16.157; 14.AH.16.158; 14.AH.16.196; 14.AH.16.223;
14.AH.16.240; 14.AH.16.244; 14.AH.16.243; 14.AH.16.247; 14.AH.18.157; 14.AH.18.158;
14.AH.18.196; 14.AH.18.223; 14.AH.18.240; 14.AH.18.244; 14.AH.18.243; 14.AH.18.247;
14.AH.26.157; 14.AH.26.158; 14.AH.26.196; 14.AH.26.223; 14.AH.26.240; 14.AH.26.244;
14.AH.26.243; 14.AH.26.247; 14.AH.27.157; 14.AH.27.158; 14.AH.27.196; 14.AH.27.223;
14.AH.27.240; 14.AH.27.244; 14.AH.27.243; 14.AH.27.247; 14.AH.29.157; 14.AH.29.158;
14.AH.29.196; 14.AH.29.223; 14.AH.29.240; 14.AH.29.244; 14.AH.29.243; 14.AH.29.247;
14.AH.54.157; 14.AH.54.158; 14.AH.54.196; 14.AH.54.223; 14.AH.54.240; 14.AH.54.244;
14.AH.54.243; 14.AH.54.247; 14.AH.55.157; 14.AH.55.158; 14.AH.55.196; 14.AH.55.223;
14.AH.55.240; 14.AH.55.244; 14.AH.55.243; 14.AH.55.247; 14.AH.56.157; 14.AH.56.158;
14.AH.56.196; 14.AH.56.223; 14.AH.56.240; 14.AH.56.244; 14.AH.56.243; 14.AH.56.247;
14.AH.157.157; 14.AH.157.158; 14.AH.157.196; 14.AH.157.223; 14.AH.157.240;
14.AH.157.244; 14.AH.157.243; 14.AH.157.247; 14.AH.196.157; 14.AH.196.158;
14.AH.196.196; 14.AH.196.223; 14.AH.196.240; 14.AH.196.244; 14.AH.196.243;
14.AH.196.247; 14.AH.223.157; 14.AH.223.158; 14.AH.223.196; 14.AH.223.223;
14.AH.223.240; 14.AH.223.244; 14.AH.223.243; 14.AH.223.247; 14.AH.240.157;
14.AH.240.158; 14.AH.240.196; 14.AH.240.223; 14.AH.240.240; 14.AH.240.244;
14.AH.240.243; 14.AH.240.247; 14.AH.244.157; 14.AH.244.158; 14.AH.244.196;
14.AH.244.223; 14.AH.244.240; 14.AH.244.244; 14.AH.244.243; 14.AH.244.247;
14.AH.247.157; 14.AH.247.158; 14.AH.247.196; 14.AH.247.223; 14.AH.247.240;
14.AH.247.244; 14.AH.247.243; 14.AH.247.247;
Prodrugs of 14.AJ 14.AJ.4.157; 14.AJ.4.158; 14.AJ.4.196; 14.AJ.4.223; 14.AJ.4.240; 14.AJ.4.244; 14.AJ.4.243;
14.AJ.4.247; 14.AJ.5.157; 14.AJ.5.158; 14.AJ.5.196; 14.AJ.5.223; 14.AJ.5.240; 14.AJ.5.244;

TABLE 100-continued

14.AJ.5.243; 14.AJ.5.247; 14.AJ.7.157; 14.AJ.7.158; 14.AJ.7.196; 14.AJ.7.223; 14.AJ.7.240;
14.AJ.7.244; 14.AJ.7.243; 14.AJ.7.247; 14.AJ.15.157; 14.AJ.15.158; 14.AJ.15.196;
14.AJ.15.223; 14.AJ.15.240; 14.AJ.15.244; 14.AJ.15.243; 14.AJ.15.247; 14.AJ.16.157;
14.AJ.16.158; 14.AJ.16.196; 14.AJ.16.223; 14.AJ.16.240; 14.AJ.16.244; 14.AJ.16.243;
14.AJ.16.247; 14.AJ.18.157; 14.AJ.18.158; 14.AJ.18.196; 14.AJ.18.223; 14.AJ.18.240;
14.AJ.18.244; 14.AJ.18.243; 14.AJ.18.247; 14.AJ.26.157; 14.AJ.26.158; 14.AJ.26.196;
14.AJ.26.223; 14.AJ.26.240; 14.AJ.26.244; 14.AJ.26.243; 14.AJ.26.247; 14.AJ.27.157;
14.AJ.27.158; 14.AJ.27.196; 14.AJ.27.223; 14.AJ.27.240; 14.AJ.27.244; 14.AJ.27.243;
14.AJ.27.247; 14.AJ.29.157; 14.AJ.29.158; 14.AJ.29.196; 14.AJ.29.223; 14.AJ.29.240;
14.AJ.29.244; 14.AJ.29.243; 14.AJ.29.247; 14.AJ.54.157; 14.AJ.54.158; 14.AJ.54.196;
14.AJ.54.223; 14.AJ.54.240; 14.AJ.54.244; 14.AJ.54.243; 14.AJ.54.247; 14.AJ.55.157;
14.AJ.55.158; 14.AJ.55.196; 14.AJ.55.223; 14.AJ.55.240; 14.AJ.55.244; 14.AJ.55.243;
14.AJ.55.247; 14.AJ.56.157; 14.AJ.56.158; 14.AJ.56.196; 14.AJ.56.223; 14.AJ.56.240;
14.AJ.56.244; 14.AJ.56.243; 14.AJ.56.247; 14.AJ.157.157; 14.AJ.157.158; 14.AJ.157.196;
14.AJ.157.223; 14.AJ.157.240; 14.AJ.157.244; 14.AJ.157.243; 14.AJ.157.247; 14.AJ.196.157;
14.AJ.196.158; 14.AJ.196.196; 14.AJ.196.223; 14.AJ.196.240; 14.AJ.196.244; 14.AJ.196.243;
14.AJ.196.247; 14.AJ.223.157; 14.AJ.223.158; 14.AJ.223.196; 14.AJ.223.223; 14.AJ.223.240;
14.AJ.223.244; 14.AJ.223.243; 14.AJ.223.247; 14.AJ.240.157; 14.AJ.240.158; 14.AJ.240.196;
14.AJ.240.223; 14.AJ.240.240; 14.AJ.240.244; 14.AJ.240.243; 14.AJ.240.247; 14.AJ.244.157;
14.AJ.244.158; 14.AJ.244.196; 14.AJ.244.223; 14.AJ.244.240; 14.AJ.244.244; 14.AJ.244.243;
14.AJ.244.247; 14.AJ.247.157; 14.AJ.247.158; 14.AJ.247.196; 14.AJ.247.223; 14.AJ.247.240;
14.AJ.247.244; 14.AJ.247.243; 14.AJ.247.247;
Prodrugs of 14.AN 14.AN.4.157; 14.AN.4.158; 14.AN.4.196; 14.AN.4.223; 14.AN.4.240; 14.AN.4.244;
14.AN.4.243; 14.AN.4.247; 14.AN.5.157; 14.AN.5.158; 14.AN.5.196; 14.AN.5.223;
14.AN.5.240; 14.AN.5.244; 14.AN.5.243; 14.AN.5.247; 14.AN.7.157; 14.AN.7.158;
14.AN.7.196; 14.AN.7.223; 14.AN.7.240; 14.AN.7.244; 14.AN.7.243; 14.AN.7.247;
14.AN.15.157; 14.AN.15.158; 14.AN.15.196; 14.AN.15.223; 14.AN.15.240; 14.AN.15.244;
14.AN.15.243; 14.AN.15.247; 14.AN.16.157; 14.AN.16.158; 14.AN.16.196; 14.AN.16.223;
14.AN.16.240; 14.AN.16.244; 14.AN.16.243; 14.AN.16.247; 14.AN.18.157; 14.AN.18.158;
14.AN.18.196; 14.AN.18.223; 14.AN.18.240; 14.AN.18.244; 14.AN.18.243; 14.AN.18.247;
14.AN.26.157; 14.AN.26.158; 14.AN.26.196; 14.AN.26.223; 14.AN.26.240; 14.AN.26.244;
14.AN.26.243; 14.AN.26.247; 14.AN.27.157; 14.AN.27.158; 14.AN.27.196; 14.AN.27.223;
14.AN.27.240; 14.AN.27.244; 14.AN.27.243; 14.AN.27.247; 14.AN.29.157; 14.AN.29.158;
14.AN.29.196; 14.AN.29.223; 14.AN.29.240; 14.AN.29.244; 14.AN.29.243; 14.AN.29.247;
14.AN.54.157; 14.AN.54.158; 14.AN.54.196; 14.AN.54.223; 14.AN.54.240; 14.AN.54.244;
14.AN.54.243; 14.AN.54.247; 14.AN.55.157; 14.AN.55.158; 14.AN.55.196; 14.AN.55.223;
14.AN.55.240; 14.AN.55.244; 14.AN.55.243; 14.AN.55.247; 14.AN.56.157; 14.AN.56.158;
14.AN.56.196; 14.AN.56.223; 14.AN.56.240; 14.AN.56.244; 14.AN.56.243; 14.AN.56.247;
14.AN.157.157; 14.AN.157.158; 14.AN.157.196; 14.AN.157.223; 14.AN.157.240;
14.AN.157.244; 14.AN.157.243; 14.AN.157.247; 14.AN.196.157; 14.AN.196.158;
14.AN.196.196; 14.AN.196.223; 14.AN.196.240; 14.AN.196.244; 14.AN.196.243;
14.AN.196.247; 14.AN.223.157; 14.AN.223.158; 14.AN.223.196; 14.AN.223.223;
14.AN.223.240; 14.AN.223.244; 14.AN.223.243; 14.AN.223.247; 14.AN.240.157;
14.AN.240.158; 14.AN.240.196; 14.AN.240.223; 14.AN.240.240; 14.AN.240.244;
14.AN.240.243; 14.AN.240.247; 14.AN.244.157; 14.AN.244.158; 14.AN.244.196;
14.AN.244.223; 14.AN.244.240; 14.AN.244.244; 14.AN.244.243; 14.AN.244.247;
14.AN.247.157; 14.AN.247.158; 14.AN.247.196; 14.AN.247.223; 14.AN.247.240;
14.AN.247.244; 14.AN.247.243; 14.AN.247.247;
Prodrugs of 14.AP 14.AP.4.157; 14.AP.4.158; 14.AP.4.196; 14.AP.4.223; 14.AP.4.240; 14.AP.4.244;
14.AP.4.243; 14.AP.4.247; 14.AP.5.157; 14.AP.5.158; 14.AP.5.196; 14.AP.5.223; 14.AP.5.240;
14.AP.5.244; 14.AP.5.243; 14.AP.5.247; 14.AP.7.157; 14.AP.7.158; 14.AP.7.196; 14.AP.7.223;
14.AP.7.240; 14.AP.7.244; 14.AP.7.243; 14.AP.7.247; 14.AP.15.157; 14.AP.15.158;
14.AP.15.196; 14.AP.15.223; 14.AP.15.240; 14.AP.15.244; 14.AP.15.243; 14.AP.15.247;
14.AP.16.157; 14.AP.16.158; 14.AP.16.196; 14.AP.16.223; 14.AP.16.240; 14.AP.16.244;
14.AP.16.243; 14.AP.16.247; 14.AP.18.157; 14.AP.18.158; 14.AP.18.196; 14.AP.18.223;
14.AP.18.240; 14.AP.18.244; 14.AP.18.243; 14.AP.18.247; 14.AP.26.157; 14.AP.26.158;
14.AP.26.196; 14.AP.26.223; 14.AP.26.240; 14.AP.26.244; 14.AP.26.243; 14.AP.26.247;
14.AP.27.157; 14.AP.27.158; 14.AP.27.196; 14.AP.27.223; 14.AP.27.240; 14.AP.27.244;
14.AP.27.243; 14.AP.27.247; 14.AP.29.157; 14.AP.29.158; 14.AP.29.196; 14.AP.29.223;
14.AP.29.240; 14.AP.29.244; 14.AP.29.243; 14.AP.29.247; 14.AP.54.157; 14.AP.54.158;
14.AP.54.196; 14.AP.54.223; 14.AP.54.240; 14.AP.54.244; 14.AP.54.243; 14.AP.54.247;
14.AP.55.157; 14.AP.55.158; 14.AP.55.196; 14.AP.55.223; 14.AP.55.240; 14.AP.55.244;
14.AP.55.243; 14.AP.55.247; 14.AP.56.157; 14.AP.56.158; 14.AP.56.196; 14.AP.56.223;
14.AP.56.240; 14.AP.56.244; 14.AP.56.243; 14.AP.56.247; 14.AP.157.157; 14.AP.157.158;
14.AP.157.196; 14.AP.157.223; 14.AP.157.240; 14.AP.157.244; 14.AP.157.243;
14.AP.157.247; 14.AP.196.157; 14.AP.196.158; 14.AP.196.196; 14.AP.196.223;
14.AP.196.240; 14.AP.196.244; 14.AP.196.243; 14.AP.196.247; 14.AP.223.157;
14.AP.223.158; 14.AP.223.196; 14.AP.223.223; 14.AP.223.240; 14.AP.223.244;
14.AP.223.243; 14.AP.223.247; 14.AP.240.157; 14.AP.240.158; 14.AP.240.196;
14.AP.240.223; 14.AP.240.240; 14.AP.240.244; 14.AP.240.243; 14.AP.240.247;
14.AP.244.157; 14.AP.244.158; 14.AP.244.196; 14.AP.244.223; 14.AP.244.240;
14.AP.244.244; 14.AP.244.243; 14.AP.244.247; 14.AP.247.157; 14.AP.247.158;
14.AP.247.196; 14.AP.247.223; 14.AP.247.240; 14.AP.247.244; 14.AP.247.243;
14.AP.247.247;

TABLE 100-continued

Prodrugs of 14.AZ

14.AZ.4.157; 14.AZ.4.158; 14.AZ.4.196; 14.AZ.4.223; 14.AZ.4.240; 14.AZ.4.244;
14.AZ.4.243; 14.AZ.4.247; 14.AZ.5.157; 14.AZ.5.158; 14.AZ.5.196; 14.AZ.5.223;
14.AZ.5.240; 14.AZ.5.244; 14.AZ.5.243; 14.AZ.5.247; 14.AZ.7.157; 14.AZ.7.158;
14.AZ.7.196; 14.AZ.7.223; 14.AZ.7.240; 14.AZ.7.244; 14.AZ.7.243; 14.AZ.7.247;
14.AZ.15.157; 14.AZ.15.158; 14.AZ.15.196; 14.AZ.15.223; 14.AZ.15.240; 14.AZ.15.244;
14.AZ.15.243; 14.AZ.15.247; 14.AZ.16.157; 14.AZ.16.158; 14.AZ.16.196; 14.AZ.16.223;
14.AZ.16.240; 14.AZ.16.244; 14.AZ.16.243; 14.AZ.16.247; 14.AZ.18.157; 14.AZ.18.158;
14.AZ.18.196; 14.AZ.18.223; 14.AZ.18.240; 14.AZ.18.244; 14.AZ.18.243; 14.AZ.18.247;
14.AZ.26.157; 14.AZ.26.158; 14.AZ.26.196; 14.AZ.26.223; 14.AZ.26.240; 14.AZ.26.244;
14.AZ.26.243; 14.AZ.26.247; 14.AZ.27.157; 14.AZ.27.158; 14.AZ.27.196; 14.AZ.27.223;
14.AZ.27.240; 14.AZ.27.244; 14.AZ.27.243; 14.AZ.27.247; 14.AZ.29.157; 14.AZ.29.158;
14.AZ.29.196; 14.AZ.29.223; 14.AZ.29.240; 14.AZ.29.244; 14.AZ.29.243; 14.AZ.29.247;
14.AZ.54.157; 14.AZ.54.158; 14.AZ.54.196; 14.AZ.54.223; 14.AZ.54.240; 14.AZ.54.244;
14.AZ.54.243; 14.AZ.54.247; 14.AZ.55.157; 14.AZ.55.158; 14.AZ.55.196; 14.AZ.55.223;
14.AZ.55.240; 14.AZ.55.244; 14.AZ.55.243; 14.AZ.55.247; 14.AZ.56.157; 14.AZ.56.158;
14.AZ.56.196; 14.AZ.56.223; 14.AZ.56.240; 14.AZ.56.244; 14.AZ.56.243; 14.AZ.56.247;
14.AZ.157.157; 14.AZ.157.158; 14.AZ.157.196; 14.AZ.157.223; 14.AZ.157.240;
14.AZ.157.244; 14.AZ.157.243; 14.AZ.157.247; 14.AZ.196.157; 14.AZ.196.158;
14.AZ.196.196; 14.AZ.196.223; 14.AZ.196.240; 14.AZ.196.244; 14.AZ.196.243;
14.AZ.196.247; 14.AZ.223.157; 14.AZ.223.158; 14.AZ.223.196; 14.AZ.223.223;
14.AZ.223.240; 14.AZ.223.244; 14.AZ.223.243; 14.AZ.223.247; 14.AZ.240.157;
14.AZ.240.158; 14.AZ.240.196; 14.AZ.240.223; 14.AZ.240.240; 14.AZ.240.244;
14.AZ.240.243; 14.AZ.240.247; 14.AZ.244.157; 14.AZ.244.158; 14.AZ.244.196;
14.AZ.244.223; 14.AZ.244.240; 14.AZ.244.244; 14.AZ.244.243; 14.AZ.244.247;
14.AZ.247.157; 14.AZ.247.158; 14.AZ.247.196; 14.AZ.247.223; 14.AZ.247.240;
14.AZ.247.244; 14.AZ.247.243; 14.AZ.247.247;

Prodrugs of 14.BF

14.BF.4.157; 14.BF.4.158; 14.BF.4.196; 14.BF.4.223; 14.BF.4.240; 14.BF.4.244;
14.BF.4.243; 14.BF.4.247; 14.BF.5.157; 14.BF.5.158; 14.BF.5.196; 14.BF.5.223; 14.BF.5.240;
14.BF.5.244; 14.BF.5.243; 14.BF.5.247; 14.BF.7.157; 14.BF.7.158; 14.BF.7.196; 14.BF.7.223;
14.BF.7.240; 14.BF.7.244; 14.BF.7.243; 14.BF.7.247; 14.BF.15.157; 14.BF.15.158;
14.BF.15.196; 14.BF.15.223; 14.BF.15.240; 14.BF.15.244; 14.BF.15.243; 14.BF.15.247;
14.BF.16.157; 14.BF.16.158; 14.BF.16.196; 14.BF.16.223; 14.BF.16.240; 14.BF.16.244;
14.BF.16.243; 14.BF.16.247; 14.BF.18.157; 14.BF.18.158; 14.BF.18.196; 14.BF.18.223;
14.BF.18.240; 14.BF.18.244; 14.BF.18.243; 14.BF.18.247; 14.BF.26.157; 14.BF.26.158;
14.BF.26.196; 14.BF.26.223; 14.BF.26.240; 14.BF.26.244; 14.BF.26.243; 14.BF.26.247;
14.BF.27.157; 14.BF.27.158; 14.BF.27.196; 14.BF.27.223; 14.BF.27.240; 14.BF.27.244;
14.BF.27.243; 14.BF.27.247; 14.BF.29.157; 14.BF.29.158; 14.BF.29.196; 14.BF.29.223;
14.BF.29.240; 14.BF.29.244; 14.BF.29.243; 14.BF.29.247; 14.BF.54.157; 14.BF.54.158;
14.BF.54.196; 14.BF.54.223; 14.BF.54.240; 14.BF.54.244; 14.BF.54.243; 14.BF.54.247;
14.BF.55.157; 14.BF.55.158; 14.BF.55.196; 14.BF.55.223; 14.BF.55.240; 14.BF.55.244;
14.BF.55.243; 14.BF.55.247; 14.BF.56.157; 14.BF.56.158; 14.BF.56.196; 14.BF.56.223;
14.BF.56.240; 14.BF.56.244; 14.BF.56.243; 14.BF.56.247; 14.BF.157.157; 14.BF.157.158;
14.BF.157.196; 14.BF.157.223; 14.BF.157.240; 14.BF.157.244; 14.BF.157.243; 14.BF.157.247;
14.BF.196.157; 14.BF.196.158; 14.BF.196.196; 14.BF.196.223; 14.BF.196.240; 14.BF.196.244;
14.BF.196.243; 14.BF.196.247; 14.BF.223.157; 14.BF.223.158; 14.BF.223.196; 14.BF.223.223;
14.BF.223.240; 14.BF.223.244; 14.BF.223.243; 14.BF.223.247; 14.BF.240.157; 14.BF.240.158;
14.BF.240.196; 14.BF.240.223; 14.BF.240.240; 14.BF.240.244; 14.BF.240.243; 14.BF.240.247;
14.BF.244.157; 14.BF.244.158; 14.BF.244.196; 14.BF.244.223; 14.BF.244.240; 14.BF.244.244;
14.BF.244.243; 14.BF.244.247; 14.BF.247.157; 14.BF.247.158; 14.BF.247.196; 14.BF.247.223;
14.BF.247.240; 14.BF.247.244; 14.BF.247.243; 14.BF.247.247;

Prodrugs of 14.CI

14.CI.4.157; 14.CI.4.158; 14.CI.4.196; 14.CI.4.223; 14.CI.4.240; 14.CI.4.244; 14.CI.4.243;
14.CI.4.247; 14.CI.5.157; 14.CI.5.158; 14.CI.5.196; 14.CI.5.223; 14.CI.5.240; 14.CI.5.244;
14.CI.5.243; 14.CI.5.247; 14.CI.7.157; 14.CI.7.158; 14.CI.7.196; 14.CI.7.223; 14.CI.7.240;
14.CI.7.244; 14.CI.7.243; 14.CI.7.247; 14.CI.15.157; 14.CI.15.158; 14.CI.15.196; 14.CI.15.223;
14.CI.15.240; 14.CI.15.244; 14.CI.15.243; 14.CI.15.247; 14.CI.16.157; 14.CI.16.158;
14.CI.16.196; 14.CI.16.223; 14.CI.16.240; 14.CI.16.244; 14.CI.16.243; 14.CI.16.247;
14.CI.18.157; 14.CI.18.158; 14.CI.18.196; 14.CI.18.223; 14.CI.18.240; 14.CI.18.244;
14.CI.18.243; 14.CI.18.247; 14.CI.26.157; 14.CI.26.158; 14.CI.26.196; 14.CI.26.223;
14.CI.26.240; 14.CI.26.244; 14.CI.26.243; 14.CI.26.247; 14.CI.27.157; 14.CI.27.158;
14.CI.27.196; 14.CI.27.223; 14.CI.27.240; 14.CI.27.244; 14.CI.27.243; 14.CI.27.247;
14.CI.29.157; 14.CI.29.158; 14.CI.29.196; 14.CI.29.223; 14.CI.29.240; 14.CI.29.244;
14.CI.29.243; 14.CI.29.247; 14.CI.54.157; 14.CI.54.158; 14.CI.54.196; 14.CI.54.223;
14.CI.54.240; 14.CI.54.244; 14.CI.54.243; 14.CI.54.247; 14.CI.55.157; 14.CI.55.158;
14.CI.55.196; 14.CI.55.223; 14.CI.55.240; 14.CI.55.244; 14.CI.55.243; 14.CI.55.247;
14.CI.56.157; 14.CI.56.158; 14.CI.56.196; 14.CI.56.223; 14.CI.56.240; 14.CI.56.244;
14.CI.56.243; 14.CI.56.247; 14.CI.157.157; 14.CI.157.158; 14.CI.157.196; 14.CI.157.223;
14.CI.157.240; 14.CI.157.244; 14.CI.157.243; 14.CI.157.247; 14.CI.196.157; 14.CI.196.158;
14.CI.196.196; 14.CI.196.223; 14.CI.196.240; 14.CI.196.244; 14.CI.196.243; 14.CI.196.247;
14.CI.223.157; 14.CI.223.158; 14.CI.223.196; 14.CI.223.223; 14.CI.223.240; 14.CI.223.244;
14.CI.223.243; 14.CI.223.247; 14.CI.240.157; 14.CI.240.158; 14.CI.240.196; 14.CI.240.223;
14.CI.240.240; 14.CI.240.244; 14.CI.240.243; 14.CI.240.247; 14.CI.244.157; 14.CI.244.158;
14.CI.244.196; 14.CI.244.223; 14.CI.244.240; 14.CI.244.244; 14.CI.244.243; 14.CI.244.247;

TABLE 100-continued

14.CI.247.157; 14.CI.247.158; 14.CI.247.196; 14.CI.247.223; 14.CI.247.240; 14.CI.247.244;
14.CI.247.243; 14.CI.247.247;
Prodrugs of 14.CO 14.CO.4.157; 14.CO.4.158; 14.CO.4.196; 14.CO.4.223; 14.CO.4.240; 14.CO.4.244;
14.CO.4.243; 14.CO.4.247; 14.CO.5.157; 14.CO.5.158; 14.CO.5.196; 14.CO.5.223;
14.CO.5.240; 14.CO.5.244; 14.CO.5.243; 14.CO.5.247; 14.CO.7.157; 14.CO.7.158;
14.CO.7.196; 14.CO.7.223; 14.CO.7.240; 14.CO.7.244; 14.CO.7.243; 14.CO.7.247;
14.CO.15.157; 14.CO.15.158; 14.CO.15.196; 14.CO.15.223; 14.CO.15.240; 14.CO.15.244;
14.CO.15.243; 14.CO.15.247; 14.CO.16.157; 14.CO.16.158; 14.CO.16.196; 14.CO.16.223;
14.CO.16.240; 14.CO.16.244; 14.CO.16.243; 14.CO.16.247; 14.CO.18.157; 14.CO.18.158;
14.CO.18.196; 14.CO.18.223; 14.CO.18.240; 14.CO.18.244; 14.CO.18.243; 14.CO.18.247;
14.CO.26.157; 14.CO.26.158; 14.CO.26.196; 14.CO.26.223; 14.CO.26.240; 14.CO.26.244;
14.CO.26.243; 14.CO.26.247; 14.CO.27.157; 14.CO.27.158; 14.CO.27.196; 14.CO.27.223;
14.CO.27.240; 14.CO.27.244; 14.CO.27.243; 14.CO.27.247; 14.CO.29.157; 14.CO.29.158;
14.CO.29.196; 14.CO.29.223; 14.CO.29.240; 14.CO.29.244; 14.CO.29.243; 14.CO.29.247;
14.CO.54.157; 14.CO.54.158; 14.CO.54.196; 14.CO.54.223; 14.CO.54.240; 14.CO.54.244;
14.CO.54.243; 14.CO.54.247; 14.CO.55.157; 14.CO.55.158; 14.CO.55.196; 14.CO.55.223;
14.CO.55.240; 14.CO.55.244; 14.CO.55.243; 14.CO.55.247; 14.CO.56.157; 14.CO.56.158;
14.CO.56.196; 14.CO.56.223; 14.CO.56.240; 14.CO.56.244; 14.CO.56.243; 14.CO.56.247;
14.CO.157.157; 14.CO.157.158; 14.CO.157.196; 14.CO.157.223; 14.CO.157.240;
14.CO.157.244; 14.CO.157.243; 14.CO.157.247; 14.CO.196.157; 14.CO.196.158;
14.CO.196.196; 14.CO.196.223; 14.CO.196.240; 14.CO.196.244; 14.CO.196.243;
14.CO.196.247; 14.CO.223.157; 14.CO.223.158; 14.CO.223.196; 14.CO.223.223;
14.CO.223.240; 14.CO.223.244; 14.CO.223.243; 14.CO.223.247; 14.CO.240.157;
14.CO.240.158; 14.CO.240.196; 14.CO.240.223; 14.CO.240.240; 14.CO.240.244;
14.CO.240.243; 14.CO.240.247; 14.CO.244.157; 14.CO.244.158; 14.CO.244.196;
14.CO.244.223; 14.CO.244.240; 14.CO.244.244; 14.CO.244.243; 14.CO.244.247; 14.CO.4.157;
14.CO.4.158; 14.CO.4.196; 14.CO.4.223; 14.CO.4.240; 14.CO.4.244; 14.CO.4.243;
14.CO.4.247;

A Cellular Accumulation Embodiment

Another embodiment of the invention is directed toward a non-nucleoside reverse transcriptase inhibitor compound capable of accumulating in human PBMCs. Accumulation in human PBMCs is described in the examples herein. Typically, the compounds of this embodiment further comprise a phosphonate or phosphonate prodrug. More typically, the phosphonate or phosphonate prodrug has the structure $A^3$ as described herein. Each of the preferred embodiments of $A^3$ described herein is a preferred embodiment of $A^3$ in the present embodiment.

Optionally, the compounds of this embodiment demonstrate improved intracellular half-life of the compounds or intracellular metabolites of the compounds in human PBMCs when compared to analogs of the compounds not having the phosphonate or phosphonate prodrug. Typically, the half-life is improved by at least about 50%, more typically at least in the range 50-100%, still more typically at least about 100%, more typically yet greater than about 100%.

In a preferred embodiment, the intracellular half-life of a metabolite of the compound in human PBMCs is improved when compared to an analog of the compound not having the phosphonate or phosphonate prodrug. In such embodiments, the metabolite is typically generated intracellularly, more typically, it is generated within human PBMCs. Still more typically, the metabolite is a product of the cleavage of a phosphonate prodrug within human PBMCs. More typically yet, the phosphonate prodrug is cleaved to form a metabolite having at least one negative charge at physiological pH. Most typically, the phosphonate prodrug is enzymatically cleaved within human PBMCs to form a phosphonate having at least one active hydrogen atom of the form P—OH.

Recursive Substituents

Selected substituents within the compounds of the invention are present to a recursive degree. In this context, "recursive substituent" means that a substituent may recite another instance of itself. Because of the recursive nature of such substituents, theoretically, a large number of compounds may be present in any given embodiment. For example, $R^x$ contains a $R^y$ substituent. $R^y$ can be $R^2$, which in turn can be $R^3$. If $R^3$ is selected to be $R^{3c}$, then a second instance of $R^x$ can be selected. One of ordinary skill in the art of medicinal chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

By way of example and not limitation, $W^3$, $R^y$ and $R^3$ are all recursive substituents in certain embodiments. Typically, each of these may independently occur 20, 19, 18, 17, 16, 15, 14, 13, 12, 11, 10, 9, 8, 7, 6, 5, 4, 3, 2, 1, or 0, times in a given embodiment. More typically, each of these may independently occur 12 or fewer times in a given embodiment. More typically yet, $W^3$ will occur 0 to 8 times, $R^y$ will occur 0 to 6 times and $R^3$ will occur 0 to 10 times in a given embodiment. Even more typically, $W^3$ will occur 0 to 6 times, $R^y$ will occur 0 to 4 times and $R^3$ will occur 0 to 8 times in a given embodiment.

Recursive substituents are an intended aspect of the invention. One of ordinary skill in the art of medicinal chemistry understands the versatility of such substituents. To the degree that recursive substituents are present in an embodiment of the invention, the total number will be determined as set forth above.

Protecting Groups

In the context of the present invention, embodiments of protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PRT" will be dependent upon the chemistry of the reaction to be protected against (e.g., acidic, basic, oxidative, reductive or other conditions) and the intended direction of the synthesis. The PRT groups do not need to be, and generally are not, the same if the compound is substituted with multiple PRT. In general, PRT will be used to protect functional groups such as carboxyl, hydroxyl or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protection. For example, protecting groups for —OH groups (whether hydroxyl, carboxylic acid, phosphonic acid, or other functions) are embodiments of "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in "Protective Groups in Organic Chemistry", Theodora W. Greene (John Wiley & Sons, Inc., New York, 1991, ISBN 0-471-62301-6) ("Greene"). See also Kocienski, Philip J.; "Protecting Groups" (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-forming Protecting Groups

Particularly of interest are ether- or ester-forming groups that are capable of functioning as chemical protecting groups in the synthetic schemes set forth herein. However, some hydroxyl and thio protecting groups are neither ether- nor ester-forming groups, as will be understood by those skilled in the art, and are included with amides, discussed below. Protecting groups capable of protecting hydroxyl or thio groups such that hydrolysis from the parental molecule yields hydroxyl or thio.

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

The phosphonate moieties of the compounds of the invention may or may not be prodrug moieties, i.e. they may or may not be susceptible to hydrolytic or enzymatic cleavage or modification. Certain phosphonate moieties are stable under most or nearly all metabolic conditions. For example, a dialkylphosphonate, where the alkyl groups are two or more carbons, may have appreciable stability in vivo due to a slow rate of hydrolysis.

Within the context of phosphonate prodrug moieties, a large number of structurally-diverse prodrugs have been described for phosphonic acids (Freeman and Ross in *Progress in Medicinal Chemistry* 34: 112-147 (1997) and are included within the scope of the present invention. An exemplary embodiment of a phosphonate ester-forming group is the phenyl carbocycle in substructure $A_3$ having the formula:

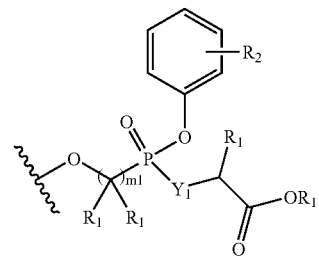

wherein m1 is 1, 2, 3, 4, 5, 6, 7 or 8, and the phenyl carbocycle is substituted with 0 to 3 $R_2$ groups. Also, in this embodiment, where $Y_1$, is O, a lactate ester is formed. Alternatively, where $Y_1$, is $N(R_2)$, $N(OR_2)$ or $N(N(R_2)_2)$, then phosphonamidate esters result. $R_1$ may be H or $C_1$-$C_{12}$ alkyl. The corollary exemplary substructure $A^3$ is included in the invention, with $Y^1$, $R^1$ and $R^2$ substituents.

In its ester-forming role, a protecting group typically is bound to any acidic group such as, by way of example and not limitation, a —$CO_2H$ or —$C(S)OH$ group, thereby resulting in —$CO_2R^x$ where $R^x$ is defined herein. Also, $R^x$ for example includes the enumerated ester groups of WO 95/07920.

Examples of protecting groups include:

$C_3$-$C_{12}$ heterocycle (described above) or aryl. These aromatic groups optionally are polycyclic or monocyclic. Examples include phenyl, spiryl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl;

$C_3$-$C_{12}$ heterocycle or aryl substituted with halo, $R^1$, $R_1$-O-$C_1$-$C_{12}$ alkylene, $C_1$-$C_{12}$ alkoxy, CN, $NO_2$, OH, carboxy, carboxyester, thiol, thioester, $C_1$-$C_{12}$ haloalkyl (1-6 halogen atoms), $C_2$-$C_{12}$ alkenyl or $C_2$-$C_{12}$ alkynyl. Such groups include 2-, 3- and 4-alkoxyphenyl ($C_1$-$C_{12}$ alkyl), 2-, 3- and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl), 2,3-, 2,4-, 2,5-, 2,6-, 3,4- and 3,5-dimethylphenyl, 2,3-, 2,4-, 2,5-, 2,6-, 3,4- and 3,5-biscarboxyethlphenyl, 2,3-, 2,4-, 2,5-, 2,6-, 3,4- and 3,5-dimethoxyphenyl, 2,3-, 2,4-, 2,5-, 2,6-, 3,4-, and 3,5-dihalophenyl (including 2,4-difluorophenyl and 3,5-difluorophenyl), 2-, 3- and 4-haloalkylphenyl (1 to 5 halogen atoms, $C_1$-$C_{12}$ alkyl including 4-trifluoromethylphenyl), 2-, 3- and 4-cyanophenyl, 2-, 3- and 4-nitrophenyl, 2-, 3- and 4-haloalkylbenzyl (1 to 5 halogen atoms, $C_1$-$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, alkylsalicylphenyl ($C_1$-$C_4$ alkyl, including 2-, 3- and 4-ethylsalicylphenyl), 2-,3- and 4- acetylphenyl, 1,8- dihydroxynaphthyl (—$C_{10}H_6$—OH) and aryloxy ethyl [$C_6$-$C_9$ aryl (including phenoxy ethyl)], 2,2'-dihydroxybiphenyl, 2-, 3- and 4-N,N-dialkylaminophenol, —$C_6H_4CH_2$—$N(CH_3)_2$, trimethoxybenzyl, triethoxybenzyl, 2-alkyl pyridinyl ($C_{1-4}$ alkyl);

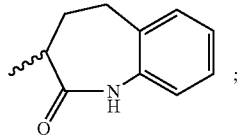

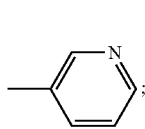

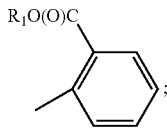

$C_4$-$C_8$ esters of 2-carboxyphenyl; and $C_1$-$C_4$ alkylene-$C_3$-$C_6$ aryl (including benzyl, —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl) substituted in the aryl moiety by 3 to 5 halogen atoms or 1 to 2 atoms or groups selected from halogen, $C_1$-$C_{12}$ alkoxy (including methoxy and ethoxy), cyano, nitro, OH, $C_1$-$C_{12}$ haloalkyl (1 to 6 halogen atoms; including —$CH_2CCl_3$), $C_1$-$C_{12}$ alkyl (including methyl and ethyl), $C_2$-$C_{12}$ alkenyl or $C_2$-$C_{12}$ alkynyl; alkoxy ethyl [$C_1$-$C_6$ alkyl including —$CH_2$—$CH_2$—O—$CH_3$ (methoxy ethyl)]; alkyl substituted by any of the groups set forth above for aryl, in particular OH or by 1 to 3 halo atoms (including —$CH_3$, —$CH(CH_3)_2$, —$C(CH_3)_3$, —$CH_2CH_3$, —$(CH_2)_2CH_3$, —$(CH_2)_3CH_3$, —$(CH_2)_4CH_3$, —$(CH_2)_5CH_3$, —$CH_2CH_2F$, —$CH_2CH_2Cl$, —$CH_2CF_3$, and —$CH_2CCl_3$);

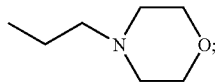

—N-2-propylmorpholino, 2,3-dihydro-6-hydroxyindene, sesamol, catechol monoester, —$CH_2$—C(O)—$N(R^1)_2$, —$CH_2$—$S(O)(R^1)$, —$CH_2$—$S(O)_2(R^1)$, —$CH_2$—CH(OC(O)$CH_2R^1$)—$CH_2(OC(O)CH_2R_1)$, cholesteryl, enolpyruvate (HOOC—C(=$CH_2$)—), glycerol;

a 5 or 6 carbon monosaccharide, disaccharide or oligosaccharide (3 to 9 monosaccharide residues);

triglycerides such as α-D-β-diglycerides (wherein the fatty acids composing glyceride lipids generally are naturally occurring saturated or unsaturated $C_{6-26}$, $C_{6-18}$ or $C_{6-10}$ fatty acid such as linoleic, lauric, myristic, palmitic, stearic, oleic, palmitoleic, linolenic and the like fatty acids) linked to acyl of the parental compounds herein through a glyceryl oxygen of the triglyceride;

phospholipids linked to the carboxyl group through the phosphate of the phospholipid;

phthalidyl (shown in FIG. 1 of Clayton et al., *Antimicrob. Agents Chemo.* (1974) 5(6):670-671;

cyclic carbonates such as (5-$R_d$-2-oxo-1,3-dioxolen-4-yl) methyl esters (Sakamoto et al., *Chem. Pharm. Bull.* (1984) 32(6)2241-2248) where $R_d$ is $R_1$, $R_4$ or aryl; and

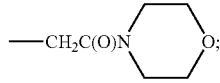

The hydroxyl groups of the compounds of this invention optionally are substituted with one of groups III, IV or V disclosed in WO 94/21604, or with isopropyl.

As further embodiments, Table A lists examples of protecting group ester moieties that for example can be bonded via oxygen to —C(O)O— and —P(O)(O—)$_2$ groups. Several amidates also are shown, which are bound directly to —C(O)— or —P(O)$_2$. Esters of structures 1-5, 8-10 and 16, 17, 19-22 are synthesized by reacting the compound herein having a free hydroxyl with the corresponding halide (chloride or acyl chloride and the like) and N,N-dicyclohexyl-N-morpholine carboxamidine (or another base such as DBU, triethylamine, $CsCO_3$, N,N-dimethylaniline and the like) in DMF (or other solvent such as acetonitrile or N-methylpyrrolidone). When the compound to be protected is a phosphonate, the esters of structures 5-7, 11, 12, 21, and 23-26 are synthesized by reaction of the alcohol or alkoxide salt (or the corresponding amines in the case of compounds such as 13, 14 and 15) with the monochlorophosphonate or dichlorophosphonate (or another activated phosphonate).

TABLE A

1. —$CH_2$—C(O)—$N(R_1)_2$*
2. —$CH_2$-$S(O)(R_1)$
3. —$CH_2$-$S(O)_2(R_1)$
4. —$CH_2$—O—C(O)—$CH_2$—$C_6H_5$
5. 3-cholesteryl
6. 3-pyridyl
7. N-ethylmorpholino
8. —$CH_2$—O—C(O)—$C_6H_5$
9. —$CH_2$—O—C(O)—$CH_2CH_3$
10. —$CH_2$—O—C(O)—$C(CH_3)_3$
11. —$CH_2$—$CCl_3$
12. —$C_6H_5$
13. —NH—$CH_2$—C(O)O—$CH_2CH_3$
14. —$N(CH_3)$—$CH_2$—C(O)O—$CH_2CH_3$
15. —$NHR_1$
16. —$CH_2$—O—C(O)—$C_{10}H_{15}$
17. —$CH_2$—O—C(O)—$CH(CH_3)_2$
18. —$CH_2$—C#H(OC(O)$CH_2R_1$)—$CH_2$—(OC(O)$CH_2R_1$)*
19. 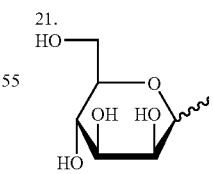
20. 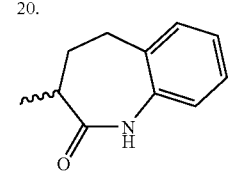
21. 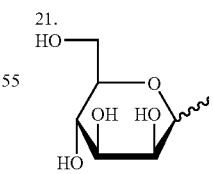
22. 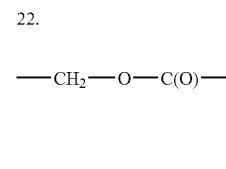
23. 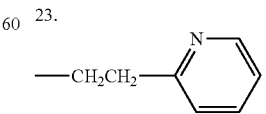
24. 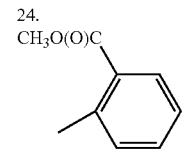
25. 
26.

TABLE A-continued

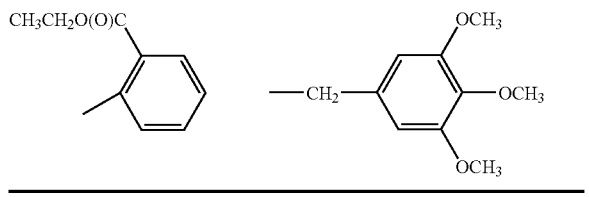

\# - chiral center is (R), (S) or racemate.

Other esters that are suitable for use herein are described in EP Patent No. 632048.

Protecting groups also includes "double ester" forming profunctionalities such as —CH$_2$OC(O)OCH$_3$,

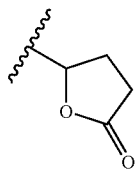

—CH$_2$SCOCH$_3$, —CH$_2$OCON(CH$_3$)$_2$, or alkyl- or aryl-acyloxyalkyl groups of the structure —CH(R$^1$ or W$^5$)O((CO)R$^{37}$) or —CH(R$^1$ or W$^5$)((CO)OR$^{38}$) (linked to oxygen of the acidic group) wherein R$^{37}$ and R$^{38}$ are alkyl, aryl, or alkylaryl groups (see U.S. Pat. No. 4,968,788). Frequently R$^{37}$ and R$^{38}$ are bulky groups such as branched alkyl, ortho-substituted aryl, meta-substituted aryl, or combinations thereof, including normal, secondary, iso- and tertiary alkyls of 1-6 carbon atoms. An example is the pivaloyloxymethyl group. These are of particular use with prodrugs for oral administration. Examples of such useful protecting groups are alkylacyloxymethyl esters and their derivatives, including —CH(CH$_2$CH$_2$OCH$_3$)OC(O)C(CH$_3$)$_3$,

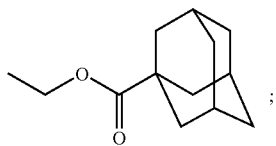

—CH$_2$OC(O)C$_{10}$H$_{15}$, —CH$_2$OC(O)C(CH$_3$)$_3$, —CH(CH$_2$OCH$_3$)OC(O)C(CH$_3$)$_3$, —CH(CH(CH$_3$)$_2$)OC(O)C(CH$_3$)$_3$, —CH$_2$OC(O)CH$_2$CH(CH$_3$)$_2$, —CH$_2$OC(O)C$_6$H$_{11}$, —CH$_2$OC(O)C$_6$H$_5$, —CH$_2$OC(O)C$_{10}$H$_{15}$, —CH$_2$OC(O)CH$_2$CH$_3$, —CH$_2$OC(O)CH(CH$_3$)$_2$, —CH$_2$OC(O)C(CH$_3$)$_3$ and —CH$_2$OC(O)CH$_2$C$_6$H$_5$.

For prodrug purposes, the ester typically chosen is one heretofore used for antibiotic drugs, in particular the cyclic carbonates, double esters, or the phthalidyl, aryl or alkyl esters.

In some embodiments the protected acidic group is an ester of the acidic group and is the residue of a hydroxyl-containing functionality. In other embodiments, an amino compound is used to protect the acid functionality. The residues of suitable hydroxyl or amino-containing functionalities are set forth above or are found in WO 95/07920. Of particular interest are the residues of amino acids, amino acid esters, polypeptides, or aryl alcohols. Typical amino acid, polypeptide and carboxyl-esterified amino acid residues are described on pages 11-18 and related text of WO 95/07920 as groups L1 or L2. WO 95/07920 expressly teaches the amidates of phosphonic acids, but it will be understood that such amidates are formed with any of the acid groups set forth herein and the amino acid residues set forth in WO 95/07920.

Typical esters for protecting acidic functionalities are also described in WO 95/07920, again understanding that the same esters can be formed with the acidic groups herein as with the phosphonate of the '920 publication. Typical ester groups are defined at least on WO 95/07920 pages 89-93 (under R$^{31}$ or R$^{35}$), the table on page 105, and pages 21-23 (as R). Of particular interest are esters of unsubstituted aryl such as phenyl or arylalkyl such benzyl, or hydroxy-, halo-, alkoxy-, carboxy- and/or alkylestercarboxy-substituted aryl or alkylaryl, especially phenyl, ortho-ethoxyphenyl, or C$_1$-C$_4$ alkylestercarboxyphenyl (salicylate C$_1$-C$_{12}$ alkylesters).

The protected acidic groups, particularly when using the esters or amides of WO 95/07920, are useful as prodrugs for oral administration. However, it is not essential that the acidic group be protected in order for the compounds of this invention to be effectively administered by the oral route. When the compounds of the invention having protected groups, in particular amino acid amidates or substituted and unsubstituted aryl esters are administered systemically or orally they are capable of hydrolytic cleavage in vivo to yield the free acid.

One or more of the acidic hydroxyls are protected. If more than one acidic hydroxyl is protected then the same or a different protecting group is employed, e.g., the esters may be different or the same, or a mixed amidate and ester may be used.

Typical hydroxy protecting groups described in Greene (pages 14-118) include substituted methyl and alkyl ethers, substituted benzyl ethers, silyl ethers, esters including sulfonic acid esters, and carbonates. For example:

Ethers (methyl, t-butyl, allyl);

Substituted Methyl Ethers (Methoxymethyl, Methylthiomethyl, t-Butylthiomethyl, (Phenyldimethylsilyl) methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydropthiopyranyl, 1-Methoxycyclohexyl, 4-Methoxytetrahydropyranyl, 4-Methoxytetrahydrothiopyranyl, 4-Methoxytetrahydropthiopyranyl S,S-Dioxido, 1-[(2-Chloro-4-methyl) phenyl]-4-methoxypiperidin-4-yl, 1,4-Dioxan-2-yl, Tetrahydrofuranyl, Tetrahydrothiofuranyl, 2,3,3a,4,5,6, 7,7a-Octahydro-7,8,8-trimethyl-4,7-methanobenzofuran-2-yl));

Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, p-Chlorophenyl, p-Methoxyphenyl, 2,4-Dinitrophenyl, Benzyl);

Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, α-Naphthyldiphenylmethyl, p-methoxyphenyldiphenylmethyl, Di(p-methoxyphenyl)phenylmethyl, Tri(p-methoxyphenyl) methyl, 4-(4'-Bromophenacyloxy)

phenyldiphenylmethyl, 4,4',4"-Tris(4,5-dichlorophthalimidophenyl)methyl, 4,4',4"-Tris(levulinoyloxyphenyl)methyl, 4,4',4"-Tris(benzoyloxyphenyl)methyl, 3-(Imidazol-1-ylmethyl)bis(4',4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido);

Silyl Ethers (Trimethylsilyl, Triethylsilyl, Triisopropylsilyl, Dimethylisopropylsilyl, Diethylisopropylsilyl, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl);

Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate));

Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate);

Groups With Assisted Cleavage (2-Iodobenzoate, 4-Azidobutyrate, 4-Nitro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3tetramethylbutyl)phenoxyacetate, 2,4-Bis(1,1-dimethylpropyl)phenoxyacetate, Chlorodiphenylacetate, Isobutyrate, Monosuccinate, (E)-2-Methyl-2-butenoate (Tigloate), o-(Methoxycarbonyl)benzoate, p-poly-Benzoate, α-Naphthoate Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

Typical 1,2-diol protecting groups (thus, generally where two OH groups are taken together with the protecting functionality) are described in Greene at pages 118-142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table B, still more typically, epoxides, acetonides, cyclic ketals and aryl acetals.

TABLE B

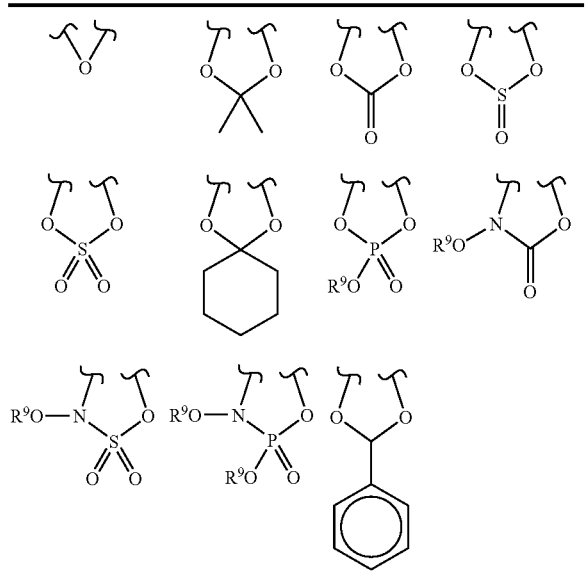

wherein $R^9$ is $C_1$-$C_6$ alkyl.

Amino Protecting Groups

Another set of protecting groups include any of the typical amino protecting groups described by Greene at pages 315-385. They include:

Carbamates: (methyl and ethyl, 9-fluorenylmethyl, 9(2-sulfo)fluorenylmethyl, 9-(2,7-dibromo)fluorenylmethyl, 2,7-di-t-butyl-[9-( 10,10-dioxo- 10,10,10,10-tetrahydrothioxanthyl)]methyl, 4-methoxyphenacyl);

Substituted Ethyl: (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl);

Groups With Assisted Cleavage: (2-methylthioethyl, 2-methylsulfonylethyl, 2-p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl);

Groups Capable of Photolytic Cleavage: (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl);

Miscellaneous Carbamates: (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-Iodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl);

Amides: (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzophenylalanyl, N-benzoyl, N-p-phenylbenzoyl);

Amides With Assisted Cleavage: (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one);

Cyclic Imide Derivatives: (N-phthalimide, N-dithiasuccinoyl, N-2,3-diphenylmaleoyl, N-2,5-dimethlpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl- 1,3-5-triazacyclohexan-2-one, 1-substituted 3,5-dinitro-4-pyridonyl);

N-Alkyl and N-Aryl Amines: (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide);

Imine Derivatives: (N- 1,1-dimethylthiomethylene, N-benzylidene, N-p-methoxybenylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenylmethylene, N-cyclohexylidene);

Enamine Derivatives: (N-(5,5-dimethyl-3-oxo-1-cyclohexenyl));

N-Metal Derivatives (N-borane derivatives, N-diphenylborinic acid derivatives, N-[phenyl(pentacarbonylchromium- or -tungsten)]carbenyl, N-copper or N-zinc chelate);

N—N Derivatives: (N-nitro, N-nitroso, N-oxide);

N—P Derivatives: (N-diphenylphosphinyl, N-dimethylthiophosphinyl, N-diphenylthiophosphinyl, N-dialkyl phosphoryl, N-dibenzyl phosphoryl, N-diphenyl phosphoryl);

N—Si Derivatives, N—S Derivatives, and N-Sulfenyl Derivatives: (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methylbenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl).

Protected amino groups include carbamates, amidines and amides, —NHC(O)OR$^1$, —NHC(O)R$^1$ or —N=CR$^1$N(R$^1$)$_2$. Another protecting group, also useful as a prodrug for amino or —NH(R$^5$), is:

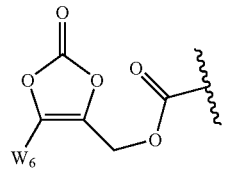

See for example Alexander, J. et al (1996) *J. Med. Chem.* 39:480-486.

Amino Acid and Polypeptide Protecting Groups and Conjugates

An amino acid or polypeptide protecting group of a compound of the invention has the structure R$^{15}$NHCH(R$^{16}$)C(O)—, where R$^{15}$ is H, an amino acid or polypeptide residue, or R$^5$, and R$^{16}$ is defined below.

R$^{16}$ is lower alkyl or lower alkyl (C$_1$-C$_6$) substituted with amino, carboxyl, amide, carboxyl ester, hydroxyl, C$_6$-C$_7$ aryl, guanidinyl, imidazolyl, indolyl, sulfhydryl, sulfoxide, and/or alkylphosphate. R$^{16}$ also is taken together with the amino acid α-N to form a proline residue (R$^{16}$=—CH$_2$)$_3$—). However, R$^{16}$ is generally the side group of a naturally-occurring amino acid such as H, —CH$_3$, —CH(CH$_3$)$_2$, —CH$_2$—CH(CH$_3$)$_2$, —CHCH$_3$—CH$_2$—CH$_3$, —CH$_2$—C$_6$H$_5$, —CH$_2$CH$_2$—S—CH$_3$, —CH$_2$OH, —CH(OH)—CH$_3$, —CH$_2$—SH, —CH$_2$—C$_6$H$_4$OH, —CH$_2$—CO—NH$_2$, —CH$_2$—CH$_2$—CO—NH$_2$, —CH$_2$—COOH, —CH$_2$—CH$_2$—COOH, —(CH$_2$)$_4$—NH$_2$ and —(CH$_2$)$_3$—NH—C(NH$_2$)—NH$_2$. R$^{16}$ also includes 1-guanidinoprop-3-yl, benzyl, 4-hydroxybenzyl, imidazol-4-yl, indol-3-yl, methoxyphenyl and ethoxyphenyl.

Another set of protecting groups include the residue of an amino-containing compound, in particular an amino acid, a polypeptide, a protecting group, —NHSO$_2$R, NHC(O)R, —N(R)$_2$, NH$_2$ or —NH(R)(H), whereby for example a carboxylic acid is reacted, i.e. coupled, with the amine to form an amide, as in C(O)NR$_2$. A phosphonic acid may be reacted with the amine to form a phosphonamidate, as in —P(O)(OR)(NR$_2$).

Amino acids have the structure R$^{17}$C(O)CH(R$^{16}$)NH—, where R$^{17}$ is —OH, —OR, an amino acid or a polypeptide residue. Amino acids are low molecular weight compounds, on the order of less than about 1000 MW and which contain at least one amino or imino group and at least one carboxyl group. Generally the amino acids will be found in nature, i.e., can be detected in biological material such as bacteria or other microbes, plants, animals or man. Suitable amino acids typically are alpha amino acids, i.e. compounds characterized by one amino or imino nitrogen atom separated from the carbon atom of one carboxyl group by a single substituted or unsubstituted alpha carbon atom. Of particular interest are hydrophobic residues such as mono- or di-alkyl or aryl amino acids, cycloalkylamino acids and the like. These residues contribute to cell permeability by increasing the partition coefficient of the parental drug. Typically, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Additionally, unnatural amino acids, for example, valanine, phenylglycine and homoarginine are also included. Commonly encountered amino acids that are not gene-encoded may also be used in the present invention. All of the amino acids used in the present invention may be either the D- or L- optical isomer. In addition, other peptidomimetics are also useful in the present invention. For a general review, see Spatola, A. F., in *Chemistry and Biochemistry of Amino Acids, Peptides and Proteins*, B. Weinstein, eds., Marcel Dekker, New York, p. 267 (1983).

When protecting groups are single amino acid residues or polypeptides they optionally are substituted at $R^3$ of substituents $A^1$, $A^2$ or $A^3$ in Formula I, or substituted at $R_3$ of substituents $A_1$, $A_2$ or $A_3$ in Formula II. These conjugates generally are produced by forming an amide bond between a carboxyl group of the amino acid (or C-terminal amino acid of a polypeptide for example). Similarly, conjugates are formed between $R^3$ (Formula I) or $R_3$ (Formula II) and an amino group of an amino acid or polypeptide. Generally, only one of any site in the scaffold drug-like compound is amidated with an amino acid as described herein, although it is within the scope of this invention to introduce amino acids at more than one permitted site. Usually, a carboxyl group of $R^3$ is amidated with an amino acid. In general, the α-amino or α-carboxyl group of the amino acid or the terminal amino or carboxyl group of a polypeptide are bonded to the scaffold parental functionalities. Carboxyl or amino groups in the amino acid side chains generally may be used to form the amide bonds with the parental compound or these groups may need to be protected during synthesis of the conjugates as described further below.

With respect to the carboxyl-containing side chains of amino acids or polypeptides it will be understood that the carboxyl group optionally will be blocked, e.g. by $R^1$, esterified with $R^5$ or amidated. Similarly, the amino side chains $R^{16}$ optionally will be blocked with $R^1$ or substituted with $R^5$.

Such ester or amide bonds with side chain amino or carboxyl groups, like the esters or amides with the parental molecule, optionally are hydrolyzable in vivo or in vitro under acidic (pH<3) or basic (pH>10) conditions. Alternatively, they are substantially stable in the gastrointestinal tract of humans but are hydrolyzed enzymatically in blood or in intracellular environments. The esters or amino acid or polypeptide amidates also are useful as intermediates for the preparation of the parental molecule containing free amino or carboxyl groups. The free acid or base of the parental compound, for example, is readily formed from the esters or amino acid or polypeptide conjugates of this invention by conventional hydrolysis procedures.

When an amino acid residue contains one or more chiral centers, any of the D, L, meso, threo or erythro (as appropriate) racemates, scalemates or mixtures thereof may be used. In general, if the intermediates are to be hydrolyzed non-enzymatically (as would be the case where the amides are used as chemical intermediates for the free acids or free amines), D isomers are useful. On the other hand, L isomers are more versatile since they can be susceptible to both non-enzymatic and enzymatic hydrolysis, and are more efficiently transported by amino acid or dipeptidyl transport systems in the gastrointestinal tract.

Examples of suitable amino acids whose residues are represented by $R^x$ or $R^y$ include the following:

Glycine;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid;

Amino acid amides such as glutamine and asparagine;

Polyamino- or polybasic-monocarboxylic acids such as arginine, lysine, β-aminoalanine, γ-aminobutyrine, ornithine, citruline, homoarginine, homocitrulline, hydroxylysine, allohydroxylsine and diaminobutyric acid;

Other basic amino acid residues such as histidine;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid;

Imino acids such as proline, hydroxyproline, allohydroxyproline, γ-methylproline, pipecolic acid, 5-hydroxypipecolic acid, and azetidine-2-carboxylic acid;

A mono- or di-alkyl (typically $C_1$-$C_8$ branched or normal) amino acid such as alanine, valine, leucine, allylglycine, butyrine, norvaline, norleucine, heptyline, α-methylserine, α-amino-α-methyl-γhydroxyvaleric acid, α-amino-α-methyl-δ-hydroxyvaleric acid, α-amino-α-methyl-εhydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid, isoleucine, alloisoleucine, tert-leucine, β-methyltryptophan and α-amino-β-ethyl-β-phenylpropionic acid;

β-phenylserinyl;

Aliphatic α-amino-β-hydroxy acids such as serine, β-hydroxyleucine, β-hydroxynorleucine, β-hydroxynorvaline, and α-amino-β-hydroxystearic acid;

α-Amino, α-, γ-, δ- or ε-hydroxy acids such as homoserine, δ-hydroxynorvaline, γ-hydroxynorvaline and ε-hydroxynorleucine residues; canavine and canaline; γ-hydroxyornithine;

2-hexosaminic acids such as D-glucosaminic acid or D-galactosaminic acid;

α-Amino-β-thiols such as penicillamine, β-thiolnorvaline or β-thiolbutyrine;

Other sulfur containing amino acid residues including cysteine; homocystine, β-phenylmethionine, methionine, S-allyl-L-cysteine sulfoxide, 2-thiolhistidine, cystathionine, and thiol ethers of cysteine or homocysteine;

Phenylalanine, tryptophan and ring-substituted α-amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4,6-trimethyl-, 2-ethoxy-5-nitro-, 2-hydroxy-5-nitro- and p-nitro-phenylalanine); furyl-, thienyl-, pyridyl-, pyrimidinyl-, purinyl- or naphthyl-alanines; and tryptophan analogues and derivatives including kynurenine, 3-hydroxykynurenine, 2-hydroxytryptophan and 4-carboxytryptophan;

α-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acids including serine, threonine, allothreonine, phosphoserine and phosphothreonine.

Polypeptides are polymers of amino acids in which a carboxyl group of one amino acid monomer is bonded to an amino or imino group of the next amino acid monomer by an amide bond. Polypeptides include dipeptides, low molecular weight polypeptides (about 1500-5000 MW) and proteins. Proteins optionally contain 3, 5, 10, 50, 75, 100 or more residues, and suitably are substantially sequence-homologous with human, animal, plant or microbial proteins. They include enzymes (e.g., hydrogen peroxidase) as well as immunogens such as KLH, or antibodies or proteins of any type against which one wishes to raise an immune response. The nature and identity of the polypeptide may vary widely.

The polypeptide amidates are useful as immunogens in raising antibodies against either the polypeptide (if it is not immunogenic in the animal to which it is administered) or against the epitopes on the remainder of the compound of this invention.

Antibodies capable of binding to the parental non-peptidyl compound are used to separate the parental compound from mixtures, for example in diagnosis or manufacturing of the parental compound. The conjugates of parental compound and polypeptide generally are more immunogenic than the polypeptides in closely homologous animals, and therefore make the polypeptide more immunogenic for facilitating raising antibodies against it. Accordingly, the polypeptide or protein may be immunogenic in an animal typically used to raise antibodies, e.g., rabbit, mouse, horse, or rat. The polypeptide optionally contains a peptidolytic enzyme cleavage site at the peptide bond between the first and second residues adjacent to the acidic heteroatom. Such cleavage sites are flanked by enzymatic recognition structures, e.g. a particular sequence of residues recognized by a peptidolytic enzyme.

Peptidolytic enzymes for cleaving the polypeptide conjugates of this invention are well known, and include carboxypeptidases which digest polypeptides by removing C-terminal residues, and are specific in many instances for particular C-terminal sequences. Such enzymes and their substrate requirements in general are well known. For example, a dipeptide (having a given pair of residues and a free carboxyl terminus) is covalently bonded through its α-amino group to the phosphorus or carbon atoms of the compounds herein. In certain embodiments, a phosphonate group substituted with an amino acid or peptide will be cleaved by the appropriate peptidolytic enzyme, leaving the carboxyl of the proximal amino acid residue to autocatalytically cleave the phosphonoamidate bond.

Suitable dipeptidyl groups (designated by their single letter code) are AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Tripeptide residues are also useful as protecting groups. When a phosphonate is to be protected, the sequence —$X^4$-pro-$X^5$— (where $X^4$ is any amino acid residue and $X^5$ is an amino acid residue, a carboxyl ester of proline, or hydrogen) will be cleaved by luminal carboxypeptidase to yield $X^4$ with a free carboxyl, which in turn is expected to autocatalytically cleave the phosphonoamidate bond. The carboxy group of $X^5$ optionally is esterified with benzyl.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J. P. F., (1992) *Pharm Res.* 9:969-978. Transport competent peptides can thus be used to enhance bioavailability of the amidate compounds. Di- or tripeptides having one or more amino acids in the D configuration may be compatible with peptide transport. Amino acids in the D configuration can be used to reduce the susceptibility of a di- or tripeptide to hydrolysis by proteases common to the brush border such as aminopeptidase N. In addition, di- or tripeptides alternatively are selected on the basis of their relative resistance to hydrolysis by proteases found in the lumen of the intestine. For example, tripeptides or polypeptides lacking asp and/or glu are poor substrates for aminopeptidase A, di- or tripeptides lacking amino acid residues on the N-terminal side of hydrophobic amino acids (leu, tyr, phe, val, trp) are poor substrates for endopeptidase, and peptides lacking a pro residue at the penultimate position at a free carboxyl terminus are poor substrates for carboxypeptidase P. Similar considerations can also be applied to the selection of peptides that are either relatively resistant or relatively susceptible to hydrolysis by cytosolic, renal, hepatic, serum or other peptidases. Such poorly cleaved polypeptide amidates are immunogens or are useful for bonding to proteins in order to prepare immunogens.

Capravirine-Like Compounds

The drugs which can be derivatized in accord with the present invention must contain at least one functional group capable of linking, i.e. bonding to the phosphorus atom in the phosphonate group. The phosphonate derivatives of Formula I and II may cleave in vivo in stages after they have reached the desired site of action, i.e. inside a cell. One mechanism of action inside a cell may entail a first cleavage, e.g. by esterase, to provide a negatively-charged "locked-in" intermediate. Cleavage of a terminal ester grouping in Formula I or II thus affords an unstable intermediate which releases a negatively charged "locked in" intermediate.

After passage inside a cell, intracellular enzymatic cleavage or modification of the phosphonate prodrug compound may result in an intracellular accumulation of the cleaved or modified compound by a "trapping" mechanism. The cleaved or modified compound may then be "locked-in" the cell, i.e. accumulate in the cell by a significant change in charge, polarity, or other physical property change which decreases the rate at which the cleaved or modified compound can exit the cell, relative to the rate at which it entered as the phosphonate prodrug. Other mechanisms by which a therapeutic effect are achieved may be operative as well. Enzymes which are capable of an enzymatic activation mechanism with the phosphonate prodrug compounds of the invention include, but are not limited to, amidases, esterases, microbial enzymes, phospholipases, cholinesterases, and phosphatases.

In selected instances in which the drug is of the nucleoside type, such as is the case of zidovudine and numerous other antiretroviral agents, it is known that the drug is activated in vivo by phosphorylation. Such activation may occur in the present system by enzymatic conversion of the "locked-in" intermediate with phosphokinase to the active phosphonate diphosphate and/or by phosphorylation of the drug itself after its release from the "locked-in" intermediate as described above. In either case, the original nucleoside-type drug will be converted, via the derivatives of this invention, to the active phosphorylated species.

From the foregoing, it will be apparent that many different drugs can be derivatized in accord with the present invention. Numerous such drugs are specifically mentioned herein. However, it should be understood that the discussion of drug families and their specific members for derivatization according to this invention is not intended to be exhaustive, but merely illustrative.

As another example, when the selected drug contains multiple reactive hydroxyl functions, a mixture of intermediates and final products may again be obtained. In the unusual case in which all hydroxy groups are approximately equally reactive, there is not expected to be a single, predominant product, as each mono-substituted product will be obtained in approximate by equal amounts, while a lesser amount of multiply-substituted product will also result. Generally speaking, however, one of the hydroxyl groups will be more susceptible to substitution than the other(s), e.g. a primary hydroxyl will be more reactive than a secondary hydroxyl, an unhindered hydroxyl will be more reactive than a hindered one. Consequently, the major product will be a mono-substituted one in which the most reactive hydroxyl has been derivatized while other mono-substituted and multiply-substituted products may be obtained as minor products.

The invention includes Capravirine-like compounds (CLC). Capravirine is described in U.S. Pat. No. 5,910,506, U.S. Pat. No. 6,083,958, U.S. Pat. No. 6,147,097, WO 96/10019, and U.S. Pat. No. 5,472,965, as well as patent applications and granted patents which are equivalents of, or related by priority claims thereto. The definition of CLC means not only the generic disclosures cited above but also each and every species set forth within the cases making up the enumerated groups. CLC compositions of the invention include a phosphonate group covalently attached as detailed in Formula I. The phosphonate group may be a phosphonate prodrug moiety. The prodrug moiety may be sensitive to hydrolysis, such as, but not limited to a pivaloyloxymethyl carbonate (POC) or POM group. Alternatively, the prodrug moiety may be sensitive to enzymatic potentiated cleavage, such as a lactate ester or a phosphonamidate-ester group. An exemplary group of phosphonate diester CLC compounds anticipated by the present invention includes:

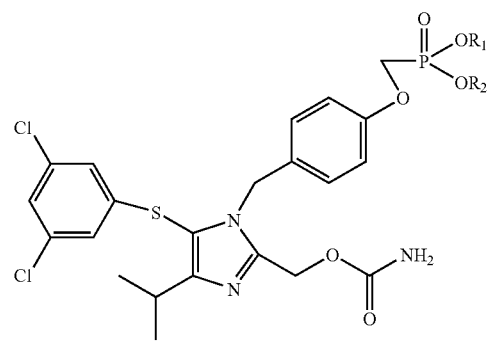

An exemplary phosphonamidate-ester CLC compound anticipated by the present invention includes:

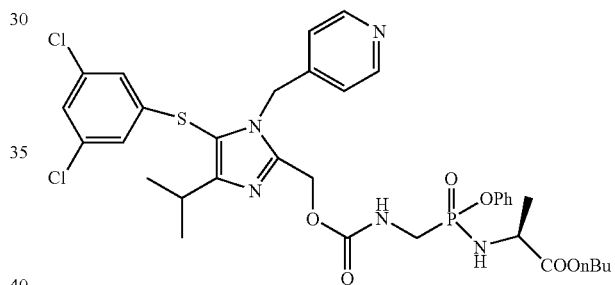

Stereoisomers

The compounds of the invention, exemplified by Formula I and II, may have chiral centers, e.g. chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. All though only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

The compositions of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid. Monovalent salts are preferred if a water soluble salt is desired.

Metal salts typically are prepared by reacting the metal hydroxide with a compound of this invention. Examples of metal salts which are prepared in this way are salts containing $Li^+$, $Na^+$, and $K^+$. A less soluble metal salt may be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of HIV RT

Another aspect of the invention relates to methods of inhibiting the activity of HIV RT comprising the step of treating a sample suspected of containing HIV RT with a compound of the invention.

Compositions of the invention may act as inhibitors of HIV RT, as intermediates for such inhibitors or have other utilities as described below. The inhibitors will bind to locations on the surface or in a cavity of HIV RT having a geometry unique to HIV RT. Compositions binding HIV RT may bind with varying degrees of reversibility. Those compounds binding substantially irreversibly are ideal candidates for use in this method of the invention. Once labeled, the substantially irreversibly binding compositions are useful as probes for the detection of HIV RT. Accordingly, the invention relates to methods of detecting HIV RT in a sample suspected of containing HIV RT comprising the steps of: treating a sample suspected of containing HIV RT with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl, amino, carboxyl, or sulfhydryl.

Within the context of the invention samples suspected of containing HIV RT include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces HIV RT, frequently a pathogenic organism such as an HIV virus. Samples can be contained in any medium including water and organic solvent/water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity of HIV RT after application of the composition can be observed by any method including direct and indirect methods of detecting HIV RT activity. Quantitative, qualitative, and semiquantitative methods of determining HIV RT activity are all contemplated. Typically one of the screening methods described above are applied, however, any other method such as observation of the physiological properties of a living organism are also applicable.

Organisms that contain HIV RT include the HIV virus. The compounds of this invention are useful in the treatment or prophylaxis of HIV infections in animals or in man.

However, in screening compounds capable of inhibiting HIV RT viruses it should be kept in mind that the results of enzyme assays may not correlate with cell culture assays. Thus, a cell based assay should be the primary screening tool.

Screens for HIV RT Inhibitors

Compositions of the invention are screened for inhibitory activity against HIV RT by any of the conventional techniques for evaluating enzyme activity. Within the context of the invention, typically compositions are first screened for inhibition of HIV RT in vitro and compositions showing inhibitory activity are then screened for activity in vivo. Certain compounds of the invention have in vitro Ki (inhibitory constants) of less then about $5 \times 10^{-6}$ M, and typically less than about $1 \times 10^{-7}$ M.

Pharmaceutical Formulations

The compounds of this invention may be formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 microns etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HIV infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active HIV infection, the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Compositions of the invention are also used in combination with other active ingredients. Such combinations are selected based on the condition to be treated, cross-reactivities of ingredients and pharmaco-properties of the combination. For example, when treating HIV viral infections the compositions of the invention are combined with other antivirals (such as RTIs, NNRTIs and other RT inhibitors).

It is possible to combine any compound of the invention with one or more other active ingredients in a unitary dosage form for simultaneous or sequential administration to an HIV infected patient. The combination therapy may be administered as a simultaneous or sequential regimen. When administered sequentially, the combination may be administered in two or more administrations. Second and third active ingredients in the combination may have anti-HIV activity and include protease inhibitors (Prt), nucleoside reverse transcriptase inhibitors (NRTI), non-nucleoside reverse transcriptase inhibitors (NNRTI), and integrase inhibitors. Exemplary active ingredients to be administered in combination with compounds of the invention are:

5,6 dihydro-5-azacytidine
5-aza 2'deoxycytidine
5-azacytidine
9 (arabinofuranosyl)guanine; 9-(2'deoxyribofuranosyl) guanine
9-(2'-deoxy 2'fluororibofuranosyl)-2,6-diaminopurine
9-(2'-deoxy 2'fluororibofuranosyl)guanine
9-(2'-deoxyribofuranosyl)-2,6diaminopurine
9-(arabinofuranosyl)-2,6diaminopurine
Abacavir, Ziagen®
Acyclovir, ACV; 9-(2-hydroxyethoxylmethyl)guanine
Adefovir (9-(2-phosphonomethoxyethyl)adenine
Adefovir dipivoxil, Hepsera®
Amprenavir, Agenerase®
BHCG; (.±.)-(1a,2b,3a)-9-[2,3-bis(hydroxymethyl)cyclobutyl]guanine
BMS200,475; 5-yl-carbocyclic 2'-deoxyguanosine
Buciclovir; (R) 9-(3,4-dihydroxybutyl)guanine
Calanolide A
Capravirine
CDG; carbocyclic 2'-deoxyguanosine
Cidofovir, HPMPC; (S)-9-(3-hydroxy-2-phosphonylmethoxypropyl)cytosine
Clevudine, L-FMAU; 2'-Fluoro-5-methyl-β-L-arabinofuranosyluracil
Cytallene; [1-(4'-hydroxy-1',2'-butadienyl)cytosine]
Cytallene; [1-(4'-hydroxy-1',2'-butadienyl)cytosine]
d4C; 3'-deoxy-2',3'-didehydrocytidine
DAPD; (−)-β-D-2,6-diaminopurine dioxolane
ddA; 2',3'-dideoxyadenosine
ddAPR; 2,6-diaminopurine-2',3'-dideoxyriboside
Delavirdine, Rescriptor®
Didanosine, ddI, Videx®; 2',3'-dideoxyinosine
DXG; dioxolane guanosine
E-5-(2-bromovinyl)-2'-deoxyuridine
Efavirenz, Sustiva®
Emtricitabine, Coviracil®, FTC; (2R,5S,cis)-4-amino-5-fluoro-1-(2-hydroxymethyl-1,3-oxathiolan-5-yl)-(1H)-pyrimidin-2-one
Enfuvirtide, Fuzeon®
FDOC; (−)-β-D-5-fluoro-1-[2-(hydroxymethyl)-1,3-dioxolane]cytosine
FEAU; 2'-deoxy-2'-fluoro-1-β-D-arabinofuranosyl-5-ethyluracil
FIAC; 1-(2-deoxy-2-fluoro-β-D-arabinofuranosyl)-5-iodocytosine
FIAU; 1-(2-deoxy-2-fluoro-β-D-arabinofuranosyl)-5-iodouridine
FLG; 2',3'-dideoxy-3'-fluoroguanosine
FLT; 3'-deoxy-3'-fluorothymidine
Fludarabine; F-ara-A; fluoroarabinosyladenosine
FMdC
Foscarnet; phosphonoformic acid
FPMPA; 9-(3-fluoro-2-phosphonylmethoxypropyl)adenine
Gancyclovir, GCV; 9-(1,3-dihydroxy-2-propoxymethyl) guanine
GS-7340; 9-[R-2-[[(S)-[[(S)-1-(isopropoxycarbonyl) ethyl]amino]-phenoxyphosphinyl]methoxy]propyl]adenine
HPMPA; (S)-9-(3-hydroxy-2-phosphonylmethoxypropyl) adenine
Hydroxyurea, Droxia®
Indinavir, Crixivan®
Lamivudine, 3TC, Epivirm™; (2R,5S,cis)-4-amino-1-(2-hydroxymethyl-1,3-oxathiolan-5-yl)-(1H)-pyrimidin-2-one
L-d4C; L-3'-deoxy-2',3'-didehydrocytidine
L-ddC; L-2',3'-dideoxycytidine
L-Fd4C; L-3'-deoxy-2',3'-didehydro-5-fluorocytidine
L-FddC; L-2',3'-dideoxy-5-fluorocytidine
Lopinavir
Nelfinavir, Viracept®
Nevirapine, Viramune®
Oxetanocin A; 9-(2-deoxy-2-hydroxymethyl-β-D-erythro-oxetanosyl)adenine Oxetanocin G; 9-(2-deoxy-2-hydroxymethyl-β-D-erythro-oxetanosyl)guanine
Penciclovir
PMEDAP; 9-(2-phosphonylmethoxyethyl)-2,6-diaminopurine
PMPA, tenofovir; (R)-9-(2-phosphonylmethoxypropyl)adenine
PPA; phosphonoacetic acid
Ribavirin
Ribavirin; 1-β-D-ribofuranosyl-1,2,4-triazole-3-carboxamide
Ritonavir, Norvir®
Saquinavir, Invirase®, Fortovase®
Sorivudine, BvaraU; 1-β-D-arabinofuranosyl-E-5-(2-bromovinyl)uracil
Stavudine, d4T, Zerit®; 2',3'-didehydro-3'-deoxythymidine
Tenofovir disoproxil; [2-(6-Amino-purin-9-yl)-1-methylethoxymethyl]-phosphonic acid diisopropoxycarbonyloxymethyl ester
Trifluorothymidine, TFT; Trifluorothymidine
Vidarabine, araA; 9-β-D-arabinofuranosyladenine
Viread®, tenofovir disoproxil fumarate (DF), Bis POC PMPA, TDF; 2,4,6,8-Tetraoxa-5-phosphanonanedioic acid, 5-[[(1R)-2-(6-amino-9H-purin-9-yl)-1-methylethoxy]methyl]-, bis(1-methylethyl) ester, 5-oxide, (2E)-2-butenedioate (1:1)
Zalcitabine, Hivid®, ddC; 2',3'-dideoxycytidine
Zidovudine, AZT, Retrovir®; 3'-azido-2',3'-dideoxythymdine
Zonavir; 5-propynyl-1-arabinosyluracil The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $^{14}C$ or $^3H$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HIV RT inhibitory activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Such compounds are suitable for use in this embodiment. Note that simply because the compounds are stable to the gastrointestinal tract does not mean that they cannot be hydrolyzed in vivo. Prodrugs typically will be stable in the digestive system but may be substantially hydrolyzed to the parental drug in the digestive lumen, liver or other metabolic organ, or within cells in general.

Exemplary Methods of Making the Compounds of the Invention

The invention provides many methods of making the compositions of the invention. The compositions are prepared by any of the applicable techniques of organic synthesis. Many such techniques are well known in the art. Such as those elaborated in "Compendium of Organic Synthetic Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., "Advanced Organic Chemistry, Third Edition", (John Wiley & Sons, New York, 1985), "Comprehensive Organic Synthesis. Selectivity, Strategy & Efficiency in Modem Organic Chemistry. In 9 Volumes", Barry M. Trost, Editor-in-Chief (Pergamon Press, New York, 1993 printing).

Dialkyl phosphonates may be prepared according to the methods of: Quast et al (1974) *Synthesis* 490; Stowell et al (1990) *Tetrahedron Lett.* 3261; U.S. Pat. No. 5,663,159.

In general, synthesis of phosphonate esters is achieved by coupling a nucleophile amine or alcohol with the corresponding activated phosphonate electrophilic precursor for example, Chlorophosphonate addition on to 5'-hydroxy of nucleoside is a well known method for preparation of nucleoside phosphate monoesters. The activated precursor can be prepared by several well known methods. Chlorophosphonates useful for synthesis of the prodrugs are prepared from the substituted-1,3-propanediol (Wissner, et al, (1992) *J. Med Chem.* 35:1650). Chlorophosphonates are made by oxidation of the corresponding chlorophospholanes (Anderson, et al, (1984) *J. Org. Chem.* 49:1304) which are obtained by reaction of the substituted diol with phosphorus trichloride. Alternatively, the chlorophosphonate agent is made by treating substituted-1,3-diols with phosphorusoxychloride (Patois, et al, (1990) *J. Chem. Soc. Perkin Trans. I,* 1577). Chlorophosphonate species may also be generated in situ from corresponding cyclic phosphites (Silverburg, et al., (1996) *Tetrahedron lett.,* 37:771-774), which in turn can be either made from chlorophospholane or phosphoramidate intermediate.

Phosphoroflouridate intermediate prepared either from pyrophosphate or phosphoric acid may also act as precursor in preparation of cyclic prodrugs (Watanabe et al., (1988) *Tetrahedron lett.*, 29:5763-66). Caution: fluorophosphonate compounds may be highly toxic!

Schemes and Examples

General aspects of these exemplary methods are described below and in the Examples. Each of the products of the following processes is optionally separated, isolated, and/or purified prior to its use in subsequent processes.

A number of exemplary methods for the preparation of the compositions of the invention are provided below. These methods are intended to illustrate the nature of such preparations are not intended to limit the scope of applicable methods.

The terms "treated", "treating", "treatment", and the like, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two.

"Treating" indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes above and in the examples (hereafter "exemplary schemes") leads to various analogs of the specific exemplary materials produce. The above cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g. an enantiomer, substantially free of its stereoisomer may be obtained by resolution of the racemic mixture using a method such as formation of diastereomers using optically active resolving agents ("Stereochemistry of Carbon Compounds," (1962) by E. L. Eliel, McGraw Hill; Lochmuller, C. H., (1975) *J. Chromatogr.*, 1 13:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g. (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase ("Chiral Liquid Chromatography" (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

All literature and patent citations above are hereby expressly incorporated by reference at the locations of their citation. Specifically cited sections or pages of the above cited works are incorporated by reference with specificity. The invention has been described in detail sufficient to allow one of ordinary skill in the art to make and use the subject matter of the following Embodiments. It is apparent that certain modifications of the methods and compositions of the following Embodiments can be made within the scope and spirit of the invention.

Scheme A (FIG. 1) shows the general interconversions of certain phosphonate compounds: acids —$P(O)(OH)_2$; monoesters —$P(O)(OR_1)(OH)$; and diesters —$P(O)(OR_1)_2$ in which the $R^1$ groups are independently selected, and defined herein before, and the phosphorus is attached through a carbon moiety (link, i.e. linker), which is attached to the rest of the molecule, e.g. drug or drug intermediate (R). The $R^1$ groups attached to the phosphonate esters in Scheme 1 may be changed using established chemical transformations. The interconversions may be carried out in the precursor compounds or the final products using the methods described below. The methods employed for a given phosphonate transformation depend on the nature of the substituent $R^1$. The preparation and hydrolysis of phosphonate esters is described in *Organic Phosphorus Compounds,* G. M. Kosolapoff, L. Maeir, eds, Wiley, 1976, p. 9ff.

The conversion of a phosphonate diester 27.1 into the corresponding phosphonate monoester 27.2 (Scheme A, Reaction 1) can be accomplished by a number of methods. For example, the ester 27.1 in which $R^1$ is an arylalkyl group such as benzyl, can be converted into the monoester compound 27.2 by reaction with a tertiary organic base such as diazabicyclooctane (DABCO) or quinuclidine, as described in *J. Org. Chem.,* 1995, 60:2946. The reaction is performed in an inert hydrocarbon solvent such as toluene or xylene, at about 110° C. The conversion of the diester 27.1 in which $R^1$ is an aryl group such as phenyl, or an alkenyl group such as allyl, into the monoester 27.2 can be effected by treatment of the ester 27.1 with a base such as aqueous sodium hydroxide in acetonitrile or lithium hydroxide in aqueous tetrahydrofuran. Phosphonate diesters 27.2 in which one of the groups $R^1$ is arylalkyl, such as benzyl, and the other is alkyl, can be converted into the monoesters 27.2 in which $R^1$ is alkyl, by hydrogenation, for example using a palladium on carbon catalyst. Phosphonate diesters in which both of the groups $R^1$ are alkenyl, such as allyl, can be converted into the monoester 27.2 in which $R^1$ is alkenyl, by treatment with chlorotris (triphenylphosphine)rhodium (Wilkinson's catalyst) in aqueous ethanol at reflux, optionally in the presence of diazabicyclooctane, for example by using the procedure described in *J. Org. Chem.,* 38:3224 1973 for the cleavage of allyl carboxylates.

The conversion of a phosphonate diester 27.1 or a phosphonate monoester 27.2 into the corresponding phosphonic acid 27.3 (Scheme A, Reactions 2 and 3) can effected by reaction of the diester or the monoester with trimethylsilyl bromide, as described in *J. Chem. Soc., Chem. Comm.,* 739, 1979. The reaction is conducted in an inert solvent such as, for example, dichloromethane, optionally in the presence of a silylating agent such as bis(trimethylsilyl)trifluoroacetamide, at ambient temperature. A phosphonate monoester 27.2 in which $R^1$ is arylalkyl such as benzyl, can be converted into the corresponding phosphonic acid 27.3 by hydrogenation over a palladium catalyst, or by treatment with hydrogen chloride in an ethereal solvent such as dioxane. A phosphonate monoester 27.2 in which $R^1$ is alkenyl such as, for example, allyl, can be converted into the phosphonic acid 27.3 by reaction with Wilkinson's catalyst in an aqueous organic solvent, for example in 15% aqueous acetonitrile, or in aqueous ethanol, for example using the procedure described in *Helv. Chim. Acta.,* 68:618, 1985. Palladium catalyzed hydrogenolysis of phosphonate esters 27.1 in which $R^1$ is benzyl is described in *J. Org. Chem.,* 24:434, 1959. Platinum-catalyzed hydrogenolysis of phosphonate esters 27.1 in which $R^1$ is phenyl is described in *J. Amer. Chem. Soc.,* 78:2336, 1956.

The conversion of a phosphonate monoester 27.2 into a phosphonate diester 27.1 (Scheme A, Reaction 4) in which the newly introduced $R^1$ group is alkyl, arylalkyl, or haloalkyl such as chloroethyl, can be effected by a number of reactions in which the substrate 27.2 is reacted with a hydroxy compound $R^1OH$, in the presence of a coupling agent. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester 27.1 to the diester 27.1 can be effected by the use of the Mitsunobu reaction. The substrate is reacted with the hydroxy compound $R^1OH$, in the presence of diethyl azodicarboxylate and a triarylphosphine such as triphenyl phosphine. Alternatively, the phosphonate monoester 27.2 can be transformed into the phosphonate diester 27.1, in which the introduced $R^1$ group is alkenyl or arylalkyl, by reaction of the monoester with the halide $R^1Br$, in which $R^1$ is as alkenyl or arylalkyl. The alkylation reaction is conducted in a polar organic solvent such as dimethylformamide or acetonitrile, in the presence of a base such as cesium carbonate. Alternatively, the phosphonate monoester can be transformed into the phosphonate diester in a two step procedure. In the first step, the phosphonate monoester 27.2 is transformed into the chloro analog —$P(O)(OR^1)Cl$ by reaction with thionyl chloride or oxalyl chloride and the like, as described in Organic Phosphorus Compounds, G. M. Kosolapoff, L. Maeir, eds, Wiley, 1976, p. 17, and the thus-obtained product —$P(O)(OR^1)Cl$ is then reacted with the hydroxy compound $R^1OH$, in the presence of a base such as triethylamine, to afford the phosphonate diester 27.1.

A phosphonic acid —$P(O)(OH)_2$ can be transformed into a phosphonate monoester —$P(O)(OR^1)(OH)$ (Scheme A, Reaction 5) by means of the methods described above of for the preparation of the phosphonate diester —$P(O)(OR^1)_2$ 27.1, except that only one molar proportion of the component $R^1OH$ or $R^1Br$ is employed.

A phosphonic acid —$P(O)(OH)_2$ 27.3 can be transformed into a phosphonate diester —$P(O)(OR^1)_2$ 27.1 (Scheme A, Reaction 6) by a coupling reaction with the hydroxy compound $R^1OH$, in the presence of a coupling agent such as Aldrithiol-2 (Aldrich) and triphenylphosphine. The reaction is conducted in a basic solvent such as pyridine. Alternatively, phosphonic acids 27.3 can be transformed into phosphonic esters 27.1 in which $R^1$ is aryl, such as phenyl, by means of a coupling reaction employing, for example, phenol and dicyclohexylcarbodiimide in pyridine at about 70° C. Alternatively, phosphonic acids 27.3 can be transformed into phosphonic esters 27.1 in which $R^1$ is alkenyl, by means of an alkylation reaction. The phosphonic acid is reacted with the alkenyl bromide $R^1Br$ in a polar organic solvent such as acetonitrile solution at reflux temperature, in the presence of a base such as cesium carbonate, to afford the phosphonic ester 27.1.

Phosphonate prodrugs of the present invention may also be prepared from the precursor free acid by Mitsunobu reactions (Mitsunobu, (1981) *Synthesis*, 1; Campbell, (1992) *J. Org. Chem.*, 52:6331), and other acid coupling reagents including, but not limited to, carbodiimides (Alexander, et al, (1994) *Collect. Czech. Chem. Commun.* 59:1853; Casara, et al, (1992) *Bioorg. Med. Chem. Lett.*, 2:145; Ohashi, et al, (1988) *Tetrahedron Lett.*, 29:1189), and benzotriazolyloxytris-(dimethylamino)phosphonium salts (Campagne, et al, (1993) *Tetrahedron Lett.*, 34:6743).

Preparation of Carboalkoxy-Substituted Phosphonate Bisamidates, Monoamidates, Diesters and Monoesters.

A number of methods are available for the conversion of phosphonic acids into amidates and esters. In one group of methods, the phosphonic acid is either converted into an isolated activated intermediate such as a phosphoryl chloride, or the phosphonic acid is activated in situ for reaction with an amine or a hydroxy compound.

The conversion of phosphonic acids into phosphoryl chlorides is accomplished by reaction with thionyl chloride, for example as described in J. Gen. Chem. USSR, 1983, 53, 480, Zh. Obschei Khim., 1958, 28, 1063, or J. Org. Chem., 1994, 59, 6144, or by reaction with oxalyl chloride, as described in J. Am. Chem. Soc., 1994, 116, 3251, or J. Org. Chem., 1994, 59, 6144, or by reaction with phosphorus pentachloride, as described in J. Org. Chem., 2001, 66, 329, or in J. Med. Chem., 1995, 38, 1372. The resultant phosphoryl chlorides are then reacted with amines or hydroxy compounds in the presence of a base to afford the amidate or ester products.

Phosphonic acids are converted into activated imidazolyl derivatives by reaction with carbonyl diimidazole, as described in J. Chem. Soc., Chem. Comm., 1991, 312, or Nucleosides Nucleotides 2000, 19, 1885. Activated sulfonyloxy derivatives are obtained by the reaction of phosphonic acids with trichloromethylsulfonyl chloride, as described in J. Med. Chem. 1995, 38, 4958, or with triisopropylbenzenesulfonyl chloride, as described in Tet. Lett., 1996, 7857, or Bioorg. Med. Chem. Lett., 1998, 8, 663. The activated sulfonyloxy derivatives are then reacted with amines or hydroxy compounds to afford amidates or esters.

Alternatively, the phosphonic acid and the amine or hydroxy reactant are combined in the presence of a diimide coupling agent. The preparation of phosphonic amidates and esters by means of coupling reactions in the presence of dicyclohexyl carbodiimide is described, for example, in J. Chem. Soc., Chem. Comm., 1991, 312, or J. Med. Chem., 1980, 23, 1299 or Coll. Czech. Chem. Comm., 1987, 52, 2792. The use of ethyl dimethylaminopropyl carbodiimide for activation and coupling of phosphonic acids is described in Tet. Lett., 2001, 42, 8841, or Nucleosides Nucleotides, 2000, 19, 1885.

A number of additional coupling reagents have been described for the preparation of amidates and esters from phosphonic acids. The agents include Aldrithiol-2, and PYBOP and BOP, as described in J. Org. Chem., 1995, 60, 5214, and J. Med. Chem., 1997, 40, 3842, mesitylene-2-sulfonyl-3-nitro-1,2,4-triazole (MSNT), as described in J. Med. Chem., 1996, 39, 4958, diphenylphosphoryl azide, as described in J. Org. Chem., 1984, 49, 1158, 1-(2,4,6-triisopropylbenzenesulfonyl-3-nitro-1,2,4-triazole (TPSNT) as described in Bioorg. Med. Chem. Lett., 1998, 8, 1013, bromotris(dimethylamino)phosphonium hexafluorophosphate (BroP), as described in Tet. Lett., 1996, 37, 3997, 2-chloro-5,5-dimethyl-2-oxo-1,3,2-dioxaphosphinane, as described in Nucleosides Nucleotides 1995, 14, 871, and diphenyl chlorophosphate, as described in J. Med. Chem., 1988, 31, 1305.

Phosphonic acids are converted into amidates and esters by means of the Mitsonobu reaction, in which the phosphonic acid and the amine or hydroxy reactant are combined in the presence of a triaryl phosphine and a dialkyl azodicarboxylate. The procedure is described in Org. Lett., 2001, 3, 643, or J. Med. Chem., 1997, 40, 3842.

Phosphonic esters are also obtained by the reaction between phosphonic acids and halo compounds, in the presence of a suitable base. The method is described, for example, in Anal. Chem., 1987, 59, 1056, or J. Chem. Soc. Perkin Trans., I, 1993, 19, 2303, or J. Med. Chem., 1995, 38, 1372, or Tet. Lett., 2002, 43, 1161.

Schemes 1-4 (FIGS. 2-5, respectively) illustrate the conversion of phosphonate esters and phosphonic acids into carboalkoxy-substituted phosphorobisamidates (Scheme 1), phosphoroamidates (Scheme 2), phosphonate monoesters (Scheme 3) and phosphonate diesters, (Scheme 4).

Scheme 1 (FIG. 2) illustrates various methods for the conversion of phosphonate diesters 1.1 into phosphorobisamidates 1.5. The diester 1.1, prepared as described previously, is hydrolyzed, either to the monoester 1.2 or to the phosphonic acid 1.6. The methods employed for these transformations are described above. The monoester 1.2 is converted into the monoamidate 1.3 by reaction with an aminoester 1.9, in which the group $R^2$ is H or alkyl, the group $R^4$ is an alkylene moiety such as, for example, $CHCH_3$, $CHPr^1$, $CH(CH_2Ph)$, $CH_2CH(CH_3)$ and the like, or a group present in natural or modified aminoacids, and the group $R^5$ is alkyl. The reactants are combined in the presence of a coupling agent such as a carbodiimide, for example dicyclohexyl carbodiimide, as described in J. Am. Chem. Soc., 1957, 79, 3575, optionally in the presence of an activating agent such as hydroxybenztriazole, to yield the amidate product 1.3. The amidate-forming reaction is also effected in the presence of coupling agents such as BOP, as described in J. Org. Chem., 1995, 60, 5214, Aldrithiol, PYBOP and similar coupling agents used for the preparation of amides and esters. Alternatively, the reactants 1.2 and 1.9 are transformed into the monoamidate 1.3 by means of a Mitsonobu reaction. The preparation of amidates by means of the Mitsonobu reaction is described in J. Med. Chem., 1995, 38, 2742. Equimolar amounts of the reactants are combined in an inert solvent such as tetrahydrofuran in the presence of a triaryl phosphine and a dialkyl azodicarboxylate. The thus-obtained monoamidate ester 1.3 is then transformed into amidate phosphonic acid 1.4. The conditions used for the hydrolysis reaction depend on the nature of the $R^1$ group, as described previously. The phosphonic acid amidate 1.4 is then reacted with an aminoester 1.9, as described above, to yield the bisamidate product 1.5, in which the amino substituents are the same or different.

An example of this procedure is shown in Scheme 1, Example 1. In this procedure, a dibenzyl phosphonate 1.14 is reacted with diazabicyclooctane (DABCO) in toluene at reflux, as described in J. Org. Chem., 1995, 60, 2946, to afford the monobenzyl phosphonate 1.15. The product is then reacted with equimolar amounts of ethyl alaninate 1.16 and dicyclohexyl carbodiimide in pyridine, to yield the amidate product 1.17. The benzyl group is then removed, for example by hydrogenolysis over a palladium catalyst, to give the monoacid product 1.18. This compound is then reacted in a Mitsonobu reaction with ethyl leucinate 1.19, triphenyl phosphine and diethylazodicarboxylate, as described in J. Med. Chem., 1995, 38, 2742, to produce the bisamidate product 1.20.

Using the above procedures, but employing, in place of ethyl leucinate 1.19 or ethyl alaninate 1.16, different aminoesters 1.9, the corresponding products 1.5 are obtained.

Alternatively, the phosphonic acid 1.6 is converted into the bisamidate 1.5 by use of the coupling reactions described above. The reaction is performed in one step, in which case the nitrogen-related substituents present in the product 1.5 are the same, or in two steps, in which case the nitrogen-related substituents can be different.

An example of the method is shown in Scheme 1, Example 2. In this procedure, a phosphonic acid 1.6 is reacted in pyridine solution with excess ethyl phenylalaninate 1.21 and dicyclohexylcarbodiimide, for example as described in J. Chem. Soc., Chem. Comm., 1991, 1063, to give the bisamidate product 1.22.

Using the above procedures, but employing, in place of ethyl phenylalaninate, different aminoesters 1.9, the corresponding products 1.5 are obtained.

As a further alternative, the phosphonic acid 1.6 is converted into the mono or bis-activated derivative 1.7, in which Lv is a leaving group such as chloro, imidazolyl, triisopropylbenzenesulfonyloxy etc. The conversion of phosphonic acids into chlorides 1.7 (Lv=Cl) is effected by reaction with thionyl chloride or oxalyl chloride and the like, as described in Organic Phosphorus Compounds, G. M. Kosolapoff, L. Maeir, eds, Wiley, 1976, p. 17. The conversion of phosphonic acids into monoimidazolides 1.7 (Lv=imidazolyl) is described in J. Med. Chem., 2002, 45, 1284 and in J. Chem. Soc. Chem. Comm., 1991, 312. Alternatively, the phosphonic acid is activated by reaction with triisopropylbenzenesulfonyl chloride, as described in Nucleosides and Nucleotides, 2000, 10, 1885. The activated product is then reacted with the aminoester 1.9, in the presence of a base, to give the bisamidate 1.5. The reaction is performed in one step, in which case the nitrogen substituents present in the product 1.5 are the same, or in two steps, via the intermediate 1.11, in which case the nitrogen substituents can be different.

Examples of these methods are shown in Scheme 1, Examples 3 and 5. In the procedure illustrated in Scheme 1, Example 3, a phosphonic acid 1.6 is reacted with ten molar equivalents of thionyl chloride, as described in Zh. Obschei Khim., 1958, 28, 1063, to give the dichloro compound 1.23. The product is then reacted at reflux temperature in a polar aprotic solvent such as acetonitrile, and in the presence of a base such as triethylamine, with butyl serinate 1.24 to afford the bisamidate product 1.25.

Using the above procedures, but employing, in place of butyl serinate 1.24, different aminoesters 1.9, the corresponding products 1.5 are obtained.

In the procedure illustrated in Scheme 1, Example 5, the phosphonic acid 1.6 is reacted, as described in J. Chem. Soc. Chem. Comm., 1991, 312, with carbonyl diimidazole to give the imidazolide 1.32. The product is then reacted in acetonitrile solution at ambient temperature, with one molar equivalent of ethyl alaninate 1.33 to yield the monodisplacement product 1.34. The latter compound is then reacted with carbonyl diimidazole to produce the activated intermediate 1.35, and the product is then reacted, under the same conditions, with ethyl N-methylalaninate 1.33a to give the bisamidate product 1.36.

Using the above procedures, but employing, in place of ethyl alaninate 1.33 or ethyl N-methylalaninate 1.33a, different aminoesters 1.9, the corresponding products 1.5 are obtained.

The intermediate monoamidate 1.3 is also prepared from the monoester 1.2 by first converting the monoester into the activated derivative 1.8 in which Lv is a leaving group such as halo, imidazolyl etc, using the procedures described above. The product 1.8 is then reacted with an aminoester 1.9 in the presence of a base such as pyridine, to give an intermediate monoamidate product 1.3. The latter compound is then converted, by removal of the $R^1$ group and coupling of the product with the aminoester 1.9, as described above, into the bisamidate 1.5.

An example of this procedure, in which the phosphonic acid is activated by conversion to the chloro derivative 1.26, is shown in Scheme 1, Example 4. In this procedure, the phosphonic monobenzyl ester 1.15 is reacted, in dichloromethane, with thionyl chloride, as described in Tet. Let., 1994, 35, 4097, to afford the phosphoryl chloride 1.26. The product is then reacted in acetonitrile solution at ambient temperature with one molar equivalent of ethyl 3-amino-2-methylpropionate 1.27 to yield the monoamidate product 1.28. The latter compound is hydrogenated in ethyl acetate over a 5% palladium on carbon catalyst to produce the monoacid product 1.29. The product is subjected to a Mitsonobu coupling procedure, with equimolar amounts of butyl alaninate 1.30, triphenyl phosphine, diethylazodicarboxylate and triethylamine in tetrahydrofuran, to give the bisamidate product 1.31.

Using the above procedures, but employing, in place of ethyl 3-amino-2-methylpropionate 1.27 or butyl alaninate 1.30, different aminoesters 1.9, the corresponding products 1.5 are obtained.

The activated phosphonic acid derivative 1.7 is also converted into the bisamidate 1.5 via the diamino compound 1.10. The conversion of activated phosphonic acid derivatives such as phosphoryl chlorides into the corresponding amino analogs 1.10, by reaction with ammonia, is described in Organic Phosphorus Compounds, G. M. Kosolapoff, L. Maeir, eds, Wiley, 1976. The diamino compound 1.10 is then reacted at elevated temperature with a haloester 1.12, in a polar organic solvent such as dimethylformamide, in the presence of a base such as dimethylaminopyridine or potassium carbonate, to yield the bisamidate 1.5.

An example of this procedure is shown in Scheme 1, Example 6. In this method, a dichlorophosphonate 1.23 is reacted with ammonia to afford the diamide 1.37. The reaction is performed in aqueous, aqueous alcoholic or alcoholic solution, at reflux temperature. The resulting diamino compound is then reacted with two molar equivalents of ethyl 2-bromo-3-methylbutyrate 1.38, in a polar organic solvent such as N-methylpyrrolidinone at ca. 150° C., in the presence of a base such as potassium carbonate, and optionally in the presence of a catalytic amount of potassium iodide, to afford the bisamidate product 1.39.

Using the above procedures, but employing, in place of ethyl 2-bromo-3-methylbutyrate 1.38, different haloesters 1.12 the corresponding products 1.5 are obtained.

The procedures shown in Scheme 1 are also applicable to the preparation of bisamidates in which the aminoester moiety incorporates different functional groups. Scheme 1, Example 7 illustrates the preparation of bisamidates derived from tyrosine. In this procedure, the monoimidazolide 1.32 is reacted with propyl tyrosinate 1.40, as described in Example 5, to yield the monoamidate 1.41. The product is reacted with carbonyl diimidazole to give the imidazolide 1.42, and this material is reacted with a further molar equivalent of propyl tyrosinate to produce the bisamidate product 1.43.

Using the above procedures, but employing, in place of propyl tyrosinate 1.40, different aminoesters 1.9, the corresponding products 1.5 are obtained. The aminoesters employed in the two stages of the above procedure can be the same or different, so that bisamidates with the same or different amino substituents are prepared.

Scheme 2 (FIG. 3) illustrates methods for the preparation of phosphonate monoamidates.

In one procedure, a phosphonate monoester 1.1 is converted, as described in Scheme 1, into the activated derivative 1.8. This compound is then reacted, as described above, with an aminoester 1.9, in the presence of a base, to afford the monoamidate product 2.1.

The procedure is illustrated in Scheme 2, Example 1. In this method, a monophenyl phosphonate 2.7 is reacted with, for example, thionyl chloride, as described in J. Gen. Chem. USSR., 1983, 32, 367, to give the chloro product 2.8. The product is then reacted, as described in Scheme 1, with ethyl alaninate 2.9, to yield the amidate 2.10.

Using the above procedures, but employing, in place of ethyl alaninate 2.9, different aminoesters 1.9, the corresponding products 2.1 are obtained.

Alternatively, the phosphonate monoester 1.1 is coupled, as described in Scheme 1, with an aminoester 1.9 to produce the amidate 2.1. If necessary, the $R^1$ substituent is then altered, by initial cleavage to afford the phosphonic acid 2.2. The procedures for this transformation depend on the nature of the $R^1$ group, and are described above. The phosphonic acid is then transformed into the ester amidate product 2.3, by reaction with the hydroxy compound $R^3OH$, in which the group $R^3$ is aryl, heteroaryl, alkyl, cycloalkyl, haloalkyl etc, using the same coupling procedures (carbodiimide, Aldrithiol-2, PYBOP, Mitsonobu reaction etc) described in Scheme 1 for the coupling of amines and phosphonic acids.

Examples of this method are shown in Scheme 2, Examples and 2 and 3. In the sequence shown in Example 2, a monobenzyl phosphonate 2.11 is transformed by reaction with ethyl alaninate, using one of the methods described above, into the monoamidate 2.12. The benzyl group is then removed by catalytic hydrogenation in ethyl acetate solution over a 5% palladium on carbon catalyst, to afford the phosphonic acid amidate 2.13. The product is then reacted in dichloromethane solution at ambient temperature with equimolar amounts of 1-(dimethylaminopropyl)-3-ethylcarbodiimide and trifluoroethanol 2.14, for example as described in Tet. Lett., 2001, 42, 8841, to yield the amidate ester 2.15.

In the sequence shown in Scheme 2, Example 3, the monoamidate 2.13 is coupled, in tetrahydrofuran solution at ambient temperature, with equimolar amounts of dicyclohexyl carbodiimide and 4-hydroxy-N-methylpiperidine 2.16, to produce the amidate ester product 2.17.

Using the above procedures, but employing, in place of the ethyl alaninate product 2.12 different monoacids 2.2, and in place of trifluoroethanol 2.14 or 4-hydroxy-N-methylpiperidine 2.16, different hydroxy compounds $R^3OH$, the corresponding products 2.3 are obtained.

Alternatively, the activated phosphonate ester 1.8 is reacted with ammonia to yield the amidate 2.4. The product is then reacted, as described in Scheme 1, with a haloester 2.5, in the presence of a base, to produce the amidate product 2.6. If appropriate, the nature of the $R^1$ group is changed, using the procedures described above, to give the product 2.3. The method is illustrated in Scheme 2, Example 4. In this sequence, the monophenyl phosphoryl chloride 2.18 is reacted, as described in Scheme 1, with ammonia, to yield the amino product 2.19. This material is then reacted in N-methylpyrrolidinone solution at 170° C. with butyl 2-bromo-3-phenylpropionate 2.20 and potassium carbonate, to afford the amidate product 2.21.

Using these procedures, but employing, in place of butyl 2-bromo-3-phenylpropionate 2.20, different haloesters 2.5, the corresponding products 2.6 are obtained.

The monoamidate products 2.3 are also prepared from the doubly activated phosphonate derivatives 1.7. In this procedure, examples of which are described in Synlett., 1998, 1, 73, the intermediate 1.7 is reacted with a limited amount of the aminoester 1.9 to give the mono-displacement product 1.11. The latter compound is then reacted with the hydroxy compound $R^3OH$ in a polar organic solvent such as dimethylformamide, in the presence of a base such as diisopropylethylamine, to yield the monoamidate ester 2.3.

The method is illustrated in Scheme 2, Example 5. In this method, the phosphoryl dichloride 2.22 is reacted in dichloromethane solution with one molar equivalent of ethyl N-methyl tyrosinate 2.23 and dimethylaminopyridine, to generate the monoamidate 2.24. The product is then reacted with phenol 2.25 in dimethylformamide containing potassium carbonate, to yield the ester amidate product 2.26.

Using these procedures, but employing, in place of ethyl N-methyl tyrosinate 2.23 or phenol 2.25, the aminoesters 1.9 and/or the hydroxy compounds $R^3OH$, the corresponding products 2.3 are obtained.

Scheme 3 (FIG. 4) illustrates methods for the preparation of carboalkoxy-substituted phosphonate diesters in which one of the ester groups incorporates a carboalkoxy substituent.

In one procedure, a phosphonate monoester 1.1, prepared as described above, is coupled, using one of the methods described above, with a hydroxyester 3.1, in which the groups $R^4$ and $R^5$ are as described in Scheme 1. For example, equimolar amounts of the reactants are coupled in the presence of a carbodiimide such as dicyclohexyl carbodiimide, as described in Aust. J. Chem., 1963, 609, optionally in the presence of dimethylaminopyridine, as described in Tet., 1999, 55, 12997. The reaction is conducted in an inert solvent at ambient temperature.

The procedure is illustrated in Scheme 3, Example 1. In this method, a monophenyl phosphonate 3.9 is coupled, in dichloromethane solution in the presence of dicyclohexyl carbodiimide, with ethyl 3-hydroxy-2-methylpropionate 3.10 to yield the phosphonate mixed diester 3.11.

Using this procedure, but employing, in place of ethyl 3-hydroxy-2-methylpropionate 3.10, different hydroxyesters 3.1, the corresponding products 3.2 are obtained.

The conversion of a phosphonate monoester 1.1 into a mixed diester 3.2 is also accomplished by means of a Mitsonobu coupling reaction with the hydroxyester 3.1, as described in Org. Lett., 2001, 643. In this method, the reactants 1.1 and 3.1 are combined in a polar solvent such as tetrahydrofuran, in the presence of a triarylphosphine and a dialkyl azodicarboxylate, to give the mixed diester 3.2. The $R^1$ substituent is varied by cleavage, using the methods described previously, to afford the monoacid product 3.3. The product is then coupled, for example using methods described above, with the hydroxy compound $R^3OH$, to give the diester product 3.4.

The procedure is illustrated in Scheme 3, Example 2. In this method, a monoallyl phosphonate 3.12 is coupled in tetrahydrofuran solution, in the presence of triphenylphosphine and diethylazodicarboxylate, with ethyl lactate 3.13 to give the mixed diester 3.14. The product is reacted with tris(triphenylphosphine) rhodium chloride (Wilkinson catalyst) in acetonitrile, as described previously, to remove the allyl group and produce the monoacid product 3.15. The latter compound is then coupled, in pyridine solution at ambient temperature, in the presence of dicyclohexyl carbodiimide, with one molar equivalent of 3-hydroxypyridine 3.16 to yield the mixed diester 3.17.

Using the above procedures, but employing, in place of the ethyl lactate 3.13 or 3-hydroxypyridine, a different hydroxyester 3.1 and/or a different hydroxy compound $R^3OH$, the corresponding products 3.4 are obtained.

The mixed diesters 3.2 are also obtained from the monoesters 1.1 via the intermediacy of the activated monoesters 3.5. In this procedure, the monoester 1.1 is converted into the activated compound 3.5 by reaction with, for example, phosphorus pentachloride, as described in J. Org. Chem., 2001, 66, 329, or with thionyl chloride or oxalyl chloride (Lv=Cl), or with triisopropylbenzenesulfonyl chloride in pyridine, as described in Nucleosides and Nucleotides, 2000, 19, 1885, or with carbonyl diimidazole, as described in J. Med. Chem., 2002, 45, 1284. The resultant activated monoester is then reacted with the hydroxyester 3.1, as described above, to yield the mixed diester 3.2.

The procedure is illustrated in Scheme 3, Example 3. In this sequence, a monophenyl phosphonate 3.9 is reacted, in acetonitrile solution at 70° C., with ten equivalents of thionyl chloride, so as to produce the phosphoryl chloride 3.19. The product is then reacted with ethyl 4-carbamoyl-2-hydroxybutyrate 3.20 in dichloromethane containing triethylamine, to give the mixed diester 3.21.

Using the above procedures, but employing, in place of ethyl 4-carbamoyl-2-hydroxybutyrate 3.20, different hydroxyesters 3.1, the corresponding products 3.2 are obtained.

The mixed phosphonate diesters are also obtained by an alternative route for incorporation of the $R^3O$ group into intermediates 3.3 in which the hydroxyester moiety is already incorporated. In this procedure, the monoacid intermediate 3.3 is converted into the activated derivative 3.6 in which Lv is a leaving group such as chloro, imidazole, and the like, as previously described. The activated intermediate is then reacted with the hydroxy compound $R^3OH$, in the presence of a base, to yield the mixed diester product 3.4.

The method is illustrated in Scheme 3, Example 4. In this sequence, the phosphonate monoacid 3.22 is reacted with trichloromethanesulfonyl chloride in tetrahydrofuran containing collidine, as described in J. Med. Chem., 1995, 38, 4648, to produce the trichloromethanesulfonyloxy product 3.23. This compound is reacted with 3-(morpholinomethyl)phenol 3.24 in dichloromethane containing triethylamine, to yield the mixed diester product 3.25.

Using the above procedures, but employing, in place of with 3-(morpholinomethyl)phenol 3.24, different carbinols $R^3OH$, the corresponding products 3.4 are obtained.

The phosphonate esters 3.4 are also obtained by means of alkylation reactions performed on the monoesters 1.1. The reaction between the monoacid 1.1 and the haloester 3.7 is performed in a polar solvent in the presence of a base such as diisopropylethylamine, as described in Anal. Chem., 1987, 59, 1056, or triethylamine, as described in J. Med. Chem., 1995, 38, 1372, or in a non-polar solvent such as benzene, in the presence of 18-crown-6, as described in Syn. Comm., 1995, 25, 3565.

The method is illustrated in Scheme 3, Example 5. In this procedure, the monoacid 3.26 is reacted with ethyl 2-bromo-3-phenylpropionate 3.27 and diisopropylethylamine in dimethylformamide at 80° C. to afford the mixed diester product 3.28.

Using the above procedure, but employing, in place of ethyl 2-bromo-3-phenylpropionate 3.27, different haloesters 3.7, the corresponding products 3.4 are obtained.

Scheme 4 (FIG. 5) illustrates methods for the preparation of phosphonate diesters in which both the ester substituents incorporate carboalkoxy groups.

The compounds are prepared directly or indirectly from the phosphonic acids 1.6. In one alternative, the phosphonic acid is coupled with the hydroxyester 4.2, using the conditions described previously in Schemes 1-3, such as coupling reactions using dicyclohexyl carbodiimide or similar reagents, or under the conditions of the Mitsonobu reaction, to afford the diester product 4.3 in which the ester substituents are identical.

This method is illustrated in Scheme 4, Example 1. In this procedure, the phosphonic acid 1.6 is reacted with three molar equivalents of butyl lactate 4.5 in the presence of Aldrithiol-2 and triphenyl phosphine in pyridine at ca. 70° C., to afford the diester 4.6.

Using the above procedure, but employing, in place of butyl lactate 4.5, different hydroxyesters 4.2, the corresponding products 4.3 are obtained.

Alternatively, the diesters 4.3 are obtained by alkylation of the phosphonic acid 1.6 with a haloester 4.1. The alkylation reaction is performed as described in Scheme 3 for the preparation of the esters 3.4.

This method is illustrated in Scheme 4, Example 2. In this procedure, the phosphonic acid 1.6 is reacted with excess ethyl 3-bromo-2-methylpropionate 4.7 and diisopropylethylamine in dimethylformamide at ca. 80° C., as described in Anal. Chem., 1987, 59, 1056, to produce the diester 4.8.

Using the above procedure, but employing, in place of ethyl 3-bromo-2-methylpropionate 4.7, different haloesters 4.1, the corresponding products 4.3 are obtained.

The diesters 4.3 are also obtained by displacement reactions of activated derivatives 1.7 of the phosphonic acid with the hydroxyesters 4.2. The displacement reaction is performed in a polar solvent in the presence of a suitable base, as described in Scheme 3. The displacement reaction is performed in the presence of an excess of the hydroxyester, to afford the diester product 4.3 in which the ester substituents are identical, or sequentially with limited amounts of different hydroxyesters, to prepare diesters 4.3 in which the ester substituents are different.

The methods are illustrated in Scheme 4, Examples 3 and 4. As shown in Example 3, the phosphoryl dichloride 2.22 is reacted with three molar equivalents of ethyl 3-hydroxy-2-(hydroxymethyl)propionate 4.9 in tetrahydrofuran containing potassium carbonate, to obtain the diester product 4.10.

Using the above procedure, but employing, in place of ethyl 3-hydroxy-2-(hydroxymethyl)propionate 4.9, different hydroxyesters 4.2, the corresponding products 4.3 are obtained.

Scheme 4, Example 4 depicts the displacement reaction between equimolar amounts of the phosphoryl dichloride 2.22 and ethyl 2-methyl-3-hydroxypropionate 4.11, to yield the monoester product 4.12. The reaction is conducted in acetonitrile at 70° C. in the presence of diisopropylethylamine. The product 4.12 is then reacted, under the same conditions, with one molar equivalent of ethyl lactate 4.13, to give the diester product 4.14.

Using the above procedures, but employing, in place of ethyl 2-methyl-3-hydroxypropionate 4.11 and ethyl lactate 4.13, sequential reactions with different hydroxyesters 4.2, the corresponding products 4.3 are obtained.

Aryl halides undergo $Ni^{+2}$ catalyzed reaction with phosphite derivatives to give aryl phosphonate containing compounds (Balthazar, et al (1980) *J. Org. Chem.* 45:5425). Phosphonates may also be prepared from the chlorophosphonate in the presence of a palladium catalyst using aromatic triflates (Petrakis, et al, (1987) *J. Am. Chem. Soc.* 109:2831; Lu, et al, (1987) *Synthesis,* 726). In another method, aryl phosphonate esters are prepared from aryl phosphates under anionic rearrangement conditions (Melvin (1981) *Tetrahedron Lett.* 22:3375; Casteel, et al, (1991) *Synthesis,* 691). N-Alkoxy aryl salts with alkali metal derivatives of cyclic alkyl phosphonate provide general synthesis for heteroaryl-2-phosphonate linkers (Redmore (1970) *J. Org. Chem.* 35:4114). These above mentioned methods can also be extended to compounds where the $W^5$ group is a heterocycle. Cyclic-1,3-propanyl prodrugs of phosphonates are also synthesized from phosphonic diacids and substituted propane-1,3-diols using a coupling reagent such as 1,3-dicyclohexylcarbodiimide (DCC) in presence of a base (e.g., pyridine). Other carbodiimide based coupling agents like 1,3-disopropylcarbodiimide or water soluble reagent, 1-(3-dimethylaminopropyl)-3-ethyl-carbodiimide hydrochloride (EDCI) can also be utilized for the synthesis of cyclic phosphonate prodrugs.

The carbamoyl group may be formed by reaction of a hydroxy group according to the methods known in the art, including the teachings of Ellis, US 2002/0103378 A1 and Hajima, U.S. Pat. No. 6,018,049.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable.

General synthetic routes to substituted imidazoles are well established. See Ogata M (1988) *Annals of the New York Academy of Sciences* 544:12-31; Takahashi et al (1985) *Heterocycles* 23:6, 1483-1492; Ogata et al (1980) *CHEM IND LONDON* 2:5-86; Yanagisawa et al U.S. Pat. No. 5,646,171; Rachwal et al US 2002/0115693 A1; Carlson et al U.S. Pat. Nos. 3,790,593; 3,761,491 and 3,773,781; Aono et al U.S. Pat. No. 6,054,591; Hajima et al U.S. Pat. No. 6,057,448; Sugimoto et al EP 00552060 and U.S. Pat. No. 5,326,780.

Figure 6A:
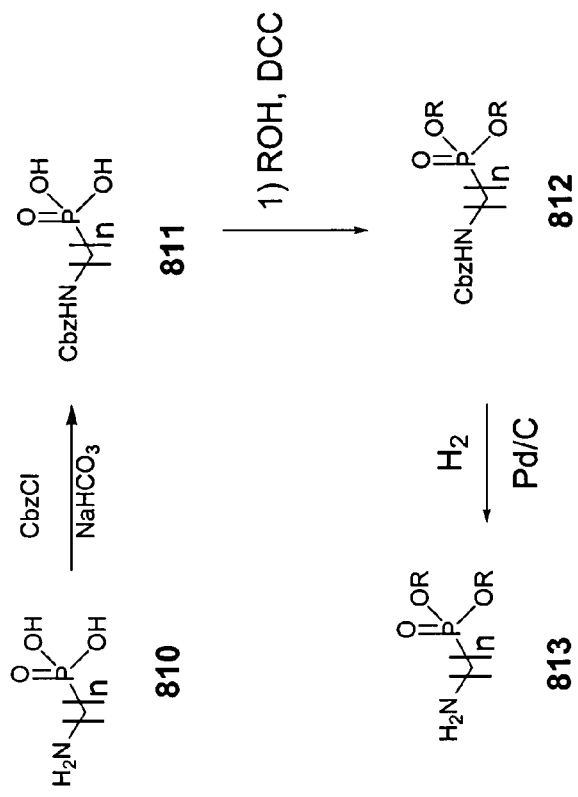
FIGS. 6A-C depict Scheme 2 which is described in detail herein below.
Figure 6B:
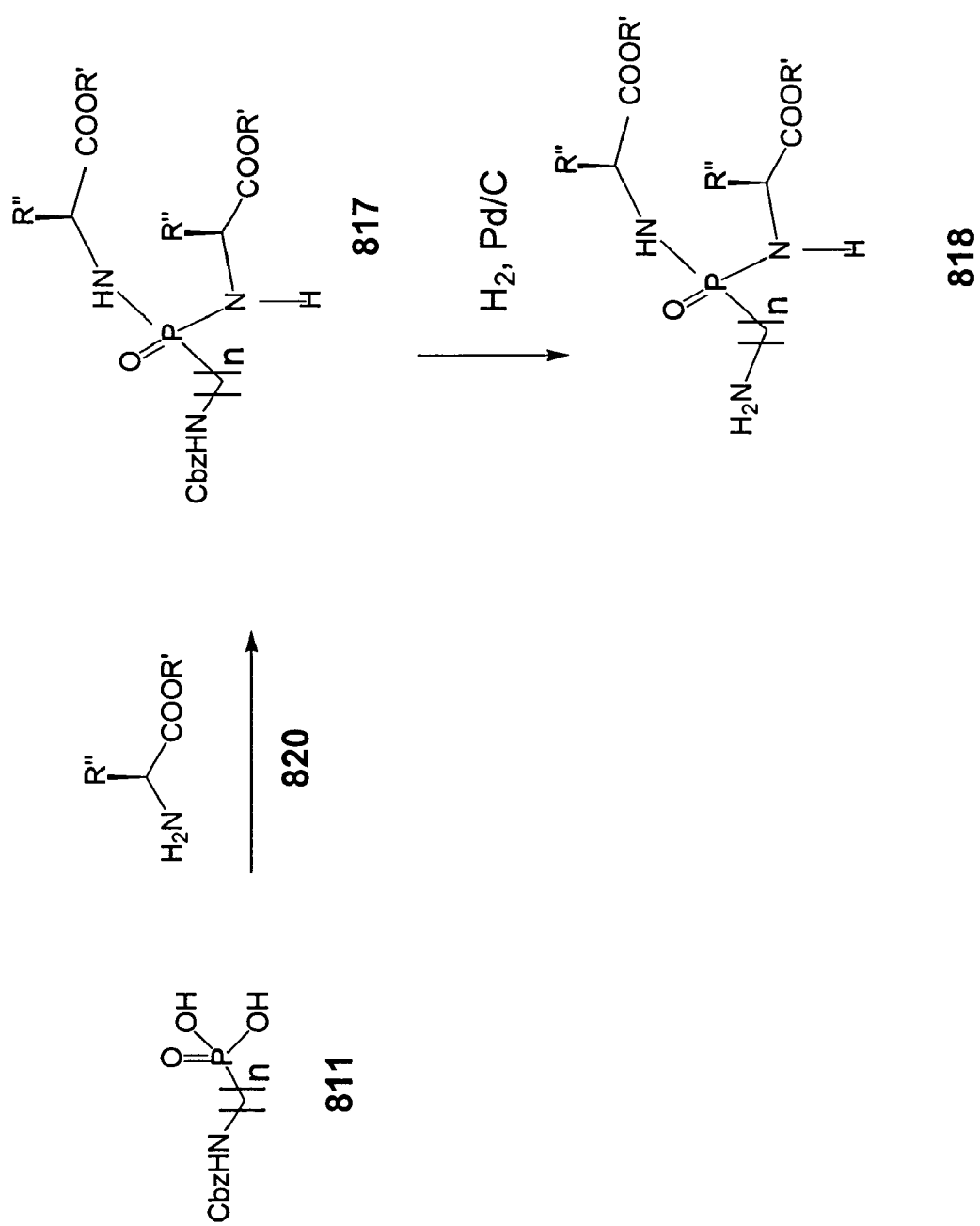
Figure 6C:
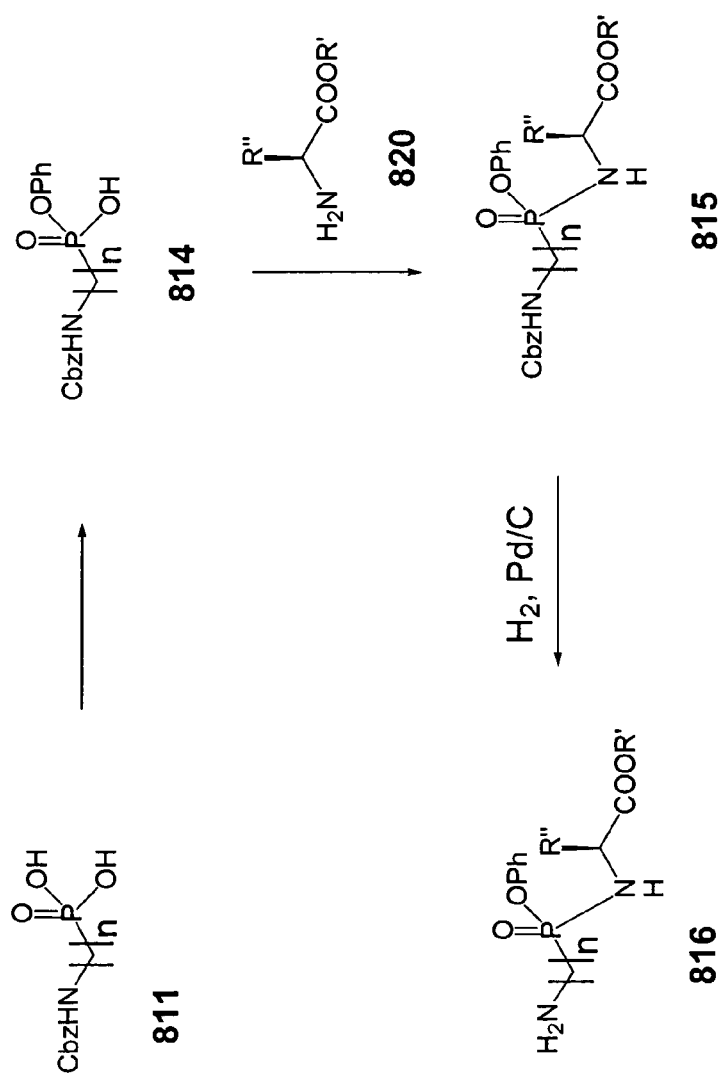

Amino alkyl phosphonate compounds 809:

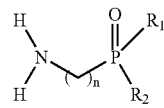

are a generic representative of compounds 811, 813, 814, 816 and 818 (Scheme 2; FIG. 6). The alkylene chain may be any length from 1 to 18 methylene groups (n=1-18). Commercial amino phosphonic acid 810 was protected as carbamate 811. The phosphonic acid 811 was converted to phosphonate 812 upon treatment with ROH in the presence of DCC or other conventional coupling reagents. Coupling of phosphonic acid 811 with esters of amino acid 820 provided bisamidate 817. Conversion of acid 811 to bisphenyl phosphonate followed by hydrolysis gave mono-phosphonic acid 814 (Cbz=$C_6H_5CH_2C(O)$—), which was then transformed to mono-phosphonic amidate 815. Carbamates 813, 816 and 818 were converted to their corresponding amines upon hydrogenation. Compounds 811, 813, 814, 816 and 818 are useful intermediates to form the phosphonate compounds of the invention.

Figure 7:
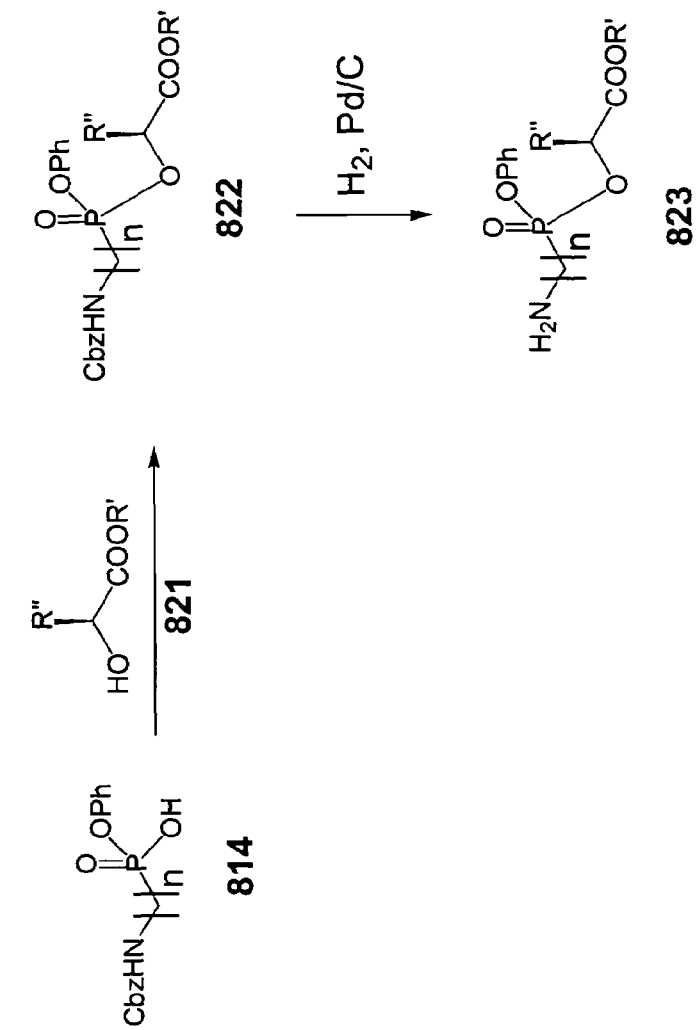
FIG. 7 depicts Scheme 3 which is described in detail herein below.

Following the similar procedures, replacement of amino acid esters 820 with lactates 821 (Scheme 3; FIG. 7) provides mono-phosphonic lactates 823. Lactates 823 are useful intermediates to form the phosphonate compounds of the invention.

EXAMPLES GENERAL SECTION

The following Examples refer to the Schemes. Some Examples have been performed multiple times. In repeated Examples, reaction conditions such as time, temperature, concentration and the like, and yields were within normal experimental ranges. In repeated Examples where significant modifications were made, these have been noted where the results varied significantly from those described. In Examples where different starting materials were used, these are noted. When the repeated Examples refer to a "corresponding" analog of a compound, such as a "corresponding ethyl ester", this intends that an otherwise present group, in this case typically a methyl ester, is taken to be the same group modified as indicated.

Example 1

To a solution of 2-aminoethylphosphonic acid (810 where n=2, 1.26 g, 10.1 mmol) in 2N NaOH (10.1 mL, 20.2 mmol) was added benzyl chloroformate (1.7 mL, 12.1 mmol). See Scheme 5. After the reaction mixture was stirred for 2 d at room temperature, the mixture was partitioned between $Et_2O$ and water. The aqueous phase was acidified with 6N HCl until pH=2. The resulting colorless solid was dissolved in MeOH (75 mL) and treated with Dowex 50WX8-200 (7 g). After the mixture was stirred for 30 minutes, it was filtered and evaporated under reduced pressure to give carbamate 28 (2.37 g, 91%) as a colorless solid.

To a solution of carbamate 28 (2.35 g, 9.1 mmol) in pyridine (40 mL) was added phenol (8.53 g, 90.6 mmol) and 1,3-dicyclohexylcarbodiimide (7.47 g, 36.2 mmol). After the reaction mixture was warmed to 70° C. and stirred for 5 h, the mixture was diluted with $CH_3CN$ and filtered. The filtrate was concentrated under reduced pressure and diluted with EtOAc. The organic phase was washed with sat. NH$_4$Cl, sat. NaHCO$_3$, and brine, then dried over Na$_2$SO$_4$, filtered, and evaporated under reduced pressure. The crude product was chromatographed on silica gel twice (eluting 40-60% EtOAc/ hexane) to give phosphonate 29 (2.13 g, 57%) as a colorless solid.

To a solution of phosphonate 29 (262 mg, 0.637 mmol) in iPrOH (5 mL) was added TFA (0.05 mL, 0.637 mmol) and 10% Pd/C (26 mg). After the reaction mixture was stirred under H$_2$ atmosphere (balloon) for 1 h, the mixture was filtered through Celite. The filtrate was evaporated under reduced pressure to give amine 30 (249 mg, 100%) as a colorless oil (Scheme 5).

Figure 8:
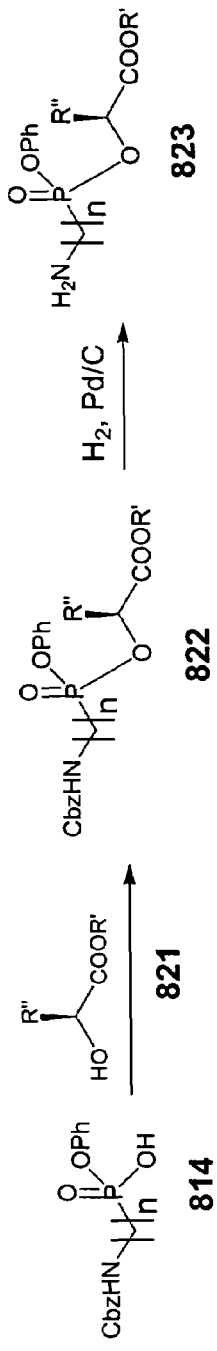
FIG. 8 depicts Scheme 6 which is described in detail herein below.

Following the similar procedures, replacement of amino acid esters with lactates (Scheme 6; FIG. 8) provided monophosphonic lactates, e.g. 823.

Figure 9:
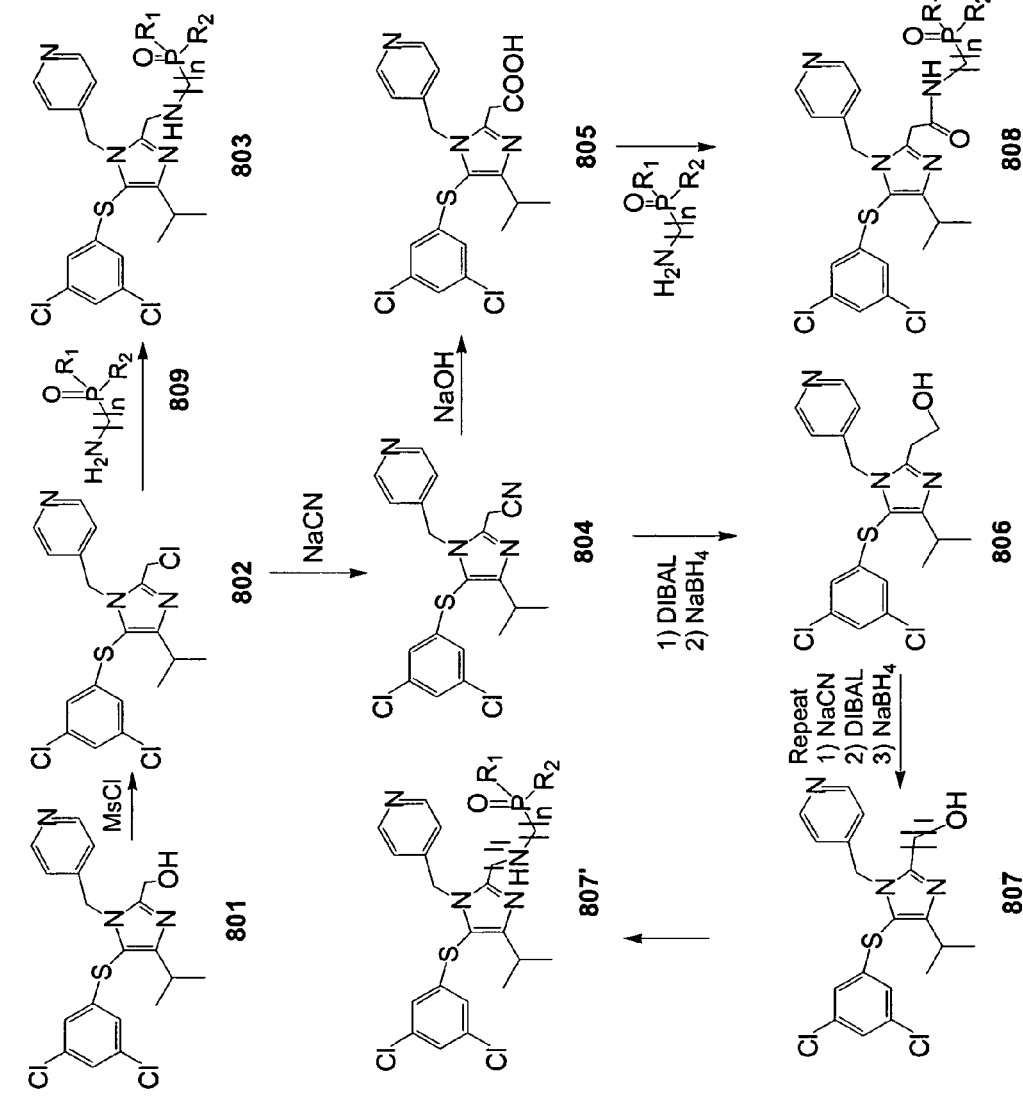
FIG. 9 depicts Scheme 7 which is described in detail herein below.

Treatment of alcohol 801 (prepared according to literature) with MsCl and TEA afforded chloride 802 (Scheme 7; FIG. 9). Chloride 802 was converted to compound 803 by reacting with 809, which preparation is detailed in Schemes 3 and 4, in the presence of base. When mesylate 802 was treated with NaCN, imidazole nitrile 804 was provided. Reduction of 804 with DIBAL followed by NaBH$_4$ yielded imidazole alcohol 806. Repeating the same procedure several times furnished alcohol 807 with the desired length. Hydrolysis of imidazole nitrile 804 provided acid 805. Coupling of acid 805 in the presence of conventional reagents afforded the amide 808. Phosphorus compound 807' was produced by transforming alcohol 807 to its corresponding mesylate followed by treating with amine 809.

Figure 10:
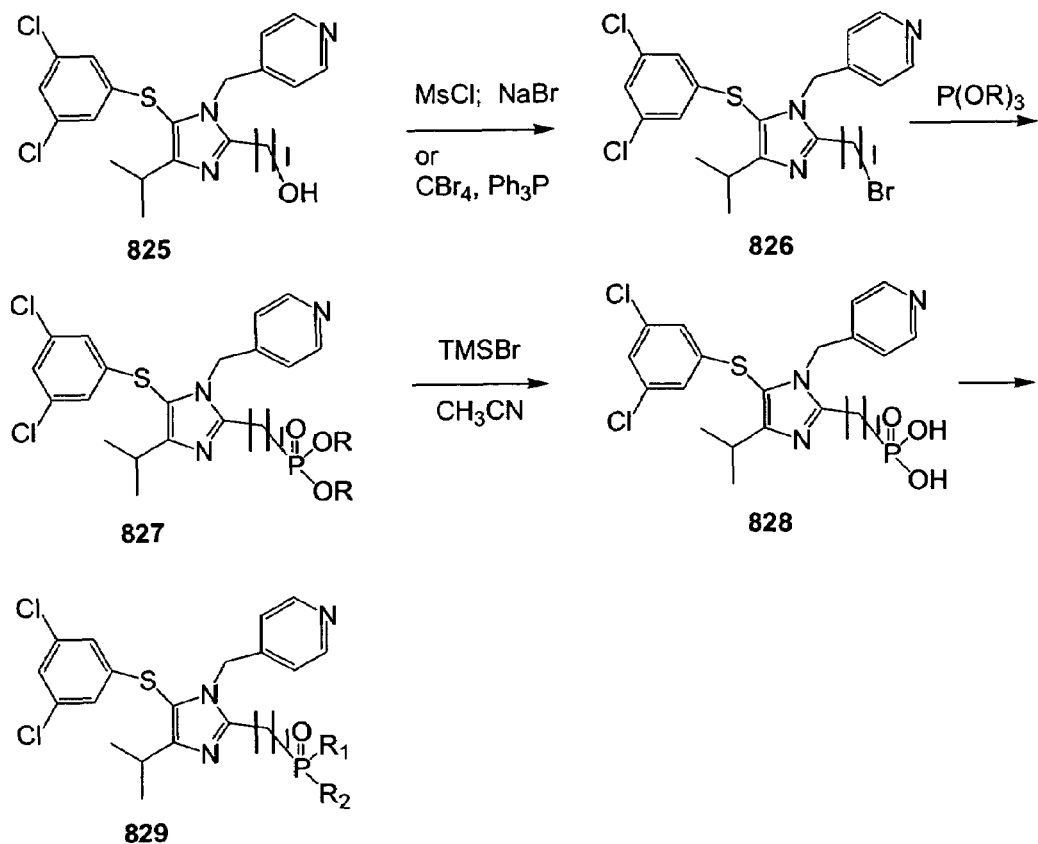
FIG. 10 depicts Scheme 8 which is described in detail herein below.

Alcohol 825 was converted to bromide 826 by first transformed to its mesylate and then treated with NaBr, this conversion was also realized by reacting alcohol 825 with Ph$_3$P and CBr$_4$ (Scheme 8; FIG. 10). Upon treating with P(OR)$_3$, phosphonate 827 was produced. Esters was then removed to form acid, and following the similar procedure described in Scheme 2 and 3, desired phosphonate, bisphosphoamidate, mono-phosphoamidate, and monophospholactate were produced.

Figure 11:
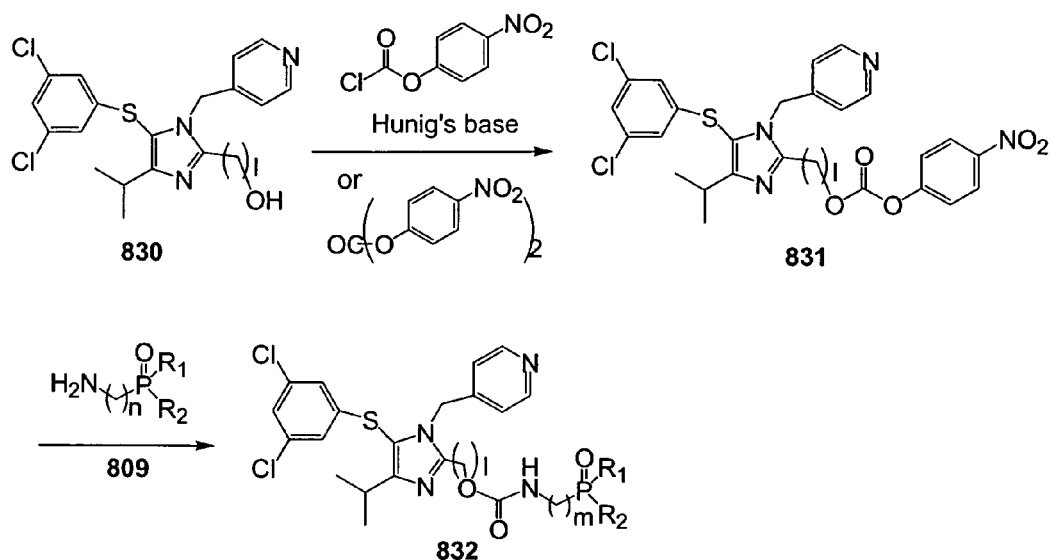
FIG. 11 depicts Scheme 9 which is described in detail herein below.

In Scheme 9 (FIG. 11), alcohol 830 was converted to carbonate 831 by reacting with either p-nitrophenyl chloroformate or p-nitrophenyl carboxy anhyride. Treatment of carbonate 831 with amine 809 in the presence of suitable base afforded desired phosphonate compounds 832.

Figure 12:
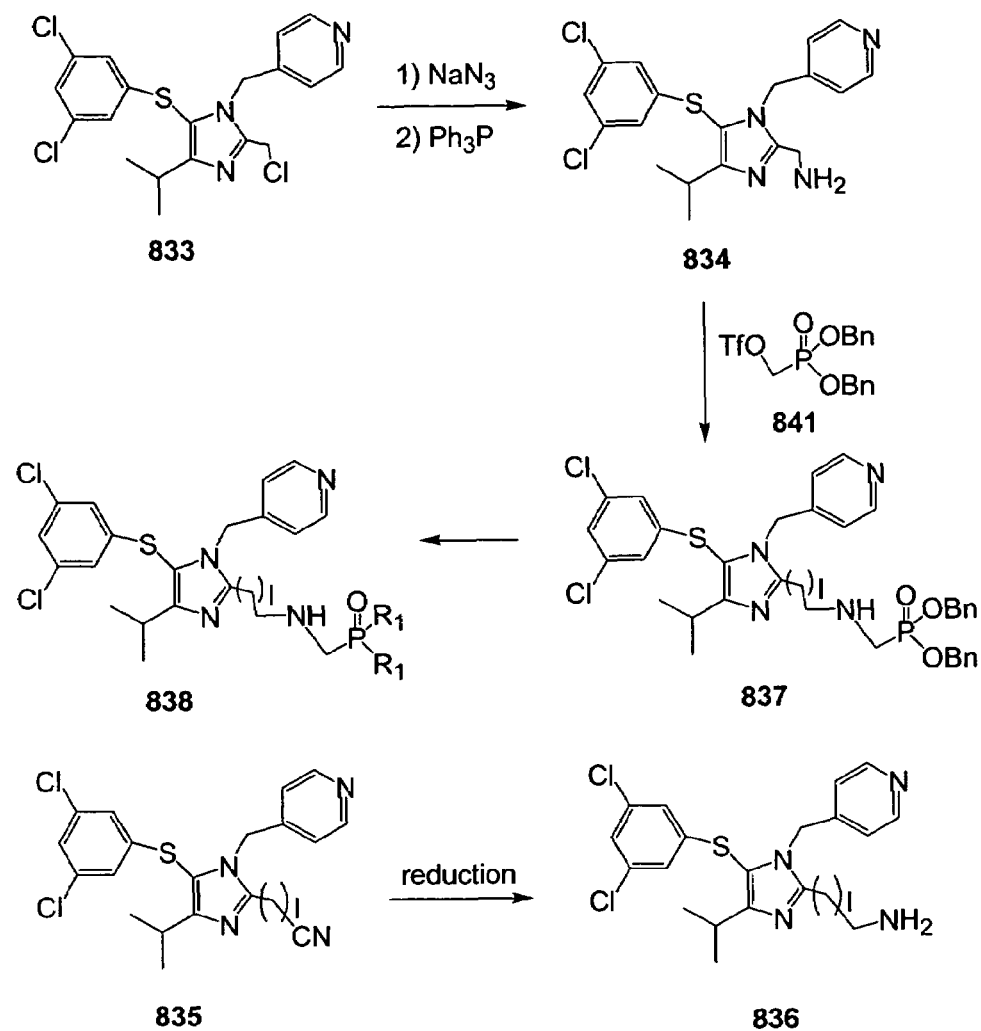
FIG. 12 depicts Scheme 10 which is described in detail herein below.

Phosphorus compound 838 was produced according to the procedures described in Scheme 10 (FIG. 12). Replacement of chloride group in compound 833 with azide followed by reduction with triphenylphosphine provided amine 834. Replacement of chloride group in compound 833 with cyanide, e.g. sodium cyanide, provided amine 835. Reduction of nitrile 835 furnished amine 836. Reaction of amines, e.g. 834 or 836, with triflate 841 in the presence of a base afforded phosphonate 837. Removal of benzyl group of 837 gave its corresponding phosphonic acid, e.g. 838 where R$_1$=H, which was converted to various phosphorus compounds according to the procedure described in the previous Schemes.

Figure 13:
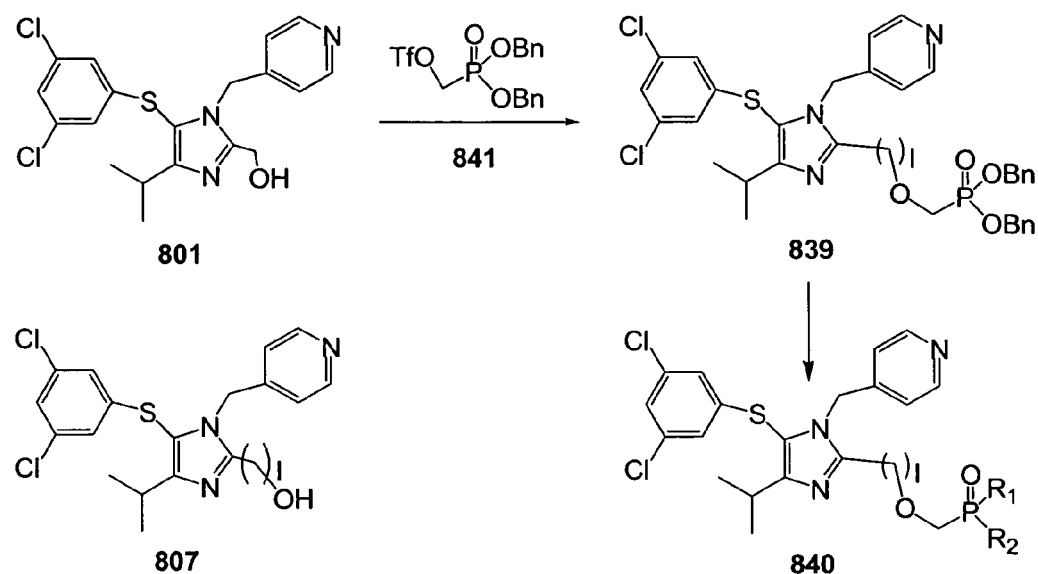
FIG. 13 depicts Scheme 11 which is described in detail herein below.

Phosphorus compound 840 was produced in a similar way as described in Scheme 10 except by replacing amines with alcohols 801, or generally, 807 (Scheme 11; FIG. 13).

Figure 14:
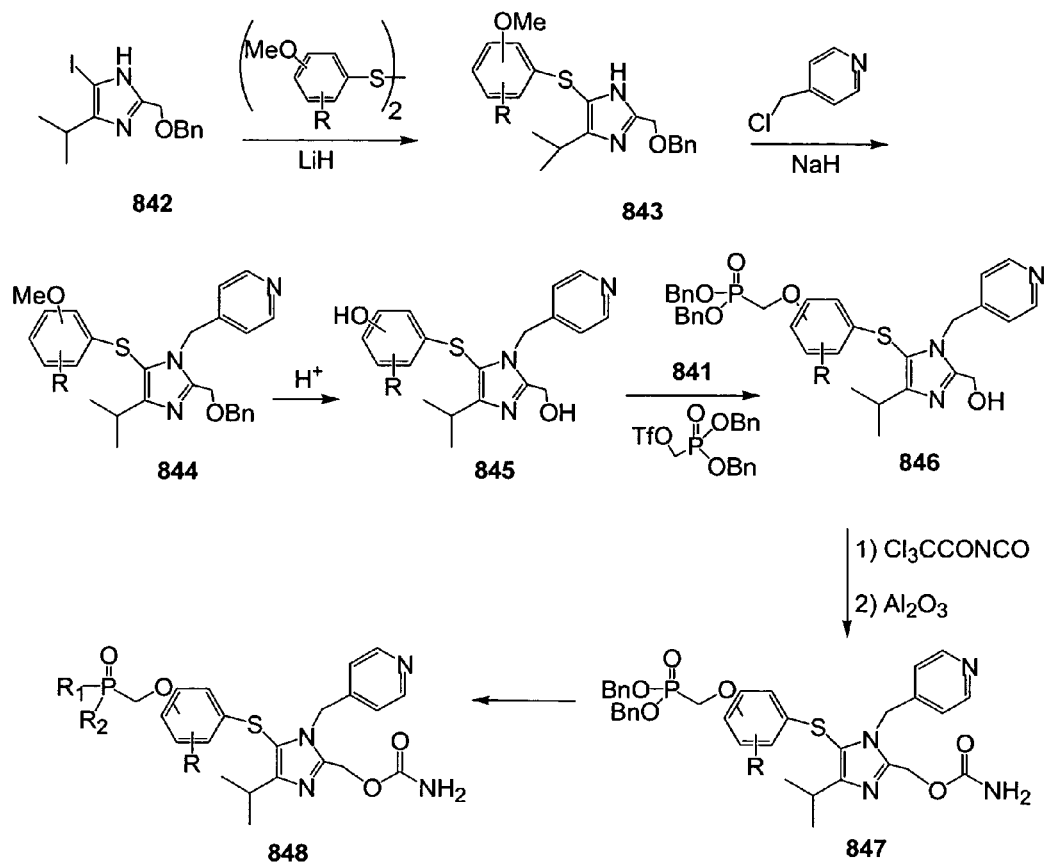
FIG. 14 depicts Scheme 12 which is described in detail herein below.

Phosphorus compound 848 was synthesized according to procedures described in Scheme 12 (FIG. 14). Iodoimidazole 842 was converted to imidazole phenyl thioether 843 by reacting with LiH and substituted phenyl disulfide (Scheme 12; FIG. 14). Treatment of imidazole with NaH and 4-picolyl chloride gave imidazole 844. Benzyl and methyl groups were removed by treating with strong acid to provide alcohol 845. Conversion of phenol 845 to phosphonate 846 was accomplished by reacting phenol 845 with triflate 841 in the presence of base. Alcohol 846 was reacting with trichloroacetyl isocyanate followed by treatment of alumina afforded carbamate 847. Phosphonate 847 was transformed to all kinds of phosphorus compound 848 followed the procedure described for 838 in Scheme 10.

Figure 15:
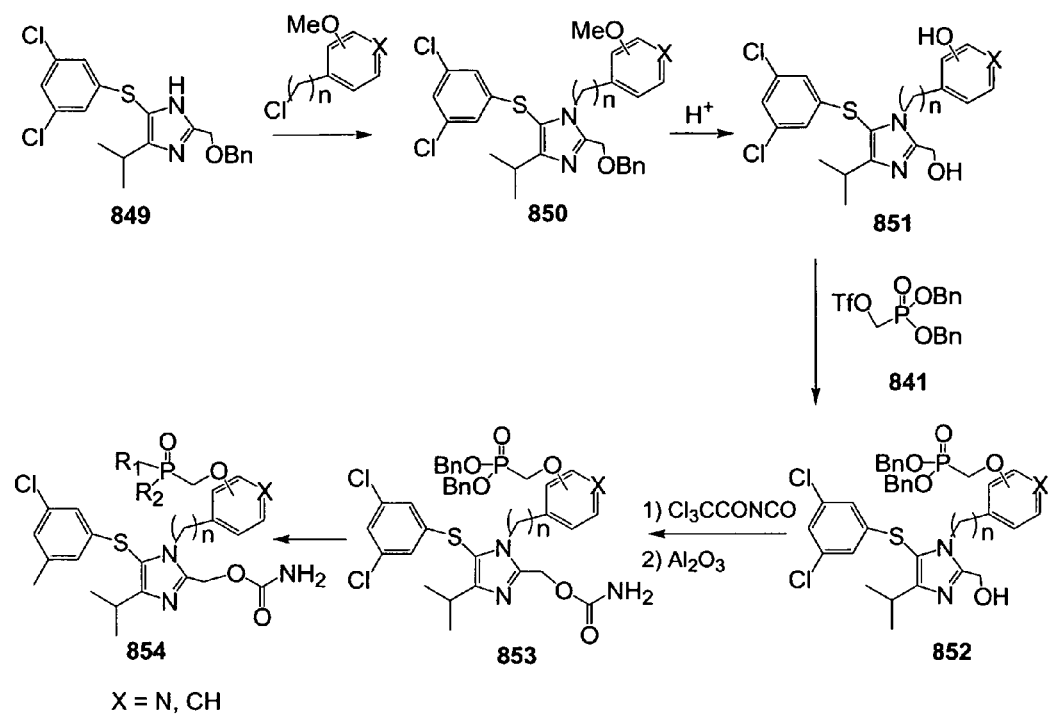
FIG. 15 depicts Scheme 13 which is described in detail herein below.

Phosphorus compound 854 was prepared as shown in Scheme 13 (FIG. 15). Imidazole 849 (prepared according to U.S. Pat. Nos. 5,910,506 and 6,057,448) was converted to 850 by reacting with chloride in the presence of base. Benzyl and methyl groups were removed by treating ether 850 with strong protonic or Lewis acid to furnish phenol 851. Treatment of phenol 851 with base followed by triflate 841 gave phosphonate 852. Following similar procedures described in Scheme 12 transforming alcohol 846 to phosphorus compound 848, alcohol 852 was converted to phosphorus compound 854.

Figure 16:
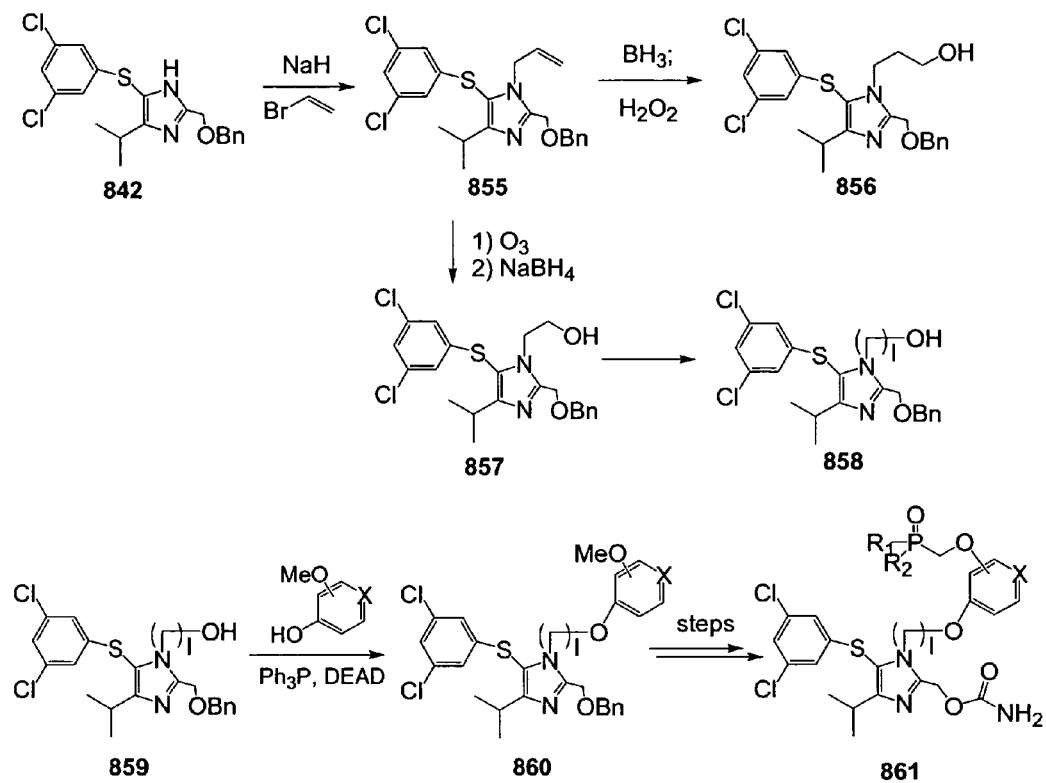
FIG. 16 depicts Scheme 14 which is described in detail herein below.

Preparation of phosphorus compound 861 is shown in Scheme 14 (FIG. 16). Imidazole 855 was synthesized by treating compound 842 with NaH followed by allyl bromide. Hydroboration followed by oxidative work up gave alcohol 856. Ozonolysis followed by reduction of the resulting aldehyde afforded alcohol 857. Alcohol 858, which has variation of length, was obtained by following the same transformation of alcohol 806 to 807 as exhibited in Scheme 7. Mitsunobu reaction of alcohol 859 with substituted phenols gave imidazole 860. Phenol ether 860 was converted to phosphonate 861 by following same procedure of transforming compound 850 to 854 as described in Scheme 13.

Figure 17:
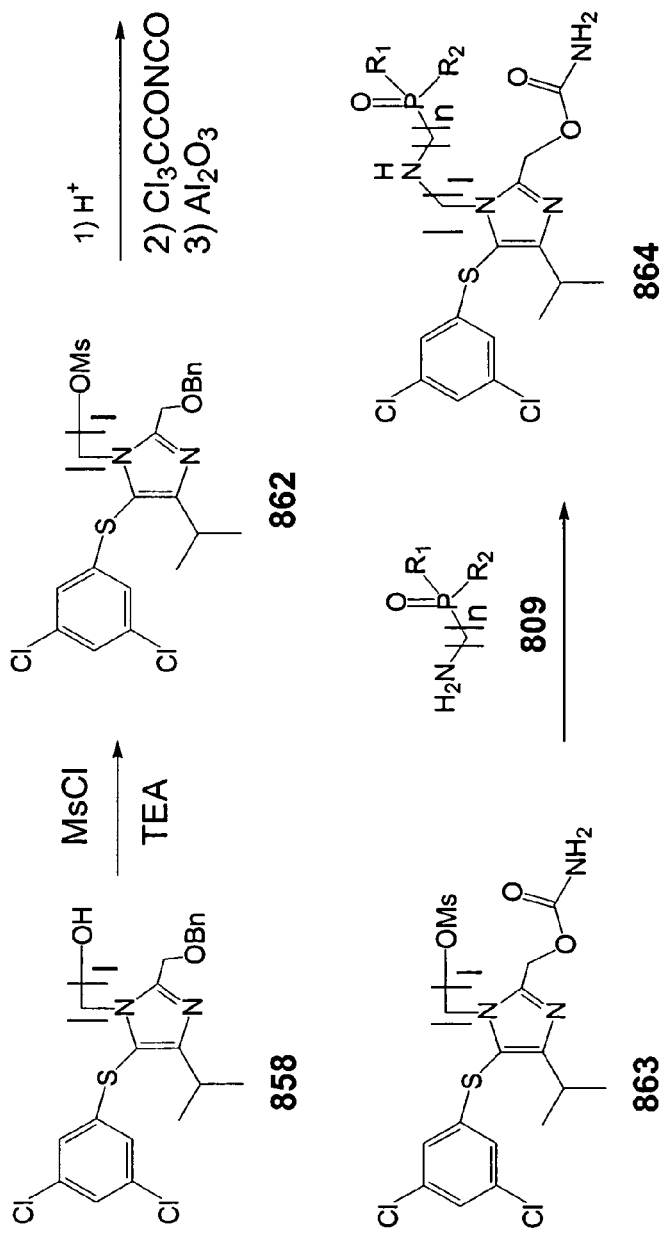
FIG. 17 depicts Scheme 15 which is described in detail herein below.

In Scheme 15 (FIG. 17), preparation of phosphorus compounds 864 is shown. Alcohol 858 was converted to mesylate 862 by reacting with MsCl. Removal of benzyl group, followed by conversion of the resultant alcohol to the corresponding carbamate (described in previous Schemes) furnished compound 863. Substitution of mesylate with amine 809 generated phosphorus compound 864.

Figure 18:
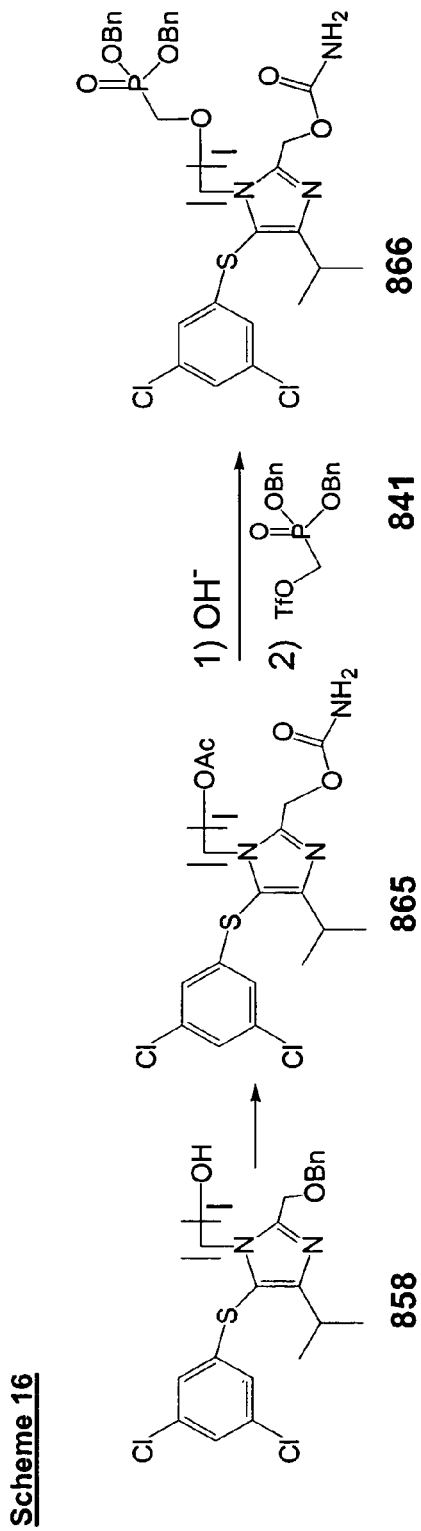
FIG. 18 depicts Scheme 16 which is described in detail herein below.

Synthesis of phosphorus compound 866 is described in Scheme 16 (FIG. 18). Protection of alcohol 858 to its acetate 865, followed by the conversion of the benzyl, —OBn group to the corresponding carbamate as described for transforming compound 862 to 863 in Scheme 15, gave compound 865. Hydrolysis of acetate, and treatment of the resultant alcohol with triflate 841 in the presence of base afforded phosphonate 866.

Figure 19:
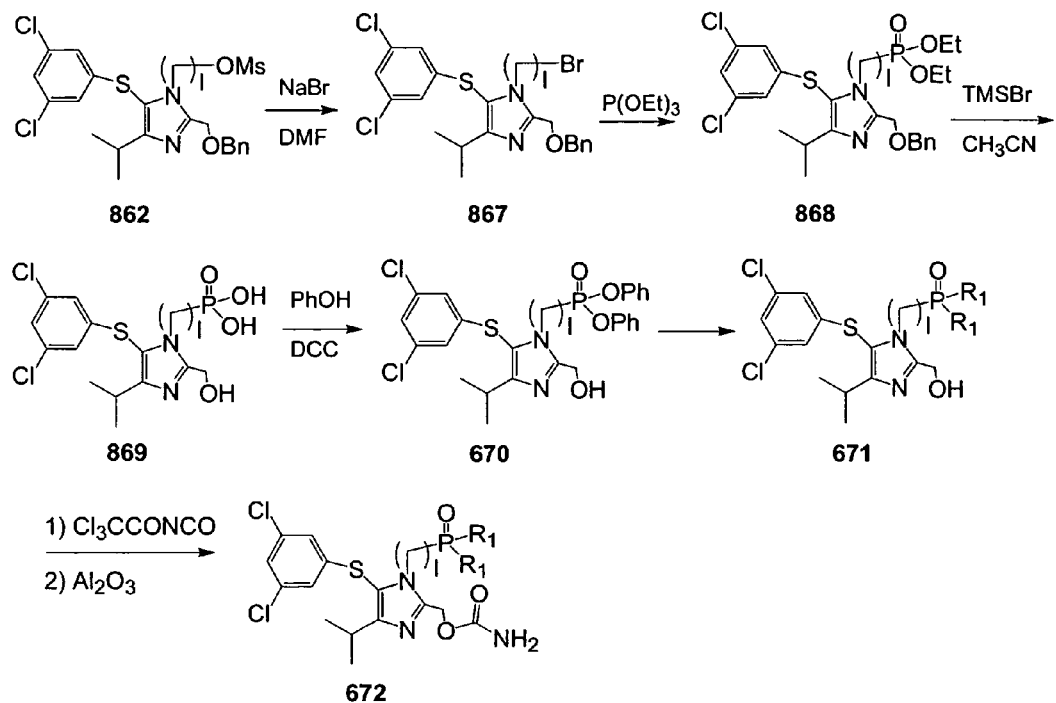
FIG. 19 depicts Scheme 17 which is described in detail herein below.

Scheme 17 (FIG. 19) describes synthesis of phosphorus compound 672. Mesylate 862 was transformed to bromide 867 by reacting with NaBr. Arbusov reaction gave phosphonate 868. Both benzyl and ethyl groups were cleaved when treated with TMSBr to yield compound 869. Coupling of phosphonic acid 869 with PhOH provided bisphenyl phosphonate 670. Compound 670 was converted to various phosphorus compounds 671 according to the procedures described in Schemes 1, 2 and 3. Phosphorus compound 672 was obtained by repeating the procedures shown before.

Figure 20:
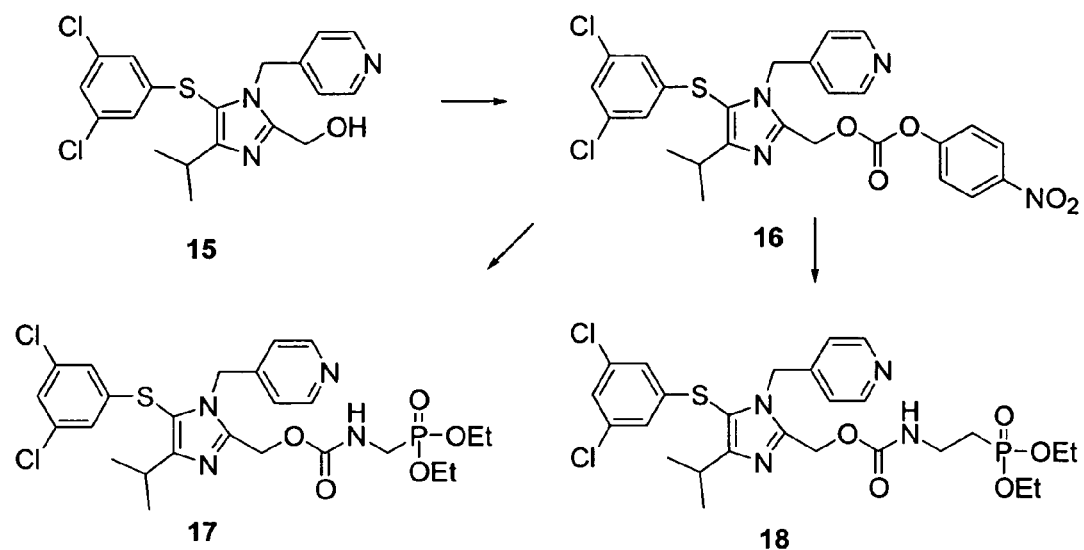
FIG. 20 depicts Scheme 18 which is described in detail herein below.

FIG. 20 depicts Scheme 18.

Example 10

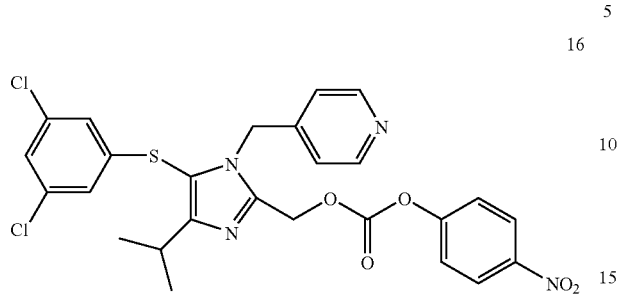

16

To a solution of alcohol 15 (42 mg, 0.10 mmol) in CH₂Cl₂ (5 mL) was added triethylamine (24 μL, 0.17 mmol) and bis(4-nitrophenyl) carbonate (46 mg, 0.15 mmol). See Scheme 18. After the reaction mixture was stirred for 4 h at room temperature, the mixture was partitioned between CH₂Cl₂ and water. The organic phase was dried over Na₂SO₄, filtered, and evaporated under reduced pressure. The crude product was chromatographed on silica gel (eluting 60-70% EtOAc/hexane) to give carbonic acid 5-(3,5-dichloro-phenylsulfanyl)-4-isopropyl-1-pyridin-4-ylmethyl-1H-imidazol-2-ylmethyl ester 4-nitro-phenyl ester 16 (47 mg, 82%) as a colorless oil.

Example 11A

17

To a solution of carbonate 16 (14 mg, 0.024 mmol) in CH₃CN (2 mL) was added diethyl(aminomethyl)phosphonate (10 mg, 0.037 mmol) and diisopropylethylamine (8 μL, 0.048 mmol). See Scheme 18 (FIG. 20). After the reaction mixture was stirred for 16 h at room temperature, the mixture was concentrated under reduced pressure. The residue was purified by preparative thin layer chromatography (eluting 5% MeOH/CH₂Cl₂) to give {[5-(3,5-dichloro-phenylsulfanyl)-4-isopropyl-1-pyridin-4-ylmethyl-1H-imidazol-2-yl-methoxycarbonylamino]-methyl}-phosphonic acid diethyl ester 17 (13 mg, 90%) as a pale yellow oil. ¹H NMR (300 MHz, CDCl₃) δ 8.44 (d, 2H), 7.04 (t, 1H), 6.78 (d, 2H), 6.68 (d, 2H), 5.25 (s, 2H), 5.19 (s, 2H), 4.98 (bt, 1H), 4.11 (dq, 4H), 3.49 (ABq, 2H), 3.17 (dq, 1H), 1.30 (m, 12H). ³¹P NMR (300 MHz, CDCl₃) δ 21.9.

Example 11B

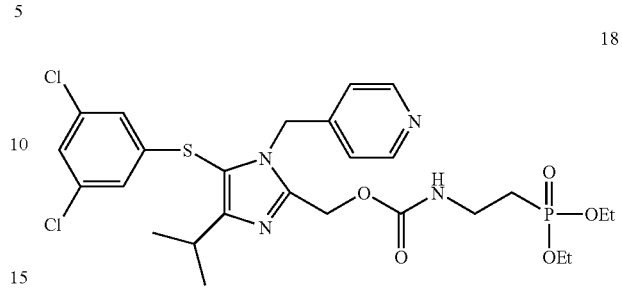

18

Figure 22:
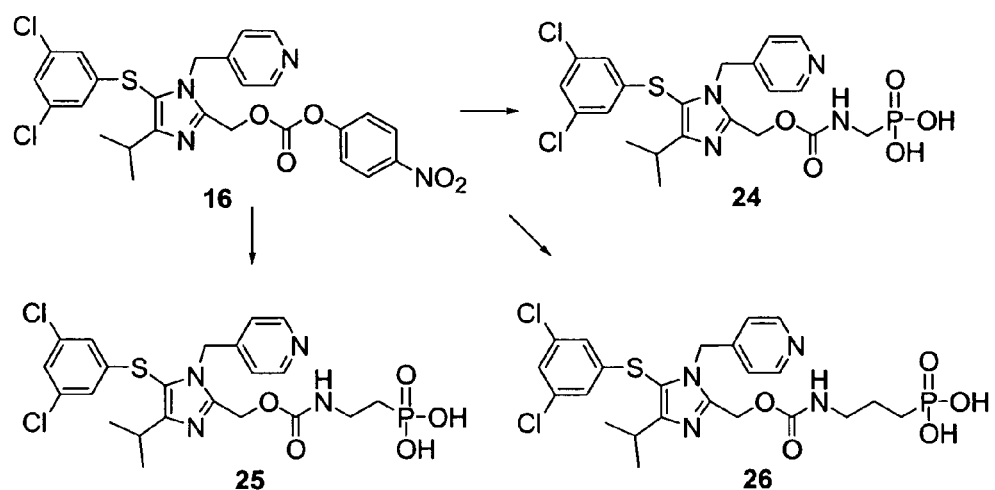
FIG. 22 depicts Scheme 20 which is described in detail herein below.

To a solution of carbonate 16 (82 mg, 0.143 mmol) in CH₃CN (5 mL) was added diethyl(aminoethyl)phosphonate (58 mg, 0.214 mmol) and diisopropylethylamine (0.05 mL, 0.286 mmol). See Scheme 20 (FIG. 22). After the reaction mixture was stirred for 16 h at room temperature, the mixture was concentrated under reduced pressure. The residue was chromatographed on silica gel (eluting 5-7.5% MeOH/CH₂Cl₂) to give {2-[5-(3,5-Dichloro-phenylsulfanyl)-4-isopropyl-1-pyridin-4-ylmethyl-1H-imidazol-2-ylmethoxycarbonylamino]-ethyl}-phosphonic acid diethyl ester 18 (79 mg, 90%) as a pale yellow oil. ¹H NMR (300 MHz, CDCl₃) δ 8.43 (d, 2H), 7.02 (s, 1H), 6.77 (d, 2H), 6.67 (s, 2H), 5.32 (t, 1H), 5.24 (s, 2H), 5.16 (s, 2H), 4.08 (m, 4H), 3.35 (m, 2H), 3.15 (m, 1H), 1.86 (m, 2H), 1.30 (m, 6H), 1.29 (s, 6H). ³¹P NMR (300 MHz, CDCl₃) δ 31.5.

FIG. 2 depicts Scheme 19.

Example 11C

23

Figure 21:
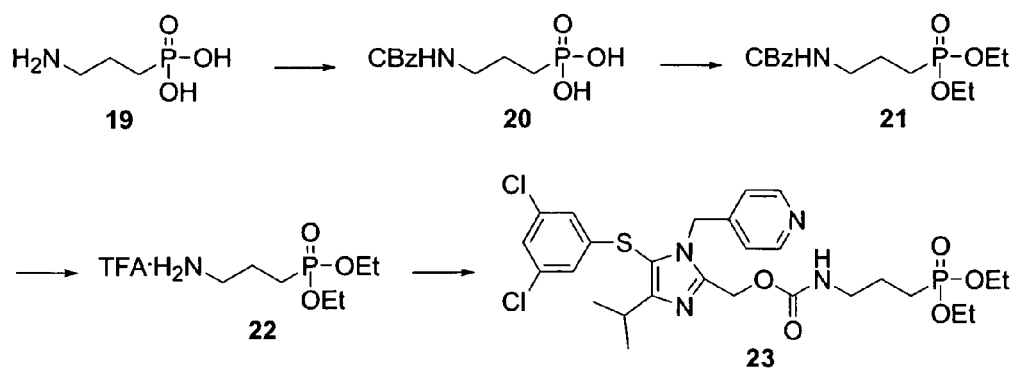
FIG. 21 depicts Scheme 19 which is described in detail herein below.

To a solution of 3-aminopropylphosphonic acid 19 (500 g, 3.59 mmol) in 2N NaOH (3.6 mL, 7.19 mmol) was added benzyl chloroformate (0.62 mL, 4.31 mmol) according to Scheme 19 (FIG. 21). After the reaction mixture was stirred for 16 hours at room temperature, the mixture was partitioned between Et₂O and water. The aqueous phase was acidified with 6N HCl until pH=2. The resulting colorless solid was dissolved in MeOH (75 mL) and treated with Dowex 50WX8-200 (2.5 g). After the mixture was stirred for 30 minutes, it was filtered and evaporated under reduced pressure to give carbamate 20 (880 mg, 90%) as a colorless solid.

To a solution of carbamate 20 (246 mg, 0.90 mmol) in benzene (5 mL) was added 1,8-diazabicyclo[5.4.0]undec-7-ene phenol (0.27 mL, 1.8 mmol) and iodoethane (0.22 mL, 2.7 mmol). After the reaction mixture was warmed to 60° C. and stirred for 16 h, the mixture was concentrated under reduced pressure and partitioned between EtOAc and sat.

NH₄Cl. The crude product was chromatographed on silica gel (eluting 3-4% MeOH/CH₂Cl₂) to give phosphonate 21 (56 mg, 19%) as a colorless oil.

To a solution of phosphonate 21 (56 mg, 0.17 mmol) in EtOH (3 mL) was added TFA (13 μL, 0.17 mmol) and 10% Pd/C (11 mg). After the reaction mixture was stirred under H₂ atmosphere (balloon) for 1 h, the mixture was filtered through Celite. The filtrate was evaporated under reduced pressure to give amine 22 (52 mg, 99%) as a colorless oil.

To a solution of carbonate 16 (15 mg, 0.026 mmol) in CH₃CN (2 mL) was added diethyl(aminopropyl)phosphonate (16 mg, 0.052 mmol) and diisopropylethylamine (11 μL, 0.065 mmol). After the reaction mixture was stirred for 16 h at room temperature, the mixture was concentrated under reduced pressure. The residue was purified by preparative thin layer chromatography (eluting 5% MeOH/CH₂Cl₂) to give {3-[5-(3,5-dichloro-phenylsulfanyl)-4-isopropyl-1-pyridin-4-ylmethyl-1H-imidazol-2-ylmethoxycarbonylamino]-propyl}-phosphonic acid diethyl ester 23 (13 mg, 79%) as a pale yellow oil. ¹H NMR (300 MHz, CDCl₃) δ 8.44 (d, 2H), 7.04 (t, 1H), 6.80 (d, 2H), 6.68 (d, 2H), 5.26 (s, 2H), 5.18 (s, 2H), 5.08 (bt, 1H), 4.08 (m, 4H), 3.15 (m, 3H), 1.72 (m, 4H), 1.31 (m, 12H). ³¹P NMR (300 MHz, CDCl₃) δ 31.5

FIG. 22 depicts Scheme 20.

Example 12A

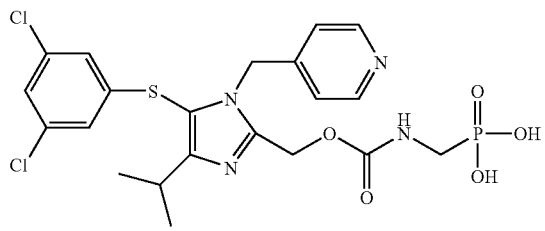

24

To a solution of aminomethylphosphonic acid (8 mg, 0.073 mmol) in water (1 mL) was added 1N NaOH (0.15 mL, 0.15 mmol) and carbonate 16 (21 mg, 0.037 mmol) in dioxane (1 mL). See Scheme 20 (FIG. 22). After the reaction mixture was stirred for 6 h at room temperature, the mixture was concentrated under reduced pressure. The residue was purified by HPLC on C18 reverse phase chromatography (eluting 30% CH₃CN/water) to give a mixture of phosphonic acid 24 and alcohol 15. The mixture was further purified by preparative thin layer chromatography (eluting 7.5% MeOH/CH₂Cl₂) to give {[5-(3,5-dichloro-(phenylsulfanyl)-4-isopropyl-1-pyridin-4-ylmethyl-1H-imidazol-2-ylmethoxycarbonyl amino]-methyl}-phosphonic acid 24 (8 mg, 40%) as a colorless solid. ¹H NMR (300 MHz, CD₃OD) δ 8.33 (bs, 2H), 7.10 (t, 1H), 7.04 (bs, (2H), 6.72 (d, 2H), 5.44 (s, 2H), 5.25 (s, 2), 3.24 (m, 2H), 3.17 (m, 1H), 1.28 (d, 6H).

Example 12B

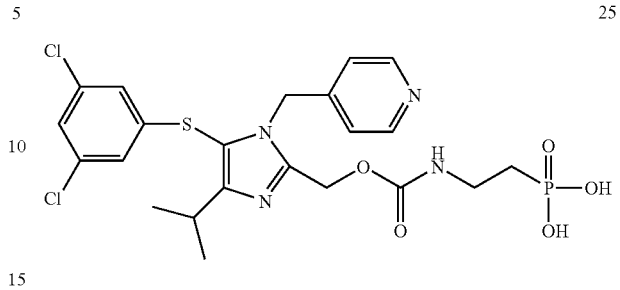

25

To a solution of 2-aminoethylphosphonic acid (12 mg, 0.098 mmol) in water (1 mL) was added 1N NaOH (0.2 mL, 0.20 mmol) and carbonate 16 (28 mg, 0.049 mmol) in dioxane (1 mL). See Scheme 20 (FIG. 22). After the reaction mixture was stirred for 6 h at room temperature, the mixture was concentrated under reduced pressure. The residue was purified by HPLC on C18 reverse phase chromatography (eluting 30% CH₃CN/water) to give a mixture of phosphonic acid 25 and alcohol 15. The mixture was further purified by preparative thin layer chromatography (eluting 7.5% MeOH/CH₂Cl₂) to give {(2-[5-(3,5-dichloro-phenylsulfanyl)-4-isopropyl-1-pyridin-4-ylmethyl-1H-imidazol-2-ylmethoxycarbonylamino]-ethyl}-phosphonic acid 25 (13 mg, 47%) as a colorless solid. ¹H NMR (300 MHz, CD₃OD) δ 8.32 (d, 2H), 7.11 (s, 1H), 7.02 (d, 2H), 6.72 (s, 2H), 5.42 (s, 2H), 5.23 (s, 2H), 3.30 (m, 2H), 3.17 (m, 1H), 1.71 (m, 2H), 1.28 (d, 6H). ³¹P NMR (300 MHz, CD₃OD) δ 20.1.

Example 12C

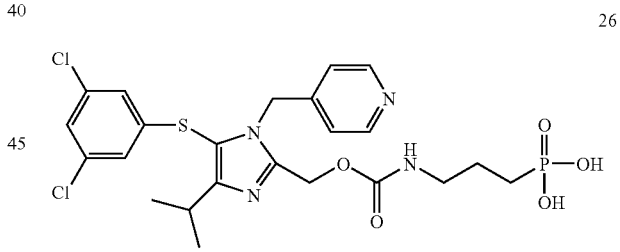

26

To a solution of 3-aminopropylphosphonic acid (12 mg, 0.084 mmol) in water (1 mL) was added 1N NaOH (0.17 mL, 0.17 mmol) and carbonate 16 (24 mg, 0.042 mmol) in dioxane (1 mL). See Scheme 20. After the reaction mixture was stirred for 6 h at room temperature, the mixture was concentrated under reduced pressure. The residue was purified by HPLC on C18 reverse phase chromatography (eluting 30% CH₃CN/water) to give a mixture of phosphonic acid 26 and alcohol 15. The mixture was further purified by preparative thin layer chromatography (eluting 7.5% MeOH/CH₂Cl₂) to give {3-[5-(3,5-dichloro-phenylsulfanyl)-4-isopropyl-1-pyridin-4-ylmethyl-1H-imidazol-2-ylmethoxycarbonylamino]-propyl}-phosphonic acid 26 (11 mg, 46%) as a colorless solid. ¹H NMR (300 MHz, CD₃OD) δ 8.34 (bs, 2H), 7.11 (s, 1H), 7.02 (bs, 2H), 6.73 (d, 2H), 5.43 (s, 2H), 5.23 (s, 2H), 3.32 (m, 1H), 3.06 (bs, 2H), 1.69 (bs, 2H), 1.50 (bs, 2H), 1.28 (d, 6H).

Example 13

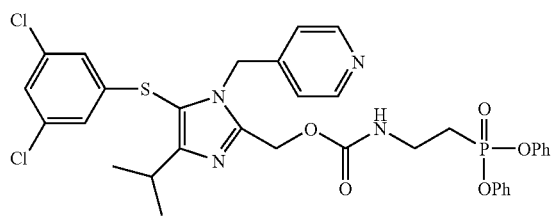

31

To a solution of 2-aminoethylphosphonic acid (1.26 g, 10.1 mmol) in 2N NaOH (10.1 mL, 20.2 mmol) was added benzyl chloroformate (1.7 mL, 12.1 mmol). See Scheme 21. After the reaction mixture was stirred for 2 d at room temperature, the mixture was partitioned between Et$_2$O and water. The aqueous phase was acidified with 6N HCl until pH=2. The resulting colorless solid was dissolved in MeOH (75 mL) and treated with Dowex 50WX8-200 (7 g). After the mixture was stirred for 30 minutes, it was filtered and evaporated under reduced pressure to give carbamate 28 (2.37 g, 91%) as a colorless solid.

To a solution of carbamate 28 (2.35 g, 9.1 mmol) in pyridine (40 mL) was added phenol (8.53 g, 90.6 mmol) and 1,3-dicyclohexylcarbodiimide (7.47 g, 36.2 mmol). After the reaction mixture was warmed to 70° C. and stirred for 5 h, the mixture was diluted with CH$_3$CN and filtered. The filtrate was concentrated under reduced pressure and diluted with EtOAc. The organic phase was washed with sat. NH$_4$Cl, sat. NaHCO$_3$, and brine, then dried over Na$_2$SO$_4$, filtered, and evaporated under reduced pressure. The crude product was chromatographed on silica gel twice (eluting 40-60% EtOAc/hexane) to give phosphonate 29 (2.13 g, 57%) as a colorless solid.

To a solution of phosphonate 29 (262 mg, 0.637 mmol) in isopropanol (iPrOH) (5 mL) was added TFA (0.05 mL, 0.637 mmol) and 10% Pd/C (26 mg). After the reaction mixture was stirred under H$_2$ atmosphere (balloon) for 1 h, the mixture was filtered through Celite. The filtrate was evaporated under reduced pressure to give amine 30 (249 mg, 100%) as a colorless oil.

To a solution of carbonate 16 (40 mg, 0.070 mmol) and amine 30 (82 mg, 0.21 mmol) in CH$_3$CN (5 mL) was added diisopropylethylamine (0.05 mL, 0.28 mmol). After the reaction mixture was stirred for 2 h at room temperature, the mixture was concentrated under reduced pressure. The residue was chromatographed on silica gel (eluting 3-4% MeOH/ CH$_2$Cl$_2$) to give {2-[5-(3,5-dichloro-phenylsulfanyl)-4-isopropyl-1-pyridin-4-ylmethyl-1H-imidazol-2-ylmethyoxycarbonylamino]-ethyl}-phosphonic acid diphenyl ester 31 (36 mg, 72%) as a colorless oil. $^1$H NMR (300 MHz, CDCl$_3$) δ 8.37 (d, 2H), 7.22 (m, 4H), 7.14 (m, 2H), 7.10 (m, 2H), 6.99 (t, 1H), 6.72 (d, 2H), 6.62 (d, 2H), 5.30 (bt, 1H), 5.18 (s, 2H), 5.13 (s, 2H), 3.50 (m, 2H), 3.12 (m, 1H), 2.21 (m, 2H), 1.26 (d, 6H). $^{31}$P NMR (300 MHz, CDCl$_3$) δ 22.4.

Example 14

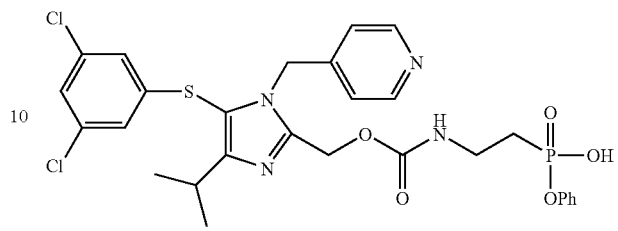

32

Figure 23:
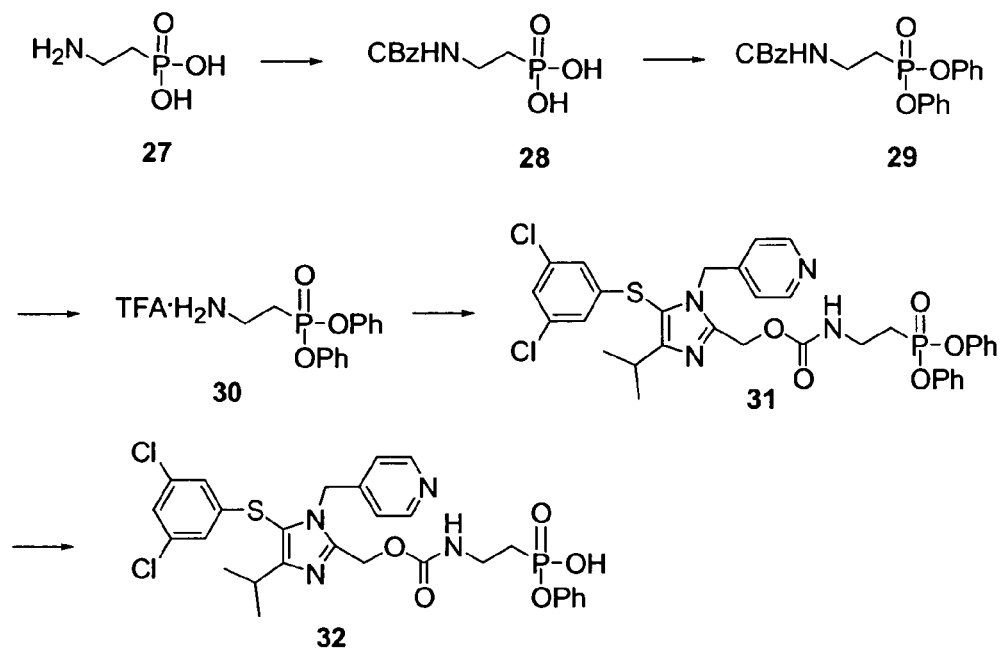
FIG. 23 depicts Scheme 21 which is described in detail herein below.

To a solution of phosphonate 31 (11 mg, 0.015 mmol) in CH$_3$CN (0.5 mL) was added 1N LiOH (46 μL, 0.046 mmol) at 0° C. See Scheme 21 (FIG. 23). After the reaction mixture was stirred for 2 h at 0° C., Dowex 50WX8-200 (26 mg) was added and stirring was continued for an additional 30 min. The reaction mixture was filtered, rinsed with CH$_3$CN, and concentrated under reduced pressure to give {2-[5-(3,5-dichloro-phenylsulfanyl)-4-isopropyl-1-pyridin-4-ylmethyl-1H-imidazol-2-ylmethoxycarbonylamino]-ethyl}-phosphonic acid monophenyl ester 32 (10 mg, 100%) as a colorless oil. $^1$H NMR (300 MHz, CD$_3$OD) δ 8.52 (d, 2H), 7.28 (m, 6H), 6.79 (m, 4H), 5.60 (s, 2H), 5.29 (s, 2H), 3.29 (m, 3H), 1.83 (m, 2H), 1.31 (d, 6H). $^{31}$P NMR (300 MHz, CD$_3$OD) δ 20.2.

Figure 24:
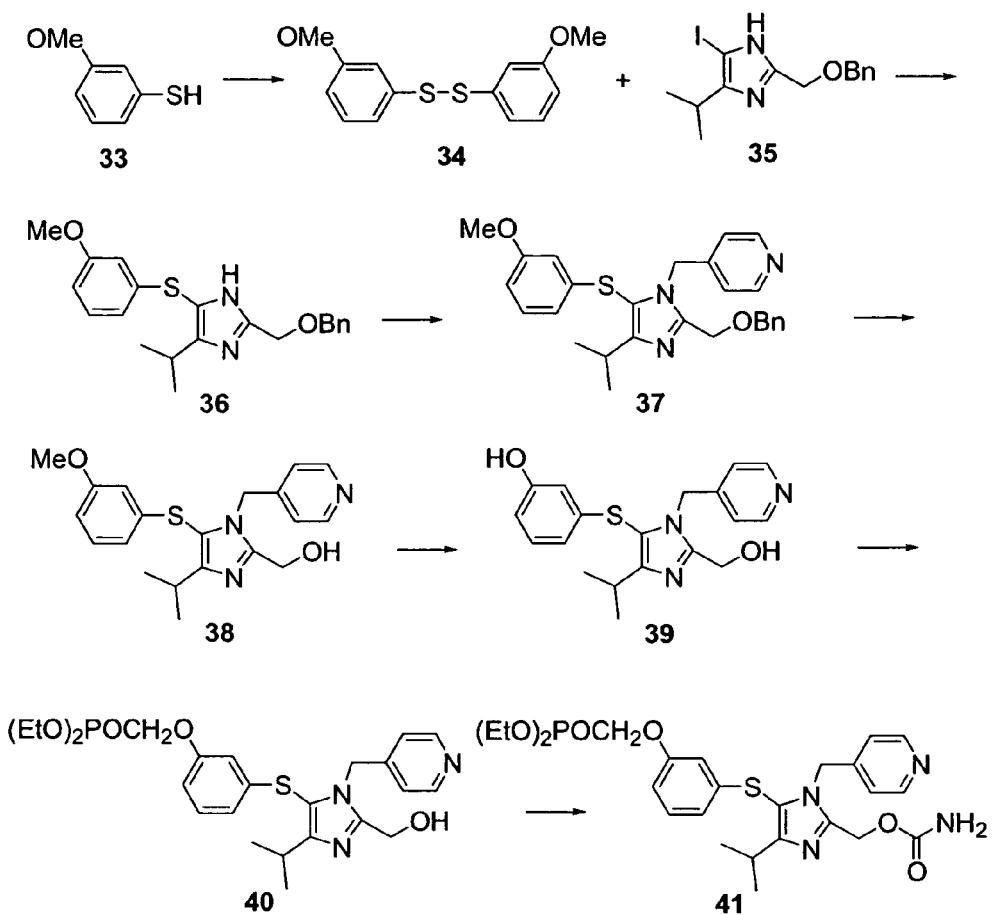
FIG. 24 depicts Scheme 22 which is described in detail herein below.

FIG. 24 depicts Scheme 22.

Example 15

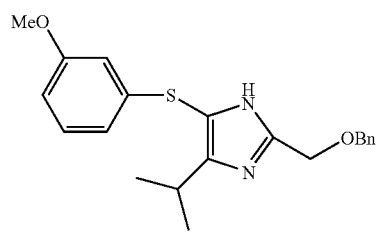

36

To a solution of 3-methoxybenzenethiol (0.88 mL, 7.13 mmol) in CH$_3$CN (15 mL) was added sodium iodide (214 mg, 1.43 mmol) and ferric chloride (232 mg, 1.43 mmol). See Scheme 22. After the reaction mixture was warmed to 60° C. and stirred for 3 d, the mixture was concentrated under reduced pressure and partitioned between CH$_2$Cl$_2$ and water. The organic phase was dried over Na$_2$SO$_4$, filtered, and evaporated under reduced pressure. The crude product was chromatographed on silica gel (eluting 5-6% EtOAc/hexane) to give disulfide 34 (851 mg, 86%) as a yellow oil. To a solution of disulfide 34 (850 mg, 3.05 mmol) in DMSO (10 mL) was added iodide 35, also denoted previously as compound 842, (1.21 g, 3.39 mmol) and lithium hydride (32 mg, 4.07 mmol). After the reaction mixture was warmed to 60° C. and stirred for 16 h, the mixture was partitioned between EtOAc and water. The organic phase was washed with brine, dried over Na$_2$SO$_4$, filtered, and evaporated under reduced pressure. The crude product was chromatographed on silica gel (eluting 30-50% EtOAc/hexane) to give 2-benzyloxymethyl-4-isopropyl-5-(3-methoxy-phenylsulfanyl)-1H-imidazole 36 (247 mg, 22%) as a yellow oil.

Example 16

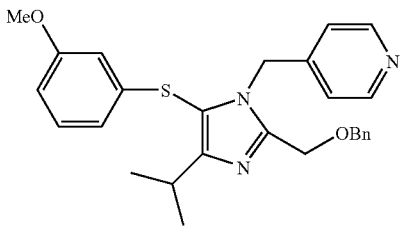

37

To a solution of sulfide 36 (247 mg, 0.67 mmol) in THF (10 mL) was added 4-picolylchloride (220 mg, 1.34 mmol), powder NaOH (59 mg, 1.47 mmol), lithium iodide (44 mg, 0.33 mmol), and tetrabutylammonium bromide (22 mg, 0.067 mmol). See Scheme 22. After the reaction mixture was stirred for 2 d at room temperature, the mixture was partitioned between EtOAc and sat. $NH_4Cl$. The organic phase was dried over $Na_2SO_4$, filtered, and evaporated under reduced pressure. The crude product was chromatographed on silica gel (eluting 60-100% EtOAc/hexane) to give 4-[2-benzyloxymethyl-4-isopropyl-5-(3-methoxy-phenylsulfanyl)-imidazol-1-ylmethyl]-pyridine 37 (201 mg, 65%) as a yellow oil.

Example 17

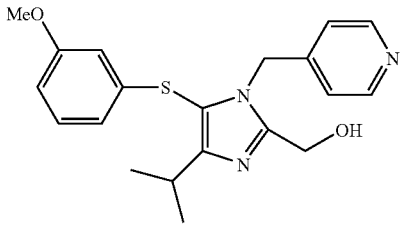

38

To a solution of amine 37 (101 mg, 0.220 mmol) in EtOH (5 mL) was added conc. HCl (5 mL). See Scheme 22 (FIG. 24). After the reaction mixture was warmed to 80° C. and stirred for 16 h, the mixture was concentrated under reduced pressure and partitioned between EtOAc and sat. $NaHCO_3$. The organic phase was dried over $Na_2SO_4$, filtered, and evaporated under reduced pressure. The crude product was chromatographed on silica gel (eluting 5-7% MeOH/$CH_2Cl_2$) to give [4-isopropyl-5-(3-methoxy-phenylsulfanyl)-1-pyridin-4-ylmethyl-1H-imidazol-2-yl]-methanol 38 (71 mg, 87%) as a pale yellow oil.

Example 18

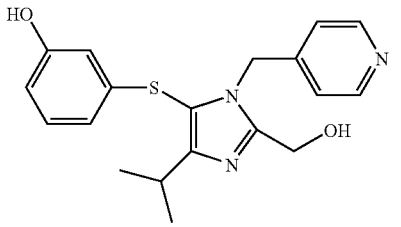

39

To a solution of alcohol 38 (56 mg, 0.15 mmol) in $CH_2Cl_2$ (2 mL) was added 1M $BBr_3$ in $CH_2Cl_2$ at 0° C. See Scheme 22 (FIG. 24). After the reaction mixture was stirred for 1 h at 0° C., the mixture was partitioned between $CH_2Cl_2$ and sat. $NaHCO_3$. The aqueous phase was neutralized with solid $NaHCO_3$ and extracted with $CH_2Cl_2$ and EtOAc. The organic phase was dried over $Na_2SO_4$, filtered, and evaporated under reduced pressure. The crude product was chromatographed on silica gel (eluting 5-10% MeOH/$CH_2Cl_2$) to give 3-(2-hydroxymethyl-5-isopropyl-3-pyridin-4-ylmethyl-3H-imidazol-4-ylsulfanyl)-phenol 39 (43 mg, 81%) as a colorless solid.

Example 19

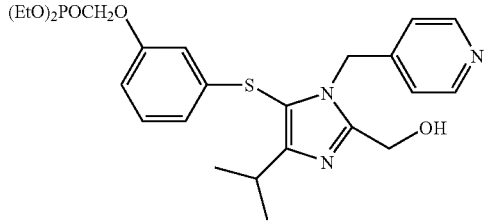

40

To a solution of phenol 39 (25 mg, 0.070 mmol) and triflate (33 mg, 0.11 mmol) in THF (2 mL) and $CH_3CN$ (2 mL) was added $Cs_2CO_3$ (46 mg, 0.14 mmol). See Scheme 22 (FIG. 24). After the reaction mixture was stirred for 1 h at room temperature, the mixture was partitioned between EtOAc and water. The organic phase was dried over $Na_2SO_4$, filtered, and evaporated under reduced pressure. The crude product was purified by preparative thin layer chromatography (eluting 10% MeOH/$CH_2Cl_2$) to give [3-(2-Hydroxymethyl-5-isopropyl-3-pyridin-4-ylmethyl-3H-imidazol-4-ylsulfanyl)-phenoxymethyl]-phosphonic acid diethyl ester 40 (10 mg, 28%) as a colorless oil.

Example 20

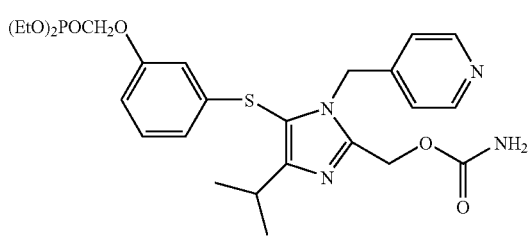

41

To a solution of diethylphosphonate 40 (10 mg, 0.020 mmol) in THF (2 mL) was added trichloroacetyl isocyanate (7 μL, 0.059 mmol). See Scheme 22 (FIG. 24). After the reaction mixture was stirred for 30 min at room temperature, the mixture was evaporated under reduced pressure. To a solution of the concentrated residue in MeOH (2 mL) was added 1M $K_2CO_3$ (0.2 mL, 0.20 mmol) at 0° C. After the reaction mixture was warmed to room temperature and stirred for 3 h, the mixture was partitioned between EtOAc and sat. $NH_4Cl$. The organic phase was dried over $Na_2SO_4$, filtered, and evaporated under reduced pressure. The crude product was purified by preparative thin layer chromatography (eluting 10% MeOH/$CH_2Cl_2$) to give [3-(2-hydroxymethyl-5-isopropyl-3-pyridin-4-ylmethyl-3H-imidazol-4-ylsulfanyl-phenoxymethyl]-phosphonic acid diethyl ester 41 (10 mg, 91%) as a colorless oil. $^1$H NMR (500 MHz, $CDCl_3$) δ 8.50 (d, 2H), 7.16 (m, 1H), 6.85 (m, 1H), 6.75 (m, 1H), 6.73 (m, 1H), 6.17 (s, 1H), 5.31 (s, 2H), 5.02 (s, 2H), 4.23 (m, 4H), 4.16 (d, 2H), 3.23 (m, 1H), 1.37 (t, 6H), 1.29 (d, 6H). $^{31}$P NMR (300 MHz, $CDCl_3$) δ 19.6.

Figure 25:
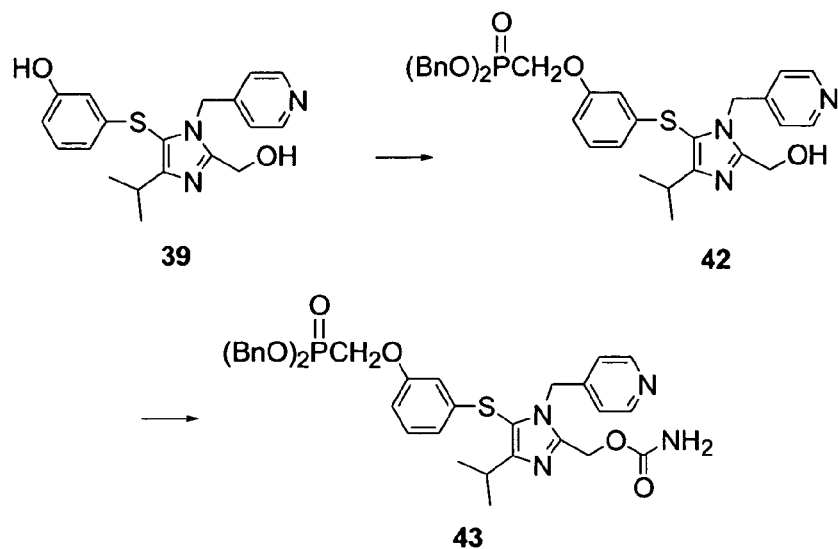
FIG. 25 depicts Scheme 23 which is described in detail herein below.

FIG. 25 depicts Scheme 23.

Example 21

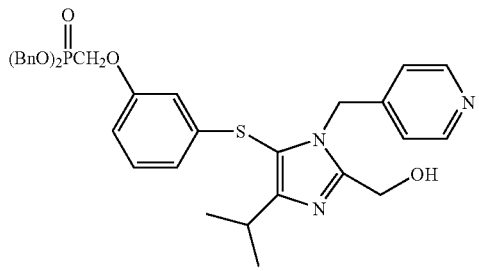

To a solution of phenol 39 (20 mg, 0.056 mmol) in THF (1 mL) and CH$_3$CN (1 mL) was added sodium hydride (60%, 5 mg, 0.112 mmol) at 0° C. See Scheme 23 (FIG. 25). After the reaction mixture was stirred for 30 min at 0° C., dibenzylphosphonyl methyltriflate (21 mg, 0.050 mmol) in THF (1 mL) was added. After the reaction mixture was stirred for 1 h at 0° C., the mixture was evaporated under reduced pressure and partitioned between EtOAc and sat. NH$_4$Cl. The organic phase was dried over Na$_2$SO$_4$, filtered, and evaporated under reduced pressure. The crude product was purified by preparative thin layer chromatography (eluting 10% MeOH/CH$_2$Cl$_2$) to give dibenzylphosphonate 42 (5 mg, 16%) as a pale yellow oil.

Example 22

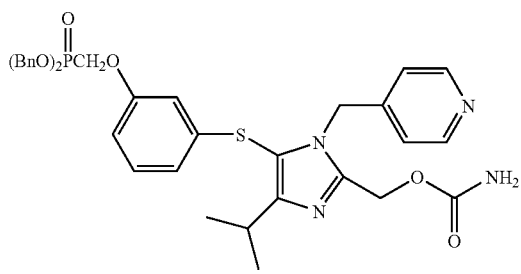

To a solution of dibenzylphosphonate 42 (5 mg, 0.0079 mmol) in CH$_2$Cl$_2$ (1 mL) was added trichloroacetyl isocyanate (5 μL, 0.049 mmol). See Scheme 23. After the reaction mixture was stirred for 15 min at room temperature, the mixture was transferred on to a 2-inch column of neutral Al$_2$O$_3$. After the reaction mixture was soaked for 30 min, the mixture was rinsed off the column with 10% MeOH/CH$_2$Cl$_2$ and evaporated under reduced pressure. The crude product was purified by preparative thin layer chromatography (eluting 10% MeOH/CH$_2$Cl$_2$) to give carbamate 43 (3 mg, 56%) as a pale yellow oil. $^1$H NMR (300 MHz, CDCl$_3$) δ 8.48 (d, 2H), 7.35 (m, 1OH), 7.12 (t, 1H), 6.88 (m, 2H), 6.70 (d, 1H), 6.66 (dd, 1H), 6.10 (t, 1H), 5.29 (s, 2H), 5.13 (dd, 6H), 5.05 (s, 2H), 4.14 (d, 2H), 3.24 (m, 1H), 1.30 (d, 6H). $^{31}$P NMR (300 MHz, CDCl$_3$) δ 20.3.

Figure 26:
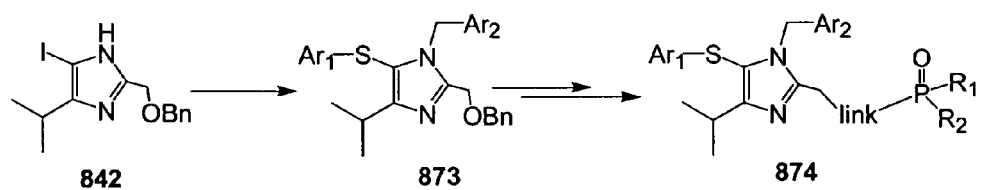
FIG. 26 depicts Scheme 24 which is described in detail herein below.

Preparation of phosphorus compound 874 was displayed in Scheme 24 (FIG. 26). Starting with imidazole 842, Ar1 and Ar2 were introduced following the procedure described in U.S. Pat. No. 5,326,780. Benzyl group was then removed and converted to phosphorus analog 874 using the procedure described previously.

Figure 27:
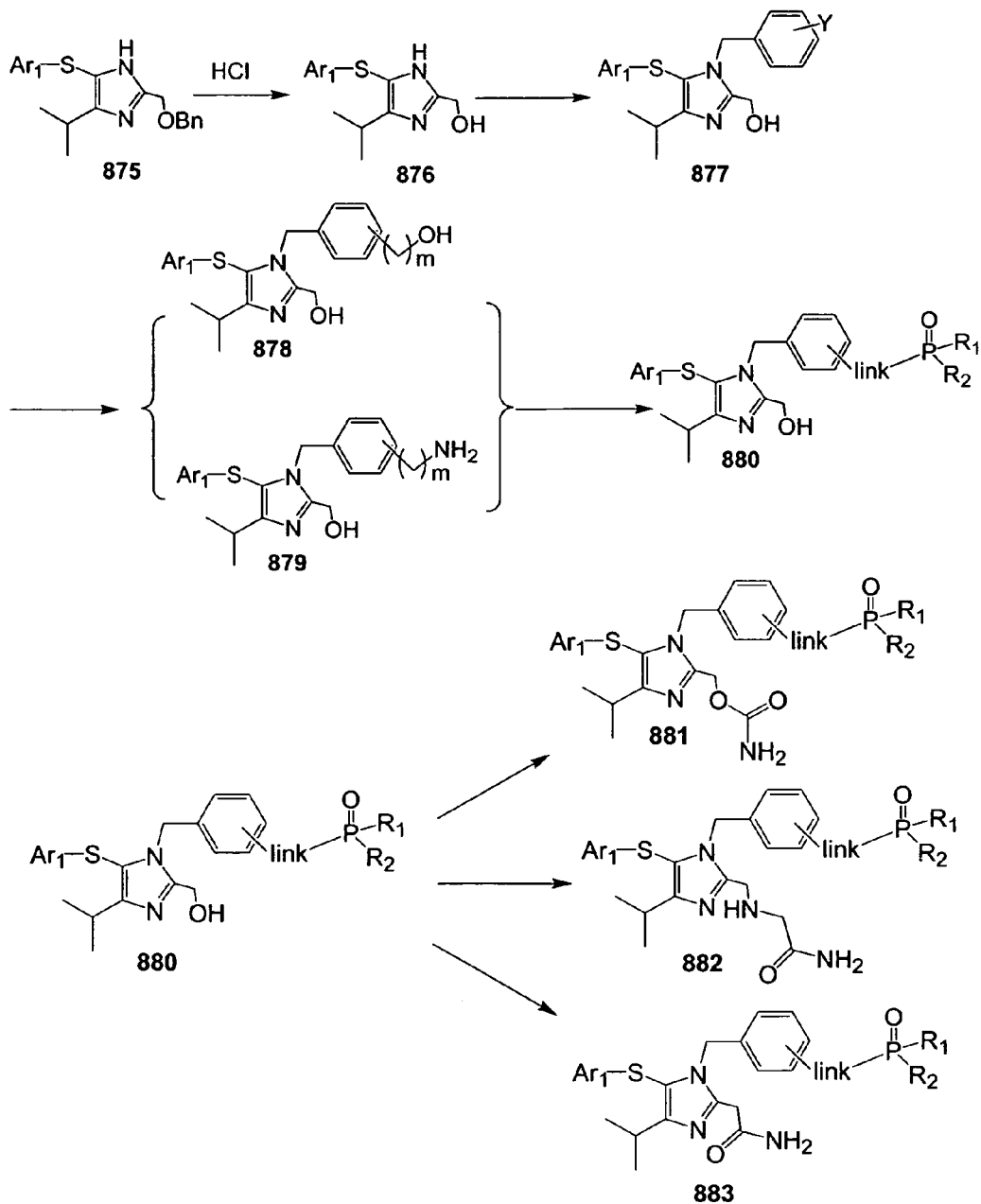
FIG. 27 depicts Scheme 25 which is described in detail herein below.

Scheme 25 (FIG. 27) describes preparation of compound 880. Compound 875 was synthesized from compound 842 using the procedures described in U.S. Pat. No. 5,326,780. Treatment of 875 with HCl removed the benzyl group to give alcohol 876, which was then introduced phenyl group with substitution of Y. Y is a function which can be converted to alcohol, aldehyde or amine, for example —NO$_2$, —COOMe, N$_3$, and etc. Conversion of Y to the amine or alcohol gave compound 878 and/or 879, which were then used as attachment site of phosphorus to afford phosphorus compound 880. Hydroxyl group in compound 880 was then converted to the desired side chain including but not limit to carbamate 881, urea 882, substituted amine 883.

Figure 28:
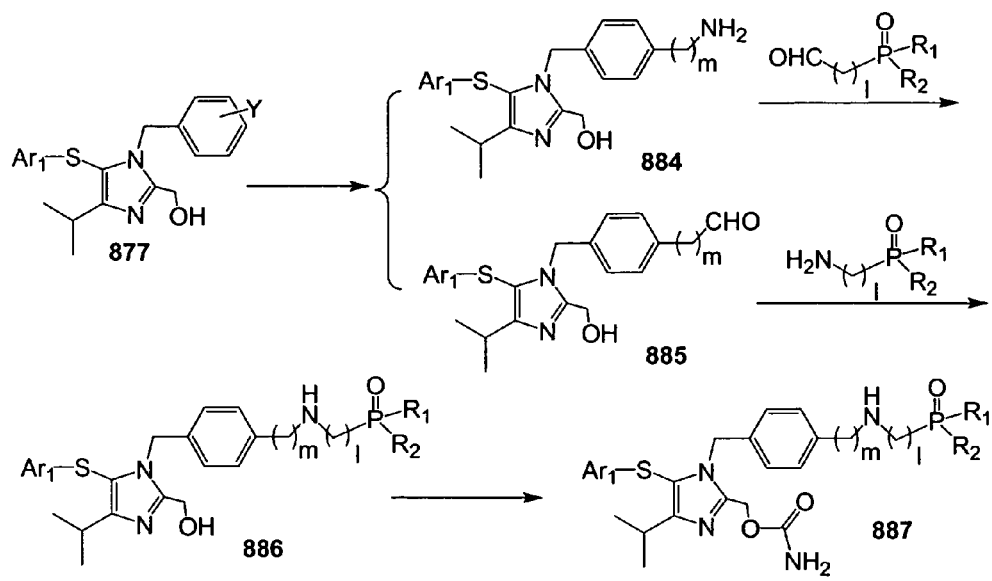
FIG. 28 depicts Scheme 26 which is described in detail herein below.

Preparation of phosphorus compound 887 is shown in Scheme 26 (FIG. 28). Compound 877 was converted to amine 884 and/or aldehyde 885, which then reacted with aldehyde and/or amine respectively to provide phosphorus compound 886. Treatment of compound 886 with Cl$_3$CCONCO provide the carbamate 887.

Example 22

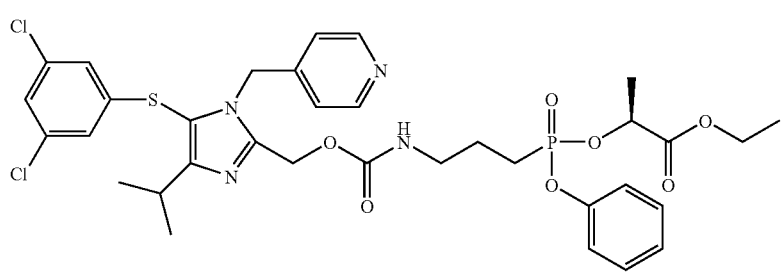

48

Figure 29:
FIG. 29 depicts the preparation of compound 48 shown in Example 22 described in detail herein below.

Compound 44 (See FIG. 29) was prepared following the sequence of steps described in Example 13, by substituting compound 20 for compound 28. Purification of the crude product on silica gel eluted with 3-4% MeOH/CH$_2$Cl$_2$ provided 37 mg of 48, the title compound. $^1$H NMR (500 MHz, CDCl$_3$) (1.3:1 diastereomeric ratio) δ 8.50 (bs, 2H), 7.35 (t, 2H), 7.20 (m, 3H), 7.06 (s, 1H), 6.90 (bs, 2H), 6.70 (s, 2H), 5.26 (bs, 2H), 5.21 (s, 2H), 4.97 (m, 1H), 4.22 (q, 2H), 3.24 (m, 2H), 3.19 (m, 1H), 2.05 (m, 2H), 1.92 (m, 2H), 1.37 (d, 3H), 1.33 (d, 6H), 1.28 (t, 3H). $^{31}$P NMR (300 MHz, CDCl$_3$) δ30.0.

Example 23

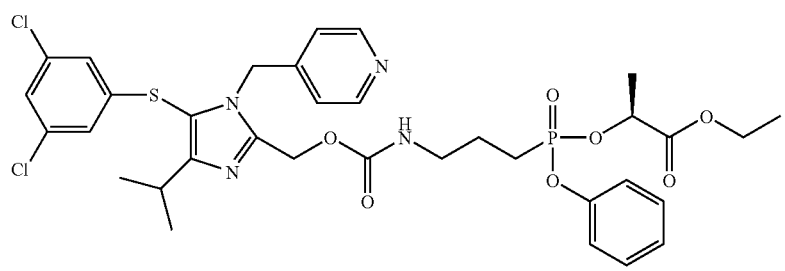

49

The title compound 49 was prepared following the sequence of steps described in Example 22, except for using scalmeric mixture 46 (around 13:1 ratio). Purification of the crude final product on silica gel eluted with 3-4% MeOH/CH$_2$Cl$_2$ provided 40 mg of the title compound. $^1$H NMR (300 MHz, CDCl$_3$) δ 8.44 (bd, 2H), 7.32 (m, 2H), 7.19 (m, 3H), 7.04 (d, 1H), 6.80 (bs, 2H), 6.68 (m, 2H), 5.27 (d, 2H), 5.19 (d, 2H), 4.96 (m, 1H), 4.15 (m, 2H), 3.18 (m, 3H), 1.93 (m, 4H), 1.55 (d, 1.5H), 1.34 (d, 1.5H), 1.31 (d, 6H), 1.21 (m, 3H). $^{31}$P NMR (300 MHz, CDCl$_3$) δ 30.0, 28.3.

Example 24

Figure 30:
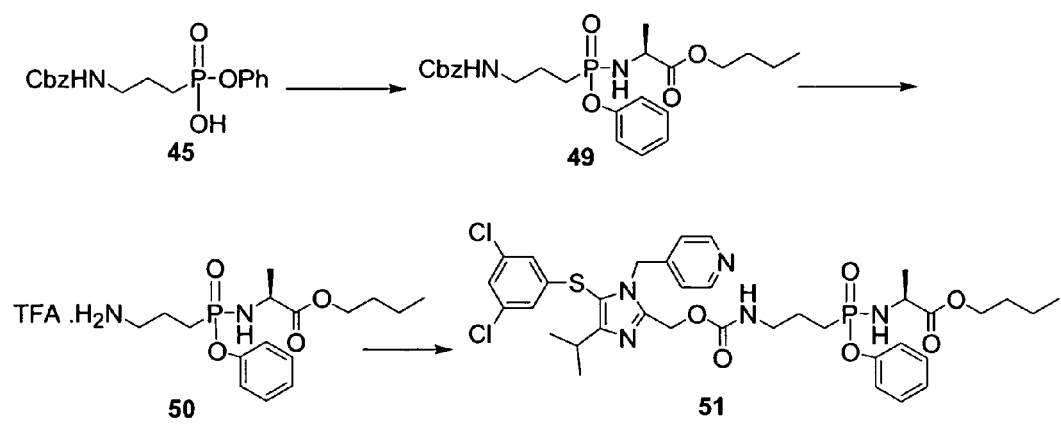
FIG. 30 depicts the preparation of compound 51 shown in Example 24 described in detail herein below.

Amidate 49 (See FIG. 30): A solution of phosphonic acid 45 (66 mg, 0.19 mmol) in CH$_3$CN (5 mL) was treated with thionyl chloride (42 μL, 0.57 mmol). After the reaction mixture was warmed to 70° C. and stirred for 2 h, the mixture was concentrated under reduced pressure. The residue was dissolved in CH$_2$Cl$_2$ (5 mL) and cooled to 0° C. Triethylamine (0.11 mL, 0.76 mmol) and L-alanine n-butyl ester (104 mg, 0.57 mmol) were added. After stirring for 1 h at 0° C. and 1 h at room temperature, the reaction mixture was neutralized with sat. NH$_4$Cl and extracted with CH$_2$Cl$_2$ and EtOAc. The organic phase was dried over Na$_2$SO$_4$, filtered, and evaporated under reduced pressure. The crude product was purified on silica gel (eluting 60-80% EtOAc/hexane) to give amidate 49 (35 mg, 39%) as a colorless oil.

Amine 50: A mixture of benzyl carbamate 49 (35 mg, 0.073 mmol), trifluoroacetic acid (8 μL, 0.11 mmol) and 10% Pd/C (7 mg) in isopropyl alcohol (2 mL) was stirred under H$_2$ atmosphere (balloon) for 1 h. The mixture was then filtered through Celite. The filtrate was evaporated under reduced pressure to give amine 50 (33 mg, 99%) as a colorless oil.

Title compound 51: A solution of 4-nitrophenylcarbonate 16 (35 mg, 0.061 mmol) in CH$_3$CN (2 mL) was treated with amine 50 (33 mg, 0.072 mmol) and iPr$_2$NEt (21 μL, 0.122 mmol). After the reaction mixture was stirred for 1 h at room temperature, the mixture was concentrated under reduced pressure. The residue was purified on silica gel (eluting 4-5% MeOH/CH$_2$Cl$_2$) to give the title compound 51(43 mg, 91%) as a pale yellow oil. $^1$H NMR (500 MHz, CDCl$_3$) δ 8.46 (bs, 2H), 7.31 (m, 2H), 7.20 (d, 2H), 7.14 (m, 1H), 7.05 (s, 1H),

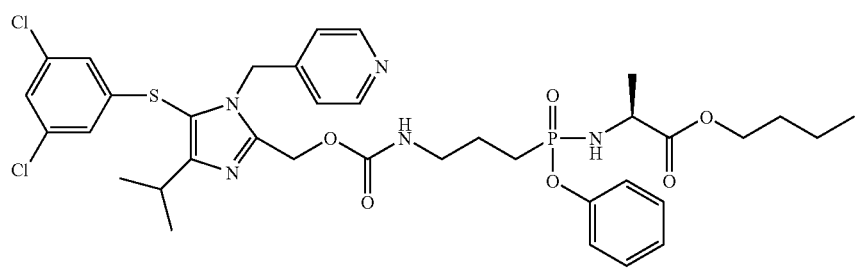

51

6.81 (bd, 2H), 6.71 (d, 2H), 5.27 (bs, 2H), 5.19 (bs, 2H), 4.07 (m, 2H), 3.98 (m, 1H), 3.63 (m, 1H), 3.18 (m, 3H), 1.83 (m, 2H), 1.80 (m, 2H), 1.58 (m, 2H), 1.35 (m, 2H), 1.32 (d, 6H), 1.30 (d, 1.5H), 1.24 (d, 1.5H), 0.93 (t, 3H). $^{31}$P NMR (300 MHz, CDCl$_3$) δ 31.6, 31.3.

Example 25

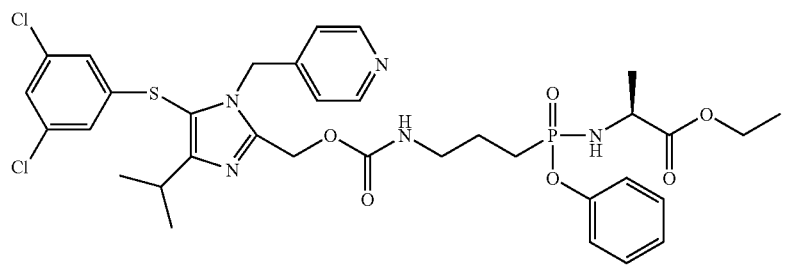

52

The title compound was prepared following the sequence of steps described in Example 24, except for substituting alanine ethyl ester for alanine n-butyl ester. Purification of the crude final product on a preparative TLC plate (5% CH₃OH/CH₂Cl₂) provided 5 mg (75%) of the title compound. $^1$H NMR(CDCl₃, 500 MHz): δ 8.46 (d, 2H), 7.32 (d, 2H), 7.20 (d, 2H), 7.15 (s, 1H), 7.05 (s, 1H), 6.82 (d, 2H), 6.70 (s, 2H), 5.27 (s, 2H), 5.19 (s, 2H), 4.12 (m, 2H), 3.70 (t, 2H), 3.19 (m, 2H), 3.12 (t, 2H), 1.48 (m, 3H), 1.47 (t, 3H), 1.25 (d,6H).

Example 26

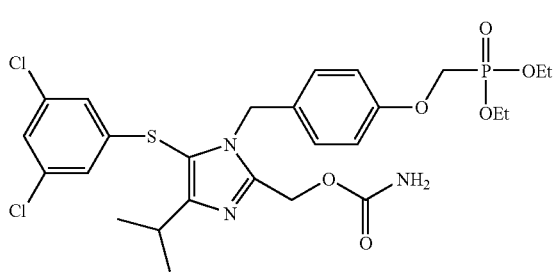

57

Figure 31:
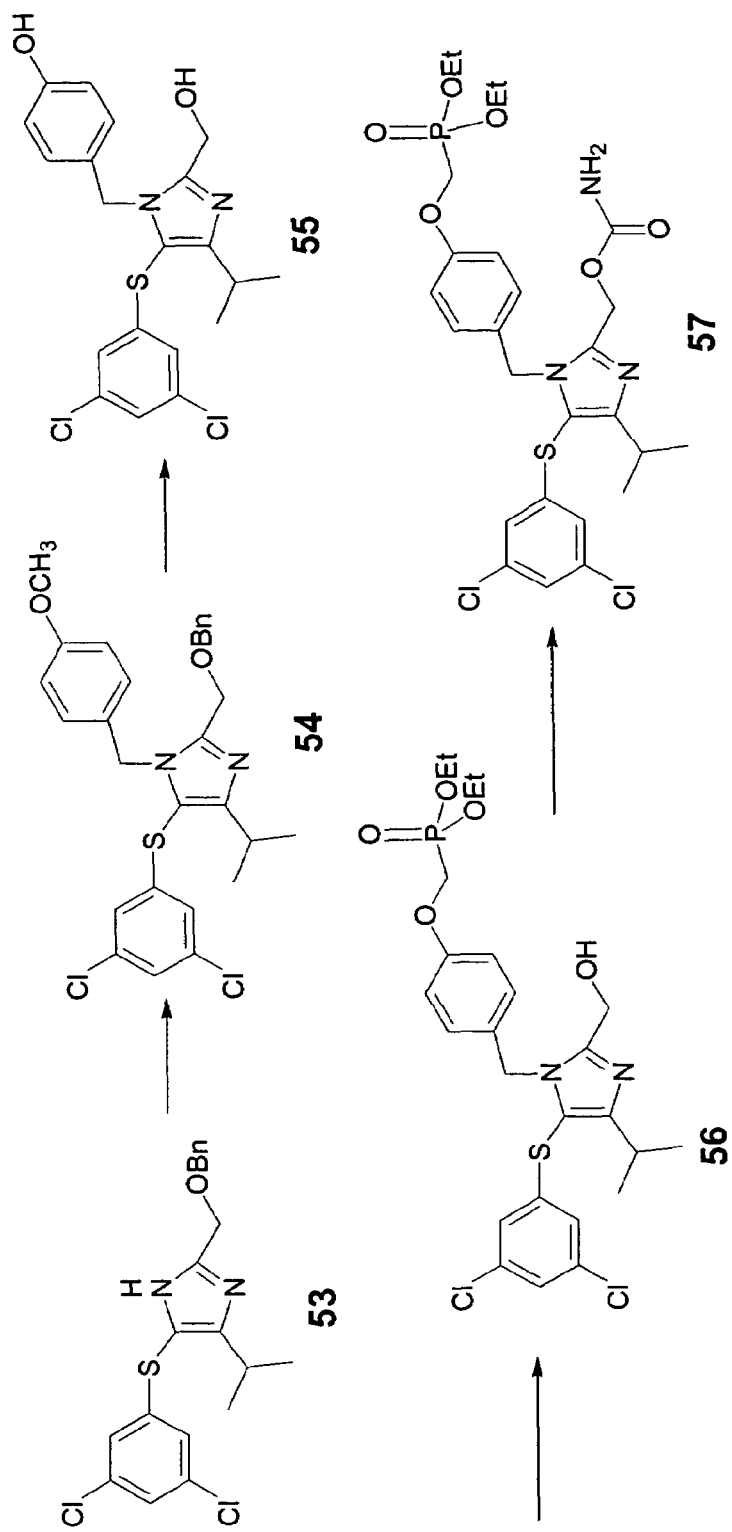
FIG. 31 depicts the preparation of compound 57 shown in Example 26 described in detail herein below.

Imidazole 54 (See FIG. 31): A solution of imidazole 53 (267 mg, 0.655 mmol) in THF (10 mL) was treated with 4-methoxybenzyl chloride (0.18 mL, 1.31 mmol), powder NaOH (105 mg, 2.62 mmol), lithium iodide (88 mg, 0.655 mmol), and tetrabutylammonium bromide (105 mg, 0.327 mmol). After stirring for 4 days at room temperature, the resulting mixture was partitioned between EtOAc and sat. NH₄Cl. The organic phase was dried over Na₂SO₄, filtered, and evaporated under reduced pressure. The crude product was purified on silica gel (eluting 20-40% EtOAc/hexane) to give imidazole 54 (289 mg, 84%) as a colorless oil.

Phenol 55: A solution of benzyl ether 54 (151 mg, 0.286 mmol) in EtOH (5 mL) was treated with conc. HCl (5 mL). After the reaction mixture was warmed to 80° C. and stirred for 2 d, the mixture was concentrated under reduced pressure and partitioned between EtOAc and sat. aqueous NaHCO₃. The organic phase was dried over Na₂SO₄, filtered, and evaporated under reduced pressure. The crude product was purified on silica gel (eluting 60-70% EtOAc/hexane) to give the alcohol (99 mg, 79%) as a colorless solid. A solution of the alcohol (77 mg, 0.18 mmol) in CH₂Cl₂ (3 mL) was added 1M BBr₃ in CH₂Cl₂ (0.90 mL, 0.90 mmol) at 0° C. After the reaction mixture was stirred for 1 h at 0° C., the mixture was neutralized with sat. NaHCO₃ and extracted with CH₂Cl₂ and EtOAc. The organic phase was dried over Na₂SO₄, filtered, and evaporated under reduced pressure. The crude product was chromatographed on silica gel (eluting 4-5% MeOH/CH₂Cl₂) to give phenol 55 (68 mg, 89%) as a colorless solid.

Diethylphosphonate 56: To a solution of phenol 55 (21 mg, 0.050 mmol) in CH₃CN (1 mL) and THF (1 mL) was added trifluoro-methanesulfonic acid diethoxy-phosphorylmethyl ester (18 mg, 0.060 mmol) in CH₃CN (1 mL). After the addition of Cs₂CO₃ (20 mg, 0.060 mmol), the reaction mixture was stirred for 2 h at room temperature. Additional triflate (18 mg, 0.060 mmol) and Cs₂CO₃ (20 mg, 0.060 mmol) were introduced. After the reaction mixture was stirred for another 2 h at room temperature, the mixture was concentrated under reduced pressure. The residue was partitioned between EtOAc and sat. NH₄Cl. The organic phase was dried over Na₂SO₄, filtered, and evaporated under reduced pressure. The crude product was purified by preparative thin layer chromatography (eluting 5% MeOH/CH₂Cl₂) to give diethylphosphonate 56 (26 mg, 91%) as a pale yellow oil.

Title compound carbamate 57: A solution of diethylphosphonate 56 (26 mg, 0.045 mmol) in CH₂Cl₂ (2 mL) was treated with trichloroacetyl isocyanate (27 μL, 0.23 mmol). After the reaction mixture was stirred for 10 min at room temperature, the mixture was concentrated under reduced pressure. The residue was transferred to an Al₂O₃ column in 10% MeOH/CH₂Cl₂. After soaking on the column for 30 min, the crude product was flushed out with 10% MeOH/CH₂Cl₂ and concentrated under reduced pressure. The crude product was purified by preparative thin layer chromatography eluted with 5% MeOH/CH₂Cl₂ to give title compound carbamate 57 (22 mg, 79%) as a pale yellow oil. $^1$H NMR (500 MHz, CDCl₃) δ 7.00 (s, 1H), 6.88 (d, 2H), 6.76 (d, 2H), 6.62 (s, 2H), 5.24 (s, 2H), 5.18 (s, 2H), 4.26 (q, 4H), 4.21 (d, 2H), 3.15 (m, 1H), 1.38 (t, 6H), 1.29 (d, 6H). $^{31}$P NMR (300 MHz, CDCl₃) δ 19.1.

Example 27

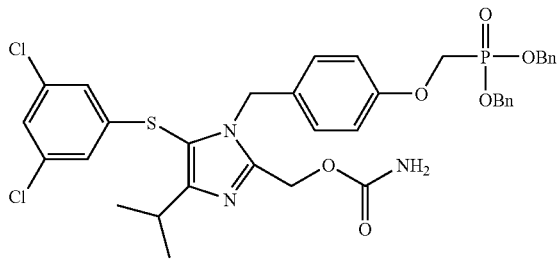

58

The title compound 58 was prepared following the sequence of steps described in Example 27 with substitution of trifluoro-methanesulfonic acid bis-benzyloxy-phosphorylmethyl ester for trifluoro-methanesulfonic acid diethoxy-phosphorylmethyl ester. Purification of the crude final product on silica gel eluted with 3-4% MeOH/CH$_2$Cl$_2$ provided 33 mg of the title compound. $^1$H NMR (500 MHz, CDCl$_3$) δ 7.37 (m, 10H), 6.96 (s, 1H), 6.85 (d, 2H), 6.70 (d, 2H), 6.62 (s, 2H), 5.23 (s, 2H), 5.17 (s, 2H), 5.13 (m, 4H), 4.18 (d, 2H), 3.16 (m, 1H), 1.30 (d, 6H). $^{31}$P NMR (300 MHz, CDCl$_3$) δ 20.1.

Example 28

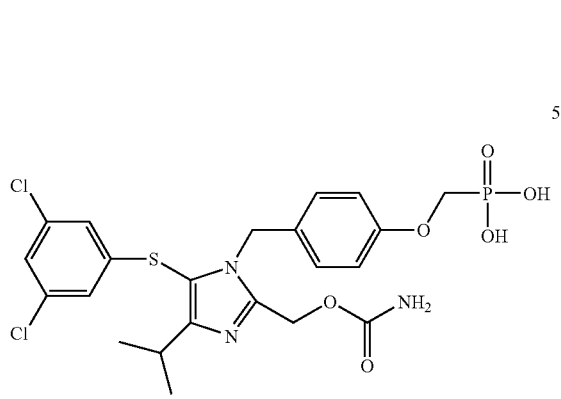

A solution of dibenzylphosphonate 58 (15 mg, 0.020 mmol) was treated 4M HCl in dioxane (1 mL). After the reaction mixture was stirred for 18 h at room temperature, the mixture was concentrated under reduced pressure. The crude product was purified on a C-18 column (eluting 30-40% CH$_3$CN/H$_2$O) to give phosphonic acid 59 (8 mg, 71%) as a colorless oil. $^1$H NMR (300 MHz, CD$_3$OD) δ 7.19 (s, 1H), 7.08 (d, 2H), 6.81 (d, 2H), 6.69 (s, 2H), 5.48 (s, 2H), 5.44 (s, 2H), 4.12 (d, 2H), 3.32 (m, 1H), 1.33 (d, 6H). 31P NMR (300 MHz, CD$_3$OD) δ 17.1.

Example 29

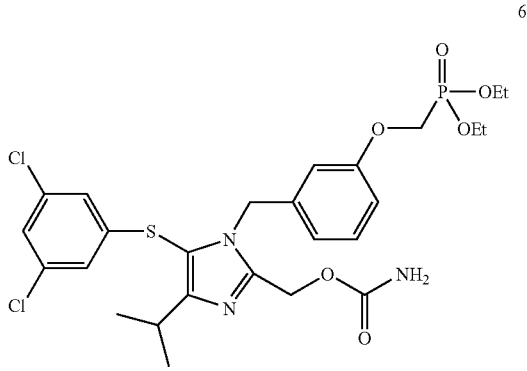

The title compound 60 was prepared following the sequence of steps described in Example 25, except for substituting 3-methoxy benzyl chloride for 4-methoxyl benzyl chloride. Purification of the crude final product on preparative thin layer chromatography eluted with 5% MeOH/CH$_2$Cl$_2$ provided 28 mg of the title compound. $^1$H NMR (500 MHz, CDCl$_3$) δ 7.12 (t, 1H), 7.03 (s, 1H), 6.75 (d, 1H), 6.66 (s, 2H), 6.60 (d, 1H), 6.55 (s, 1H), 5.24 (s, 2H), 5.19 (s, 2H), 4.22 (q, 4H), 4.20 (d, 2H), 3.17 (m, 1H), 1.37 (t, 6H), 1.31 (d, 6H). $^{31}$P NMR (300 MHz, CDCl$_3$) δ 19.2.

Example 30

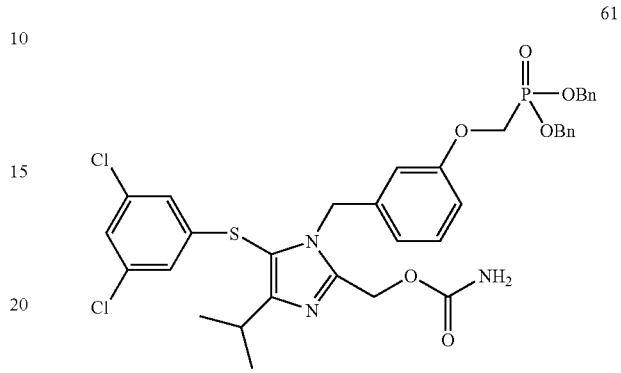

The title compound 61 was prepared following the sequence of steps described in Example 26, except for substituting 3-methoxy benzyl chloride for 4-methoxyl benzyl chloride. Purification of the crude final product on silica gel eluted with 3-4% MeOH/CH$_2$Cl$_2$ provided 36 mg of the title compound. $^1$H NMR (500 MHz, CDCl$_3$) δ 7.36 (m, 10 H), 7.10 (t, 1H), 7.00 (s, 1H), 6.68 (d, 1H), 6.64 (s, 2H), 6.59 (d, 1H), 6.53 (s, 1H), 5.23 (s, 2H), 5.17 (s, 2H), 5.11 (m, 4H), 4.18 (d, 2H), 3.16 (m, 1H), 1.31 (d, 6H). $^{31}$P NMR (300 MHz, CDCl$_3$) δ 20.2.

Example 31

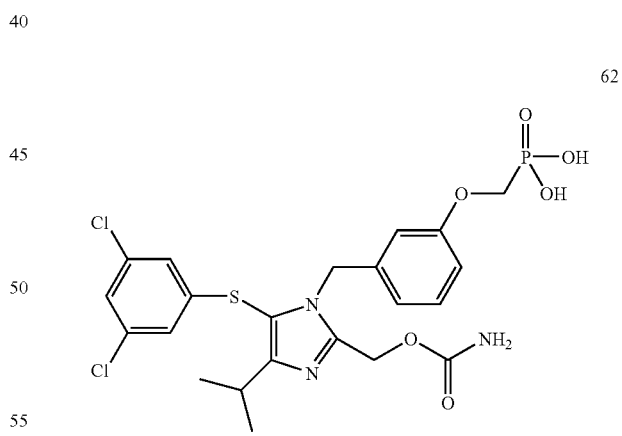

The title compound 62 was prepared following the sequence of steps described in Example 29, except for substituting compound 61 for compound 58. Purification of the crude final product with HPLC (eluting 30-40% CH$_3$CN/H$_2$O) provided 7 mg of the title compound. $^1$H NMR (300 MHz, CD$_3$OD) δ 7.18 (s, 1H), 7.13 (t, 1H), 6.81 (d, 1H), 6.77 (s, 2H), 6.72 (s, 1H), 6.68 (d, 1H), 5.49 (s, 2H), 5.37 (s, 2H), 4.12 (d, 2H), 3.33 (m, 1H), 1.34 (d, 6H). $^{31}$P NMR (300 MHz, CD$_3$OD) δ 17.0.

Example 32

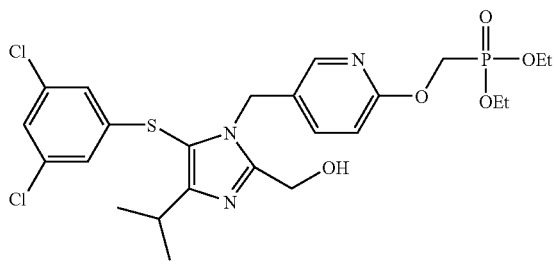

68

Figure 32:
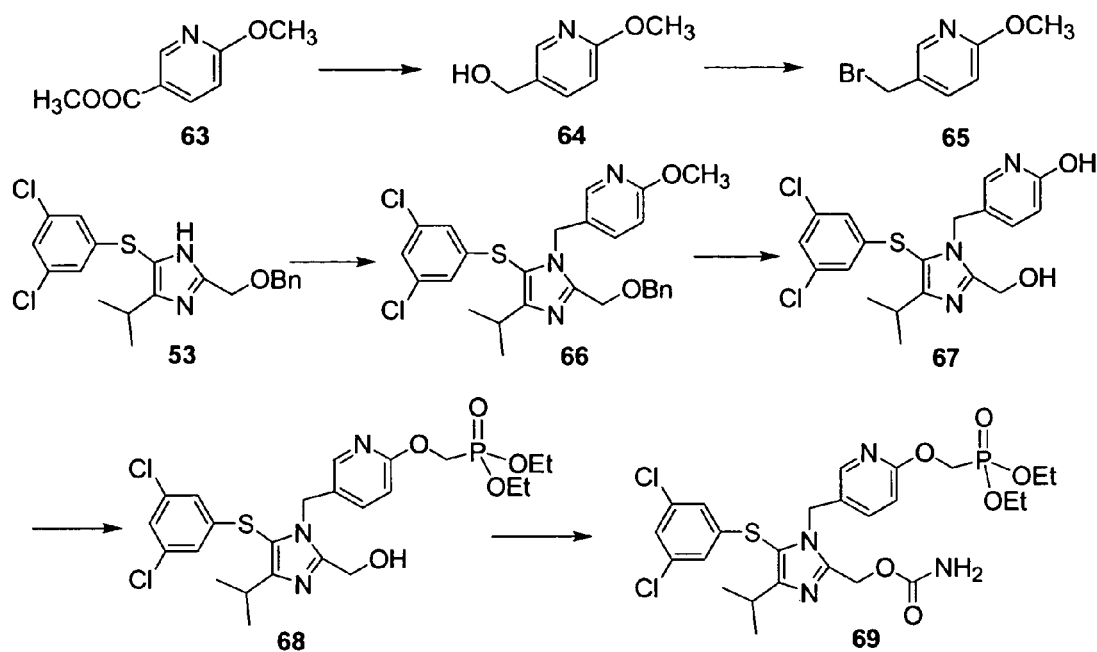
FIG. 32 depicts the preparation of compounds 68 and 69 shown in Example 32 described in detail herein below.

Alcohol 64 (See FIG. 32): A solution of methyl 6-methoxynicotinate 63 (2.0 g, 12 mmol) in Et$_2$O (50 mL) was treated with 1.5M DIBAL-H in toluene (16.8 mL, 25.1 mmol) at 0° C. After the reaction mixture was stirred for 1 h at 0° C, the mixture was quenched with 1M sodium potassium tartrate and stirred for an additional 2 h. The aqueous phase was extracted with Et$_2$O and concentrated to give alcohol 64 (1.54 g, 92%) as a pale yellow oil.

Bromide 65: A solution of alcohol 64 (700 mg, 5.0 mmol) in CH$_2$Cl$_2$ (50 mL) was treated with carbon tetrabromide (2.49 g, 7.5 mmol) and triphenylphosphine (1.44 g, 5.5 mmol) at 0C. After the reaction mixture was stirred for 30 min at room temperature, the mixture was partitioned between CH$_2$Cl$_2$ and sat. aqueous NaHCO$_3$. The organic phase was dried over Na$_2$SO$_4$, filtered, and evaporated under reduced pressure. The crude product was purified on silica gel (eluting 5-10% MeOH/CH$_2$Cl$_2$) to give bromide 65 (754 mg, 75%) as colorless crystals.

Imidazole 66 (See FIG. 32): A solution of imidazole 53 (760 mg, 1.86 mmol) and bromide 65 (752 mg, 3.72 mmol) in THF (10 mL) was treated with powder NaOH (298 mg, 7.44 mmol), lithium iodide (249 mg, 1.86 mmol), and tetrabutylammonium bromide (300 mg, 0.93 mmol). After stirring for 14 h at room temperature, the mixture was partitioned between EtOAc and sat. NH$_4$Cl. The organic phase was dried over Na$_2$SO$_4$, filtered, and evaporated under reduced pressure. The crude product was purified on silica gel (eluting 20-30% EtOAc/hexane) to give imidazole 66 (818 mg, 83%) as a pale yellow oil.

Diol 67: A solution of benzyl ether 66 (348 mg, 0.658 mmol) in EtOH (3 mL) was treated with conc. HCl (3 mL). After the reaction mixture was warmed to 80° C. and stirred for 18 h, the mixture was concentrated under reduced pressure. The crude product was chromatographed on silica gel (eluting 5-10% MeOH/CH$_2$Cl$_2$) to give diol 67 (275 mg, 98%) as a colorless solid.

Title compound diethylphosphonate 68: A solution of diol 67 (40 mg, 0.094 mmol) in THF (1 mL) was treated with trifluoro-methanesulfonic acid diethoxy-phosphorylmethyl ester (114 mg, 0.38 mmol) in THF (1 mL). After the addition of Ag$_2$CO$_3$ (52 mg, 0.19 mmol), the reaction mixture was stirred for 5 d at room temperature. The mixture was quenched with sat. NaHCO$_3$ and sat. NaCl, and extracted with EtOAc. The organic phase was dried over Na$_2$SO$_4$, filtered, and evaporated under reduced pressure. The crude product was chromatographed by silica gel (eluting 3-4% MeOH/CH$_2$Cl$_2$) and by preparative thin layer chromatography (eluting 4% MeOH/CH$_2$Cl$_2$) to give the title compound diethylphosphonate 68 (23 mg, 43%) as a colorless oil. $^1$H NMR (300 MHz, CDCl$_3$) δ 7.92 (s, 1H), 7.39 (d, 1H), 7.00 (s, 1H), 6.65 (d, 1H), 6.55 (d, 2H), 5.20 (s, 2H), 4.81 (s, 2H), 4.55 (d, 2H), 4.21 (m, 4H), 3.08 (m, 1H), 1.35 (t, 6H), 1.20 (d, 6H). $^{31}$P NMR (300 MHz, CDCl$_3$) δ 20.7.

Example 33

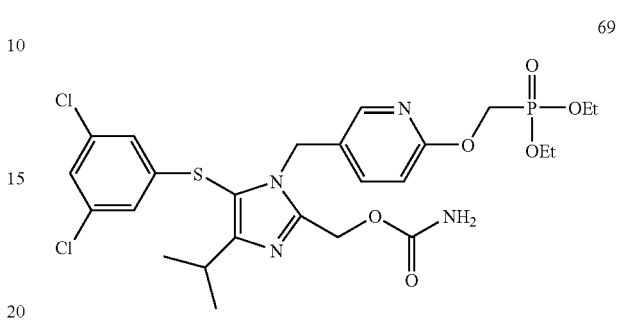

69

A solution of diethylphosphonate 68 (13 mg, 0.023 mmol) in CH$_2$Cl$_2$ (0.5 mL) was treated with trichloroacetyl isocyanate (13 µL, 0.11 mmol). After the reaction mixture was stirred for 10 min at room temperature, the mixture was concentrated under reduced pressure. The residue was transferred to an Al$_2$O$_3$ column in 10% MeOH/CH$_2$Cl$_2$. After soaking on the column for 30 min, the crude product was flushed out with 10% MeOH/CH$_2$Cl$_2$ and concentrated under reduced pressure. The crude product was purified by preparative thin layer chromatography (eluting 5% MeOH/CH$_2$Cl$_2$) to give carbamate 69 (13 mg, 92%) as a pale yellow oil. $^1$H NMR (300 MHz, CDCl$_3$) δ 7.78 (d, 1H), 7.20 (dd, 1H), 7.03 (t, 1H), 6.65 (d, 1H), 6.62 (d, 2H), 5.24 (s, 2H), 5.16 (s, 2H), 4.74 (bs, 2H), 4.58 (d, 2H), 4.20 (m, 1H), 1.35 (t, 6H), 1.27 (d, 6H). $^{31}$P NMR (300 MHz, CDCl$_3$) δ 20.7.

Example 34

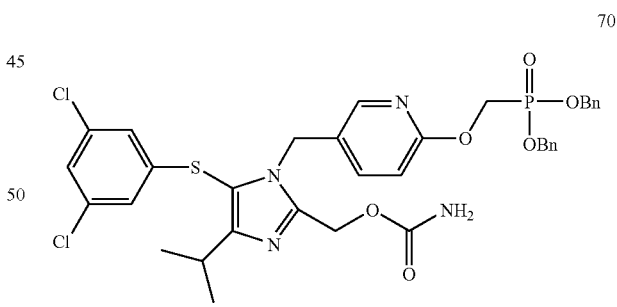

70

The title compound 70 was prepared following the sequence of steps described in Example 32, except for substituting trifluoro-methanesulfonic acid bis-benzyloxy-phosphorylmethyl ester for trifluoro-methanesulfonic acid diethoxy-phosphorylmethyl ester. Purification of the crude final product on silica gel eluted with 50-60% CH$_3$CN/H$_2$O provided 12 mg of the title compound. $^1$H NMR (300 MHz, CDCl$_3$) δ 7.78 (s, 1H), 7.34 (m, 10H), 7.19 (dd, 1H), 7.02 (t, 1H), 6.63 (s, 1H), 6.61 (d, 2H), 5.38 (s, 2H), 5.25 (s, 2H), 5.11 (m, 4H), 4.62 (d, 2H), 3.24 (m, 1H), 1.33 (d, 6H). $^{31}$P NMR (300 MHz, CDCl$_3$) δ 21.4.

Example 35

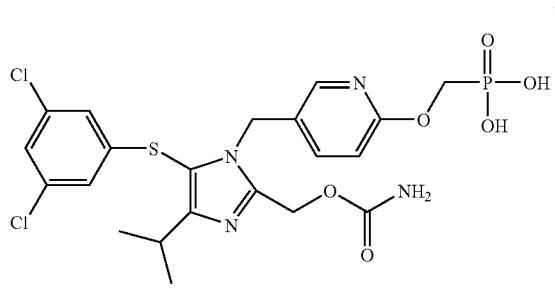

71

The title compound 71 was prepared following the sequence of steps described in Example 29, except for substituting compound 70 for compound 28. Purification of the crude final product with HPLC provided 2 mg of the title compound. $^1$H NMR (300 MHz, CD$_3$OD) δ 7.90 (s, 1H), 7.44 (d, 1H), 7.13 (t, 1H), 6.72 (m, 3H), 5.39 (s, 2H), 5.34 (s, 2H), 4.39 (d, 2H), 3.30 (m, 1H), 1.28 (d, 6H).

Example 36

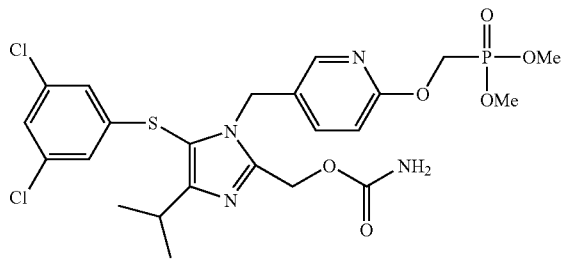

72

To a solution of phosphonic acid 72 (33 mg, 0.058 mmol) in DMF (2 mL) was added benzotriazol-1-yloxytripyrrolidino-phosphonium hexafluorophosphate (91 mg, 0.175 mmol), iPr$_2$NEt (30 μL, 0.175 mmol), and MeOH (0.24 mL, 5.83 mmol). After the reaction mixture was stirred for 2 d at room temperature, the mixture was partitioned between EtOAc and sat. NH$_4$Cl. The organic phase was dried over Na$_2$SO$_4$, filtered, and evaporated under reduced pressure. Purification of the crude final product on silica gel eluted with 3-5% MeOH/CH$_2$Cl$_2$ and by preparative thin layer chromatography (eluting 5% MeOH/CH$_2$Cl$_2$) provided 6 mg of the title compound as a colorless solid. $^1$H NMR (300 MHz, CDCl$_3$) δ 7.79 (d, 1H), 7.21 (dd, 1H), 7.04 (s, 1H), 6.66 (d, 1H), 6.62 (d, 2H), 5.25 (s, 2H), 5.17 (s, 2H), 4.70 (bs, 2H), 4.63 (d, 2H), 3.84 (d, 6H), 3.14 (m, 1H), 1.28 (d, 6H). $^{31}$P NMR (300 MHz, CDCl$_3$) δ 23.2.

Example 37

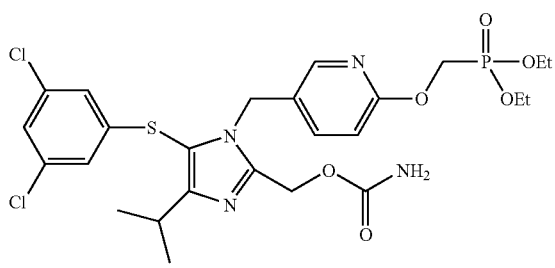

73

A solution of diol 67 (50 mg, 0.118 mmol) in CH$_2$Cl$_2$ (5 mL) was treated with diethyl (2-bromoethyl)-phosphonate (64 μL, 0.354 mmol) and Ag$_2$CO$_3$ (65 mg, 0.236 mmol). After the reaction mixture was stirred for 3 d at 40° C., additional phosphonate (64 μL, 0.354 mmol), Ag$_2$CO$_3$ (65 mg, 0.236 mmol), and benzene (5 mL) were introduced. After the reaction mixture was stirred for another 4 days at 70° C., the mixture was filtered through a medium-fritted funnel. The crude product was chromatographed by silica gel (eluting 4-5% MeOH/CH$_2$Cl$_2$) to give diethylphosphonate 74 (8 mg, 12%) as a colorless oil. $^1$H NMR (300 MHz, CDCl$_3$) δ 7.81 (bs, 1H), 7.17 (dd, 1H), 7.03 (t, 1H), 6.60 (d, 2H), 6.52 (d, 2H), 5.25 (s, 2H), 5.15 (s, 2H), 4.71 (bs, 2H), 4.47 (m, 2H), 4.14 (m, 4H), 3.12 (m, 1H), 2.27 (m, 2H), 1.34 (t, 6H), 1.27 (d, 6H), $^{31}$P NMR (300 MHz, CDCl$_3$) δ 28.0.

Example 38

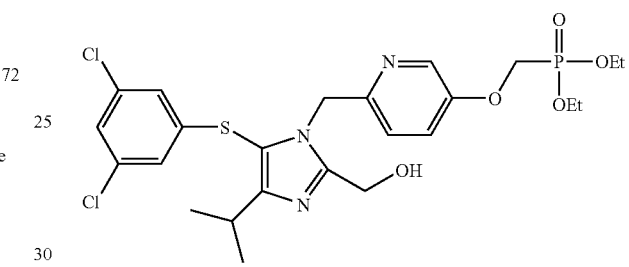

74

The title compound 74 was prepared following the sequence of steps described in Example 33, except for substituting 6-bromomethyl-3-methoxy pyridine for 5-bromomethyl-2-methoxy pyridine 65. Purification of the crude final product on silica gel with 4-5% MeOH/CH$_2$Cl$_2$ provided 66 mg of the title compound. $^1$H NMR (300 MHz, CDCl$_3$) δ 8.17 (d, 1H), 7.01 (d, 1H), 6.93 (m, 2H), 6.41 (d, 2H), 5.26 (s, 2H), 4.94 (s, 2H), 4.22 (a, 4H), 4.12 (m, 2H), 3.08 (m, 1H), 1.38 (t, 6H), 1.25 (d, 6H). $^{31}$P NMR (300 MHz, CDCl$_3$) δ 17.7.

Example 39

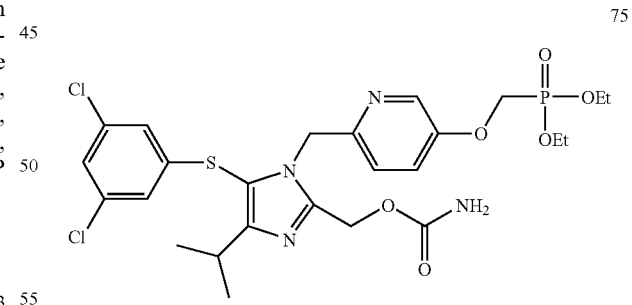

75

The title compound 75 was prepared following the sequence of steps described in Example 34, except for substituting compound 74 for compound 33. Purification of the crude final product on preparative thin layer chromatography eluted with 5% MeOH/CH$_2$Cl$_2$ provided 15 mg the title compound. $^1$H NMR (500 MHz, CDCl$_3$) δ 8.18 (d, 1H), 6.98 (m, 1H), 6.96 (m, 1H), 6.79 (d, 1H), 6.58 (d, 2H), 5.35 (s, 2H), 5.32 (s, 2H), 4.83 (bs, 2H) 4.25 (a, 4H), 4.24 (m, 2H), 3.14 (m, 1H), 1.39 (t, 6H), 1.28 (d, 6H). $^{31}$P NMR (300 MHz, CDCl$_3$) δ 18.1.

Example 40

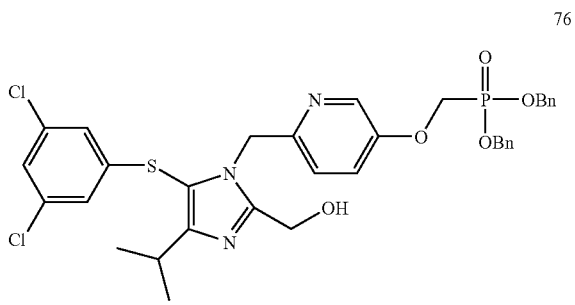

The title compound 76 was prepared following the sequence of steps described in Example 39, except for substituting trifluoro-methanesulfonic acid bis-benzyloxy-phosphorylmethyl ester for trifluoro-methanesulfonic acid diethoxy-phosphorylmethyl ester. Purification of the crude final product on silica gel eluted with 4% MeOH/CH$_2$Cl$_2$ provided 67 mg of the title compound. $^1$H NMR (300 MHz, CDCl$_3$) δ 8.05 (d, 1H), 7.36 (m, 10H), 6.95 (d, 1H), 6.81 (m, 2H), 6.37 (d, 2H), 5.22 (s, 2H), 5.13 (m, 4H), 4.91 (s, 2H), 4.11 (d, 2H), 3.05 (m, 1H), 1.22 (d, 6H). $^{31}$P NMR (300 MHz, CDCl$_3$) δ 18.8.

Example 41

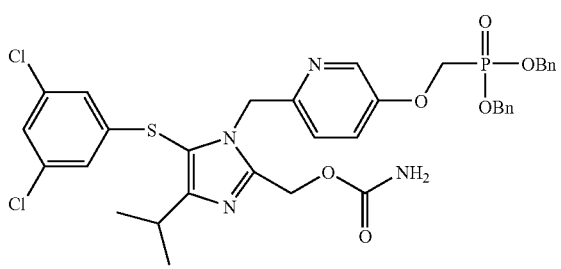

The title compound 77 was prepared following the sequence of steps described in Example 34, except for substituting compound 76 for compound 33. Purification of the crude final product on silica gel eluted with 4-5% MeOH/CH$_2$Cl$_2$ provided 35 mg of the title compound. $^1$H NMR (300 MHz, CDCl$_3$) δ 8.07 (d, 1H), 7.36 (m, 10H), 6.85 (m, 2H), 6.72 (d, 1H), 6.55 (d, 2H), 5.35 (s, 2H), 5.29 (s, 2H), 5.13 (m, 4H), 4.74 (bs, 2H), 4.15 (d, 2H), 3.13 (m, 1H), 1.28 (d, 6H). $^{31}$P NMR (300 MHz, CDCl$_3$) δ 19.2.

Example 42

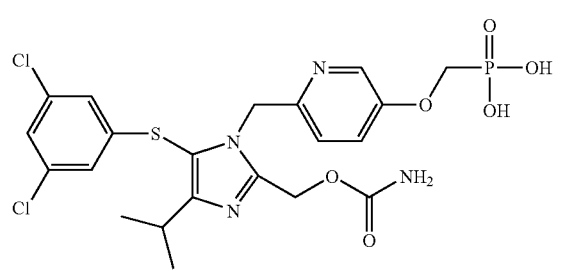

The title compound 78 was prepared following the sequence of steps described in Example 29, except for substituting compound 77 for compound 28. Purification of the crude final product on a C-18 column eluted with 30% CH$_3$CN/H$_2$O provided 6 mg of the title compound. $^1$H NMR (300 MHz, CD$_3$OD) δ 8.16 (bs, 1H), 7.21 (bs, 2H), 7.18 (bs, 1H), 6.70 (d, 2H), 5.64 (s, 2H), 5.49 (s, 2H), 4.21 (d, 2H), 3.34 (m, 1H), 1.34 (d, 6H). $^{31}$P NMR (300 MHz, CD$_3$OD) δ 16.0.

Example 43

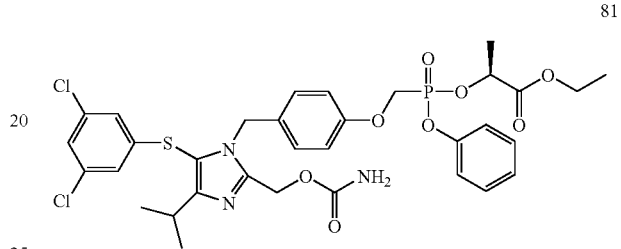

Figure 33:
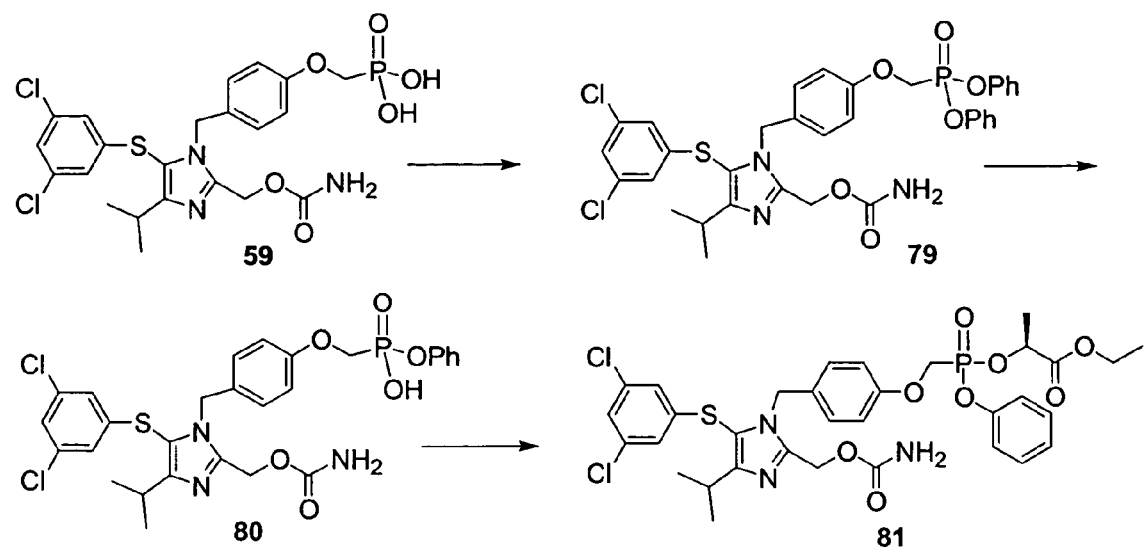
FIG. 33 depicts the preparation of compound 81 shown in Example 43 described in detail herein below.

Diphenylphosphonate 79 (FIG. 33): A solution of phosphonic acid 59 (389 mg, 0.694 mmol) in pyridine (5 mL) was treated with phenol (653 mg, 6.94 mmol) and 1,3-dicyclohexylcarbodiimide (573 mg, 2.78 mmol). After stirring at 70° C. for 2 h, the mixture was diluted with CH$_3$CN and filtered through a fritted funnel. The filtrate was partitioned between EtOAc and sat. NH$_4$Cl, and extracted with EtOAc. The organic phase was dried over Na$_2$SO$_4$, filtered, and evaporated under reduced pressure. The crude product was purified on silica gel (eluting 60-80% EtOAc/hexane) to give diphenylphosphonate 79 (278 mg, 56%) as a colorless oil.

Phosphonic acid 80 (FIG. 33): A solution of diphenylphosphonate 79 (258 mg, 0.362 mmol) in CH$_3$CN (20 mL) was treated with 1N NaOH (0.72 mL, 0.724 mmol) at 0° C. After the reaction mixture was stirred for 3 h at 0° C., the mixture was filtered through Dowex 50WX8-400 acidic resin (380 mg), rinsed with MeOH, and concentrated under reduced pressure to give phosphonic acid 80 (157 mg, 68%) as a colorless solid.

Title compound 81: A solution of phosphonic acid 80 (35 mg, 0.055 mmol) in CH$_3$CN (1 mL) and THF (1 mL) was treated with thionyl chloride (12 μL, 0.16 mmol). After the reaction mixture was warmed to 70° C. and stirred for 2 h, the mixture was concentrated under reduced pressure. The residue was then dissolved in CH$_2$Cl$_2$ (2 mL) and cooled to 0° C. Triethylamine (31 μL, 0.22 mmol) and ethyl S-(−)-lactate (19 μL, 0.16 mmol) were added. After stirring for 1 h at 0° C. and 1 h at room temperature, the reaction mixture was neutralized with sat. NH$_4$Cl and extracted with CH$_2$Cl$_2$ and EtOAc. The organic phase was dried over Na$_2$SO$_4$, filtered, and evaporated under reduced pressure. The crude product was purified by preparative thin layer chromatography (eluting 70% EtOAc/hexane) to give ethyl lactate 81 (7 mg, 17%) as a colorless solid. $^1$H NMR (300 MHz, CDCl$_3$) δ 7.30 (m, 5H), 6.99 (d, 1H), 6.82 (m, 4H), 6.63 (d, 2H), 5.23 (s, 2H), 5.18 (s, 2H), 5.14 (m, 1H), 4.67 (bs, 2H), 4.51 (d, 2H), 4.20 (m, 2H), 3.16 (m, 1H), 1.61 (d, 1.5H), 1.50 (d, 1.5H), 1.30 (d, 6H), 1.24 (m, 3H). $^{31}$P NMR (300 MHz, CDCl$_3$) δ 17.0, 15.0.

Example 44

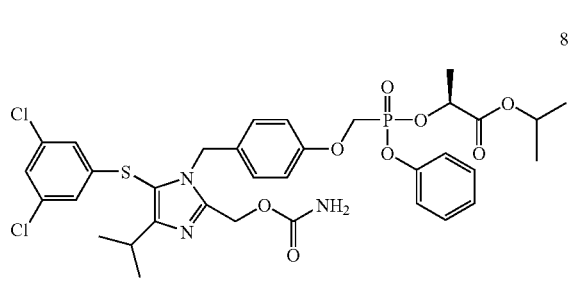

82

The title compound 82 was prepared following the sequence of steps described in Example 44, except for reacting monophosphonic acid 80 with isopropyl lactate. Purification of the crude final product on silica gel eluted with 70-90% EtOAc/hexane provided 5.4 mg of the title compound. $^1$H NMR (300 MHz, CDCl$_3$) δ 7.35 (m, 3H), 7.25 (m, 3H), 7.0 (s, 0.5H), 6.98 (s, 0.5H), 6.86 (m, 2H), 6.79 (m, 2H), 6.64 (s, 1H), 6.61 (s, 1H), 5.22 (s, 2H), 5.17 (s, 2H), 5.06 (b, 1H), 4.62 (b, 2H), 4.53 (m, 2H), 4.38 (q, 1H), 3.15 (m, 1H), 1.60 (d, 1.5H), 1.48 (d, 1.5H), 1.30 (d, 3H), 1.28 (d, 3H), 1.20 (d, 6H). $^{31}$P NMR (300 MHz, CDCl$_3$) δ 17.04, 14.94 (1:1 diastereomeric ratio).

Example 45

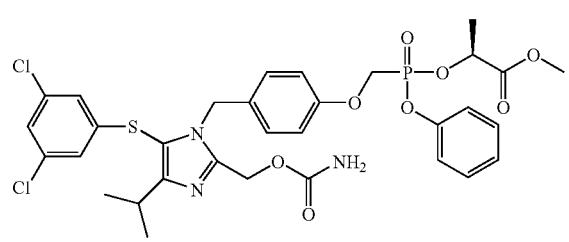

83

The title compound 83 was prepared following the sequence of steps described in Example 44, except for reacting monophosphonic acid 80 with methyl lactate. Purification of the crude final product on silica gel eluted with 70-90% EtOAc/hexane provided 2.7 mg of the title compound. $^1$H NMR (300 MHz, CD$_3$CN) δ 7.40 (m, 2H), 7.25 (m, 3H), 7.08 (s, 1H), 6.98 (d, 2H), 6.77 (d, 2H), 6.64 (s, 2H), 5.20 (s, 2H), 5.16 (s, 2H), 5.13 (b, 1H), 4.47 (m, 2H), 3.72 (s, 2H), 3.67 (s, 1H), 3.09 (m, 1H), 1.56 (d, 1H), 1.51 (d, 2H), 1.20 (d, 6H). $^{31}$P NMR (300 MHz, CD$_3$CN) δ 16.86, 15.80 (2.37:1 diastereomeric ratio).

Example 46

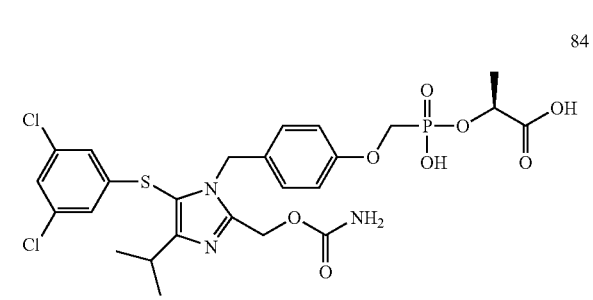

84

A solution of mono-lactate phosphonate compound 83 (131 mg, 0.18 mmol) in DMSO/MeCN (1 mL/2 mL) and PBS buffer (10 mL) was treated with esterase (400 μL). After the reaction mixture was warmed to 40° C. and stirred for 7 days, the mixture was filtered and concentrated under reduced pressure. Purification of the crude product on C$_{18}$ column eluted with MeCN/H$_2$O provided 17.3 mg (15%) of the title compound 84. $^1$H NMR (300 MHz, CD$_3$OD) δ 7.20 (s, 1H), 7.02 (d, 2H), 6.79 (d, 2H), 6.71 (s, 2H), 5.40 (s, 2H), 5.35 (s, 2H), 5.34 (b, 1H) 4.10 (bd, 2H), 3.26 (m, 1H), 1.50 (d, 3H), 1.30 (d, 6H). $^{31}$P NMR (300 MHz, CD$_3$OD) δ 14.2.

Example 47

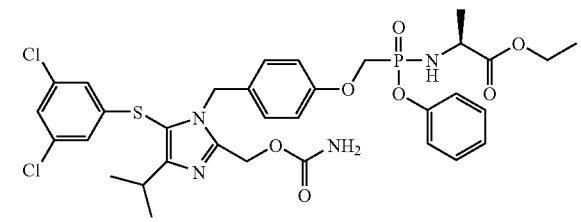

85

The title compound 85 was prepared following the sequence of steps described in Example 44, except for reacting monophosphonic acid 80 with L-alanine ethyl ester. Purification of the crude final product on preparative thin layer chromatography eluted with 80% EtOAc/hexane provided 7 mg of the title compound. $^1$H NMR (300 MHz, CDCl$_3$) δ 7.26 (m, 5H), 6.98 (d, 1H), 6.87 (d, 2H), 6.73 (t,211), 6.62 (s, 2H), 5.21 (s, 2H), 5.17 (s, 2H), 4.28 (bs, 2H), 4.25 (m, 2H), 4.10 (m, 2H), 4.02 (m, 1H), 3.66 (m, 1H1), 3.14 (m, 1H), 1.28 (d, 6H), 1.24 (m, 6H). $^{31}$P NMR (300 MHz, CDCl$_3$) δ 20.2, 19.1.

Example 48

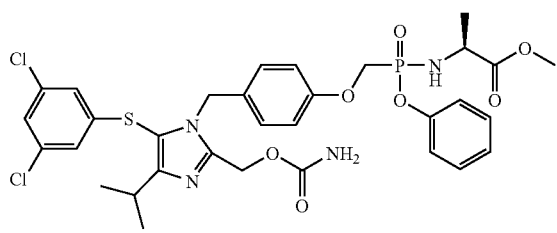

86

The title compound 86 was prepared following the sequence of steps described in Example 44, except for reacting monophosphonic acid 80 with L-alanine methyl ester. Purification of the crude final product on preparative thin layer chromatography eluted with 80% EtOAc/hexane provided 8 mg of the title compound. $^1$H NMR (300 MHz, CDCl$_3$) δ 7.25 (m, 5H), 6.98 (d, 1H), 6.88 (d, 2H), 6.73 (t, 2H), 6.61 (bs, 2H), 5.21 (d, 2H), 5.17 (s, 2H), 4.66 (bs, 2H), 4.25 (m, 3H), 3.66 (s, 1.5H), 3.64 (m, 1H), 3.59 (m, 1.5H), 3.14 (m, 1H), 1.36 (t, 6H), 1.28 (d, 6H). $^{31}$P NMR (300 MHz, CDCl$_3$) δ 20.2, 19.0.

Example 49

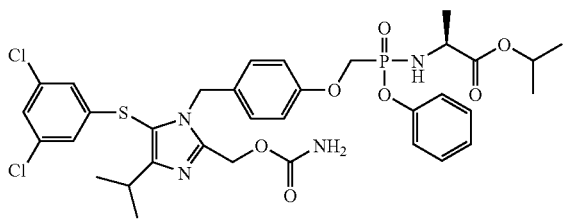

87

The title compound 87 was prepared following the sequence of steps described in Example 44, except for reacting monophosphonic acid 80 with L-alanine isopropyl ester. Purification of the crude final product on preparative thin layer chromatography eluted with 80% EtOAc/hexane provided 7 mg of the title compound. $^1$H NMR (300 MHz, CDCl$_3$) δ 7.25 (m, 5H), 6.98 (m, 1H), 6.87 (d, 2H), 6.74 (m, 2H), 6.61 (bs, 2H), 5.22 (d, 2H), 5.18 (s, 2H), 4.93 (m, 1H), 4.68 (bs, 2H), 4.25 (m, 3H), 3.66 (s, 1H), 3.15 (m, 1H), 1.34 (m, 3H), 1.29 (d, 6H), 1.17 (m, 6H). $^{31}$P NMR (300 MHz, CDCl$_3$) δ 20.1, 19.1.

Example 50

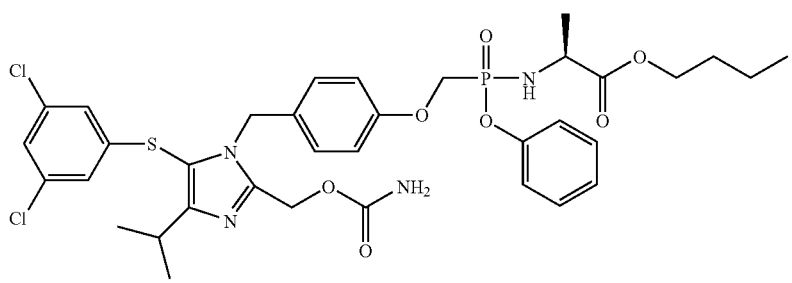

88

The title compound 88 was prepared following the sequence of steps described in Example 44, except for reacting monophosphonic acid 80 with L-alanine n-butyl ester. Purification of the crude final product on preparative thin layer chromatography eluted with 80% EtOAc/hexane provided 6 mg of the title compound. $^1$H NMR (300 MHz, CDCl$_3$) δ 7.25 (m, 5H), 6.98 (bd, 1H), 6.88 (d, 2H), 6.73 (t, 2H), 6.61 (d, 2H), 5.22 (d, 2H), 5.17 (s, 2H), 4.63 (bs, 2H), 4.25 (m, 3H), 4.06 (m, 2H), 3.65 (m, 1H), 3.14 (m, 1H), 1.58 (m, 4H), 1.36 (m, 3H), 1.28 (d, 6H), 0.90 (t, 3H). $^{31}$P NMR (300 MHz, CDCl$_3$) δ 20.2, 19.1.

Example 51

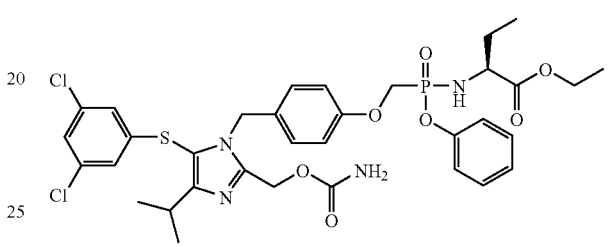

89

The title compound 89 was prepared following the sequence of steps described in Example 44, except for reacting monophosphonic acid 80 with L-alanine n-butyl ester. Purification of the crude final product on preparative thin layer chromatography eluted with 80% EtOAc/hexane provided 4 mg of the title compound. $^1$H NMR (300 MHz, CDCl$_3$) δ 7.24 (m, 5H), 6.98 (m, 1H), 6.87 (d, 2H), 6.74 (t, 2H), 6.62 (d, 2H), 5.21 (d, 2H), 5.17 (s, 2H), 4.64 (bs, 2H), 4.24 (m, 2H), 4.11 (m, 3H), 3.58 (m, 1H), 3.15 (m, 1H), 1.28 (d, 6H), 1.19 (m, 5H), 0.84 (m, 3H). $^{31}$P NMR (300 MHz, CDCl$_3$) δ 20.4, 19.4.

Example 52

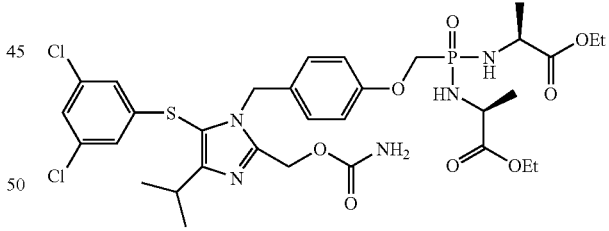

90

To a solution of phosphonic acid 59 (61 mg, 0.11 mmol) in DMF (1 mL) was added benzotriazol-1-yloxytripyrrolidinophosphonium hexafluorophosphate (169 mg, 0.32 mmol), L-alanine ethyl ester (50 mg, 0.32 mmol), and DIEA (151 µL, 0.87 mmol). The reaction mixture was stirred for 5 hours at room temperature. Then the mixture was concentrated under reduced pressure. The residue was dissolved in EtOAc, washed with HCl (5% aq), and extracted with EtOAc (3×). The organic phase was washed with sat. NaHCO$_3$, dried over Na$_2$SO$_4$, and evaporated under reduced pressure. The crude product was purified on silica gel eluted with 5-8% MeOH/CH$_2$Cl$_2$ to give 5.5 mg of compound bis-amidate 90 as white solid. $^1$H NMR (300 MHz, CDCl$_3$) δ 7.06 (s, 1H), 6.88 (d, 2H), 6.73 (d, 2H), 6.62 (s, 2H), 5.23 (s, 2H), 5.17 (s, 2H), 4.70 (bs, 2H), 4.25 (bm, 8H), 3.40 (q, 2H), 3.16 (m, 1H), 1.44 (t, 6H), 1.24 (d, 6H), $^{31}$P NMR (300 MHz, CDCl$_3$) δ 19.41.

Example 53

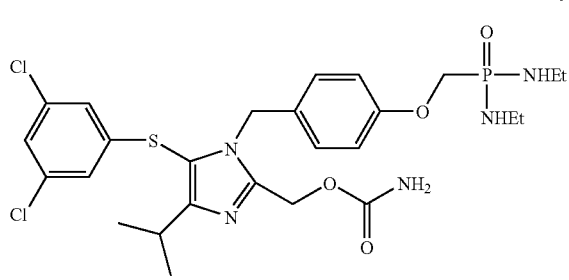

91

The title compound 91 was prepared following the sequence of steps described in Example 52, except for substituting ethyl amine for L-alanine ethyl ester. Purification of the crude final product on silica gel eluted with 4-10% MeOH/CH$_2$Cl$_2$ provided 14.8 mg of the title compound. $^1$H NMR (300 MHz, CD$_3$OD) δ 7.07 (s, 1H), 6.99 (d, 2H), 6.77 (d, 2H), 6.60 (s, 2H), 5.27 (s, 2H), 5.22 (s, 2H), 4.07 (d, 2H), 3.09 (m, 1H), 3.01 (bm, 4H), 1.24 (d, 6H), 1.16 (t, 6H). $^{31}$P NMR (300 MHz, CD$_3$OD) δ 24.66.

Example 54

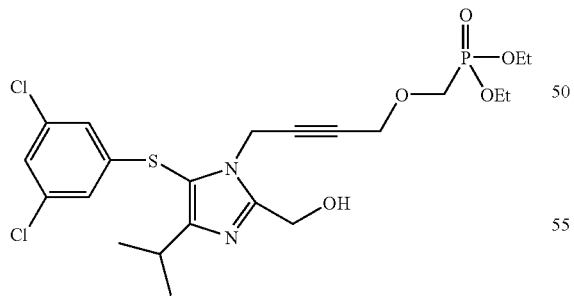

97

Figure 34:
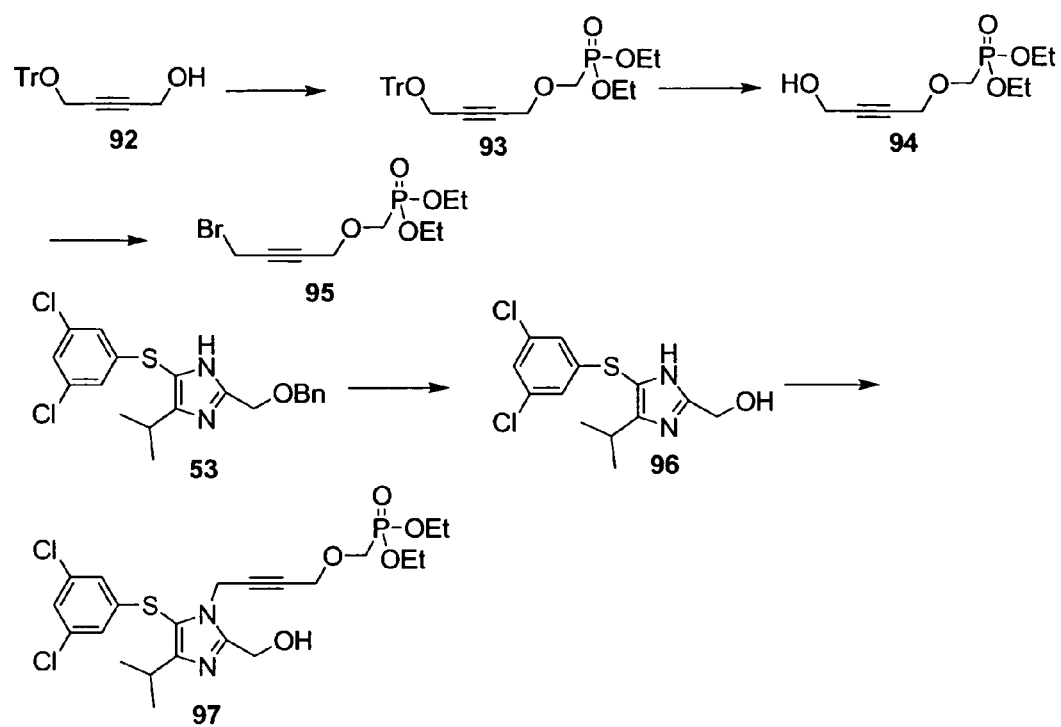
FIG. 34 depicts the preparation of compound 97 shown in Example 54 described in detail herein below.

Diethylphosphonate 93 (FIG. 34): A solution of alcohol 92 (200 mg, 0.609 mmol) in THF (5 mL) was treated with 60% NaH in mineral oil (37 mg, 0.914 mmol) at 0° C. After the reaction mixture was stirred for 5 min at 0° C., trifluoromethanesulfonic acid diethoxy-phosphorylmethyl ester (219 mg, 0.731 mmol) was added in THF (3 mL). After the reaction mixture was stirred for an additional 30 min, the mixture was quenched with sat. NH$_4$Cl and extracted with EtOAc. The organic phase was dried over Na$_2$SO$_4$, filtered, and evaporated under reduced pressure to give crude diethylphosphonate 93 as a colorless oil.

Alcohol 94 (FIG. 34): A solution of diethylphosphonate 93 (291 mg, 0.609 mmol) in CH$_2$Cl$_2$ (5 mL) was treated with trifluoroacetic acid (0.5 mL). After the reaction mixture was stirred for 30 min at room temperature, the mixture was concentrated under reduced pressure. The crude product was purified on silica gel (eluting 4-5% MeOH/CH$_2$Cl$_2$) to give alcohol 94 (135 mg, 94% over 2 steps) as a colorless oil.

Bromide 95 (FIG. 34): A solution of alcohol 94 (134 mg, 0.567 mmol) in CH$_2$Cl$_2$ (5 mL) was treated with carbon tetrabromide (282 mg, 0.851 mmol) and triphenylphosphine (164 mg, 0.624 mmol). After stirring at room temperature for 1 h, the mixture was partitioned between CH$_2$Cl$_2$ and sat. NaHCO$_3$. The organic phase was dried over Na$_2$SO$_4$, filtered, and evaporated under reduced pressure. The crude product was purified twice on silica gel (eluting 60-100% EtOAc/hexane, followed by eluting 0-2% MeOH/CH$_2$Cl$_2$) to give bromide 95 (80 mg, 47%) as a colorless oil.

Imidazole 96 (FIG. 34): A solution of benzyl ether 53 (2.58 g, 6.34 mmol) in EtOH (60 mL) was treated with conc. HCl (60 mL). After the reaction mixture was warmed to 100° C. and stirred for 18 h, the mixture was concentrated under reduced pressure. The residue was partitioned between EtOAc and sat. NaHCO$_3$. The organic phase was dried over Na$_2$SO$_4$, filtered, and evaporated under reduced pressure. The crude product was chromatographed on silica gel (eluting 8-9% MeOH/CH$_2$Cl$_2$) to give imidazole 96 (1.86 g, 93%) as a colorless solid.

Title compound 97: A solution of imidazole 96 (54 mg, 0.170 mmol) and bromide 95 (56 mg, 0.187 mmol) in THF (3 mL) was treated with powder NaOH (14 mg, 0.340 mmol), lithium iodide (23 mg, 0.170 mmol), and tetrabutylammonium bromide (27 mg, 0.085 mmol) were then added. After stirring at room temperature for 2 h, the mixture was partitioned between EtOAc and sat. NH$_4$Cl. The organic phase was dried over Na$_2$SO$_4$, filtered, and evaporated under reduced pressure. The crude product was purified on silica gel (eluting 3-4% MeOH/CH$_2$Cl$_2$) and by preparative thin layer chromatography (eluting 5% MeOH/CH$_2$Cl$_2$) to give alcohol 97 (42 mg, 46%) as a pale yellow oil. $^1$H NMR (300 MHz, CDCl$_3$) δ 7.13 (bs, 1H), 6.86 (d, 2H), 4.92 (s, 2H), 4.87 (s, 2H), 4.16 (m, 6H), 3.73 (d, 2H), 3.10 (m, 1H), 1.34 (t, 6H), 1.21 (d, 6H). $^{31}$P NMR (300 MHz, CDCl$_3$) δ 20.8.

Example 55

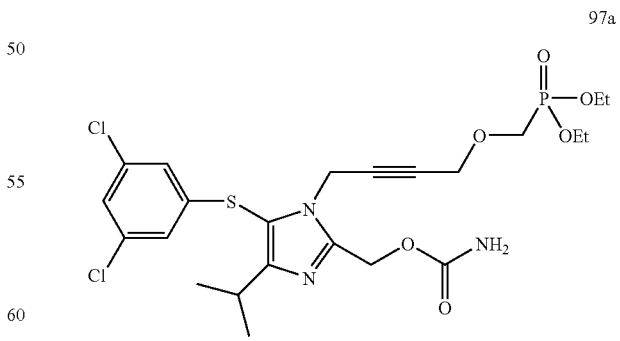

97a

The title compound 97a was prepared following the sequence of steps described in Example 32 by substituting compound 97a for compound 68. Purification of the crude final product on silica gel eluted with 3-4% MeOH/CH$_2$Cl$_2$ provided 13 mg of the title compound. $^1$H NMR (300 MHz, CDCl$_3$) δ 7.13 (t, 1H), 6.87 (d, 2H), 5.29 (s, 2H), 4.87 (s, 2H), 4.14 (m, 6H), 3.72 (d, 2H), 3.13 (m, 1H), 1.33 (t, 6H), 1.26 (d, 6H). $^{31}$P NMR (300 MHz, CDCl$_3$) δ 2.12.

Example 56

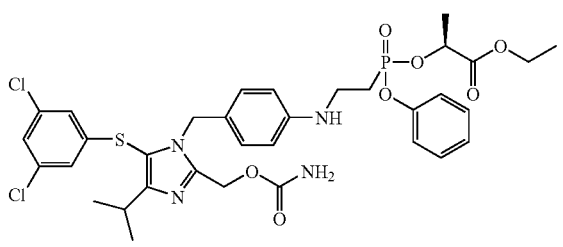

Figure 35A:
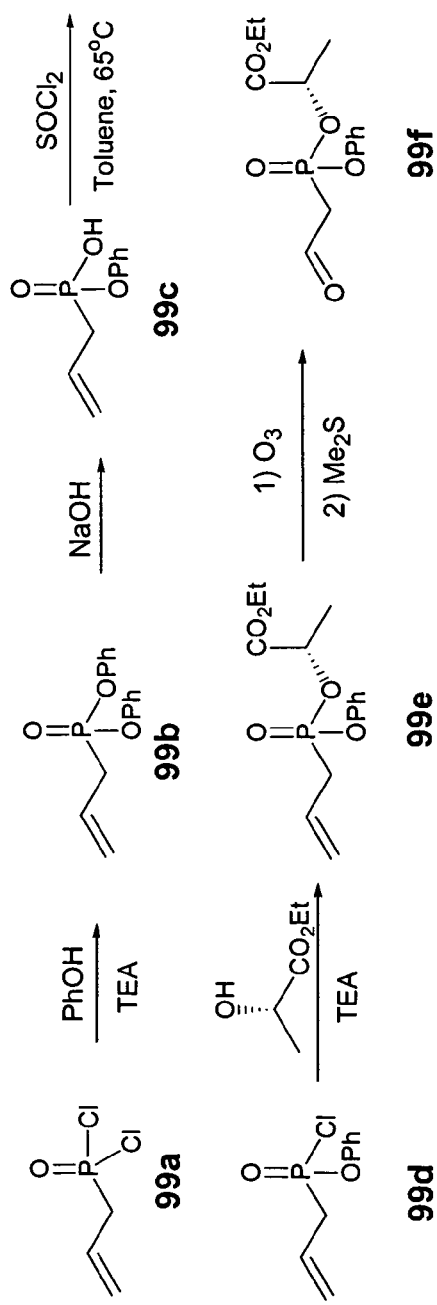
FIGS. 35A-B depict the preparation of compound 101 shown in Example 56 described in detail herein below.
Figure 35B:
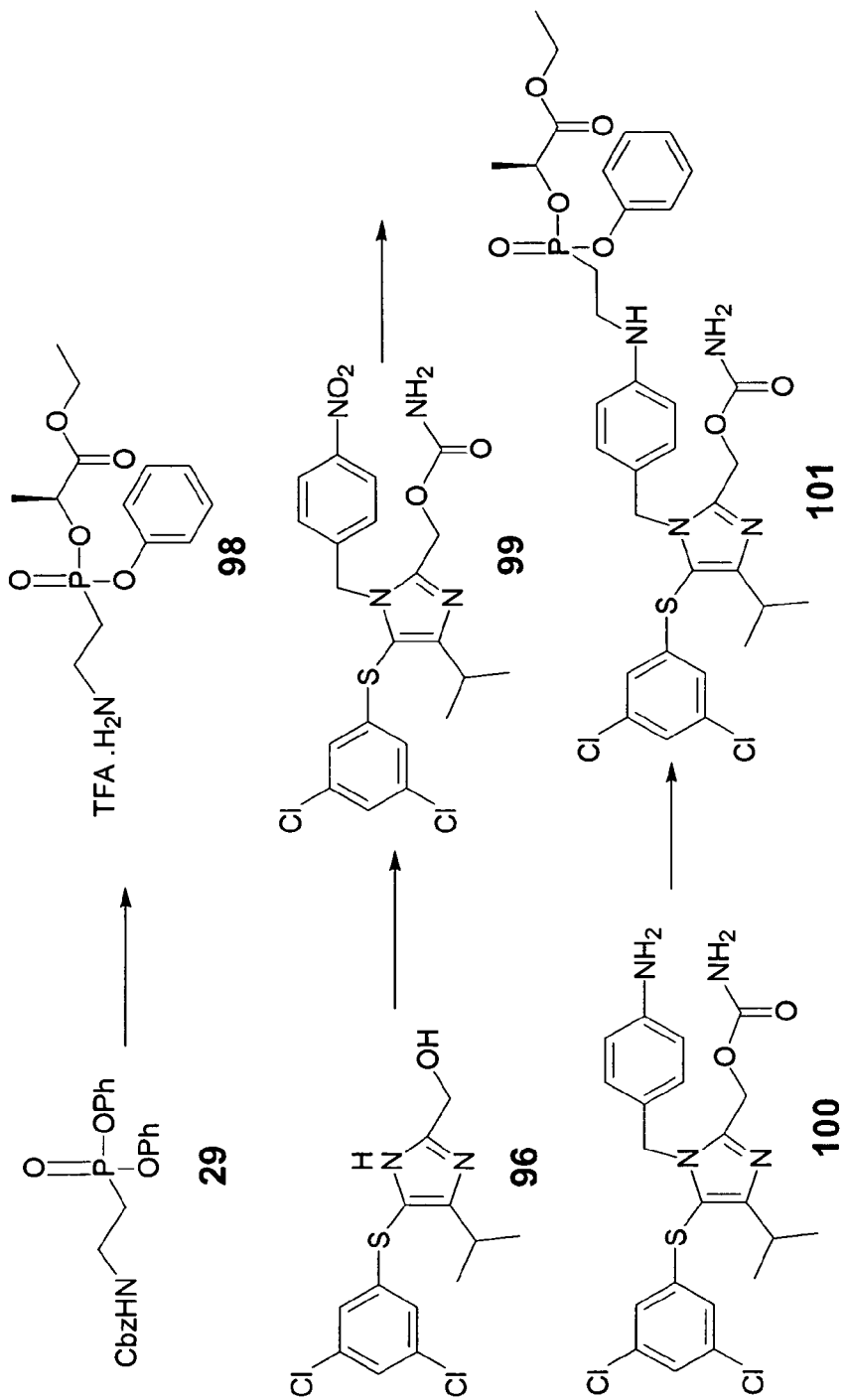

Monophenol Allylphosphonate 99c (FIG. 35): To a solution of allylphosphonic dichloride 99a (4 g, 25.4 mmol) and phenol (5.2 g, 55.3 mmol) in CH$_2$Cl$_2$ (40 mL) at 0° C. was added TEA (8.4 mL, 60 mmol). After stirred at room temperature for 1.5 h, the mixture was diluted with hexane-ethyl acetate and washed with HCl (0.3 N) and water. The organic phase was dried over MgSO$_4$, filtered and concentrated under reduced pressure. The residue was filtered through a pad of silica gel (eluted with 2:1 hexane-ethyl acetate) to afford crude product diphenol allylphosphonate 99b (7.8 g, containing the excessive phenol) as an oil which was used directly without any further purification. The crude material was dissolved in CH$_3$CN (60 mL), and NaOH (4.4N, 15 mL) was added at 0° C. The resulted mixture was stirred at room temperature for 3 h, then neutralized with acetic acid to pH=8 and concentrated under reduced pressure to remove most of the acetonitrile. The residue was dissolved in water (50 mL) and washed with CH$_2$Cl$_2$ (3×25 mL). The aqueous phase was acidified with concentrated HCl at 0° C. and extracted with ethyl acetate. The organic phase was dried over MgSO$_4$, filtered, evaporated and co-evaporated with toluene under reduced pressure to yield desired monophenol allylphosphonate 99c (4.75 g, 95%) as an oil.

Monolactate Allylphosphonate 99e (FIG. 35): A solution of monophenol allylphosphonate 99c (4.75 g, 24 mmol) in toluene (30 mL) was treated with SOCl$_2$ (5 mL, 68 mmol) and DMF (0.05 mL). After stirred at 65° C. for 4 h, the reaction was completed as shown by $^{31}$P NMR. The reaction mixture was evaporated and co-evaporated with toluene under reduced pressure to give mono chloride 99d (5.5 g) as an oil. A solution of chloride 99d in CH$_2$Cl$_2$ (25 mL) at 0° C. was added ethyl (s)-lactate (3.3 mL, 28.8 mmol), followed by TEA. The mixture was stirred at 0° C. for 5 min then at room temperature for 1 h, and concentrated under reduced pressure. The residue was partitioned between ethyl acetate and HCl (0.2N), the organic phase was washed with water, dried over MgSO$_4$, filtered and concentrated under reduced pressure. The residue was purified by chromatography on silica gel to afford desired monolactate 99e (5.75 g, 80%) as an oil (2:1 mixture of two isomers).

Aldehyde 99f (FIG. 35): A solution of allylphosphonate 99e (2.5 g, 8.38 mmol) in CH$_2$Cl$_2$ (30 mL) was bubbled with ozone air at -78° C. until the solution became blue, then bubbled with nitrogen until the blue color disappeared. Methyl sulfide (3 mL) was added at -78° C. The mixture was warmed up to room temperature, stirred for 16 h and concentrated under reduced pressure to give desired aldehyde 99f (3.2 g, as a 1:1 mixture of DMSO).

Compound 98 (FIG. 35) was prepared from compound 29 following the sequence of steps described in Example 22. Compound 99 was prepared from compound 96 following the sequence of steps described in Example 54 and 55, except for substituting 4-nitro benzyl bromide for compound 95.

Aniline 100 (FIG. 35): To a solution of compound 99 (100 mg, 0.202 mmol) in EtOH (2 mL) was added acetic acid (2 mL) and zinc dust (40 mg, 0.606 mmol). After the reaction mixture was stirred for 30 min at room temperature, the mixture was concentrated under reduced pressure. The crude product was purified on silica gel (eluting 5-6% MeOH/CH$_2$Cl$_2$) to give aniline 100 (43 mg, 41%) as a yellow oil.

Title compound phosphonate 101: To a solution of aniline 100 (22 mg, 0.042 mmol) and aldehyde 99f (17 mg, 0.046 mmol) in MeOH (2 mL) was added acetic acid (10 μL, 0.17 mmol) and 4 Å molecular sieves (10 mg). After the reaction mixture was stirred for 2 h at room temperature, NaCNBH$_3$ (5 mg, 0.084 mmol) was added. After the reaction mixture was stirred for an additional 4 h at room temperature, the mixture was concentrated under reduced pressure. The residue was partitioned between EtOAc and sat. NaHCO$_3$. The organic phase was dried over Na$_2$SO$_4$, filtered, and evaporated under reduced pressure. The crude product was purified on silica gel (eluting 5-6% MeOH/CH$_2$Cl$_2$) to give title compound phosphonate 101 (25 mg, 79%) as a colorless oil. $^1$H NMR (500 MHz, CDCl$_3$) δ 7.34 (dd, 2H), 7.21 (m, 3H), 7.02 (bs, 1H), 6.79 (d, 2H), 6.64 (t, 2H), 6.42 (dd, 2H), 5.21 (s, 2H), 5.10 (s, 2H), 5.02 (m, 1H), 4.75 (bs, 2H), 4.20 (m, 2H), 3.53 (m, 2H), 3.13 (m, 1H), 2.31 (m, 2H), 1.58 (d, 1.5H), 1.38 (d, 1.5 H), 1.28 (d, 6H), 1.25 (t, 3H). $^{31}$P NMR (300 MHz, CDCl$_3$) δ 28.4, 26.5.

Example 57

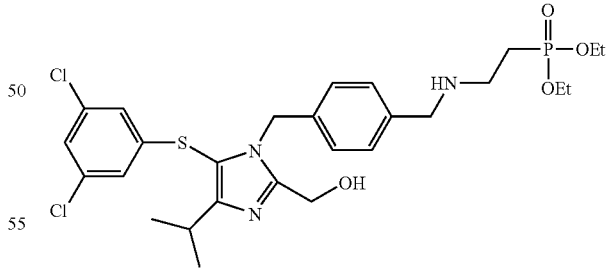

Figure 36:
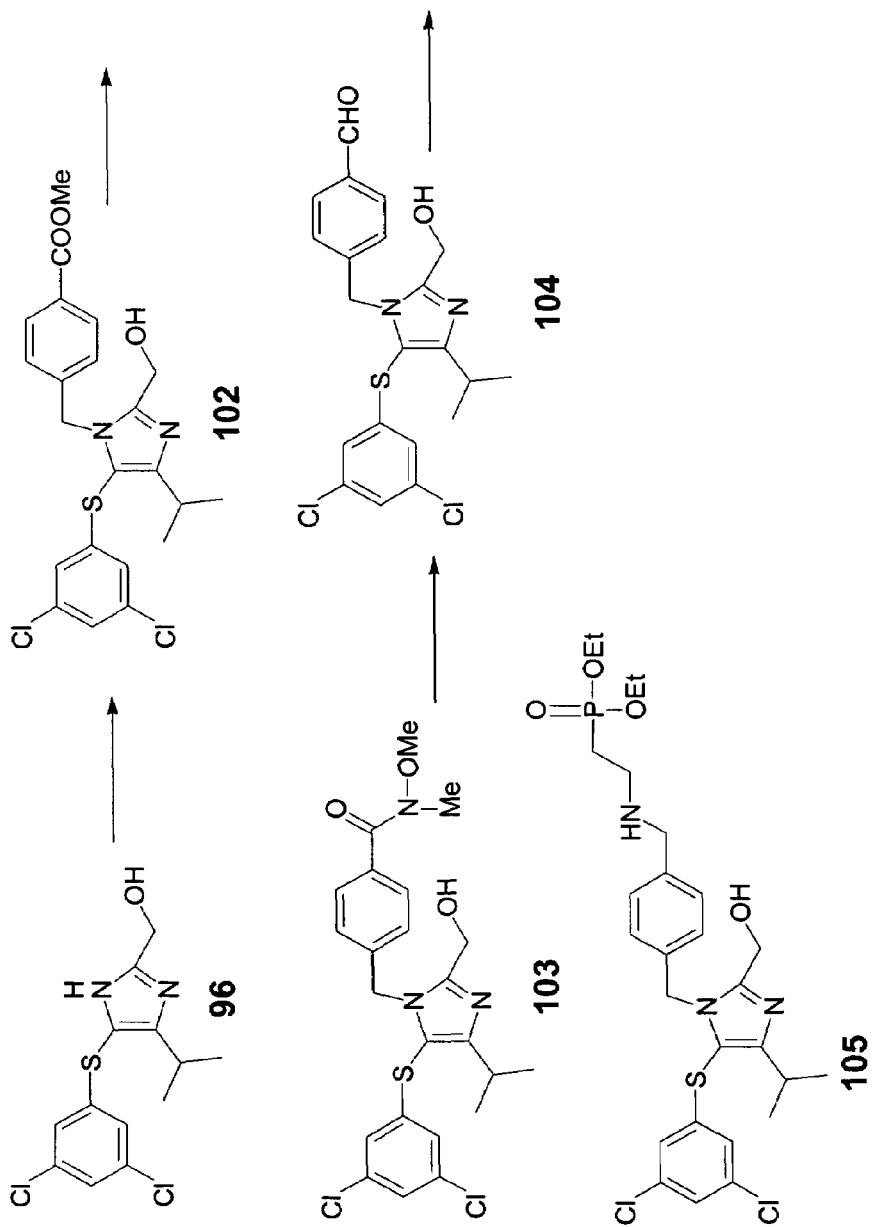
FIG. 36 depicts the preparation of compound 105 shown in Example 57 described in detail herein below.

Compound 102 (FIG. 36): was prepared from compound 96 following the sequence of steps described in Example 54, except for substituting methyl 4-bromomethyl benzoate for compound 95.

Amide 103 (FIG. 36): A solution of ester 102 (262 mg, 0.563 mmol) in THF (5 mL) and CH$_3$CN (2 mL) was treated with 1N NaOH (1.13 mL, 1.13 mmol). After the reaction mixture was stirred for 2 h at 60° C., the mixture was concentrated under reduced pressure. The residue was partitioned between EtOAc and 1N HCl. The organic phase was dried over Na$_2$SO$_4$, filtered, and evaporated under reduced pressure. The crude product was chromatographed on silica gel (eluting 5-10% MeOH/CH$_2$Cl$_2$) to give the carboxylic acid (120 mg, 47%) as a colorless oil. A solution of the above carboxylic acid (120 mg, 0.266 mmol) and N,O-dimethylhydroxylamine (29 mg, 0.293 mmol) in DMF (3 mL) was treated with 1-(3-dimethylaminopropyl)-3-ethylcarbodiimide hydrochloride (61 mg, 0.319 mmol), 1-hydroxybenzotriazole hydrate (43 mg, 0.319 mmol), and triethylamine (55 μL, 0.399 mmol). After the reaction mixture was stirred for 18 h at room temperature, the mixture was partitioned between EtOAc and H$_2$O. The organic phase was dried over Na$_2$SO$_4$, filtered, and evaporated under reduced pressure. The crude product was chromatographed on silica gel (eluting 3-4% MeOH/CH$_2$Cl$_2$) to give the amide 103 (107 mg, 81%) as a colorless oil.

Aldehyde 104 (FIG. 36): A solution of amide 103 (106 mg, 0.214 mmol) in THF (5 mL) was treated with 1.5M DIBAL-H in toluene (0.43 mL, 0.642 mmol) at 0° C. After the reaction mixture was stirred for 1 h at 0° C., the mixture was quenched with 1M sodium potassium tartrate and stirred for an additional 3 d. The aqueous phase was extracted with EtOAc, and the organic phase was dried over Na$_2$SO$_4$, filtered, and evaporated under reduced pressure to give crude aldehyde 104 as a colorless oil.

Title compound 105: To a solution of aldehyde 104 (91 mg, 0.21 mmol) in MeOH (5 mL) was added diethyl(aminoethyl) phosphonate (63 mg, 0.231 mmol), acetic acid (48 μL, 0.231 mmol) and 4 Å molecular sieves (10 mg). After the reaction mixture was stirred for 2 h at room temperature, NaCNBH$_3$ (26 mg, 0.42 mmol) was added. After the reaction mixture was stirred for an additional 18 h at room temperature, the mixture was concentrated under reduced pressure. The residue was partitioned between EtOAc and sat. NaHCO$_3$. The organic phase was dried over Na$_2$SO$_4$, filtered, and evaporated under reduced pressure. The crude product was chromatographed on silica gel (eluting 5-10% MeOH/CH$_2$Cl$_2$) to give phosphonate 105 (10 mg, 8% over 2 steps) as a colorless oil. $^1$H NMR (300 MHz, CD$_3$OD) δ 7.15 (d, 2H), 7.10 (t, 1H), 7.06 (d, 2H), 6.65 (t, 2H), 5.34 (s, 2H), 4.73 (s, 2H), 4.09 (m, 4H), 3.68 (s, 2H), 3.12 (m, 1H), 2.83 (m, 2H), 2.04 (m, 2H), 1.30 (t, 6H), 1.24 (d, 6H). $^{31}$P NMR (300 MHz, CD$_3$OD) δ 30.6.

Example 58

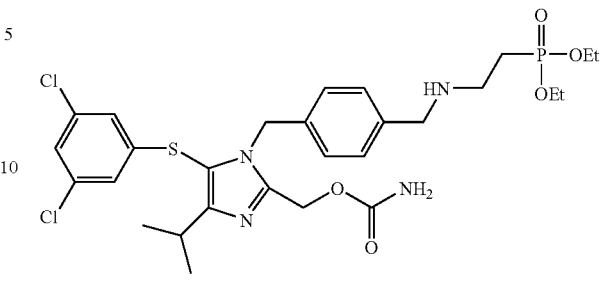

The title compound 106 was prepared following the sequence of steps described in Example 34, except for substituting compound 105 for compound 68. Purification of the crude final product on preparative thin layer chromatography eluted with 7% MeOH/CH$_2$Cl$_2$ provided 6 mg of the title compound. $^1$H NMR (300 MHz, CDCl$_3$) δ 7.15 (d, 2H), 7.02 (bs, 1H), 6.88 (d, 2H), 6.67 (t, 2H), 5.21 (s, 2H), 5.17 (s, 2H), 4.76 (bs, 2H), 4.08 (m, 4H), 3.70 (s, 2H), 3.15 (m, 1H), 2.86 (m, 2H), 1.97 (m, 2H), 1.31 (t, 6H), 1.29 (d, 6H). $^{31}$P NMR (300 MHz, CDCl$_3$) δ 30.6.

Example 59

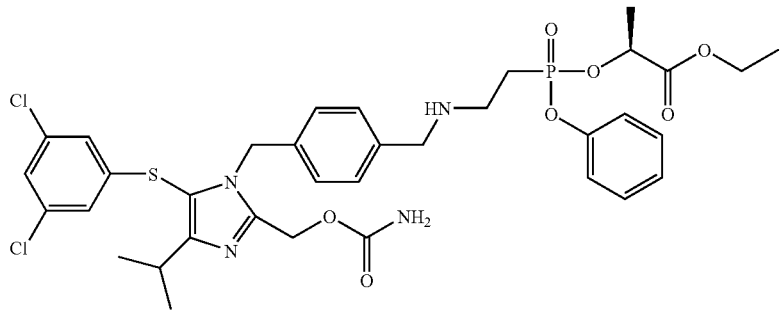

Figure 37:
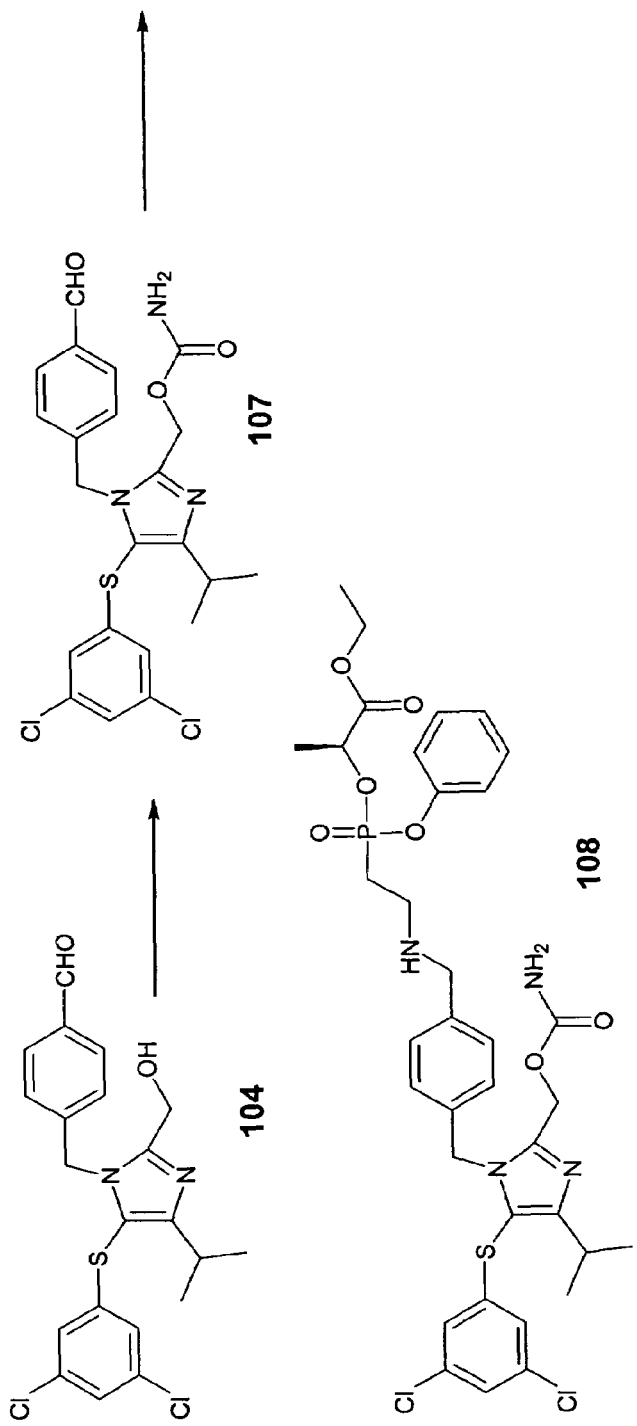
FIG. 37 depicts the preparation of compound 108 shown in Example 59 described in detail herein below.

Compound 107 (FIG. 37) was prepared following the sequence of steps described in Example 34, except for substituting compound 104 for compound 68. The title compound was prepared following the sequence of steps described in Example 58, except for substituting compound 98 for aminoethyl phosphonic acid diethyl ester. Purification of the crude final product on preparative thin layer chromatography eluted with 7% MeOH/CH$_2$Cl$_2$ provided 24 mg of the title compound 108. $^1$H NMR (300 MHz, CDCl$_3$) (5:1 diastereomeric ratio) δ 7.34 (t, 2H), 7.17 (m, 5H), 7.01 (t, 1H), 6.86 (d, 2H), 6.66 (t, 2H), 5.20 (bs, 4H), 4.96 (m, 1H), 4.63 (bs, 2H), 4.19 (m, 2H), 3.73 (s, 2H), 3.15 (m, 1H), 3.02 (m, 2H), 2.27 (m, 2H), 1.36 (d, 3H), 1.29 (d, 6H) 1.27 (m, 3H). $^{31}$P NMR (300 MHz, CDCl$_3$) δ 29.1, 27.4.

Example 60

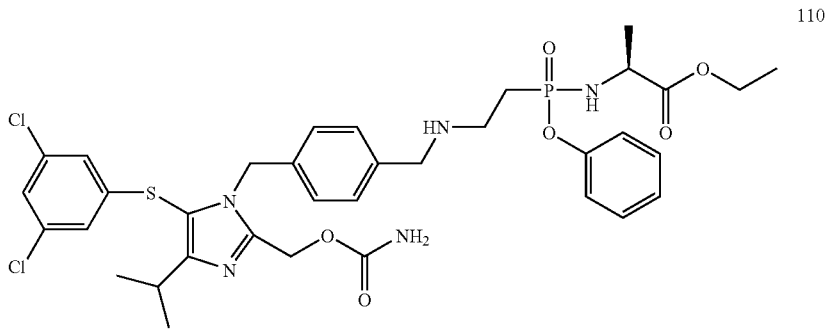

Figure 38:
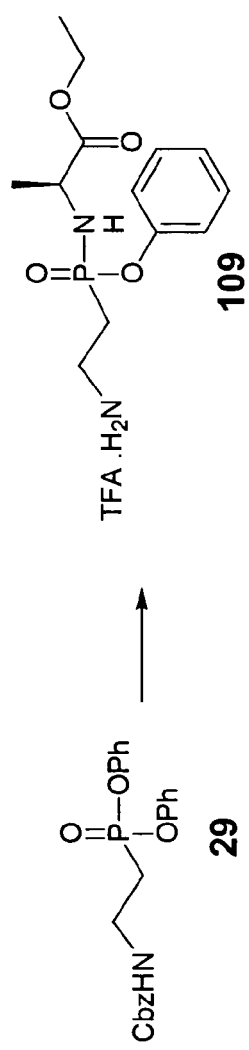
FIG. 38 depicts the preparation of compound 109 shown in Example 60 described in detail herein below.

Compound 109 (FIG. 38) was prepared from compound 29 following the sequence of steps described in Example 22. The title compound was prepared following the sequence of steps described in Example 58, except for substituting compound 109 for aminoethyl phosphonic acid diethyl ester. Purification of the crude final product on silica gel eluted with 5-6% MeOH/CH$_2$Cl$_2$ provided 8 mg of the title compound. $^1$H NMR (300 MHz, CDCl$_3$) (1.8:1 diastereomeric ratio) δ 7.31 (m, 2H), 7.16 (m, 5H), 7.01 (bs, 1H), 6.88 (d, 2H), 6.66 (bs, 2H), 5.21 (s, 2H), 5.20 (s, 2H), 4.69 (bd, 2H), 4.27 (bt, 1H), 4.12 (m, 3H), 3.75 (m, 2H), 3.16 (m, 1H), 2.99 (m, 2H), 2.11 (m, 2H), 1.30 (d, 6H), 1.22 (m, 6H). $^{31}$P NMR (300 MHz, CDCl$_3$) δ 31.3, 30.8.

Example 61

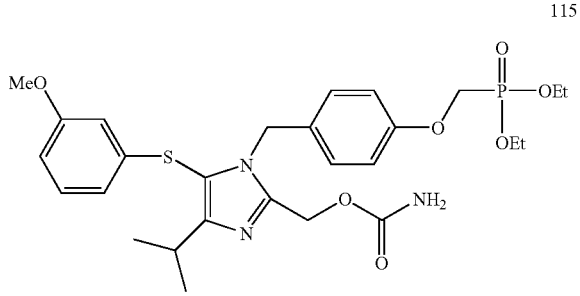

Figure 39:
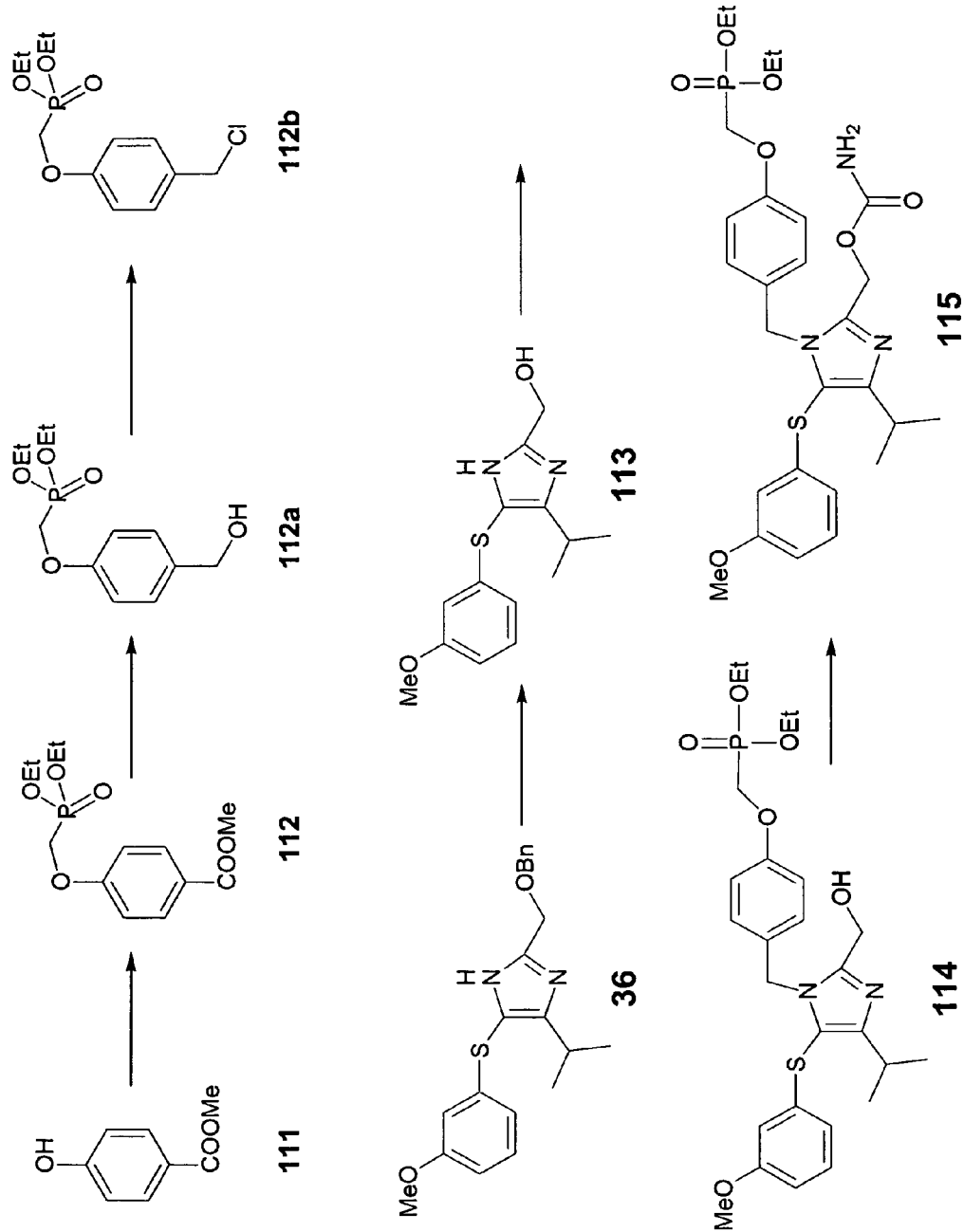
FIG. 39 depicts the preparation of compound 115 shown in Example 61 described in detail herein below.

Compound 112 (FIG. 39): A solution of methyl 4-hydroxybenzoate 111 (0.977 g, 6.42 mmol) and trifluoro-methanesulfonic acid diethoxy-phosphorylmethl ester (2.12 g, 7.06 mmol) in THF (50 mL) was treated with Cs$_2$CO$_3$ (4.18 g, 12.84 mmol). The resulting reaction mixture was stirred for 1 h at room temperature before it was partitioned between EtOAc and sat. aqueous NH$_4$Cl and extracted with EtOAc (3×). The organic phase was washed with brine, dried over Na$_2$SO$_4$, and evaporated under reduced pressure. Purification of the crude product on silica gel (eluted with 60-90% EtOAc/hexane) provided 1.94 g (quantitative) of methyl phosphonobenzoate compound 112 as a clear oil.

Alcohol 112a (FIG. 39): A solution of 112 (1.94 g, 6.42 mmol) in Et$_2$O (40 mL) was treated with LiBH$_4$ (0.699 g, 32.1 mmol) and THF (10 mL). After the reaction mixture was stirred for 12 h at room temperature, the mixture was quenched with water and extracted with EtOAc (3×). The organic phase was dried over Na$_2$SO$_4$ and evaporated under reduced pressure. The crude product was purified on silica gel (eluted with 2-5% MeOH/CH$_2$Cl$_2$) to give 1.48 g (84%) of alcohol compound 112a as a colorless oil.

Chloride 112b (FIG. 39): A solution of 112a (315 mg, 1.15 mmol) in MeCN (6 mL) was treated with methanesulfonyl chloride (97.6 µL, 1.26 mmol), TEA (175 µL, 1.26 mmol), LiCl (74.5 mg, 1.72 mmol). After stirring at room temperature for 30 min., the mixture was concentrated under reduced pressure, partitioned between EtOAc and sat. NaHCO$_3$, and extracted with EtOAc (3×). The organic phase was dried over Na$_2$SO$_4$ and evaporated under reduced pressure. Purification of the crude product on silica gel (eluted with 2-4% MeOH/CH$_2$Cl$_2$) provided 287 mg (85%) of chloride compound 112b as a clear pale yellow oil.

Alcohol compound 113 (FIG. 39): A solution of benzyl ether 36 (120 mg, 0.326 mmol) in EtOH (2 mL) was treated with conc. HCl (2 mL). After the reaction mixture was refluxed at 100° C. for 1 day, the mixture was concentrated under reduced pressure, partitioned between EtOAc and sat. NaHCO$_3$, and extracted with EtOAc (3×). The organic phase was dried over Na$_2$SO$_4$ and evaporated under reduced pressure to provide the crude alcohol compound 113 (90 mg, 99%) as a white solid.

Compound 114 (FIG. 39): A solution of alcohol compound 113 (16.8 mg, 0.060 mmol) and chloride compound 112b (21.1 mg, 0.072 mmol) in THF (1.5 mL) was treated with powder NaOH (3.5 mg, 0.090 mmol), lithium iodide (12.0 mg, 0.090 mmol), and tetrabutylammonium bromide (9.70 mg, 0.030 mmol). After the reaction mixture was stirred at room temperature for 15 h, the mixture was partitioned between EtOAc and sat. NH$_4$Cl. The organic phase was dried over Na$_2$SO$_4$, filtered, and evaporated under reduced pressure. The crude product was purified on silica gel (eluted with 3-6% MeOH/CH$_2$Cl$_2$) to give compound 114 (19.7 mg, 61%) as a colorless oil.

Title compound 115: A solution of 114 (19.7 mg, 0.037 mmol) in CH$_2$Cl$_2$ (1 mL) was treated with trichloroacetyl isocyanate (13.2 µL, 0.111 mmol). After the reaction mixture was stirred at room temperature for 20 min, 2 mL of CH$_2$Cl$_2$ (saturated with NH3) was added to the mixture. After stirring at room temperature for 1 h, the mixture was bubbled with N$_2$ for 1 h. The mixture was then concentrated under reduced pressure and purified on silica gel (eluted with 4-6% MeOH/CH$_2$Cl$_2$) to give the titled compound 115 (18.5 mg, 87%) as a clear oil. $^1$H NMR (300 MHz, CDCl$_3$) δ 7.09 (t, 1H), 6.90 (d, 2H), 6.78 (d, 2H), 6.63 (dd, 1H), 6.51 (dd, 1H), 6.40 (t, 1H), 5.15 (s, 2H), 5.11 (s, 2H), 4.70 (b, 2H), 4.21 (m, 6H), 3.70 (s, 3H), 3.22 (m, 1H), 1.36 (t, 6H), 1.29 (d, 6H). $^{31}$P NMR (300 MHz, CDCl$_3$) δ 19.2.

Example 62

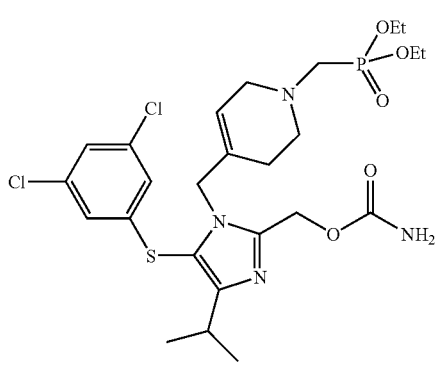

118

Figure 40:
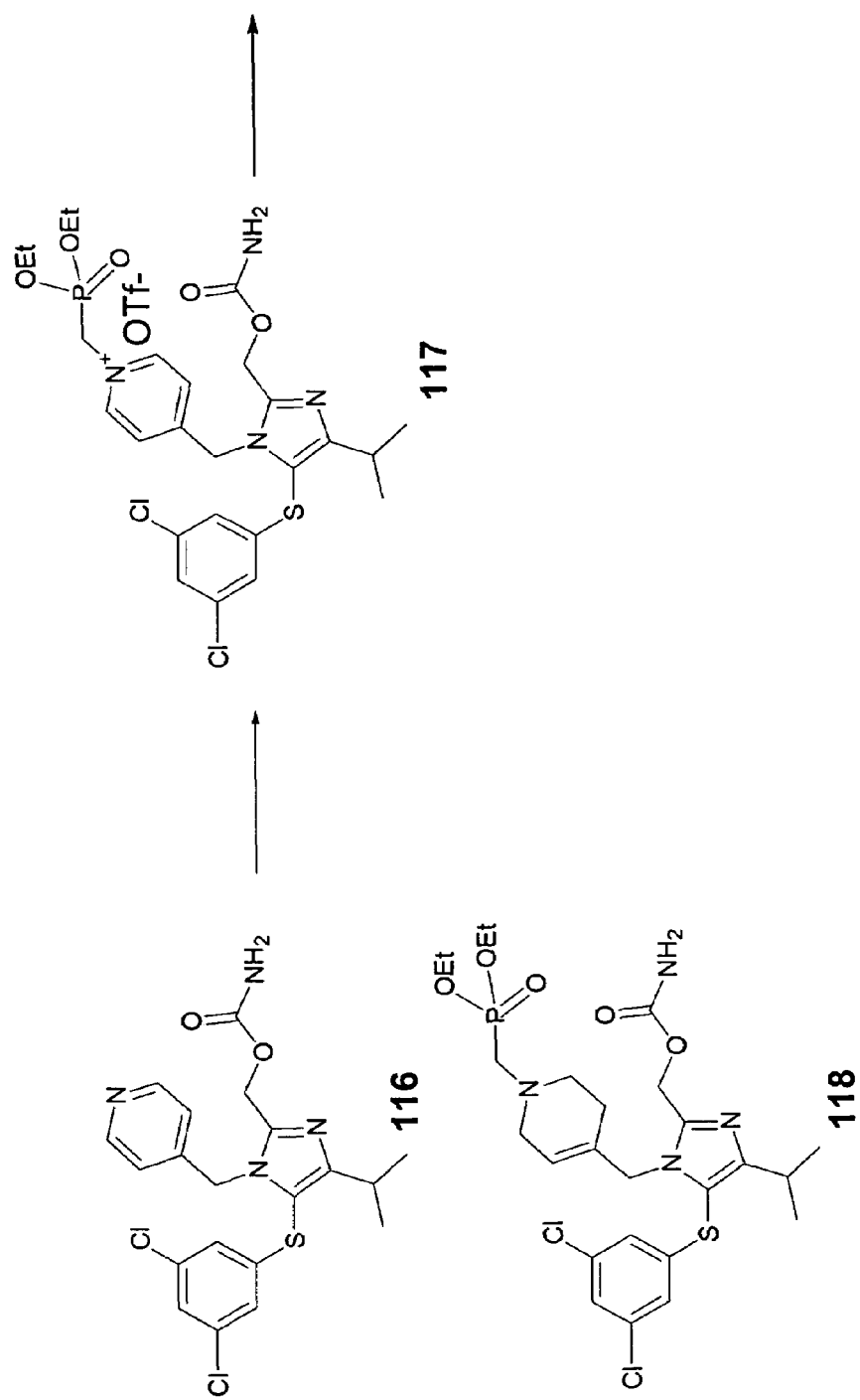
FIG. 40 depicts the preparation of compound 118 shown in Example 62 described in detail herein below.

A suspension of compound 116 (FIG. 40) (15 mg, 0.03 mmol) in acetone d-6 was treated with trifluoro-methanesulfonic acid diethoxy-phosphorylmethyl ester (12 mg, 0.04 mmol). The solution was stirred overnight at ambient temperature. Concentration afforded compound 117. Compound 117 (22 mg, 0.03 mmol) was suspended in EtOH (2mL) and an excess of sodium borohydride(15 mg, 0.39 mmol) was added. The solution was stirred at room temperature. After 30 minutes, sodium borohydride (15 mg, 0.39 mmol) was added again. Acetic acid (1 ml) in EtOH was added 2 hours later followed by the addition of sodium borohydride (15 mg, 0.39 mmol). After 30 minutes, the solution was concentrated. The residue was dissolved in saturated aqueous NaHCO$_3$ and extracted with EtOAc (×3). The organic layers were washed with brine and dried over MgSO$_4$. The solution was filtered, concentrated and purified using a TLC plate (5% CH$_3$OH/CH$_2$Cl$_2$) to give 14 mg (80%) of the desired product. $^1$H NMR (CDCl$_3$, 500mHz): 7.13 (s, 1H), 6.83 (s, 2H), 5.16 (s, 2H), 5.01 (s, 1H), 4.51 (s, 2H), 4.14 (m, 4H), 3.15 (m, 1H), 3.00 (s, 2H), 2.80 (d, 2H), 2.68 (t, 2H), 1.97 (s, 2H), 1.33 (t, 6H), 1.29 (d, 6H).

Example 63

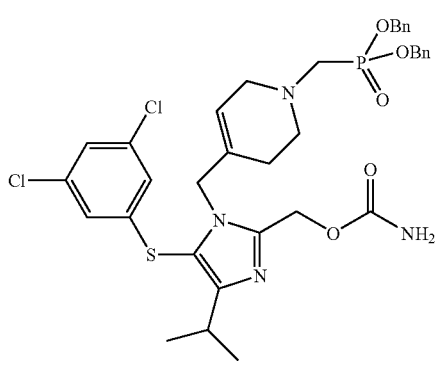

119

Title compound 119 was prepared following the sequence of steps described in Example 62 by substituting trifluoro-methanesulfonic acid bis-benzyloxy-phosphorylmethyl ester for trifluoro-methanesulfonic acid diethoxy-phosphorylmethyl ester. Purification of the crude final product on silica gel eluted with (2.5% -5% CH$_3$OH/CH$_2$Cl$_2$) provided 71 mg (65%) of the title compound. $^1$H NMR (CDCl$_3$, 500 MHz): 7.35 (s, 10H), 7.11 (s,1H) 6.82 (s, 2H), 5.16 (s, 2H), 5.04 (d, 4H), 4.99 (s, 1H), 4.49 (s, 2H), 3.15 (m, 1H), 2.96 (s, 2H), 2.81 (d, 2H), 2.63 (t, 2H), 1.91 (s, 2H), 1.29 ppm(d, 6H).

Example 64

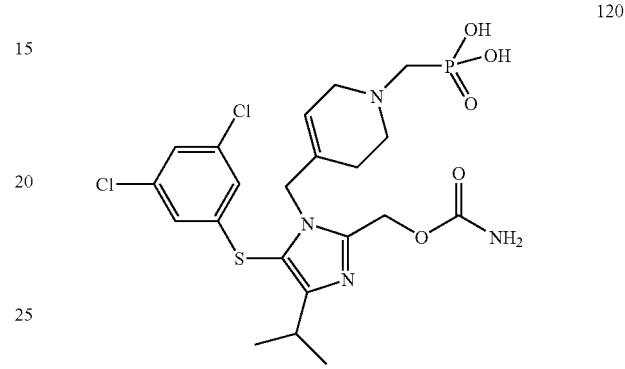

120

Compound 119 was stirred in 4M HCl/dioxane overnight at ambient temperature. The mixture was concentrated and purified using HPLC (20% CH$_3$CN/H$_2$O) to provide 20 mg of the title compound 120. $^1$H NMR (CD$_3$OD$_3$, 500 MHz) 7.33 (s,1H) 7.00 (s, 2H), 5.22 (s, 2H), 5.12 (s, 1H), 4.79 (s, 2H), 3.80 (s, 2H), 3.49 (s, 2H), 3.23 (m, 2H), 3.21 (m, 1H), 2.40 (s, 2H), 1.28 (d, 6H).

Example 65

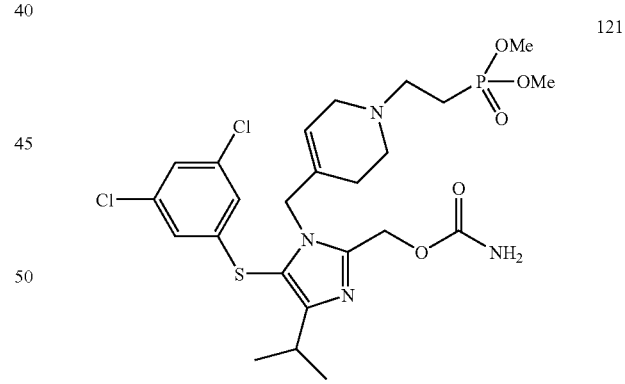

121

Compound 121 was prepared following the sequence of steps described in Example 62 by substituting trifluoro-methanesulfonic acid dimethoxy-phosphorylethyl ester for trifluoro-methanesulfonic acid diethoxy-phosphorylmethyl ester. Purification of the crude final product on TLC plate eluted with (5% CH$_3$OH/CH$_2$Cl$_2$) provided 11 mg (65%) of the title compound. $^1$H NMR (CDCl$_3$, 500 MHz): 7.34 (d, 2H). 7.20 (d, 2H), 7.19 (d,1H) 7.13 (s, 1H), 6.83 (s, 2H), 5.18 (s, 2H), 5.03 (s, 1H), 4.98 (m, 1H), 4.52 (s, 2H), 4.22 (m, 2H), 3.15 (m, 1H), 2.91 (s, 2H), 2.81 (s, 2H), 2.54 (s, 2H), 2.29 (m, 2H), 2.01 (d, 2H), 1.56 (d, 3H), 1.38 (d,3H), 1.28 (q, 3H), 1.28 (d, 6H).

Example 66

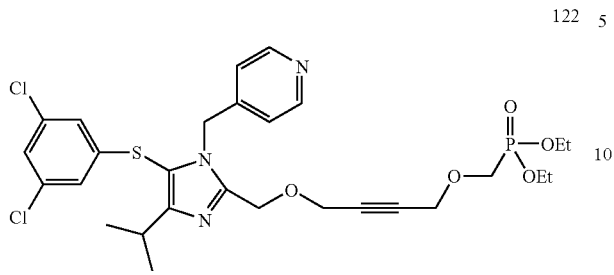

122

Figure 41:
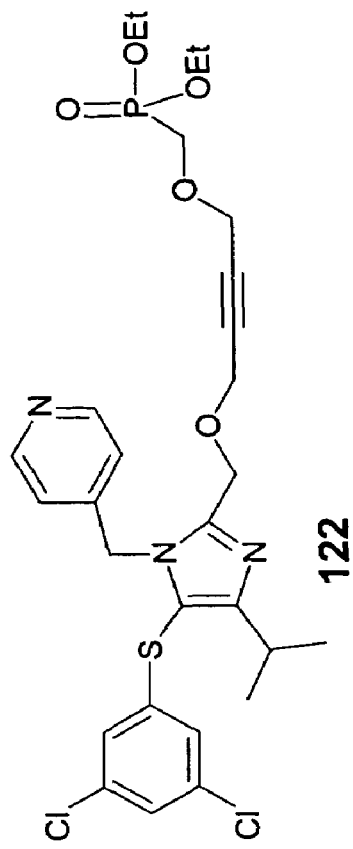
FIG. 41 depicts the preparation of compound 122 shown in Example 66 described in detail herein below.
Figure 41:
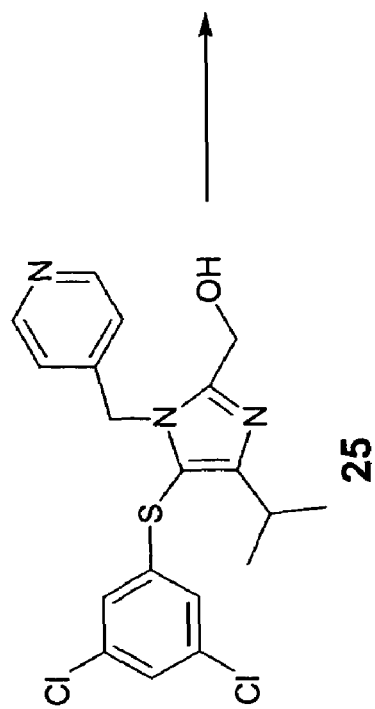

A solution of 25 (FIG. 41) (33.2 mg, 0.081 mmol) in DMF (3 mL) under $N_2$ at 0° C. was treated with NaH. After stirring at 0° C. for 10 min, 95 (23 mg, 0.077 mmol) was added, and the resulting mixture was slowly raised to room temperature and stirred at room temperature for 8 h. The mixture was then poured into water, and extracted with EtOAc. The combined organic layers were washed with brine, dried ($Na_2SO_4$), filtered, and evaporated under reduced pressure. The crude product was purified on TLC plate (eluted with 3% MeOH/$CH_2Cl_2$) to provide 17.9 mg of the title compound 122. $^1$H NMR (500 MHz, $CDCl_3$) δ 8.45 (d, 2H), 7.04 (t, 1H), 6.88 (d, 2H), 6.67 (d, 2H), 5.24 (s, 2H), 4.67 (s, 2H), 5.02 (m, 1H), 4.27 (bs, 2H), 4.22 (bs, 2H), 4.19 (m, 4H), 3.82 (m, 2H), 3.16 (m, 1H), 1.35 (t, 6H), 1.30 (d, 6H). $^{31}$P NMR (300 MHz, $CDCl_3$) δ 20.8.

Example 67

Anti-HIV-1 Cell Culture Assay

The assay is based on quantification of the HIV-1-associated cytopathic effect by a colorimetric detection of the viability of virus-infected cells in the presence or absence of tested inhibitors. The HIV-1-induced cell death is determined using a metabolic substrate 2,3-bis(2-methoxy-4-nitro-5-sulfophenyl)-2H-tetrazolium-5-carboxanilide (XTT) which is converted only by intact cells into a product with specific absorption characteristics as described by Weislow O S, Kiser R, Fine D L, Bader J, Shoemaker R H and Boyd M R (1989) *J Natl Cancer Inst* 81, 577.

Assay Protocol for Determination of EC50:
1. Maintain MT2 cells in RPMI-1640 medium supplemented with 5% fetal bovine serum and antibiotics.
2. Infect the cells with the wild-type HIV-1 strain IIIB (Advanced Biotechnologies, Columbia, Md.) for 3 hours at 37° C. using the virus inoculum corresponding to a multiplicity of infection equal to 0.01.
3. Distribute the infected cells into a 96-well plate (20,000 cells in 100 µL/well) and add various concentrations of the tested inhibitor in triplicate (100 µL/well in culture media). Include untreated infected and untreated mock-infected control cells.
4. Incubate the cells for 5 days at 37° C.
5. Prepare XTT solution (6 ml per assay plate) at a concentration of 2 mg/mL in a phosphate-buffered saline pH 7.4. Heat the solution in water-bath for 5 min at 55° C. Add 50 µL of N-methylphenazonium methasulfate (5 µg/mL) per 6 mL of XTT solution.
6. Remove 100 µL media from each well on the assay plate.
7. Add 100 µL of the XTT substrate solution per well and incubate at 37° C. for 45 to 60 min in a $CO_2$ incubator.
8. Add 20 µL of 2% Triton X-100 per well to inactivate the virus.
9. Read the absorbance at 450 nm with subtracting off the background absorbance at 650 nm.
10. Plot the percentage absorbance relative to untreated control and estimate the EC50 value as drug concentration resulting in a 50% protection of the infected cells.

Example 68

Cytotoxicity Cell Culture Assay (Determination of CC50)

The assay is based on the evaluation of cytotoxic effect of tested compounds using a metabolic substrate 2,3-bis(2-methoxy-4-nitro-5-sulfophenyl)-2H-tetrazolium-5-carboxanilide (XTT) as described by Weislow O S, Kiser R, Fine D L, Bader J, Shoemaker R H and Boyd M R (1989) *J Natl Cancer Ins* 81, 577.

Assay Protocol for Determination of CC50:
1. Maintain MT-2 cells in RPMI-1640 medium supplemented with 5% fetal bovine serum and antibiotics.
2. Distribute the cells into a 96-well plate (20,000 cell in 100 µL media per well) and add various concentrations of the tested compound in triplicate (100 µL/well). Include untreated control.
3. Incubate the cells for 5 days at 37° C.
4. Prepare XTT solution (6 ml per assay plate) in dark at a concentration of 2 mg/mL in a phosphate-buffered saline pH 7.4. Heat the solution in a water-bath at 55° C. for 5 min. Add 50 µL of N-methylphenazonium methasulfate (5 µg/mL) per 6 mL of XTT solution.
5. Remove 100 µL media from each well on the assay plate and add 100 µL of the XTT substrate solution per well. Incubate at 37° C. for 45 to 60 min in a $CO_2$ incubator.
6. Add 20 µL of 2% Triton X-100 per well to stop the metabolic conversion of XTT.
7. Read the absorbance at 450 nm with subtracting off the background at 650 nm.
8. Plot the percentage absorbance relative to untreated control and estimate the CC50 value as drug concentration resulting in a 50% inhibition of the cell growth. Consider the absorbance being directly proportional to the cell growth.

PETT-Like Phosphonate NNRTI Compounds

The PETT class of compound has demonstrated activity in inhibiting HIV replication. The present invention provides novel analogs of PETT class of compound. Such novel PETT analogs possess all the utilities of PETT and optionally provide cellular accumulation as set forth below.

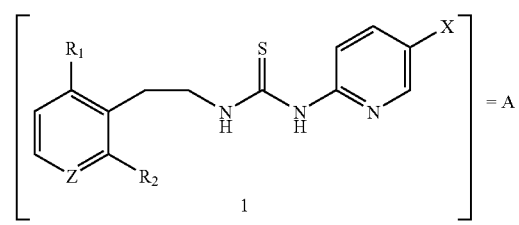

$R_1$ = H, F, Cl, OMe  Z = CH
$R_2$ = H, F, Cl, OMe  Z = N when $R_1$ and $R_2$ are H
X = Cl, Br, CN

275

-continued

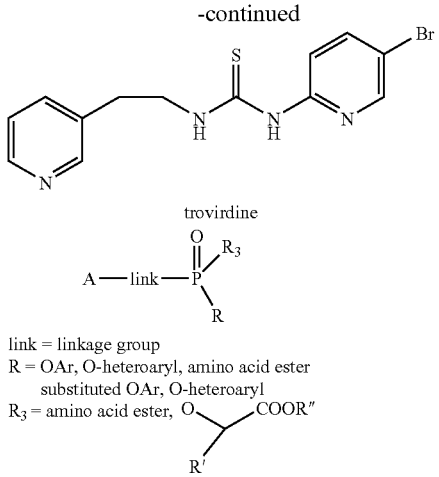

trovirdine link = linkage group
R = OAr, O-heteroaryl, amino acid ester substituted OAr, O-heteroaryl
$R_3$ = amino acid ester, The intermediate phosphonate esters required for conversion into the prodrug phosphonate moieties bearing amino acid, or lactate esters are shown in Table 2.

TABLE 2

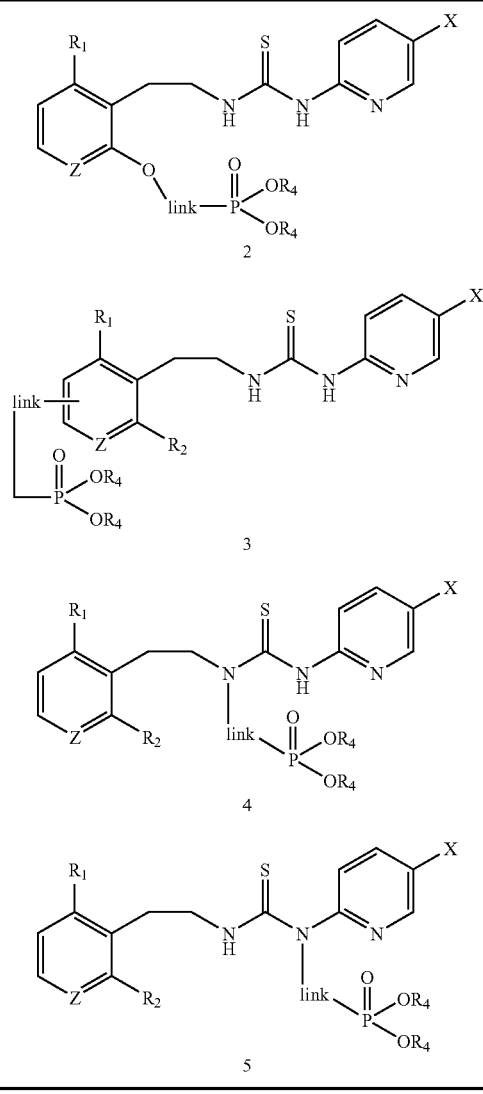

276

Figure 42A:
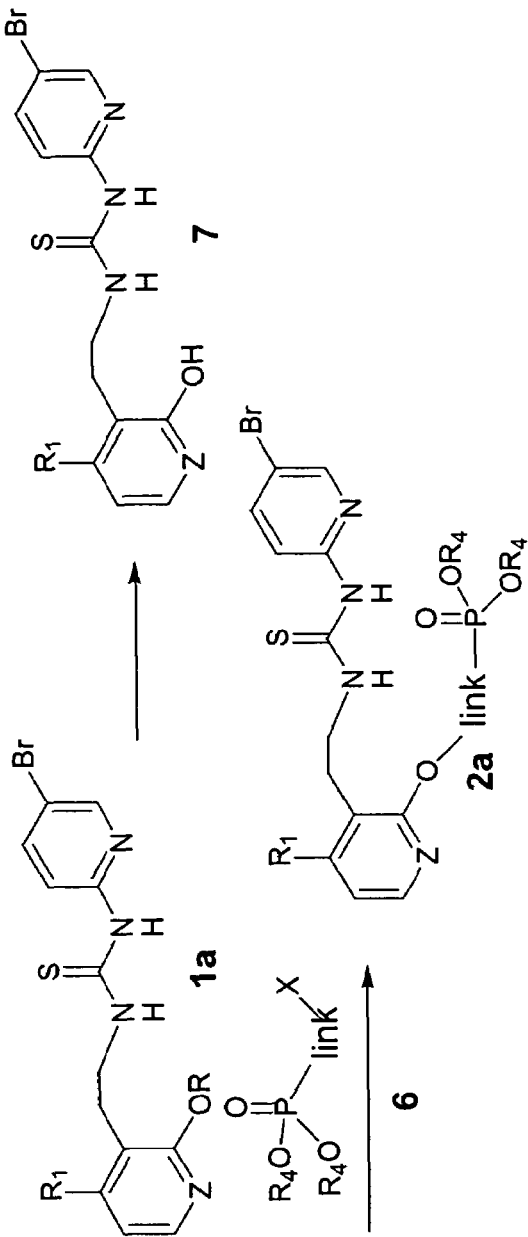
FIGS. 42A-B depict Scheme 1 which is described in detail herein below.
Figure 42B:
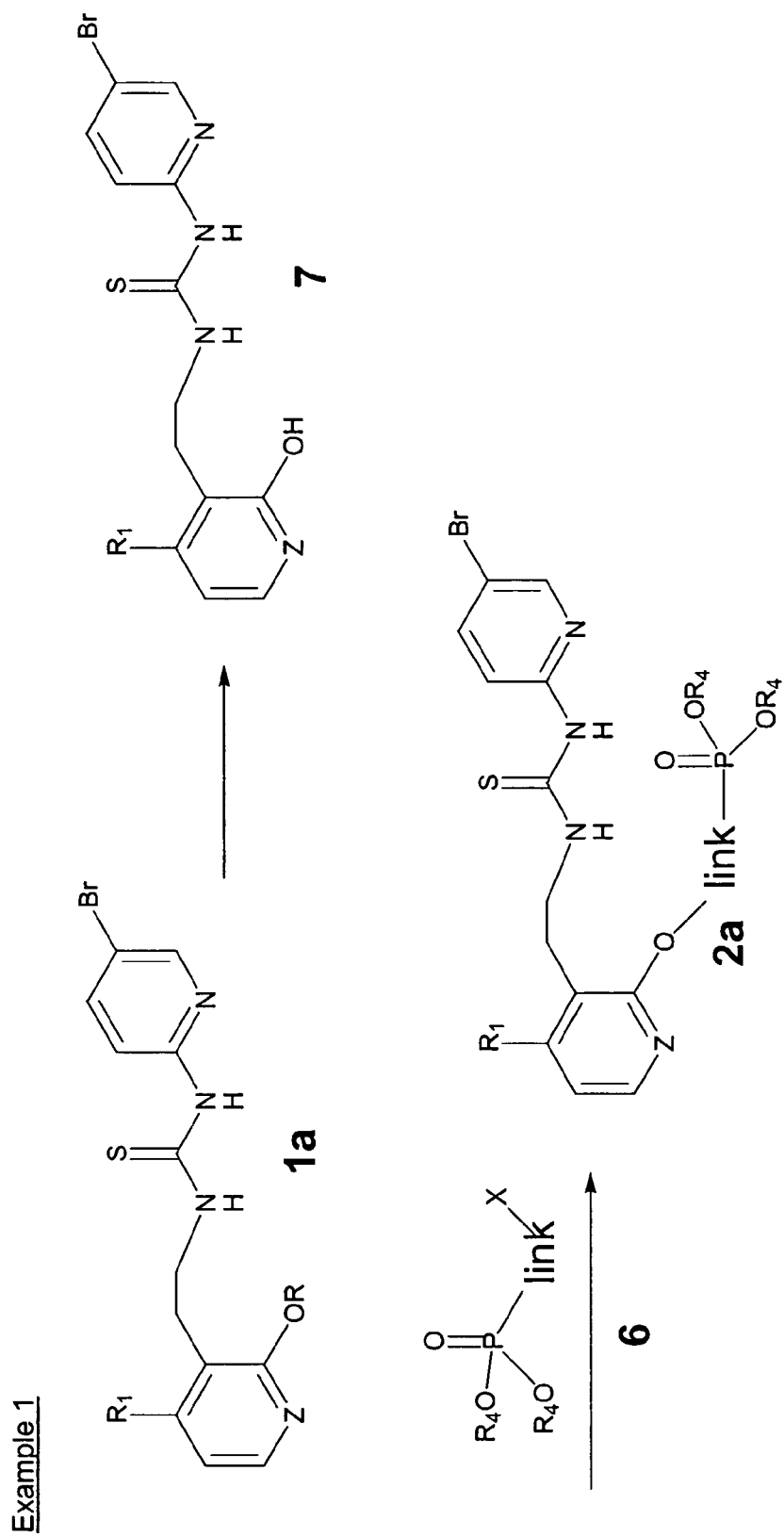

PETT 1 compounds, analogs of trovirdine, are obtained following the procedures described in WO/9303022 and *J. Med. Chem.* 1995, 38, 4929-4936 and 1996, 39,4261-4274. Preparation of PETT-like phosphonate NNRTI compounds, e.g. phosphonate analog type 2 is outlined in Scheme 1 (FIG. 42). PETT analog 1a is obtained following the above mentioned literature procedure. Alkyl group of 1a is then removed using such as, for example $BCl_3$ to give phenol 7, many examples are described in Greene and Wuts, Protecting Groups in Organic Synthesis, $3^{rd}$ Edition, John Wiley and Sons Inc. Conversion of 7 to the desired phosphonate analogs is realized by treatment of 7 with the phosphonate reagent 6 under suitable conditions.

For example (Example 1; FIG. 42), PETT 1a is treated with BCl3 to give phenol 7. Treatment of 7 with phosphonate 6.1 in the presence of base, for example, Cs2CO3, affords the phosphonate 2a.1. Using the above procedure but employing a different phosphonate reagent 5 in place of 6. 1, corresponding products 2 with different linking groups are obtained.

Figure 43A:
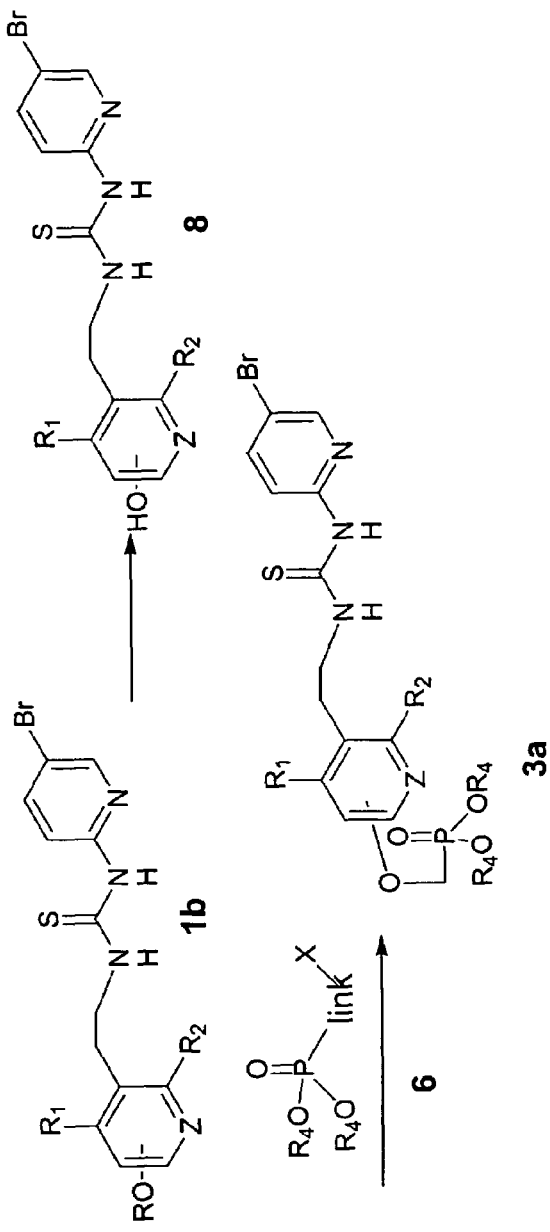
FIGS. 43A-B depict Scheme 2 which is described in detail herein below.
Figure 43B:
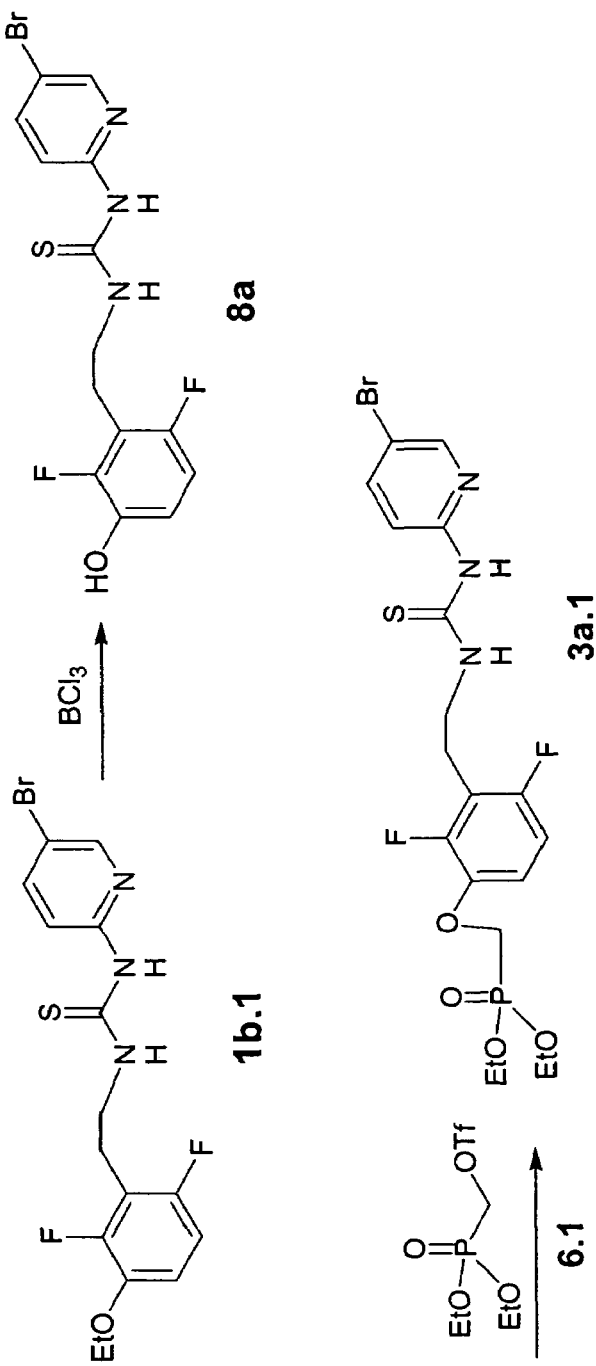

Scheme 2 (FIG. 43) shows the preparation of phosphonate type 3 in Table 2. PETT 1b is obtained as described in WO/9303022 and *J. Med. Chem.* 1995, 38, 4929-4936 and 1996, 39,4261-4274. Alkyl group of 1b is then removed using such as, for example $BCl_3$ to give phenol 8, many examples are described in Greene and Wuts, Protecting Groups in Organic Synthesis, $3^{rd}$ Edition, John Wiley and Sons Inc. Conversion of 8 to the desired phosphonate analogs is realized by treatment of 8 with the phosphonate reagent 6 under suitable conditions.

For example (Example 1), PETT 1a is treated with BC13 to give phenol 7. Treatment of 7 with triflate methyl phosphonic acid diethyl ester 6.1 in the presence of base, for example, Cs2CO3, affords the phosphonate 2a.1. Using the above procedure but employing a different phosphonate reagent 6 in place of 6. 1, corresponding products 3 with different linking groups are obtained.

Figure 44A:
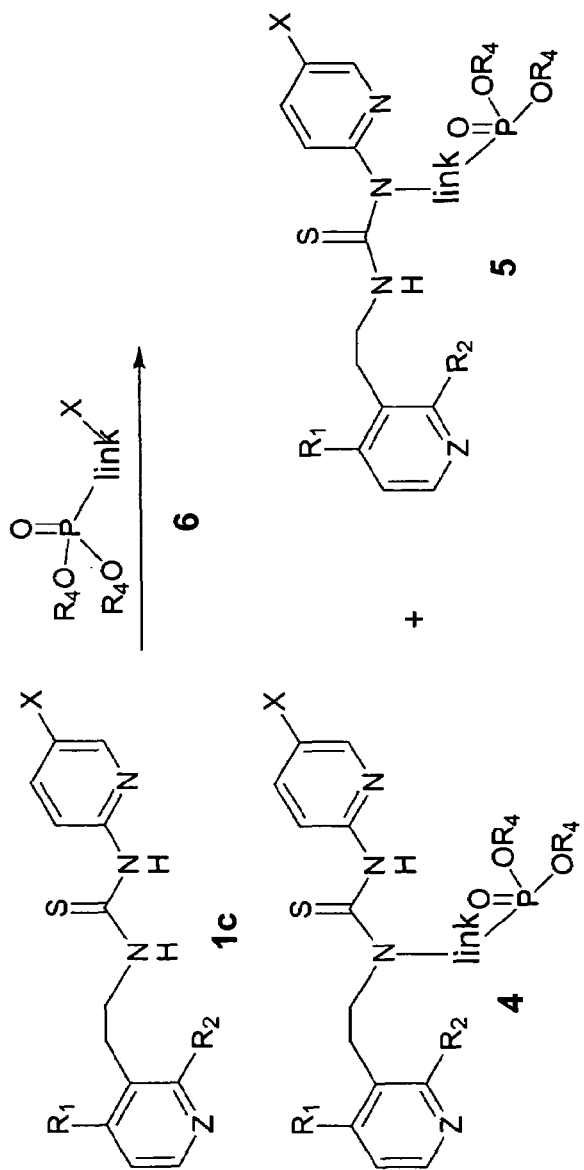
FIGS. 44A-B depict Scheme 3 which is described in detail herein below.
Figure 44B:
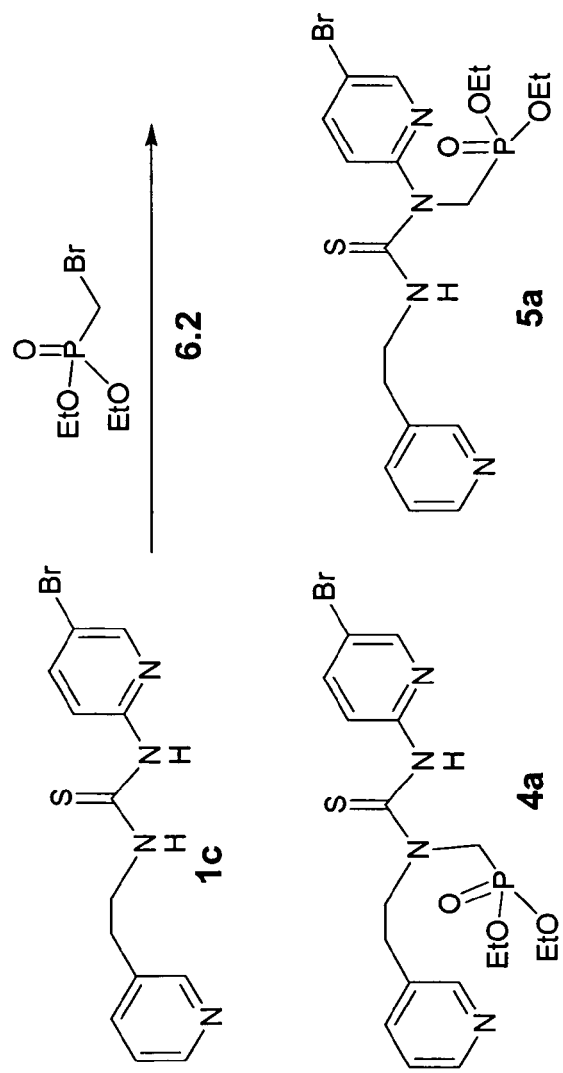

Scheme 3 (FIG. 44) shows of the preparation of the phosphonate linkage of type 4 and 5 to PETT. PETT 1c is first treated with a suitable base to remove the thiourea proton, the product is then treated with 1 equivalent of a phosphonate reagent 5 bearing a leaving group such as, for example, bromine, mesyl, tosyl etc to give the alkylated product 4 and 5. The phosphonates 4 and 5 are separated by chromatography. For example (Example 3; FIG. 44)), PETT 1, in DMF, is treated with sodium hydride followed by one equivalent of bromomethyl phosphonic acid dibenzyl ester 6.2 to give phosphonate 4a and 5a. Phosphonate product 4a and 5a are then separated by chromatography to give pure 4a and 5a respectively. Using the above procedure but employing a different phosphonate reagent 5 in place of 6.2, corresponding products 4 and 5 with different linking groups are obtained.

Pyrazole-Like Phosphonate NNRTI Compounds

The present invention includes pyrazole-like phosphonate NNRTI compounds and describes methods for their preparation. Pyrazole-like phosphonate NNRTI compounds are potential anti-HIV agents.

TABLE 3

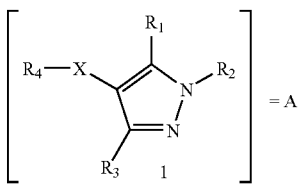

$R_1$, $R_2$, $R_3$ and $R_4$, X are defined as described in Patent WO02/04424.

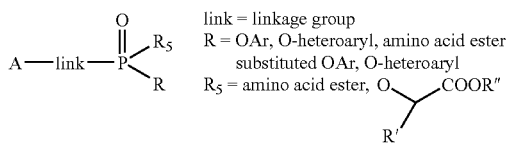

link = linkage group
R = OAr, O-heteroaryl, amino acid ester substituted OAr, O-heteroaryl
$R_5$ = amino acid ester, O⏜COOR″

A link group includes a portion of the structure that links two substructures, one of which is pyrazole class of HIV inhibiting agents having the general formula shown above, the other is a phosphonate group bearing the appropriate R and $R_5$ groups. The link has at least one uninterrupted chain of atoms other than hydrogen.

Pyrazole class of compounds has shown to be inhibitors of HIV RT. The present invention provides novel analogs of pyrazole class of compound. Such novel pyrazole analogs possess all the utilities of pyrazoles and optionally provide cellular accumulation as set forth below.

The intermediate phosphonate esters required for conversion into the prodrug phosphonate moieties bearing amino acid, or lactate esters are shown in Table 4, where $R_1$, $R_2$, $R_3$, $R_4$ and X are as described in WO02/04424.

TABLE 4

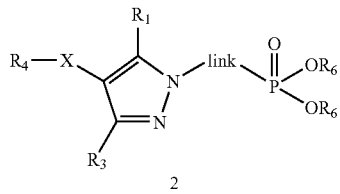

2

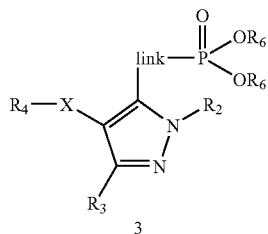

3

Pyrazole 1 is obtained following the procedures described in WO02/04424.

Figure 45A:
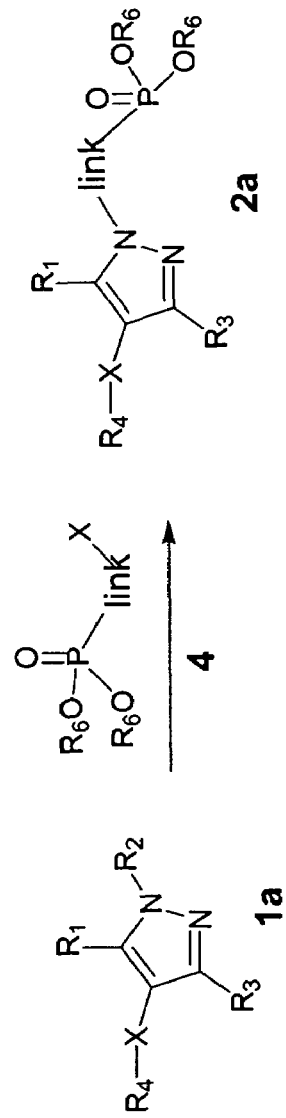
FIGS. 45A-B depict Scheme 1 which is described in detail herein below.
Figure 45B:
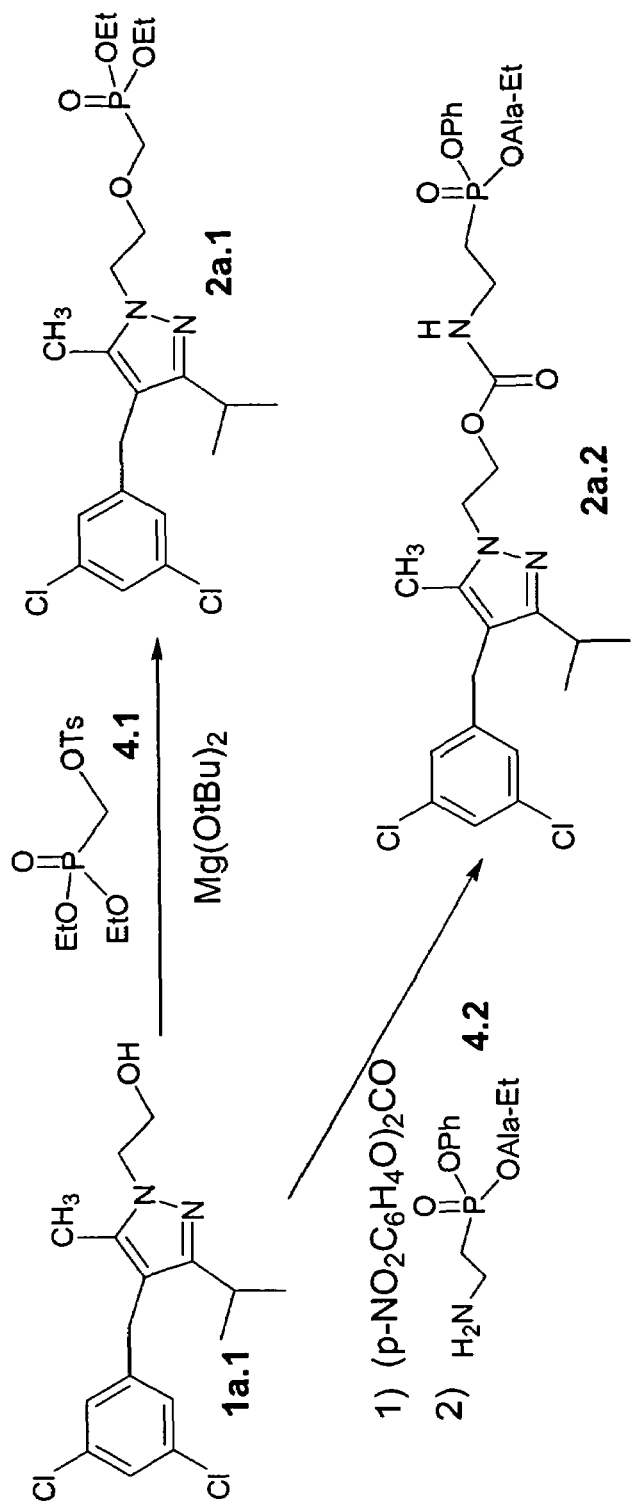
Figure 46A:
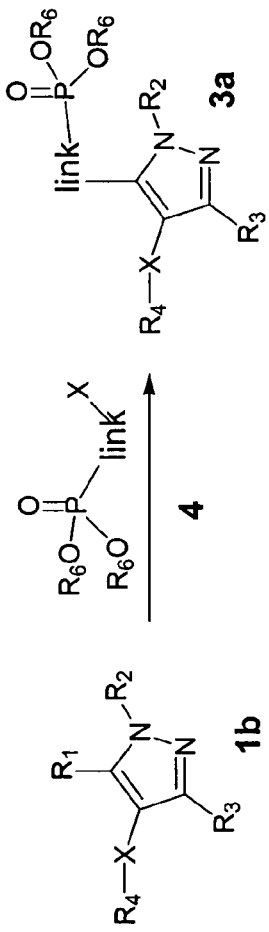
FIGS. 46A-D depict Scheme 2 which is described in detail herein below.
Figure 46B:
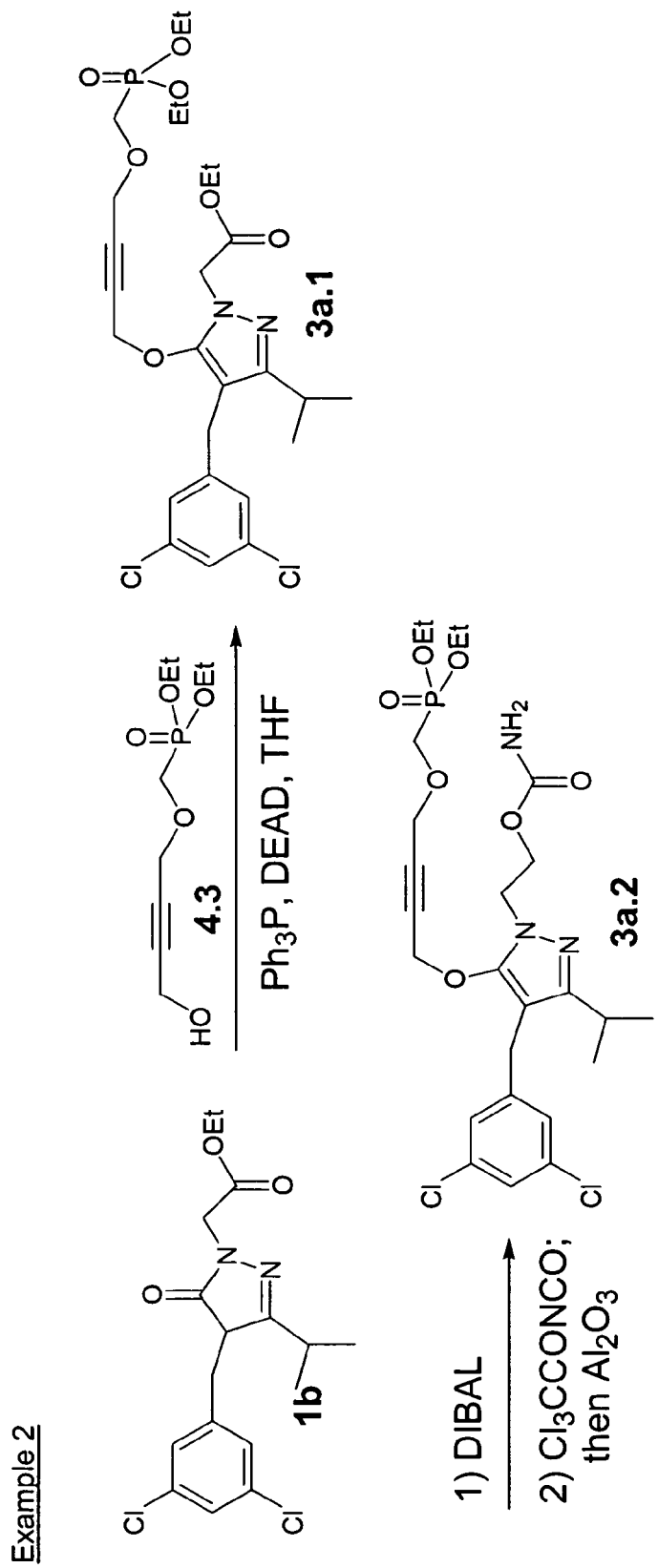
Figure 46C:
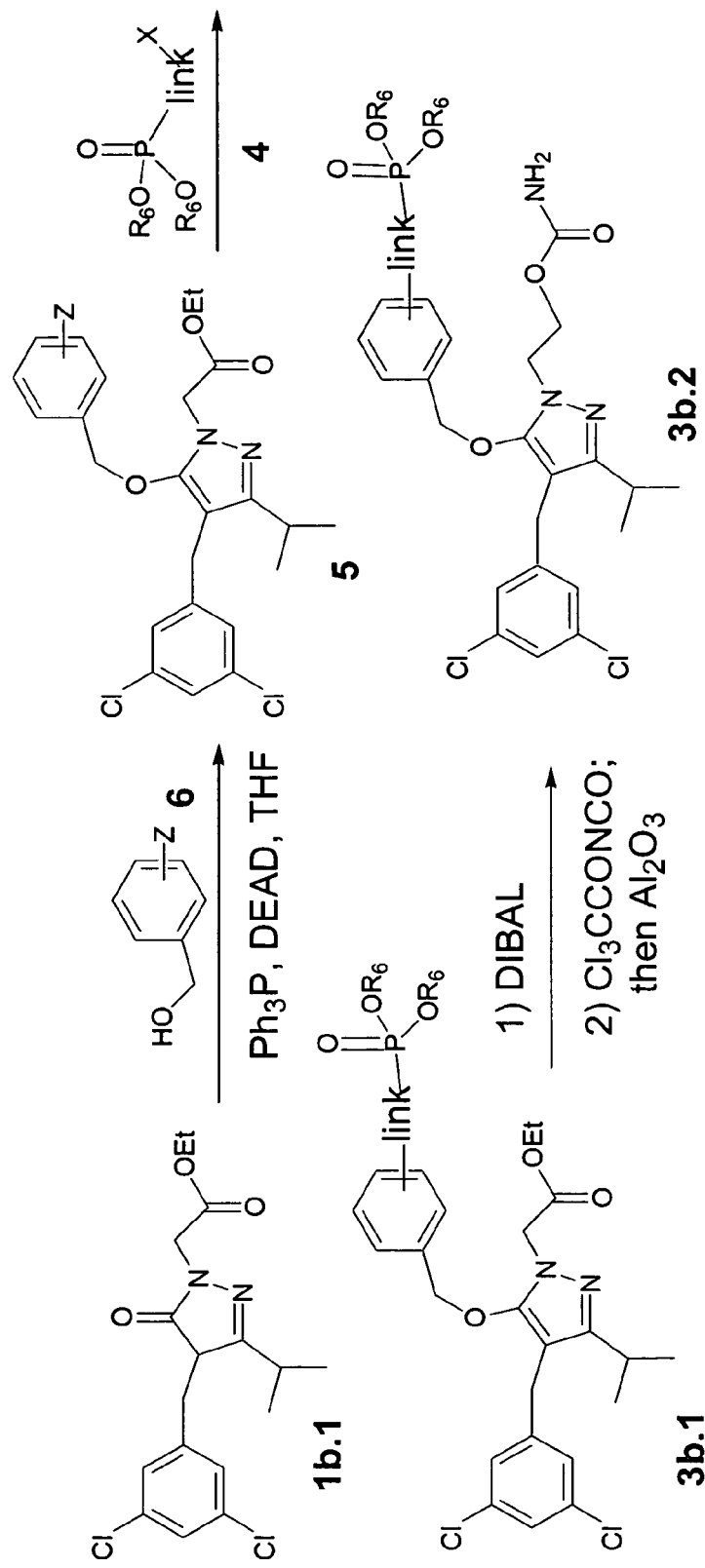
Figure 46D:
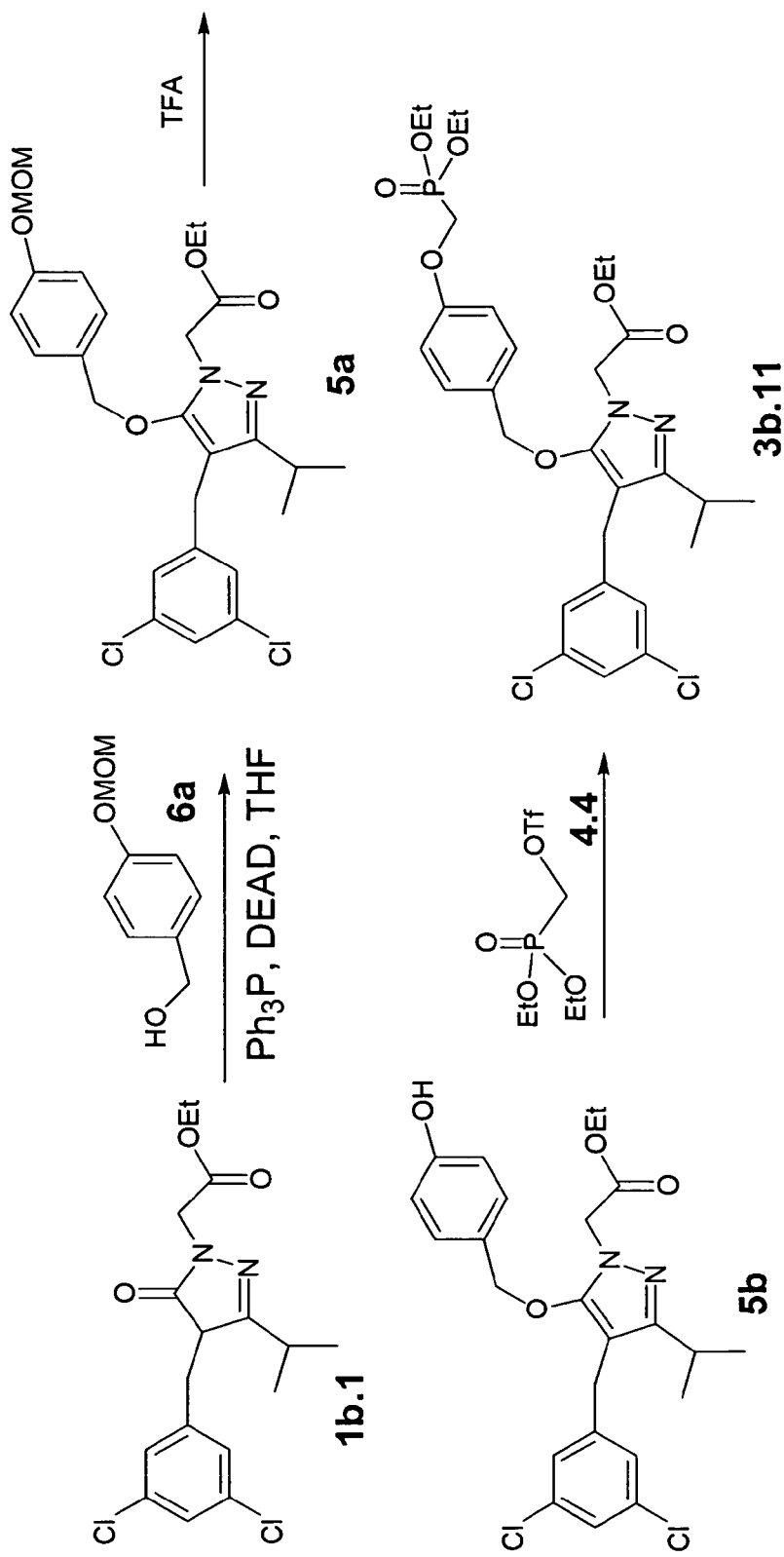

Preparation of phosphonate analog type 2 is outlined in Scheme 1 (FIG. 45). Pyrazole analog 1a, which $R_2$ bears a function group can be used as attaching site for phosphonate prodrug, is obtained as described in the above mentioned literature. Conversion of 1a to the desired phosphonate analogs is realized by treatment of 2a with the phosphonate reagent 4 under suitable conditions.

For example (Example 1; FIG. 45), treatment of pyrazole 1a.1 with phosphonate 4.1 in the presence of base, for example, $Mg(OtBu)_2$, affords the phosphonate 2a.1. Using the above procedure but employing a different phosphonate reagent 4 in place of 4.1, corresponding products 2a with different linking groups are obtained. Alternatively, activation of the hydroxyl group with bis(4-nitrophenyl) carbonate, following by treatment with amino ethyl phosphonate 4.2 provides phosphonate 2a.2. Using different phosphonate 4 in place of 4.2 and/or different methods for linking them together affords 2 with different linker.

Scheme 2 (FIG. 46) shows the preparation of phosphonate type 3 conjugate to pyrazole in Table 4. Pyrazole 1b, bearing a functional group at position $R_1$ can be used as attaching site for phosphonate prodrug, is obtained as described in WO02/04424. Conversion of 1b to the desired phosphonate 3 analogs is realized by treatment of 1b with the phosphonate reagent 4 under suitable conditions. For example (Example 2; FIG. 46), pyrazole 1b reacts with phosphonate 4.3 in the presence of triphenyl phosphine and DEAD in THF, affords the phosphonate 3a.1. Phosphonate 3a.2 is obtained by first reducing the ester to alcohol, and then by treating the resulting alcohol with trichloroacetyl isocyanate, and followed by alumina. Using the above procedure but employing a different phosphonate reagent 4 in place of 4.3, corresponding products 3 with different linking groups are obtained.

Alternatively, as shown in Example 3 (FIG. 46), reaction of pyrazolone 1b.1 with a moiety bearing a protected function group which can be used to attach phosphonate, for example benzyl alcohol with a protected hydroxyl or amino group, under Mitsunobu condition affords compound 5. The protecting group of Z is then removed, and the resulting product is reacted with phosphonate reagent yields phosphonate 3b.1. Phosphonate 3b.1 is converted to phosphonate 3b.2 following the procedures described Example 2. Reaction of pyrazolone 1b.1 with benzyl alcohol 6b with $Ph_3P/DEAD$ produces 5a. The protecting group MOM—is then removed with TFA to give phenol 5b. Treatment of phenol with triflate methyl phosphonic acid dibenzyl ester 4a to give phosphonate 3b.11, which is also converted to 3b.2 type of compound.

Urea-PETT-Like Phosphonate NNRTI Compounds

The present invention include describes Urea-PETT-like phosphonate NNRTI compounds and methods for their preparation. Urea-PETT-like phosphonate NNRTI compounds are potential anti-HIV agents.

TABLE 5

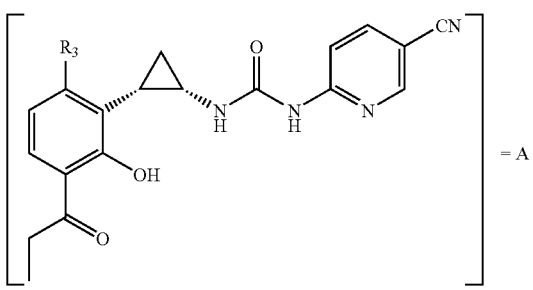

$R_3$ = F, Cl, OMe

1

TABLE 5-continued

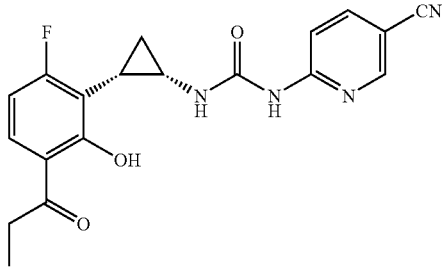

MIV-150

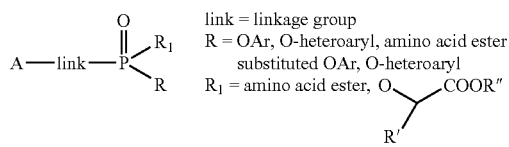

link = linkage group
R = OAr, O-heteroaryl, amino acid ester substituted OAr, O-heteroaryl
R₁ = amino acid ester, $O\underset{R'}{\overset{}{\diagdown}}COOR''$ A link group includes a portion of the structure that links two substructures, one of which is urea-PETT class of HIV inhibiting agents having the general formula shown above, the other is a phosphonate group bearing the appropriate R and R1 groups. The link has at least one uninterrupted chain of atoms other than hydrogen.

Urea-PETT class of compound has demonstrated activity in inhibiting HIV replication. The present invention provides novel analogs of urea-PETT class of compound. Such novel urea-PETT analogs possess all the utilities of urea-PETT and optionally provide cellular accumulation as set forth below.

The intermediate phosphonate esters required for conversion into the prodrug phosphonate moieties bearing amino acid, or lactate esters are shown in Table 6.

TABLE 6

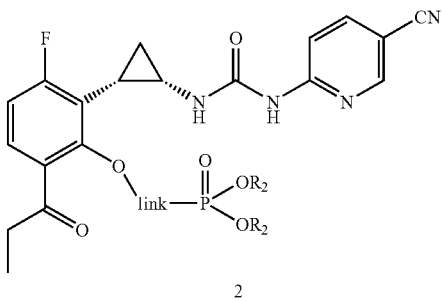

2

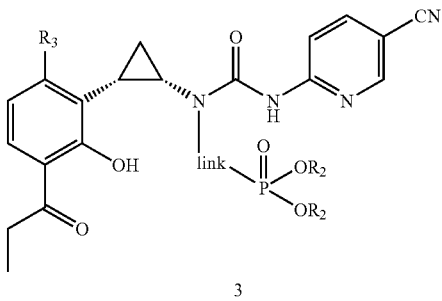

3

TABLE 6-continued

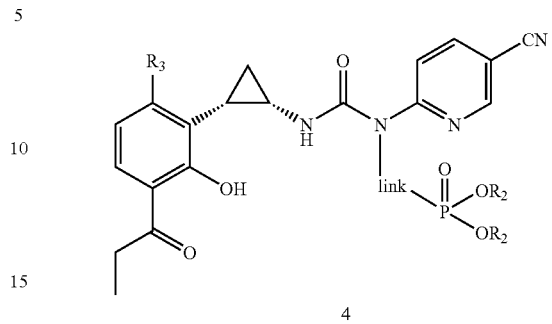

4

Figure 47A:
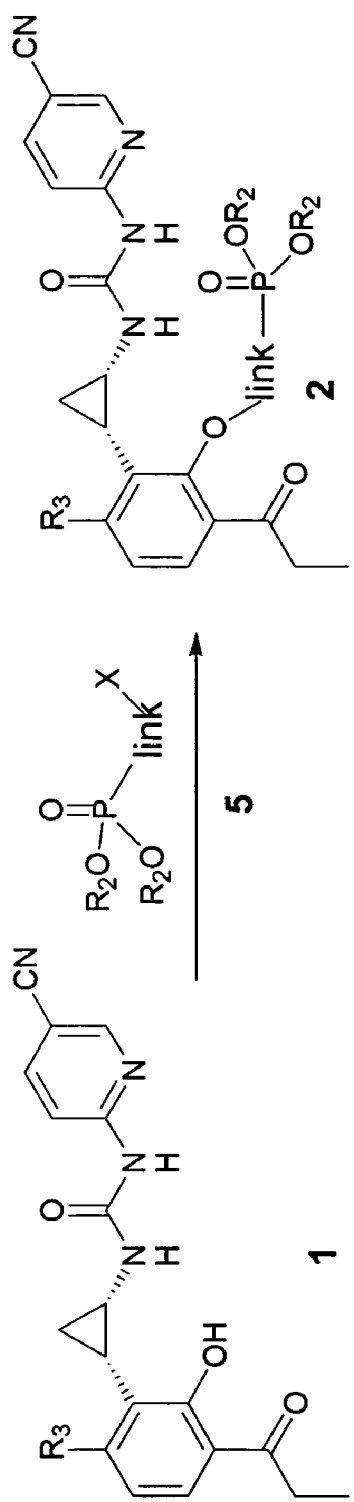
FIGS. 47A-B depict Scheme 1 which is described in detail herein below.
Figure 47B:
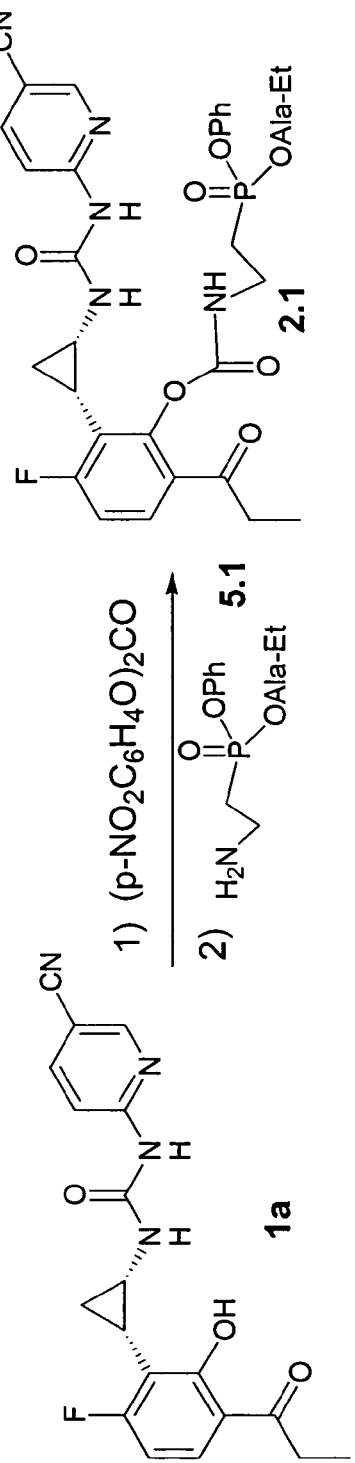

Preparation of phosphonate analog type 2 is outlined in Scheme 1 (FIG. 47). Urea-PETT 1 is described in U.S. Pat. No. 6,486,183 and *J. Med. Chem.* 1999, 42, 4150-4160. Conversion of 1 to the desired phosphonate analogs is realized by treatment of 1 with the phosphonate reagent 5 under suitable conditions. For example (Example 1; FIG. 47)), urea-PETT 1a is activated as it p-nitro-phenol carbonate by reacting with bis(4-nitrophenyl)carbonate. Reaction of the resulting carbonate with amino ethyl phosphonate 5.1 in the presence of base, for example, Hunig's base, affords the phosphonate 2.1.

Figure 48A:
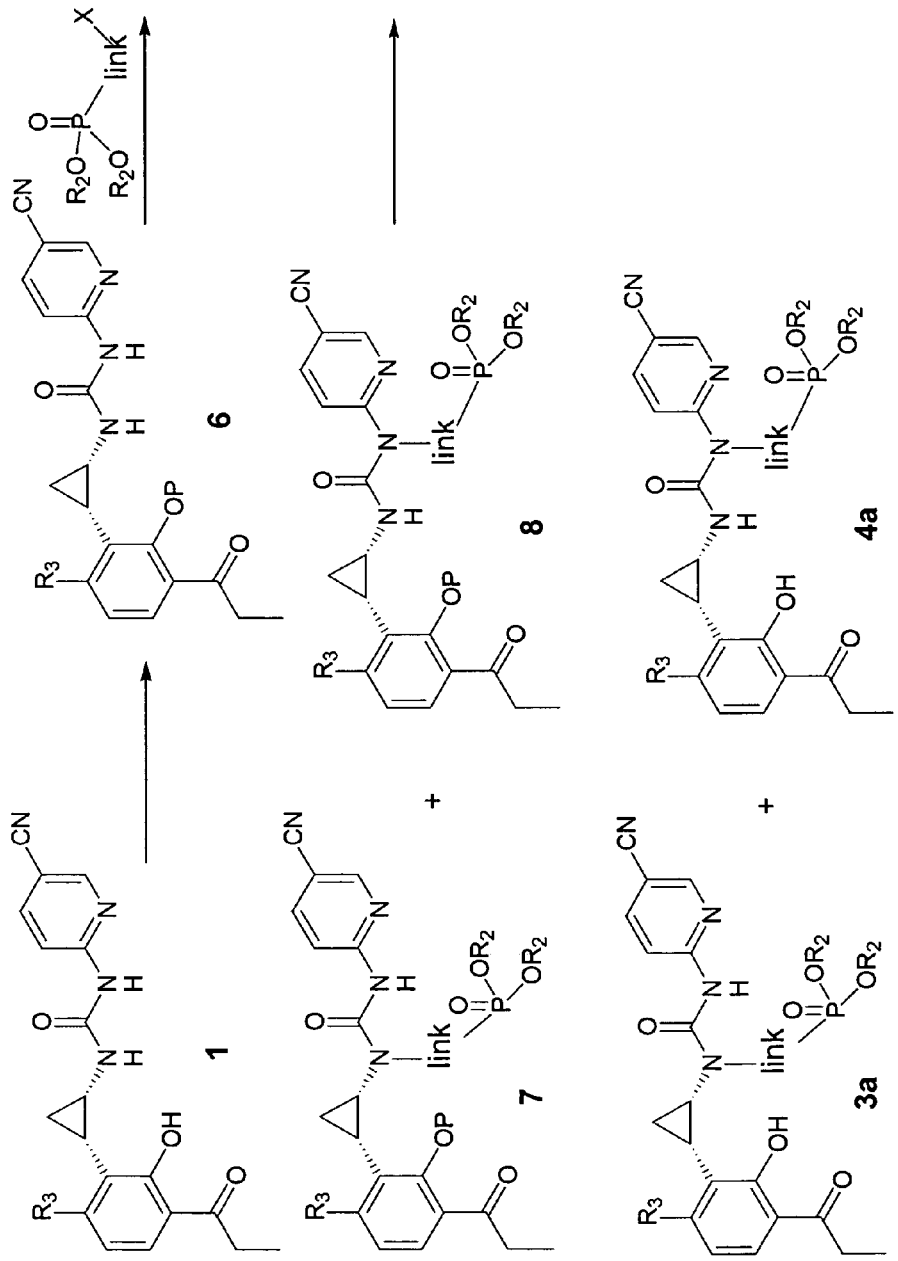
FIGS. 48A-B illustrate Scheme 2 which is described in detail herein below.
Figure 48B:
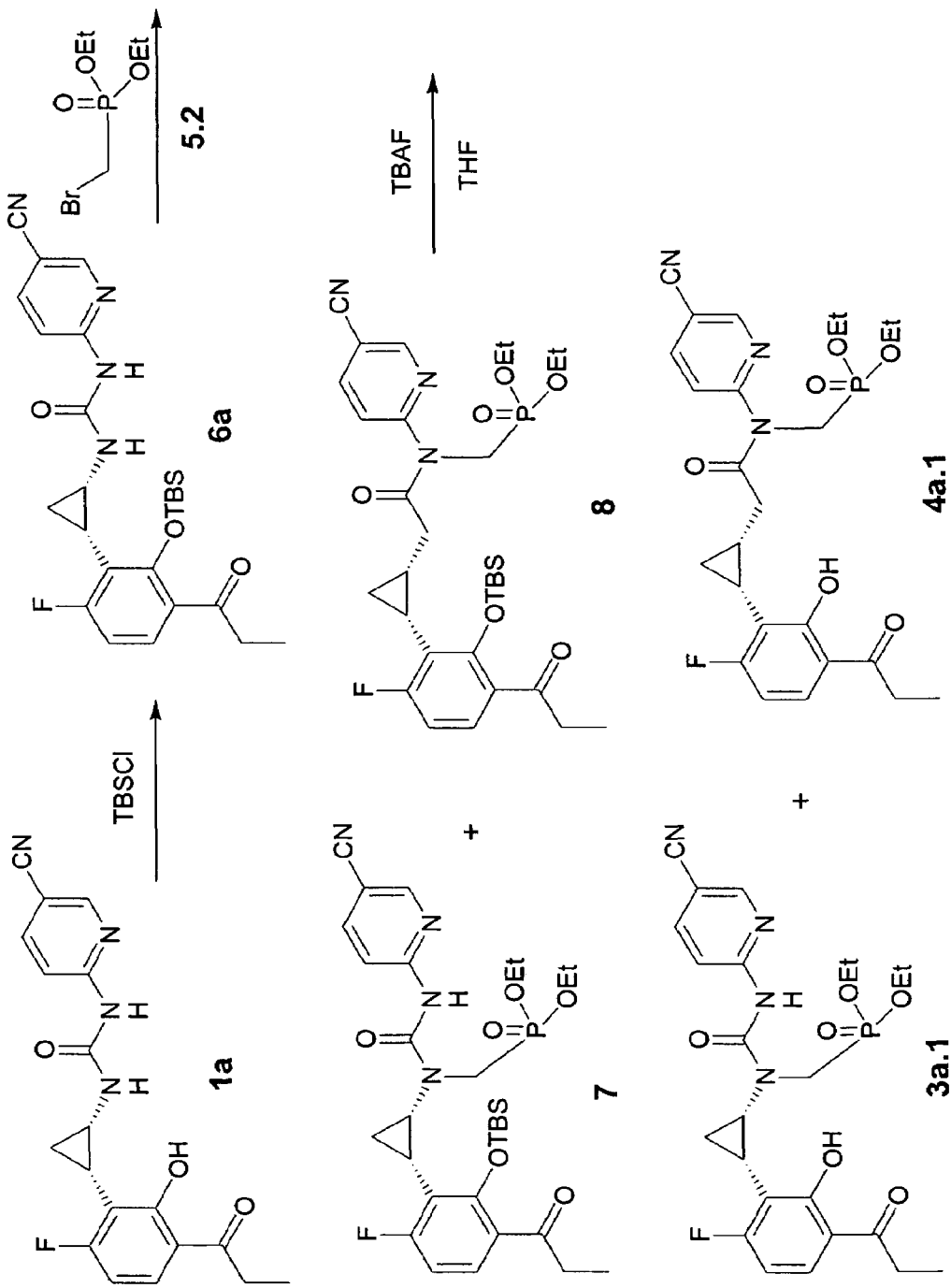

Scheme 2 (FIG. 48) shows of the preparation of the phosphonate linkage of type 2 and 3 to urea-PETT. The hyroxyl group of urea-PETT 1 is protected with a suitable protecting group, for example, trityl, silyl, benzyl or MOM- etc to give 6 as described in Greene and Wuts, Protecting Groups in Organic Synthesis, 3$^{rd}$ Edition, John Wiley and Sons Inc. The resulting protected urea-PETT 6 is first treated with a suitable base to remove the urea proton, the product is then treated with 1 equivalent of a phosphonate reagent 5 bearing a leaving group such as, for example, bromine, mesyl, tosyl etc to give the alkylated product 7 and 8. The phosphonates 7 and 8 are separated by chromatography and independently deprotected using conventional conditions described in Greene and Wuts, Protecting Groups in Organic Synthesis, 3$^{rd}$ Edition, John Wiley and Sons Inc. p116-121. For example (Example 2; FIG. 48), urea-PETT 1 is protected as t-butyl dimethyl silyl ether 6a by reacting with TBSCl and imidazole. Compound 6a, in DMF, is treated with sodium hydride followed by one equivalent of bromomethyl phosphonic acid dibenzyl ester 5.2 to give phosphonate 7a and 8a respectively. phosphonates 7a and 8a are separated by chromatography, and then independently deprotected by treatment with TBAF in an aprotic solvent such as THF or acetonitrile to give 3a and 4a respectively in which the linkage is a methylene group. Using the above procedure but employing a different phosphonate reagent 5 in place of 5.2, corresponding products 3 and 4 with different linking groups are obtained.

Nevaripine-Like Phosphonate NNRTI Compounds

The present invention describes methods for the preparation of phosphonate analogs of nevaripine class of HIV inhibiting agents shown in Table 7 that are potential anti-HIV agents.

TABLE 7

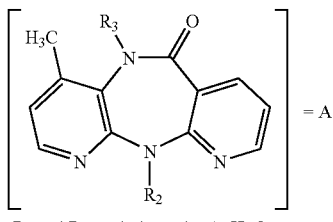

R₂ and R₃ are independently H, $C_{1-6}$ alkyl and $C_{1-6}$ cycloalkyl

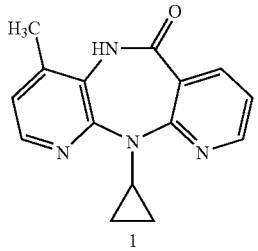

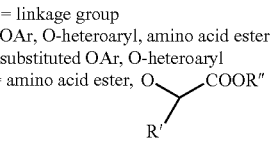

link = linkage group
R = OAr, O-heteroaryl, amino acid ester substituted OAr, O-heteroaryl
$R_1$ = amino acid ester, O—CR'—COOR''

A link group includes a portion of the structure that links two substructures, one of which is nevapine class of HIV inhibiting agents having the general formula shown above, the other is a phosphonate group bearing the appropriate R and R1 groups. The link has at least one uninterrupted chain of atoms other than hydrogen. Nevirapine-type compounds are inhibitors of HIV RT, and nevirapine is currently used in clinical for treatment of HIV infection and AIDs. The present invention provides novel analogs of nevirapine class of compound. Such novel nevirapine analogs possess all the utilities of nevirapine and optionally provide cellular accumulation as set forth below.

The intermediate phosphonate esters required for conversion into the prodrug phosphonate moieties bearing amino acid, or lactate esters are shown in Table 8.

TABLE 8

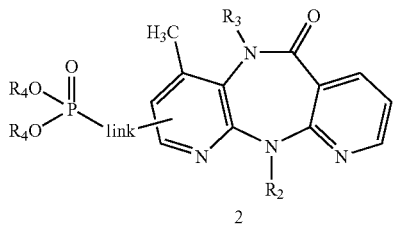

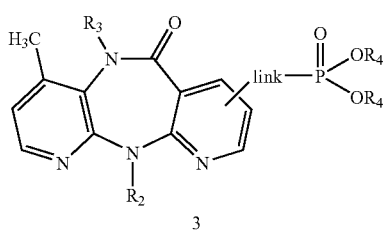

TABLE 8-continued

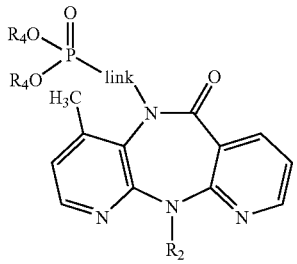

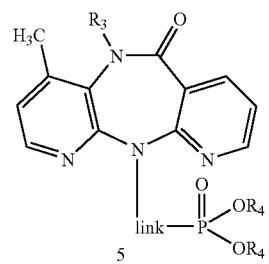

Figure 49A:
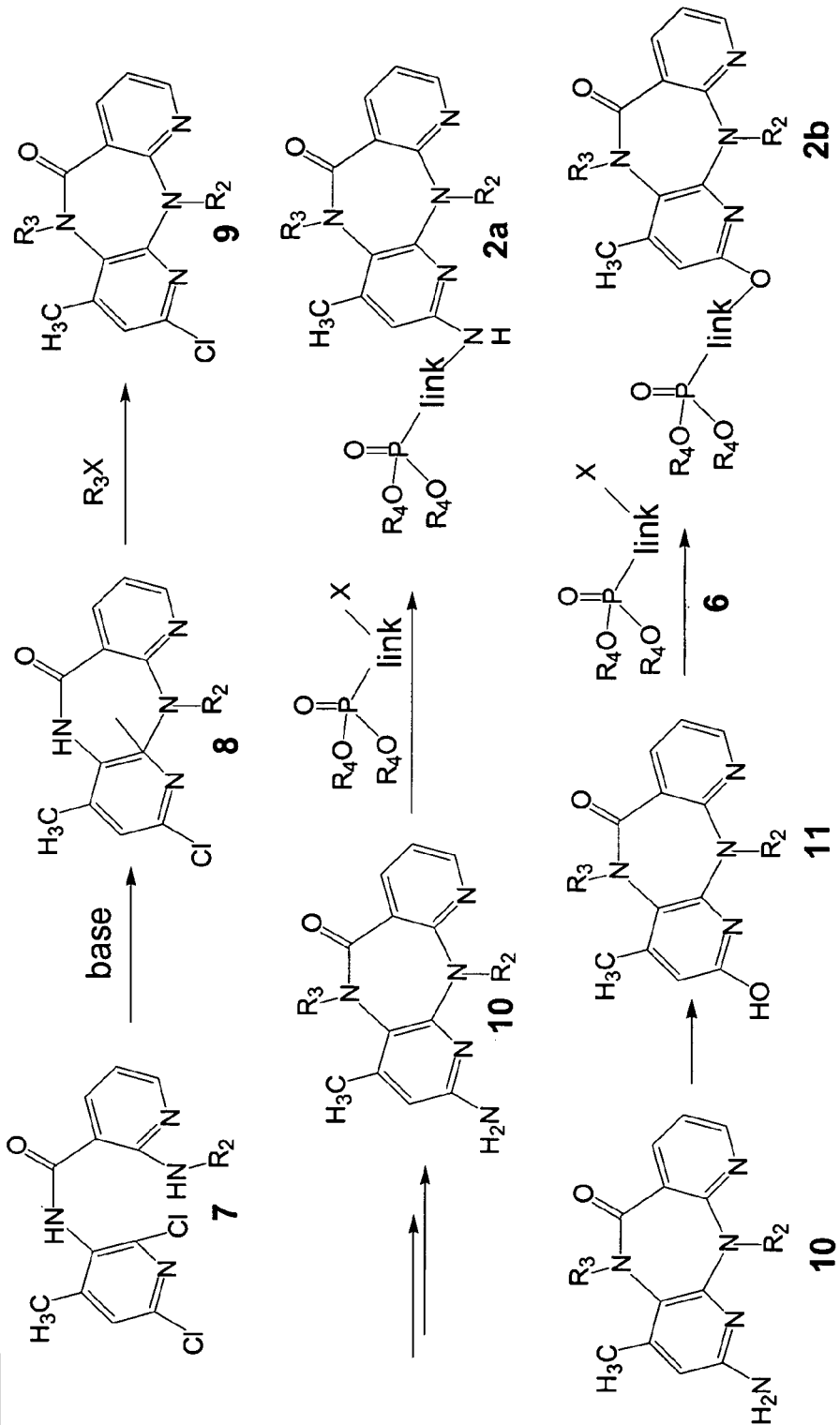
FIGS. 49A-B depict Scheme 1 which is described in detail herein below.
Figure 49B:
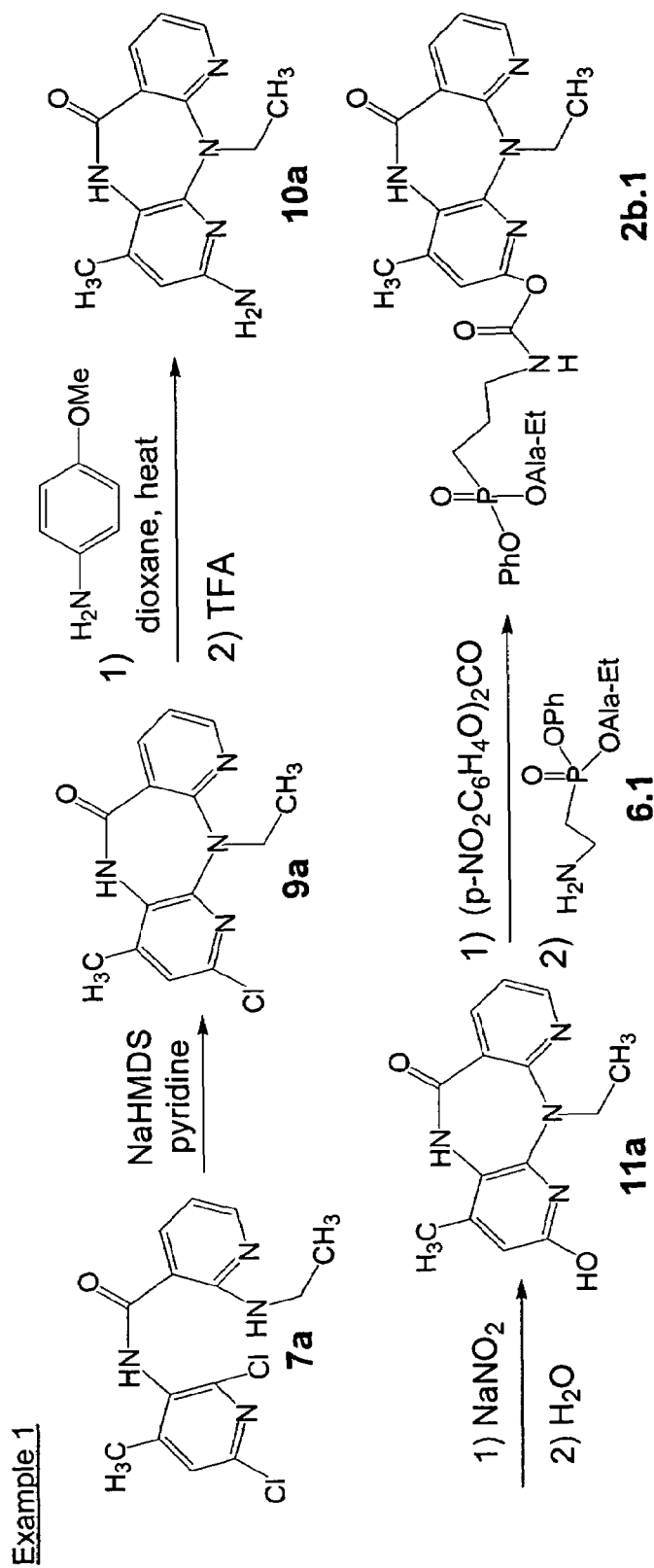
Figure 50A:
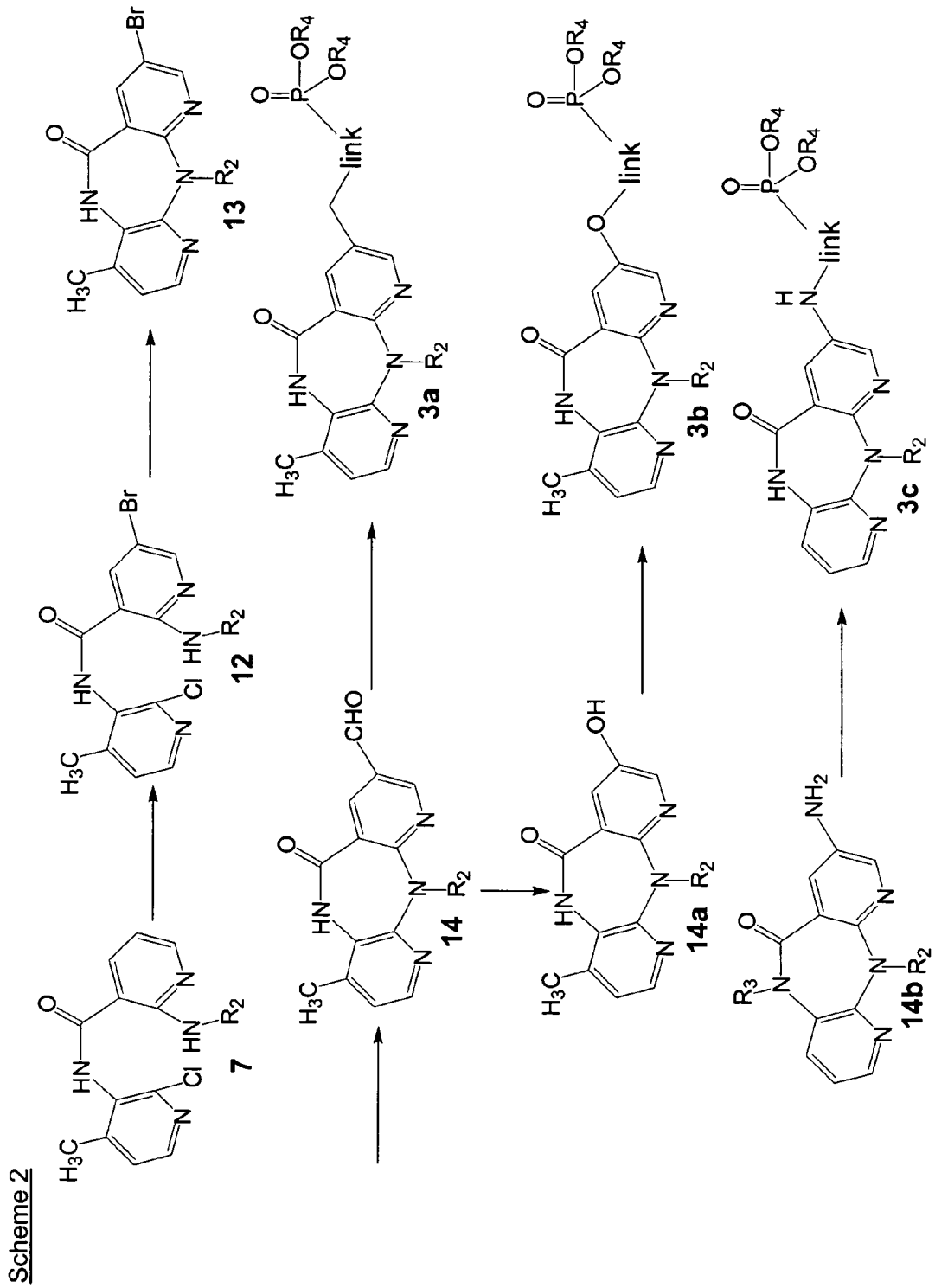
FIGS. 50A-B depict Scheme 2 which is described in detail herein below.
Figure 50B:
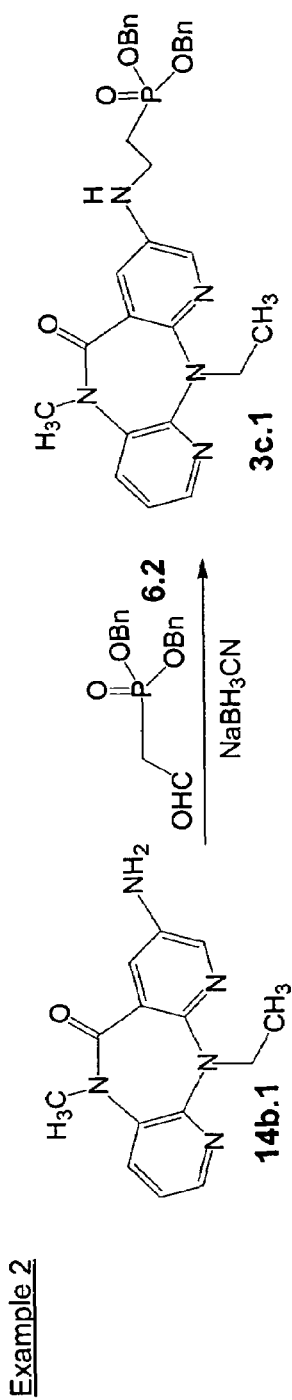

Compound 1 is synthesized as described in U.S. Pat. No. 5,366,972 and *J. Med. Chem.* 1991, 34, 2231. Preparation of phosphonate analog 2 is outlined in Scheme 1 (FIG. 49) and 2 (FIG. 50). Amide 7 is prepared as described in U.S. Pat. No. 5,366,972 and *J. Med. Chem.* 1998, 41, 2960-2971 and 2972-2984. Amide 7 is converted to dipyridodizaepinone 10 following the procedures described in U.S. Pat. No. 5,336,972 and *J. Med. Chem.* 1998, 41, 2960-2971 and 2972-2984. Namely, treatment of dipyridine amide 7 with base provides the dipyridodizaepinone 8. Alkylation of the amide N— is achieved with base and alkyls bearing a leaving group, such as, for example, bromide, iodide, mesylate etc. Displacement of chloride with p-methoxybenzylamine, followed by removal of the p-methoxybenzyl group affords amine 10. The amine group serves as the attachment site for introduction of a phosphonate group. Reaction of amine 10 with reagent 6 provides 2 with different linker attached to amine.

Alternatively (Scheme 2; FIG. 50), amine 10 is transformed to phenol 11 as described in *J. Med. Chem.* 1998, 41, 2972-2984, many examples are also described in R. C. Larock, Comprehensive Organic Transformation, John Wiley & Sons, 2ⁿᵈ Ed. the hydroxyl group then serves as the linking site for a suitable phosphonate group. Reaction of amine 11 with reagent 6 provides 2 with different linker attached to hydroxyl group. For example (Example 1), amide 7a, obtained as described in *J Med. Chem.* 1998, 41, 2960-2971 and 2972-2984, is treated with sodium hexamethyldisilazane in pyridine to give diazepinone 9a. Amine 10a is synthesized from 9a by displacement of the chloride with p-methoxybenzylamine followed by removal of the protecting group of amine. Diazotization of the amine 10a and subsequent in situ conversion to hydroxy yields phenol 11a. Phosphonate with different linker is then able to be attached at the phenol site. For example, the phenol is activated as p-nitro-benzyl carbonate, subsequent treatment with amino ethyl phosphonate 6.1 in the presence of Hunig's base affords carbamate 2b.1.

Scheme 2 (FIG. 50) shows the preparation of phosphonate conjugates compounds type 3 in Table 8. Diazapinone 13 is obtained from dipyrido amide 7 following the procedure described in *J. Med. Chem.* 1998, 41, 2960-2971 and 2972-2984, which is then converted to aldehyde 14 and phenol 14a following the procedures in the same literature. Aldehyde 14 and phenol 14a are then converted to 3a and 3b respectively by reacting with suitable phosphonate reagents 6. Amine 14b is obtained using the method described in *J. Med. Chem.* 1998, 41, 2960-2971, which is converted to phosphonate 3c.

For example (Example 2; FIG. 50), amine 14b.1, obtained by using the procedures described in *J. Med. Chem.* 1998, 41, 2960-2971, reacts with phosphonic acid dibenzyl ester 6.2 under reductive amination conditions to give phosphonate 3c.1.

Figure 51A:
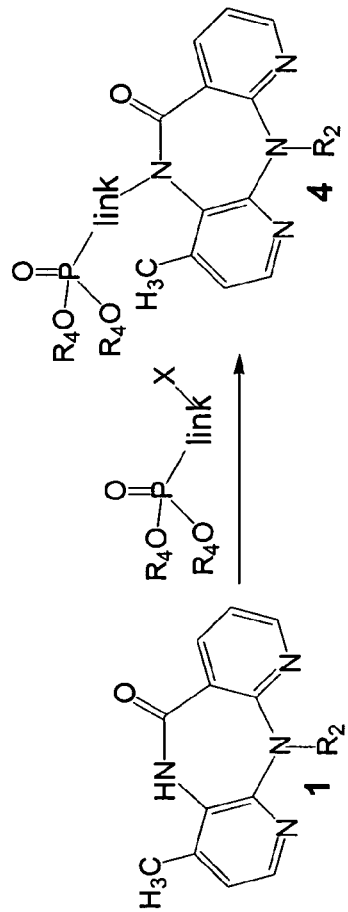
FIGS. 51A-B depict Scheme 3 which is described in detail herein below.
Figure 51B:
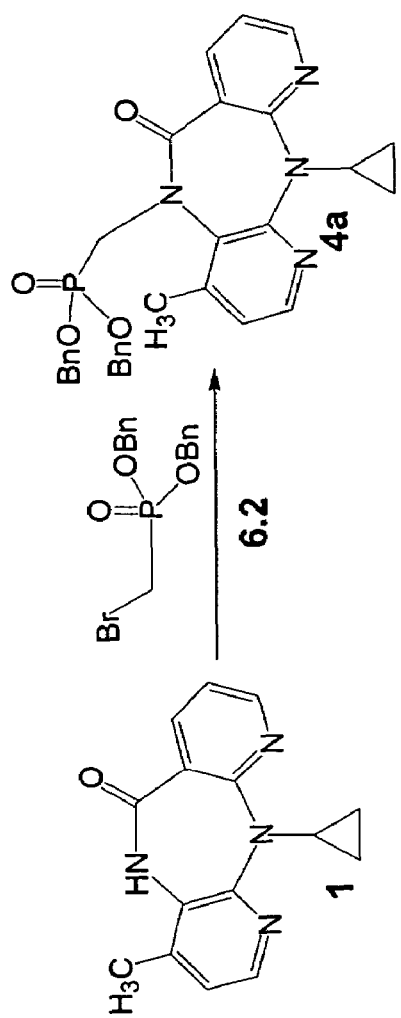

Preparation of phosphonate analog type 4 in Table 8 is shown in Scheme 3 (FIG. 51). Nevirapine analog 1 is dissolved in suitable solvent such as, for example, DMF or other protic solvent, and treated with the phosphonate reagent 9, bearing a leaving group, such as, for example, bromine, mesyl, tosyl, or triflate, in the presence of a suitable organic or inorganic base, to give phosphonate 4. For example, 1 was dissolved in DMF, is treated with sodium hydride and 1 equivalent of bromomethyl phosphonic acid dibenzyl ester 6.2 to give phosphonate 4a in which the linkage is a methylene group.

Figure 52A:
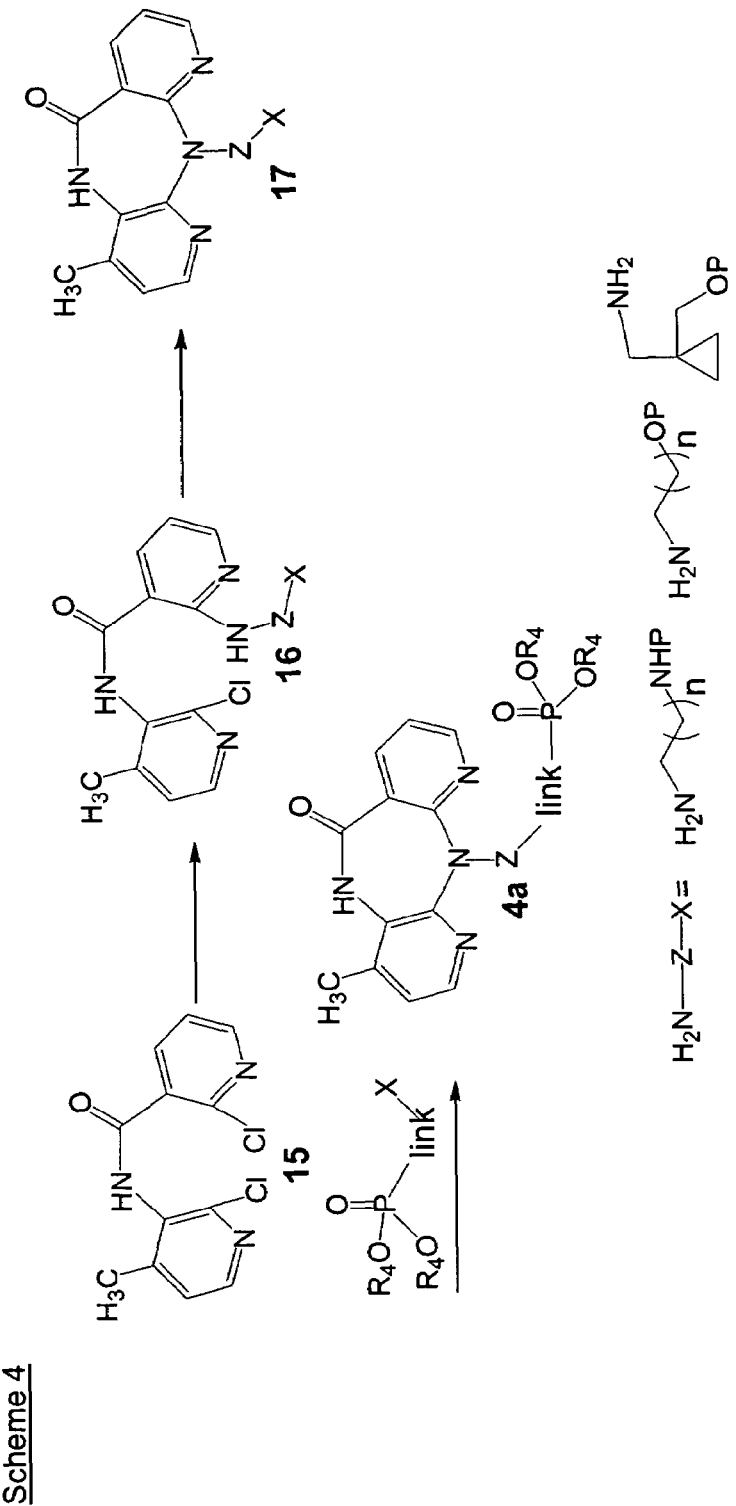
FIGS. 52A-B depict Scheme 4 which is described in detail herein below.
Figure 52B:
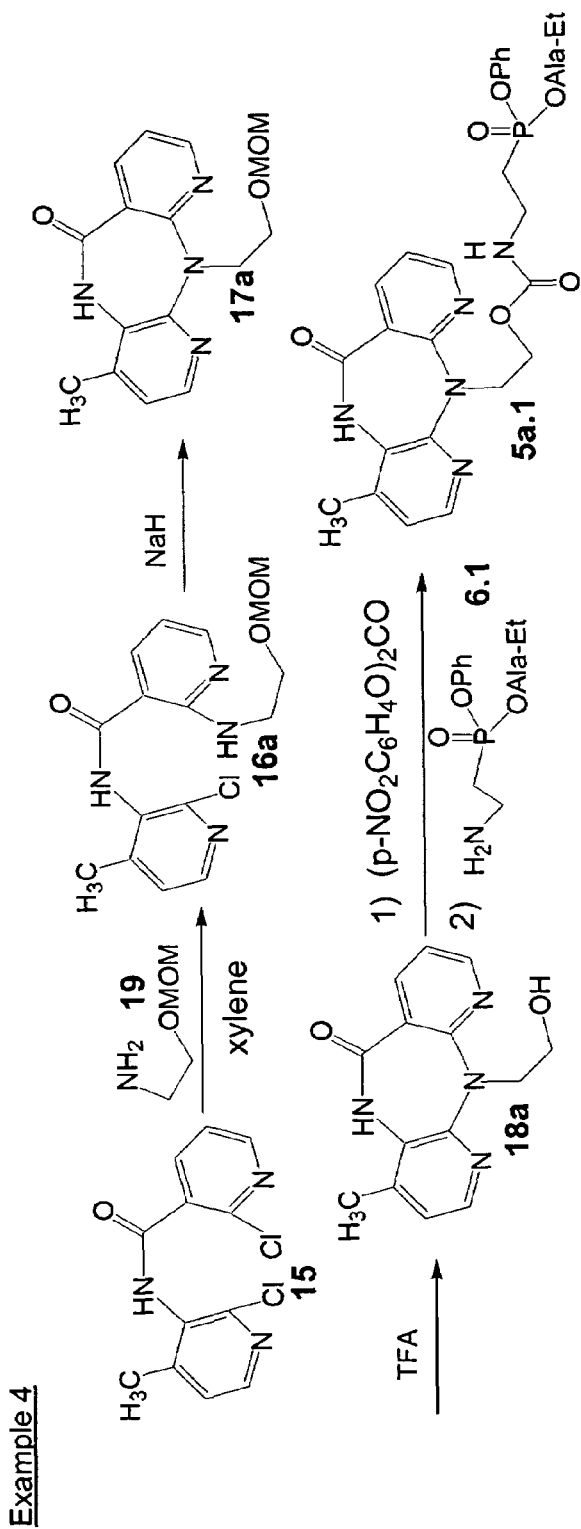

Scheme 4 (FIG. 52) shows the preparation of phosphonate type 5 in Table 8. Amine 15 is prepared according to the procedures described in U.S. Pat. No. 5,336,972 and *J. Med. Chem.* 1998, 41, 2960-2971 and 2972-2984. Substituted alkyl amines, which bearing a protected amino or hydroxyl group, or a precursor of amino group, are used in displacement of alkyls described in U.S. Pat. No. 5,336,972 and *J. Med. Chem.* 1998, 41, 2960-2971 and 2972-2984, react with the chloropyridine 15 in the presence of base to give amine 16. These alkyl amines include but not limit to examples in Scheme 4. These substituted alkyl amines are obtained from commercial sources by protection of the amino or hydroxyl group with a suitable protecting group, for example trityl, silyl, benzyl etc as described in Greene and Wuts, Protecting Groups in Organic Synthesis, $3^{rd}$ Edition, John Wiley and Sons Inc. Formation of the diazepinone ring in the presence of a suitable base produces 17. Removal of protecting group or conversion to amine group from a precursor, such as a nitro group, followed by treatment with reagent 6 yield 5a. For example (Example 4; FIG. 52), the hydroxyl group of 2-hydroxy ethylamine is protected as its MOM-ether (19). Selective displacement of 2'-chloro substituent of the pyridinecarboxamide ring with substituted ethylamine 19 produce 16a. Formation of the diazepinone ring in the presence of sodium hexamethyldisilazane affords 17a. MOM—is then removed to provide alcohol 18a. The hydroxyl group is then used for attaching the phosphonate group. The alcohol is first converted to carbonate by reacting with bis(4-nitrobenzyl)carbonate, subsequent treatment of the resulting carbonate with aminoethyl phosphonate 6.2 provides phosphonate 5a.1.

Quinazolinone-Like Phosphonate NNRTI Compounds

The present invention describes methods for the preparation of phosphonate analogs of quinazolinones shown in Table 9 that are potential anti-HIV agents.

TABLE 9

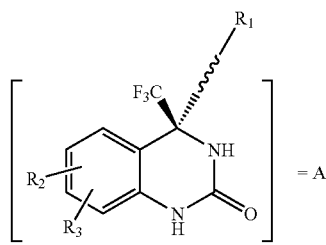

⌒⌒⌒ = signl, double, triple bond

TABLE 9-continued $R_1$ = substituted $C_{3-5}$ alkyl, $C_{3-5}$ cycloalkyl
phenyl and heterocyclic, substituents
are $C_{1-4}$ alkyls, OH, $C_{1-4}$alkoxyl, halides, $NH_2$, $NHR_1'$,
$NR_1'R_1'$, $NHCOR_1'$ $R_2$ = H, MeO, F, Cl $R_3$ = H, F, Cl

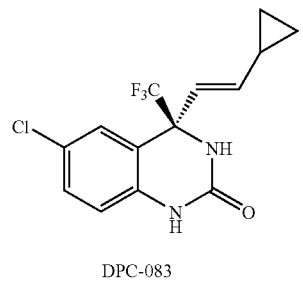

DPC-083

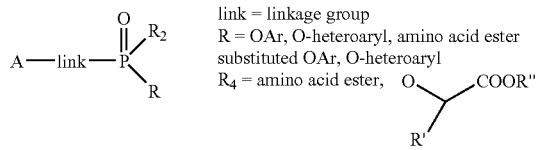

link = linkage group
R = OAr, O-heteroaryl, amino acid ester
substituted OAr, O-heteroaryl
$R_4$ = amino acid ester, A link group includes a portion of the structure that links two substructures, one of which is quinazolinones having the general formula shown above, the other is a phosphonate group bearing the appropriate R and R4 groups. The link has at least one uninterrupted chain of atoms other than hydrogen.

Quinozolinone class of compound, act as NNRTI, has demonstrated to inhibit HIV replication. DPC-083, one of representative analogs of this class of compounds, is in clinical phase II studies for treatment of HIV infection and AIDs. The present invention provides novel analogs of quinozolinone class of compound. Such novel quinozolinone analogs possess all the utilities of quinozolinone and optionally provide cellular accumulation as set forth below.

The intermediate phosphonate esters required for conversion into the prodrug phosphonate moieties bearing amino acid, or lactate esters are shown in Table 10.

TABLE 10

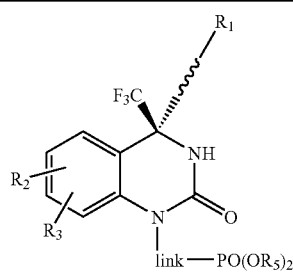

TABLE 10-continued

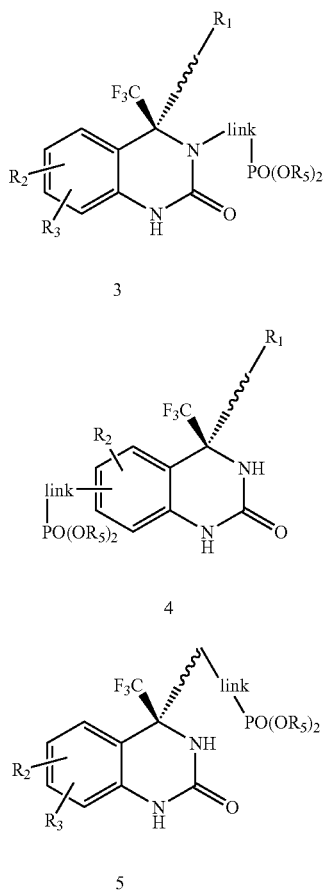

3

4

5

Figure 53A:
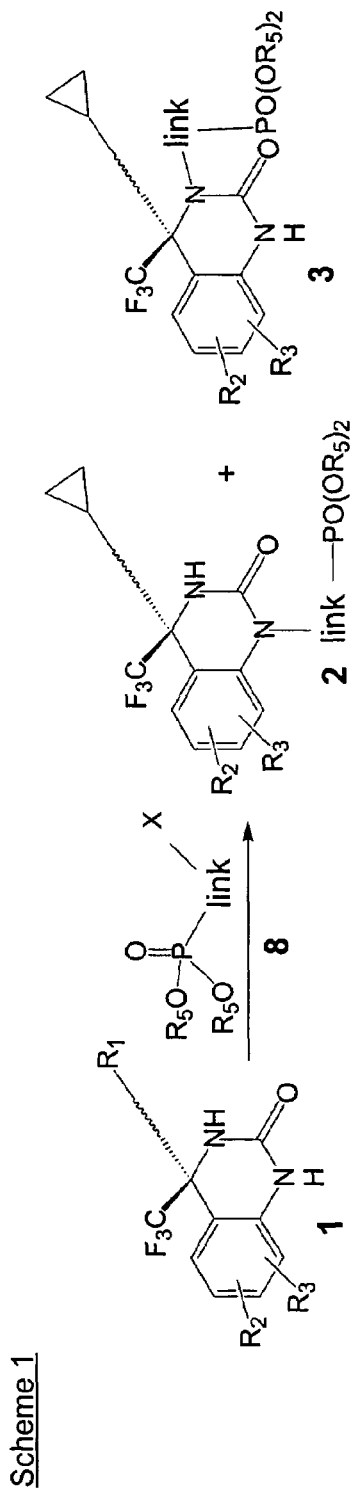
FIGS. 53A-B illustrate Scheme 1 which is described in detail herein below.
Figure 53B:
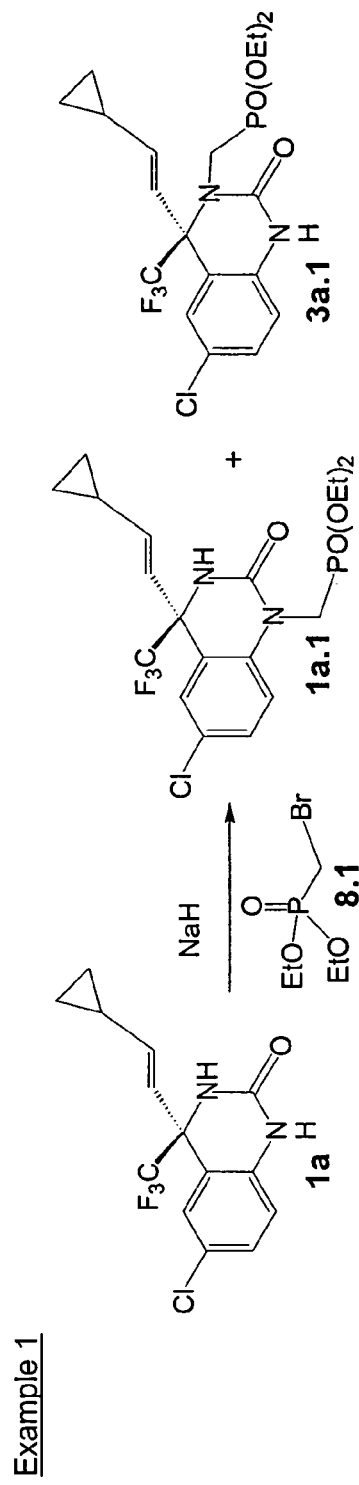

Preparation of phosphonate 2 is outlined in Scheme 1 (FIG. 53). Quinazolinone 1, synthesized as described in Patent EP0530994, WO93/04047 and U.S. Pat. No. 6,423,718, is dissolved in suitable solvent such as, for example, DMF or other protic solvent is first treated with a suitable base to remove the urea proton, the product is then treated with 1 equivalent of a phosphonate reagent 8 bearing a leaving group such as, for example, bromine, mesyl, tosyl etc to give the alkylated product 2 and 3. The phosphonates 2 and 3 are separated by chromatography. For example, 1 is dissolved in DMF, is treated with sodium hydride and 1 equivalent of bromomethyl phosphonic acid diethyl ester 8.1 prepared to give quinazolinone phosphonate 2 in which the linkage is a methylene group. Using the above procedure but employing different phosphonate reagents 8 in place of 8.1, the corresponding products 2 and 3 are obtained bearing different linking group.

Figure 54:
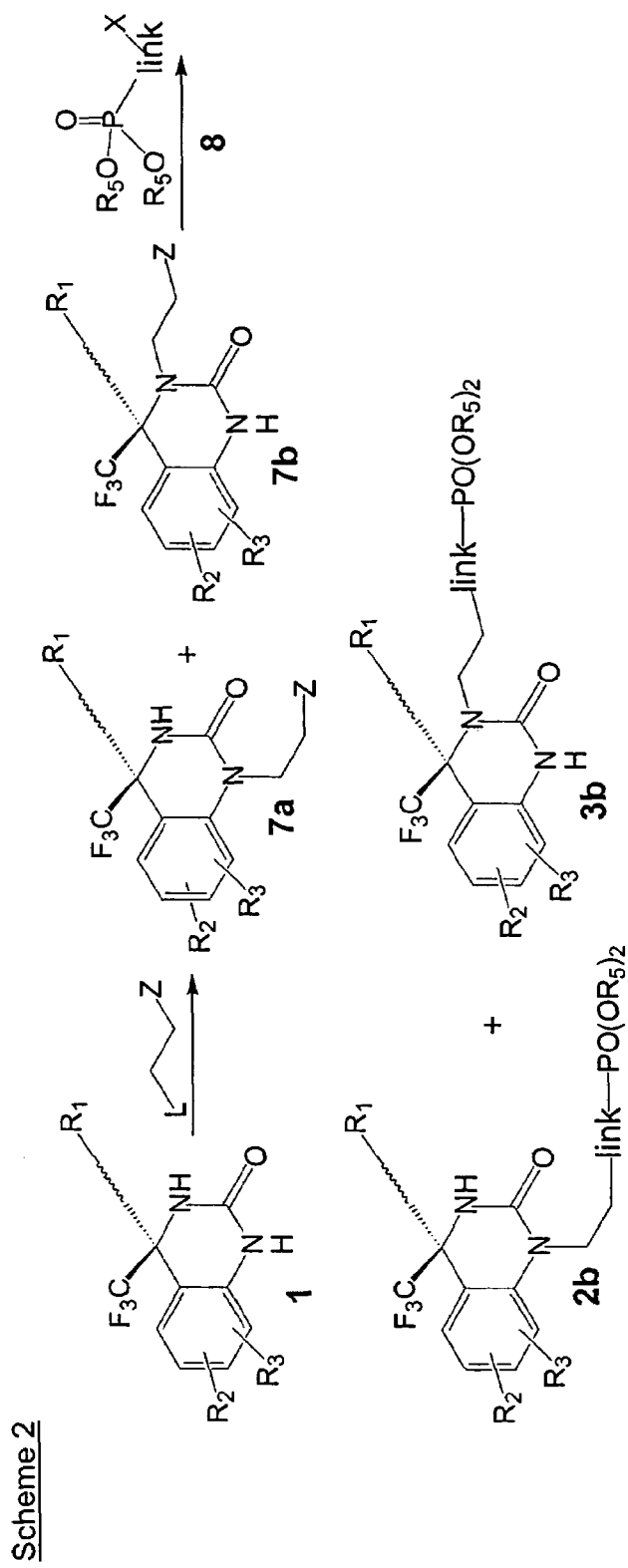
FIG. 54 depicts Scheme 2 which is described in detail herein below.

Scheme 2 (FIG. 54) shows the preparation of phosphonate analogs type 2 and 3 attached with an alternative way. Quinazolinone 1, dissolved in a suitable solvent such as, for example, DMF or other protic solvents, is first treated with a suitable base to remove the urea proton, the product is then treated with 1 equivalent of reagent B, which bears a leaving group such as, for example, bromine, mesyl, tosyl etc, to give the alkylated product 7a and 7b. Compound B possesses a protected NH2 or OH group, or a precursor for them. The alkylated product 7a and 7b are separated by chromatography. Protecting group is then removed, and the resulting alcohol or amine then reacts with reagent 8 to afford 2b and 3b respectively.

Figure 55:
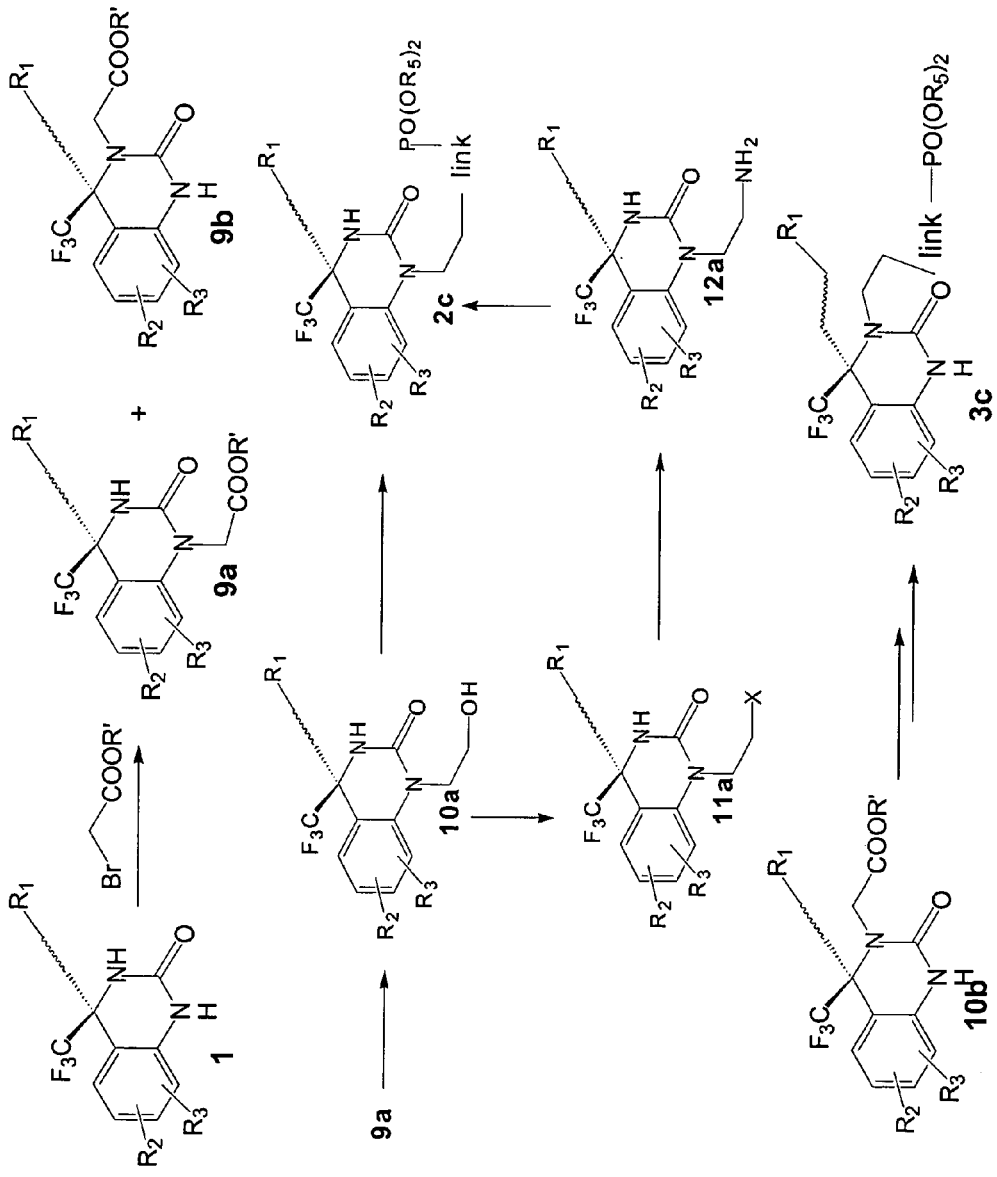
FIG. 55 depicts Scheme 3 which is described in detail herein below.

Alternatively (Scheme 3; FIG. 55), alkylation of 1 with bromoacetate provides 9a and 9b, which are separated by chromatography. The ester group of 9 is reduced to alcohol to give 10. The alcohol 11 is also transformed to amine 12 under conventional conditions, many examples are described in R. C. Larock, Comprehensive Organic Transformation, John Wiley & Sons, 2nd Ed. The hydroxyl group of 10 and amino group of 12 then serve as the attachment site for linking phosphonate to provide 2c. Similarly, ester 10a is converted to phosphonate 3c following the procedures of transformation of 10 to 2c.

Figure 56:
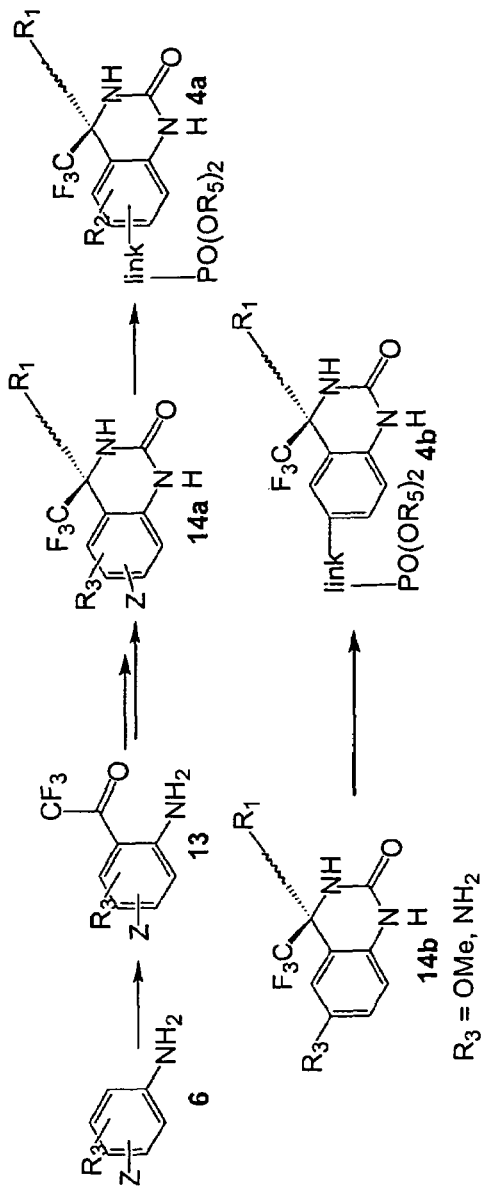
FIG. 56 depicts Scheme 4 which is described in detail herein below.
Figure 57A:
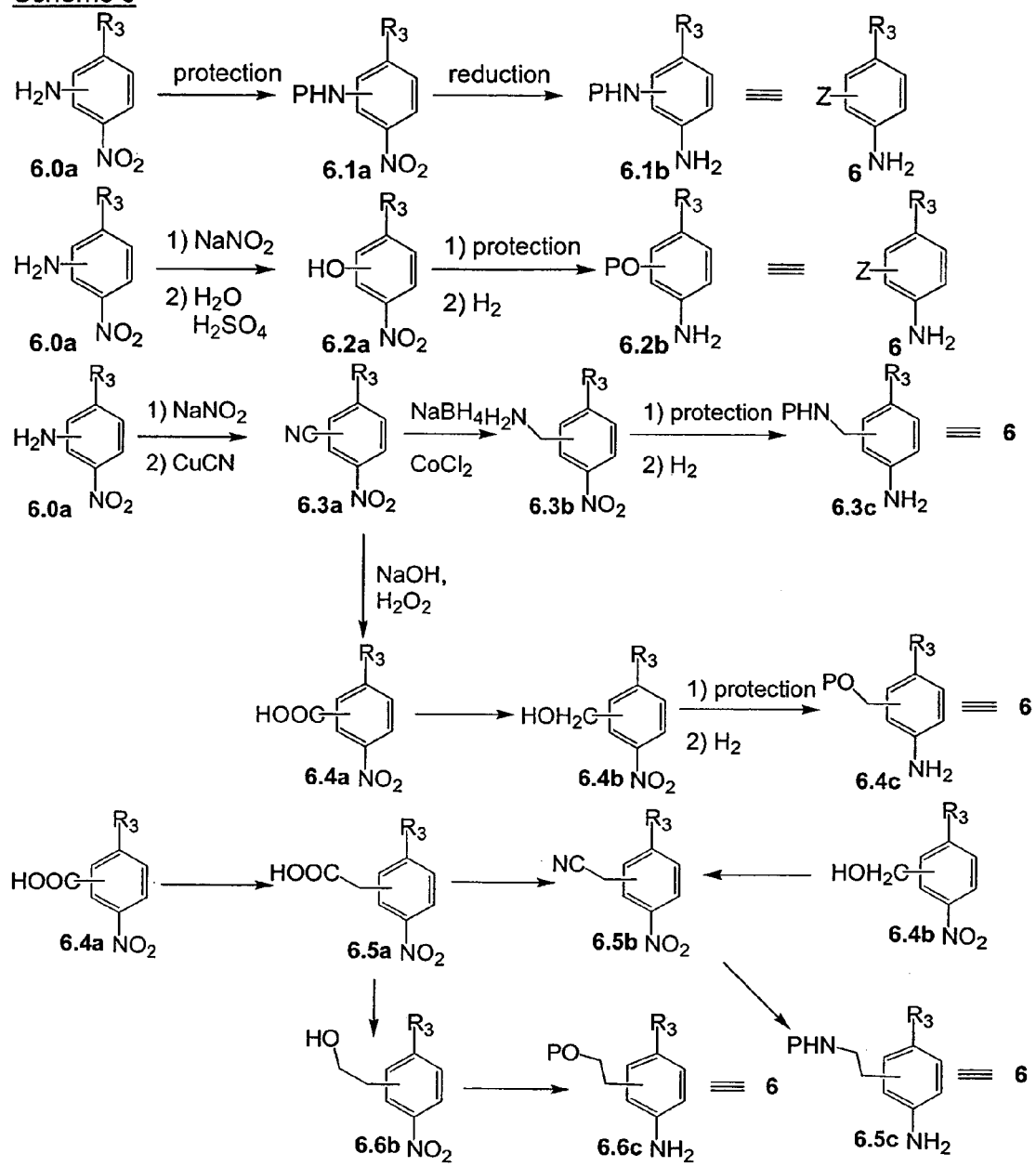
FIGS. 57A-C depict Scheme 5 which is described in detail herein below.
Figure 57B:
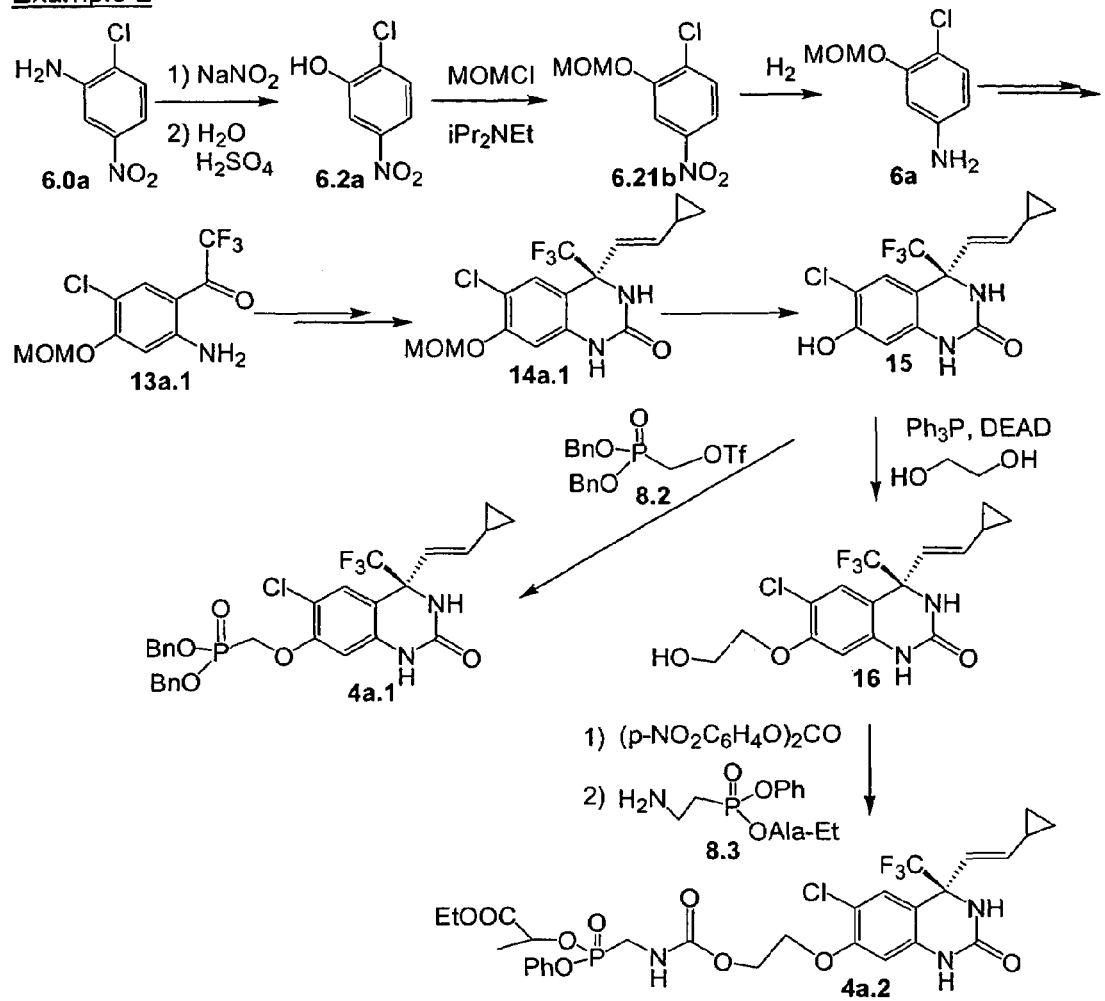
Figure 57C:
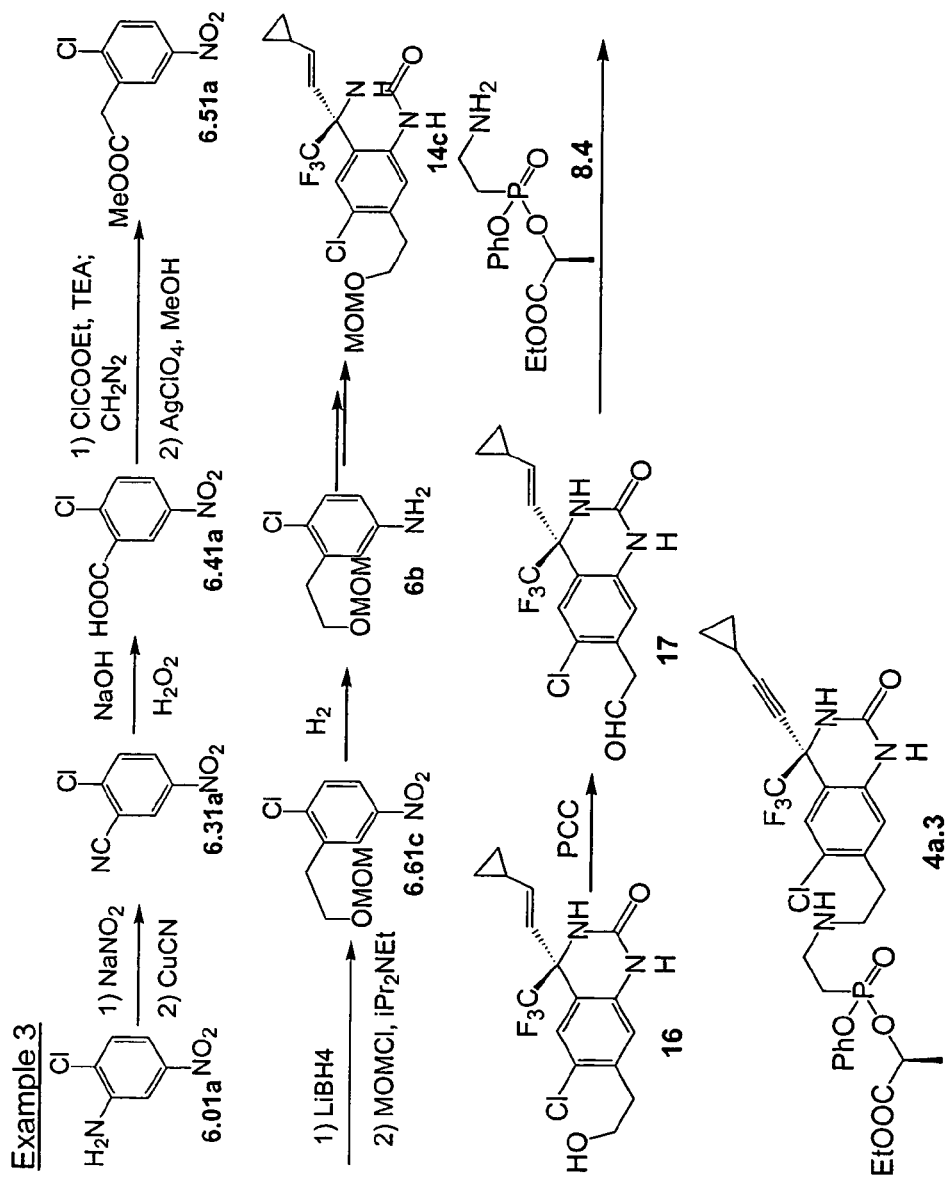

Scheme 4 (FIG. 56) shows the preparation of quinazolinone-phosphonate conjugates type 4 in Table 10. Substituted aniline 6 with a functional group Z, which is bearing a protected alcohol or amino group, or protected alcohol or amino alkyl, is converted to trifluoromethyl phenyl ketone 13, which is subsequently converted to quinozolinone 14a, following the procedure described in U.S. Pat. No. 6,423,718. Deprotection of the protecting group, followed by reacting with reagents 8 under suitable conditions give the desired the phosphonate 4a. Quinazoline 14b, prepared according to U.S. Pat. No. 6,423,718, is converted to phosphonate 4b by reacting with phosphonate reagent 8 directly ($R_3=NH_2$), or after deprotection ($R_3=OMe$) under the condition such as for example, $BCl_3$, many examples are described in Greene and Wuts, Protecting Groups in Organic Synthesis, $3^{rd}$ Edition, John Wiley and Sons Inc. Synthesis of compound 6 is described in Scheme 5 (FIG. 57).

Scheme 5 (FIG. 57) shows compounds 6 are obtained through modification of commercial available material 2-halo-5-nitroaniline, or 5-halo-2-nitroaniline (6.0a). The amino group of 6.0a is first protected with a suitable protecting group, for example trityl, Cbz, or Boc etc as described in Greene and Wuts, Protecting Groups in Organic Synthesis, $3^{rd}$ Edition, John Wiley and Sons Inc. Reduction of the nitro group of 6.1 a with a reducing agent, many examples are described in R. C. Larock, Comprehensive Organic Transformation, John Wiley & Sons, $2^{nd}$ Ed, gives 6.1b, which is then used in the transformation described in Scheme 4 (FIG. 56).

The amino group of 6.0a is converted to hydroxyl group to give 6.2a by established procedures, for example, diazotization followed by treatment with $H_2O/H_2SO_4$, many examples are described in R. C. Larock, Comprehensive Organic Transformation, John Wiley & Sons, $2^{nd}$ Ed. The hydroxyl group is then protected with a suitable protecting group, for example trityl ethers, silyl ethers, methoxy methyl ethers etc as described in Greene and Wuts, Protecting Groups in Organic Synthesis, $3^{rd}$ Edition, John Wiley and Sons Inc. The nitro group of the resulting compound is then reduced with the above mentioned methods to give 6.2b, which is then used in the transformation described in Scheme 4 (FIG. 56).

The hydroxyl or amino alkyls are obtained using the following methods. The amino group of 6.0a is converted to nitrile 6.3a with the known method, for example diazotization followed by treatment with cuprous cyanide, many examples are described in R. C. Larock, Comprehensive Organic Transformation, John Wiley & Sons, $2^{nd}$ Ed. The nitrile group is then selectively reduced with a reducing agent, many examples are described in R. C. Larock, Comprehensive Organic Transformation, John Wiley & Sons, $2^{nd}$ Ed, to give amine 6.3b. With the mentioned methods above, the amino group is protected and nitro group is reduced respectively to give 6.3c. Alternatively, the nitrile 6.3a is converted to acid 6.4a and the acid is subsequently reduced to alcohol to give 6.4b using the examples described in R. C. Larock, Comprehensive Organic Transformation, John Wiley & Sons, $2^{nd}$ Ed. Similarly, protection of hydroxyl group followed by reduction of nitro to amine gives 6.4c. Compound 6.3c and 6.4c are used in Scheme 4 (FIG. 56) respectively.

The homologated hydroxyl or amino alkyls are obtained using the following methods (Scheme 3). The acid 6.4a are extended to acid 6.5a, which is transformed to nitrile 6.5b, these two transformation are described in R. C. Larock, Comprehensive Organic Transformation, John Wiley & Sons, 2 Ed, Nitrile 6.5b is converted to aniline 6.5c using the similar methods described above. Alternatively, nitrile 6.5b is obtained by first convert benzyl alcohol 6.4b to benzyl halide, then treated with CN— nucleophile. Reduction of acid 6.5a provided alcohol 6.6b, which is protected using the protecting groups described above to give the required aniline 6.6c. Compound 6.5c and 6.6c are used in Scheme 4 (FIG. 56) respectively.

For example aniline 6.0a (Example 2; FIG. 57) is treated with $NaNO_2$ in the presence of acid at 0° C., then the resulting mixture was heated in $H_2O$ to give phenol 6.2a. The hydroxyl group is then protected as methoxyl methyl ether by treating phenol 6.2a with MOMCl in the presence of Hunig's base to yield 6.21b. Hydrogenation of nitrobenzene affords aniline 6a. Aniline 6a is converted to phenyl trifluoromethyl ketone 13a.1, which is subsequently transformed to quinazolinone analog 14a.1, using the method described in U.S. Pat. No. 6,423,718. Deprotection of the MOM-ether with trifluoroacidic acid provides phenol 15. Treatment of 15, in acetonitrile, with triflate methyl phosphonic acid dibenzyl ester 8.2 in the presence of $Cs_2CO_3$ gives 4a.1. Alternatively, reaction of phenol 15 with ethylenediol under the Mitsunobu condition produces 16. Hydroxyl group of 16 as activated as carbamate, subsequent treatment with amino methyl phosphonate 8.3 affords phosphonate analog 4a.2.

Example 3 (FIG. 57) shows 2-chloro-5-nitro aniline 6.0b transformed to nitrile 6.31a by reacting with $NaNO_2$ and then CuCN subsequently. Hydrolysis of nitrile 6.31a gives acid 6.41a. Treatment of 6.41a with ClCOOEt in the presence of base at 0° C. followed by $CH_2N_2$ provides diazoketone, which is converted to methyl ester 6.51a upon treating with silver perchlorate in methanol. The ester group is then reduced to give alcohol, which is protected as MOM-ether to provide 6.61c. The nitro group is then reduced to amine to afford 6b. Aniline 6b is converted to quinazolinone analog 14 using the method described in U.S. Pat. No. 6,423,718. Deprotection of the MOM-ether with trifluoroacidic acid provide alcohol 16. The aldehyde 17 is obtained by oxidation of alcohol. Reductive amination of 17 with amino ethyl phosphonate 8.4 afford analog 4a.3.

Figure 58A:
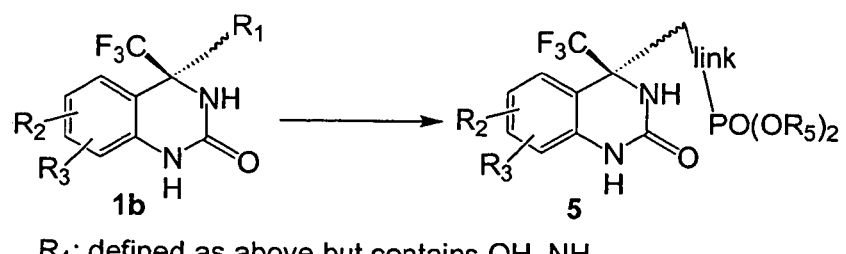
FIGS. 58A-B illustrate Scheme 6 which is described in detail herein below.
Figure 58B:
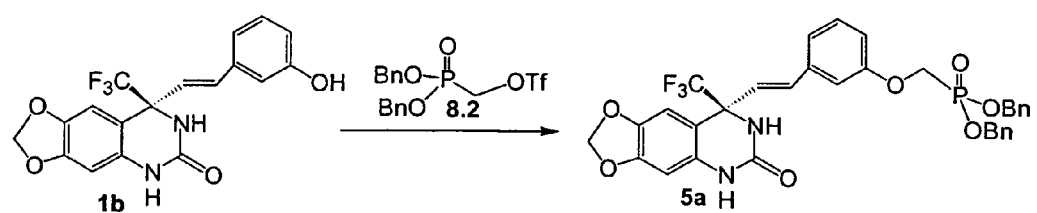

Preparation of phosphonate analog type 5 from quinazolinone 1 is outlined in Scheme 6 (FIG. 58). Quinazolinone 1, which $R_1$ contains OH, or $NH_2$ or $NHR_1'$ as the attachment site for connecting phosphonate, reacts with reagent 8 under suitable conditions to provide phosphonate analog 5. For example (Example 4; FIG. 58), Quinozalinone 1b.1, obtained as described in U.S. Pat. No. 6,423,718, is treated with phosphonate reagents 8.2 in the presence of $Cs_2CO_3$, give phosphonate 5a.

Efavirenz-Like Phosphonate NNRTI Compounds

The present invention includes efavirenz-like phosphonate NNRTI compounds and methods for the preparation of efavirenz phosphonate analogs shown in Table 11.

TABLE 11

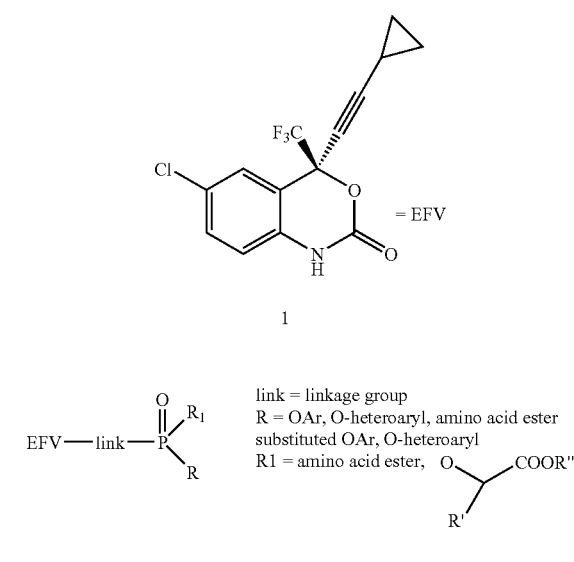

A link group includes a portion of the structure that links two substructures, one of which is efavirenz having the general formula shown above, the other is a phosphonate group bearing the appropriate R and $R_1$ groups. The link has at least one uninterrupted chain of atoms other than hydrogen.

Efavirenz and its analogs have demonstrated therapeutic acitivity against HIV replication, and efavirenz is currently used in clinical for treatment of HIV infection and AIDS. The present invention provides novel analogs of efavirenz. Such novel efavirenz analogs possess all the utilities of efavirenz and optionally provide cellular accumulation as set forth below.

The intermediate phosphonate esters required for conversion into the prodrug phosphonate moieties bearing amino acid, or lactate esters are shown in Table 12.

TABLE 12

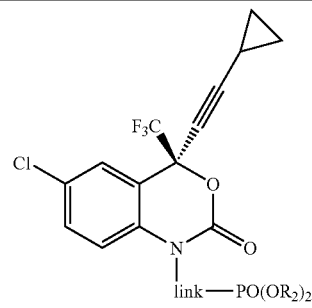

TABLE 12-continued

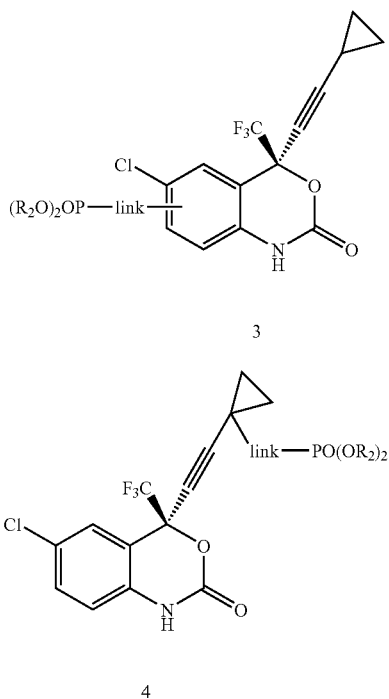

3

4

Figure 59A:
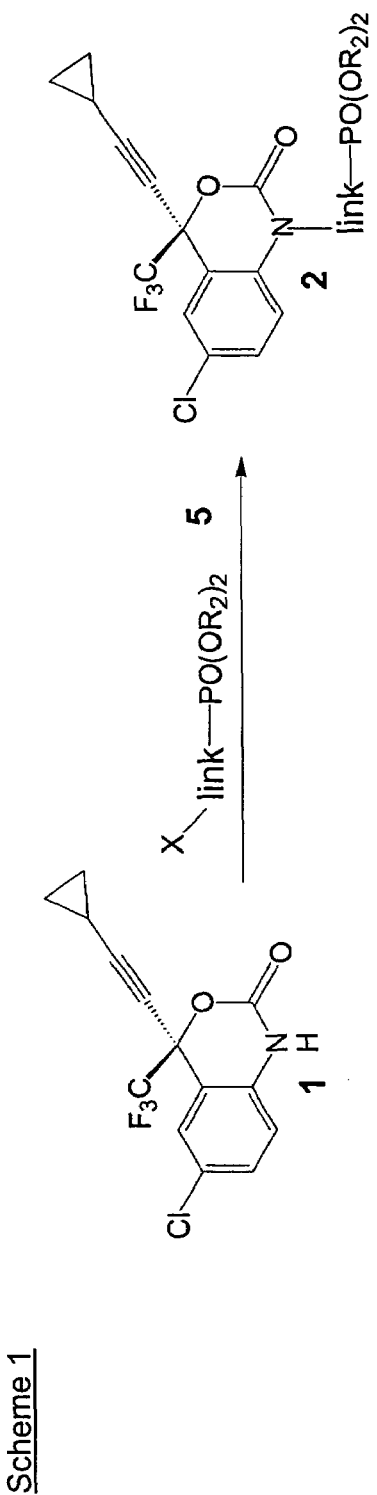
FIGS. 59A-B depict Scheme 1 which is described in detail herein below.
Figure 59B:
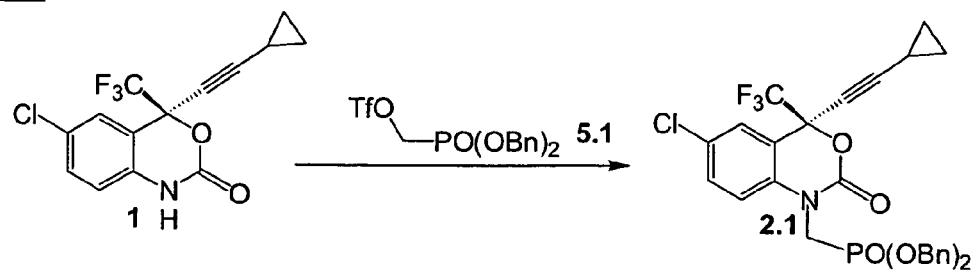

Compound 1 can be synthesized as described in U.S. Pat. No. 5,519,021. Preparation of compound 2 from efavirenz 1 is outlined in Scheme1 (FIG. 59). Efavirenz 1 is dissolved in suitable solvent such as, for example, DMF or other protic solvent, and treated with the phosphonate reagent 5 in the presence of a suitable organic or inorganic base. For example, 1 is dissolved in DMF, is treated with sodium hydride and 1 equivalent of triflate methyl phosphonic acid dibenzyl ester 5.1 prepared to give EFV phosphonate 2 in which the linkage is a methylene group. Using the above procedure but employing different phosphonate reagents 5 in place of 5.1, the corresponding products 2 are obtained bearing different linking group.

Scheme 2 (FIG. 60) shows the preparation of EFV-phosphonate conjugates compounds 3 in Table 12. p-Chloro aniline with functional group Z, which bears a protected alcohol or amino group, or protected alcohol or amino alkyl, is converted to compound 7 following the procedure described in U.S. Pat. No. 5,519,021. Deprotection of the protecting group, followed by reacting with reagent 5 in the above mentioned conditions give the desired the compound 3. As shown in Scheme 3 (FIG. 61), compounds 6 are obtained through modification of commercial available material 2-chloro-5-nitroaniline, or 5-chloro-2-nitroaniline (6.0a).

Figure 61A:
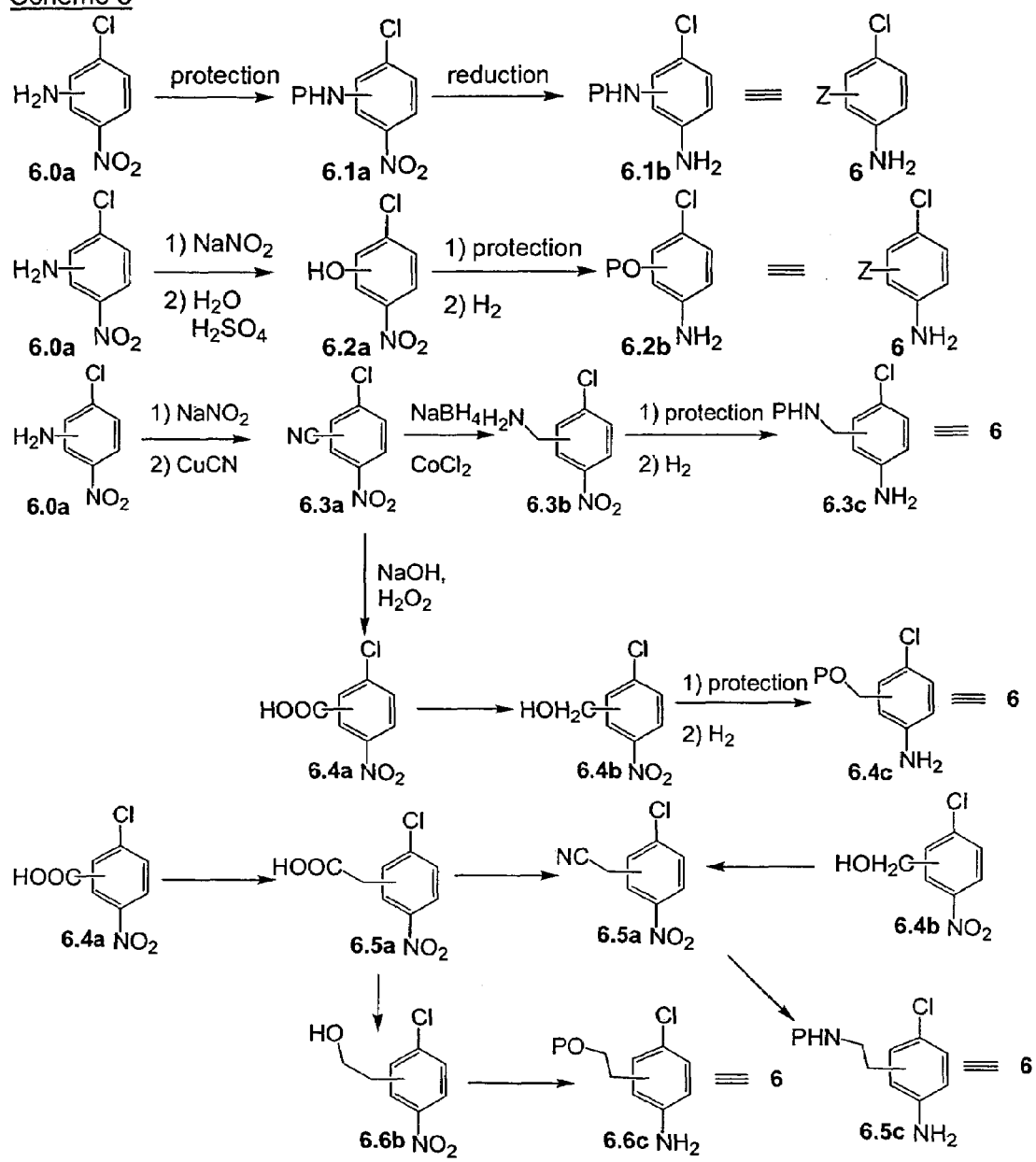
FIGS. 61A-C depict Scheme 3 which is described in detail herein below.
Figure 61B:
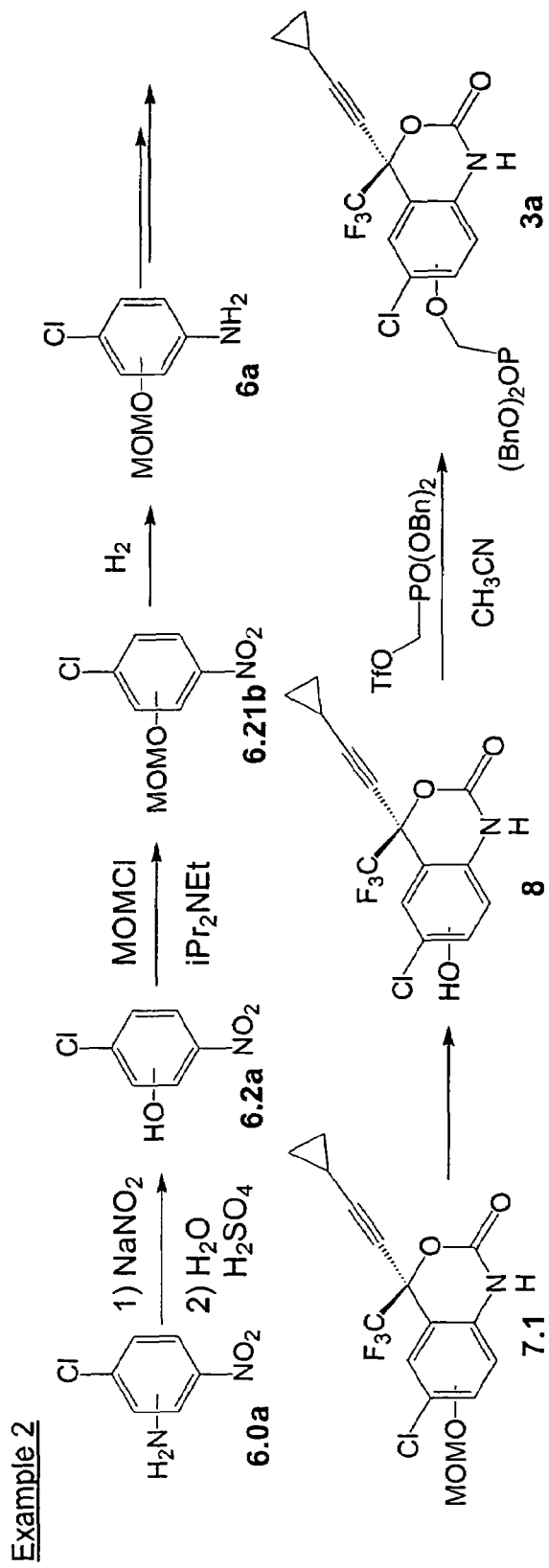
Figure 61C:
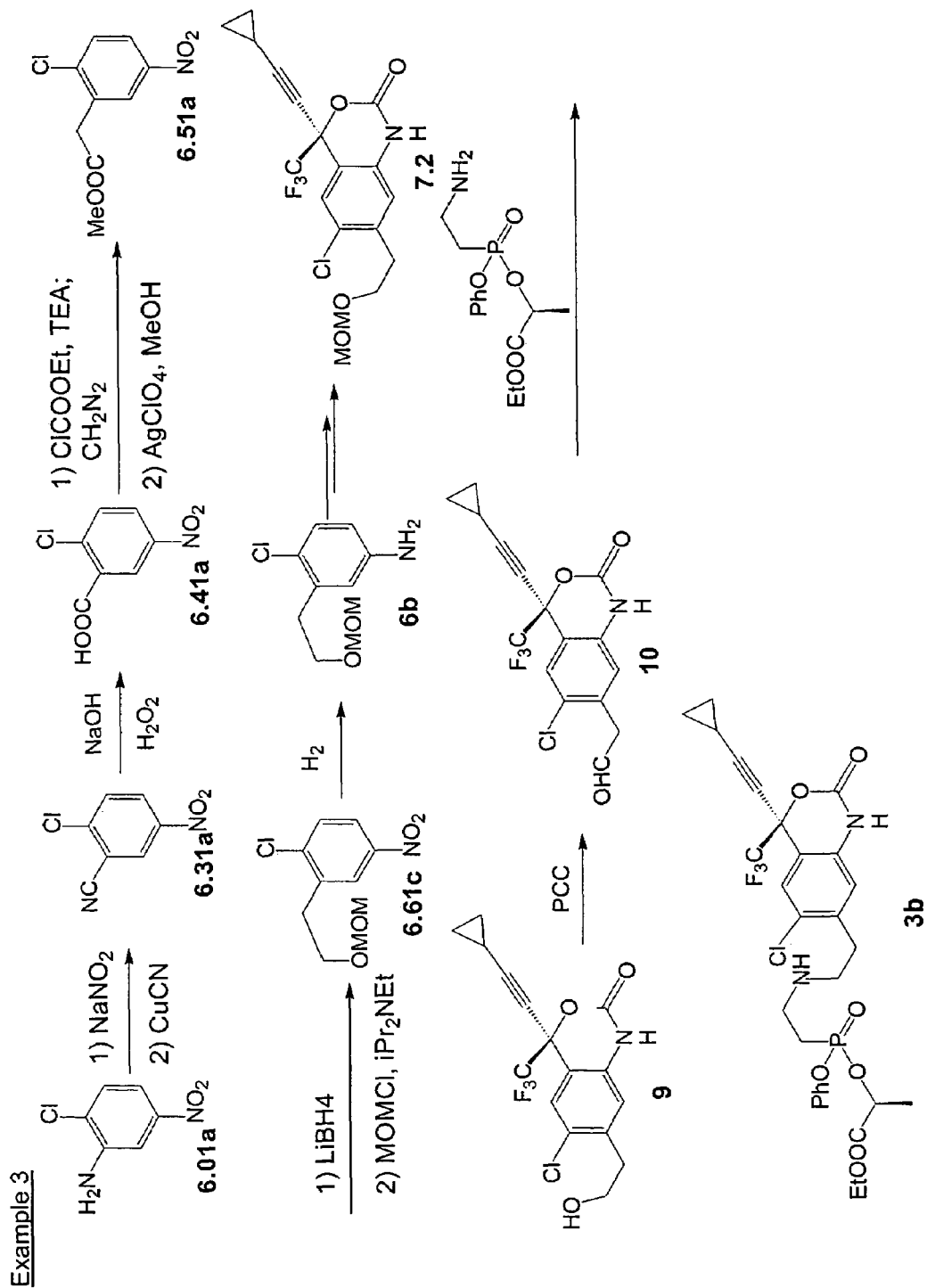

The amino group of 6.0a is first protected with a suitable protecting group (Scheme 3; FIG. 61), for example trityl, Cbz, or Boc etc as described in Greene and Wuts, Protecting Groups in Organic Synthesis, $3^{rd}$ Edition, John Wiley and Sons Inc. Reduction of the nitro group in 6.1a with a reducing agent, many examples are described in R. C. Larock, Comprehensive Organic Transformation, John Wiley & Sons, $2^{nd}$ Ed, give 6.1b, which is then used in the transformation described in Scheme 2.

Figure 60:
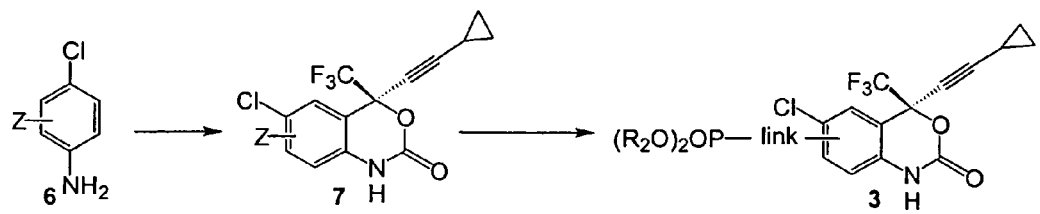
FIG. 60 depicts Scheme 2 which is described in detail herein below.

Alternatively, the amino group of 6.0a is converted to hydroxyl group to give 6.2a by established procedures, for example, diazotization followed by treatment with $H_2O/H_2SO_4$, many examples are described in R. C. Larock, Comprehensive Organic Transformation, John Wiley & Sons, 2nd Ed. The hydroxyl group is then protected with a suitable protecting group, for example trityl ethers, silyl ethers, methoxy methyl ethers etc as described in Greene and Wuts, Protecting Groups in Organic Synthesis, $3^{rd}$ Edition, John Wiley and Sons Inc. The nitro group of the resulting compound is then reduced with the above mentioned methods to give 6.2b, which is then used in the transformation described in Scheme 2 (FIG. 60).

The hydroxyl or amino alkyls are obtained using the following methods. The amino group in 6.0a is converted to nitrile 6.3a with the known method, for example diazotization followed by treatment with cuprous cyanide, many examples are described in R. C. Larock, Comprehensive Organic Transformation, John Wiley & Sons, $2^{nd}$ Ed. The nitrile group is then selectively reduced with a reducing agent, many examples are described in R. C. Larock, Comprehensive Organic Transformation, John Wiley & Sons, $2^{nd}$ Ed, to give amine 6.3b. With the mentioned methods above, the amino group is protected and nitro group is reduced respectively to give 6.3c. In addition, the nitrile 6.3a is converted to acid 6.4a and the acid is subsequently reduced to alcohol to give 6.4b, and the reduction of nitro to amine give 6.4c, using the methods described in R. C. Larock, Comprehensive Organic Transformation, John Wiley & Sons, $2^{nd}$ Ed. Both 6.3c and 6.4c used in the transformation described in Scheme 2.

The homologated hydroxyl or amino alkyls are obtained using the following methods (Scheme 3; FIG. 61). The acid 6.4a are extended to acid 6.5a, which is transformed to nitrile 6.5b, these two transformation are described in R. C. Larock, Comprehensive Organic Transformation, John Wiley & Sons, 2 Ed, Nitrile 6.5b is converted to aniline 6.5c using the similar methods described above. Alternatively, nitrile 6.5b is obtained by first convert benzyl alcohol 6.4b to benzyl halide, then treated with CN— nucleophile. Reduction of acid 6.5a provided alcohol 6.6b, which is protected using the protecting groups described above to give the required aniline 6.6c. Both 6.5c and 6.6c used in the transformation described in Scheme 2 (FIG. 60).

For example aniline 6.0a (Example 2; FIG. 61) is treated with $NaNO_2$ in the presence of acid at 0° C., then the resulting mixture was heated in $H_2O$ to give phenol 6.2a. The hydroxyl group is then protected as methoxyl methyl ether by treating phenol 6.2a with MOMCl in the presence of Hunig's base to yield 6.21b. Hydrogenation of nitrobenzene affords aniline 6.2a. Aniline 6a is converted to efavirenz analog 7.1. Deprotection of the MOM-ether with trifluoroacidic acid provides phenol 8. Treatment of 8 in acetonitrile with (trifluorosulfonylmethyl)-phosphonic acid dibenzyl ester 5.1 in the presence of $Cs_2CO_3$ gives 3a.

In Example 3 (FIG. 61), 2-chloro-5-nitro aniline 6.0b is transformed to nitrile 6.31a by reacting with $NaNO_2$ and then CuCN subsequently. Hydrolysis of nitrile 6.31a gives acid 6.41a. Treatment of 6.41a with ClCOOEt in the presence of base at 0° C. followed by $CH_2N_2$ provides diazoketone, which is converted to methyl ester 6.51a upon treating with silver perchlorate in methanol. The ester group is then reduced to give alcohol, which is protected as MOM-ether to provide 6.61c. The nitro group is then reduced to amine to afford 6b. Aniline 6a is converted to efavirenz analog 7.1. Deprotection of the MOM-ether with trifluoroacetic acid provides phenol 9. The aldehyde 10 is obtained by oxidation of alcohol. Reductive amination of 10 with agent 5.2 affords analog 3b.

Figure 62A:
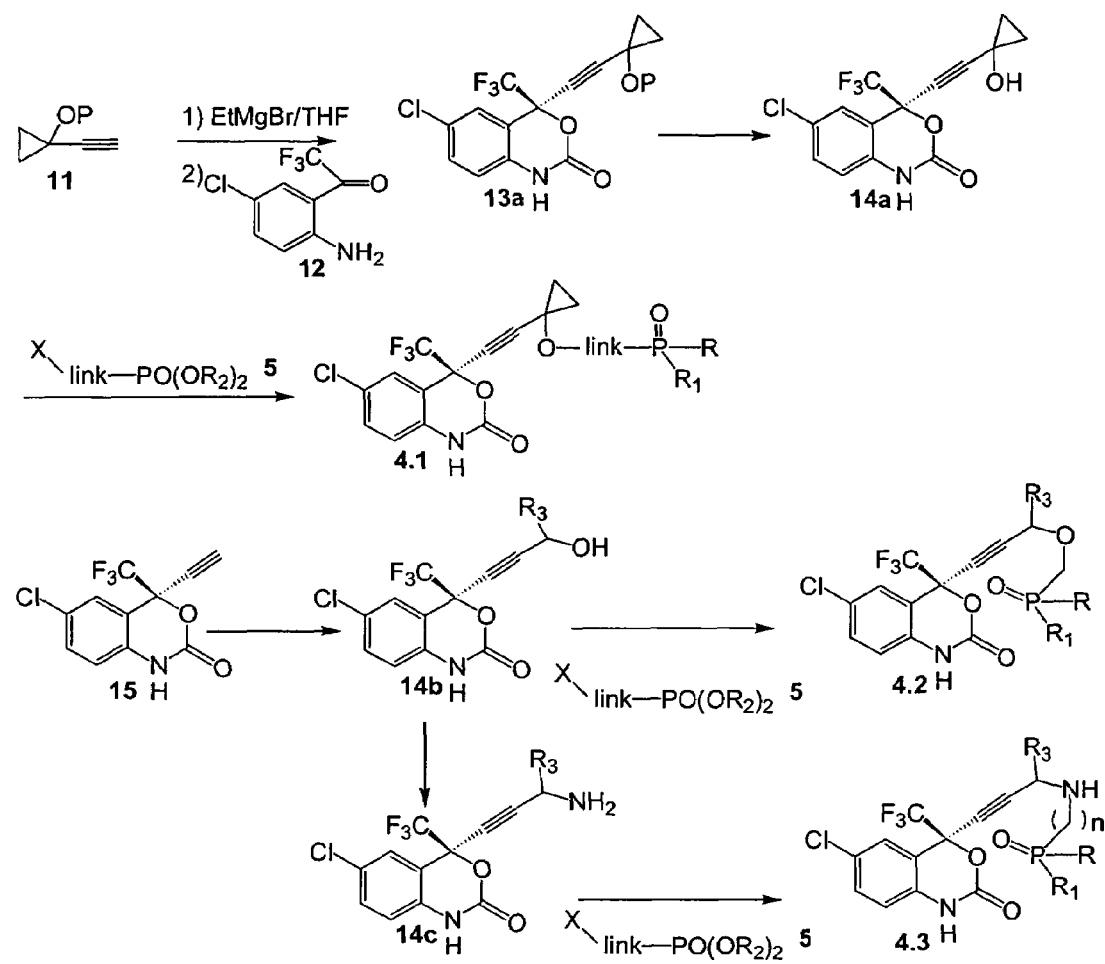
FIGS. 62A-B depict Scheme 4 which is described in detail herein below.
Figure 62B:
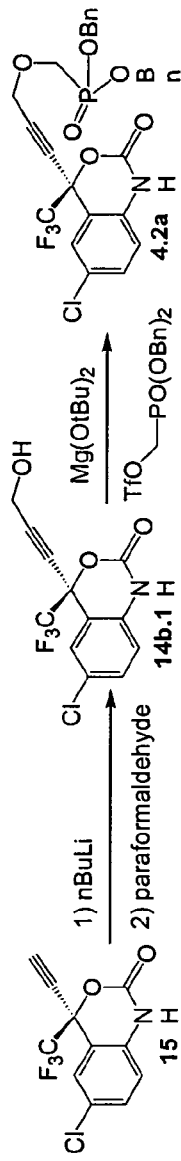

Preparation of compound 2 from efavirenz 1 is outlined in Scheme 4 (FIG. 62). Compound 12, obtained as described in U.S. Pat. No. 5,519,021, reacting with Grignard reagent, generated from protected acetylene 11 following the procedure described in U.S. Pat. No. 5,519,021, gives compound 13a. The hydroxyl group in 11 is protected as its silyl ether, trityl ether etc. Removal of the protecting group of 13a yields alcohol 14a. Alkylation of 14a with agent 5 affords phosphonate 4.1. Alternatively, compound 15, obtained as described in U.S. Pat. No. 5,519,021, reacts with aldehyde or ketone to give alcohol 14b, which is converted to analog 4b using the conditions described above. Amine 14c is obtained from alcohol 14b under the standard conditions. Amine 14c is converted to phosphonate 4c either by reacting with agent 5 or reductive amination with a phosphonate reagents containing an aldehyde group. For example, treatment of compound 14 with n-BuLi followed by paraformaldehyde gives alcohol 14b.1. Treatment of alcohol 14b.1 with Mg(OtBu)$_2$ followed by phosphonate provides phosphonate 4.2b.

Benzophenone-Like Phosphonate NNRTI Compounds

The present invention describes methods for the preparation of phosphonate analogs of benzophenone class of HIV inhibiting pyrimidines shown in Table 13 that are potential anti-HIV agents.

TABLE 13

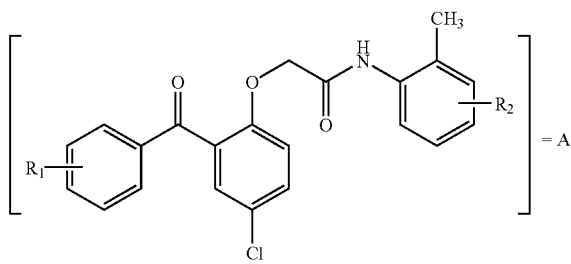

1 GW4751

TABLE 13-continued

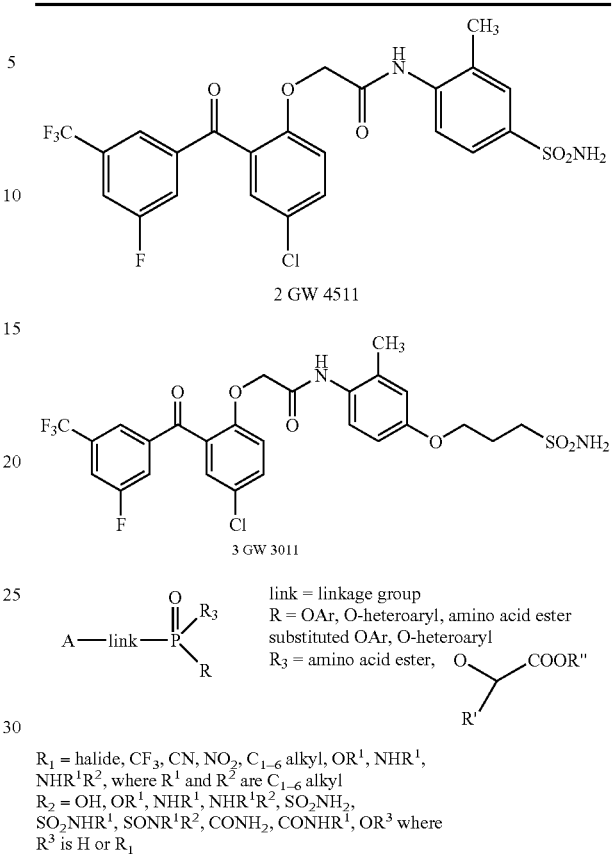

$R_1$ = halide, $CF_3$, CN, $NO_2$, $C_{1-6}$ alkyl, $OR^1$, $NHR^1$, $NHR^1R^2$, where $R^1$ and $R^2$ are $C_{1-6}$ alkyl
$R_2$ = OH, $OR^1$, $NHR^1$, $NHR^1R^2$, $SO_2NH_2$, $SO_2NHR^1$, $SONR^1R^2$, $CONH_2$, $CONHR^1$, $OR^3$ where $R^3$ is H or $R_1$ A link group includes a portion of the structure that links two substructures, one of which is benzophenone class of HIV inhibiting agents having the general formula shown above, the other is a phosphonate group bearing the appropriate R and $R_3$ groups. The link has at least one uninterrupted chain of atoms other than hydrogen.

Benzophenone class of compounds has shown to be inhibitors of HIV RT. The present invention provides novel analogs of benzophenone class of compound. Such novel benzophenone analogs possess all the utilities of benzophenone and optionally provide cellular accumulation as set forth below.

The intermediate phosphonate esters required for conversion into the prodrug phosphonate moieties bearing amino acid, or lactate esters are shown in Table 14.

TABLE 14

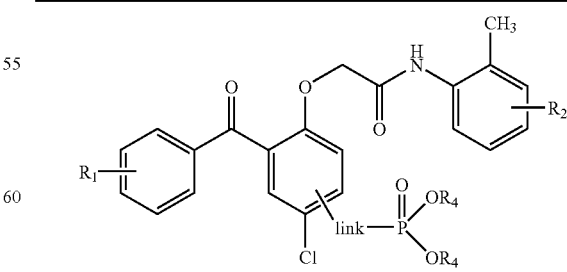

4

TABLE 14-continued

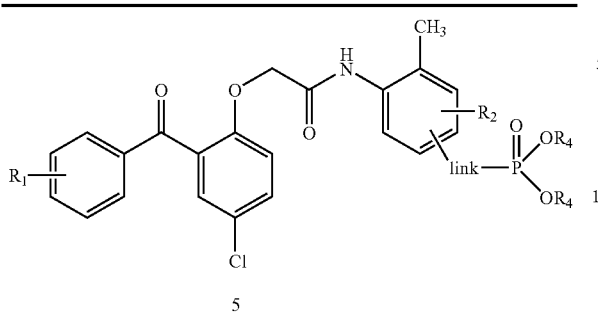

5

Figure 63A:
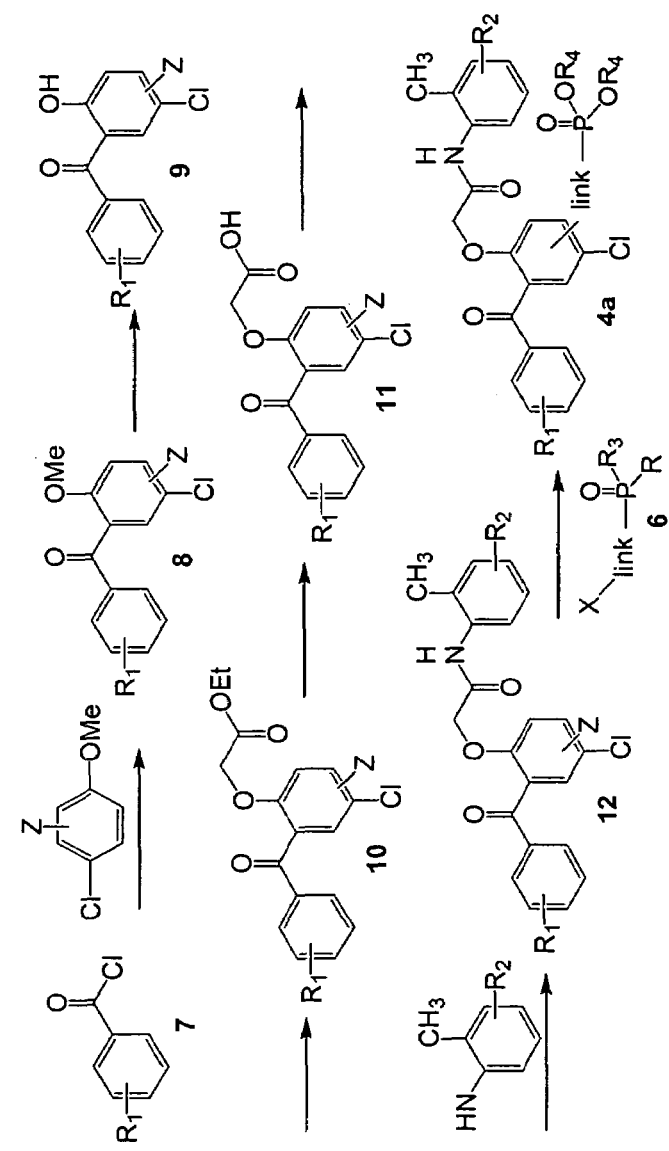
FIGS. 63A-B depict Scheme 1 which is described in detail herein below.
Figure 63B:
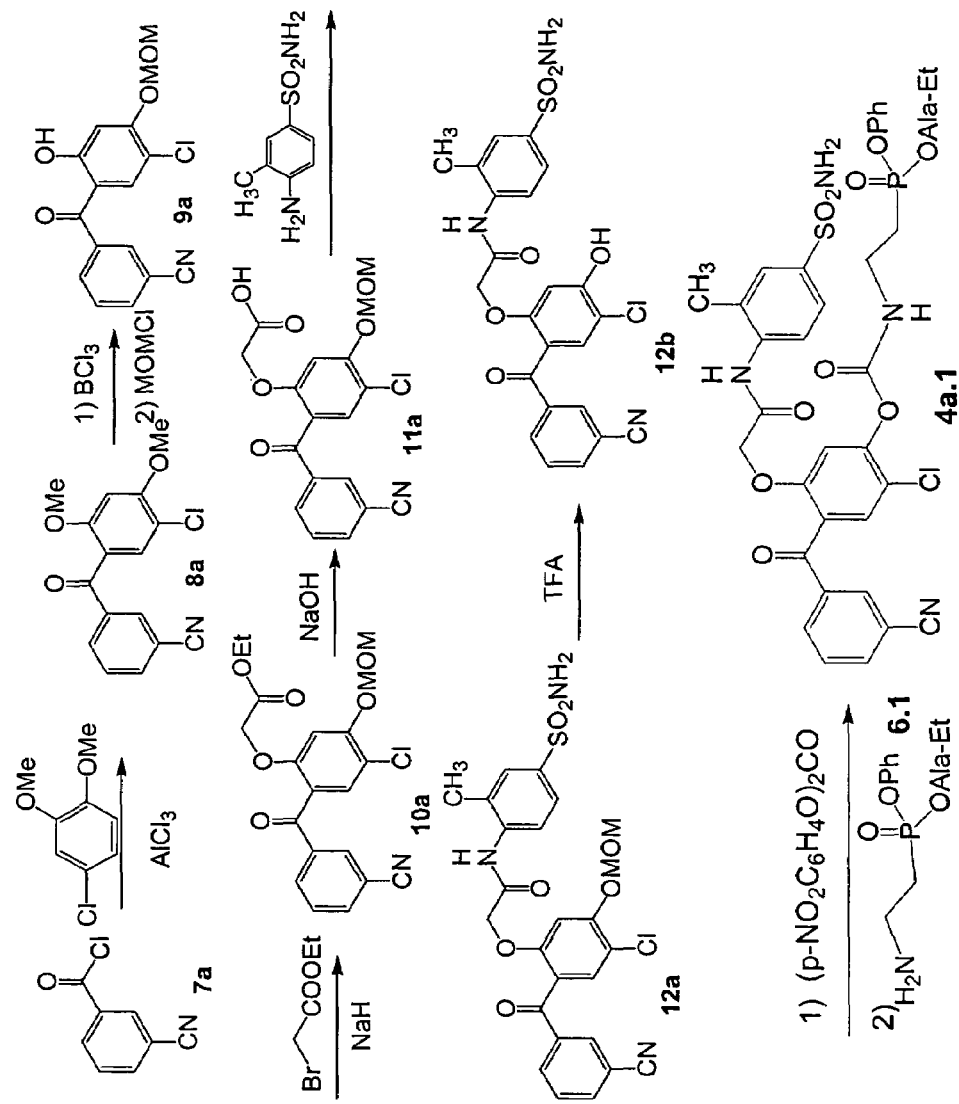

Preparation of phosphonate analog 4 is outlined in Scheme 1 (FIG. 63). Benzophenone 8 is obtained from Freidel-Crafts reaction of substituted benzoyl chloride 7 and 4-chloro-phenol methyl ether which bearing a protected amine or hydroxyl group Z. Phenol ether is obtained by selective protection of commercially available 4-chlorophenol substituted with amino- or hydroxyl group. Benzoyl chloride is obtained either from commercial sources or prepared from commercial available benzoic acid. Benzophenone 8 is also obtained from oxidation of the corresponding alcohol, which in turn is obtained from the reaction of benzaldehyde and anion. Removal of methyl provides phenol 9. Alkylation of phenol with bromoacetate such as ethyl bromoacetate affords ester 10. The ester is then converted to acid. Formation of amide 12 from acid 11 and aniline 10 is achieved following the standard amide formation methods, many examples are described in R. C. Larock, Comprehensive Organic Transformation, John Wiley & Sons, $2^{nd}$ Ed. Removal of the protecting group of Z followed by reacting with reagent 6 affords phosphonate analog 4a.

For example (Example 1; FIG. 63), commercially available 3-cyanobenzoyl chloride is treated with trichloroaluminum followed by 3,4-dimethoxy chlorobenzene to give benzophenone 8a. Treatment of 8 with $BCl_3$ removes the methyl to give diphenol, which is selectively protected as its mono MOM-ether to give 9a. Alkylation of phenol 9a with ethyl bromoacetate gives ester 10a. Hydrolysis of the ester affords acid 11a. Coupling if the acid 11a with aniline produces 12a. The MOM- group is then removed to yield phenol 12b. Phenol is then activated as its 4-nitro-phenyl carbonate by reacting with bis(4-nitro-phenyl)carbonate, which is subsequently treated with aminoethyl phosphonate to give 4a.1.

Figure 64A:
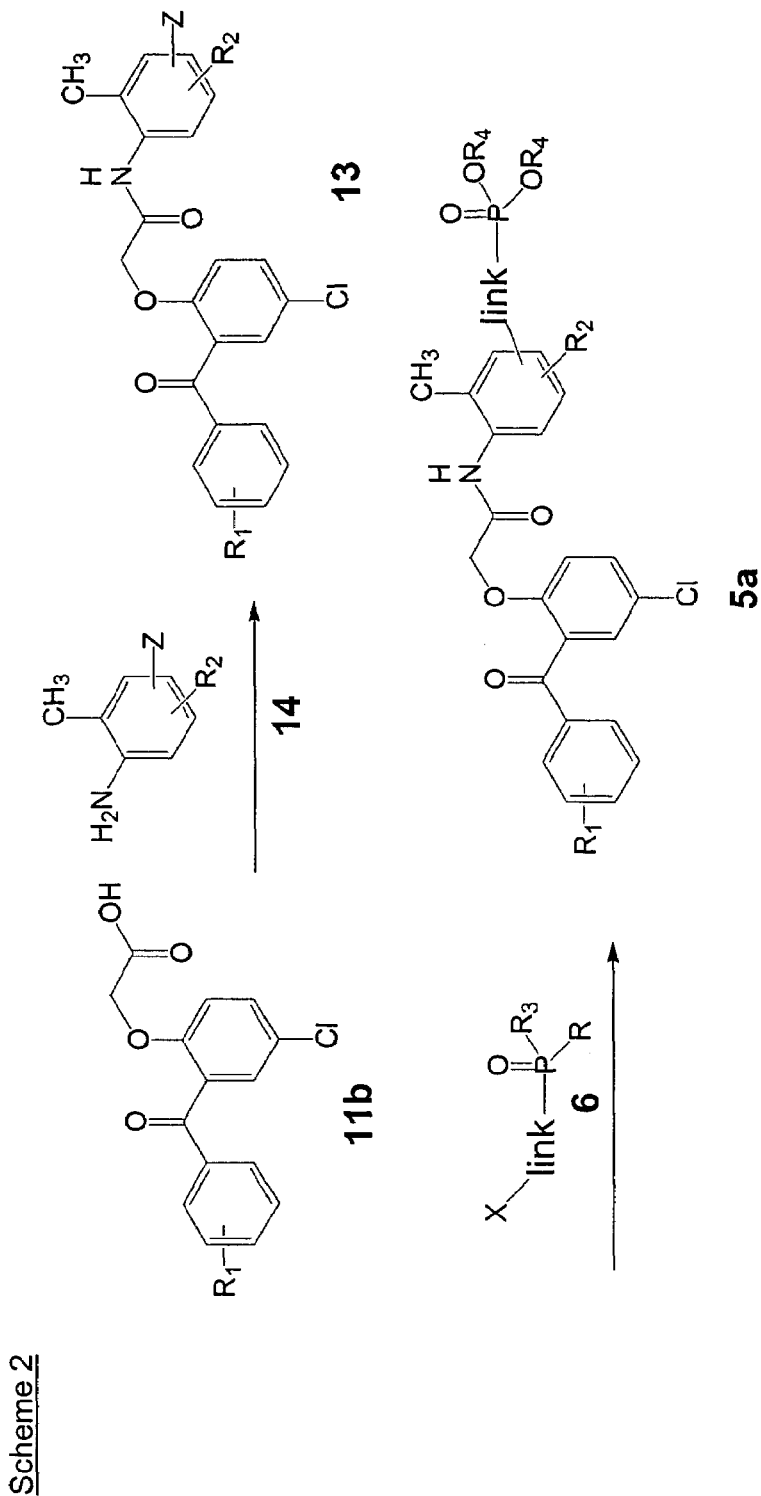
FIGS. 64A-B depict Scheme 2 which is described in detail herein below.
Figure 64B:
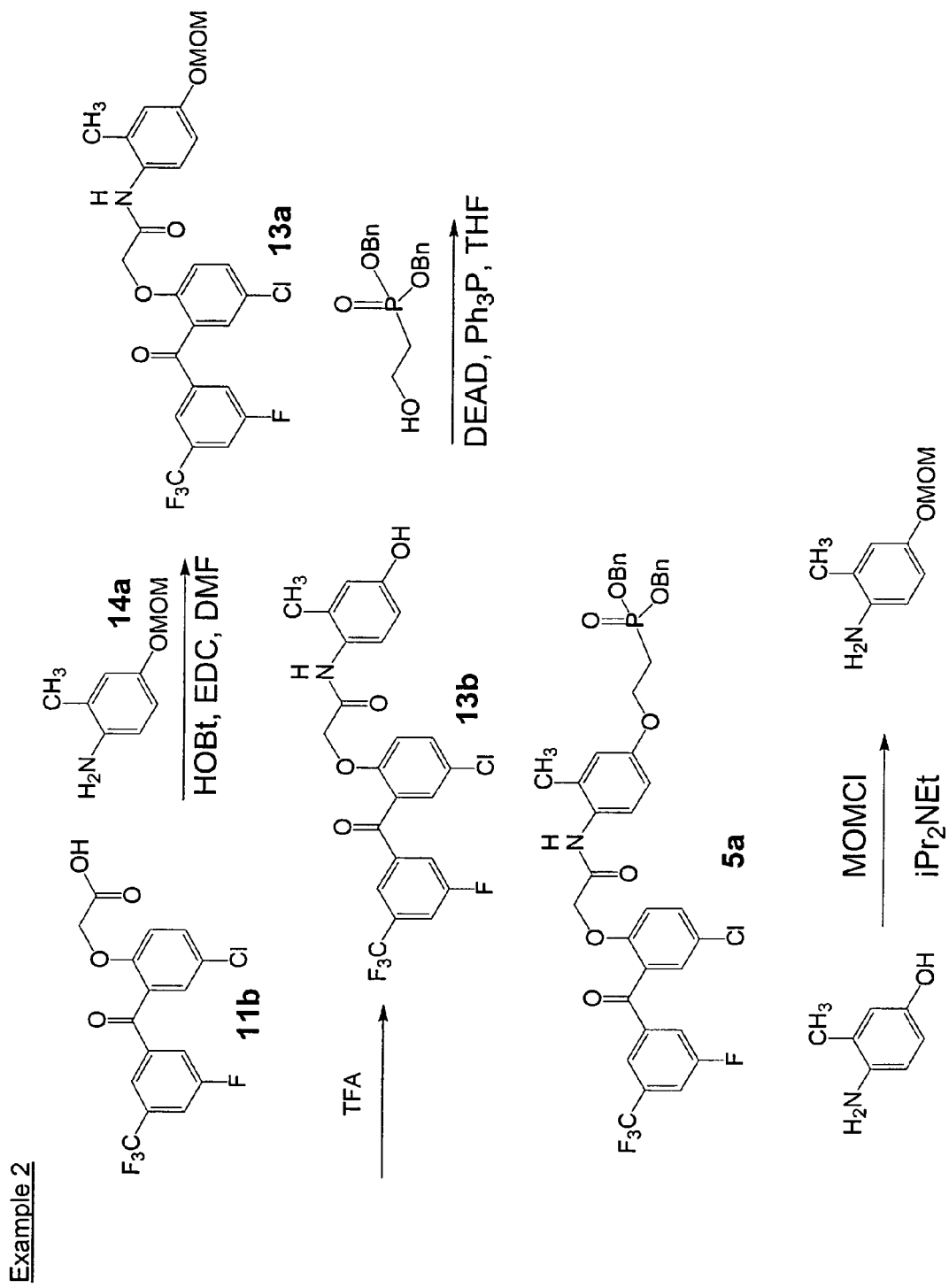

Alternatively (Scheme 2; FIG. 64), amine 10 is transformed to phenol 11 as described in, the hydroxyl group is then serves as the linking site for a suitable phosphonate group.

Scheme 2 (FIG. 64) shows the preparation of phosphonate analog type 5. Benzophenone 11b reacts with aniline 14, bearing a protect hydroxyl or amino group, gives amide 13. Formation of amide 13 from acid 1ib and aniline 14 is achieved following the standard amide formation methods, many examples are described in R. C. Larock, Comprehensive Organic Transformation, John Wiley & Sons, $2^{nd}$ Ed. Removal of the protecting group of Z followed by reacting with reagent 6 affords phosphonate analog 5a. For example (Example 2; FIG. 64), acid 11b couples with aniline 14 provides amide 13a. The MOM-group is then deprotected with TFA to afford phenol 13b, which is then coupled with hydroxy ethyl phosphonic acid dibenzyl ester in the presence of Ph3P/DEAD to give phosphonate 5a. Protected aniline 14a is obtained by treating the commercially available 4-amino-m-cresol with MOMCl in the presence of base, for example Hunig's base.

Pyrimidine-Like Phosphonate NNRTI Compounds

The present invention includes Pyrimidine-like phosphonate NNRTI compounds. The present invention also includes methods for the preparation of phosphonate analogs of TMC-125 and TMC-120 class of HIV inhibiting pyrimidines as shown in Table 15 which are potential anti-HIV agents.

TABLE 15

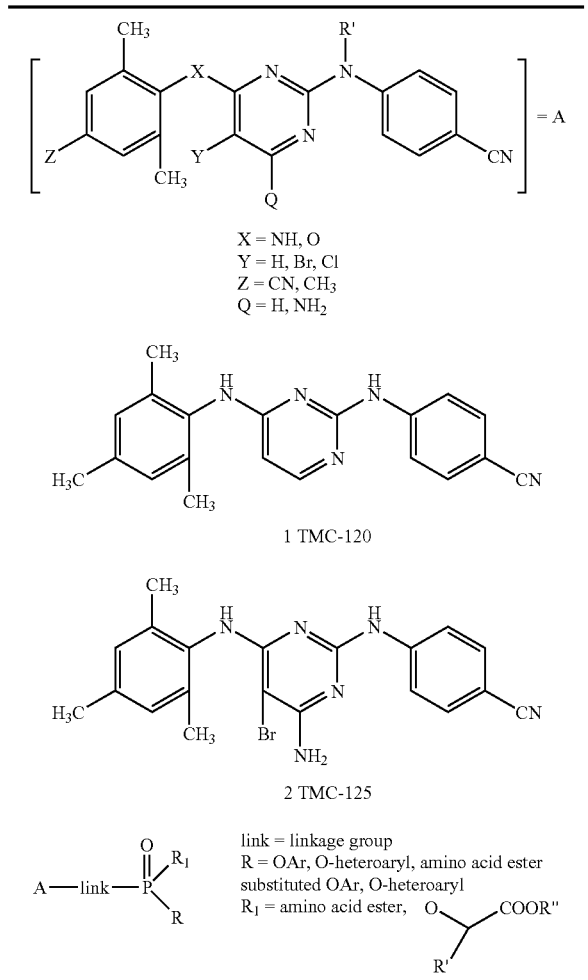

A link group includes a portion of the structure that links two substructures, one of which is TMC-120 and TMC-125 class of pyrimidines having the general formula shown above, the other is a phosphonate group bearing the appropriate R and R1 groups. The link has at least one uninterrupted chain of atoms other than hydrogen.

TMC-125 and TMC-120 class of pyrimidines have demonstrated to be potent in inhibition of HIV replication. Both TMC-125 and TMC-120 are currently in clinical phase II studies for treatment of HIV infection and AIDs. The present invention provides novel analogs of TMC-120 and TMC-125 class of compound. Such novel TMC-120 and TMC-125 class analogs possess all the utilities of TMC-120 and TMC-125 class and optionally provide cellular accumulation as set forth below.

The intermediate phosphonate esters required for conversion into the prodrug phosphonate moieties bearing amino acid, or lactate esters are shown in Table 16.

TABLE 16

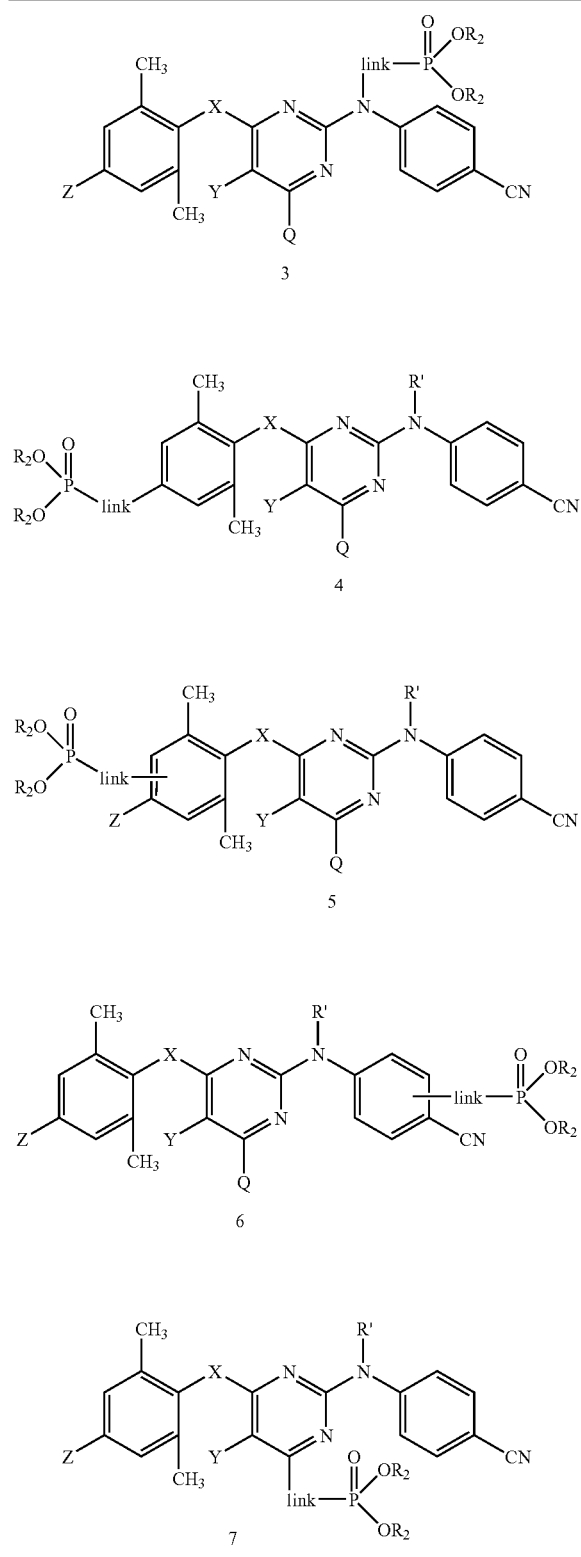

TABLE 16-continued

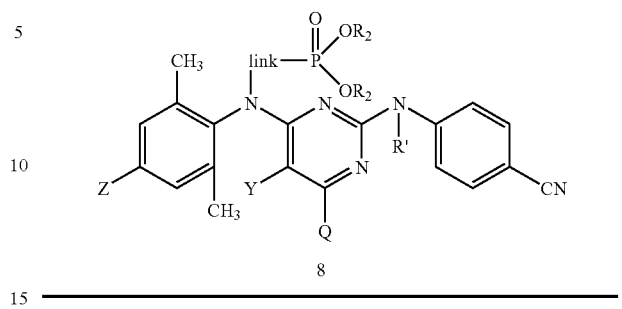

Figure 65A:
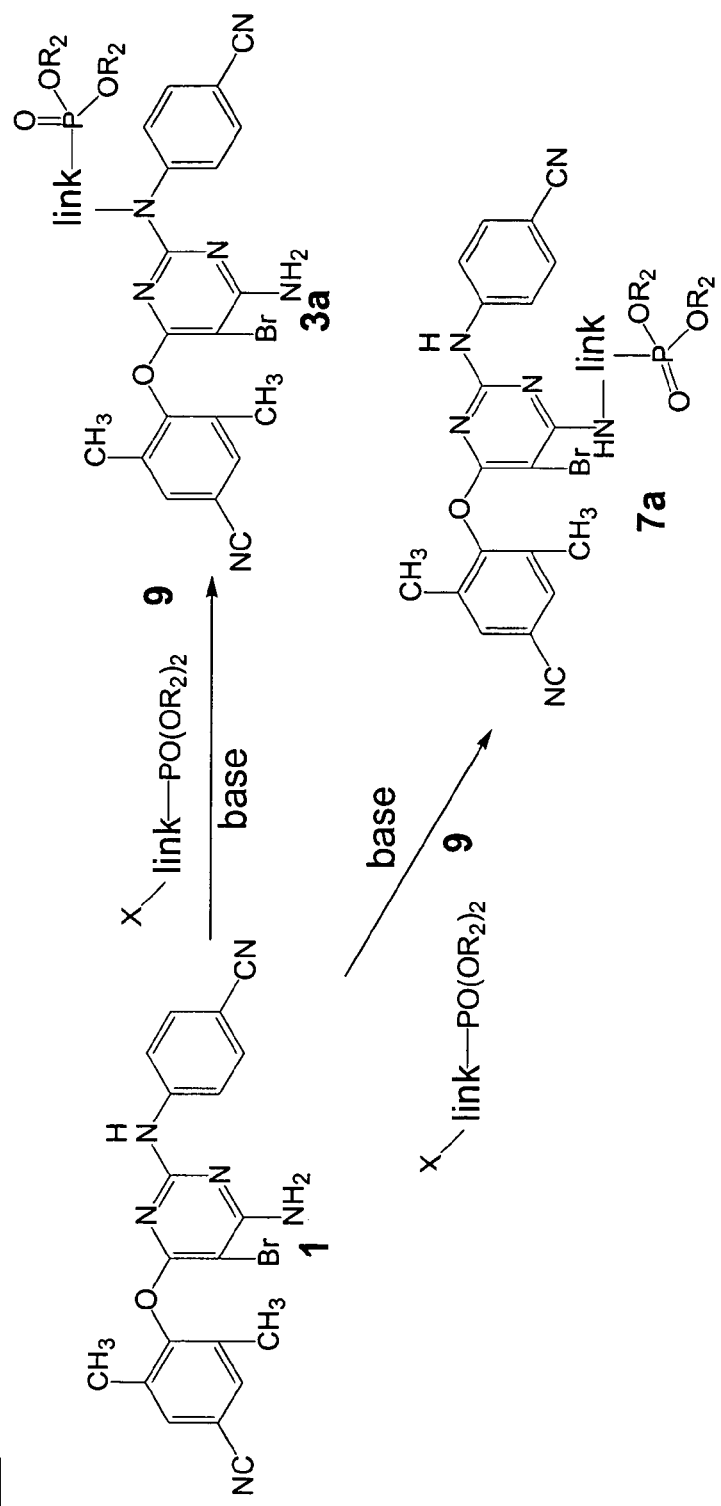
FIGS. 65A-B illustrate Scheme 2 which is described in detail herein below.
Figure 65B:
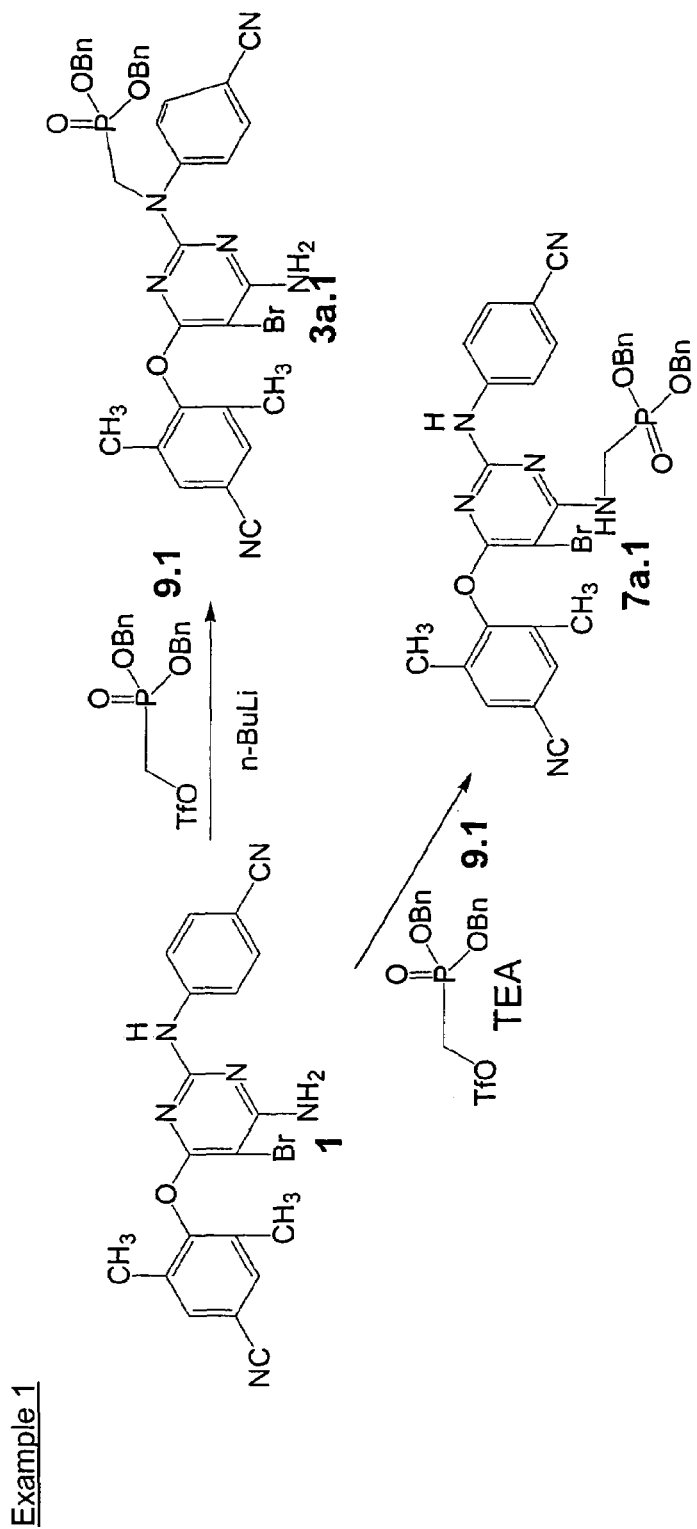

Compounds 1 and 2 can be synthesized as described in U.S. Pat. No. 6,197,779 and WO 0027825. Preparation of phosphonate analog 3 and 7 is outlined in Scheme 1 (FIG. 65). TMC-125 1 is dissolved in suitable solvent such as, for example, DMF or other protic solvent, and treated with the phosphonate reagent 9, bearing a leaving group, such as, for example, bromine, mesyl, tosyl, or trifluoromethanesulfonyl in the presence of a suitable organic or inorganic base, either 3a or 7a is obtained as the major product depending on the base. For example, 1 was dissolved in DMF, is treated with n-butyl lithium and 1 equivalent of triflate methyl phosphonic acid dibenzyl ester 9.1 prepared to give phosphonate 3a.1 as the major product. Alternatively, treatment of 1 with 9.1 in acetonitrile in the presence of triethylamine provides 7a.1 as the major product. The above procedure provides phosphonate analog 3 in which the linkage is a methylene group. Using the above procedure but employing different phosphonate reagents 9 in place of 9.1, the corresponding products 3 and 7 are obtained bearing different linking group.

Figure 66A:
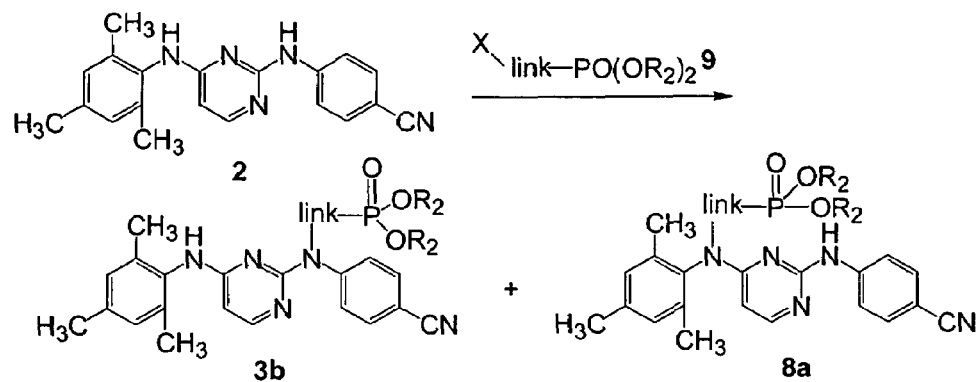
FIGS. 66A-B depict Scheme 2 which is described in detail herein below.
Figure 66B:
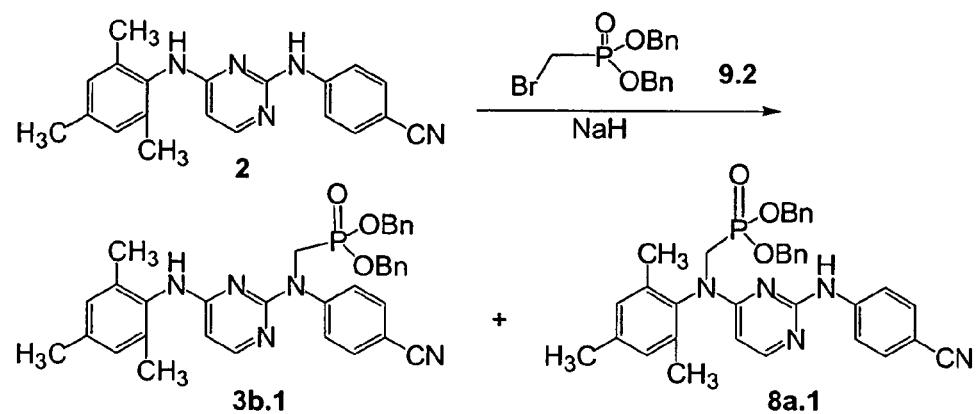

Scheme 2 (FIG. 66) shows the preparation of phosphonate conjugates compounds type 3 and 8 in Table 16. TMC-120 2 is treated with base, and subsequently treated with phosphonate reagent 9 bearing a leaving group, such as, for example, bromine, mesyl, tosyl, or trifluoromethanesulfonyl. The alkylated products are then separated by chromatography. For example (Example 2; FIG. 66), treatment of TMC-120 2 with NaH in DMF, followed by bromomethyl phosphonic acid dibenzyl ester 9.2 gives phosphonate 3b.1 and 8a.1. The mixture of phosphonates 3b.1 and 8a.1 is separated by chromatography to give pure 3b.1 and 8a.1 respectively.

Figure 67:
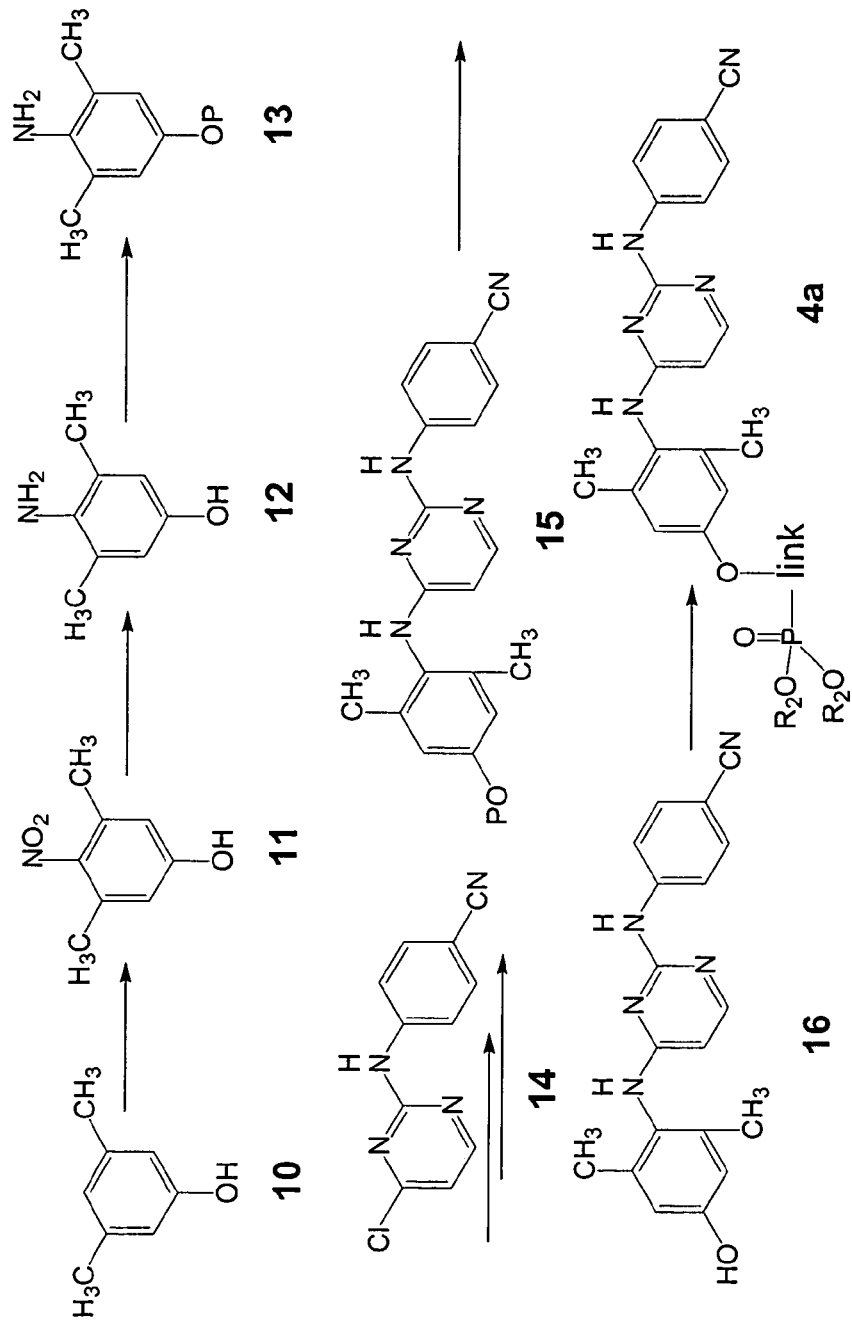
FIG. 67 depicts Scheme 3 which is described in detail herein below.
Figure 68:
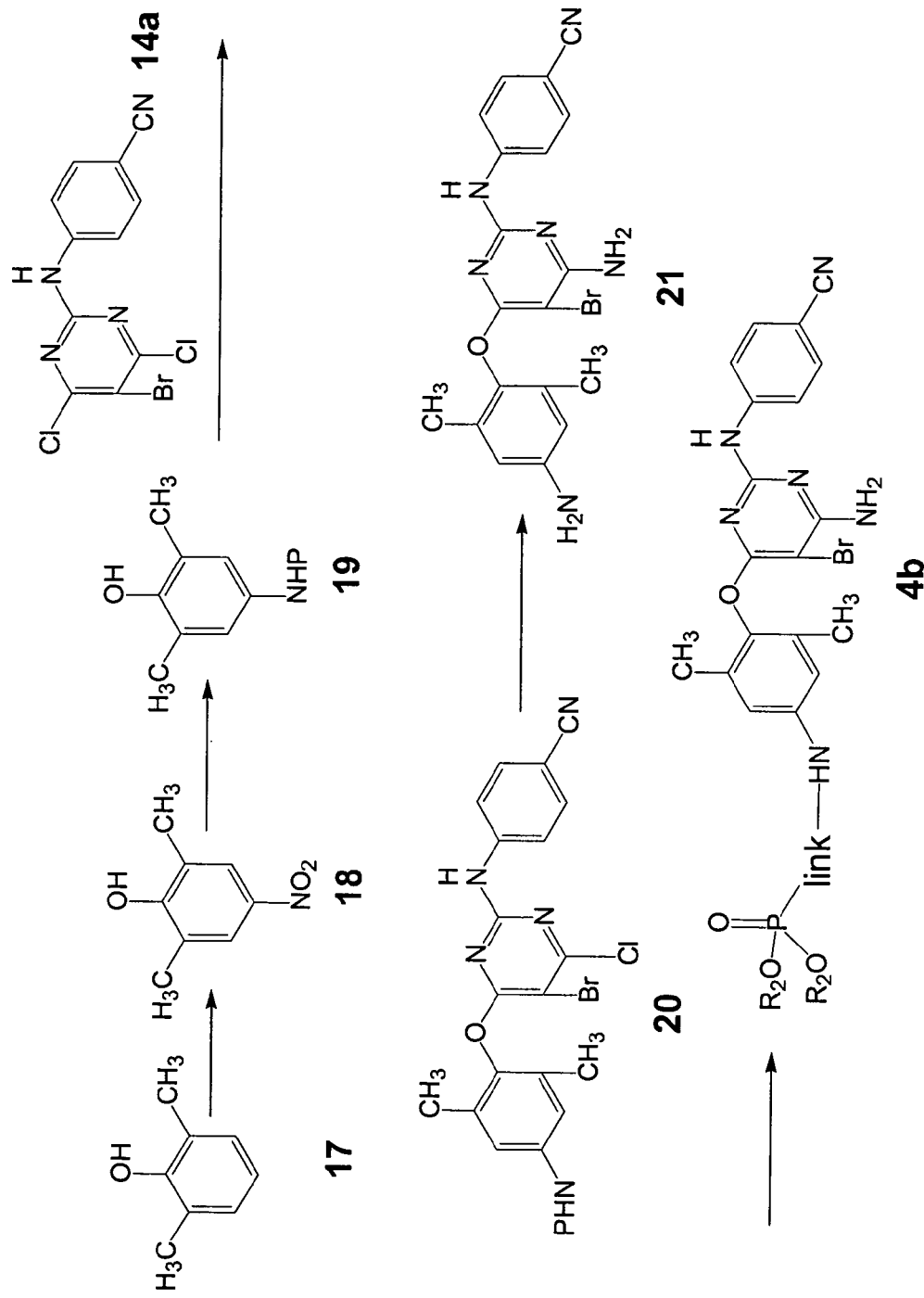
FIG. 68 depicts Scheme 4 which is described in detail herein below.
Figure 69A:
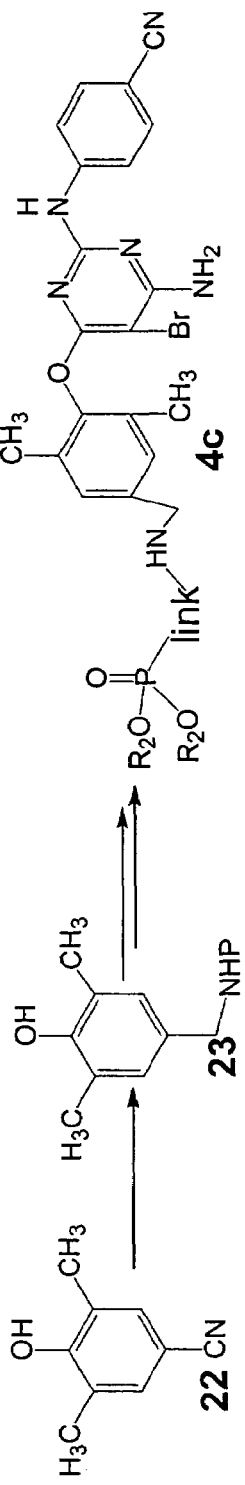
FIGS. 69A-B depict Scheme 5 which is described in detail herein below.
Figure 69B:
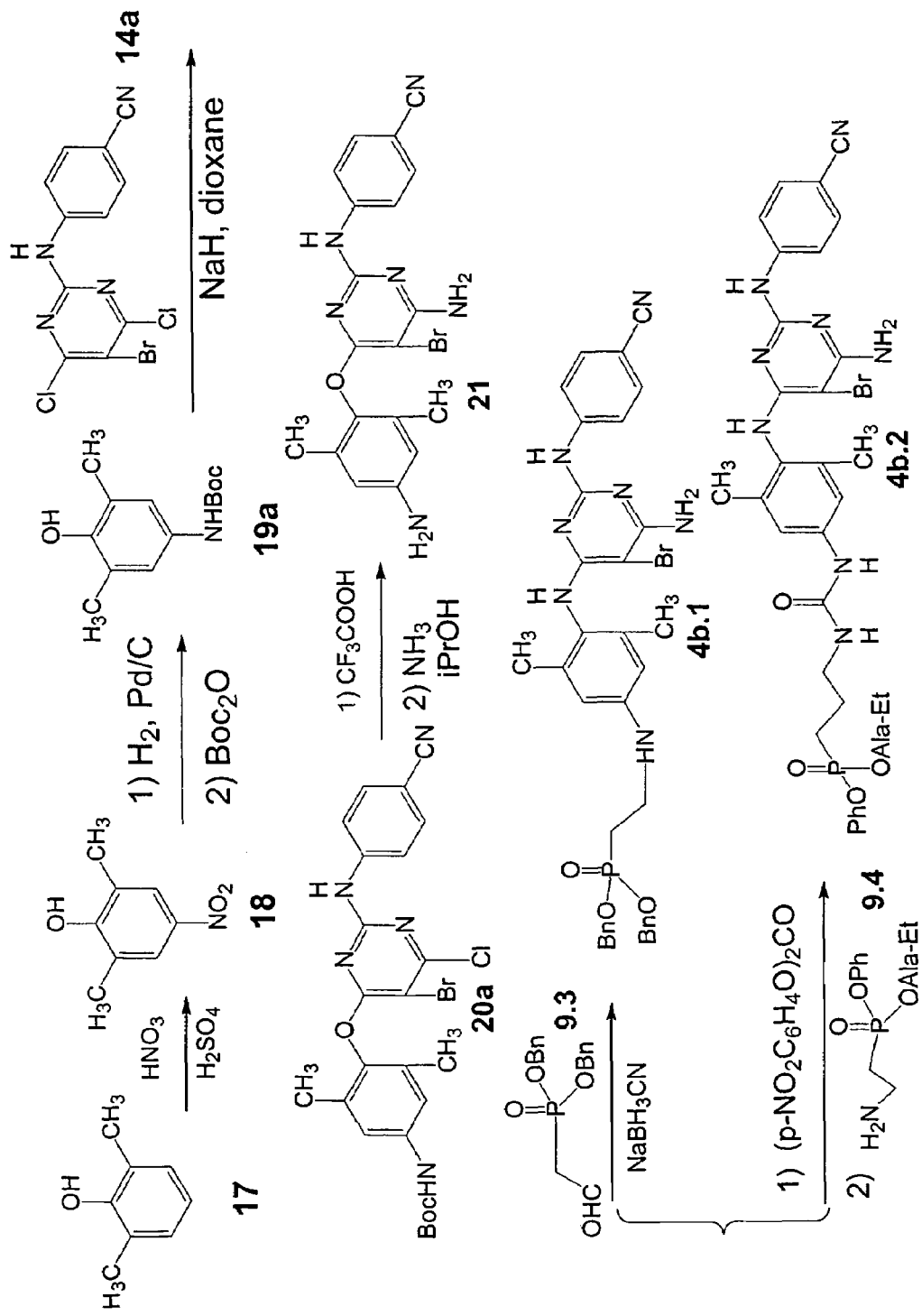

Preparation of phosphonate analogs type 4 in Table 16 is shown in Scheme 3 (FIG. 67), 4 (FIG. 68) and 5 (FIG. 69). Nitration of commercially available 3,5-dimethyl phenol 10 gives 11, subsequent reduction of the resulting nitrobenzene 11 provide 12, many examples are described in R. C. Larock, Comprehensive Organic Transformation, John Wiley & Sons, $2^{nd}$ Ed. The hydroxyl group of phenol 12 is protected with a suitable protecting group, for example trityl, silyl, benzyl or MOM- etc to give 13 as described in Greene and Wuts, Protecting Groups in Organic Synthesis, $3^{rd}$ Edition, John Wiley and Sons Inc. Treatment of 14 with 13 following the procedures described in U.S. Pat. No. 6,197,779 and WO 0027825 give 15. Removal of the protecting group gives phenol 16. Reaction of phenol 16 with phosphonate reagent 9 in the presence of base in a protic solvent provides 4a. Nitration (Scheme 4; FIG. 68) of commercially available 2,6-dimethyl phenol provides 18. Reduction of nitro group to amine, followed by protection of the resultant amine with protecting group, for example, such as trityl, Boc, Cbz etc as described in Greene and Wuts, Protecting Groups in Organic Synthesis, $3^{rd}$ Edition, John Wiley and Sons Inc. Treatment of 14a with 19 following the procedures described in U.S. Pat. No. 6,197,779 and WO 0027825 give 20. Phenol 21 is obtained by treating 20 with NH3 using the procedure described in U.S. Pat. No. 6,197,779 and WO 0027825, followed by removal of the protecting group. Reaction of phenol 21 with phosphonate reagent 9 provides 4b. As shown in Scheme 5, the commercially available 2,6-dimethyl-4-cyanophenol 22 is reduced to benzyl amine, and the resultant amine is protected as described above. Phenol 23 is converted to phosphonate 4c following the procedure described above for the transformation 19 to 4b, just replace 19 with 23. For example (Example 3; FIG. 69), nitration of 2,6-dimethyl phenol with $HNO_3$ in $H_2SO_4$ gives phenol 18. The nitro group is reduced under catalytic hydrogenation condition, and subsequent protection of the resulting amine with Boc- gives phenol 19a. Treatment of phenol 18 with sodium hydride, followed by reacting the resulting sodium phenoxide with 13 in dioxane provides 20a. Removal of the Boc- with TFA followed by treatment of the resulting product with NH3 in isopropyl alcohol according to U.S. Pat. No. 6,197,779 and WO 0027825 replaces the Cl— with $NH_2$ group to give 21. The amine group in the phenyl ring is used as attachment site for introduction of phosphonate. Reductive amination of amine with aldehyde 9.3 provides 4b.1. Treatment of 21 with p-nitro-phenyl carbonate, followed by aminoethyl phosphonate 9.4 affords urea linker 4b.2.

Figure 70A:
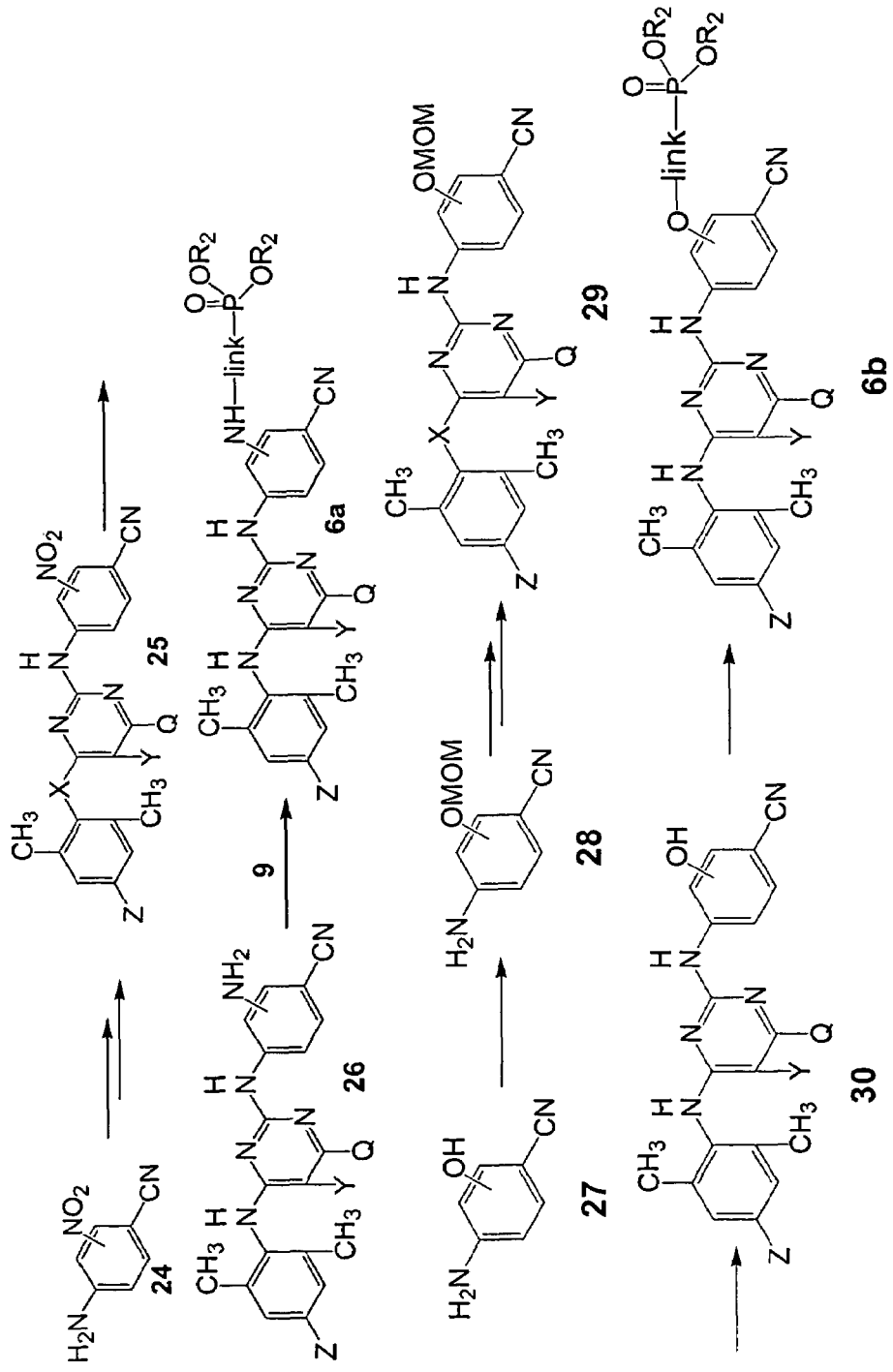
FIGS. 70A-B depict Scheme 6 which is described in detail herein below.
Figure 70B:
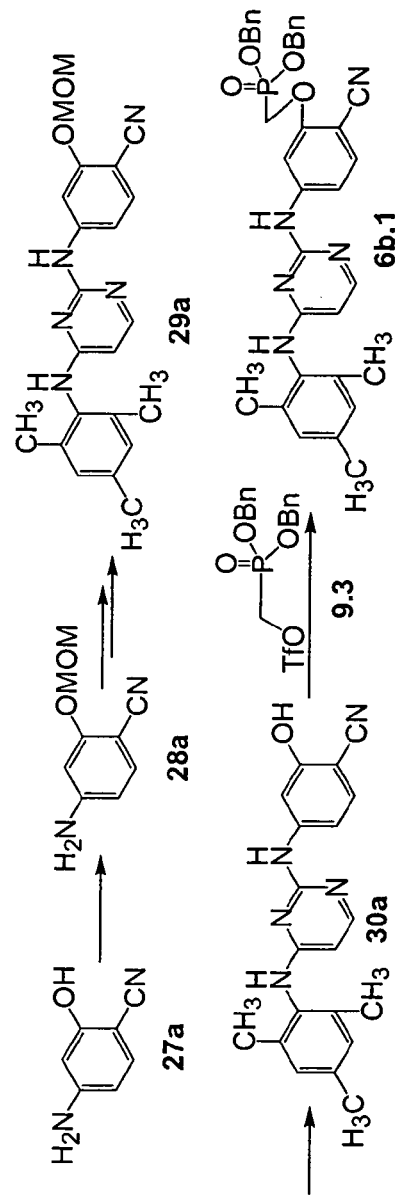

Scheme 6 (FIG. 70) shows the preparation of phosphonate type 6 in Table 16. Substituted 4-amino-benzonitriles 24 or 27, which bearing a protected amino or hydroxyl group, or a precursor of amino group, are used in the replacement of 4-amino-benzonitrile for the preparation of TMC-125 and TMC-120 class of analogs as described in U.S. Pat. No. 6,197,779 and WO 0027825. TMC-120 and TMC-125 analogs 25 and 29 are thus obtained. Removal of protecting group or conversion to amine group from a precursor, such as a nitro group, provide 26 or 30 respectively. Treatment of 26 and/or 30 with reagent 9 yield 6a and/or 6b respectively. For example (Example 4; FIG. 70), the hydroxyl group of 4-amino-2-hyroxy-benzonitrile 27a is protected as its MOM-ether to give 28a. Following the procedure in U.S. Pat. No. 6,197,779 and WO 0027825, 28a is converted to TMC-120 analog 29a. Removal of MOM-ether with TFA provides phenol 30a, which is treated with trifluoromethylsulfonyl phosphonic acid benzyl ester together with $Cs_2CO_3$ in acetonitrile affords phosphonate analog 6b.1.

Figure 71A:
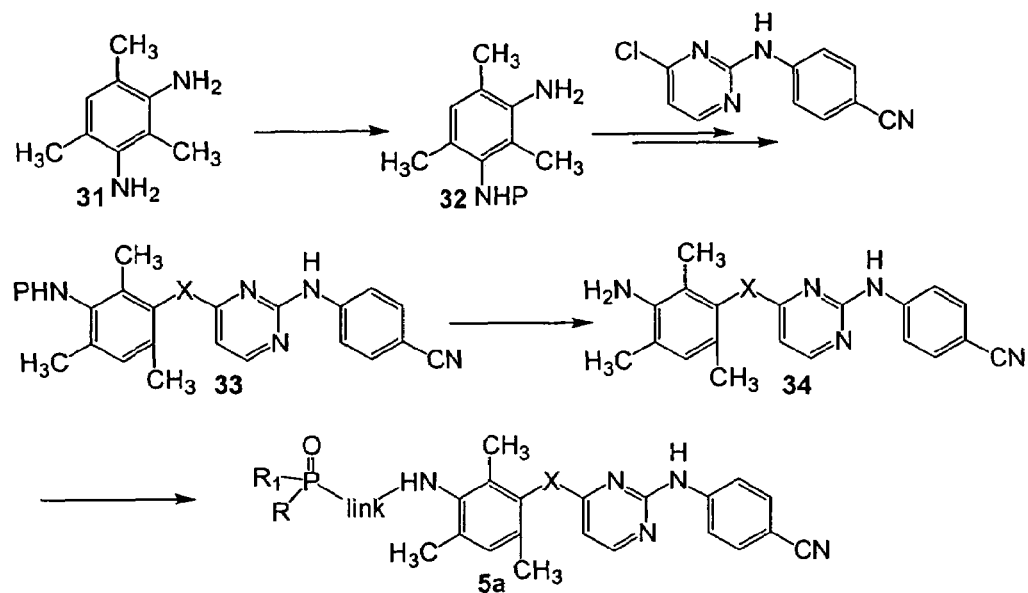
FIGS. 71A-B illustrate Scheme 7 which is described in detail herein below.
Figure 71B:
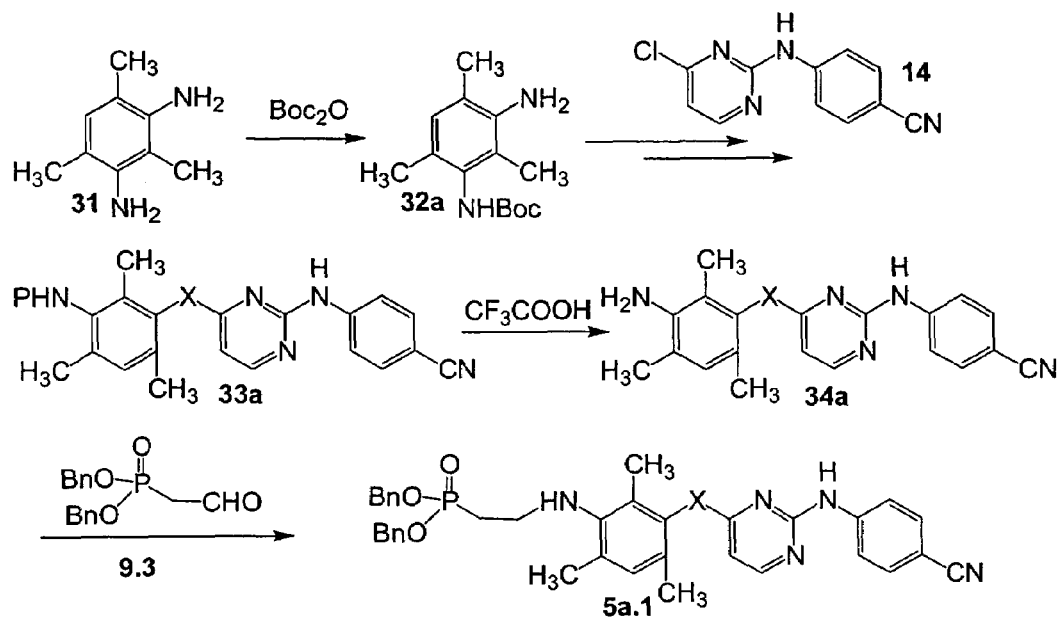

Preparation of phosphonate analog type 5 in Table 16 is shown in Scheme 7 (FIG. 71). Substituted aniline, which bearing a protected amino or hydroxyl group, is converted to TMC-120 or TMC-125 analogs following the procedures described in U.S. Pat. No. 6,197,779 and WO 0027825. Removal of the protecting group gives analog 34. The amino or hydroxyl group in 33 serves as attachment site for introduction of phosphonate. Reaction of 33 with reagent 9 provides 5a. For example (Example 5; FIG. 71), commercially available 2-amino-2,4,6-trimethyl-aniline is selectively protected as Boc- carbamate. Reaction of 32a with 13 provides 33a. Removal of Boc with TFA affords aniline 34a. Reductive amination with reagent 9.2 yields phosphonate analog 5a.1.

SJ3366-Like Phosphonate NNRTI Compounds

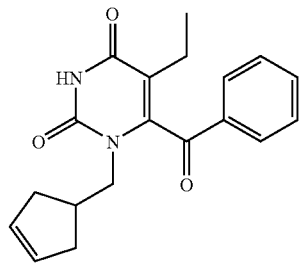

SJ3366

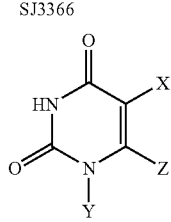

X = alkyl $C_1$–$C_{12}$ branched or straight
Y = alkyl, alkoxy, with or without link-PO($R_1$)($R_2$)
Z = $Y_2$-link-PO($R_1$)($R_2$) or
    $Y_2$-Aryl (optionally substituted)
    or $Y_2$-alkyl
$Y_2$ = $CR_2$, O, S, NR (R = H, alkyl $C_1$–$C_{12}$), C = O, COH

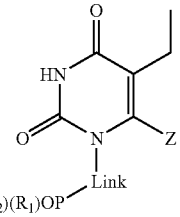

Type A [Y = link PO($R_1$)($R_2$)]

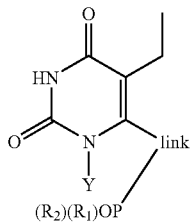

Type B [Z = link PO($R_1$)($R_2$)]

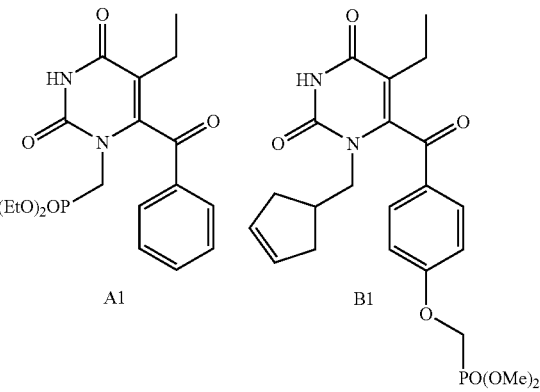

A1                                B1

SJ3366 is described in U.S. Pat. No. 5,922,727. The present invention provides novel phosphonate analogs of SJ3366 which possess all the utilities of SJ3366 and optionally provide cellular accumulation as set forth below.

The present invention also relates to the delivery of SJ3366-like phosphonate compounds which are optionally targeted for site-specific accumulation in cells, tissues or organs. More particularly, this invention relates to analogs of SJ3366 which comprise SJ3366 linked to a $PO(R_1)(R_2)$ moiety.

SJ3366 may be covalently bonded directly or indirectly by a link to the $PO(R_1)(R_2)$ moiety. An R group of the $PO(R_1)(R_2)$ moiety can possibly be cleaved within the desired delivery site, thereby forming an ionic species which does not exit the cell easily. This may cause accumulation within the cell and can optionally protect the SJ3366 analog from exposure to metabolic enzymes which would metabolize the analog if not protected within the cell. The cleavage may occur as a result of normal displacement by cellular nucleophiles or enzymatic action, but is preferably caused to occur selectively at a predetermined release site. The advantage of this method is that the SJ3366 analog may optionally be delivered site-specifically, may optionally accumulate within the cell and may optionally be shielded from metabolic enzymes.

The following examples illustrate various aspects of the present invention and are not to be construed to limit the types of analogs that may employ this strategy of linking SJ3366 or an SJ3366 analog to a $PO(R_1)(R_2)$ moiety in any manner whatsoever.

Preparation of compounds of type A require a link which can react with SJ3366 or an intermediate or analog thereof, to result in a covalent bond between the link and the drug-like compound. The link is also attached to the phosphorous containing moiety as shown in an example of type A, namely A1.

Examples of type A can be made by 1-alkylation of the 3-phenacyl derivatives 35 and 36 (synthesis described in J. Med. Chem. 1995, 38, 1860-2865, and so numbered 35 and 36 therein) with alkyl halide containing links followed by deprotection of the 3-phenacyl group.

Figure 72:
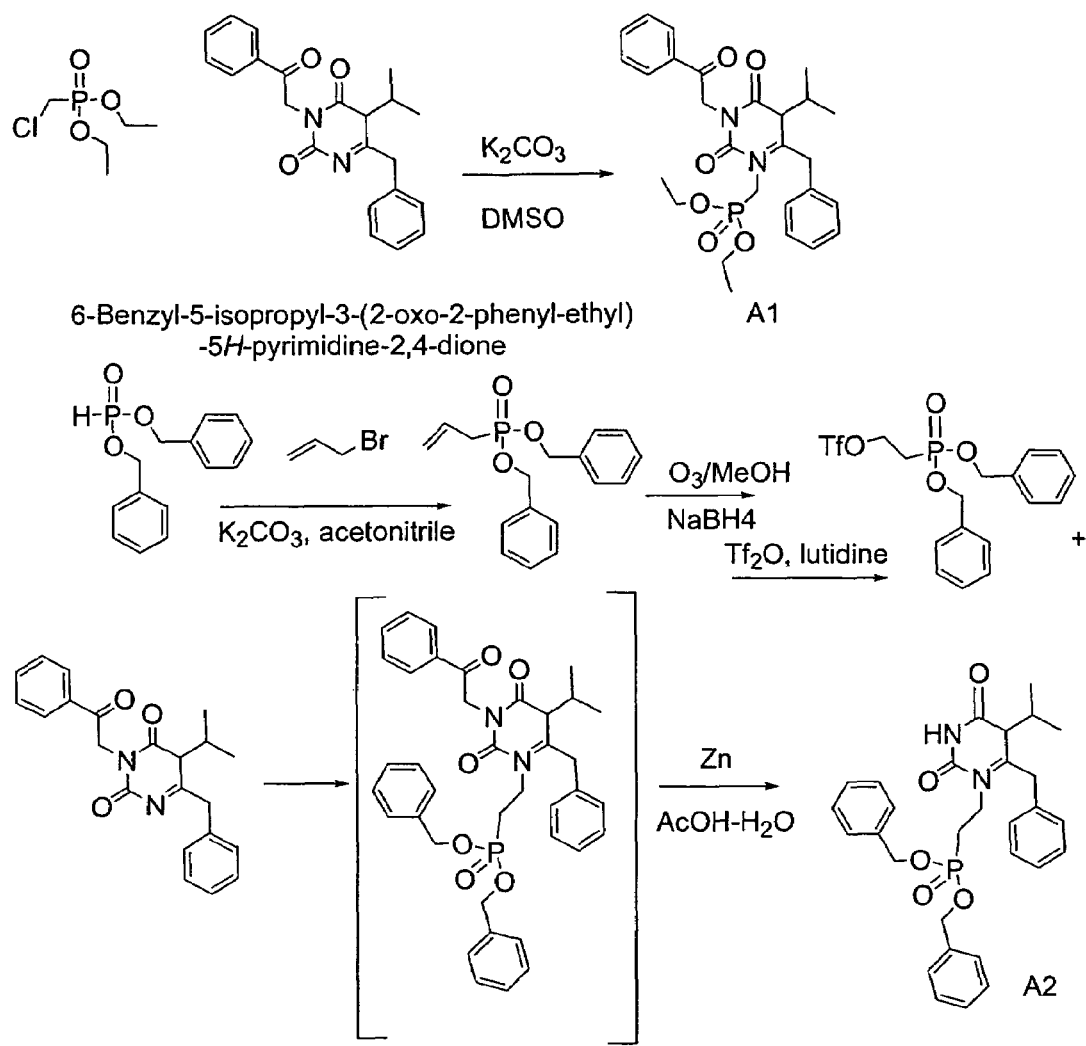
FIG. 72 depicts Scheme 1 which is described in detail herein below.

An example synthesis is as follows, and is shown in Scheme 1 (FIG. 72). 6-Benzyl-5-isopropyl-3-(2-phenyl-allyl)-dihydro-pyrimidine-2,4-dione, as prepared in J. Med. Chem. 1995, 38, 15, 2860-2865, is treated analogously to the reference article authors' treatment in preparing their compounds 37-40, but in the case of compound A1, commercially available chloromethyldiethylphosphonate is used as the alkylating agent. Alternatively the link is connected by starting with the same drug-like compound and using a triflated link. The triflated link is prepared, for example, by reaction of allyl bromide with dibenzylphosphite and potassium carbonate in acetonitrile at 65° C. Ozonolysis of the double bond followed by treatment with sodium borohydride would provide the alcohol, which could then be reacted with triflic anhydride with 2,6 lutidine in dichloromethane to produce the triflate. The triflated material could then be attached by stirring it with, for example 6-Benzyl-5-isopropyl-3-(2-phenyl-allyl)-dihydro-pyrimidine-2,4-dione with 2,6 lutidine or other base in an appropriate solvent such as acetone. This procedure will provide examples A1 and A2.

Scheme 1 (FIG. 72) can be extended to include analogs with various moieties at C6 in addition to substituted benzyl rings. For example, the LDA treatment described in J. Med. Chem. 1995, 38, 15, 2860-2865 followed by disulfide addition provides intermediates which can then be treated similarly to those in scheme 1 (FIG. 72) to install the link $PO(R_1)(R_2)$ at the 1 position.

Figure 74:
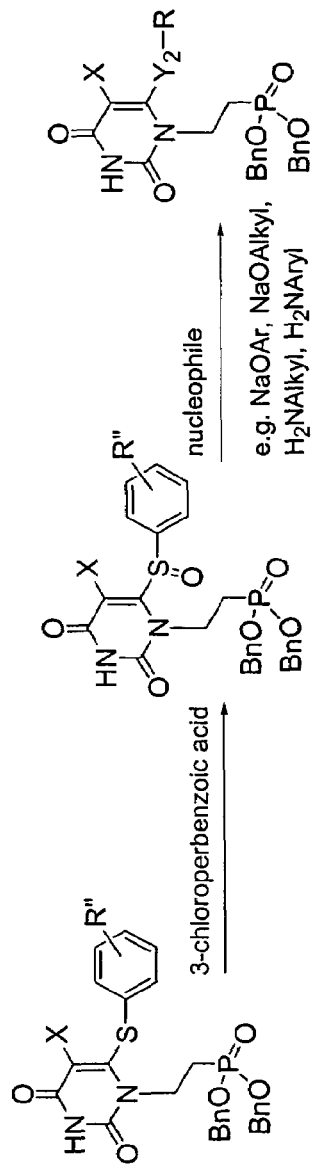
FIG. 74 depicts Scheme 3 which is described in detail herein below.

Scheme 3 (FIG. 74) also demonstrates a method to prepare analogs with oxygen or nitrogen at $Y_2$ attached to the 6 position. This method is explained fully in J. Med. Chem. 1991, 34,1, 349-357. Using this method allows for aryl and alkyl groups to be attached to the 6 position by either oxygen or nitrogen. A specific example is shown in the bottom row of the boxes in Scheme 7 below.

Figure 73:
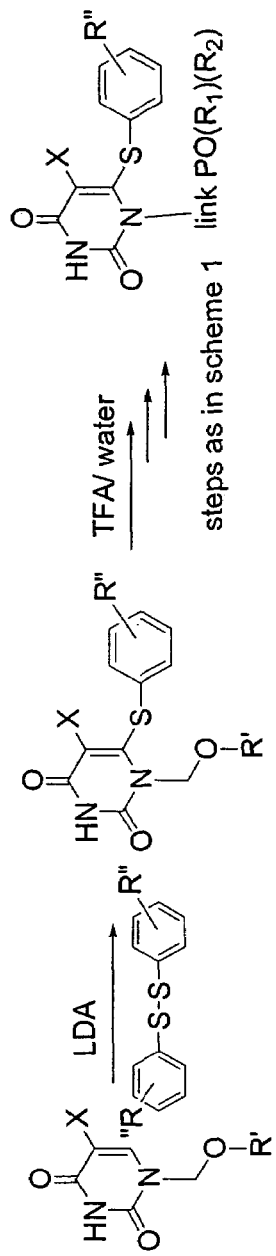
FIG. 73 depicts Scheme 2 which is described in detail herein below.
Figure 75:
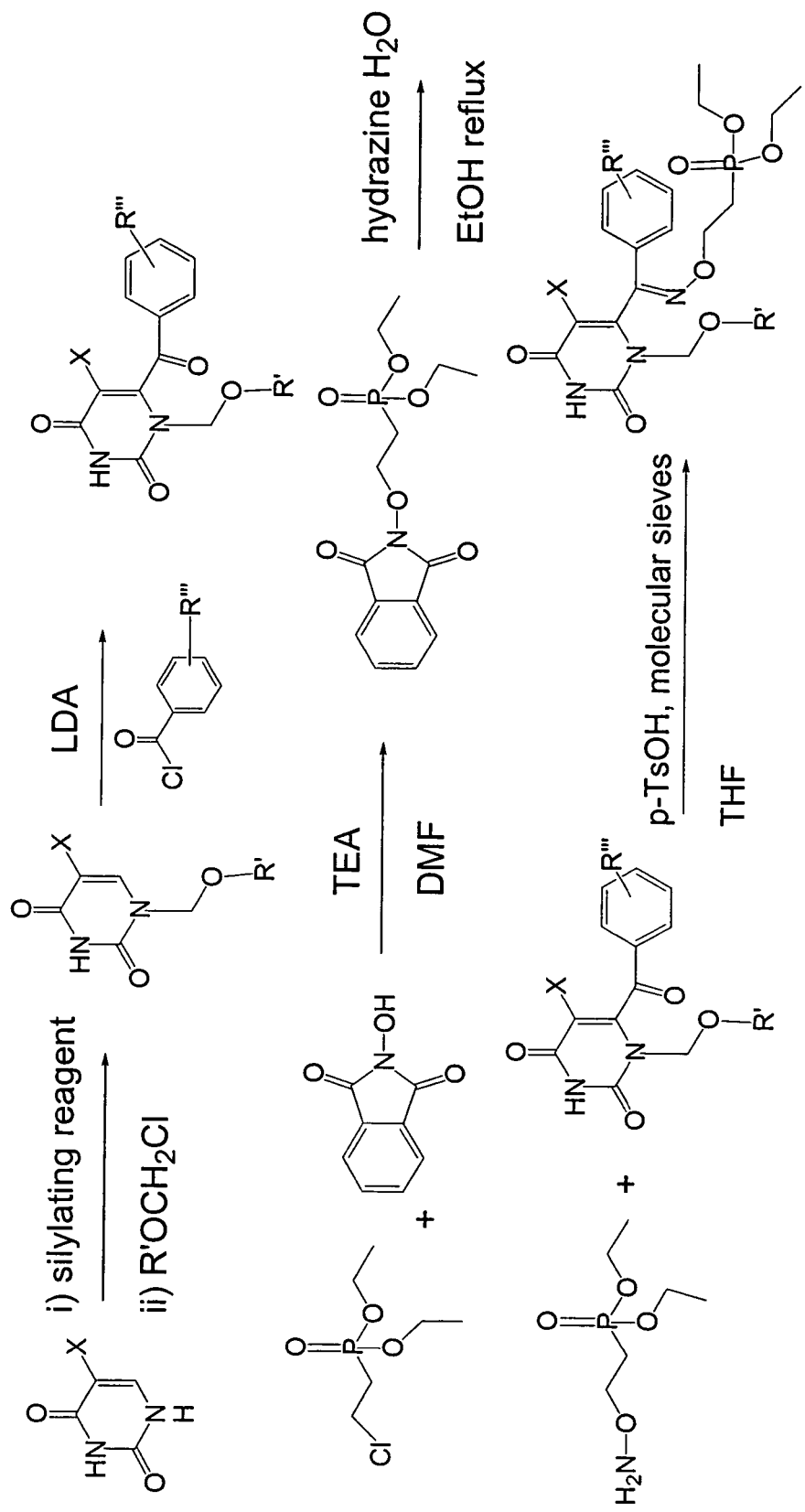
FIG. 75 depicts Scheme 4 which is described in detail herein below.
Figure 76:
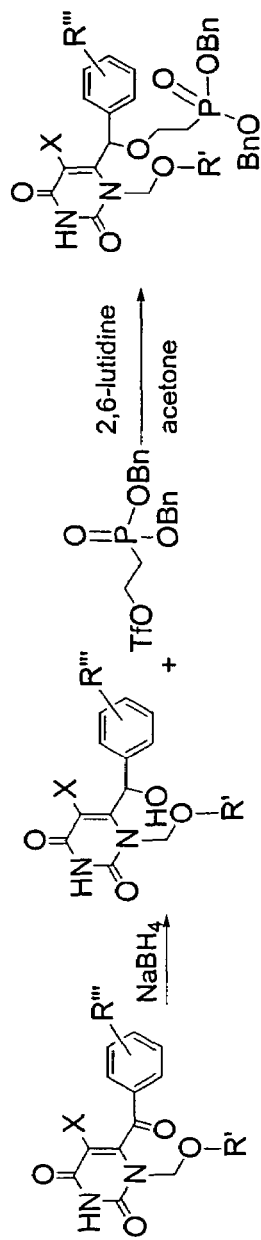
FIG. 76 depicts Scheme 5 which is described in detail herein below.
Figure 77:
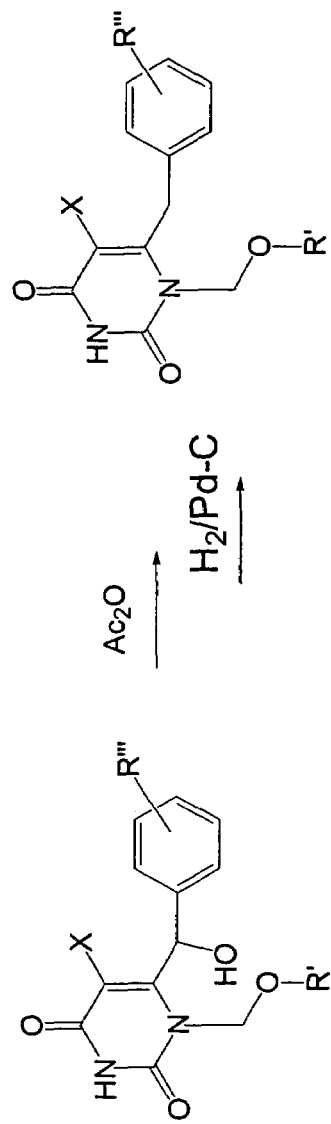
FIG. 77 depicts Scheme 6 which is described in detail herein below.

Alternatively the 5 position may be functionalized after the nucleophile is appended by the TFA/water deprotection and alkylation strategy shown in Scheme 2 (FIG. 73). Analogs with methylene, a secondary alcohol or a ketone at the 6 position are readily prepared following the LDA procedure in Scheme 2 (FIG. 73), but using substituted or unsubstituted PhCOCl in place of a disulfide, as is done in J. Med. Chem. 1991, 34, 1 page 351. The resultant ketone can be converted to an oxime ether (Scheme 4; FIG. 75), an ether (Scheme 5; FIG. 76) or reduced to a methylene (Scheme 6; FIG. 77). Scheme 6 can be extended with the deprotection and alkylation steps described in Scheme 2. The methylene, secondary alcohol and ether are all described in J. Med. Chem. 1991, 34, 1 page 349-357, and the oxime ether can be prepared as described below (Scheme 4; FIG. 75).

Alternatively the ketone containing compound could undergo deprotection at the 1 position and attachment of the link $PO(R_1)(R_2)$ as in Scheme 2 above.

Figure 78A:
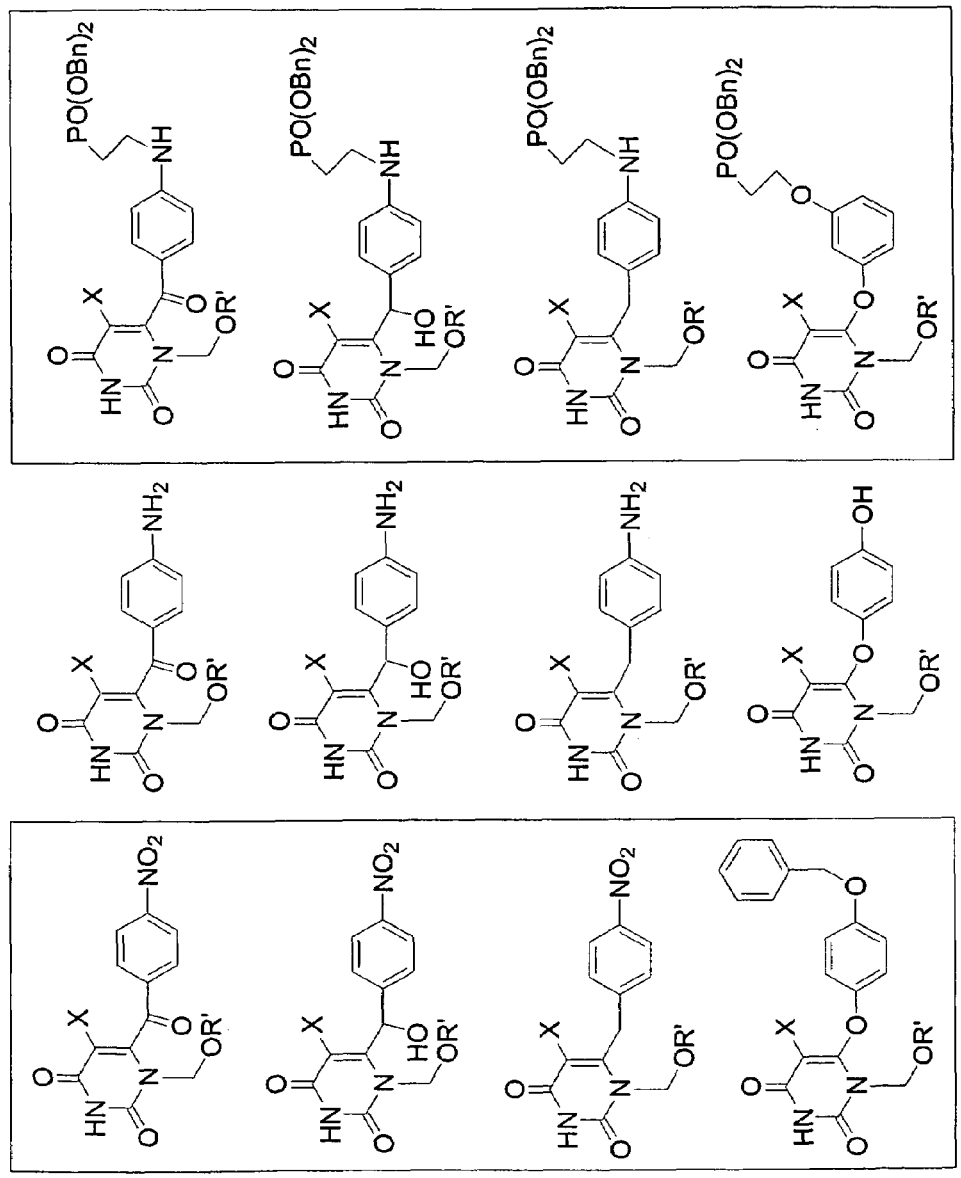
FIGS. 78A-B depict Scheme 7 which is described in detail herein below.
Figure 78B:
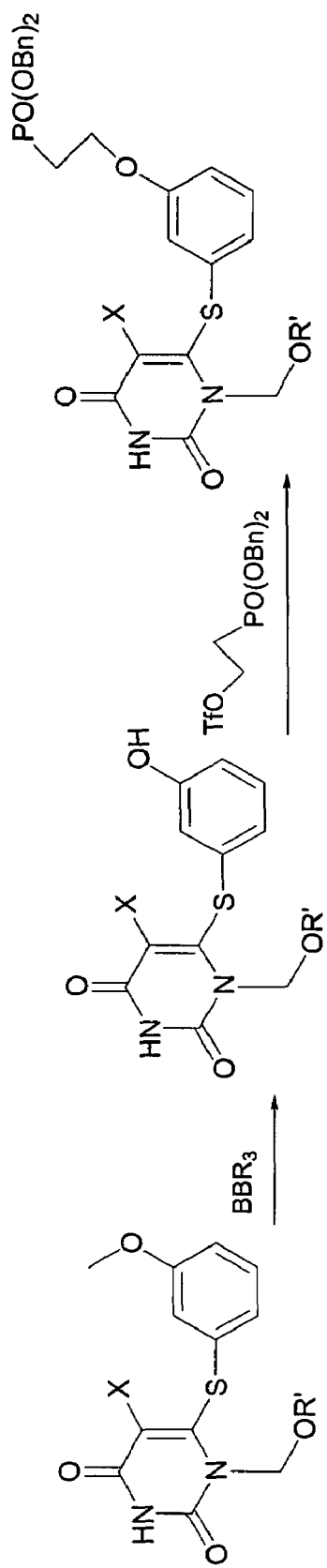

The above shown compounds could also have a reactive group at the aryl or alkyl substituent on the 5 or the 6 position that would allow for attachment of the $PO(R_1)(R_2)$ group. These reactive groups are protected by a protecting group, or be present in the form of a masked functionality, such as the manner in which a nitro group would mask an amine. Scheme 7 (FIG. 78) shows some more representative examples of the many ways an attachment of a $PO(R_1)(R_2)$ is made. The chemistry involved is explained above, except for the BBr3 demethylation, which is a common procedure (J. F. W. McOmie and D. E. West, Org. Synth. Collect. Vol. V, 412, (1973) for demethylating methoxyaryl rings. The compounds in box A are treated with hydrogen gas and stirred in a solvent such as ethanol or methanol with a suspension of 10% palladium on carbon. The anilines or alcohols are then treated with a triflated $PO(R_1)(R_2)$ containing group as described above.

Delavirdine-Like Phosphonate NNRTI Compounds

Diaromatic compounds refer to any diaromatic substituted compound, more specifically, bis(heteroaryl) piperazine (BHAP), more specifically 1 {5-methanesulfonamidoindolyl-2-carbonyl}-4-{3-(1-methylethylamino)-2-pyridinyl}piperazine as found in U.S. Pat. No. 5,563,142 claim 8 column 90 line 49-51, and pharmaceutically acceptable salts thereof.

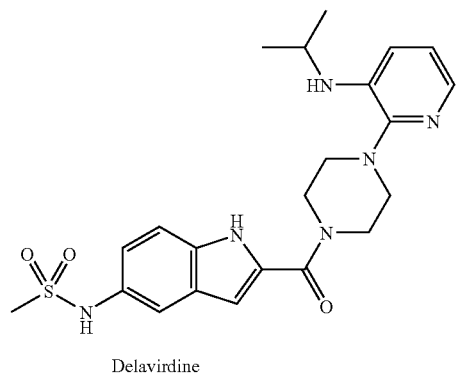

Delavirdine

Preparation of compounds of type A, B, and C require a link which can react with a drug-like compound which is either 1 {5-methanesulfonamidoindolyl-2-carbonyl}-4-{3-

(1-methylethylamino)-2-pyridinyl}piperazine or an intermediate thereof, to result in a covalent bond between the link and the drug-like compound. The link is also attached to the phosphorous containing moiety shown in examples of type A, B and C, namely A1, B1 and C1.

Figure 79:
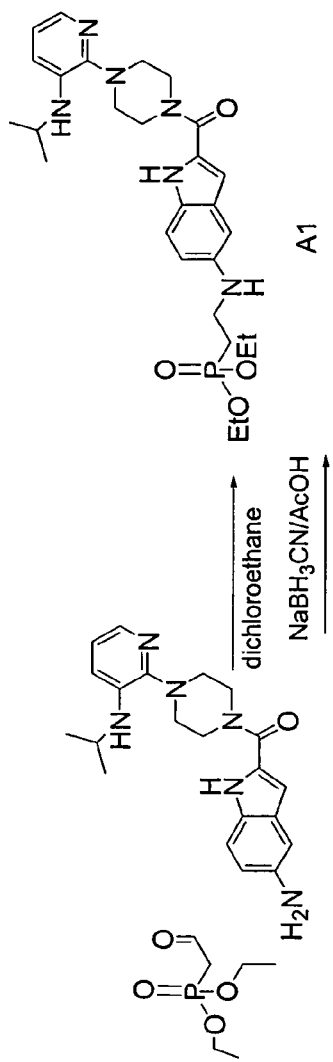
FIG. 79 illustrates Scheme 1 which is described in detail herein below.

Examples of type A can be made by reacting the aminoindole $NH_2$ of the immediate precursor to delavirdine (1-[5-amidoindolyl-2-carbonyl]-4-[3-(1 -methylethylamino)-2-pyridinyl]piperazine, such as example 101 in U.S. Pat. No. 5,563,142, synthesis described therein, with the phosphorous containing moiety having an aldehyde as the reactive part of the link. The aldehyde and $NH_2$ group react through a reductive amination reaction, which can be performed by stirring both reagents in, for example dichloroethane, for approximately two hours and then adding acetic acid and sodium cyanoborohydride, or by other standard methods known to most organic chemists. Commercially available aldehyde containing phosphonates such as that shown in scheme 1 (FIG. 79) can be used to prepare example A1.

This method may be extended to synthesize molecules with the link attached at other positions on the indole phenyl ring by following the procedures described in U.S. Pat. No. 5,563,142 but substituting starting materials as relevant to obtain the indole with the desired substitution pattern.

Figure 80:
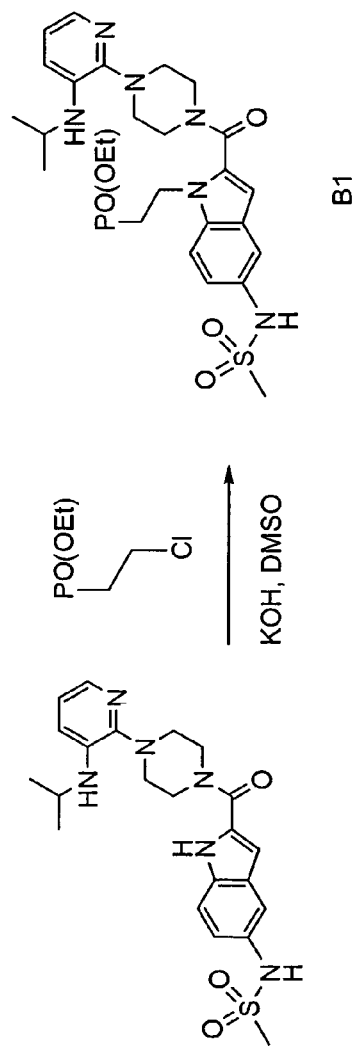
FIG. 80 illustrates Scheme 2 which is described in detail herein below.
Figure 81A:
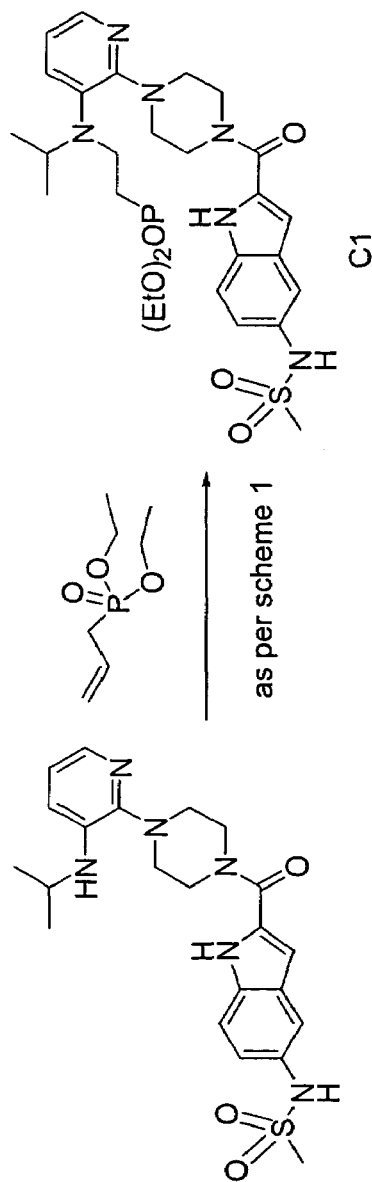
FIGS. 81A-F illustrate Scheme 3 which is described in detail herein below.
Figure 81B:
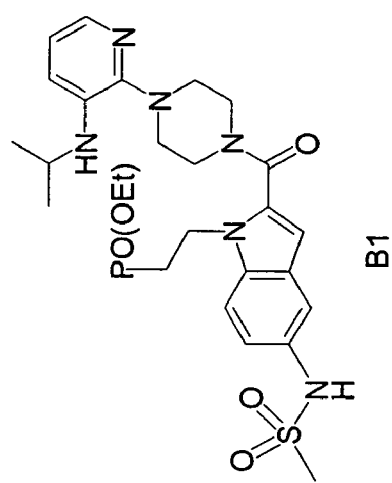
Figure 81C:
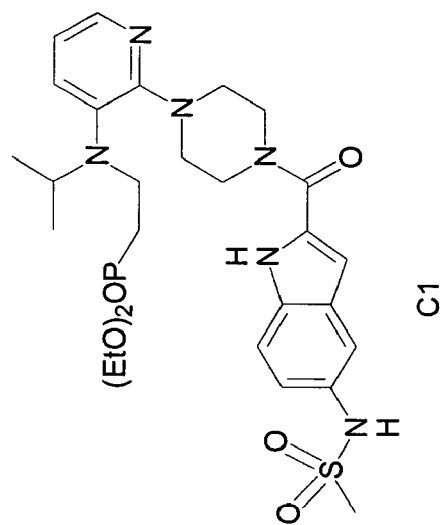
Figure 81D:
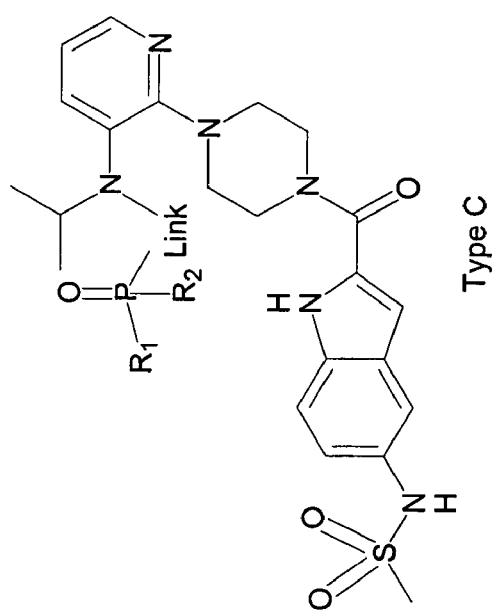
Figure 81E:
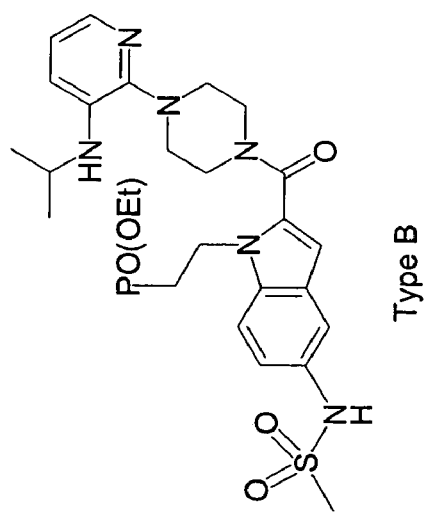
Figure 81F:
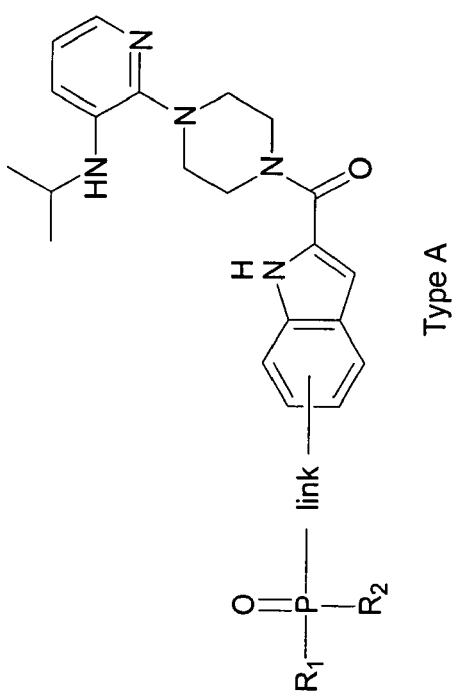

Examples of type B can be prepared by reacting the indole NH of delavirdine with, for example, a link which contains an alkyl chloride in the presence of KOH in DMSO as described in J. Med. Chem. 34, 3, 1991, 1099-1110. The alkyl chloride link is for example commercially available chloromethyl diethoxyphosphonate, giving example B1 (Scheme 2, FIG. 80).

Examples of type C can be made by reacting the secondary amine of delavirdine with the phosphorous containing moiety having an aldehyde as the reactive part of the link (Scheme 3; FIG. 81). The aldehyde and NH group react through a reductive amination reaction, which can be performed by stirring both reagents in, for example dichloroethane, for approximately two hours and then adding acetic acid and sodium cyanoborohydride, or by other standard methods known to most organic chemists. In this example the aldehyde containing phosphonate is commercially available. This procedure will provide example C1.

The present invention provides novel analogs of 1 {5-methanesulfonamidoindolyl-2-carbonyl}-4-{3-(1-methylethylamino)-2-pyridinyl}piperazine. Such novel 1 {5-methanesulfonaidioindolyl-2-carbonyl}-4-{3-(1-methylethylamino)-2-pyridinyl}piperazine analogs possess all the utilities of 1 {5-methanesulfonamidoindolyl-2-carbonyl}-4-{3-(1-methylethylamino)-2-pyridinyl}piperazine and optionally provide cellular accumulation as set forth below.

Emivirine-Like Phosphonate NNRTI Compounds

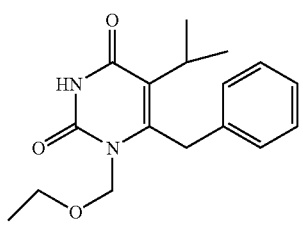

-continued

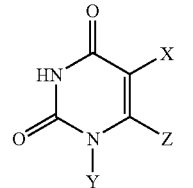

X = alkyl $C_1$–$C_{12}$ branched or straight
Y = alkyl, alkoxy, with or without link-$PO(R_1)(R_2)$
Z = $Y^2$-link-$PO(R_1)(R_2)$ or
    $Y^2$-Aryl (optionally substituted)
    or $Y^2$-alkyl
$Y^2$ = $CR_2$, O, S, NR (R = H, alkyl $C_1$–$C_{12}$), C = O, COH

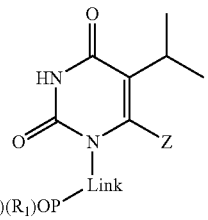

Type A [Y = link $PO(R_1)(R_2)$]

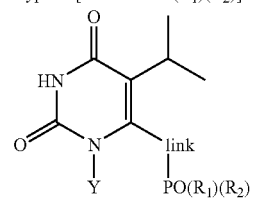

Type B [Z = link $PO(R_1)(R_2)$]

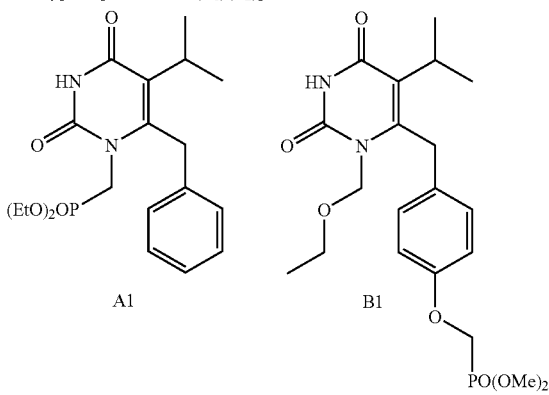

A1                B1

The present invention provides novel phosphonate analogs of Emivirine and pharmaceutically acceptable salts thereof. Emivirine is described in U.S. Pat. No. 5,461,060. Such novel Emivirine analogs possess all the utilities of Emivirine and optionally provide cellular accumulation as set forth below.

The present invention also relates to the delivery of Emivirine-like phosphonate compounds which are optionally targeted for site-specific accumulation in cells, tissues or organs. More particularly, this invention relates to analogs of Emivirine which comprise Emivirine linked to a $PO(R_1)(R_2)$ moiety.

Emivirine is covalently bonded directly or indirectly by a link to the $PO(R_1)(R_2)$ moiety. An R group of the $PO(R_1)(R_2)$ moiety can possibly be cleaved within the desired delivery site, thereby forming an ionic species which does not exit the cell easily. This may cause accumulation within the cell and can optionally protect the Emivirine analog from exposure to metabolic enzymes which would metabolize the analog if not protected within the cell. The cleavage may occur as a result of normal displacement by cellular nucleophiles or enzymatic action, but is preferably caused to occur selectively at a predetermined release site. The advantage of this method is that the Emivirine analog may optionally be delivered site-specifically, may optionally accumulate within the cell and may optionally be shielded from metabolic enzymes.

Link: an atom or molecule which covalently binds together two components. In the present invention, a link is intended to include atoms and molecules which can be used to covalently bind Emivirine or an analog thereof at one end of the link to the $PO(R_1)(R_2)$ at the other end of the link. The link must not prevent the binding of the analog with its appropriate receptor. Examples of suitable links include, but are not limited to, polymethylene [—$(CH_2)_n$, where n is 1-10], ester, amine, carbonate, carbamate, ether, olefin, aromatic ring, acetal, heteroatom containing ring, or any combination of two or more of these units. The $PO(R_1)(R_2)$ may also be directly attached. A skilled artisan will readily recognize other links which can be used in accordance with the present invention.

The preceding Schemes 1-7 for SJ3366-like phosphonate NNRTI compounds illustrate various aspects of the present invention and are not to be construed to limit the types of analogs that may employ this strategy of linking Emivirine or an Emivirine analog to a $PO(R_1)(R_2)$ moiety in any manner whatsoever.

Loviride-Like Phosphonate NNRTI Compounds

The present invention relates to Loviride-like phosphonate NNRTI compounds and their delivery to cells, tissue or organs which are optionally targeted for site-specific accumulation. More particularly, this invention relates to phosphonate analogs of Loviride, and their pharmaceutically acceptable salts and formulations, which comprise Loviride linked to a phosphonate, i.e. $PO(R_1)(R_2)$ moiety.

The groups $R_1$-$R_{10}$ are as described in U.S. Pat. No. 5,556,886, and also can be link $PO(R_1)(R_2)$. The present invention provides novel phosphonate analogs of Loviride. Such novel Loviride analogs possess all the utilities of NNRTI properties as Loviride and optionally provide cellular accumulation as set forth below.

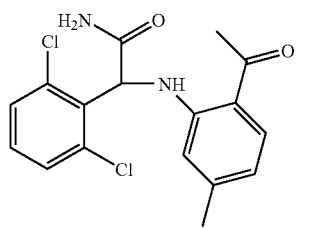

Loviride

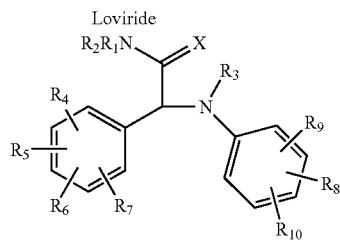

Loviride may be covalently bonded directly or indirectly by a link to the $PO(R_1)(R_2)$ moiety. An R group of the $PO(R_1)(R_2)$ moiety can possibly be cleaved within the desired delivery site, thereby forming an ionic species which does not exit the cell easily. This may cause accumulation within the cell and can optionally protect the Loviride analog from exposure to metabolic enzymes which would metabolize the analog if not charged or protected within the cell. The cleavage may occur as a result of normal displacement by cellular nucleophiles or enzymatic action, but is preferably caused to occur selectively at a predetermined release site. The advantage of this method is that the Loviride analog may optionally be delivered site-specifically, may optionally accumulate within the cell and may optionally be shielded from metabolic enzymes.

The following examples illustrate various aspects of the present invention and are not to be construed to limit the types of analogs that may employ this strategy of linking Loviride or an Loviride analog to a $PO(R_1)(R_2)$ moiety in any manner whatsoever.

UC781-Like Phosphonate NNRTI Compounds

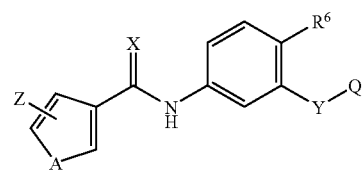

The present invention includes UC781-like phosphonate compounds and pharmaceutically acceptable salts thereof. UC781 is described in U.S. Pat. No. 6,143,780.

A, X, Y, Q and $R^6$ in the formula above are as defined in U.S. Pat. No. 6,143,780. Z represents any substitution of the heteroatom ring. Also the heteroatom ring may be six membered. The present invention provides novel phosphonate analogs of UC781. Such novel UC781 analogs possess all the utilities of Emivirine and optionally provide cellular accumulation as set forth below. The present invention also relates to the delivery of UC781-like phosphonate compounds which are optionally targeted for site-specific accumulation in cells, tissues or organs. More particularly, this invention relates to analogs of UC781 which comprise UC781 linked to a $PO(R_1)(R_2)$ moiety.

UC781 is covalently bonded directly or indirectly by a link to the $PO(R_1)(R_2)$ moiety. An R group of the $PO(R_1)(R_2)$ moiety can possibly be cleaved within the desired delivery site, thereby forming an ionic species which does not exit the cell easily. This may cause accumulation within the cell and can optionally protect the UC781e analog from exposure to metabolic enzymes which would metabolize the analog if not protected within the cell. The cleavage may occur as a result of normal displacement by cellular nucleophiles or enzymatic action, but is preferably caused to occur selectively at a predetermined release site. The advantage of this method is that the UC781 analog may optionally be delivered site-specifically, may optionally accumulate within the cell and may optionally be shielded from metabolic enzymes.

Link is any moiety which covalently binds together UC781 or an analog of UC781 and a phosphonate group. In the present invention, a link is intended to include atoms and molecules which can be used to covalently bind UC781 or an analog thereof at one end of the link to the $PO(R_1)(R_2)$ at the other end of the link. The link should not prevent the binding of the analog with its appropriate receptor. Examples of suitable links include, but are not limited to, polymethylene [—$(CH_2)_n$, where n is 1-10], ester, amine, carbonate, carbamate, ether, olefin, aromatic ring, acetal, heteroatom containing ring or any combination of two or more of these units. Direct attachment of the PO($R_1$)($R_2$) is also possible. A skilled artisan will readily recognize other links which can be used in accordance with the present invention.

The following examples illustrate various aspects of the present invention and are not to be construed to limit the types of analogs that may employ this strategy of linking UC781 or an UC781 analog to a PO($R_1$)($R_2$) moiety in any manner whatsoever.

Preparation of compounds of type A may proceed via a link which can react with UC781 or an analog or intermediate thereof, to result in a covalent bond between the link and the drug-like compound. The link is also attached to the phosphorous containing moiety as shown in an example of type A, namely A1.

Figure 82:
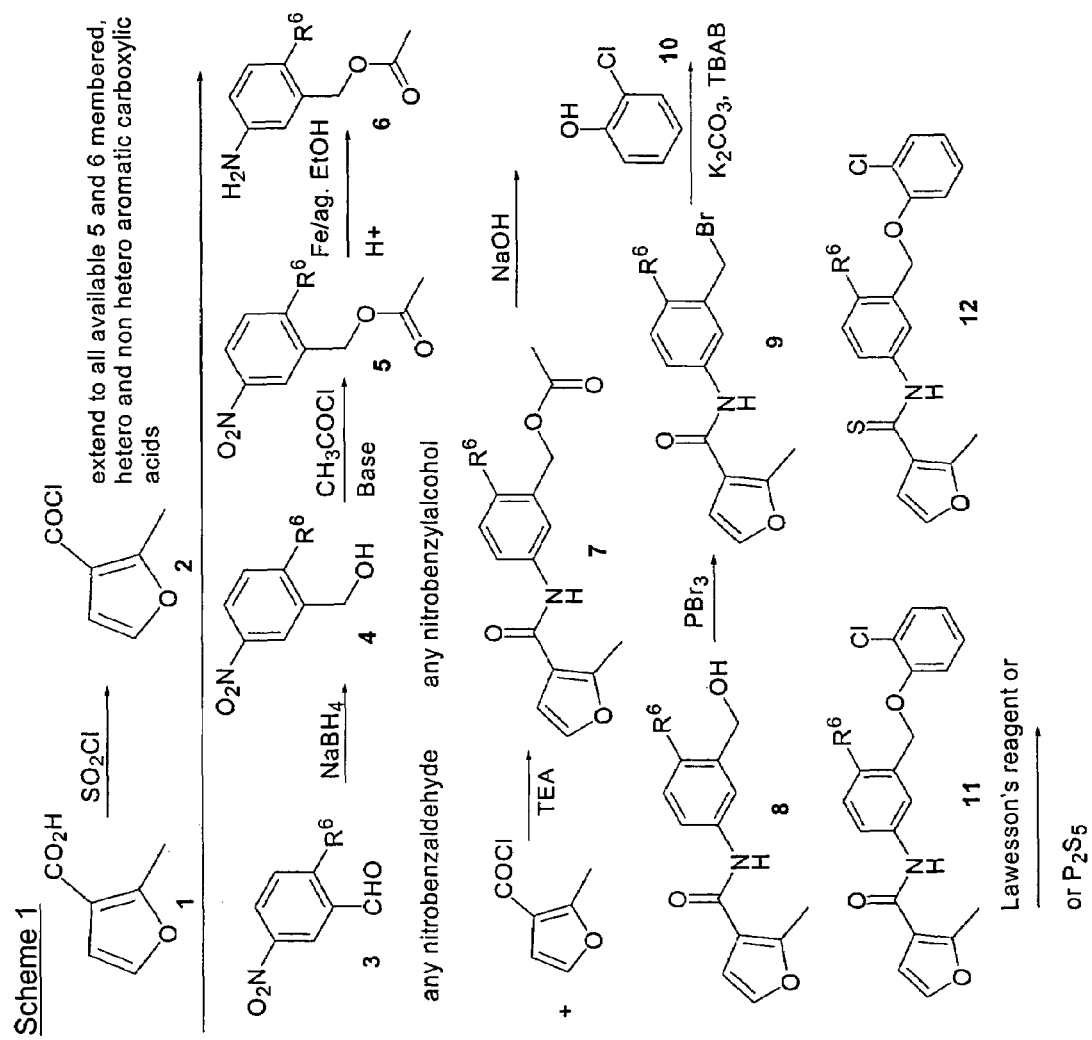
FIG. 82 illustrates Scheme 1 which is described in detail herein below.

Preparation of N-3-((2-chlorophenoxy)methyl)-4-chlorophenyl-2-methyl-3-furancarbothioamide, compound 12 in scheme 1 (FIG. 82) and intermediates 2, 4-11, as per U.S. Pat. No. 6,143,780.

Step 1: Preparation of 2-chloro-5-nitrobenzoyl alcohol 30 g of 2-chloro-5-nitrobenzaldehyde was dissolved in 500 mL of methanol and cooled to 0° C. A solution of 10 g of sodium borohydride in 100 mL of water was then added dropwise over 90 minutes while maintaining the temperature below 10° C. The resultant reaction mixture was then stirred for one hour, then acidified with 2N HCl and left stirring overnight. The solids were then, washed with water and dried, to produce 27 g of 2-chloro-5-nitrobenzyl alcohol as a white solid.

Step 2: Preparation of 2-chloro-5-nitrobenzoyl acetate 27 g of the 2-chloro-5-nitrobenzyl alcohol prepared above in Step 1, was dissolved in 122 mL of toluene. 22 mL of triethylamine was then added. The resultant reaction mixture was cooled to 20° C. and then a solution of 10.2 mL of acetyl chloride in 10 mL of toluene, was added dropwise, keeping the temperature below 20° C. The reaction mixture was then stirred overnight. 2.1 mL of triethylamine and 1.1 mL of acetyl chloride/toluene solution were then added and the reaction mixture was stirred for one hour. 100 mL of water was then added, followed by 50 mL of ether. The resulting organic phase was separated, washed with 2N HCl, aqueous sodium bicarbonate solution and water. The washed organic phase was then dried over magnesium sulfate and the solvent was evaporated, to produce 29.6 g of 2-chloro-5-nitrobenzoyl acetate as a white solid.

Step 3: Preparation of 5-amino-2-chlorobenzoyl acetate 24 g of iron powder was added to a solution of 1.6 mL of concentrated HCl, 16.8 mL of water, and 70 mL of ethanol. 29.6 g of the 2-chloro-5-nitrobenzoyl acetate prepared above in Step 2 dissolved in 45 mL of ethanol, was then added to the mixture in three equal portions. The resultant reaction mixture was refluxed for 5 hours. An additional 2.4 g of iron and 0.1 mL of concentrated HCl was then added to the reaction mixture. The reaction mixture was then refluxed for an additional one hour, filtered through Celite and evaporated. 100 mL of water was then added to the evaporated material and the resultant mixture was extracted with 100 mL of ether. The ether solution was washed with water, dried over magnesium sulfate, and evaporated, to produce 22.9 g of 5-amino-2-chlorobenzoyl acetate as an oil.

Step 4: Preparation of N-(3-acetoxymethyl-4-chlorophenyl)-2-methyl-3-furancarboxanilide. A solution of 22.8 g of the 5-amino-2-chlorobenzoyl acetate from Step 3 above and 17.2 mL of triethylamine in 118 mL ether was prepared and then added dropwise to a second solution of 16.6 g 2-methyl-3-thiophenecarboxylic acid chloride in 118 mL ether at 0° C. to 10° C. and the resultant mixture was stirred at room temperature overnight. 100 mL of water and 100 mL of ethyl acetate were then added to the mixture, the organic phase separated, washed with 2N hydrochloric acid and water, dried over magnesium sulfate, and the solvents removed in vacuo, to produce 29.87 g of N-(3-acetoxymethyl-4-chlorophenyl)-2-methyl-3-furancarboxamide as a beige solid.

Step 5: Preparation of N-(4-chloro-3-hydroxymethylphenyl)-2-methyl-3-furancarboxamide. A solution of 29 g of the N-(3-acetoxymethyl-4-chlorophenyl)-2-methyl-3-furancarboxamide prepared in Step 4 above and 14.5 g potassium hydroxide in 110 mL water, was prepared. The solution was then heated at 70° C. for 16 hours and then acidified with 2N hydrochloric. The resulting solid was collected, washed with water, and dried, producing 23.65 g of N-(4-chloro-3-hydroxymethylphenyl)-2-methyl-3-furancarboxamide as a white solid.

Step 6: Preparation of N-(3-bromomethyl-4-chlorophenyl)-2-methyl-3-furancarboxamide. 12 g of the N-(4-chloro-3-hydroxymethylphenyl)-2-methyl-3-furancarboxamide prepared in Step 5 above, was dissolved in 180 mL ethyl acetate. 1.8 mL of phosphorus tribromide was then added. The resultant mixture was stirred for 90 minutes at room temperature. 100 mL of water was then added to the mixture. The resultant organic phase was separated, washed with water, aqueous sodium bicarbonate solution and water, and then dried over magnesium sulfate. The solvent was evaporated off to produce 12.97 g of N-(3-bromomethyl-4-chlorophenyl)-2-methyl-3-furancarboxamide as a solid.

Step 7: Preparation of N-3-((2-chlorophenoxy)methyl)-4-chlorophenyl-2-methyl-3-furancarboxamide. 2 g of the N-(3-bromomethyl-4-chlorophenyl)-2-methyl-3-furancarboxamide produced in Step 6, was dissolved in 20 mL of 2-butanone to produce a solution. 0.84 g of potassium carbonate, 0.79 g of 2-chlorophenol and 0.2 g of tetrabutylammonium bromide were then added to the solution. The resultant reaction mixture was stirred at room temperature overnight, the solvents removed in vacuo, and the residue extracted with ethyl acetate, to produce a second solution. This second solution was washed with 2N aqueous sodium hydroxide and water, and then dried over magnesium sulfate. The solvent was removed to produce 2.7 g of a solid, which was purified by dissolving in ethyl acetate:hexane (20:80) and running the resultant solution through a plug of silica gel. Removal of solvent produced 2.0 g of N-3-((2-chlorophenoxy)methyl)-4-chlorophenyl-2-methyl-3-furancarboxamide as a white solid.

Step 8: Preparation of N-3-((2-chlorophenoxy)methyl)-4-chlorophenyl-2-methyl-3-furancarbothioamide. 1.5 g of the N-3-((2-chlorophenoxy)methyl)-4-chlorophenyl-2-methyl-3-furancarboxamide prepared in Step 7 above, 0.8 g of Lawesson's reagent (0.8 g) and 1.6 g of sodium bicarbonate were added to 35 mL of toluene, and the resultant reaction mixture was refluxed for five hours. The reaction mixture was then passed through a plug of neutral aluminum oxide, eluted with 1:1 ether/hexane and purified by column chromatography on silica gel, to produce 0.77 g of N-3-((2-chlorophenoxy)methyl)-4-chlorophenyl-2-methyl-3-furancarbothioamide.

The above protocol can easily be modified to attach the link—PO($R_1$)($R_2$).

To prepare compounds of type A in Table 17, the following route is performed. Compound 8 above, when $R^6$ is chloro, is transformed into a triflate by reacting it with triflic anhydride and 2,6 lutidine in dichloromethane at −40° C. The addition of hydroxyethyldimethoxyphosphonate will effect the attachment of the link PO($R_1$)($R_2$) group. Treatment with Lawesson's reagent as above will provide compound A2.

TABLE 17

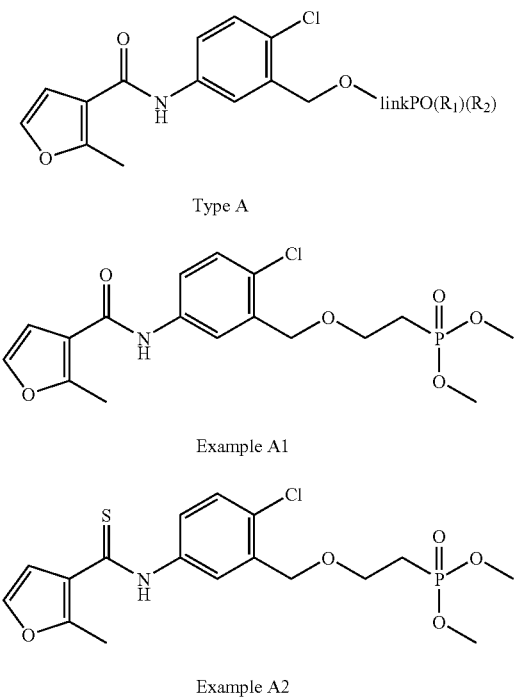

By replacing 2-chloro 5-nitrobenzaldehyde with other nitrobenzaldehyes and following a similar procedure as that used to make compound A2, the relative positions of attachment of the ether and the amide is changed. Furthermore, the chloro substituent shown as $R^6$ above is switched to other positions, and other substituents are used in combination with or without the chloro atom or other substituents anywhere on the ring (shown as Q below). This would allow for compounds of type B2 of Table 18 to be prepared. As with all analogs that are amenable to such treatment, Lawesson's reagent would then be used to convert to the corresponding sulfamide.

TABLE 18

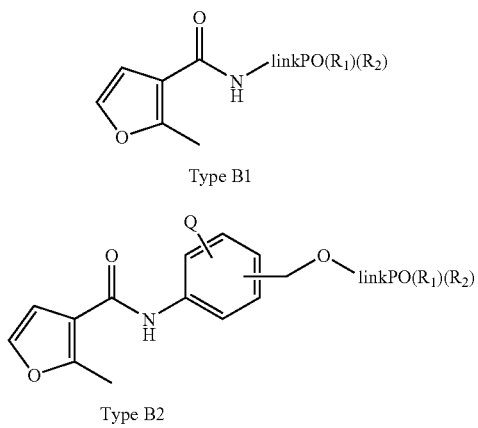

Figure 83:
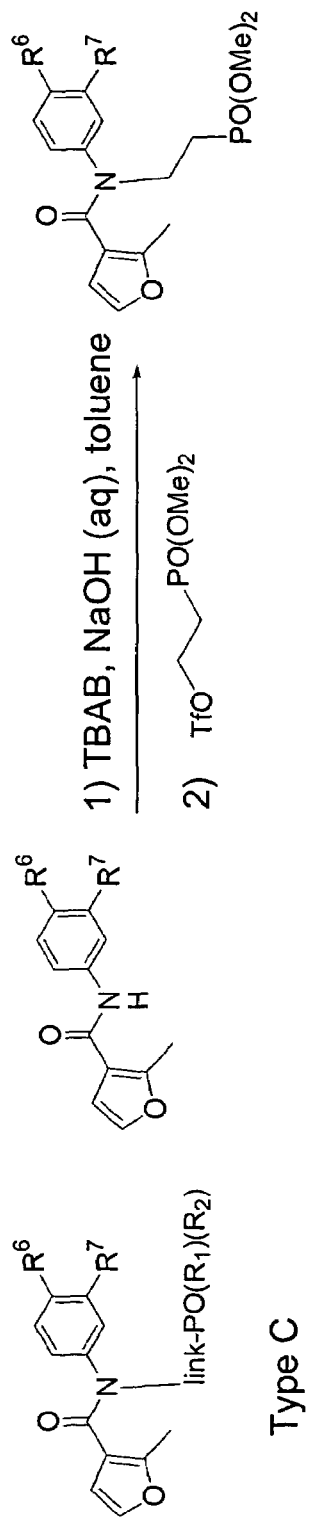
FIG. 83 depicts a reaction with compounds of the general form Type C which is described in detail herein below.
Figure 84A:
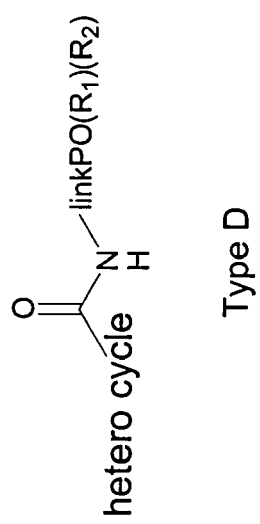
FIGS. 84A-F depict compounds of the general form Type D which is described in detail herein below and reactions therewith.
Figure 84B:
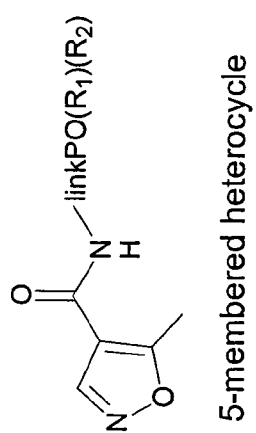
Figure 84C:
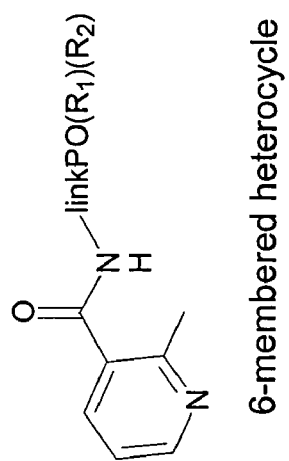
Figure 84D:
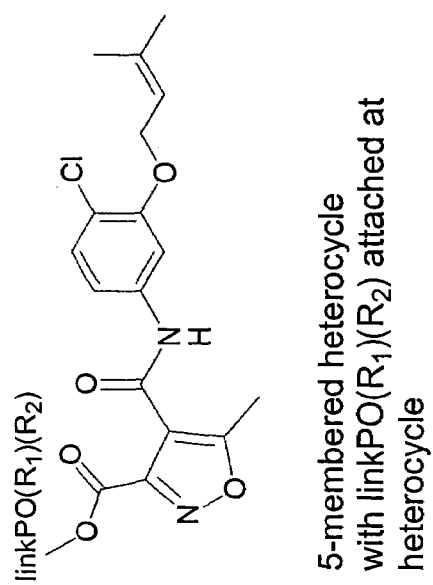
Figure 84E:
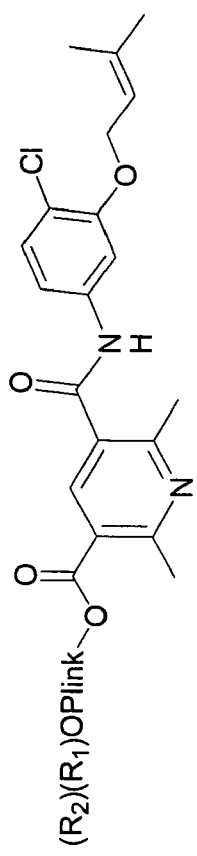
Figure 84F:
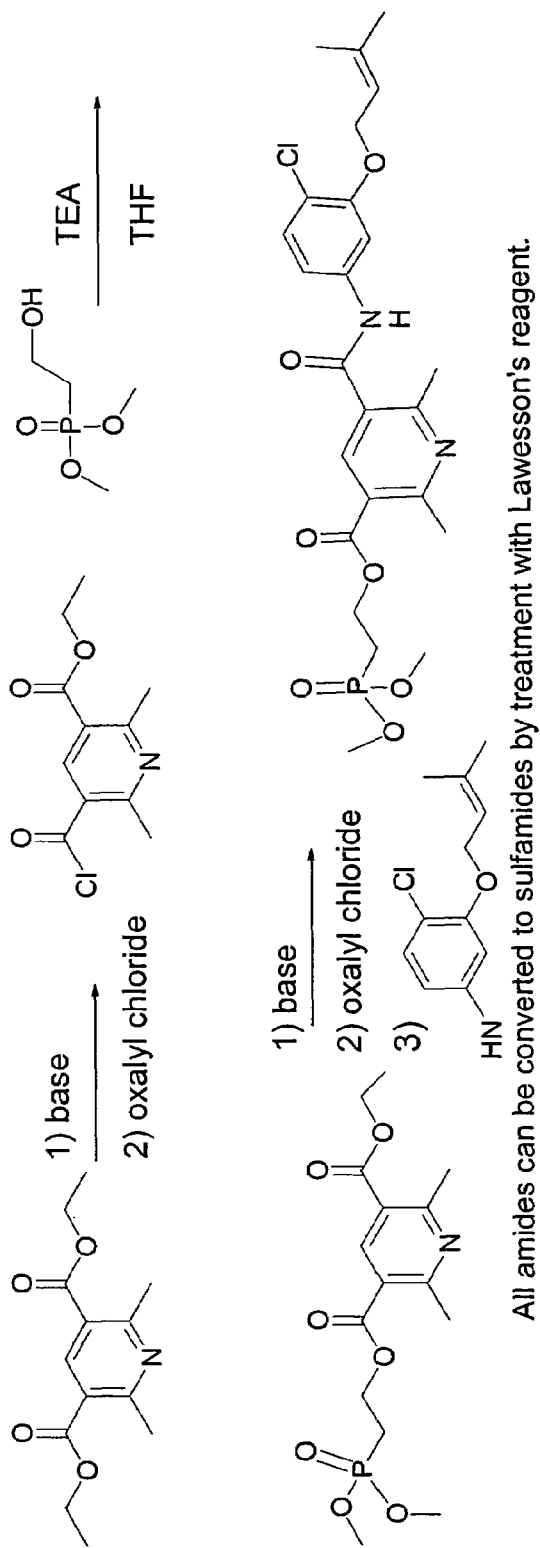
Figure 85A:
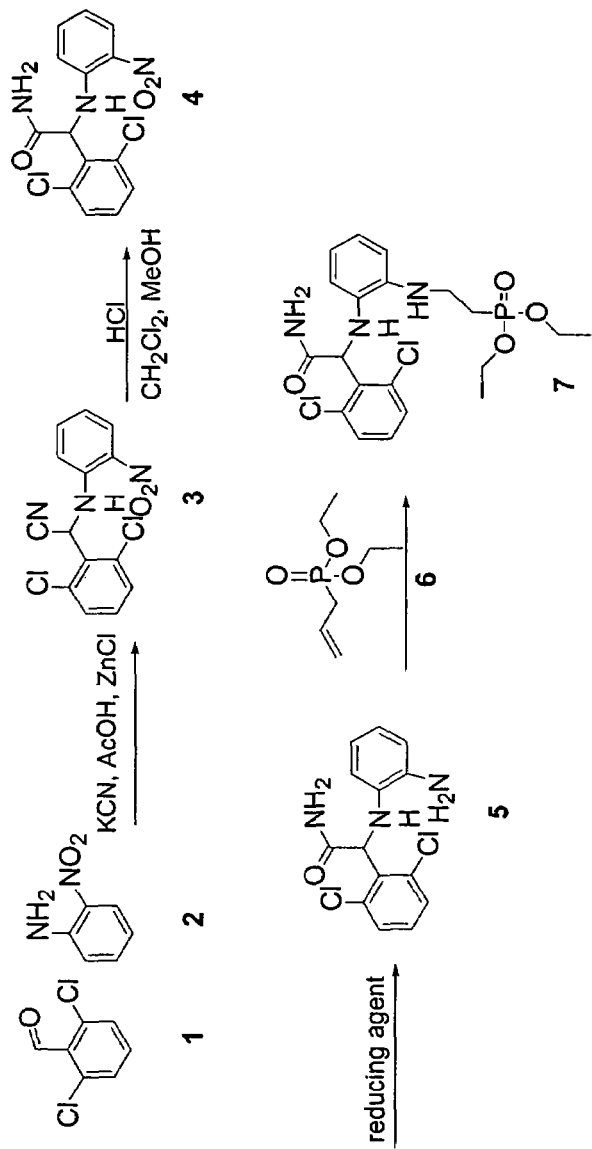
FIGS. 85A-D illustrate Scheme 1 which is described in detail herein below.
Figure 85B:
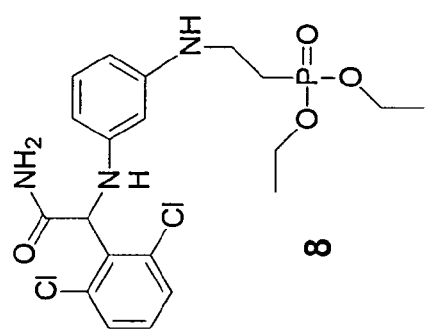
Figure 85C:
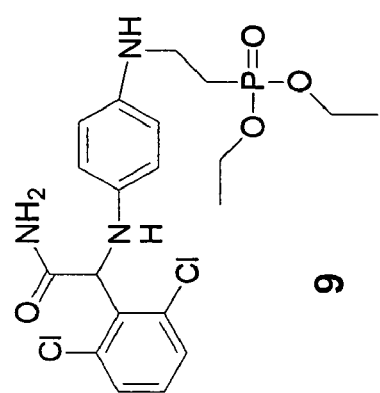
Figure 85D:
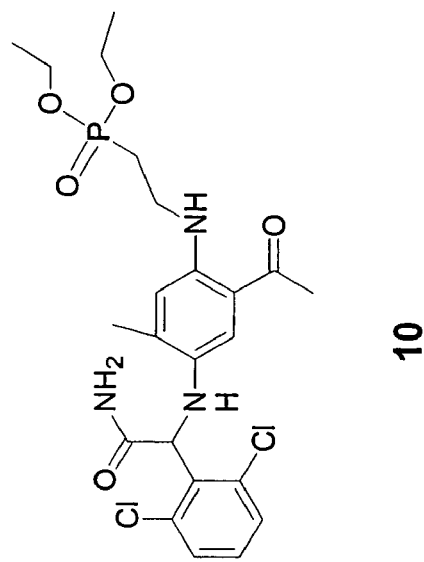

Type B1 compounds would include Type B2 and are prepared using the above steps with the center aryl ring being considered part of the link. Prior to treatment with Lawesson's reagent the amide proton is abstracted by treatment with base to allow for attachment of the PO(R$_1$)(R$_2$) moiety. Lawesson's reagent would then be used to convert to the corresponding sulfamide. This would allow for compounds of the general form Type C shown in FIG. 83.

The furan ring of UC781 is switched to 5 or 6-membered heterocycles easily by substituting different heterocyclic acid chlorides for 2-methyl-3-thiophenecarboxylic acid chloride in step 4 in the above written synthesis of N-3-((2-chlorophenoxy)methyl)-4-chlorophenyl-2-methyl-3-furancarbothioamide. This will afford Type D compounds as exemplified in FIG. 84. The link PO(R$_1$)(R$_2$) moiety is attached directly to the heterocycle by starting with for example the diester of the desired heterocycle. Mono acid formation of the heterocycle by hydrolysis of one ester would allow for attachment of the PO(R$_1$)(R$_2$) group. This would be followed by hydrolysis of the remaining ester by base, acid chloride formation as above and amide formation by reaction with the desired amine. D1, a specific exemplification of Type D compounds having in this case R$_1$ and R$_2$=OMe and link=CH$_2$CH$_2$ is prepared as shown below in FIG. 84.

The details of the first two steps of Scheme 1 (FIG. 85) shown above are thoroughly covered in U.S. Pat. No. 5,556,886. The synthesis can be extended as shown to allow for the attachment of the link PO(R$_1$)(R$_2$) at various sites on either aryl ring.

To attach on the ortho, meta or para positions of the ring that starts out as the substituted aniline, a moiety must be present that will allow for such an attachment of the PO(R$_1$)(R$_2$) moiety. In this case a nitro group is used as an amine precursor. The reduction of the nitro can be effected by tin chloride and acetic acid in an appropriate solvent, or through some other catalytic hydrogenation method. From there, compounds such as compound 5 with a free anilino NH$_2$ can be reacted with, for example, a commercially available phosphonate such as compound 6 above in a reductive amination reaction. This reductive amination is performed using dichloroethane as solvent, and after stirring under dry conditions, sodium cyanoborohydride and acetic acid is added to complete the reaction giving compound 7. Using commercially available meta and para nitroanilines leads to compounds 8, 9 and 10. Other substitution patterns are also possible. Also, other means of attachment are also possible to attach the drug-like compound to the PO(R$_1$)(R$_2$) piece. By varying the position of the nitro group, the PO(R$_1$)(R$_2$) is attached at any position on the anilino ring. Depicted below are examples of nitroanilines that allow for the attachment at various positions.

Figure 86:
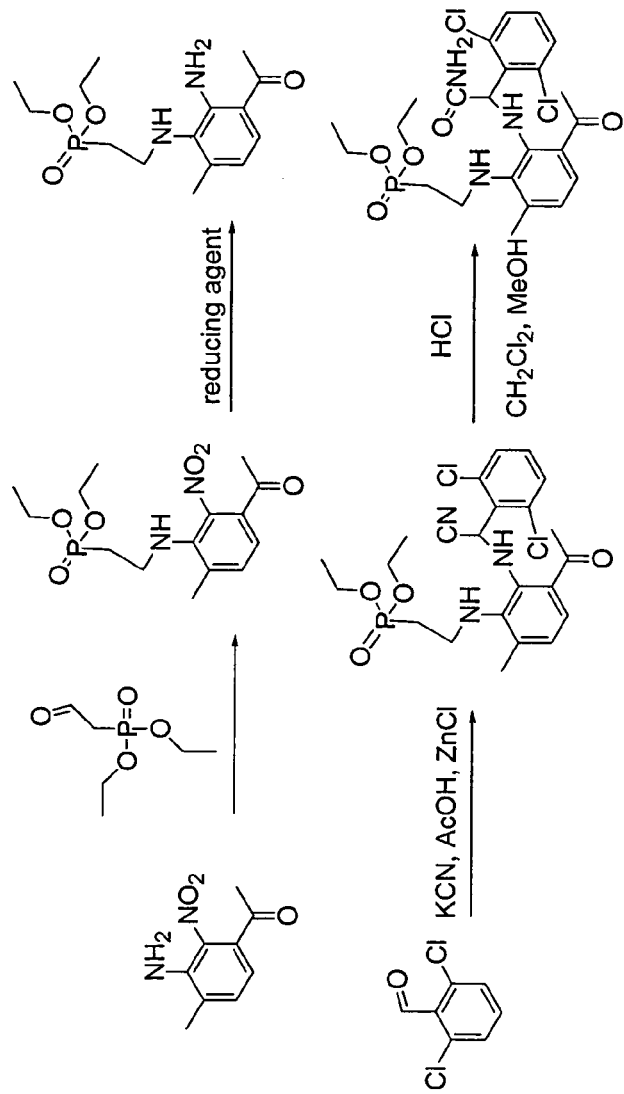
FIG. 86 depicts Scheme 2 which is described in detail herein below.

Alternatively, the nitroanilines is attached to the PO(R$_1$)(R$_2$) moiety prior to coupling with the aldehyde. The nitro is then reduced to form the aniline needed for coupling with the aldehyde. Hydrolysis of the cyano group to the amide is conducted as above, as illustrated in Scheme 2 (FIG. 86).

Figure 87:
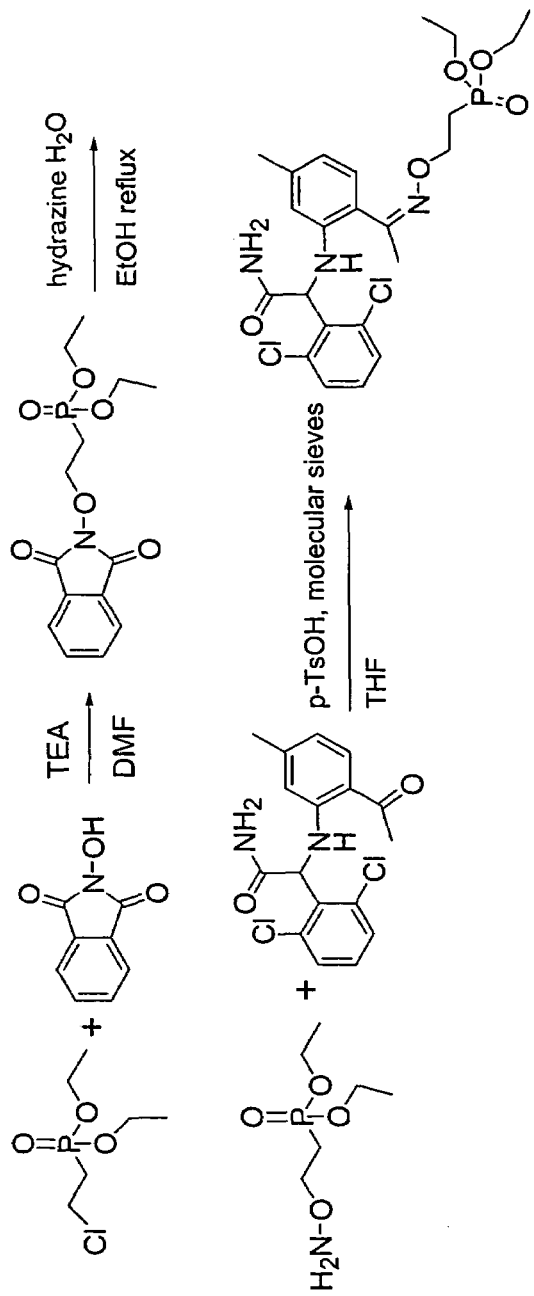
FIG. 87 depicts Scheme 3 which is described in detail herein below.

The ketone of Loviride or Loviride analogs also serves as a point of attachment for the PO(R$_1$)(R$_2$) group. The synthesis of such an attachment is shown in Scheme 3 (FIG. 87).

By using a variation of the benzaldehyde shown as compound 1 in Scheme 1 (FIG. 85), further points of attachment are also attainable. By using, for example, 2,6-dichloro (3,4, or 5 nitro) benzaldehyde, and following Scheme 1 (FIG. 85), the PO(R$_1$)(R$_2$) is attached at any position of the ring which starts out as the benzaldehyde. Further examples of compounds that can be made in this way are compounds 11, 12 and 13 below.

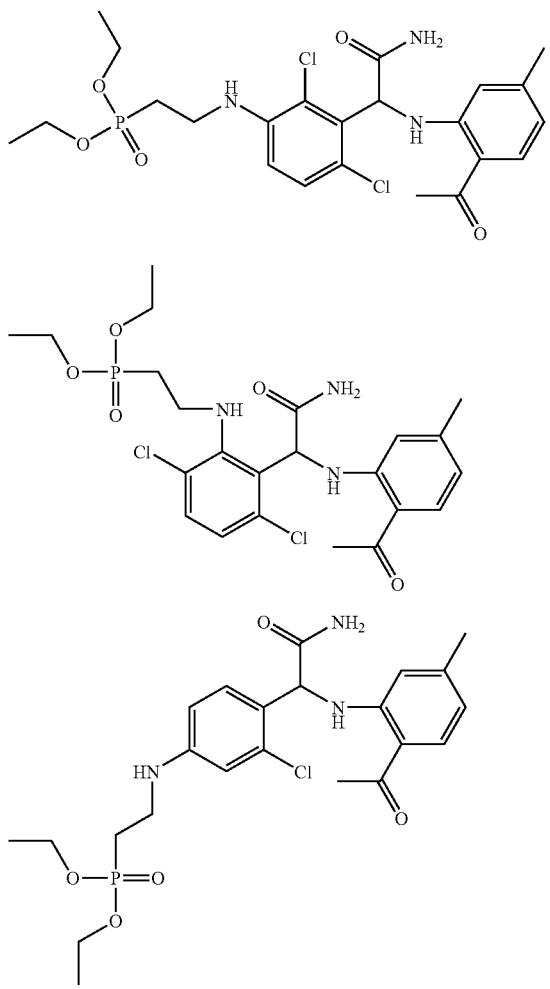

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the claims of the invention.

We claim:

1. A phosphonate anolog of Efavirenz or a pharmaceutically acceptable salt, thereof.
2. A compound according to claim 1 of the Formula:

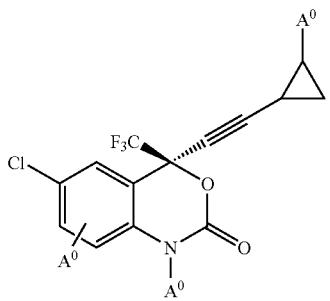

wherein $A^0$ is $A^1$, $A^2$ or $W^3$ with the proviso that the compound includes at least one $A^1$;

$A^1$ is: 

$A^2$ is: 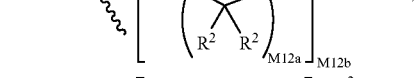

$A^3$ is:

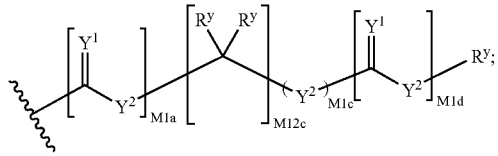

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, —$S(O)_{M2}$—, or —$S(O)_{M2}$—$S(O)_{M2}$—;

$R^x$ is independently H, $R^1$, $W^3$, a protecting group, or the formula:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups, or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or —$NO_2$;

$R^{3b}$ is $Y^1$;

$R^{3c}$ is —$R^x$, —$N(R^x)(R^x)$, —$SR^x$, —$S(O)R^x$, —$S(O)_2R^x$, —$S(O)(OR^x)$, —$S(O)_2(OR^x)$, —$OC(Y^1)R^x$, —$OC(Y^1)OR^x$, —$OC(Y^1)(N(R^x))$, —$SC(Y^1)R^x$, —$SC(Y^1)OR^x$, —$SC(Y^1)(N(R^x)(R^x))$, —$N(R^x)C(Y^1)R^x$, —$N(R^x)C(Y^1)OR^x$, or —$N(R^x)C(Y^1)(N(R^x)(R^x))$;

$R^{3d}$ is —$C(Y^1)R^x$, —$C(Y^1)OR^x$ or —$C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ $R^4$ wherein each $R^4$ is substituted with 0 to 3 $R^3$ groups;

$W^3$ is $W^4$ or $W^5$;

$W^4$ is $R^5$, —$C(Y^1)R^5$, —$C(Y^1)W^5$, —$SO_2R^5$, or —$SO_2W^5$;

$W^5$ is carbocycle or heterocycle wherein $W^5$ is independently substituted with 0 to 3 $R^2$ groups;

$W^6$ is $W^3$ are independently substituted with 1, 2, or 3 $A^3$ groups;

M2 is 0, 1 or 2;
M12a is 1, 2, 3, 4, 3, 6, 7, 8, 9, 10, 11 or 12;
M12b is 0, 1, 2, 3, 4, 5, 6, 7, 8, 9, 10, 11 or 12.
M1a, M1c, and M1d are independently 0 or 1; and
M12c is 0, 1, 2, 3, 4, 5, 6, 7, 8, 9, 10, 11 or 12.

3. A compound of claim 2 having the formulas:

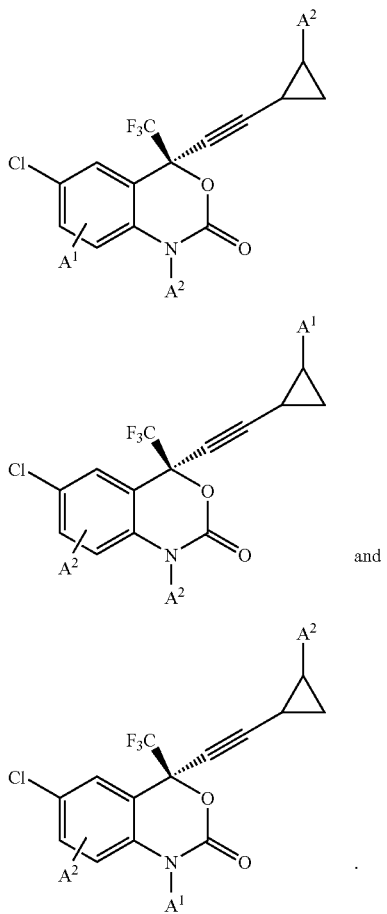

and

.

4. The compound of claim 2 wherein $A^1$ is of the formula:

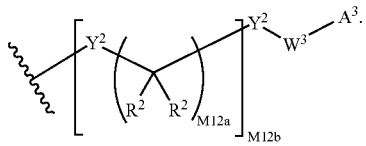

5. The compound of claim 4 wherein $A^1$ is of the formula:

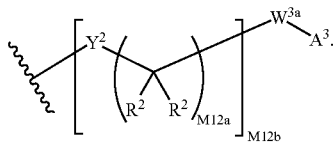

6. The compound of claim 5 wherein $A^1$ is of the formula:

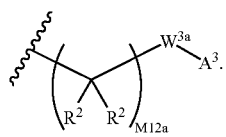

7. The compound of claim 6 wherein $A^1$ is of the formula:

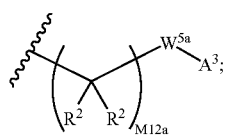

and $W^{5a}$ is a carbocycle or a hetero cycle where $W^{5a}$ is independently substituted with 0 or 1 $R^2$ groups.

8. The compound of claim 7 wherein M12a is 1.

9. The compound of claim 7 wherein $A^1$ is selected from the formulas:

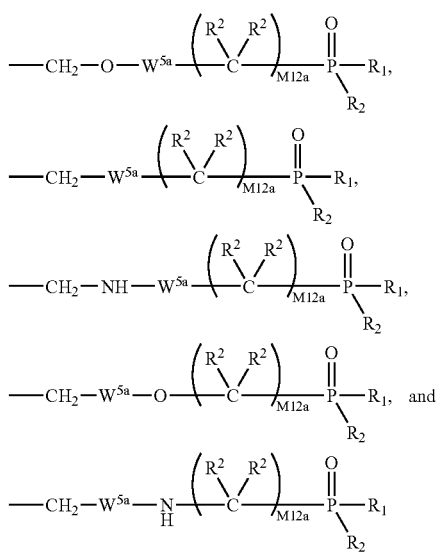

$R_1$ and $R_2$ are independently selected from hydroxy, methoxy, ethoxy, trifluoroethoxy, isopropoxy, phenoxy, benzyloxy, O-pivaloyloxymethyl, an amino acid ester and a lactate ester; and $W^{5a}$ is selected from the formulas:

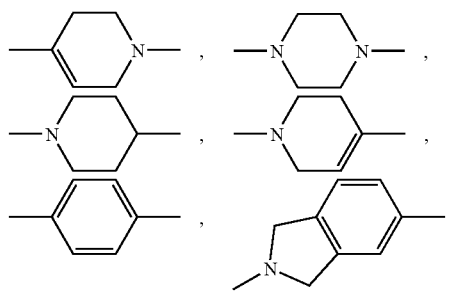

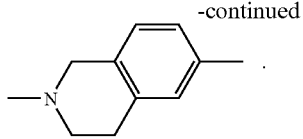

10. The compound of claim 2 wherein $A^3$ is of the formula:

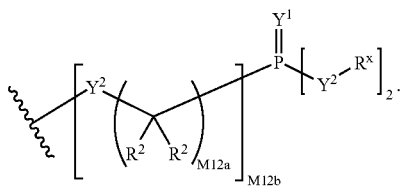

11. The compound of claim 10 wherein $A^3$ is of the formula:

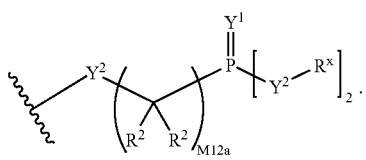

12. The compound of claim 11 wherein $A^3$ is of the formula:

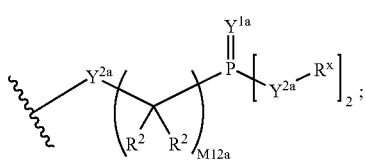

$Y^{1a}$ is O or S; and
$Y^{2a}$ is O, $N(R^x)$ or S.

13. The compound of claim 12 wherein $A^3$ is of the formula:

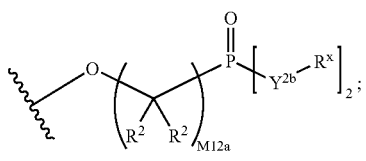

and $Y^{2b}$ is O or $N(R^x)$.

14. The compound of claim 13 wherein $A^3$ is of the formula:

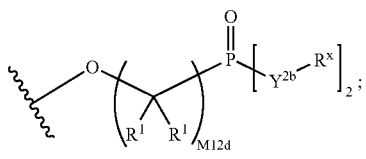

$Y^{2b}$ is O or $N(R^x)$; and
M12d is 1, 2, 3, 4, 5, 6, 7 or 8.

15. The compound of claim 14 wherein $A^3$ is of the formula:

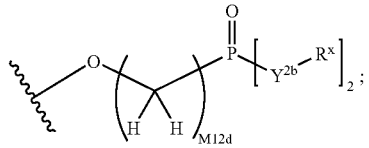

$Y^{2b}$ is O or $N(R^x)$; and
M12d is 1, 2, 3, 4, 5, 6, 7 or 8.

16. The compound of claim 15 wherein M12d is 1.

17. The compound of claim 2 wherein $A^3$ is of the formula:

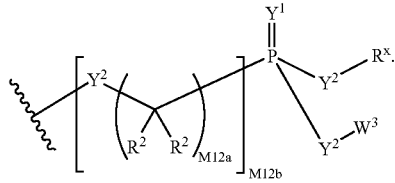

18. The compound of claim 17 wherein $A^3$ is of the formula:

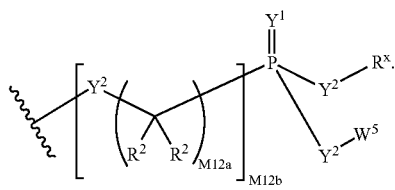

19. The compound of claim 18 wherein $W^5$ is a carbocycle.

20. The compound of claim 19 wherein $A^3$ is of the formula:

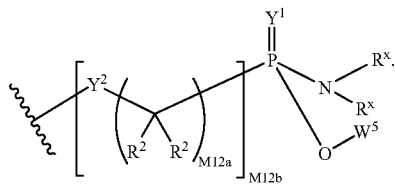

21. The compound of claim 20 wherein $W^5$ is phenyl.

22. The compound of claim 17 wherein M12b is 1.

23. The compound of claim 22 wherein $A^3$ is of the formula:

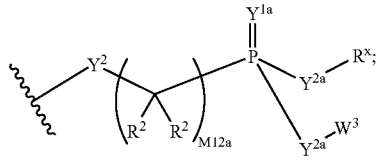

$Y^{1a}$ is O or S; and
$Y^{2a}$ is O, N($R^x$) or S.

24. The compound of claim 23 wherein $A^3$ is of the formula:

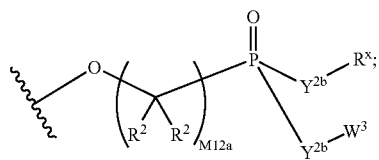

and $Y^{2b}$ is O or N($R^x$).

25. The compound of claim 24 wherein $A^3$ is of the formula:

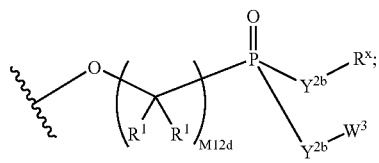

$Y^{2b}$ is O or N($R^x$); and
M12d is 1, 2, 3, 4, 5, 6, 7 or 8.

26. The compound of claim 25 wherein $R^1$ is H.

27. The compound of claim 25 wherein M12d is 1.

28. The compound of claim 25 wherein $A^3$ is of the formula:

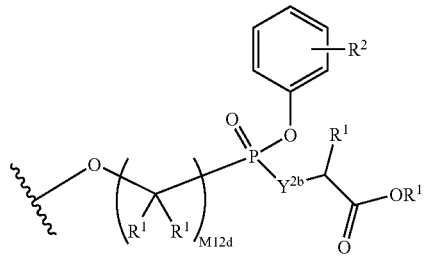

wherein the phenyl carbocycle is substituted with 0 to 3 $R^2$ groups, and $R^1$ is H or $C_1$-$C_{18}$ alkyl.

29. The compound of claim 28 wherein $Y^{2b}$ is N($R^x$).

30. The compound of claim 29 wherein $A^3$ is of the formula:

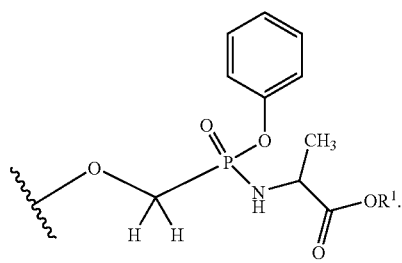

31. The compound of claim 28 wherein $A^3$ is of the formula:

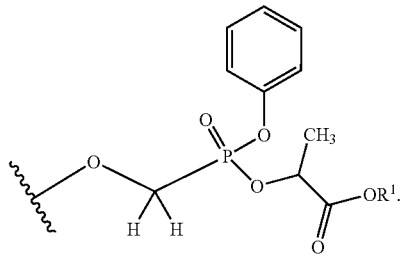

32. A compound of claim 2 wherein $R^x$ is of the formula:

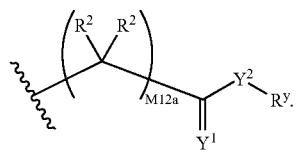

33. A compound of claim 32 wherein $R^x$ is of the formula:

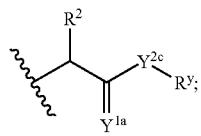

$Y^{1a}$ is O or S; and
$Y^{2c}$ is O, N($R^y$) or S.

34. A compound of claim 32 wherein $R^x$ is of the formula:

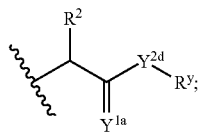

and $Y^{2d}$ is O or N($R^y$).

35. A compound of claim 34 wherein $R^x$ is of the formula:

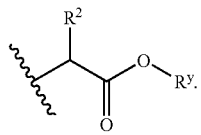

36. A compound of claim 35 wherein $R^x$ is of the formula:

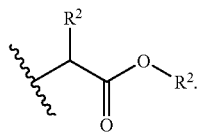

37. The compound of claim 2 wherein $R^x$ is of the formula:

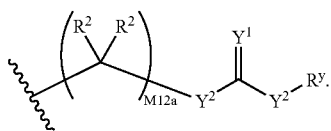

38. The compound of claim 37 wherein $A^3$ is of the formula:

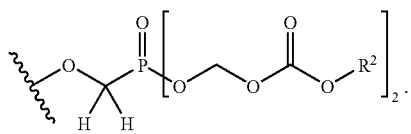

39. The compound of claim 2 wherein $A^3$ is of the formula:

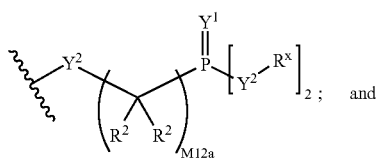

$R^x$ is of the formula:

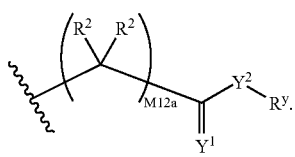

40. The compound of claim 39 wherein $A^3$ is of the formula:

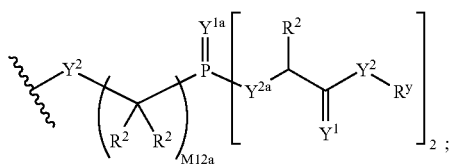

$Y^{1a}$ is O or S; and
$Y^{2a}$ is O, $N(R^2)$ or S.

41. The compound of claim 40 wherein $A^3$ is of the formula:

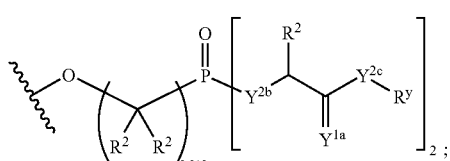

$Y^{2b}$ is O or $N(R^2)$; and
$Y^{2c}$ is O, $N(R^y)$ or S.

42. The compound of claim 41 wherein $A^3$ is of the formula:

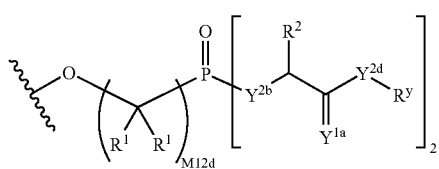

$Y^{1a}$ is O or S;
$Y^{2b}$ is O or $N(R^2)$;
$Y^{2d}$ is O or $N(R^y)$; and
M12d is 1, 2, 3, 4, 5, 6, 7 or 8.

43. The compound of claim 42 wherein $A^3$ is of the formula:

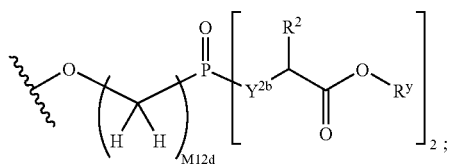

$Y^{2b}$ is O or $N(R^2)$; and
M12d is 1, 2, 3, 4, 5, 6, 7 or 8.

44. The compound of claim 43 wherein $A^3$ is of the formula:

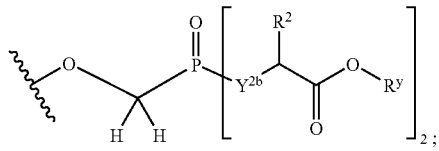

and $Y^{2b}$ is O or $N(R^2)$.

45. The compound of claim 44 wherein $A^3$ is of the formula:

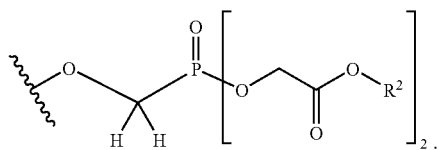

46. The compound of claim 2 wherein $A^3$ is of the formula:

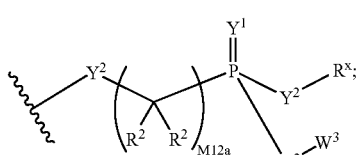

$R^x$ is of the formula:

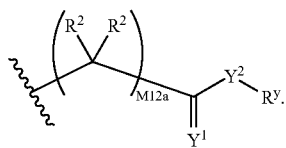

47. The compound of claim 46 wherein $A^3$ is of the formula:

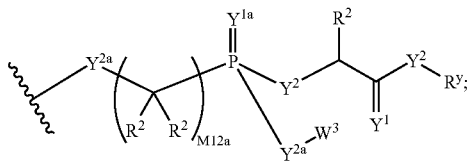

$Y^{1a}$ is O or S; and
$Y^{2a}$ is O, $N(R^2)$ or S.

48. The compound of claim 47 wherein $A^3$ is of the formula:

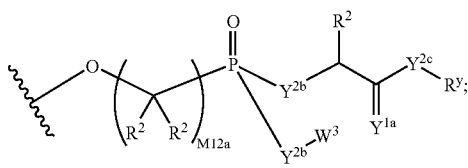

$Y^{2b}$ is O or $N(R^2)$; and
$Y^{2c}$ is O, $N(R^y)$ or S.

49. The compound of claim 48 wherein $A^3$ is of the formula:

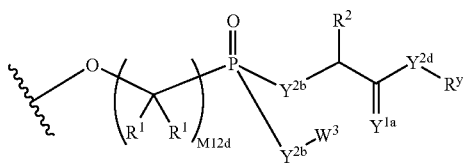

$R^1$ is H or $C_1$-$C_{18}$ alkyl;
$Y^{2d}$ is O or $N(R^y)$; and
M12d is 1, 2, 3, 4, 5, 6, 7 or 8.

50. The compound of claim 49 wherein $R^1$ is H; and $Y^{1a}$ and $Y^{2d}$ are O.

51. The compound of claim 50 wherein M12d is 1.

52. The compound of claim 2 wherein $A^1$ is of the formula:

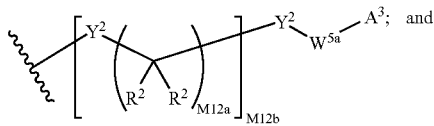

$A^3$ is of the formula:

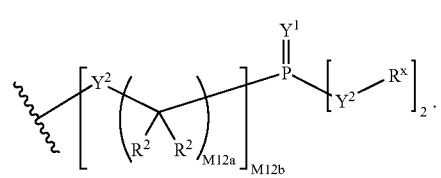

53. The compound of claim 52 wherein $A^1$ is of the formula:

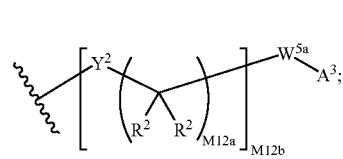

$A^3$ is of the formula:

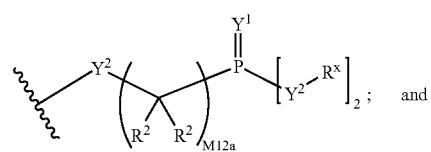

$R^x$ is of the formula:

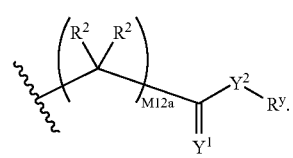

54. The compound of claim 53 wherein $A^1$ is of the formula:

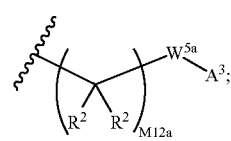

$A^3$ is of the formula:

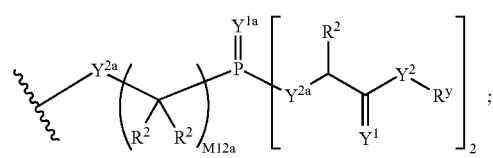

$Y^{1a}$ is O or S; and
$Y^{2a}$ is O, $N(R^2)$ or S.

55. The compound of claim 54 wherein $A^1$ is of the formula:

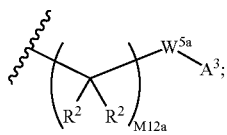

$W^{5a}$ is a carbocycle independently substituted with 0 or 1 $R^2$ groups;

$A^3$ is of the formula:

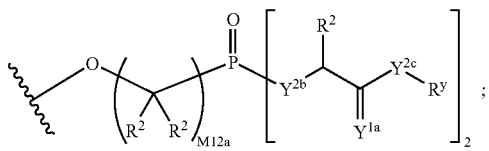

$Y^{1a}$ is O or $Y^{2b}$ is O or $N(R^2)$; and $Y^{2c}$ is O, $N(R^y)$ or S.

56. The compound of claim 55 wherein $A^1$ is of the formula:

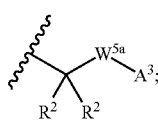

$W^{5a}$ is a carbocycle independently substituted with 0 or 1 $R^2$ groups;

$A^3$ is of the formula:

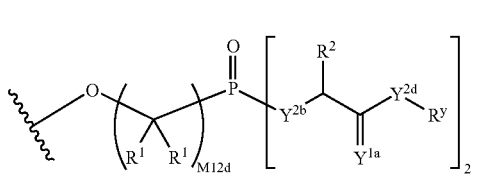

$Y^{1a}$ is O or S;

$Y^{2b}$ is O or $N(R^2)$ $Y^{2d}$ is O or $N(R^y)$; and

M12d is 1, 2, 3, 4, 5, 6, 7 or 8.

57. The compound of claim 56 wherein $A^1$ is of the formula:

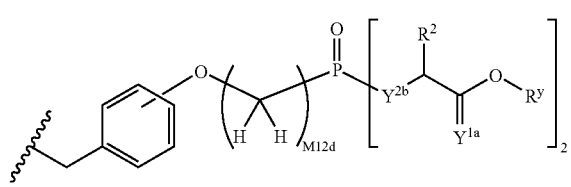

$Y^{2b}$ is O or $N(R^2)$; and

M12d is 1, 2, 3, 4, 5, 6, 7 or 8.

58. The compound of claim 2 wherein $A^1$ is of the formula:

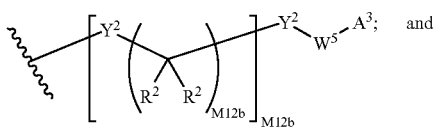

and $A^3$ is of the formula:

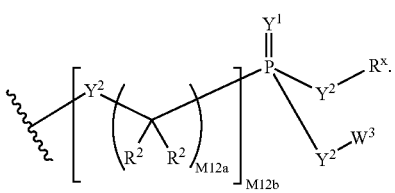

59. The compound of claim 58 wherein $A^1$ is of the formula:

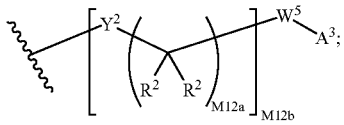

$A^3$ is of the formula:

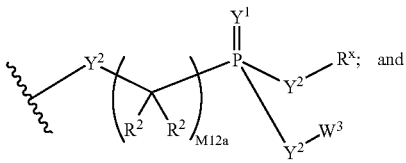

and $R^x$ is of the formula:

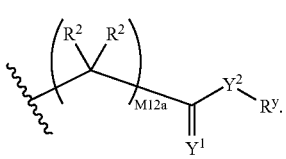

60. The compound of claim 59 wherein $A^1$ is of the formula:

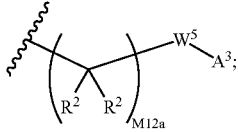

$A^3$ is of the formula:

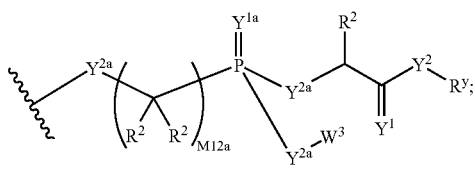

$Y^{1a}$ is O or S; and
$Y^{2a}$ is O, $N(R^2)$ or S.

61. The compound of claim 60 wherein $A^1$ is of the formula:

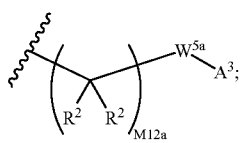

$W^{5a}$ is a carbocycle independently substituted with 0 or 1 $R^2$ groups;
$A^3$ is of the formula:

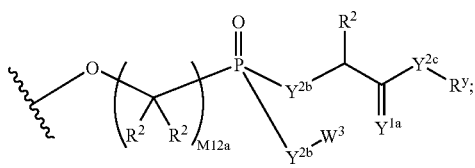

$Y^{1a}$ is O or S;
$Y^{2b}$ is O or $N(R^2)$; and
$Y^{2c}$ is O, $N(R^y)$ or S.

62. The compound of claim 61 wherein $A^3$ is of the formula:

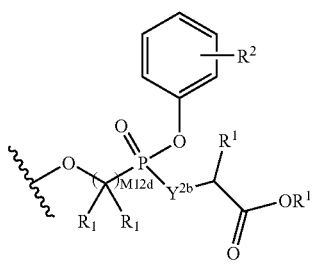

wherein the phenyl carbocycle is substituted with 0 to 3 $R^2$ groups.

63. The compound of claim 59 wherein $A^1$ is of the formula:

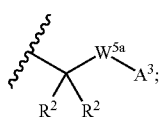

$W^{5a}$ is a carbocycle or heterocyle where $W^{5a}$ is independently substituted with 0 or 1 $R^2$ groups;

$A^3$ is of the formula:

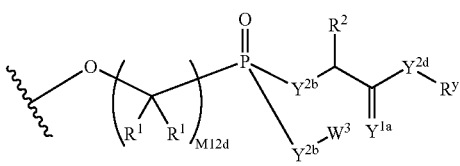

$Y^{1a}$ is O or S;
$Y^{2b}$ is O or $N(R^2)$;
$Y^{2d}$ is O or $N(R^y)$; and
M12d is 1, 2, 3, 4, 5, 6, 7 or 8.

64. The compound of claim 63 wherein $A^1$ is of the formula:

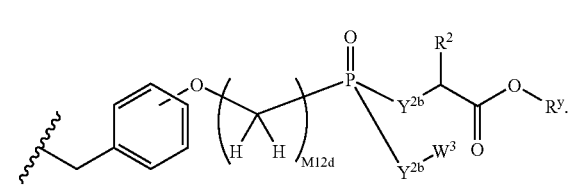

65. The compound of claim 2 wherein $A^2$ is of the formula:

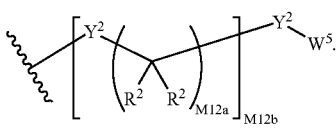

66. The compound of claim 65 wherein $A^2$ is of the formula:

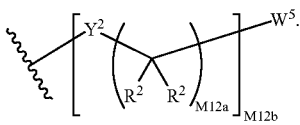

67. The compound of claim 66 wherein M12b is 1.

68. The compound of claim 66 where M12b is 0, $Y^2$ is a bond and $W^5$ is a carbocycle or heterocycle where $W^5$ is optionally and independently substituted with 1, 2, or 3 $R^2$ groups.

69. The compound of claim 66 wherein $A^2$ is of the formula:

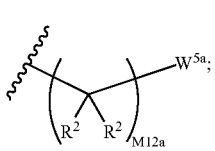

and $W^{5a}$ is a carbocycle or heterocycle where $W^{5a}$ is optionally and independently substituted with 1, 2, or 3 $R^2$ groups.

70. The compound of claim 69 wherein M12a is 1.

71. The compound of claim 70 wherein $A^2$ is selected from phenyl, substituted phenyl, benzyl, substituted benzyl, pyridyl and substituted pyridyl.

72. The compound of claim 2 wherein $A^2$ is of the formula:

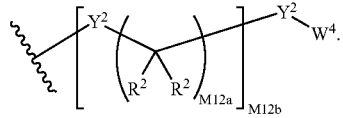

73. The compound of claim 72 wherein $A^2$ is of the formula:

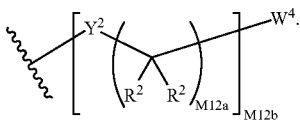

74. The compound of claim 73 wherein M12b is 1.

75. The compound of claim 1 wherein the half-life is improved by at least about 100%.

* * * * *